(12) United States Patent
Qian et al.

(10) Patent No.: US 10,653,701 B2
(45) Date of Patent: May 19, 2020

(54) SUBSTITUTED QUINAZOLINES FOR INHIBITING KINASE ACTIVITY

(71) Applicant: NeuPharma, Inc., Foster City, CA (US)

(72) Inventors: Xiangping Qian, Foster City, CA (US); Yong-Liang Zhu, Fremont, CA (US)

(73) Assignee: NEUPHARMA, INC., Foster City, CA (US)

( * ) Notice: Subject to any disclaimer, the term of this patent is extended or adjusted under 35 U.S.C. 154(b) by 0 days.

(21) Appl. No.: 16/188,852

(22) Filed: Nov. 13, 2018

(65) Prior Publication Data

US 2019/0307767 A1 Oct. 10, 2019

Related U.S. Application Data

(60) Continuation of application No. 15/806,165, filed on Nov. 7, 2017, now Pat. No. 10,172,868, which is a continuation of application No. 15/359,370, filed on Nov. 22, 2016, now Pat. No. 9,849,139, which is a division of application No. 14/466,896, filed on Aug. 22, 2014, now Pat. No. 9,550,770.

(60) Provisional application No. 62/000,946, filed on May 20, 2014, provisional application No. 61/900,283, filed on Nov. 5, 2013, provisional application No. 61/869,596, filed on Aug. 23, 2013.

(51) Int. Cl.
| | |
|---|---|
| A61K 31/517 | (2006.01) |
| A61K 31/553 | (2006.01) |
| A61K 31/5377 | (2006.01) |
| A61K 45/06 | (2006.01) |
| C07D 239/84 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 405/12 | (2006.01) |
| C07D 413/12 | (2006.01) |
| C07D 471/04 | (2006.01) |
| C07C 57/145 | (2006.01) |
| C12Q 1/6886 | (2018.01) |
| G01N 33/574 | (2006.01) |

(52) U.S. Cl.
CPC .......... *A61K 31/553* (2013.01); *A61K 31/517* (2013.01); *A61K 31/5377* (2013.01); *A61K 45/06* (2013.01); *C07C 57/145* (2013.01); *C07D 239/84* (2013.01); *C07D 401/04* (2013.01); *C07D 401/12* (2013.01); *C07D 401/14* (2013.01); *C07D 403/04* (2013.01); *C07D 403/12* (2013.01); *C07D 405/12* (2013.01); *C07D 413/12* (2013.01); *C07D 471/04* (2013.01); *C12Q 1/6886* (2013.01); *G01N 33/57484* (2013.01); *C12Q 2600/156* (2013.01); *C12Q 2600/158* (2013.01)

(58) Field of Classification Search
CPC ................................................. A61K 31/553
See application file for complete search history.

(56) References Cited

U.S. PATENT DOCUMENTS

| | | | |
|---|---|---|---|
| 5,033,252 | A | 7/1991 | Carter et al. |
| 5,052,558 | A | 10/1991 | Carter et al. |
| 5,323,907 | A | 6/1994 | Kalvelage et al. |
| 5,846,514 | A | 12/1998 | Foster et al. |
| 6,334,997 | B1 | 1/2002 | Foster et al. |
| 6,399,603 | B1 | 6/2002 | Jacobs et al. |
| 6,579,868 | B1 | 6/2003 | Asano et al. |
| 7,932,262 | B2 | 4/2011 | Ramurthy et al. |
| 8,946,235 | B2 | 2/2015 | Butterworth et al. |
| 9,550,770 | B2 | 1/2017 | Qian et al. |
| 9,849,139 | B2 | 12/2017 | Qian et al. |
| 10,172,868 | B2 | 1/2019 | Qian et al. |
| 2010/0048561 | A1 | 2/2010 | Ramurthy et al. |
| 2010/0144707 | A1 | 6/2010 | Bartolozzi et al. |
| 2013/0059847 | A1 | 3/2013 | Bearss et al. |
| 2013/0109693 | A1 | 5/2013 | Routier et al. |
| 2014/0080848 | A1 | 3/2014 | Shiau et al. |
| 2014/0255428 | A1 | 9/2014 | Li et al. |
| 2015/0175601 | A1 | 6/2015 | Xiangping et al. |
| 2016/0304471 | A1 | 10/2016 | Xiangping et al. |
| 2017/0050936 | A1 | 2/2017 | Qian et al. |
| 2017/0313683 | A1 | 11/2017 | Wang et al. |
| 2018/0072688 | A1 | 3/2018 | Qian et al. |
| 2018/0125855 | A1 | 5/2018 | Qian et al. |

FOREIGN PATENT DOCUMENTS

| | | |
|---|---|---|
| CN | 1211252 A | 3/1999 |
| CN | 101454294 A | 6/2009 |
| CN | 102260263 A | 11/2011 |
| CN | 103889962 A | 6/2014 |
| CN | 104203924 A | 12/2014 |
| EP | 2269993 A1 | 1/2011 |
| GB | 587936 A | 5/1947 |

(Continued)

OTHER PUBLICATIONS

Pinedo et al. (2000).*

(Continued)

*Primary Examiner* — Paul V Ward

(74) *Attorney, Agent, or Firm* — Wilson Sonsini Goodrich & Rosati

(57) ABSTRACT

Chemical entities that are kinase inhibitors, pharmaceutical compositions and methods of treatment of cancer are described.

22 Claims, No Drawings

(56) References Cited

FOREIGN PATENT DOCUMENTS

| | | |
|---|---|---|
| WO | WO-9722596 A1 | 6/1997 |
| WO | WO-9729106 A1 | 8/1997 |
| WO | WO-9730035 A1 | 8/1997 |
| WO | WO-9732856 A1 | 9/1997 |
| WO | WO-9813354 A1 | 4/1998 |
| WO | WO-9902166 A1 | 1/1999 |
| WO | WO-0040529 A1 | 7/2000 |
| WO | WO-0041669 A2 | 7/2000 |
| WO | WO-0047212 A1 | 8/2000 |
| WO | WO-0121598 A1 | 3/2001 |
| WO | WO-0192224 A1 | 12/2001 |
| WO | WO-0204434 A1 | 1/2002 |
| WO | WO-0208213 A1 | 1/2002 |
| WO | WO-2004082606 A2 | 9/2004 |
| WO | WO-2007117607 A2 | 10/2007 |
| WO | WO-2011046964 A2 | 4/2011 |
| WO | WO-2011135259 A1 | 11/2011 |
| WO | WO-2013013031 A1 | 1/2013 |
| WO | WO-2013130660 A1 | 9/2013 |
| WO | WO-2014037750 A1 | 3/2014 |
| WO | WO-2015027222 A2 | 2/2015 |
| WO | WO-2015193740 A2 | 12/2015 |
| WO | WO-2016133935 A1 | 8/2016 |
| WO | WO-2018035061 A1 | 2/2018 |

OTHER PUBLICATIONS

McMahon et al. (2000).*
Chen et al., Targeting the epidermal growth factor receptor in non-small cell lung cancer cells: the effect of combining RNA interference with tyrosine kinase inhibitors or cetuximab. BMC Medicine. 10(28):1-15 (2012).
Dille, et al. CAPLUS Abstract of: Journal of Organic Chemistry (1955), 20, 171-7.
The United States Department of Health and Human Services, Food and Drug Administration, "Guidance for Industry, Q1A(R2) Stability testing of New Drug Substances and Drug Products" Nov. 2003, Revision 2, pp. 1-25.
Basu, et al., Structure-based design and synthesis of covalent-reversible inhibitors to overcome drug resistance in EGFR. Bioorganic & Medicinal chemistry. 2015; 23(12):2767-2780.
Bundgaard. Design of Prodrugs. Elsevier, 1985.
Bursavich, et al. Novel Mps1 kinase inhibitors: from purine to pyrrolopyrimidine and quinazoline leads. Bioorg Med Chem Lett. Dec. 15, 2013;23(24):6829-33. doi: 10.1016/j.bmcl.2013.10.008. Epub Oct. 11, 2013.
CAS Registry No. 1026642-77-2; STN entry date: Jun. 8, 2008.
CAS Registry No. 1082700-91-1; STN entry date: Dec. 10, 2008.
Cho, et al. Synthesis and antitumor activity of 3-arylisoquinoline derivatives. Arch Pharm Res. Jun. 1997;20(3):264-8.
EP17195141.1 Office Action dated Apr. 18, 2019.
European Search Report dated Feb. 2, 2017 for EP Application No. 14838403.5.
Evans. Synthesis of radiolabeled compounds, J. Radioanal. Chem. 1981; 64(1-2):9-32.
Han, et al., Balancing potency, metabolic stability and permeability in pyrrolopyrimidine-based EGFR inhibitors. European Journal of medicinal chemistry. 2016; 124: 583-607.
He, et al. Synthesis and Sar of novel quinazolines as potent and brain-penetrant c-jun N-terminal kinase (JNK) inhibitors. Bioorg Med Chem Lett. Mar. 15, 2011;21(6):1719-23. doi: 10.1016/j.bmcl. 2011.01.079. Epub Jan. 22, 2011.
Higuchi, et al. Pro-drugs as novel drug delivery systems. American Chemical Society. ACS symposium series 14. 1975.
International search report and written opinion dated Feb. 10, 2015 for PCT Application No. US2014/52409.
International search report and written opinion dated Jul. 25, 2016 for PCT Application No. US2016/018129.
"International Search Report and Written Opinion dated Nov. 30, 2017 for International PCT Patent Application No. PCT/US2017/046819".
Kalbalka, et al. The Synthesis of Radiolabeled Compounds via Organometallic Intermediates, Tetrahedron. 1989; 45(21):6601-21.
Kubinyi, et al., 3D QSAR in Drug Design:Ligand-Protein Interactions and Molecular Similarity. 1998; vol. 2-3: 243-244.
McMahon. VEGF receptor signaling in tumor angiogenesis. The Oncologist. 2000; 5(suppl 1):3-10.
Notice of Allowance dated Aug. 24, 2017 for U.S. Appl. No. 15/359,370.
Notice of allowance dated Aug. 27, 2018 for U.S. Appl. No. 15/806,165.
Notice of allowance dated Sep. 30, 2016 for U.S. Appl. No. 14/466,896.
Office Action dated Jan. 13, 2017 for U.S. Appl. No. 15/044,966.
Office action dated Jan. 21, 2016 for U.S. Appl. No. 14/466,896.
Office action dated Jan. 29, 2018 for U.S. Appl. No. 15/044,966.
Office Action dated Apr. 26, 2017 for U.S. Appl. No. 15/359,370.
Office Action dated Aug. 21, 2017 for U.S. Appl. No. 15/044,966.
Office action dated Aug. 24, 2016 for U.S. Appl. No. 14/466,896.
Pinedo, et al. Translational research: The role of VEGF in tumor angiogenesis. The Oncologist. 2000; 5(suppl 1):1-2.
PubChem. Compound Summary for CID 68388374. Create date: Nov. 30, 2012.
Remington's Pharamceutical Sciences. 18th Edition, Mack Publishing Company (1990).
Remington: The Science and Practice of Pharmacy. 21st Edition, Lippincott Williams & Wilkins (2005).
Roche. Bioreversible Carriers in Drug Design, American Pharmaceutical Association and Pergamon Press, 1987.
Troger, et al. (CAPLUS Abstract of: Journal fuer Praktische Chemie (Leipzig) (1927), 117, p. 117-41).
Warmuth, C. The Practice of Medicinal Chemistry. 2nd edition. 2003.Elsevier. chs. 9-10.
Golub et al., Molecular classification of cancer: class discovery and class prediction by gene expression monitoring. Science. 286(5439):531-537 (1999).
Lala, et al., Role of Nitric and Oxide in Tumor Progression: Lessons from Experimental Tumors. Cancer Metastasis Reviews. 17(1):91-106 (1998).
MedlinePlus. Cancer. https://medlineplus.gov/cancer.html#. 1-12 (2019).
Georgescu et al., New Pyrrolo[1,2-c]Pyrimidine Derivatives. Revue Roumaine de Chimie 42(1): 11-15 (1997).
Georgescu et al., Preparation of some new pyrrolo [1,2-c]pyrimidine derivatives. Revista de Chimie 34(12): 1130-1131 (1983). [Abstract included].

* cited by examiner

SUBSTITUTED QUINAZOLINES FOR INHIBITING KINASE ACTIVITY

CROSS-REFERENCE

This application is a continuation application of U.S. application Ser. No. 15/806,165, filed Nov. 7, 2017, which is a continuation of U.S. application Ser. No. 15/359,370, filed Nov. 22, 2016, which is a divisional application of U.S. application Ser. No. 14/466,896, filed on Aug. 22, 2014, now U.S. Pat. No. 9,550,770, which claims the benefit of priority to U.S. Provisional Application No. 62/000,946, filed May 20, 2014; U.S. Provisional Application No. 61/900,283, filed on Nov. 5, 2013; and U.S. Provisional Application No. 61/869,596, filed on Aug. 23, 2013, which applications are incorporated herein by reference.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

The identification of effective small compounds which specifically inhibit signal transduction and cellular proliferation by modulating the activity of tyrosine and serine/threonine kinases to regulate and modulate abnormal or inappropriate cell proliferation, differentiation, or metabolism is therefore desirable. In particular, the identification of compounds that specifically inhibit the function of a kinase which is essential for processes leading to cancer would be beneficial.

SUMMARY OF THE INVENTION

In one aspect, the present disclosure provides a compound of Formula I

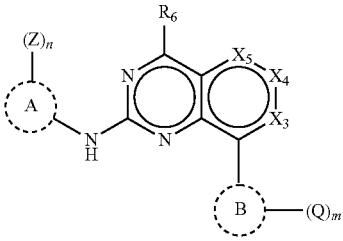

Formula I or a pharmaceutically acceptable salt thereof, wherein
$X_3$ is C—$R_{12}$, or N;
$X_4$ is C—$R_{13}$, or N;
$X_5$ is C—$R_{14}$, or N;
n is 0, 1, 2, 3, 4, or 5;
m is 0, 1, 2, 3, 4, or 5;

is aryl or heteroaryl;

is aryl, heteroaryl, or heterocycloalkyl;
$R_6$, $R_{12}$, $R_{13}$, $R_{14}$, and each Z is independently hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;

each Q is independently hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; wherein E is an electrophilic group capable of forming a covalent bond with a nucleophile.

In some embodiments,

is selected from the group consisting of pyrrolyl, furanyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridinyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, tetrazinyl, and phenyl; and

is selected from the group consisting of piperazinyl, morpholinyl, piperidinyl, thiomorpholinyl, pyrrolidinyl, tetrahydrofuranyl, diazepanyl, azetidinyl, oxetanyl, oxiranyl, aziridinyl, pyrrolyl, furanyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridinyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, tetrazinyl, and phenyl. For example

is selected from the group consisting of phenyl, pyridinyl, pyrimidinyl, pyrazinyl, thiazolyl, oxazolyl, imidazolyl, pyrazolyl, isoxazolyl, and thienyl. For example,

is selected from the group consisting of phenyl, pyridinyl, pyrimidinyl, pyrazinyl, thiazolyl, oxazolyl, imidazolyl, pyrazolyl, isoxazolyl, and thienyl. In some embodiments,

is phenyl or pyridinyl. In other embodiments,

is phenyl or pyridinyl. In some embodiments,

is selected from the group consisting of piperazinyl, morpholinyl, piperidinyl, thiomorpholinyl, pyrrolidinyl, tetrahydrofuranyl, diazepanyl, azetidinyl, oxetanyl, oxiranyl, and aziridinyl. In some embodiments,

is selected from the group consisting of: piperazinyl, morpholinyl, piperidinyl, pyrrolidinyl, tetrahydrofuranyl, and diazepanyl. In some embodiments,

is selected from the group consisting of: piperazinyl, morpholinyl, piperidinyl, and pyrrolidinyl.

In some embodiments, m is 1, 2, or 3; and at least one Q is E. In some embodiments, n is 1 and Z is an optionally substituted heterocycloalkyl. In some embodiments, Z is optionally substituted piperazinyl. For example, Z is methylpiperazinyl or acetylpiperazinyl. In some embodiments, Z is amino optionally substituted with optionally substituted heterocycloalkyl.

In another aspect, the present disclosure provides the compound or pharmaceutically acceptable salt of Formula I wherein

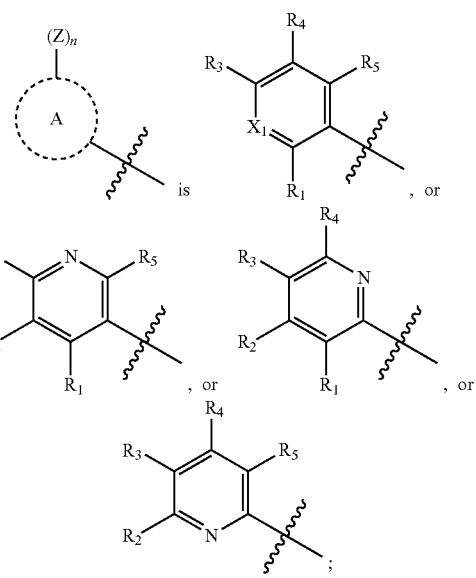

$X_1$ is C—$R_2$, or N; and
$R_1$, $R_2$, $R_3$, $R_4$, and $R_5$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl. Another embodiment of the invention described wherein

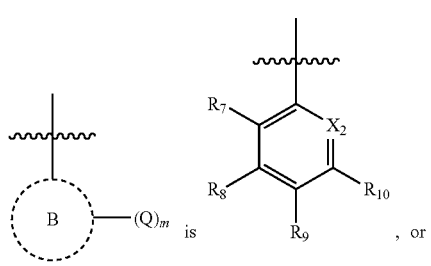

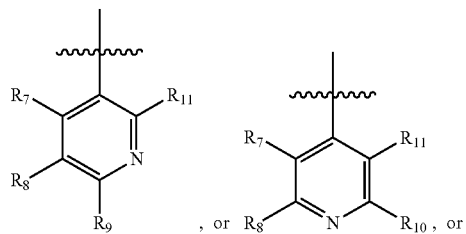

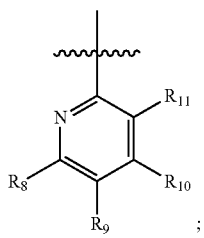

$X_2$ is C—$R_{11}$, or N; and $R_{11}$, $R_7$, $R_8$, $R_9$, and $R_{10}$ are independently, hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl or E; wherein E is an electrophilic group capable of forming a covalent bond with a nucleophile.

In some embodiments, the compound of Formula I is a compound of Formula Ia

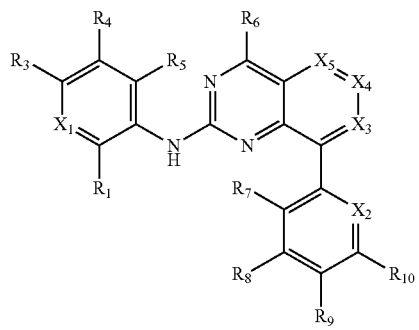

Formula Ia or a pharmaceutically acceptable salt thereof, wherein $X_1$ is C—$R_2$, or N;

$X_2$ is C—$R_{11}$, or N;

$X_3$ is C—$R_{12}$, or N;

$X_4$ is C—$R_{13}$, or N;

$X_5$ is C—$R_{14}$, or N;

$R_1$, $R_2$, $R_3$, $R_4$, $R_5$, $R_6$, $R_7$, $R_1$, $R_{12}$, $R_{13}$, and $R_{14}$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;

$R_8$, $R_9$, and $R_{10}$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; wherein E can be an electrophilic group capable of forming a covalent bond with a nucleophile. In some embodiments, at least one of $R_8$, $R_9$, and $R_{10}$ is E. In some embodiments, $R_3$ is amino optionally substituted with optionally substituted heterocycloalkyl. In some embodiments, $R_4$ is amino optionally substituted with optionally substituted heterocycloalkyl.

In some embodiments, the compound or pharmaceutically acceptable salt has the Formula Ib:

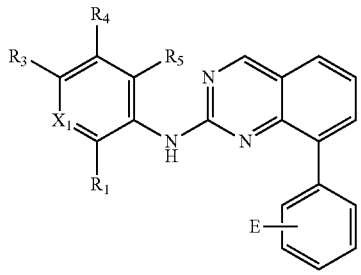

Formula Ib wherein:
$X_1$ is N or C—$R_2$;
each $R_1$, $R_2$, $R_4$, or $R_5$ is independently H or halo;
$R_3$ is optionally substituted heterocycloalkyl; and
E is an electrophilic group capable of forming a covalent bond with a nucleophile.

For example, the compound or pharmaceutically acceptable salt has the Formula Ib':

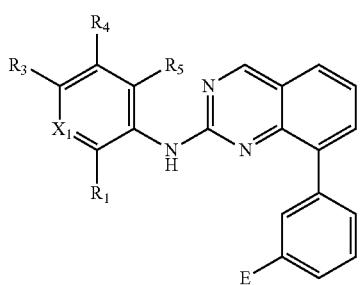

Formula Ib'

In some embodiments, $X_1$ is C—$R_2$. In some embodiments, $R_1$ and $R_2$ are independently hydrogen or halo. In some embodiments, $R_1$ and $R_2$ are hydrogen. In some embodiments, $R_1$ is hydrogen and $R_2$ is halo. In some embodiments, $R_1$ is hydrogen and $R_2$ is fluoro. In some embodiments, $R_1$ is halo and $R_2$ is hydrogen. In some embodiments, $R_1$ is fluoro and $R_2$ is hydrogen. In some embodiments, $R_1$ and $R_2$ are halo. In some embodiments, $R_1$ and $R_2$ are fluoro.

In some embodiments, $R_3$ is optionally substituted morpholinyl, optionally substituted piperazinyl, optionally substituted pyrrolidinyl, optionally substituted piperidinyl, optionally substituted azetidinyl, or substituted amino. For example, $R_3$ is optionally substituted morpholinyl, pyrrolidinyl, piperazinyl, or piperidinyl.

In some embodiments, $R_3$ is piperazinyl, morpholinyl, piperidinyl, or pyrrolidinyl, optionally substituted with —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(O^{Rb})OR^c$ sulfanyl (such as $SR^b$), sulfinyl (such as —$SOR^a$) or sulfonyl (such as —$SO_2R^a$ and —$SO_2NR^bR^c$), where $R^a$ is optionally substituted $C_1$-$C_6$ alkyl, optionally substituted cycloalkyl, optionally substituted heterocycloalkyl, optionally substituted alkenyl, optionally substituted alkynyl, optionally substituted aryl, or optionally substituted heteroaryl;
$R^b$ is hydrogen, optionally substituted $C_1$-$C_6$ alkyl, optionally substituted cycloalkyl, optionally substituted heterocycloalkyl, optionally substituted aryl, or optionally substituted heteroaryl; and
$R^c$ is hydrogen or optionally substituted $C_1$-$C_4$ alkyl; or $R^b$ and $R^c$, and the nitrogen to which they are attached, form an optionally substituted heterocycloalkyl group; and
where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

In some embodiments, $R_3$ is

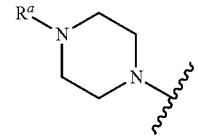

In some embodiments, $R_a$ is $C_1$-$C_6$ alkyl, optionally substituted with $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, or —$NHSO_2(C_1$-$C_4$ haloalkyl).

In some embodiments, $R_a$ is $C_1$-$C_6$ alkyl, optionally substituted with —OH, halo, $C_1$-$C_4$ alkyl, or —$OC_1$-$C_4$ alkyl. In some embodiments, $R_a$ is —$CH_3$, —$CH_2CH_2OH$, —$CH_2CH_2F$, —$CH_2CH_2OMe$, —$CH_2C(CH_3)_2OH$, or —$CH_2CH(CH_3)OH$.

In another aspect, the present disclosure provides a pharmaceutical composition comprising a pharmaceutically acceptable carrier and a compound or pharmaceutically acceptable salt of any one of compounds described herein. The pharmaceutical composition may be formulated in a form which is a tablet, capsule, powder, liquid, suspension, suppository, or aerosol. The pharmaceutical composition may be packaged with instructions for using the composition to treat a subject suffering from cancer.

In another aspect, the present disclosure provides a method of treating cancer in a subject which comprises administering to a subject in need thereof a therapeutically effective amount of a compound or pharmaceutically acceptable salt of any one of the compounds described herein. The cancer may be colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In a further embodiment, the cancer is melanoma, non-small cell lung cancer, thyroid cancer, ovarian cancer, or colon cancer. The melanoma may be unresectable or metastatic melanoma.

In another aspect, the present disclosure provides a method of treating a disorder mediated by EGFR kinase or EGFR mutants in a subject in need thereof, comprising administering to the subject a therapeutically effective amount of a compound or pharmaceutically acceptable salt of any one of the compounds described herein.

In another aspect, the present disclosure provides a method of treating a disorder in a subject in need thereof, comprising: a) determining the presence or absence of a EGFR mutation in a biological sample isolated from the subject; and b) if a EGFR mutation is determined to be present in the subject, administering to the subject a therapeutically effective amount of a compound or pharmaceutically acceptable salt of any one of the compounds described herein.

Somatic activating mutations of the EGFR gene, increased gene copy number and certain clinical and pathological features have been found in certain types of cancer. The specific types of activating mutations may be Exon 19 deletion (del E746-A750) mutations, the single-point substitution mutation L858R in exon 21 and the point mutation T790M. A specific type of activating mutation may also be the double mutations of L858R and T790M. In some embodiments, determining the presence or absence of the EGFR mutation comprises amplifying EGFR nucleic acid from a biological sample and sequencing the amplified nucleic acid. In some other embodiments, determining the presence or absence of the EGFR mutation comprises detecting a mutant EGFR polypeptide in a biological sample using a binding agent to a mutant EGFR polypeptide. The binding agent may be an antibody. The biological sample may be isolated from a tumor of the subject. In some embodiments, determining the presence or absence of the both L858R and T790M EGFR mutations comprises amplifying EGFR nucleic acid from the biological sample and sequencing the amplified nucleic acid, or detecting a double mutant EGFR polypeptide from the biological sample.

In some embodiments, the disorder is cancer. The cancer may be colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In a further embodiment, the cancer is melanoma, non-small cell lung cancer, thyroid cancer, ovarian cancer, or colon cancer. The melanoma may be unresectable or metastatic melanoma.

The treatment method described herein may further comprise administering an additional anti-cancer and/or cytotoxic agent.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION OF THE INVENTION

As used herein, the following words and phrases are generally intended to have the meanings as set forth below, except to the extent that the context in which they are used indicates otherwise.

The following abbreviations and terms have the indicated meanings throughout:
AcOH=acetic acid
Boc=tert-butoxycarbonyl
c-=cyclo DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
i-=iso
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
n-=normal
NaOAc=sodium acetate
PE=petroleum ether
Ph=phenyl
Prep=preparative
quant.=quantitative
RP-HPLC=reverse phase-high pressure liquid chromatography
rt, r.t., or RT=room temperature
s-=sec-=secondary
t-=tert-=tertiary
THF=tetrahydrofuran
TLC=thin layer chromatography
UV=ultraviolet As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH$_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C$=$O)$—.

As used herein, "formyl" refers to the group —C(O)H.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —$CONR^bR^c$, where $R^b$ is H, optionally substituted $C_1$-$C_6$ alkyl, optionally substituted cycloalkyl, optionally substituted heterocycloalkyl, optionally substituted aryl, optionally substituted heteroaryl, or optionally substituted alkoxy; and $R^c$ is hydrogen or optionally substituted $C_1$-$C_4$ alkyl; or $R^b$ and $R^c$ taken together with the nitrogen to which they are bound, form an optionally substituted 4- to 8-membered nitrogen-containing heterocycloalkyl which optionally includes 1 or 2 additional heteroatoms chosen from O, N, and S in the heterocycloalkyl ring;

where each substituted group is independently substituted with one or more substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$N(phenyl), —$NHSO_2$($C_1$-$C_4$ alkyl), —$NHSO_2$(phenyl), or —$NHSO_2$($C_1$-$C_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—NH2.

As used herein, "substituted carbamimidoyl" refers to the group —C(=$NR^e$)—$NR^fR^g$ where $R^e$ is hydrogen, cyano, optionally substituted alkyl, optionally substituted cycloalkyl, optionally substituted aryl, optionally substituted heteroaryl, or optionally substituted heterocycloalkyl; and $R^f$ and $R^g$ are independently hydrogen optionally substituted alkyl, optionally substituted cycloalkyl, optionally substituted aryl, optionally substituted heteroaryl, or optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —OP(O)($OR^b$)$OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted aryl, or optionally substituted heteroaryl;

$R^b$ is H, optionally substituted C1-C6 alkyl, optionally substituted aryl, or optionally substituted heteroaryl; and $R^c$ is hydrogen or optionally substituted C1-C4 alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO2($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), or —$NHSO_2$($C_1$-$C_4$ haloalkyl).

As used herein, E refers to the electrophilic group capable of forming a covalent bond with a nucleophile. In some embodiments, compounds comprising E can undergo a spontaneous reaction with a protein. In some embodiments, compounds comprising E can undergo a spontaneous reaction with a protein to form a new covalent bond under moderate reaction conditions. In some embodiments, compounds comprising E can undergo a spontaneous reaction with a protein to form a new covalent bond wherein the new covalent bond forms between the compound and the nitrogen or sulfur of an amino acid residue sidechain. Some non-limiting examples of the amino acid can be lysine or cysteine, for example. In some embodiments, moderate reaction conditions can be at a temperature below about 50° C., 45° C., 40° C., 39° C., 38° C., 37° C., 36° C., 35° C., 34° C., 33° C., 30° C., 27° C., 25° C., 20° C., or 5 OC in an aqueous solution at a concentration of protein and compound below about 1M for example. In some embodiments, E is an electrophilic group capable of forming a covalent bond with a cysteine residue of a protein. In some embodiments, compounds comprising E are capable of forming a covalent bond with a cysteine residue of a protein. Examples of E include, but are not limited to, the following groups:

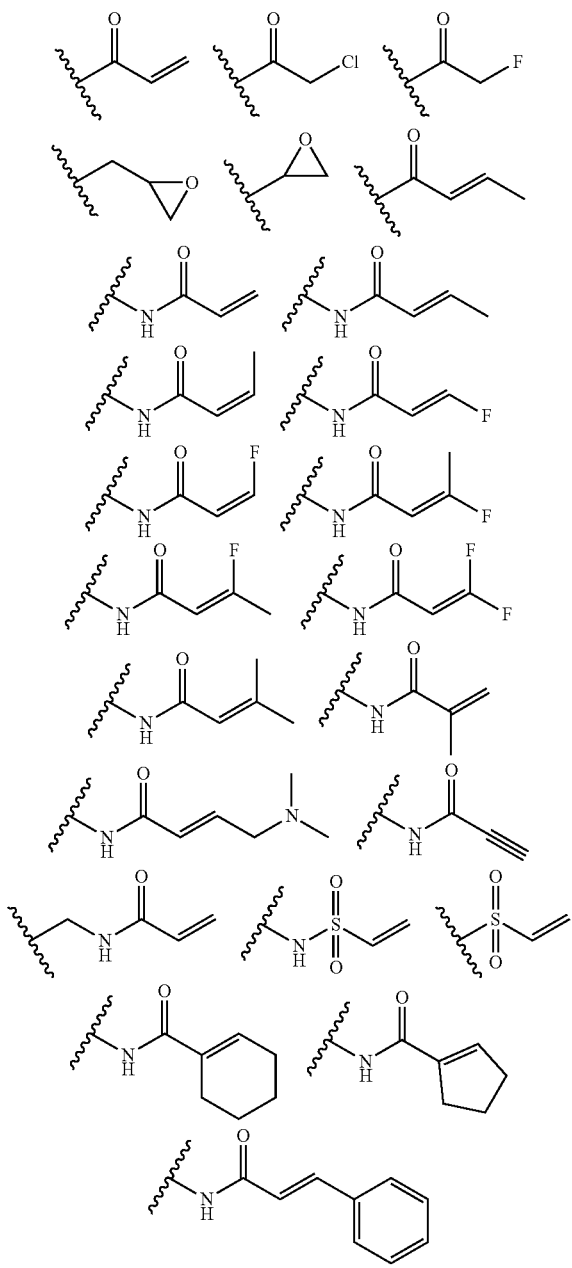

-continued

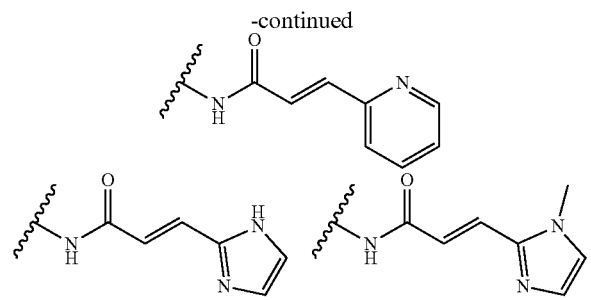

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, pyridyl, pyrazinyl, pyrimidinyl, pyrazolinyl, imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein.

Substituted heteroaryl also includes ring systems substituted with one or more oxide (—O—) substituents, such as pyridinyl N-oxides.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include but are not limited to, for example, pyrrolidinyl, morpholinyl, piperidinyl, piperazinyl, azetidinyl, diazepanyl, diazocanyl, pyrrolidinyl, morpholinyl, piperidinyl, piperazinyl, imidazolidinyl, pyrazolidinyl, dihydrofuranyl, and tetrahydrofuranyl. Substituted heterocycloalkyl can also include ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteroatoms independently chosen from oxygen, sulfur, and nitrogen and is not aromatic.

As used herein, "sulfanyl" refers to the groups: —S-(optionally substituted ($C_1$-$C_6$)alkyl), —S-(optionally substituted cycloalkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

As used herein, "sulfinyl" refers to the groups: —S(O)-(optionally substituted ($C_1$-$C_6$)alkyl), —S(O)-(optionally substituted cycloalkyl), —S(O)-(optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S($O_2$)-(optionally substituted ($C_1$-$C_6$)alkyl), —S($O_2$)-(optionally substituted cycloalkyl), —S($O_2$)-(optionally substituted aryl), —S($O_2$)-(optionally substituted heteroaryl), —S($O_2$)-(optionally substituted heterocycloalkyl), and —S($O_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(^O)(OR^b)OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted cycloalkyl, optionally substituted heterocycloalkyl, optionally substituted alkenyl, optionally substituted alkynyl, optionally substituted aryl, or optionally substituted heteroaryl; $R^b$ is hydrogen, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), or —$NHSO_2$($C_1$-$C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —OP(O)($OR^b$)$OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), or —NHSO$_2$($C_1$-$C_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), or —NHSO$_2$($C_1$-$C_4$ haloalkyl).

In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5.

Another substituted alkoxy group is hydroxyalkoxy or —OCH$_2$(CH$_2$)$_y$OH, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), or —NHSO$_2$($C_1$-$C_4$ haloalkyl).

As used herein, "substituted amino" refers to the group —NHR$^d$ or —NR$^d$R$^e$ wherein R$^d$ is hydroxyl, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is chosen from optionally substituted alkyl, optionally substituted cycloalkyl, optionally substituted aryl, optionally substituted heteroaryl, or optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)$ $OR^c$, sulfanyl (such as $SR^b$), sulfinyl (such as —$SOR^a$), or sulfonyl (such as —$SO_2R^a$ and —$SO_2NR^bR^c$), wherein $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and wherein each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)$ $OC_1$-$C_4$ alkyl, —$CON(C_1$-$C_4$ alkyl)($C_1$-$C_4$ alkyl), —$CONH$ ($C_1$-$C_4$ alkyl), —$CONH_2$, —$NHC(O)(C_1$-$C_4$ alkyl), —$NHC$ (O)(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$ (phenyl), —$NHSO_2(C_1$-$C_4$ alkyl), —$NHSO_2$(phenyl), or —$NHSO_2(C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable forms" of compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, pharmaceutically acceptable salts include "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen-.group containing a ring nitrogen or a heteroaryl group containing a ring nitrogen.

The compounds disclosed herein can be used in different enriched isotopic forms, e.g., enriched in the content of $^2H$, $^3H$, $^{11}C$, $^{13}C$ and/or $^{14}C$. In one particular embodiment, the compound is deuterated at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, carbonate, phosphate, hydrogenphosphate, diphosphate, hydrobromate, sulfate, sulfinate, nitrate, and like salts; as well as salts with an organic acid, such as malate, malonate, maleate, fumarate, tartrate, succinate, citrate, acetate, lactate, gluconate, methanesulfonate, Tris (hydroxymethylaminomethane), p-toluenesulfonate, priopionate, 2-hydroxyethylsulfonate, benzoate, salicylate, stearate, oxalate, pamoate, and alkanoate such as acetate, $HOOC-(CH_2)_n-COOH$ where n is 0-4, and like salts. Other salts include sulfate, methasulfonate, bromide, trifluoracetate, picrate, sorbate, benzilate, salicilate, nitrate, phthalate or morpholine. Pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-Cycloalkyl, $(C_3-C_7)$-Cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^Y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein, the terms "group", "radical" or "fragment" are synonymous and are intended to indicate functional groups or fragments of molecules attachable to a bond or other fragments of molecules.

As used herein, the term "leaving group" refers to the meaning conventionally associated with it in synthetic organic chemistry, i.e., an atom or group displaceable under nucleophilic displacement conditions. Examples of leaving groups include, but are not limited to, dimethylhydroxylamino (e.g. Weinreb amide), halogen, alkane- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

As used herein, the term "protective group" or "protecting group" refers to a group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block certain reactive sites present in the reactants. Examples of protecting groups can be found in Wuts et al., *Green's Protective Groups in Organic Synthesis*, (J. Wiley, 4th ed. 2006).

As used herein, the term "deprotection" or "deprotecting" refers to a process by which a protective group is removed after a selective reaction is completed. Certain protective groups may be preferred over others due to their convenience or relative ease of removal. Without being limiting, deprotecting reagents for protected amino or anilino group include strong acid such as trifluoroacetic acid (TFA), concentrated HCl, $H_2SO_4$, or HBr, and the like.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anti-cancer therapeutic.

As used herein, "significant" refers to any detectable change that is statistically significant in a standard parametric test of statistical significance such as Student's T-test, where $p<0.05$.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

As used herein, the term EGFR is used to refer the epidermal growth factor receptor (EGFR), a receptor tyrosine kinase of the ErbB family. The terms "EGFR", "Her1", "ErbB1" and the like are used interchangeably to refer to the gene or protein product of the gene.

A. Compounds

In one aspect, provided is a compound of Formula I

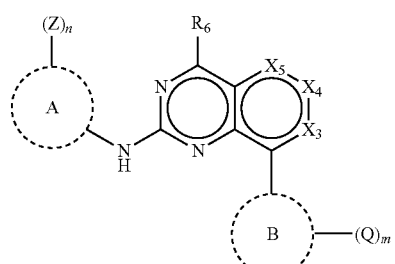

Formula I or a pharmaceutically acceptable salt thereof, wherein
$X_3$ is C—$R_{12}$, or N;
$X_4$ is C—$R_{13}$, or N;
$X_5$ is C—$R_{14}$, or N;
n is 0, 1, 2, 3, 4, or 5;
m is 0, 1, 2, 3, 4, or 5;

is aryl or heteroaryl;

is aryl, heteroaryl, or heterocycloalkyl;

$R_6$, $R_{12}$, $R_{13}$, $R_{14}$, and each Z is independently hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;

each Q is independently hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; wherein E is an electrophilic group capable of forming a covalent bond with a nucleophile.

In some embodiments,

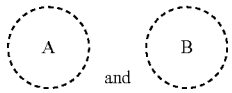

are each independently 5-membered aryl, 6-membered aryl, 5-membered heteroaryl, or 6-membered heteroaryl.

In some embodiments,

is 5-membered aryl, 6-membered aryl, 5-membered heteroaryl, or 6-membered heteroaryl; and

independently 5-membered aryl, 6-membered aryl, 5-membered heteroaryl, 6-membered heteroaryl, 5-membered heterocycloalkyl, or 6-membered heterocycloalkyl.

In some embodiments,

is selected from the group consisting of: pyrrolyl, furanyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridinyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, tetrazinyl, and phenyl; and

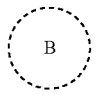

is selected from the group consisting of: piperazinyl, morpholinyl, piperidinyl, thiomorpholinyl, pyrrolidinyl, tetrahydrofuranyl, diazepanyl, azetidinyl, oxetanyl, oxiranyl, aziridinyl, pyrrolyl, furanyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridinyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, tetrazinyl, and phenyl.

In some embodiments,

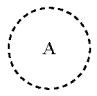

is selected from the group consisting of: phenyl, pyridinyl, pyrimidinyl, pyrazinyl, thiazolyl, oxazolyl, imidazolyl, pyrazolyl, isoxazolyl, and thienyl.

In some embodiments,

is selected from the group consisting of: phenyl, pyridinyl, pyrimidinyl, pyrazinyl, thiazolyl, oxazolyl, imidazolyl, pyrazolyl, isoxazolyl, and thienyl. In some embodiments, m is 1, 2, or 3; and at least one Q is E.

In some embodiments,

is selected from the group consisting of: piperazinyl, morpholinyl, piperidinyl, thiomorpholinyl, pyrrolidinyl, tetrahydrofuranyl, diazepanyl, azetidinyl, oxetanyl, oxiranyl, aziridinyl. In some embodiments,

is selected from the group consisting of: piperazinyl, morpholinyl, piperidinyl, pyrrolidinyl, and tetrahydrofuranyl, and diazepanyl. In some embodiments,

is selected from the group consisting of: piperazinyl, morpholinyl, piperidinyl, and pyrrolidinyl. In some embodiments,

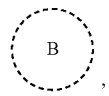

is attached to the core via a carbon-carbon bond. In some embodiments,

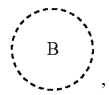

is attached to the core via a carbon-nitrogen bond. In some embodiments,

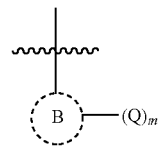

is selected from the group consisting of:

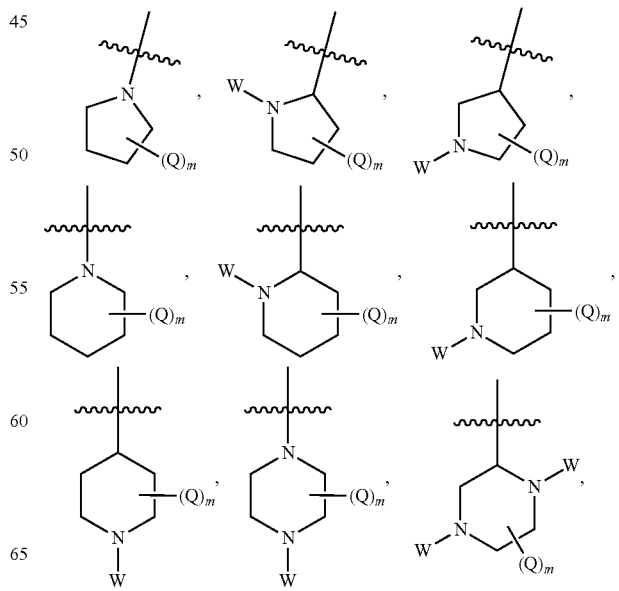

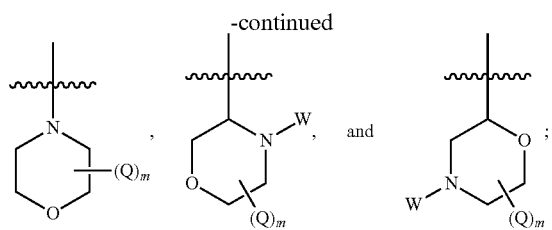

wherein each W is independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; wherein E is an electrophilic group capable of forming a covalent bond with a nucleophile. In some embodiments, W is E; wherein E is an electrophilic group capable of forming a covalent bond with a nucleophile. In some embodiments, at least one W is E. In some embodiments, W is selected from the group consisting of H, optionally substituted alkyl, and

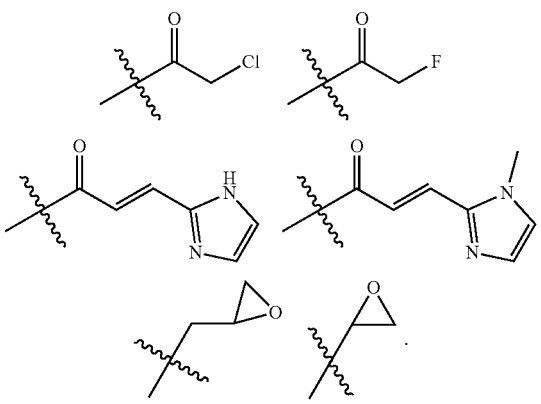

In some embodiments, each W is selected from the group consisting of H, $C_1$-$C_4$ alkyl, and

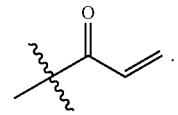 [SMILES: *C(=O)C=C]

In some embodiments, at least one Q is E; wherein E is an electrophilic group capable of forming a covalent bond with a cysteine residue of a protein. In some embodiments, E is selected from

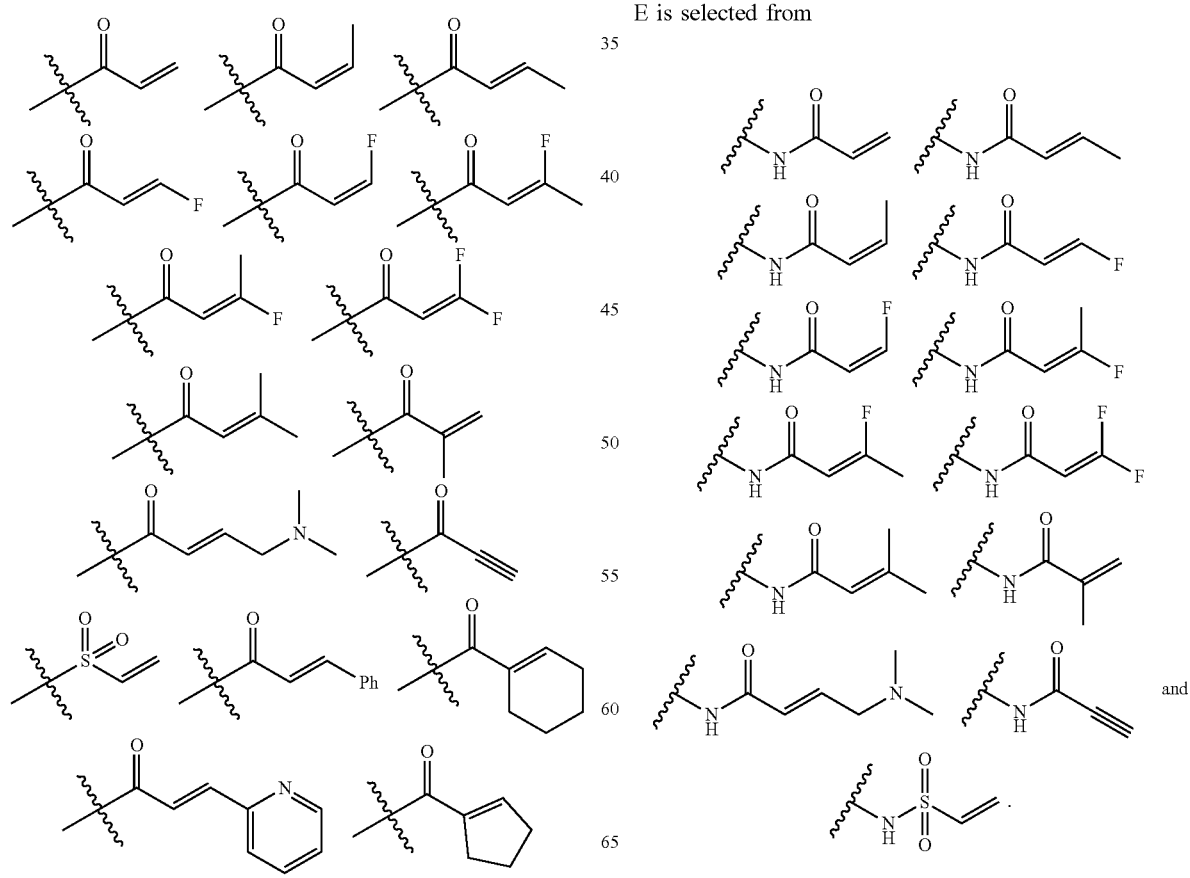

For example, in some embodiments, E is

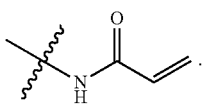 [SMILES: *NC(=O)C=C]

In some embodiments, E is

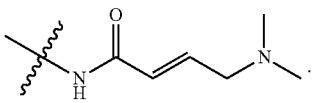 [SMILES: *NC(=O)/C=C/CN(C)C]

Another embodiment, provided is the compound or pharmaceutically acceptable salt of Formula I wherein

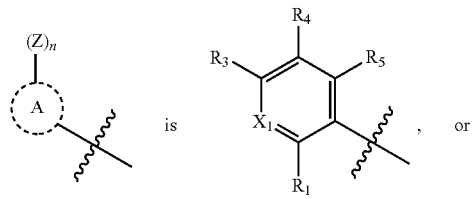

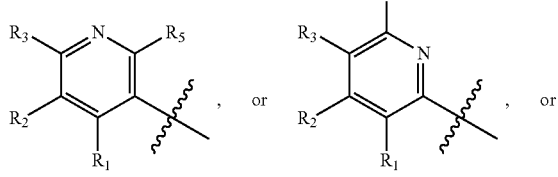

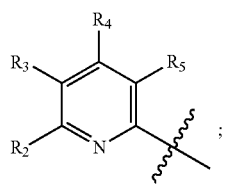

$X_1$ is C—$R_2$, or N; and $R_1$, $R_2$, $R_3$, $R_4$, and $R_5$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl.

Another embodiment, provided is the compound or pharmaceutically acceptable salt of Formula I wherein

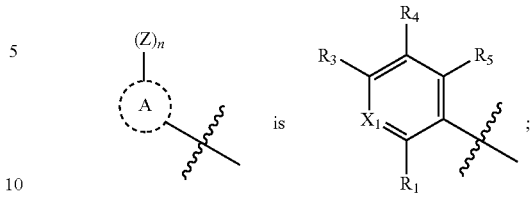

$X_1$ is C—$R_2$, or N; and $R_1$, $R_2$, $R_3$, $R_4$, and $R_5$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl.

Another embodiment of the invention described wherein

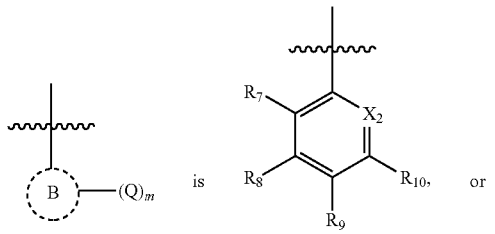

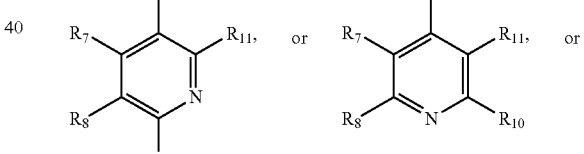

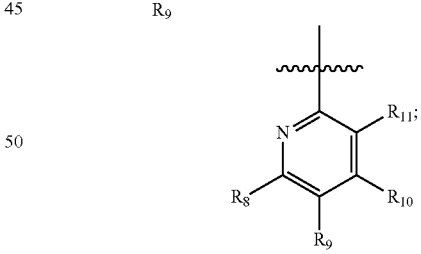

$X_2$ is C—$R_{11}$, or N; and $R_{11}$, $R_7$, $R_8$, $R_9$, and $R_{10}$ are independently, hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl or E; wherein E is an electrophilic group capable of forming a covalent bond with a nucleophile.

Another embodiment of the invention described wherein

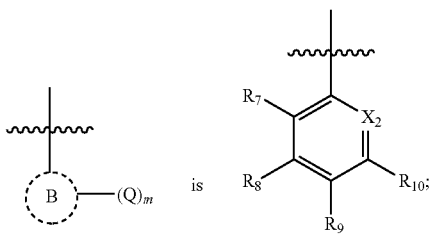

is $X_2$ is C—$R_{11}$, or N; and $R_{11}$, $R_7$, $R_8$, $R_9$, and $R_{10}$ are independently, hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl or E; wherein E is an electrophilic group capable of forming a covalent bond with a nucleophile.

In some embodiments, the compound is of Formula Ia

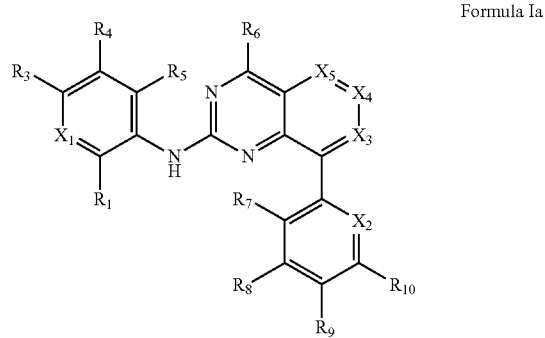

Formula Ia or a pharmaceutically acceptable salt thereof, wherein $X_1$ is C—$R_2$, or N;
$X_2$ is C—$R_{11}$, or N;
$X_3$ is C—$R_{12}$, or N;
$X_4$ is C—$R_{13}$, or N;
$X_5$ is C—$R_{14}$, or N;

$R_1$, $R_2$, $R_3$, $R_4$, $R_5$, $R_6$, $R_7$, $R_{11}$, $R_{12}$, $R_{13}$, and $R_{14}$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;

$R_8$, $R_9$, and $R_{10}$ are independently hydrogen, cyano, halo, hydroxy, azido, nitro, carboxy, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; where E is an electrophilic group capable of forming a covalent bond with a nucleophile. In some embodiments, E is electrophilic group capable of forming a covalent bond with a cysteine residue of a protein.

In some embodiments, the compound or pharmaceutically acceptable salt has the Formula Ib:

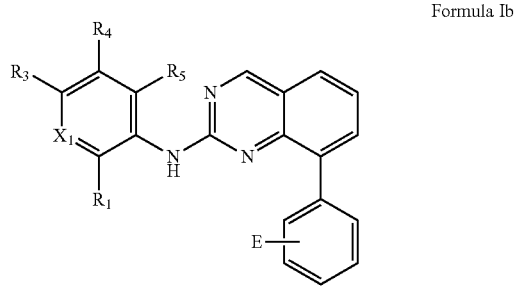

Formula Ib wherein:
$X_1$ is N or C—$R_2$;
each $R_1$, $R_2$, $R_4$, or $R_5$ is independently H or halo;
$R_3$ is optionally substituted heterocycloalkyl; and
E is an electrophilic group capable of forming a covalent bond with a nucleophile.

In some embodiments, the compound or pharmaceutically acceptable salt has the Formula Ib':

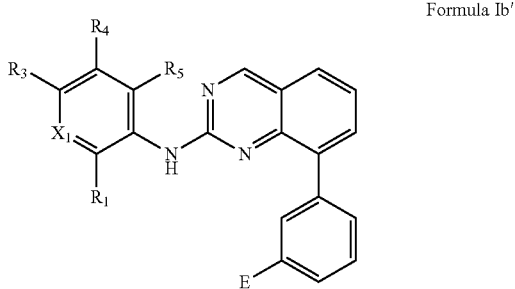

Formula Ib'

In some embodiments, $R_1$ is hydrogen, cyano, halo, hydroxy, —$CONH_2$, optionally substituted alkoxy, or optionally substituted cycloalkyloxy. In some embodiments, $R_1$ is hydrogen, cyano, fluoro, chloro, hydroxy, hydroxymethyl, —$CONH_2$, or methoxy. In some embodiments, $R_1$ is hydrogen, cyano, fluoro, chloro, hydroxy, or methoxy. In some embodiments, $R_1$ is hydrogen. In some embodiments, $R_1$ is methoxy. In some embodiments, $R_1$ is fluoro.

In some embodiments, $R_2$, $R_3$, and $R_4$ are independently hydrogen, cyano, halo, hydroxy, carboxy, optionally substituted alkoxy, optionally substituted lower alkyl, optionally substituted heterocycloalkyl, optionally substituted aryl, optionally substituted heteroaryl, optionally substituted amino, optionally substituted acyl, optionally substituted alkoxycarbonyl, or optionally substituted aminocarbonyl.

In some embodiments, $R_2$ is hydrogen. In some embodiments, $R_2$ is fluoro.

In some embodiments, $R_3$ is hydrogen, optionally substituted alkoxy, optionally substituted lower alkyl, optionally substituted heterocycloalkyl, optionally substituted aryl, optionally substituted heteroaryl, or optionally substituted amino. In some embodiments, $R_3$ is optionally substituted heterocycloalkyl, or optionally substituted heteroaryl. In some embodiments, $R_3$ is optionally substituted morpholinyl, optionally substituted piperazinyl, optionally substituted pyrrolidinyl, optionally substituted piperidinyl, optionally substituted imidazolidinyl, optionally substituted pyrazolidinyl, optionally substituted azetidinyl, optionally substituted 1,4-diazepanyl, optionally substituted 1,4-diazocanyl, optionally substituted pyranyl, optionally substituted imidazolyl, optionally substituted pyrazolyl, or optionally substituted pyridyl. In some embodiments, $R_3$ is pyrrolidin-1-yl, morpholin-4-yl, piperidin-1-yl, piperazin-1-yl, 4-methylpiperazin-1-yl, azetidin-1-yl, 1,4-diazepan-1-yl, or 1,4-diazocan-1-yl, each of which is optionally substituted with one or two groups independently hydroxyl, methoxy, amino, fluoro, oxo, or lower alkyl optionally substituted with hydroxy, methoxy, fluoro or amino. In some embodiments, $R_3$ is pyrrolidin-2-yl, morpholin-2-yl, piperidin-2-yl, piperazin-2-yl, 4-methylpiperazin-2-yl, azetidin-2-yl, 1,4-diazepan-2-yl, 1,4-diazocan-2-yl, pyrrolidin-3-yl, morpholin-3-yl, piperidin-3-yl, piperidin-4-yl, piperazin-3-yl, azetidin-3-yl, 1,4-diazepan-3-yl, or 1-4,-diazocan-3-yl, each of which is optionally substituted with one or two groups independently hydroxyl, methoxy, amino, fluoro, oxo, or lower alkyl optionally substituted with hydroxy, methoxy, fluoro or amino. In some embodiments, $R_3$ is 2,4-imidazolidinyl, 2,3-pyrazolidinyl, 2,3-dihydrofuranyl, or 2,5-dihydrofuranyl, piperidinyl N-oxide, morpholinyl-N-oxide, 1-oxo-1-thiomorpholinyl or 1,1-dioxo-1-thiomorpholinyl, each of which is optionally substituted with one or two independent groups consisting of hydroxyl, methoxy, amino, fluoro, oxo, or lower alkyl optionally substituted with hydroxy, methoxy, fluoro or amino.

In some embodiments, $R_3$ is

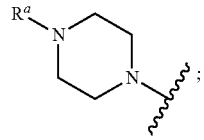

wherein $R^a$ is $C_1$-$C_6$ alkyl, optionally substituted with $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), or —$NHSO_2(C_1$-$C_4$ haloalkyl).

In some embodiments, $R^a$ is $C_1$-$C_6$ alkyl, optionally substituted with —OH, halo, $C_1$-$C_4$ alkyl, or —$OC_1$-$C_4$ alkyl. In some embodiments, $R^a$ is —$CH_3$, —$CH_2CH_2OH$, —$CH_2CH_2F$, —$CH_2CH_2OMe$, —$CH_2C(CH_3)_2OH$, or —$CH_2CH(CH_3)OH$.

In some embodiments, $R_4$ is hydrogen, optionally substituted alkoxy, optionally substituted lower alkyl, optionally substituted heterocycloalkyl, optionally substituted aryl, optionally substituted heteroaryl, or optionally substituted amino. In some embodiments, $R_4$ is hydrogen, optionally substituted heterocycloalkyl, or optionally substituted heteroaryl. In some embodiments, $R_4$ is optionally substituted morpholinyl, optionally substituted piperazinyl, optionally substituted pyrrolidinyl, optionally substituted piperidinyl, optionally substituted imidazolidinyl, optionally substituted pyrazolidinyl, optionally substituted azetidinyl, optionally substituted 1,4-diazepanyl, optionally substituted 1,4-diazocanyl, optionally substituted pyranyl, optionally substituted imidazolyl, optionally substituted pyrazolyl, or optionally substituted pyridyl. In some embodiments, $R_4$ is pyrrolidin-1-yl, morpholin-4-yl, piperidin-1-yl, piperazin-1-yl, 4-methylpiperazin-1-yl, azetidin-1-yl, 1,4-diazepan-1-yl, or 1,4-diazocan-1-yl, each of which is optionally substituted with one or two groups independently hydroxyl, amino, fluoro, oxo, or lower alkyl optionally substituted with hydroxy, fluoro, or amino. In some embodiments, $R_4$ is pyrrolidin-2-yl, morpholin-2-yl, piperidin-2-yl, piperazin-2-yl, 4-methylpiperazin-2-yl, azetidin-2-yl, 1,4-diazepan-2-yl, 1,4-diazocan-2-yl, pyrrolidin-3-yl, morpholin-3-yl, piperidin-3-yl, piperidin-4-yl, piperazin-3-yl, azetidin-3-yl, 1,4-diazepan-3-yl, or 1-4,-diazocan-3-yl, each of which is optionally substituted with one or two groups independently hydroxyl, amino, fluoro, oxo, or lower alkyl optionally substituted with hydroxy, fluoro, or amino. In some embodiments, $R_4$ is 2,4-imidazolidinyl, 2,3-pyrazolidinyl, 2,3-dihydrofuranyl, or 2,5-dihydrofuranyl, piperidinyl N-oxide, morpholinyl-N-oxide, 1-oxo-1-thiomorpholinyl or 1,1-dioxo-1-thiomorpholinyl, each of which is optionally substituted with one or two groups independently hydroxyl, amino, fluoro, oxo, or lower alkyl optionally substituted with hydroxy, fluoro, or amino.

In some embodiments, $R_2$ and $R_4$ are hydrogen, and $R_3$ is optionally substituted heterocycloalkyl. In some embodiments, $R_2$ and $R_4$ are hydrogen and $R_3$ is optionally substituted morpholinyl, optionally substituted piperazinyl, optionally substituted pyrrolidinyl, optionally substituted piperidinyl, optionally substituted azetidinyl, optionally substituted 1,4-diazepanyl, or optionally substituted 1,4-diazocanyl. In some embodiments, $R_2$ and $R_4$ are hydrogen and $R_3$ is pyrrolidin-1-yl, morpholin-4-yl, piperidin-1-yl, piperazin-1-yl, 4-methylpiperazin-1-yl, azetidin-1-yl, 1,4-diazepan-1-yl, or 1-4,-diazocan-1-yl, each of which is optionally substituted with one or two groups independently hydroxyl, amino, fluoro, oxo, or lower alkyl optionally substituted with hydroxy, fluoro, or amino.

In some embodiments, $R_2$ and $R_4$ are hydrogen, and $R_3$ is optionally substituted amino. In some embodiments, $R_2$ and $R_4$ are hydrogen and $R_3$ is substituted amino, which is substituted with optionally substituted heterocycloalkyl. In some embodiments, $R_2$ and $R_4$ are hydrogen, and $R_3$ is substituted amino, which is substituted with optionally substituted morpholinyl, optionally substituted piperazinyl, optionally substituted pyrrolidinyl, optionally substituted piperidinyl, optionally substituted azetidinyl, optionally substituted 1,4-diazepanyl, or optionally substituted 1,4-diazocanyl.

In some embodiments, $R_2$ and $R_3$ are hydrogen, and $R_4$ is optionally substituted heterocycloalkyl. In some embodiments, $R_2$ and $R_3$ are hydrogen, and $R_4$ is optionally substituted morpholinyl, optionally substituted piperazinyl, optionally substituted pyrrolidinyl, optionally substituted piperidinyl, optionally substituted azetidinyl, optionally substituted 1,4-diazepanyl, or optionally substituted 1,4-diazocanyl. In some embodiments, $R_2$ and $R_4$ are hydrogen and $R_3$ is pyrrolidin-1-yl, morpholin-4-yl, piperidin-1-yl, piperazin-1-yl, 4-methylpiperazin-1-yl, azetidin-1-yl, 1,4-diazepan-1-yl, or 1-4,-diazocan-1-yl, each of which is optionally substituted with one or two groups independently hydroxyl, amino, fluoro, oxo, or lower alkyl optionally substituted with hydroxy, fluoro, or amino.

In some embodiments, $R_2$ and $R_3$ are hydrogen, and $R_4$ is optionally substituted amino. In some embodiments, $R_2$ and $R_4$ are hydrogen and $R_3$ is substituted amino, which is substituted with optionally substituted heterocycloalkyl. In some embodiments, $R_2$ and $R_4$ are hydrogen, and $R_3$ is substituted amino, which is substituted with optionally substituted morpholinyl, optionally substituted piperazinyl, optionally substituted pyrrolidinyl, optionally substituted piperidinyl, optionally substituted azetidinyl, optionally substituted 1,4-diazepanyl, or optionally substituted 1,4-diazocanyl.

In some embodiments, $R_5$ is hydrogen, halo, cyano, optionally substituted alkoxy, or optionally substituted alkyl. In some embodiments, $R_5$ is hydrogen.

In some embodiments, $R_6$ is hydrogen or optionally substituted amino. In some embodiments, $R_6$ is hydrogen or amino. In some embodiments, $R_6$ is hydrogen. In some embodiments, $R_6$ is amino.

In some embodiments, $R_7$, $R_{11}$, $R_{13}$, and $R_{14}$ are independently hydrogen, cyano, optionally substituted lower alkyl, halo, or methoxy. In some embodiments, $R_7$, $R_{11}$, $R_{13}$, and $R_{14}$ are independently hydrogen, cyano, fluoro, chloro, methyl, hydroxymethyl, —CH$_2$F, or methoxy. In some embodiments, $R_7$, $R_{11}$, $R_{13}$, and $R_{14}$ are hydrogen. In some embodiments, $R_7$ is fluoro or chloro, and $R_{11}$, $R_{13}$, and $R_{14}$ are hydrogen. In some embodiments, $R_{11}$ is fluoro or chloro, and $R_7$, $R_{13}$, and $R_{14}$ are hydrogen.

In some embodiments, $R_8$, $R_9$, and $R_{10}$ are independently hydrogen, cyano, halo, hydroxy, carboxy, optionally substituted alkoxy, optionally substituted cycloalkyloxy, optionally substituted alkyl, optionally substituted alkenyl, optionally substituted alkynyl, optionally substituted amino, optionally substituted acyl, optionally substituted alkoxycarbonyl, optionally substituted aminocarbonyl, or E.

In some embodiments, at least one of $R_8$, $R_9$, and $R_{10}$ is halo. In some embodiments, at least one of $R_8$, $R_9$, and $R_{10}$ is fluoro or chloro. In some embodiments, at least one of $R_8$, $R_9$, and $R_{10}$ is optionally substituted amino. In some embodiments, at least one of $R_8$, $R_9$, and $R_{10}$ is optionally substituted alkoxy. In some embodiments, at least one of $R_8$, $R_9$, and $R_{10}$ is alkoxy substituted with optionally substituted amino or optionally substituted heterocycloalkyl.

In some embodiments, at least one of $R_8$, $R_9$, and $R_{10}$ is E, where E is an electrophilic group capable of forming a covalent bond with a cysteine residue of a protein.

In some embodiments, at least one of $R_8$, $R_9$, and $R_{10}$ is selected from

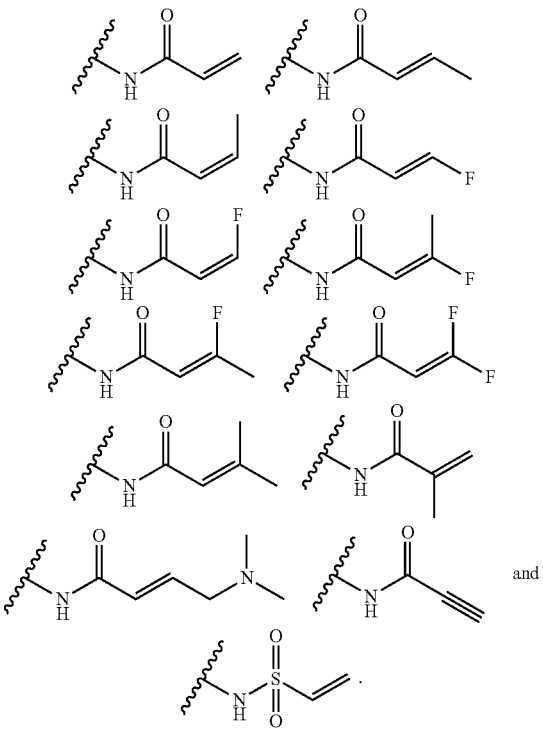

and

In some embodiments, at least one of $R_8$, $R_9$, and $R_{10}$ is

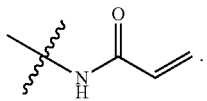 [SMILES: *NC(=O)C=C]

In some embodiments, at least one of $R_8$, $R_9$, and $R_{10}$ is

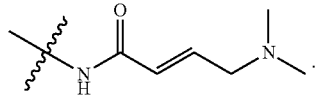

In some embodiments, $R_8$ is

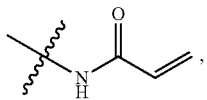 [SMILES: *NC(=O)C=C]

and $R_9$ and $R_{10}$ are hydrogen. In some embodiments, $R_8$ is

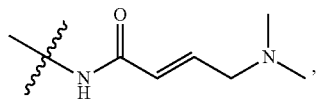 [SMILES: *NC(=O)/C=C/CN(C)C]

and $R_9$ and $R_{10}$ are hydrogen. In some embodiments, $R_{10}$ is

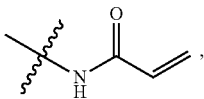 [SMILES: *NC(=O)C=C]

and $R_8$ and $R_9$ are hydrogen. In some embodiments, $R_{10}$ is

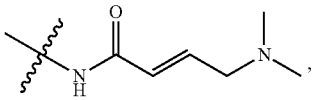

and $R_8$ and $R_9$ are hydrogen.

In some embodiments, $R_8$ is fluoro, and $R_9$ and $R_{10}$ are hydrogen. In some embodiments, $R_8$ is chloro, and $R_9$ and $R_{10}$ are hydrogen. In some embodiments, $R_{10}$ is fluoro, and $R_8$ and $R_9$ are hydrogen. In some embodiments, $R_{10}$ is chloro, and $R_8$ and $R_9$ are hydrogen.

In some embodiments, $R_8$ is optionally substituted alkoxy, and $R_9$ and $R_{10}$ are hydrogen. In some embodiments, $R_9$ is optionally substituted alkoxy, and $R_8$ and $R_{10}$ are hydrogen.

In some embodiments, $R_{12}$ is hydrogen, halo, cyano, —CONH$_2$, —NHCOCH$_3$, or optionally substituted lower alkyl. In some embodiments, $R_{12}$ is hydrogen, fluoro, chloro, cyano, methyl, ethyl, propyl, —CF$_3$, —CH$_2$F, —CHF$_2$, —CH$_2$CF$_3$, —CH$_2$CH$_2$F, —CH$_2$CHF$_2$, —CH$_2$OH, —CONH$_2$, —CH$_2$CONH$_2$, or —NHCOCH$_3$. In some embodiments, $R_{12}$ is hydrogen. In some embodiments, $R_{12}$ is fluoro. In some embodiments, $R_{12}$ is methyl. In some embodiments, $R_{12}$ is —CH$_2$OH.

In some embodiments, $X_1$ is C—$R_2$ or N, $X_2$ is C—$R_{11}$ or N, $X_3$ is C—$R_{12}$ or N, $X_4$ is C—$R_{13}$ or N, and $X_5$ is C—$R_{14}$ or N.

In some embodiments, $X_1$ is C—$R_2$, $X_2$ is C—$R_{11}$, $X_3$ is C—$R_{12}$, $X_4$ is C—$R_{13}$, and $X_5$ is C—$R_{14}$.

In some embodiments, $X_1$ is N, $X_2$ is C—$R_{11}$, $X_3$ is C—$R_{12}$, $X_4$ is C—$R_{13}$, and $X_5$ is C—$R_{14}$.

In some embodiments, $X_1$ is C—$R_2$, $X_2$ is N, $X_3$ is C—$R_{12}$, $X_4$ is C—$R_{13}$, and $X_5$ is C—$R_{14}$.

In some embodiments, $X_1$ is C—$R_2$, $X_2$ is C—$R_{11}$, $X_3$ is N, $X_4$ is C—$R_{13}$, and $X_5$ is C—$R_{14}$.

In some embodiments, $X_1$ is C—$R_2$, $X_2$ is C—$R_{11}$, $X_3$ is C—$R_{12}$, $X_4$ is N, and $X_5$ is C—$R_{14}$.

In some embodiments, $X_1$ is C—$R_2$, $X_2$ is C—$R_{11}$, $X_3$ is C—$R_{12}$, $X_4$ is C—$R_{13}$, and $X_5$ is N.

In some embodiments, $X_1$ is N, $X_2$ is N, $X_3$ is C—$R_{12}$, $X_4$ is C—$R_{13}$, and $X_5$ is C—$R_{14}$.

In some embodiments, $X_1$ is N, $X_2$ is C—$R_{11}$, $X_3$ is N, $X_4$ is C—$R_{13}$, and $X_5$ is C—$R_{14}$.

In some embodiments, $X_1$ is C—$R_2$, $X_2$ is N, $X_3$ is N, $X_4$ is C—$R_{13}$, and $X_5$ is C—$R_{14}$.

In some embodiments, $X_1$ is N, $X_2$ is N, $X_3$ is N, $X_4$ is C—$R_{13}$, and $X_5$ is C—$R_{14}$.

In another aspect, the present disclosure provides a compound or pharmaceutically acceptable salt thereof, wherein the compound is chosen from the group consisting of:

N-(3-(2-((4-(piperazin-1-yl)phenyl)amino)pyrido[3,2-d]pyrimidin-8-yl)phenyl)acetamide N-(3-(2-((4-(piperazin-1-yl)phenyl)amino)pyrido[4,3-d]pyrimidin-8-yl)phenyl)acetamide N-(3-(2-((4-(piperazin-1-yl)phenyl)amino)pyrido[3,4-d]pyrimidin-8-yl)phenyl)acetamide 8-(2-fluorophenyl)-N-(4-morpholinophenyl)pyrido[4,3-d]pyrimidin-2-amine 8-(2-fluorophenyl)-N-(4-morpholinophenyl)pyrido[3,2-d]pyrimidin-2-amine 8-(2-fluorophenyl)-N-(4-morpholinophenyl)pyrido[3,4-d]pyrimidin-2-amine 8-(5-chloro-2-fluorophenyl)-N-(4-morpholinophenyl)pyrido[3,4-d]pyrimidin-2-amine 8-(3-chlorophenyl)-N-(4-morpholinophenyl)pyrido[3,4-d]pyrimidin-2-amine 8-(3-fluorophenyl)-N-(4-morpholinophenyl)pyrido[3,4-d]pyrimidin-2-amine 8-(2,6-difluorophenyl)-N-(4-morpholinophenyl)pyrido[3,4-d]pyrimidin-2-amine 8-(2-fluoro-5-(2-morpholinoethoxy)phenyl)-N-(4-morpholinophenyl)pyrido[3,4-d]pyrimidin-2-amine 8-(5-(2-(dimethylamino)ethoxy)-2-fluorophenyl)-N-(4-morpholinophenyl)pyrido[3,4-d]pyrimidin-2-amine 8-(3-(2-morpholinoethoxy)phenyl)-N-(4-morpholinophenyl)pyrido[3,4-d]pyrimidin-2-amine 8-(3-(2-(dimethylamino)ethoxy)phenyl)-N-(4-morpholinophenyl)pyrido[3,4-d]pyrimidin-2-amine 8-(4-(2-morpholinoethoxy)phenyl)-N-(4-morpholinophenyl)pyrido[3,4-d]pyrimidin-2-amine 8-(4-(2-(dimethylamino)ethoxy)phenyl)-N-(4-morpholinophenyl)pyrido[3,4-d]pyrimidin-2-amine 8-(2-fluoro-4-(2-morpholinoethoxy)phenyl)-N-(4-morpholinophenyl)pyrido[3,4-d]pyrimidin-2-amine 8-(4-(2-(dimethylamino)ethoxy)-2-fluorophenyl)-N-(4-morpholinophenyl)pyrido[3,4-d]pyrimidin-2-amine 8-phenyl-N-(4-(piperazin-1-yl)phenyl)pyrido[3,4-d]pyrimidin-2-amine 8-(2-fluorophenyl)-N-(4-(piperazin-1-yl)phenyl)pyrido[3,4-d]pyrimidin-2-amine 8-(2-chlorophenyl)-N-(4-(piperazin-1-yl)phenyl)pyrido[3,4-d]pyrimidin-2-amine 8-(2,6-difluorophenyl)-N-(4-(piperazin-1-yl)phenyl)pyrido[3,4-d]pyrimidin-2-amine 8-(5-chloro-2-fluorophenyl)-N-(4-(piperazin-1-yl)phenyl)pyrido[3,4-d]pyrimidin-2-amine 8-(3-chlorophenyl)-N-(4-(piperazin-1-yl)phenyl)pyrido[3,4-d]pyrimidin-2-amine 8-(3-fluorophenyl)-N-(4-(piperazin-1-yl)phenyl)pyrido[3,4-d]pyrimidin-2-amine N-(4-fluoro-3-(2-((4-(piperazin-1-yl)phenyl)amino)pyrido[3,4-d]pyrimidin-8-yl)phenyl)acetamide 8-(2-fluoro-5-(2-morpholinoethoxy)phenyl)-N-(4-(piperazin-1-yl)phenyl)pyrido[3,4-d]pyrimidin-2-amine 8-(5-(2-(dimethylamino)ethoxy)-2-fluorophenyl)-N-(4-(piperazin-1-yl)phenyl)pyrido[3,4-d]pyrimidin-2-amine 8-(3-(2-morpholinoethoxy)phenyl)-N-(4-(piperazin-1-yl)phenyl)pyrido[3,4-d]pyrimidin-2-amine 8-(3-(2-(dimethylamino)ethoxy)phenyl)-N-(4-(piperazin-1-yl)phenyl)pyrido[3,4-d]pyrimidin-2-amine 8-(4-(2-morpholinoethoxy)phenyl)-N-(4-(piperazin-1-yl)phenyl)pyrido[3,4-d]pyrimidin-2-amine 8-(4-(2-(dimethylamino)ethoxy)phenyl)-N-(4-(piperazin-1-yl)phenyl)pyrido[3,4-d]pyrimidin-2-amine 8-(2-fluoro-4-(2-morpholinoethoxy)phenyl)-N-(4-(piperazin-1-yl)phenyl)pyrido[3,4-d]pyrimidin-2-amine 8-(4-(2-(dimethylamino)ethoxy)-2-fluorophenyl)-N-(4-(piperazin-1-yl)phenyl)pyrido[3,4-d]pyrimidin-2-amine N1-(1-(2-fluoroethyl)azetidin-3-yl)-N4-(8-(2-fluorophenyl)pyrido[3,4-d]pyrimidin-2-yl)benzene-1,4-diamine N1-(1-(2-fluoroethyl)azetidin-3-yl)-N4-(8-(3-(2-morpholinoethoxy)phenyl)pyrido[3,4-d]pyrimidin-2-yl)benzene-1,4-diamine N1-(8-(2-fluoro-5-(2-morpholinoethoxy)phenyl)pyrido[3,4-d]pyrimidin-2-yl)-N4-(1-(2-fluoroethyl)azetidin-3-yl)benzene-1,4-diamine
N1-(8-(5-chloro-2-fluorophenyl)pyrido[3,4-d]pyrimidin-2-yl)-N4-(1-(2-fluoroethyl)azetidin-3-yl)benzene-1,4-diamine
8-(3-aminophenyl)-N-(4-morpholinophenyl)quinazolin-2-amine
8-(3-aminophenyl)-N-(4-(piperazin-1-yl)phenyl)quinazolin-2-amine
8-(3-aminophenyl)-N-(4-(4-methylpiperazin-1-yl)phenyl)quinazolin-2-amine
N-(3-(2-((4-morpholinophenyl)amino)quinazolin-8-yl)phenyl)acetamide
N-(3-(2-((4-(piperazin-1-yl)phenyl)amino)quinazolin-8-yl)phenyl)acetamide
N-(3-(2-((4-(4-methylpiperazin-1-yl)phenyl)amino)quinazolin-8-yl)phenyl)acetamide
N-(4-morpholinophenyl)-8-phenylquinazolin-2-amine
8-(2-fluorophenyl)-N-(4-morpholinophenyl)quinazolin-2-amine
8-(2-chlorophenyl)-N-(4-morpholinophenyl)quinazolin-2-amine
8-(5-chloro-2-fluorophenyl)-N-(4-morpholinophenyl)quinazolin-2-amine
8-(3-chlorophenyl)-N-(4-morpholinophenyl)quinazolin-2-amine
8-(3-fluorophenyl)-N-(4-morpholinophenyl)quinazolin-2-amine
8-(2,6-difluorophenyl)-N-(4-morpholinophenyl)quinazolin-2-amine
8-(2-fluoro-5-(2-morpholinoethoxy)phenyl)-N-(4-morpholinophenyl)quinazolin-2-amine
8-(5-(2-(dimethylamino)ethoxy)-2-fluorophenyl)-N-(4-morpholinophenyl)quinazolin-2-amine
8-(3-(2-morpholinoethoxy)phenyl)-N-(4-morpholinophenyl)quinazolin-2-amine
8-(3-(2-(dimethylamino)ethoxy)phenyl)-N-(4-morpholinophenyl)quinazolin-2-amine
8-(4-(2-morpholinoethoxy)phenyl)-N-(4-morpholinophenyl)quinazolin-2-amine
8-(4-(2-(dimethylamino)ethoxy)phenyl)-N-(4-morpholinophenyl)quinazolin-2-amine
8-(2-fluoro-4-(2-morpholinoethoxy)phenyl)-N-(4-morpholinophenyl)quinazolin-2-amine
8-(4-(2-(dimethylamino)ethoxy)-2-fluorophenyl)-N-(4-morpholinophenyl)quinazolin-2-amine
8-phenyl-N-(4-(piperazin-1-yl)phenyl)quinazolin-2-amine
8-(2-fluorophenyl)-N-(4-(piperazin-1-yl)phenyl)quinazolin-2-amine
8-(2-chlorophenyl)-N-(4-(piperazin-1-yl)phenyl)quinazolin-2-amine
8-(2,6-difluorophenyl)-N-(4-(piperazin-1-yl)phenyl)quinazolin-2-amine
8-(5-chloro-2-fluorophenyl)-N-(4-(piperazin-1-yl)phenyl)quinazolin-2-amine
8-(3-chlorophenyl)-N-(4-(piperazin-1-yl)phenyl)quinazolin-2-amine
8-(3-fluorophenyl)-N-(4-(piperazin-1-yl)phenyl)quinazolin-2-amine
N-(4-fluoro-3-(2-((4-(piperazin-1-yl)phenyl)amino)quinazolin-8-yl)phenyl)acetamide
8-(2-fluoro-5-(2-morpholinoethoxy)phenyl)-N-(4-(piperazin-1-yl)phenyl)quinazolin-2-amine
8-(5-(2-(dimethylamino)ethoxy)-2-fluorophenyl)-N-(4-(piperazin-1-yl)phenyl)quinazolin-2-amine
8-(3-(2-morpholinoethoxy)phenyl)-N-(4-(piperazin-1-yl)phenyl)quinazolin-2-amine
8-(3-(2-(dimethylamino)ethoxy)phenyl)-N-(4-(piperazin-1-yl)phenyl)quinazolin-2-amine
8-(4-(2-morpholinoethoxy)phenyl)-N-(4-(piperazin-1-yl)phenyl)quinazolin-2-amine
8-(4-(2-(dimethylamino)ethoxy)phenyl)-N-(4-(piperazin-1-yl)phenyl)quinazolin-2-amine
8-(2-fluoro-4-(2-morpholinoethoxy)phenyl)-N-(4-(piperazin-1-yl)phenyl)quinazolin-2-amine
8-(4-(2-(dimethylamino)ethoxy)-2-fluorophenyl)-N-(4-(piperazin-1-yl)phenyl)quinazolin-2-amine
N1-(1-(2-fluoroethyl)azetidin-3-yl)-N4-(8-(2-fluorophenyl)quinazolin-2-yl)benzene-1,4-diamine
N1-(1-(2-fluoroethyl)azetidin-3-yl)-N4-(8-(3-(2-morpholinoethoxy)phenyl)quinazolin-2-yl)benzene-1,4-diamine
N1-(8-(2-fluoro-5-(2-morpholinoethoxy)phenyl)quinazolin-2-yl)-N4-(1-(2-fluoroethyl)azetidin-3-yl)benzene-1,4-diamine
N1-(8-(5-chloro-2-fluorophenyl)quinazolin-2-yl)-N4-(1-(2-fluoroethyl)azetidin-3-yl)benzene-1,4-diamine
N-(3-(2-((4-morpholinophenyl)amino)pyrido[3,4-d]pyrimidin-8-yl)phenyl)acrylamide
N-(3-(2-((4-(piperazin-1-yl)phenyl)amino)pyrido[3,4-d]pyrimidin-8-yl)phenyl)acrylamide
N-(3-(2-((4-morpholinophenyl)amino)pyrido[3,2-d]pyrimidin-8-yl)phenyl)acrylamide
N-(3-(2-((4-morpholinophenyl)amino)pyrido[4,3-d]pyrimidin-8-yl)phenyl)acrylamide
N-(3-(2-((4-(4-methylpiperazin-1-yl)phenyl)amino)pyrido[3,4-d]pyrimidin-8-yl)phenyl)acrylamide
N-(3-(2-((4-(4-methylpiperazin-1-yl)phenyl)amino)pyrido[3,2-d]pyrimidin-8-yl)phenyl)acrylamide
N-(3-(2-((4-(4-methylpiperazin-1-yl)phenyl)amino)pyrido[4,3-d]pyrimidin-8-yl)phenyl)acrylamide
N-(3-(2-((4-(4-ethylpiperazin-1-yl)phenyl)amino)pyrido[3,4-d]pyrimidin-8-yl)phenyl)acrylamide
N-(3-(2-((4-(piperidin-1-yl)phenyl)amino)pyrido[3,4-d]pyrimidin-8-yl)phenyl)acrylamide
N-(3-(2-((4-(azetidin-3-ylamino)phenyl)amino)pyrido[3,4-d]pyrimidin-8-yl)phenyl)acrylamide
N-(3-(2-((4-((1-methylazetidin-3-yl)amino)phenyl)amino)pyrido[3,4-d]pyrimidin-8-yl)phenyl)acrylamide tert-butyl 3-((4-((8-(3-acrylamidophenyl)pyrido[3,4-d]pyrimidin-2-yl)amino)phenyl)amino)azetidine-1-carboxylate
N-(3-(2-((4-((1-acetylazetidin-3-yl)amino)phenyl)amino)pyrido[3,4-d]pyrimidin-8-yl)phenyl)acrylamide
N-(3-(2-((4-((1-(2-fluoroethyl)azetidin-3-yl)amino)phenyl)amino)pyrido[3,4-d]pyrimidin-8-yl)phenyl)acrylamide
N-(3-(2-((4-((1-(2-fluoroethyl)azetidin-3-yl)amino)phenyl)amino)pyrido[3,2-d]pyrimidin-8-yl)phenyl)acrylamide
N-(3-(2-((4-((1-(2-fluoroethyl) azetidin-3-yl)amino)phenyl)amino)pyrido[4,3-d]pyrimidin-8-yl)phenyl)acrylamide
N-(3-(2-((4-(piperidin-4-ylamino)phenyl)amino)pyrido[3,4-d]pyrimidin-8-yl)phenyl)acrylamide
N-(3-(2-((4-((1-methylpiperidin-4-yl)amino)phenyl)amino)pyrido[3,4-d]pyrimidin-8-yl)phenyl)acrylamide
N-(3-(2-((4-(pyrrolidin-3-ylamino)phenyl)amino)pyrido[3,4-d]pyrimidin-8-yl)phenyl)acrylamide
(R)—N-(3-(2-((4-(pyrrolidin-3-ylamino)phenyl)amino)pyrido[3,4-d]pyrimidin-8-yl)phenyl)acrylamide
(S)—N-(3-(2-((4-(pyrrolidin-3-ylamino)phenyl)amino)pyrido[3,4-d]pyrimidin-8-yl)phenyl)acrylamide
(S)—N-(3-(2-((4-(2-(hydroxymethyl)morpholino)phenyl)amino)pyrido[3,4-d]pyrimidin-8-yl)phenyl)acrylamide
(R)—N-(3-(2-((4-(2-(hydroxymethyl)morpholino)phenyl)amino)pyrido[3,4-d]pyrimidin-8-yl)phenyl)acrylamide (R)—N-(3-(2-((4-(2-(aminomethyl)morpholino)phenyl)amino)pyrido[3,4-d]pyrimidin-8-yl)phenyl)acrylamide
(S)—N-(3-(2-((4-(2-(aminomethyl)morpholino)phenyl)amino)pyrido[3,4-d]pyrimidin-8-yl)phenyl)acrylamide
(R)—N-(3-(2-((4-(3-(aminomethyl)morpholino)phenyl)amino)pyrido[3,4-d]pyrimidin-8-yl)phenyl)acrylamide
(S)—N-(3-(2-((4-(3-(aminomethyl)morpholino)phenyl)amino)pyrido[3,4-d]pyrimidin-8-yl)phenyl)acrylamide
N-(3-(2-((2-methoxy-4-morpholinophenyl)amino)pyrido[3,4-d]pyrimidin-8-yl)phenyl)acrylamide
N-(3-(2-((2-methoxy-4-morpholinophenyl)amino)pyrido[3,2-d]pyrimidin-8-yl)phenyl)acrylamide
N-(3-(2-((2-methoxy-4-morpholinophenyl)amino)pyrido[4,3-d]pyrimidin-8-yl)phenyl)acrylamide
N-(3-(2-((2-methoxy-4-(4-methylpiperazin-1-yl)phenyl)amino)pyrido[3,4-d]pyrimidin-8-yl)phenyl)acrylamide
N-(3-(2-((2-methoxy-4-(4-methylpiperazin-1-yl)phenyl)amino)pyrido[3,2-d]pyrimidin-8-yl)phenyl)acrylamide
N-(3-(2-((2-methoxy-4-(4-methylpiperazin-1-yl)phenyl)amino)pyrido[4,3-d]pyrimidin-8-yl)phenyl)acrylamide
N-(3-(2-((2-methoxy-4-((1-methylazetidin-3-yl)amino)phenyl)amino)pyrido[3,4-d]pyrimidin-8-yl)phenyl)acrylamide
N-(3-(2-((4-((1-(2-fluoroethyl)azetidin-3-yl)amino)-2-methoxyphenyl)amino)pyrido[3,4-d]pyrimidin-8-yl)phenyl)acrylamide
N-(3-(2-((2-methoxy-4-((1-methylpiperidin-4-yl)amino)phenyl)amino)pyrido[3,4-d]pyrimidin-8-yl)phenyl)acrylamide
N-(3-(2-((2-methoxy-4-morpholinophenyl)amino)quinazolin-8-yl)phenyl)acrylamide
N-(3-(2-((2-methoxy-4-(piperazin-1-yl)phenyl)amino)quinazolin-8-yl)phenyl)acrylamide
N-(3-(2-((2-methoxy-4-(4-methylpiperazin-1-yl)phenyl)amino)quinazolin-8-yl)phenyl)acrylamide
N-(3-(2-((4-(4-ethylpiperazin-1-yl)-2-methoxyphenyl)amino)quinazolin-8-yl)phenyl)acrylamide
N-(3-(2-((2-methoxy-4-(piperidin-1-yl)phenyl)amino)quinazolin-8-yl)phenyl)acrylamide
N-(3-(2-((4-(azetidin-3-ylamino)-2-methoxyphenyl)amino)quinazolin-8-yl)phenyl)acrylamide
N-(3-(2-((2-methoxy-4-((1-methylazetidin-3-yl)amino)phenyl)amino)quinazolin-8-yl)phenyl)acrylamide tert-butyl 3-((4-((8-(3-acrylamidophenyl)quinazolin-2-yl)amino)-3-methoxyphenyl)amino)azetidine-1-carboxylate
N-(3-(2-((4-((1-acetylazetidin-3-yl)amino)-2-methoxyphenyl)amino)quinazolin-8-yl)phenyl) acrylamide
N-(3-(2-((4-((1-(2-fluoroethyl) azetidin-3-yl)amino)-2-methoxyphenyl)amino)quinazolin-8-yl)phenyl)acrylamide
N-(3-(2-((2-methoxy-4-(piperidin-4-ylamino)phenyl)amino)quinazolin-8-yl)phenyl)acrylamide
N-(3-(2-((2-methoxy-4-((1-methylpiperidin-4-yl)amino)phenyl)amino)quinazolin-8-yl)phenyl)acrylamide
N-(3-(2-((2-methoxy-4-(pyrrolidin-3-ylamino)phenyl)amino)quinazolin-8-yl)phenyl)acrylamide
(R)—N-(3-(2-((2-methoxy-4-(pyrrolidin-3-ylamino)phenyl)amino)quinazolin-8-yl)phenyl)acrylamide
(S)—N-(3-(2-((2-methoxy-4-(pyrrolidin-3-ylamino)phenyl)amino)quinazolin-8-yl)phenyl)acrylamide
(S)—N-(3-(2-((4-(2-(hydroxymethyl)morpholino)-2-methoxyphenyl)amino)quinazolin-8-yl)phenyl)acrylamide
(R)—N-(3-(2-((4-(2-(hydroxymethyl)morpholino)-2-methoxyphenyl)amino)quinazolin-8-yl)phenyl)acrylamide
(R)—N-(3-(2-((4-(2-(aminomethyl)morpholino)-2-methoxyphenyl)amino)quinazolin-8-yl)phenyl)acrylamide
(S)—N-(3-(2-((4-(2-(aminomethyl)morpholino)-2-methoxyphenyl)amino)quinazolin-8-yl)phenyl)acrylamide
(R)—N-(3-(2-((4-(3-(aminomethyl)morpholino)-2-methoxyphenyl)amino)quinazolin-8-yl)phenyl)acrylamide
(S)—N-(3-(2-((4-(3-(aminomethyl)morpholino)-2-methoxyphenyl)amino)quinazolin-8-yl)phenyl)acrylamide
N-(3-(7-fluoro-2-((4-morpholinophenyl)amino)quinazolin-8-yl)phenyl)acrylamide
N-(3-(7-fluoro-2-((2-methoxy-4-morpholinophenyl)amino)quinazolin-8-yl)phenyl)acrylamide
N-(3-(7-chloro-2-((4-morpholinophenyl)amino)quinazolin-8-yl)phenyl)acrylamide
N-(3-(7-chloro-2-((2-methoxy-4-morpholinophenyl)amino)quinazolin-8-yl)phenyl)acrylamide
N-(3-(7-methyl-2-((4-morpholinophenyl)amino)quinazolin-8-yl)phenyl)acrylamide
N-(3-(2-((2-methoxy-4-morpholinophenyl)amino)-7-methylquinazolin-8-yl)phenyl)acrylamide
N-(3-(7-ethyl-2-((4-morpholinophenyl)amino)quinazolin-8-yl)phenyl)acrylamide
N-(3-(7-fluoro-2-((4-(piperazin-1-yl)phenyl)amino)quinazolin-8-yl)phenyl)acrylamide
N-(3-(7-fluoro-2-((4-(4-methylpiperazin-1-yl)phenyl)amino)quinazolin-8-yl)phenyl)acrylamide
N-(3-(7-fluoro-2-((2-methoxy-4-(4-methylpiperazin-1-yl)phenyl)amino)quinazolin-8-yl)phenyl)acrylamide
N-(3-(7-chloro-2-((4-(4-methylpiperazin-1-yl)phenyl)amino)quinazolin-8-yl)phenyl)acrylamide
N-(3-(7-chloro-2-((2-methoxy-4-(4-methylpiperazin-1-yl)phenyl)amino)quinazolin-8-yl)phenyl)acrylamide
N-(3-(7-methyl-2-((4-(4-methylpiperazin-1-yl)phenyl)amino)quinazolin-8-yl)phenyl)acrylamide
N-(3-(2-((2-methoxy-4-(4-methylpiperazin-1-yl)phenyl)amino)-7-methylquinazolin-8-yl)phenyl)acrylamide
N-(3-(7-ethyl-2-((4-(4-methylpiperazin-1-yl)phenyl)amino)quinazolin-8-yl)phenyl)acrylamide
N-(3-(2-((4-(4-ethylpiperazin-1-yl)phenyl)amino)-7-fluoroquinazolin-8-yl)phenyl)acrylamide
N-(3-(7-fluoro-2-((4-(piperidin-1l-yl)phenyl)amino)quinazolin-8-yl)phenyl)acrylamide
N-(3-(2-((4-(azetidin-3-ylamino)phenyl)amino)-7-fluoroquinazolin-8-yl)phenyl)acrylamide
N-(3-(7-fluoro-2-((4-((1-methylazetidin-3-yl)amino)phenyl)amino)quinazolin-8-yl)phenyl)acrylamide tert-butyl 3-((4-((8-(3-acrylamidophenyl)-7-fluoroquinazolin-2-yl)amino)phenyl)amino)azetidine-1-carboxylate
N-(3-(2-((4-((1-acetylazetidin-3-yl)amino)phenyl)amino)-7-fluoroquinazolin-8-yl)phenyl)acrylamide
N-(3-(7-fluoro-2-((4-((1-(2-fluoroethyl)azetidin-3-yl)amino)phenyl)amino)quinazolin-8-yl)phenyl)acrylamide
N-(3-(7-chloro-2-((4-((1-(2-fluoroethyl)azetidin-3-yl)amino)phenyl)amino)quinazolin-8-yl)phenyl)acrylamide
N-(3-(2-((4-((1-(2-fluoroethyl)azetidin-3-yl)amino)phenyl)amino)-7-methylquinazolin-8-yl)phenyl)acrylamide
N-(3-(7-ethyl-2-((4-((1-(2-fluoroethyl)azetidin-3-yl)amino)phenyl)amino)quinazolin-8-yl)phenyl)acrylamide
N-(3-(7-fluoro-2-((4-(piperidin-4-ylamino)phenyl)amino)quinazolin-8-yl)phenyl)acrylamide
N-(3-(7-fluoro-2-((4-((1-methylpiperidin-4-yl)amino)phenyl)amino)quinazolin-8-yl)phenyl)acrylamide N-(3-(7-fluoro-2-((4-(pyrrolidin-3-ylamino)phenyl)amino)quinazolin-8-yl)phenyl)acrylamide
(R)—N-(3-(7-fluoro-2-((4-(pyrrolidin-3-ylamino)phenyl)amino)quinazolin-8-yl)phenyl)acrylamide
(S)—N-(3-(7-fluoro-2-((4-(pyrrolidin-3-ylamino)phenyl)amino)quinazolin-8-yl)phenyl)acrylamide
(S)—N-(3-(7-fluoro-2-((4-(2-(hydroxymethyl)morpholino)phenyl)amino)quinazolin-8-yl)phenyl)acrylamide
(R)—N-(3-(7-fluoro-2-((4-(2-(hydroxymethyl)morpholino)phenyl)amino)quinazolin-8-yl)phenyl)acrylamide
(R)—N-(3-(2-((4-(2-(aminomethyl)morpholino)phenyl)amino)-7-fluoroquinazolin-8-yl)phenyl)acrylamide
(S)—N-(3-(2-((4-(2-(aminomethyl)morpholino)phenyl)amino)-7-fluoroquinazolin-8-yl)phenyl)acrylamide
(R)—N-(3-(2-((4-(3-(aminomethyl)morpholino)phenyl)amino)-7-fluoroquinazolin-8-yl)phenyl)acrylamide
(S)—N-(3-(2-((4-(3-(aminomethyl)morpholino)phenyl)amino)-7-fluoroquinazolin-8-yl)phenyl)acrylamide
N-(3-(2-((4-morpholinophenyl)amino)quinazolin-8-yl)phenyl)acrylamide
N-(3-(2-((4-(piperazin-1-yl)phenyl)amino)quinazolin-8-yl)phenyl)acrylamide
N-(3-(2-((4-(4-methylpiperazin-1-yl)phenyl)amino)quinazolin-8-yl)phenyl)acrylamide
N-(3-(2-((4-(4-ethylpiperazin-1-yl)phenyl)amino)quinazolin-8-yl)phenyl)acrylamide
N-(3-(2-((4-(piperidin-1-yl)phenyl)amino)quinazolin-8-yl)phenyl)acrylamide
N-(3-(2-((4-(azetidin-3-ylamino)phenyl)amino)quinazolin-8-yl)phenyl)acrylamide
N-(3-(2-((4-((1-methylazetidin-3-yl)amino)phenyl)amino)quinazolin-8-yl)phenyl)acrylamide
tert-butyl 3-((4-((8-(3-acrylamidophenyl)quinazolin-2-yl)amino)phenyl)amino)azetidine-1-carboxylate
N-(3-(2-((4-((1-acetylazetidin-3-yl)amino)phenyl)amino)quinazolin-8-yl)phenyl)acrylamide
N-(3-(2-((4-((1-(2-fluoroethyl)azetidin-3-yl)amino)phenyl)amino)quinazolin-8-yl)phenyl)acrylamide
N-(3-(2-((4-(piperidin-4-ylamino)phenyl)amino)quinazolin-8-yl)phenyl)acrylamide
N-(3-(2-((4-((1-methylpiperidin-4-yl)amino)phenyl)amino)quinazolin-8-yl)phenyl)acrylamide
N-(3-(2-((4-(pyrrolidin-3-ylamino)phenyl)amino)quinazolin-8-yl)phenyl)acrylamide
(R)—N-(3-(2-((4-(pyrrolidin-3-ylamino)phenyl)amino)quinazolin-8-yl)phenyl)acrylamide
(S)—N-(3-(2-((4-(pyrrolidin-3-ylamino)phenyl)amino)quinazolin-8-yl)phenyl)acrylamide
(S)—N-(3-(2-((4-(2-(hydroxymethyl)morpholino)phenyl)amino)quinazolin-8-yl)phenyl)acrylamide
(R)—N-(3-(2-((4-(2-(hydroxymethyl)morpholino)phenyl)amino)quinazolin-8-yl)phenyl)acrylamide
(R)—N-(3-(2-((4-(2-(aminomethyl)morpholino)phenyl)amino)quinazolin-8-yl)phenyl)acrylamide
(S)—N-(3-(2-((4-(2-(aminomethyl)morpholino)phenyl)amino)quinazolin-8-yl)phenyl)acrylamide
(R)—N-(3-(2-((4-(3-(aminomethyl)morpholino)phenyl)amino)quinazolin-8-yl)phenyl)acrylamide
(S)—N-(3-(2-((4-(3-(aminomethyl)morpholino)phenyl)amino)quinazolin-8-yl)phenyl)acrylamide
N-(3-(2-((6-(piperazin-1-yl)pyridin-3-yl)amino)pyrido[3,2-d]pyrimidin-8-yl)phenyl)acetamide
N-(3-(2-((6-(piperazin-1-yl)pyridin-3-yl)amino)pyrido[4,3-d]pyrimidin-8-yl)phenyl)acetamide
N-(3-(2-((6-(piperazin-1-yl)pyridin-3-yl)amino)pyrido[3,4-d]pyrimidin-8-yl)phenyl)acetamide
8-(2-fluorophenyl)-N-(6-morpholinopyridin-3-yl)pyrido[4,3-d]pyrimidin-2-amine
8-(2-fluorophenyl)-N-(6-morpholinopyridin-3-yl)pyrido[3,2-d]pyrimidin-2-amine
8-(2-fluorophenyl)-N-(6-morpholinopyridin-3-yl)pyrido[3,4-d]pyrimidin-2-amine
8-(5-chloro-2-fluorophenyl)-N-(6-morpholinopyridin-3-yl)pyrido[3,4-d]pyrimidin-2-amine
8-(3-chlorophenyl)-N-(6-morpholinopyridin-3-yl)pyrido[3,4-d]pyrimidin-2-amine
8-(3-fluorophenyl)-N-(6-morpholinopyridin-3-yl)pyrido[3,4-d]pyrimidin-2-amine
8-(2,6-difluorophenyl)-N-(6-morpholinopyridin-3-yl)pyrido[3,4-d]pyrimidin-2-amine
8-(2-fluoro-5-(2-morpholinoethoxy)phenyl)-N-(6-morpholinopyridin-3-yl)pyrido[3,4-d]pyrimidin-2-amine
8-(5-(2-(dimethylamino)ethoxy)-2-fluorophenyl)-N-(6-morpholinopyridin-3-yl)pyrido[3,4-d]pyrimidin-2-amine
8-(3-(2-morpholinoethoxy)phenyl)-N-(6-morpholinopyridin-3-yl)pyrido[3,4-d]pyrimidin-2-amine
8-(3-(2-(dimethylamino)ethoxy)phenyl)-N-(6-morpholinopyridin-3-yl)pyrido[3,4-d]pyrimidin-2-amine
8-(4-(2-morpholinoethoxy)phenyl)-N-(6-morpholinopyridin-3-yl)pyrido[3,4-d]pyrimidin-2-amine
8-(4-(2-(dimethylamino)ethoxy)phenyl)-N-(6-morpholinopyridin-3-yl)pyrido[3,4-d]pyrimidin-2-amine
8-(2-fluoro-4-(2-morpholinoethoxy)phenyl)-N-(6-morpholinopyridin-3-yl)pyrido[3,4-d]pyrimidin-2-amine
8-(4-(2-(dimethylamino)ethoxy)-2-fluorophenyl)-N-(6-morpholinopyridin-3-yl)pyrido[3,4-d]pyrimidin-2-amine
8-phenyl-N-(6-(piperazin-1-yl)pyridin-3-yl)pyrido[3,4-d]pyrimidin-2-amine
8-(2-fluorophenyl)-N-(6-(piperazin-1-yl)pyridin-3-yl)pyrido[3,4-d]pyrimidin-2-amine
8-(2-chlorophenyl)-N-(6-(piperazin-1-yl)pyridin-3-yl)pyrido[3,4-d]pyrimidin-2-amine
8-(2,6-difluorophenyl)-N-(6-(piperazin-1-yl)pyridin-3-yl)pyrido[3,4-d]pyrimidin-2-amine
8-(5-chloro-2-fluorophenyl)-N-(6-(piperazin-1-yl)pyridin-3-yl)pyrido[3,4-d]pyrimidin-2-amine
8-(3-chlorophenyl)-N-(6-(piperazin-1-yl)pyridin-3-yl)pyrido[3,4-d]pyrimidin-2-amine
8-(3-fluorophenyl)-N-(6-(piperazin-1-yl)pyridin-3-yl)pyrido[3,4-d]pyrimidin-2-amine
N-(4-fluoro-3-(2-(((6-(piperazin-1-yl)pyridin-3-yl)amino)pyrido[3,4-d]pyrimidin-8-yl)phenyl)acetamide
8-(2-fluoro-5-(2-morpholinoethoxy)phenyl)-N-(6-(piperazin-1-yl)pyridin-3-yl)pyrido[3,4-d]pyrimidin-2-amine
8-(5-(2-(dimethylamino)ethoxy)-2-fluorophenyl)-N-(6-(piperazin-1-yl)pyridin-3-yl)pyrido[3,4-d]pyrimidin-2-amine
8-(3-(2-morpholinoethoxy)phenyl)-N-(6-(piperazin-1-yl)pyridin-3-yl)pyrido[3,4-d]pyrimidin-2-amine
8-(3-(2-(dimethylamino)ethoxy)phenyl)-N-(6-(piperazin-1-yl)pyridin-3-yl)pyrido[3,4-d]pyrimidin-2-amine
8-(4-(2-morpholinoethoxy)phenyl)-N-(6-(piperazin-1-yl)pyridin-3-yl)pyrido[3,4-d]pyrimidin-2-amine
8-(4-(2-(dimethylamino)ethoxy)phenyl)-N-(6-(piperazin-1-yl)pyridin-3-yl)pyrido[3,4-d]pyrimidin-2-amine
8-(2-fluoro-4-(2-morpholinoethoxy)phenyl)-N-(6-(piperazin-1-yl)pyridin-3-yl)pyrido[3,4-d]pyrimidin-2-amine
8-(4-(2-(dimethylamino)ethoxy)-2-fluorophenyl)-N-(6-(piperazin-1-yl)pyridin-3-yl)pyrido[3,4-d]pyrimidin-2-amine
N2-(1-(2-fluoroethyl)azetidin-3-yl)-N5-(8-(2-fluorophenyl)pyrido[3,4-d]pyrimidin-2-yl)pyridine-2,5-diamine N2-(1-(2-fluoroethyl)azetidin-3-yl)-N5-(8-(3-(2-morpholinoethoxy)phenyl)pyrido[3,4-d]pyrimidin-2-yl)pyridine-2,5-diamine
N5-(8-(2-fluoro-5-(2-morpholinoethoxy)phenyl)pyrido[3,4-d]pyrimidin-2-yl)-N2-(1-(2-fluoroethyl)azetidin-3-yl)pyridine-2,5-diamine
N5-(8-(5-chloro-2-fluorophenyl)pyrido[3,4-d]pyrimidin-2-yl)-N2-(1-(2-fluoroethyl)azetidin-3-yl)pyridine-2,5-diamine
8-(3-aminophenyl)-N-(6-morpholinopyridin-3-yl)quinazolin-2-amine
8-(3-aminophenyl)-N-(6-(piperazin-1-yl)pyridin-3-yl)quinazolin-2-amine
8-(3-aminophenyl)-N-(6-(4-methylpiperazin-1-yl)pyridin-3-yl)quinazolin-2-amine
N-(3-(2-((6-morpholinopyridin-3-yl)amino)quinazolin-8-yl)phenyl)acetamide
N-(3-(2-((6-(piperazin-1-yl)pyridin-3-yl)amino)quinazolin-8-yl)phenyl)acetamide
N-(3-(2-((6-(4-methylpiperazin-1-yl)pyridin-3-yl)amino)quinazolin-8-yl)phenyl)acetamide
N-(6-morpholinopyridin-3-yl)-8-phenylquinazolin-2-amine
8-(2-fluorophenyl)-N-(6-morpholinopyridin-3-yl)quinazolin-2-amine
8-(2-chlorophenyl)-N-(6-morpholinopyridin-3-yl)quinazolin-2-amine
8-(5-chloro-2-fluorophenyl)-N-(6-morpholinopyridin-3-yl)quinazolin-2-amine
8-(3-chlorophenyl)-N-(6-morpholinopyridin-3-yl)quinazolin-2-amine
8-(3-fluorophenyl)-N-(6-morpholinopyridin-3-yl)quinazolin-2-amine
8-(2,6-difluorophenyl)-N-(6-morpholinopyridin-3-yl)quinazolin-2-amine
8-(2-fluoro-5-(2-morpholinoethoxy)phenyl)-N-(6-morpholinopyridin-3-yl)quinazolin-2-amine
8-(5-(2-(dimethylamino)ethoxy)-2-fluorophenyl)-N-(6-morpholinopyridin-3-yl)quinazolin-2-amine
8-(3-(2-morpholinoethoxy)phenyl)-N-(6-morpholinopyridin-3-yl)quinazolin-2-amine
8-(3-(2-(dimethylamino)ethoxy)phenyl)-N-(6-morpholinopyridin-3-yl)quinazolin-2-amine
8-(4-(2-morpholinoethoxy)phenyl)-N-(6-morpholinopyridin-3-yl)quinazolin-2-amine
8-(4-(2-(dimethylamino)ethoxy)phenyl)-N-(6-morpholinopyridin-3-yl)quinazolin-2-amine
8-(2-fluoro-4-(2-morpholinoethoxy)phenyl)-N-(6-morpholinopyridin-3-yl)quinazolin-2-amine
8-(4-(2-(dimethylamino)ethoxy)-2-fluorophenyl)-N-(6-morpholinopyridin-3-yl)quinazolin-2-amine
8-phenyl-N-(6-(piperazin-1-yl)pyridin-3-yl)quinazolin-2-amine
8-(2-fluorophenyl)-N-(6-(piperazin-1-yl)pyridin-3-yl)quinazolin-2-amine
8-(2-chlorophenyl)-N-(6-(piperazin-1-yl)pyridin-3-yl)quinazolin-2-amine
8-(2,6-difluorophenyl)-N-(6-(piperazin-1-yl)pyridin-3-yl)quinazolin-2-amine
8-(5-chloro-2-fluorophenyl)-N-(6-(piperazin-1-yl)pyridin-3-yl)quinazolin-2-amine
8-(3-chlorophenyl)-N-(6-(piperazin-1-yl)pyridin-3-yl)quinazolin-2-amine
8-(3-fluorophenyl)-N-(6-(piperazin-1-yl)pyridin-3-yl)quinazolin-2-amine
N-(4-fluoro-3-(2-((6-(piperazin-1-yl)pyridin-3-yl)amino)quinazolin-8-yl)phenyl)acetamide
8-(2-fluoro-5-(2-morpholinoethoxy)phenyl)-N-(6-(piperazin-1-yl)pyridin-3-yl)quinazolin-2-amine
8-(5-(2-(dimethylamino)ethoxy)-2-fluorophenyl)-N-(6-(piperazin-1-yl)pyridin-3-yl)quinazolin-2-amine
8-(3-(2-morpholinoethoxy)phenyl)-N-(6-(piperazin-1-yl)pyridin-3-yl)quinazolin-2-amine
8-(3-(2-(dimethylamino)ethoxy)phenyl)-N-(6-(piperazin-1-yl)pyridin-3-yl)quinazolin-2-amine
8-(4-(2-morpholinoethoxy)phenyl)-N-(6-(piperazin-1-yl)pyridin-3-yl)quinazolin-2-amine
8-(4-(2-(dimethylamino)ethoxy)phenyl)-N-(6-(piperazin-1-yl)pyridin-3-yl)quinazolin-2-amine
8-(2-fluoro-4-(2-morpholinoethoxy)phenyl)-N-(6-(piperazin-1-yl)pyridin-3-yl)quinazolin-2-amine
8-(4-(2-(dimethylamino)ethoxy)-2-fluorophenyl)-N-(6-(piperazin-1-yl)pyridin-3-yl)quinazolin-2-amine
N2-(1-(2-fluoroethyl)azetidin-3-yl)-N5-(8-(2-fluorophenyl)quinazolin-2-yl)pyridine-2,5-diamine
N2-(1-(2-fluoroethyl)azetidin-3-yl)-N5-(8-(3-(2-morpholinoethoxy)phenyl)quinazolin-2-yl)pyridine-2,5-diamine
N5-(8-(2-fluoro-5-(2-morpholinoethoxy)phenyl)quinazolin-2-yl)-N2-(1-(2-fluoroethyl)azetidin-3-yl)pyridine-2,5-diamine
N5-(8-(5-chloro-2-fluorophenyl)quinazolin-2-yl)-N2-(1-(2-fluoroethyl)azetidin-3-yl)pyridine-2,5-diamine
N-(3-(2-((6-morpholinopyridin-3-yl)amino)pyrido[3,4-d]pyrimidin-8-yl)phenyl)acrylamide
N-(3-(2-((6-(piperazin-1-yl)pyridin-3-yl)amino)pyrido[3,4-d]pyrimidin-8-yl)phenyl)acrylamide
N-(3-(2-((6-morpholinopyridin-3-yl)amino)pyrido[3,2-d]pyrimidin-8-yl)phenyl)acrylamide
N-(3-(2-((6-morpholinopyridin-3-yl)amino)pyrido[4,3-d]pyrimidin-8-yl)phenyl)acrylamide
N-(3-(2-((6-(4-methylpiperazin-1-yl)pyridin-3-yl)amino)pyrido[3,4-d]pyrimidin-8-yl)phenyl)acrylamide
N-(3-(2-((6-(4-methylpiperazin-1-yl)pyridin-3-yl)amino)pyrido[3,2-d]pyrimidin-8-yl)phenyl)acrylamide
N-(3-(2-((6-(4-methylpiperazin-1-yl)pyridin-3-yl)amino)pyrido[4,3-d]pyrimidin-8-yl)phenyl)acrylamide
N-(3-(2-((6-(4-ethylpiperazin-1-yl)pyridin-3-yl)amino)pyrido[3,4-d]pyrimidin-8-yl)phenyl)acrylamide
N-(3-(2-((6-(piperidin-1-yl)pyridin-3-yl)amino)pyrido[3,4-d]pyrimidin-8-yl)phenyl)acrylamide
N-(3-(2-((6-(azetidin-3-ylamino)pyridin-3-yl)amino)pyrido[3,4-d]pyrimidin-8-yl)phenyl)acrylamide
N-(3-(2-((6-((1-methylazetidin-3-yl)amino)pyridin-3-yl)amino)pyrido[3,4-d]pyrimidin-8-yl)phenyl)acrylamide
tert-butyl 3-((5-((8-(3-acrylamidophenyl)pyrido[3,4-d]pyrimidin-2-yl)amino)pyridin-2-yl)amino)azetidine-1-carboxylate
N-(3-(2-((6-((1-acetylazetidin-3-yl)amino)pyridin-3-yl)amino)pyrido[3,4-d]pyrimidin-8-yl)phenyl)acrylamide
N-(3-(2-((6-((1-(2-fluoroethyl)azetidin-3-yl)amino)pyridin-3-yl)amino)pyrido[3,4-d]pyrimidin-8-yl)phenyl)acrylamide
N-(3-(2-((6-((1-(2-fluoroethyl)azetidin-3-yl)amino)pyridin-3-yl)amino)pyrido[3,2-d]pyrimidin-8-yl)phenyl)acrylamide
N-(3-(2-((6-((1-(2-fluoroethyl)azetidin-3-yl)amino)pyridin-3-yl)amino)pyrido[4,3-d]pyrimidin-8-yl)phenyl)acrylamide
N-(3-(2-((6-(piperidin-4-ylamino)pyridin-3-yl)amino)pyrido[3,4-d]pyrimidin-8-yl)phenyl)acrylamide
N-(3-(2-((6-((1-methylpiperidin-4-yl)amino)pyridin-3-yl)amino)pyrido[3,4-d]pyrimidin-8-yl)phenyl)acrylamide
N-(3-(2-((6-(pyrrolidin-3-ylamino)pyridin-3-yl)amino)pyrido[3,4-d]pyrimidin-8-yl)phenyl)acrylamide (R)—N-(3-(2-((6-(pyrrolidin-3-ylamino)pyridin-3-yl)amino)pyrido[3,4-d]pyrimidin-8-yl)phenyl)acrylamide
(S)—N-(3-(2-((6-(pyrrolidin-3-ylamino)pyridin-3-yl)amino)pyrido[3,4-d]pyrimidin-8-yl)phenyl)acrylamide
(S)—N-(3-(2-((6-(2-(hydroxymethyl)morpholino)pyridin-3-yl)amino)pyrido[3,4-d]pyrimidin-8-yl)phenyl)acrylamide
(R)—N-(3-(2-((6-(2-(hydroxymethyl)morpholino)pyridin-3-yl)amino)pyrido[3,4-d]pyrimidin-8-yl)phenyl)acrylamide
(R)—N-(3-(2-((6-(2-(aminomethyl)morpholino)pyridin-3-yl)amino)pyrido[3,4-d]pyrimidin-8-yl)phenyl)acrylamide
(S)—N-(3-(2-((6-(2-(aminomethyl)morpholino)pyridin-3-yl)amino)pyrido[3,4-d]pyrimidin-8-yl)phenyl)acrylamide
(R)—N-(3-(2-((6-(3-(aminomethyl)morpholino)pyridin-3-yl)amino)pyrido[3,4-d]pyrimidin-8-yl)phenyl)acrylamide
(S)—N-(3-(2-((6-(3-(aminomethyl)morpholino)pyridin-3-yl)amino)pyrido[3,4-d]pyrimidin-8-yl)phenyl)acrylamide
N-(3-(2-((2-methoxy-6-morpholinopyridin-3-yl)amino)pyrido[3,4-d]pyrimidin-8-yl)phenyl)acrylamide
N-(3-(2-((2-methoxy-6-morpholinopyridin-3-yl)amino)pyrido[3,2-d]pyrimidin-8-yl)phenyl)acrylamide
N-(3-(2-((2-methoxy-6-morpholinopyridin-3-yl)amino)pyrido[4,3-d]pyrimidin-8-yl)phenyl)acrylamide
N-(3-(2-((2-methoxy-6-(4-methylpiperazin-1-yl)pyridin-3-yl)amino)pyrido[3,4-d]pyrimidin-8-yl)phenyl)acrylamide
N-(3-(2-((2-methoxy-6-(4-methylpiperazin-1-yl)pyridin-3-yl)amino)pyrido[3,2-d]pyrimidin-8-yl)phenyl)acrylamide
N-(3-(2-((2-methoxy-6-(4-methylpiperazin-1-yl)pyridin-3-yl)amino)pyrido[4,3-d]pyrimidin-8-yl)phenyl)acrylamide
N-(3-(2-((2-methoxy-6-((1-methylazetidin-3-yl)amino)pyridin-3-yl)amino)pyrido[3,4-d]pyrimidin-8-yl)phenyl)acrylamide
N-(3-(2-((6-((1-(2-fluoroethyl)azetidin-3-yl)amino)-2-methoxypyridin-3-yl)amino)pyrido[3,4-d]pyrimidin-8-yl)phenyl)acrylamide
N-(3-(2-((2-methoxy-6-((1-methylpiperidin-4-yl)amino)pyridin-3-yl)amino)pyrido[3,4-d]pyrimidin-8-yl)phenyl)acrylamide
N-(3-(2-((2-methoxy-6-morpholinopyridin-3-yl)amino)quinazolin-8-yl)phenyl)acrylamide
N-(3-(2-((2-methoxy-6-(piperazin-1-yl)pyridin-3-yl)amino)quinazolin-8-yl)phenyl)acrylamide
N-(3-(2-((2-methoxy-6-(4-methylpiperazin-1-yl)pyridin-3-yl)amino)quinazolin-8-yl)phenyl)acrylamide
N-(3-(2-((6-(4-ethylpiperazin-1-yl)-2-methoxypyridin-3-yl)amino)quinazolin-8-yl)phenyl)acrylamide
N-(3-(2-((2-methoxy-6-(piperidin-1-yl)pyridin-3-yl)amino)quinazolin-8-yl)phenyl)acrylamide
N-(3-(2-((6-(azetidin-3-ylamino)-2-methoxypyridin-3-yl)amino)quinazolin-8-yl)phenyl)acrylamide
N-(3-(2-((2-methoxy-6-((1-methylazetidin-3-yl)amino)pyridin-3-yl)amino)quinazolin-8-yl)phenyl)acrylamide
tert-butyl 3-((5-((8-(3-acrylamidophenyl)quinazolin-2-yl)amino)-6-methoxypyridin-2-yl)amino)azetidine-1-carboxylate
N-(3-(2-((6-((1-acetylazetidin-3-yl)amino)-2-methoxypyridin-3-yl)amino) quinazolin-8-yl)phenyl)acrylamide
N-(3-(2-((6-((1-(2-fluoroethyl)azetidin-3-yl)amino)-2-methoxypyridin-3-yl)amino)quinazolin-8-yl)phenyl)acrylamide
N-(3-(2-((2-methoxy-6-(piperidin-4-ylamino)pyridin-3-yl)amino)quinazolin-8-yl)phenyl)acrylamide
N-(3-(2-((2-methoxy-6-((1-methylpiperidin-4-yl)amino)pyridin-3-yl)amino)quinazolin-8-yl)phenyl)acrylamide
N-(3-(2-((2-methoxy-6-(pyrrolidin-3-ylamino)pyridin-3-yl)amino)quinazolin-8-yl)phenyl)acrylamide
(R)—N-(3-(2-((2-methoxy-6-(pyrrolidin-3-ylamino)pyridin-3-yl)amino)quinazolin-8-yl)phenyl)acrylamide
(S)—N-(3-(2-((2-methoxy-6-(pyrrolidin-3-ylamino)pyridin-3-yl)amino)quinazolin-8-yl)phenyl)acrylamide
(S)—N-(3-(2-((6-(2-(hydroxymethyl)morpholino)-2-methoxypyridin-3-yl)amino)quinazolin-8-yl)phenyl)acrylamide
(R)—N-(3-(2-((6-(2-(hydroxymethyl)morpholino)-2-methoxypyridin-3-yl)amino)quinazolin-8-yl)phenyl)acrylamide
(R)—N-(3-(2-((6-(2-(aminomethyl)morpholino)-2-methoxypyridin-3-yl)amino)quinazolin-8-yl)phenyl)acrylamide
(S)—N-(3-(2-((6-(2-(aminomethyl)morpholino)-2-methoxypyridin-3-yl)amino)quinazolin-8-yl)phenyl)acrylamide
(R)—N-(3-(2-((6-(3-(aminomethyl)morpholino)-2-methoxypyridin-3-yl)amino)quinazolin-8-yl)phenyl)acrylamide
(S)—N-(3-(2-((6-(3-(aminomethyl)morpholino)-2-methoxypyridin-3-yl)amino)quinazolin-8-yl)phenyl)acrylamide
N-(3-(7-fluoro-2-((6-morpholinopyridin-3-yl)amino)quinazolin-8-yl)phenyl)acrylamide
N-(3-(7-fluoro-2-((2-methoxy-6-morpholinopyridin-3-yl)amino)quinazolin-8-yl)phenyl)acrylamide
N-(3-(7-chloro-2-((6-morpholinopyridin-3-yl)amino)quinazolin-8-yl)phenyl)acrylamide
N-(3-(7-chloro-2-((2-methoxy-6-morpholinopyridin-3-yl)amino)quinazolin-8-yl)phenyl)acrylamide
N-(3-(7-methyl-2-((6-morpholinopyridin-3-yl)amino)quinazolin-8-yl)phenyl)acrylamide
N-(3-(2-((2-methoxy-6-morpholinopyridin-3-yl)amino)-7-methylquinazolin-8-yl)phenyl)acrylamide
N-(3-(7-ethyl-2-((6-morpholinopyridin-3-yl)amino)quinazolin-8-yl)phenyl)acrylamide
N-(3-(7-fluoro-2-((6-(piperazin-1-yl)pyridin-3-yl)amino)quinazolin-8-yl)phenyl)acrylamide
N-(3-(7-fluoro-2-((6-(4-methylpiperazin-1-yl)pyridin-3-yl)amino) quinazolin-8-yl)phenyl)acrylamide
N-(3-(7-fluoro-2-((2-methoxy-6-(4-methylpiperazin-1-yl)pyridin-3-yl)amino) quinazolin-8-yl)phenyl)acrylamide
N-(3-(7-chloro-2-((6-(4-methylpiperazin-1-yl)pyridin-3-yl)amino)quinazolin-8-yl)phenyl)acrylamide
N-(3-(7-chloro-2-((2-methoxy-6-(4-methylpiperazin-1-yl)pyridin-3-yl)amino)quinazolin-8-yl)phenyl)acrylamide
N-(3-(7-methyl-2-((6-(4-methylpiperazin-1-yl)pyridin-3-yl)amino)quinazolin-8-yl)phenyl)acrylamide
N-(3-(2-((2-methoxy-6-(4-methylpiperazin-1-yl)pyridin-3-yl)amino)-7-methylquinazolin-8-yl)phenyl)acrylamide
N-(3-(7-ethyl-2-((6-(4-methylpiperazin-1-yl)pyridin-3-yl)amino)quinazolin-8-yl)phenyl)acrylamide
N-(3-(2-((6-(4-ethylpiperazin-1-yl)pyridin-3-yl)amino)-7-fluoroquinazolin-8-yl)phenyl)acrylamide
N-(3-(7-fluoro-2-((6-(piperidin-1-yl)pyridin-3-yl)amino) quinazolin-8-yl)phenyl)acrylamide
N-(3-(2-((6-(azetidin-3-ylamino)pyridin-3-yl)amino)-7-fluoroquinazolin-8-yl)phenyl)acrylamide N-(3-(7-fluoro-2-((6-((1-methylazetidin-3-yl)amino)pyridin-3-yl)amino)quinazolin-8-yl)phenyl)acrylamide tert-butyl 3-((5-((8-(3-acrylamidophenyl)-7-fluoroquinazolin-2-yl)amino)pyridin-2-yl)amino)azetidine-1-carboxylate N-(3-(2-((6-((1-acetylazetidin-3-yl)amino)pyridin-3-yl)amino)-7-fluoroquinazolin-8-yl)phenyl)acrylamide N-(3-(7-fluoro-2-((6-((1-(2-fluoroethyl)azetidin-3-yl)amino)pyridin-3-yl)amino)quinazolin-8-yl)phenyl)acrylamide N-(3-(7-chloro-2-((6-((1-(2-fluoroethyl)azetidin-3-yl)amino)pyridin-3-yl)amino)quinazolin-8-yl)phenyl)acrylamide N-(3-(2-((6-((1-(2-fluoroethyl)azetidin-3-yl)amino)pyridin-3-yl)amino)-7-methylquinazolin-8-yl)phenyl)acrylamide N-(3-(7-ethyl-2-((6-((1-(2-fluoroethyl)azetidin-3-yl)amino)pyridin-3-yl)amino)quinazolin-8-yl)phenyl)acrylamide N-(3-(7-fluoro-2-((6-(piperidin-4-ylamino)pyridin-3-yl)amino)quinazolin-8-yl)phenyl)acrylamide N-(3-(7-fluoro-2-((6-((1-methylpiperidin-4-yl)amino)pyridin-3-yl)amino)quinazolin-8-yl)phenyl)acrylamide N-(3-(7-fluoro-2-((6-(pyrrolidin-3-ylamino)pyridin-3-yl)amino)quinazolin-8-yl)phenyl) acrylamide (R)—N-(3-(7-fluoro-2-((6-(pyrrolidin-3-ylamino)pyridin-3-yl)amino)quinazolin-8-yl)phenyl)acrylamide (S)—N-(3-(7-fluoro-2-((6-(pyrrolidin-3-ylamino)pyridin-3-yl)amino)quinazolin-8-yl)phenyl)acrylamide (S)—N-(3-(7-fluoro-2-((6-(2-(hydroxymethyl)morpholino)pyridin-3-yl)amino)quinazolin-8-yl)phenyl)acrylamide (R)—N-(3-(7-fluoro-2-((6-(2-(hydroxymethyl)morpholino)pyridin-3-yl)amino)quinazolin-8-yl)phenyl)acrylamide (R)—N-(3-(2-((6-(2-(aminomethyl)morpholino)pyridin-3-yl)amino)-7-fluoroquinazolin-8-yl)phenyl)acrylamide (S)—N-(3-(2-((6-(2-(aminomethyl)morpholino)pyridin-3-yl)amino)-7-fluoroquinazolin-8-yl)phenyl)acrylamide (R)—N-(3-(2-((6-(3-(aminomethyl)morpholino)pyridin-3-yl)amino)-7-fluoroquinazolin-8-yl)phenyl)acrylamide (S)—N-(3-(2-((6-(3-(aminomethyl)morpholino)pyridin-3-yl)amino)-7-fluoroquinazolin-8-yl)phenyl)acrylamide N-(3-(2-((6-morpholinopyridin-3-yl)amino)quinazolin-8-yl)phenyl)acrylamide N-(3-(2-((6-(piperazin-1-yl)pyridin-3-yl)amino)quinazolin-8-yl)phenyl)acrylamide N-(3-(2-((6-(4-methylpiperazin-1-yl)pyridin-3-yl)amino)quinazolin-8-yl)phenyl)acrylamide N-(3-(2-((6-(4-ethylpiperazin-1-yl)pyridin-3-yl)amino)quinazolin-8-yl)phenyl)acrylamide N-(3-(2-((6-(piperidin-1-yl)pyridin-3-yl)amino)quinazolin-8-yl)phenyl)acrylamide N-(3-(2-((6-(azetidin-3-ylamino)pyridin-3-yl)amino)quinazolin-8-yl)phenyl)acrylamide N-(3-(2-((6-((1-methylazetidin-3-yl)amino)pyridin-3-yl)amino) quinazolin-8-yl)phenyl)acrylamide tert-butyl 3-((5-((8-(3-acrylamidophenyl)quinazolin-2-yl)amino)pyridin-2-yl)amino)azetidine-1-carboxylate N-(3-(2-((6-((1-acetylazetidin-3-yl)amino)pyridin-3-yl)amino)quinazolin-8-yl)phenyl)acrylamide N-(3-(2-((6-((1-(2-fluoroethyl)azetidin-3-yl)amino)pyridin-3-yl)amino)quinazolin-8-yl)phenyl)acrylamide N-(3-(2-((6-(piperidin-4-ylamino)pyridin-3-yl)amino)quinazolin-8-yl)phenyl)acrylamide N-(3-(2-((6-((1-methylpiperidin-4-yl)amino)pyridin-3-yl)amino)quinazolin-8-yl)phenyl)acrylamide N-(3-(2-((6-(pyrrolidin-3-ylamino)pyridin-3-yl)amino)quinazolin-8-yl)phenyl)acrylamide (R)—N-(3-(2-((6-(pyrrolidin-3-ylamino)pyridin-3-yl)amino)quinazolin-8-yl)phenyl)acrylamide (S)—N-(3-(2-((6-(pyrrolidin-3-ylamino)pyridin-3-yl)amino)quinazolin-8-yl)phenyl)acrylamide (S)—N-(3-(2-((6-(2-(hydroxymethyl)morpholino)pyridin-3-yl)amino)quinazolin-8-yl)phenyl)acrylamide (R)—N-(3-(2-((6-(2-(hydroxymethyl)morpholino)pyridin-3-yl)amino)quinazolin-8-yl)phenyl)acrylamide (R)—N-(3-(2-((6-(2-(aminomethyl)morpholino)pyridin-3-yl)amino)quinazolin-8-yl)phenyl)acrylamide (S)—N-(3-(2-((6-(2-(aminomethyl)morpholino)pyridin-3-yl)amino)quinazolin-8-yl)phenyl)acrylamide (R)—N-(3-(2-((6-(3-(aminomethyl)morpholino)pyridin-3-yl)amino)quinazolin-8-yl)phenyl)acrylamide (S)—N-(3-(2-((6-(3-(aminomethyl)morpholino)pyridin-3-yl)amino)quinazolin-8-yl)phenyl)acrylamide 8-(4-aminopyridin-2-yl)-N-(4-morpholinophenyl)quinazolin-2-amine 8-(4-aminopyridin-2-yl)-N-(4-(piperazin-1-yl)phenyl)quinazolin-2-amine 8-(4-aminopyridin-2-yl)-N-(4-(4-methylpiperazin-1-yl)phenyl)quinazolin-2-amine N-(2-(2-((4-morpholinophenyl)amino)quinazolin-8-yl)pyridin-4-yl)acetamide N-(2-(2-((4-(4-methylpiperazin-1-yl)phenyl)amino)quinazolin-8-yl)pyridin-4-yl)acetamide N-(4-morpholinophenyl)-8-(pyridin-2-yl)quinazolin-2-amine 8-(4-(2-morpholinoethoxy)pyridin-2-yl)-N-(4-morpholinophenyl)quinazolin-2-amine 8-(4-(2-(dimethylamino)ethoxy)pyridin-2-yl)-N-(4-morpholinophenyl)quinazolin-2-amine 8-(5-(2-morpholinoethoxy)pyridin-2-yl)-N-(4-morpholinophenyl)quinazolin-2-amine 8-(5-(2-(dimethylamino)ethoxy)pyridin-2-yl)-N-(4-morpholinophenyl)quinazolin-2-amine N-(4-(piperazin-1-yl)phenyl)-8-(pyridin-2-yl)quinazolin-2-amine N-(2-(2-((4-(piperazin-1-yl)phenyl)amino)quinazolin-8-yl)pyridin-4-yl)acetamide 8-(4-(2-morpholinoethoxy)pyridin-2-yl)-N-(4-(piperazin-1-yl)phenyl)quinazolin-2-amine 8-(4-(2-(dimethylamino)ethoxy)pyridin-2-yl)-N-(4-(piperazin-1-yl)phenyl)quinazolin-2-amine 8-(5-(2-morpholinoethoxy)pyridin-2-yl)-N-(4-(piperazin-1-yl)phenyl)quinazolin-2-amine 8-(5-(2-(dimethylamino)ethoxy)pyridin-2-yl)-N-(4-(piperazin-1-yl)phenyl)quinazolin-2-amine N1-(1-(2-fluoroethyl)azetidin-3-yl)-N4-(8-(4-(2-morpholinoethoxy)pyridin-2-yl)quinazolin-2-yl)benzene-1,4-diamine N-(2-(2-((2-methoxy-4-morpholinophenyl)amino)pyrido[3,4-d]pyrimidin-8-yl)pyridin-4-yl)acrylamide N-(2-(2-((2-methoxy-4-morpholinophenyl)amino)pyrido[3,2-d]pyrimidin-8-yl)pyridin-4-yl)acrylamide N-(2-(2-((2-methoxy-4-morpholinophenyl)amino)pyrido[4,3-d]pyrimidin-8-yl)pyridin-4-yl)acrylamide N-(2-(2-((2-methoxy-4-(4-methylpiperazin-1-yl)phenyl)amino)pyrido[3,4-d]pyrimidin-8-yl)pyridin-4-yl)acrylamide N-(2-(2-((2-methoxy-4-(4-methylpiperazin-1-yl)phenyl)amino)pyrido[3,2-d]pyrimidin-8-yl)pyridin-4-yl)acrylamide N-(2-(2-((2-methoxy-4-(4-methylpiperazin-1-yl)phenyl)amino)pyrido[4,3-d]pyrimidin-8-yl)pyridin-4-yl)acrylamide N-(2-(2-((2-methoxy-4-((1-methylazetidin-3-yl)amino)phenyl)amino)pyrido[3,4-d]pyrimidin-8-yl)pyridin-4-yl)acrylamide N-(2-(2-((4-((1-(2-fluoroethyl)azetidin-3-yl)amino)-2-methoxyphenyl)amino)pyrido[3,4-d]pyrimidin-8-yl)pyridin-4-yl)acrylamide N-(2-(2-((2-methoxy-4-((1-methylpiperidin-4-yl)amino)phenyl)amino)pyrido[3,4-d]pyrimidin-8-yl)pyridin-4-yl)acrylamide N-(2-(2-((2-methoxy-4-morpholinophenyl)amino)quinazolin-8-yl)pyridin-4-yl)acrylamide N-(2-(2-((2-methoxy-4-(piperazin-1-yl)phenyl)amino)quinazolin-8-yl)pyridin-4-yl)acrylamide N-(2-(2-((2-methoxy-4-(4-methylpiperazin-1-yl)phenyl)amino)quinazolin-8-yl)pyridin-4-yl)acrylamide N-(2-(2-((4-(4-ethylpiperazin-1-yl)-2-methoxyphenyl)amino)quinazolin-8-yl)pyridin-4-yl)acrylamide N-(2-(2-((2-methoxy-4-(piperidin-1-yl)phenyl)amino)quinazolin-8-yl)pyridin-4-yl)acrylamide N-(2-(2-((4-(azetidin-3-ylamino)-2-methoxyphenyl)amino)quinazolin-8-yl)pyridin-4-yl)acrylamide N-(2-(2-((2-methoxy-4-((1-methylazetidin-3-yl)amino)phenyl)amino)quinazolin-8-yl)pyridin-4-yl)acrylamide tert-butyl 3-((4-((8-(4-acrylamidopyridin-2-yl)quinazolin-2-yl)amino)-3-methoxyphenyl)amino)azetidine-1-carboxylate N-(2-(2-((4-((1-acetylazetidin-3-yl)amino)-2-methoxyphenyl)amino)quinazolin-8-yl)pyridin-4-yl)acrylamide N-(2-(2-((4-((1-(2-fluoroethyl)azetidin-3-yl)amino)-2-methoxyphenyl)amino)quinazolin-8-yl)pyridin-4-yl)acrylamide N-(2-(2-((2-methoxy-4-(piperidin-4-ylamino)phenyl)amino)quinazolin-8-yl)pyridin-4-yl)acrylamide N-(2-(2-((2-methoxy-4-((1-methylpiperidin-4-yl)amino)phenyl)amino)quinazolin-8-yl)pyridin-4-yl)acrylamide N-(2-(2-((2-methoxy-4-(pyrrolidin-3-ylamino)phenyl)amino)quinazolin-8-yl)pyridin-4-yl)acrylamide (R)—N-(2-(2-((2-methoxy-4-(pyrrolidin-3-ylamino)phenyl)amino)quinazolin-8-yl)pyridin-4-yl)acrylamide (S)—N-(2-(2-((2-methoxy-4-(pyrrolidin-3-ylamino)phenyl)amino)quinazolin-8-yl)pyridin-4-yl)acrylamide (S)—N-(2-(2-((4-(2-(hydroxymethyl)morpholino)-2-methoxyphenyl)amino)quinazolin-8-yl)pyridin-4-yl)acrylamide (R)—N-(2-(2-((4-(2-(hydroxymethyl)morpholino)-2-methoxyphenyl)amino)quinazolin-8-yl)pyridin-4-yl)acrylamide (R)—N-(2-(2-((4-(2-(aminomethyl)morpholino)-2-methoxyphenyl)amino)quinazolin-8-yl)pyridin-4-yl)acrylamide (S)—N-(2-(2-((4-(2-(aminomethyl)morpholino)-2-methoxyphenyl)amino)quinazolin-8-yl)pyridin-4-yl)acrylamide (R)—N-(2-(2-((4-(3-(aminomethyl)morpholino)-2-methoxyphenyl)amino)quinazolin-8-yl)pyridin-4-yl)acrylamide (S)—N-(2-(2-((4-(3-(aminomethyl)morpholino)-2-methoxyphenyl)amino)quinazolin-8-yl)pyridin-4-yl)acrylamide N-(2-(2-((4-morpholinophenyl)amino)pyrido[3,4-d]pyrimidin-8-yl)pyridin-4-yl)acrylamide N-(2-(2-((4-(piperazin-1-yl)phenyl)amino)pyrido[3,4-d]pyrimidin-8-yl)pyridin-4-yl)acrylamide N-(2-(2-((4-morpholinophenyl)amino)pyrido[3,2-d]pyrimidin-8-yl)pyridin-4-yl)acrylamide N-(2-(2-((4-morpholinophenyl)amino)pyrido[4,3-d]pyrimidin-8-yl)pyridin-4-yl)acrylamide N-(2-(2-((4-(4-methylpiperazin-1-yl)phenyl)amino)pyrido[3,4-d]pyrimidin-8-yl)pyridin-4-yl)acrylamide N-(2-(2-((4-(4-methylpiperazin-1-yl)phenyl)amino)pyrido[3,2-d]pyrimidin-8-yl)pyridin-4-yl)acrylamide N-(2-(2-((4-(4-methylpiperazin-1-yl)phenyl)amino)pyrido[4,3-d]pyrimidin-8-yl)pyridin-4-yl)acrylamide N-(2-(2-((4-(4-ethylpiperazin-1-yl)phenyl)amino)pyrido[3,4-d]pyrimidin-8-yl)pyridin-4-yl)acrylamide N-(2-(2-((4-(piperidin-1-yl)phenyl)amino)pyrido[3,4-d]pyrimidin-8-yl)pyridin-4-yl)acrylamide N-(2-(2-((4-(azetidin-3-ylamino)phenyl)amino)pyrido[3,4-d]pyrimidin-8-yl)pyridin-4-yl)acrylamide N-(2-(2-((4-((1-methylazetidin-3-yl)amino)phenyl)amino)pyrido[3,4-d]pyrimidin-8-yl)pyridin-4-yl)acrylamide tert-butyl 3-((4-((8-(4-acrylamidopyridin-2-yl)pyrido[3,4-d]pyrimidin-2-yl)amino)phenyl)amino)azetidine-1-carboxylate N-(2-(2-((4-((1-acetylazetidin-3-yl)amino)phenyl)amino)pyrido[3,4-d]pyrimidin-8-yl)pyridin-4-yl)acrylamide N-(2-(2-((4-((1-(2-fluoroethyl)azetidin-3-yl)amino)phenyl)amino)pyrido[3,4-d]pyrimidin-8-yl)pyridin-4-yl)acrylamide N-(2-(2-((4-((1-(2-fluoroethyl)azetidin-3-yl)amino)phenyl)amino)pyrido[3,2-d]pyrimidin-8-yl)pyridin-4-yl)acrylamide N-(2-(2-((4-((1-(2-fluoroethyl)azetidin-3-yl)amino)phenyl)amino)pyrido[4,3-d]pyrimidin-8-yl)pyridin-4-yl)acrylamide N-(2-(2-((4-(piperidin-4-ylamino)phenyl)amino)pyrido[3,4-d]pyrimidin-8-yl)pyridin-4-yl)acrylamide N-(2-(2-((4-((1-methylpiperidin-4-yl)amino)phenyl)amino)pyrido[3,4-d]pyrimidin-8-yl)pyridin-4-yl)acrylamide N-(2-(2-((4-(pyrrolidin-3-ylamino)phenyl)amino)pyrido[3,4-d]pyrimidin-8-yl)pyridin-4-yl)acrylamide (R)—N-(2-(2-((4-(pyrrolidin-3-ylamino)phenyl)amino)pyrido[3,4-d]pyrimidin-8-yl)pyridin-4-yl)acrylamide (S)—N-(2-(2-((4-(pyrrolidin-3-ylamino)phenyl)amino)pyrido[3,4-d]pyrimidin-8-yl)pyridin-4-yl)acrylamide (S)—N-(2-(2-((4-(2-(hydroxymethyl)morpholino)phenyl)amino)pyrido[3,4-d]pyrimidin-8-yl)pyridin-4-yl)acrylamide (R)—N-(2-(2-((4-(2-(hydroxymethyl)morpholino)phenyl)amino)pyrido[3,4-d]pyrimidin-8-yl)pyridin-4-yl)acrylamide (R)—N-(2-(2-((4-(2-(aminomethyl)morpholino)phenyl)amino)pyrido[3,4-d]pyrimidin-8-yl)pyridin-4-yl)acrylamide (S)—N-(2-(2-((4-(2-(aminomethyl)morpholino)phenyl)amino)pyrido[3,4-d]pyrimidin-8-yl)pyridin-4-yl)acrylamide (R)—N-(2-(2-((4-(3-(aminomethyl)morpholino)phenyl)amino)pyrido[3,4-d]pyrimidin-8-yl)pyridin-4-yl)acrylamide (S)—N-(2-(2-((4-(3-(aminomethyl)morpholino)phenyl)amino)pyrido[3,4-d]pyrimidin-8-yl)pyridin-4-yl)acrylamide N-(2-(7-fluoro-2-((4-morpholinophenyl)amino)quinazolin-8-yl)pyridin-4-yl)acrylamide N-(2-(7-fluoro-2-((2-methoxy-4-morpholinophenyl)amino)quinazolin-8-yl)pyridin-4-yl)acrylamide N-(2-(7-chloro-2-((4-morpholinophenyl)amino)quinazolin-8-yl)pyridin-4-yl)acrylamide N-(2-(7-chloro-2-((2-methoxy-4-morpholinophenyl)amino)quinazolin-8-yl)pyridin-4-yl)acrylamide N-(2-(7-methyl-2-((4-morpholinophenyl)amino)quinazolin-8-yl)pyridin-4-yl)acrylamide N-(2-(2-((2-methoxy-4-morpholinophenyl)amino)-7-methylquinazolin-8-yl)pyridin-4-yl)acrylamide N-(2-(7-ethyl-2-((4-morpholinophenyl)amino)quinazolin-8-yl)pyridin-4-yl)acrylamide
N-(2-(7-fluoro-2-((4-(piperazin-1-yl)phenyl)amino)quinazolin-8-yl)pyridin-4-yl)acrylamide
N-(2-(7-fluoro-2-((4-(4-methylpiperazin-1-yl)phenyl)amino)quinazolin-8-yl)pyridin-4-yl)acrylamide
N-(2-(7-fluoro-2-((2-methoxy-4-(4-methylpiperazin-1-yl)phenyl)amino)quinazolin-8-yl)pyridin-4-yl)acrylamide
N-(2-(7-chloro-2-((4-(4-methylpiperazin-1-yl)phenyl)amino)quinazolin-8-yl)pyridin-4-yl)acrylamide
N-(2-(7-chloro-2-((2-methoxy-4-(4-methylpiperazin-1-yl)phenyl)amino)quinazolin-8-yl)pyridin-4-yl)acrylamide
N-(2-(7-methyl-2-((4-(4-methylpiperazin-1-yl)phenyl)amino)quinazolin-8-yl)pyridin-4-yl)acrylamide
N-(2-(2-((2-methoxy-4-(4-methylpiperazin-1-yl)phenyl)amino)-7-methylquinazolin-8-yl)pyridin-4-yl)acrylamide
N-(2-(7-ethyl-2-((4-(4-methylpiperazin-1-yl)phenyl)amino)quinazolin-8-yl)pyridin-4-yl)acrylamide
N-(2-(2-((4-(4-ethylpiperazin-1-yl)phenyl)amino)-7-fluoroquinazolin-8-yl)pyridin-4-yl)acrylamide
N-(2-(7-fluoro-2-((4-(piperidin-1l-yl)phenyl)amino)quinazolin-8-yl)pyridin-4-yl)acrylamide
N-(2-(2-((4-(azetidin-3-ylamino)phenyl)amino)-7-fluoroquinazolin-8-yl)pyridin-4-yl)acrylamide
N-(2-(7-fluoro-2-((4-((1-methylazetidin-3-yl)amino)phenyl)amino)quinazolin-8-yl)pyridin-4-yl)acrylamide
tert-butyl 3-((4-((8-(4-acrylamidopyridin-2-yl)-7-fluoroquinazolin-2-yl)amino)phenyl)amino)azetidine-1-carboxylate
N-(2-(2-((4-((1-acetylazetidin-3-yl)amino)phenyl)amino)-7-fluoroquinazolin-8-yl)pyridin-4-yl)acrylamide
N-(2-(7-fluoro-2-((4-((1-(2-fluoroethyl)azetidin-3-yl)amino)phenyl)amino)quinazolin-8-yl)pyridin-4-yl)acrylamide
N-(2-(7-chloro-2-((4-((1-(2-fluoroethyl)azetidin-3-yl)amino)phenyl)amino)quinazolin-8-yl)pyridin-4-yl)acrylamide
N-(2-(2-((4-((1-(2-fluoroethyl)azetidin-3-yl)amino)phenyl)amino)-7-methylquinazolin-8-yl)pyridin-4-yl)acrylamide
N-(2-(7-ethyl-2-((4-((1-(2-fluoroethyl)azetidin-3-yl)amino)phenyl)amino)quinazolin-8-yl)pyridin-4-yl)acrylamide
N-(2-(7-fluoro-2-((4-(piperidin-4-ylamino)phenyl)amino)quinazolin-8-yl)pyridin-4-yl)acrylamide
N-(2-(7-fluoro-2-((4-((1-methylpiperidin-4-yl)amino)phenyl)amino)quinazolin-8-yl)pyridin-4-yl)acrylamide
N-(2-(7-fluoro-2-((4-(pyrrolidin-3-ylamino)phenyl)amino)quinazolin-8-yl)pyridin-4-yl)acrylamide
(R)—N-(2-(7-fluoro-2-((4-(pyrrolidin-3-ylamino)phenyl)amino)quinazolin-8-yl)pyridin-4-yl)acrylamide
(S)—N-(2-(7-fluoro-2-((4-(pyrrolidin-3-ylamino)phenyl)amino)quinazolin-8-yl)pyridin-4-yl)acrylamide
(S)—N-(2-(7-fluoro-2-((4-(2-(hydroxymethyl)morpholino)phenyl)amino)quinazolin-8-yl)pyridin-4-yl)acrylamide
(R)—N-(2-(7-fluoro-2-((4-(2-(hydroxymethyl)morpholino)phenyl)amino)quinazolin-8-yl)pyridin-4-yl)acrylamide
(R)—N-(2-(2-((4-(2-(aminomethyl)morpholino)phenyl)amino)-7-fluoroquinazolin-8-yl)pyridin-4-yl)acrylamide
(S)—N-(2-(2-((4-(2-(aminomethyl)morpholino)phenyl)amino)-7-fluoroquinazolin-8-yl)pyridin-4-yl)acrylamide
(R)—N-(2-(2-((4-(3-(aminomethyl)morpholino)phenyl)amino)-7-fluoroquinazolin-8-yl)pyridin-4-yl)acrylamide
(S)—N-(2-(2-((4-(3-(aminomethyl)morpholino)phenyl)amino)-7-fluoroquinazolin-8-yl)pyridin-4-yl)acrylamide
N-(2-(2-((4-morpholinophenyl)amino)quinazolin-8-yl)pyridin-4-yl)acrylamide
N-(2-(2-((4-(piperazin-1-yl)phenyl)amino)quinazolin-8-yl)pyridin-4-yl)acrylamide
N-(2-(2-((4-(4-methylpiperazin-1-yl)phenyl)amino)quinazolin-8-yl)pyridin-4-yl)acrylamide
N-(2-(2-((4-(4-ethylpiperazin-1-yl)phenyl)amino)quinazolin-8-yl)pyridin-4-yl)acrylamide
N-(2-(2-((4-(piperidin-1-yl)phenyl)amino)quinazolin-8-yl)pyridin-4-yl)acrylamide
N-(2-(2-((4-(azetidin-3-ylamino)phenyl)amino)quinazolin-8-yl)pyridin-4-yl)acrylamide
N-(2-(2-((4-((1-methylazetidin-3-yl)amino)phenyl)amino)quinazolin-8-yl)pyridin-4-yl)acrylamide
tert-butyl 3-((4-((8-(4-acrylamidopyridin-2-yl)quinazolin-2-yl)amino)phenyl)amino)azetidine-1-carboxylate
N-(2-(2-((4-((1-acetylazetidin-3-yl)amino)phenyl)amino)quinazolin-8-yl)pyridin-4-yl)acrylamide
N-(2-(2-((4-((1-(2-fluoroethyl)azetidin-3-yl)amino)phenyl)amino)quinazolin-8-yl)pyridin-4-yl)acrylamide
N-(2-(2-((4-(piperidin-4-ylamino)phenyl)amino)quinazolin-8-yl)pyridin-4-yl)acrylamide
N-(2-(2-((4-((1-methylpiperidin-4-yl)amino)phenyl)amino)quinazolin-8-yl)pyridin-4-yl)acrylamide
N-(2-(2-((4-(pyrrolidin-3-ylamino)phenyl)amino)quinazolin-8-yl)pyridin-4-yl)acrylamide
(R)—N-(2-(2-((4-(pyrrolidin-3-ylamino)phenyl)amino)quinazolin-8-yl)pyridin-4-yl)acrylamide
(S)—N-(2-(2-((4-(pyrrolidin-3-ylamino)phenyl)amino)quinazolin-8-yl)pyridin-4-yl)acrylamide
(S)—N-(2-(2-((4-(2-(hydroxymethyl)morpholino)phenyl)amino)quinazolin-8-yl)pyridin-4-yl)acrylamide
(R)—N-(2-(2-((4-(2-(hydroxymethyl)morpholino)phenyl)amino)quinazolin-8-yl)pyridin-4-yl)acrylamide
(R)—N-(2-(2-((4-(2-(aminomethyl)morpholino)phenyl)amino)quinazolin-8-yl)pyridin-4-yl)acrylamide
(S)—N-(2-(2-((4-(2-(aminomethyl)morpholino)phenyl)amino)quinazolin-8-yl)pyridin-4-yl)acrylamide
(R)—N-(2-(2-((4-(3-(aminomethyl)morpholino)phenyl)amino)quinazolin-8-yl)pyridin-4-yl)acrylamide
(S)—N-(2-(2-((4-(3-(aminomethyl)morpholino)phenyl)amino)quinazolin-8-yl)pyridin-4-yl)acrylamide
N-(2-(2-((6-(piperazin-1-yl)pyridin-3-yl)amino)pyrido[3,2-d]pyrimidin-8-yl)pyridin-4-yl)acetamide
N-(2-(2-((6-(piperazin-1-yl)pyridin-3-yl)amino)pyrido[4,3-d]pyrimidin-8-yl)pyridin-4-yl)acetamide
N-(6-morpholinopyridin-3-yl)-8-(pyridin-2-yl)pyrido[4,3-d]pyrimidin-2-amine
N-(6-morpholinopyridin-3-yl)-8-(pyridin-2-yl)pyrido[3,2-d]pyrimidin-2-amine
N-(6-morpholinopyridin-3-yl)-8-(pyridin-2-yl)pyrido[3,4-d]pyrimidin-2-amine
8-(4-(2-morpholinoethoxy)pyridin-2-yl)-N-(6-morpholinopyridin-3-yl)pyrido[3,4-d]pyrimidin-2-amine
8-(4-(2-(dimethylamino)ethoxy)pyridin-2-yl)-N-(6-morpholinopyridin-3-yl)pyrido[3,4-d]pyrimidin-2-amine
8-(5-(2-morpholinoethoxy)pyridin-2-yl)-N-(6-morpholinopyridin-3-yl)pyrido[3,4-d]pyrimidin-2-amine
8-(5-(2-(dimethylamino)ethoxy)pyridin-2-yl)-N-(6-morpholinopyridin-3-yl)pyrido[3,4-d]pyrimidin-2-amine
N-(6-(piperazin-1-yl)pyridin-3-yl)-8-(pyridin-2-yl)pyrido[3,4-d]pyrimidin-2-amine
N-(2-(2-((6-(piperazin-1-yl)pyridin-3-yl)amino)pyrido[3,4-d]pyrimidin-8-yl)pyridin-4-yl)acetamide
8-(4-(2-morpholinoethoxy)pyridin-2-yl)-N-(6-(piperazin-1-yl)pyridin-3-yl)pyrido[3,4-d]pyrimidin-2-amine
8-(4-(2-(dimethylamino)ethoxy)pyridin-2-yl)-N-(6-(piperazin-1-yl)pyridin-3-yl)pyrido[3,4-d]pyrimidin-2-amine
8-(5-(2-morpholinoethoxy)pyridin-2-yl)-N-(6-(piperazin-1-yl)pyridin-3-yl)pyrido[3,4-d]pyrimidin-2-amine 8-(5-(2-(dimethylamino)ethoxy)pyridin-2-yl)-N-(6-(piperazin-1-yl)pyridin-3-yl)pyrido[3,4-d]pyrimidin-2-amine N2-(1-(2-fluoroethyl)azetidin-3-yl)-N5-(8-(4-(2-morpholinoethoxy)pyridin-2-yl)pyrido[3,4-d]pyrimidin-2-yl)pyridine-2,5-diamine 8-(4-aminopyridin-2-yl)-N-(6-morpholinopyridin-3-yl)quinazolin-2-amine 8-(4-aminopyridin-2-yl)-N-(6-(piperazin-1-yl)pyridin-3-yl)quinazolin-2-amine 8-(4-aminopyridin-2-yl)-N-(6-(4-methylpiperazin-1-yl)pyridin-3-yl)quinazolin-2-amine N-(2-(2-((6-morpholinopyridin-3-yl)amino)quinazolin-8-yl)pyridin-4-yl)acetamide N-(2-(2-((6-(piperazin-1-yl)pyridin-3-yl)amino)quinazolin-8-yl)pyridin-4-yl)acetamide N-(2-(2-((6-(4-methylpiperazin-1-yl)pyridin-3-yl)amino)quinazolin-8-yl)pyridin-4-yl)acetamide N-(6-morpholinopyridin-3-yl)-8-(pyridin-2-yl)quinazolin-2-amine 8-(4-(2-morpholinoethoxy)pyridin-2-yl)-N-(6-morpholinopyridin-3-yl)quinazolin-2-amine 8-(4-(2-(dimethylamino)ethoxy)pyridin-2-yl)-N-(6-morpholinopyridin-3-yl)quinazolin-2-amine 8-(5-(2-morpholinoethoxy)pyridin-2-yl)-N-(6-morpholinopyridin-3-yl)quinazolin-2-amine 8-(5-(2-(dimethylamino)ethoxy)pyridin-2-yl)-N-(6-morpholinopyridin-3-yl)quinazolin-2-amine N-(6-(piperazin-1-yl)pyridin-3-yl)-8-(pyridin-2-yl)quinazolin-2-amine 8-(4-(2-morpholinoethoxy)pyridin-2-yl)-N-(6-(piperazin-1-yl)pyridin-3-yl)quinazolin-2-amine 8-(4-(2-(dimethylamino)ethoxy)pyridin-2-yl)-N-(6-(piperazin-1-yl)pyridin-3-yl)quinazolin-2-amine 8-(5-(2-morpholinoethoxy)pyridin-2-yl)-N-(6-(piperazin-1-yl)pyridin-3-yl)quinazolin-2-amine 8-(5-(2-(dimethylamino)ethoxy)pyridin-2-yl)-N-(6-(piperazin-1-yl)pyridin-3-yl)quinazolin-2-amine N2-(1-(2-fluoroethyl)azetidin-3-yl)-N5-(8-(4-(2-morpholinoethoxy)pyridin-2-yl)quinazolin-2-yl)pyridine-2,5-diamine N-(2-(2-((2-methoxy-6-morpholinopyridin-3-yl)amino)pyrido[3,4-d]pyrimidin-8-yl)pyridin-4-yl)acrylamide N-(2-(2-((2-methoxy-6-morpholinopyridin-3-yl)amino)pyrido[3,2-d]pyrimidin-8-yl)pyridin-4-yl)acrylamide N-(2-(2-((2-methoxy-6-morpholinopyridin-3-yl)amino)pyrido[4,3-d]pyrimidin-8-yl)pyridin-4-yl)acrylamide N-(2-(2-((2-methoxy-6-(4-methylpiperazin-1-yl)pyridin-3-yl)amino)pyrido[3,4-d]pyrimidin-8-yl)pyridin-4-yl)acrylamide N-(2-(2-((2-methoxy-6-(4-methylpiperazin-1-yl)pyridin-3-yl)amino)pyrido[3,2-d]pyrimidin-8-yl)pyridin-4-yl)acrylamide N-(2-(2-((2-methoxy-6-(4-methylpiperazin-1-yl)pyridin-3-yl)amino)pyrido[4,3-d]pyrimidin-8-yl)pyridin-4-yl)acrylamide N-(2-(2-((2-methoxy-6-((1-methylazetidin-3-yl)amino)pyridin-3-yl)amino)pyrido[3,4-d]pyrimidin-8-yl)pyridin-4-yl)acrylamide N-(2-(2-((6-((1-(2-fluoroethyl)azetidin-3-yl)amino)-2-methoxypyridin-3-yl)amino)pyrido[3,4-d]pyrimidin-8-yl)pyridin-4-yl)acrylamide N-(2-(2-((2-methoxy-6-((1-methylpiperidin-4-yl)amino)pyridin-3-yl)amino)pyrido[3,4-d]pyrimidin-8-yl)pyridin-4-yl)acrylamide N-(2-(2-((2-methoxy-6-morpholinopyridin-3-yl)amino)quinazolin-8-yl)pyridin-4-yl)acrylamide N-(2-(2-((2-methoxy-6-(piperazin-1-yl)pyridin-3-yl)amino)quinazolin-8-yl)pyridin-4-yl)acrylamide N-(2-(2-((2-methoxy-6-(4-methylpiperazin-1-yl)pyridin-3-yl)amino)quinazolin-8-yl)pyridin-4-yl)acrylamide N-(2-(2-((6-(4-ethylpiperazin-1-yl)-2-methoxypyridin-3-yl)amino)quinazolin-8-yl)pyridin-4-yl)acrylamide N-(2-(2-((2-methoxy-6-(piperidin-1-yl)pyridin-3-yl)amino)quinazolin-8-yl)pyridin-4-yl)acrylamide N-(2-(2-((6-(azetidin-3-ylamino)-2-methoxypyridin-3-yl)amino)quinazolin-8-yl)pyridin-4-yl)acrylamide N-(2-(2-((2-methoxy-6-((1-methylazetidin-3-yl)amino)pyridin-3-yl)amino)quinazolin-8-yl)pyridin-4-yl)acrylamide tert-butyl 3-((5-((8-(4-acrylamidopyridin-2-yl)quinazolin-2-yl)amino)-6-methoxypyridin-2-yl)amino)azetidine-1-carboxylate N-(2-(2-((6-((1-acetylazetidin-3-yl)amino)-2-methoxypyridin-3-yl)amino)quinazolin-8-yl)pyridin-4-yl)acrylamide N-(2-(2-((6-((1-(2-fluoroethyl)azetidin-3-yl)amino)-2-methoxypyridin-3-yl)amino)quinazolin-8-yl)pyridin-4-yl)acrylamide N-(2-(2-((2-methoxy-6-(piperidin-4-ylamino)pyridin-3-yl)amino)quinazolin-8-yl)pyridin-4-yl)acrylamide N-(2-(2-((2-methoxy-6-((1-methylpiperidin-4-yl)amino)pyridin-3-yl)amino)quinazolin-8-yl)pyridin-4-yl)acrylamide N-(2-(2-((2-methoxy-6-(pyrrolidin-3-ylamino)pyridin-3-yl)amino)quinazolin-8-yl)pyridin-4-yl)acrylamide (R)—N-(2-(2-((2-methoxy-6-(pyrrolidin-3-ylamino)pyridin-3-yl)amino)quinazolin-8-yl)pyridin-4-yl)acrylamide (S)—N-(2-(2-((2-methoxy-6-(pyrrolidin-3-ylamino)pyridin-3-yl)amino)quinazolin-8-yl)pyridin-4-yl)acrylamide (S)—N-(2-(2-((6-(2-(hydroxymethyl)morpholino)-2-methoxypyridin-3-yl)amino)quinazolin-8-yl)pyridin-4-yl)acrylamide (R)—N-(2-(2-((6-(2-(hydroxymethyl)morpholino)-2-methoxypyridin-3-yl)amino)quinazolin-8-yl)pyridin-4-yl)acrylamide (R)—N-(2-(2-((6-(2-(aminomethyl)morpholino)-2-methoxypyridin-3-yl)amino)quinazolin-8-yl)pyridin-4-yl)acrylamide (S)—N-(2-(2-((6-(2-(aminomethyl)morpholino)-2-methoxypyridin-3-yl)amino)quinazolin-8-yl)pyridin-4-yl)acrylamide (R)—N-(2-(2-((6-(3-(aminomethyl)morpholino)-2-methoxypyridin-3-yl)amino)quinazolin-8-yl)pyridin-4-yl)acrylamide (S)—N-(2-(2-((6-(3-(aminomethyl)morpholino)-2-methoxypyridin-3-yl)amino)quinazolin-8-yl)pyridin-4-yl)acrylamide N-(2-(2-((6-morpholinopyridin-3-yl)amino)pyrido[3,4-d]pyrimidin-8-yl)pyridin-4-yl)acrylamide N-(2-(2-((6-(piperazin-1-yl)pyridin-3-yl)amino)pyrido[3,4-d]pyrimidin-8-yl)pyridin-4-yl)acrylamide N-(2-(2-((6-morpholinopyridin-3-yl)amino)pyrido[3,2-d]pyrimidin-8-yl)pyridin-4-yl)acrylamide N-(2-(2-((6-morpholinopyridin-3-yl)amino)pyrido[4,3-d]pyrimidin-8-yl)pyridin-4-yl)acrylamide N-(2-(2-((6-(4-methylpiperazin-1-yl)pyridin-3-yl)amino)pyrido[3,4-d]pyrimidin-8-yl)pyridin-4-yl)acrylamide N-(2-(2-((6-(4-methylpiperazin-1-yl)pyridin-3-yl)amino)pyrido[3,2-d]pyrimidin-8-yl)pyridin-4-yl)acrylamide N-(2-(2-((6-(4-methylpiperazin-1-yl)pyridin-3-yl)amino)pyrido[4,3-d]pyrimidin-8-yl)pyridin-4-yl)acrylamide N-(2-(2-((6-(4-ethylpiperazin-1-yl)pyridin-3-yl)amino)pyrido[3,4-d]pyrimidin-8-yl)pyridin-4-yl)acrylamide N-(2-(2-((6-(piperidin-1-yl)pyridin-3-yl)amino)pyrido[3,4-d]pyrimidin-8-yl)pyridin-4-yl)acrylamide
N-(2-(2-((6-(azetidin-3-ylamino)pyridin-3-yl)amino)pyrido[3,4-d]pyrimidin-8-yl)pyridin-4-yl)acrylamide
N-(2-(2-((6-((1-methylazetidin-3-yl)amino)pyridin-3-yl)amino)pyrido[3,4-d]pyrimidin-8-yl)pyridin-4-yl)acrylamide
tert-butyl 3-((5-((8-(4-acrylamidopyridin-2-yl)pyrido[3,4-d]pyrimidin-2-yl)amino)pyridin-2-yl)amino)azetidine-1-carboxylate
N-(2-(2-((6-((1-acetylazetidin-3-yl)amino)pyridin-3-yl)amino)pyrido[3,4-d]pyrimidin-8-yl)pyridin-4-yl)acrylamide
N-(2-(2-((6-((1-(2-fluoroethyl)azetidin-3-yl)amino)pyridin-3-yl)amino)pyrido[3,4-d]pyrimidin-8-yl)pyridin-4-yl)acrylamide
N-(2-(2-((6-((1-(2-fluoroethyl)azetidin-3-yl)amino)pyridin-3-yl)amino)pyrido[3,2-d]pyrimidin-8-yl)pyridin-4-yl)acrylamide
N-(2-(2-((6-((1-(2-fluoroethyl)azetidin-3-yl)amino)pyridin-3-yl)amino)pyrido[4,3-d]pyrimidin-8-yl)pyridin-4-yl)acrylamide
N-(2-(2-((6-(piperidin-4-ylamino)pyridin-3-yl)amino)pyrido[3,4-d]pyrimidin-8-yl)pyridin-4-yl)acrylamide
N-(2-(2-((6-((1-methylpiperidin-4-yl)amino)pyridin-3-yl)amino)pyrido[3,4-d]pyrimidin-8-yl)pyridin-4-yl)acrylamide
N-(2-(2-((6-(pyrrolidin-3-ylamino)pyridin-3-yl)amino)pyrido[3,4-d]pyrimidin-8-yl)pyridin-4-yl)acrylamide
(R)—N-(2-(2-((6-(pyrrolidin-3-ylamino)pyridin-3-yl)amino)pyrido[3,4-d]pyrimidin-8-yl)pyridin-4-yl)acrylamide
(S)—N-(2-(2-((6-(pyrrolidin-3-ylamino)pyridin-3-yl)amino)pyrido[3,4-d]pyrimidin-8-yl)pyridin-4-yl)acrylamide
(S)—N-(2-(2-((6-(2-(hydroxymethyl)morpholino)pyridin-3-yl)amino)pyrido[3,4-d]pyrimidin-8-yl)pyridin-4-yl)acrylamide
(R)—N-(2-(2-((6-(2-(hydroxymethyl)morpholino)pyridin-3-yl)amino)pyrido[3,4-d]pyrimidin-8-yl)pyridin-4-yl)acrylamide
(R)—N-(2-(2-((6-(2-(aminomethyl)morpholino)pyridin-3-yl)amino)pyrido[3,4-d]pyrimidin-8-yl)pyridin-4-yl)acrylamide
(S)—N-(2-(2-((6-(2-(aminomethyl)morpholino)pyridin-3-yl)amino)pyrido[3,4-d]pyrimidin-8-yl)pyridin-4-yl)acrylamide
(R)—N-(2-(2-((6-(3-(aminomethyl)morpholino)pyridin-3-yl)amino)pyrido[3,4-d]pyrimidin-8-yl)pyridin-4-yl)acrylamide
(S)—N-(2-(2-((6-(3-(aminomethyl)morpholino)pyridin-3-yl)amino)pyrido[3,4-d]pyrimidin-8-yl)pyridin-4-yl)acrylamide
N-(2-(7-fluoro-2-((6-morpholinopyridin-3-yl)amino)quinazolin-8-yl)pyridin-4-yl)acrylamide
N-(2-(7-fluoro-2-((2-methoxy-6-morpholinopyridin-3-yl)amino)quinazolin-8-yl)pyridin-4-yl)acrylamide
N-(2-(7-chloro-2-((6-morpholinopyridin-3-yl)amino)quinazolin-8-yl)pyridin-4-yl)acrylamide
N-(2-(7-chloro-2-((2-methoxy-6-morpholinopyridin-3-yl)amino)quinazolin-8-yl)pyridin-4-yl)acrylamide
N-(2-(7-methyl-2-((6-morpholinopyridin-3-yl)amino)quinazolin-8-yl)pyridin-4-yl)acrylamide
N-(2-(2-((2-methoxy-6-morpholinopyridin-3-yl)amino)-7-methylquinazolin-8-yl)pyridin-4-yl)acrylamide
N-(2-(7-ethyl-2-((6-morpholinopyridin-3-yl)amino)quinazolin-8-yl)pyridin-4-yl)acrylamide
N-(2-(7-fluoro-2-((6-(piperazin-1-yl)pyridin-3-yl)amino)quinazolin-8-yl)pyridin-4-yl)acrylamide
N-(2-(7-fluoro-2-((6-(4-methylpiperazin-1-yl)pyridin-3-yl)amino)quinazolin-8-yl)pyridin-4-yl)acrylamide
N-(2-(7-fluoro-2-((2-methoxy-6-(4-methylpiperazin-1-yl)pyridin-3-yl)amino)quinazolin-8-yl)pyridin-4-yl)acrylamide
N-(2-(7-chloro-2-((6-(4-methylpiperazin-1-yl)pyridin-3-yl)amino)quinazolin-8-yl)pyridin-4-yl)acrylamide
N-(2-(7-chloro-2-((2-methoxy-6-(4-methylpiperazin-1-yl)pyridin-3-yl)amino)quinazolin-8-yl)pyridin-4-yl)acrylamide
N-(2-(7-methyl-2-((6-(4-methylpiperazin-1-yl)pyridin-3-yl)amino)quinazolin-8-yl)pyridin-4-yl)acrylamide
N-(2-(2-((2-methoxy-6-(4-methylpiperazin-1-yl)pyridin-3-yl)amino)-7-methylquinazolin-8-yl)pyridin-4-yl)acrylamide
N-(2-(7-ethyl-2-((6-(4-methylpiperazin-1-yl)pyridin-3-yl)amino)quinazolin-8-yl)pyridin-4-yl)acrylamide
N-(2-(2-((6-(4-ethylpiperazin-1-yl)pyridin-3-yl)amino)-7-fluoroquinazolin-8-yl)pyridin-4-yl)acrylamide
N-(2-(7-fluoro-2-((6-(piperidin-1-yl)pyridin-3-yl)amino)quinazolin-8-yl)pyridin-4-yl)acrylamide
N-(2-(2-((6-(azetidin-3-ylamino)pyridin-3-yl)amino)-7-fluoroquinazolin-8-yl)pyridin-4-yl)acrylamide
N-(2-(7-fluoro-2-((6-((1-methylazetidin-3-yl)amino)pyridin-3-yl)amino)quinazolin-8-yl)pyridin-4-yl)acrylamide
tert-butyl 3-((5-((8-(4-acrylamidopyridin-2-yl)-7-fluoroquinazolin-2-yl)amino)pyridin-2-yl)amino)azetidine-1-carboxylate
N-(2-(2-((6-((1-acetylazetidin-3-yl)amino)pyridin-3-yl)amino)-7-fluoroquinazolin-8-yl)pyridin-4-yl)acrylamide
N-(2-(7-fluoro-2-((6-((1-(2-fluoroethyl)azetidin-3-yl)amino)pyridin-3-yl)amino)quinazolin-8-yl)pyridin-4-yl)acrylamide
N-(2-(7-chloro-2-((6-((1-(2-fluoroethyl)azetidin-3-yl)amino)pyridin-3-yl)amino)quinazolin-8-yl)pyridin-4-yl)acrylamide
N-(2-(2-((6-((1-(2-fluoroethyl)azetidin-3-yl)amino)pyridin-3-yl)amino)-7-methylquinazolin-8-yl)pyridin-4-yl)acrylamide
N-(2-(7-ethyl-2-((6-((1-(2-fluoroethyl)azetidin-3-yl)amino)pyridin-3-yl)amino)quinazolin-8-yl)pyridin-4-yl)acrylamide
N-(2-(7-fluoro-2-((6-(piperidin-4-ylamino)pyridin-3-yl)amino)quinazolin-8-yl)pyridin-4-yl)acrylamide
N-(2-(7-fluoro-2-((6-((1-methylpiperidin-4-yl)amino)pyridin-3-yl)amino)quinazolin-8-yl)pyridin-4-yl)acrylamide
N-(2-(7-fluoro-2-((6-(pyrrolidin-3-ylamino)pyridin-3-yl)amino)quinazolin-8-yl)pyridin-4-yl)acrylamide
(R)—N-(2-(7-fluoro-2-((6-(pyrrolidin-3-ylamino)pyridin-3-yl)amino)quinazolin-8-yl)pyridin-4-yl)acrylamide
(S)—N-(2-(7-fluoro-2-((6-(pyrrolidin-3-ylamino)pyridin-3-yl)amino)quinazolin-8-yl)pyridin-4-yl)acrylamide
(S)—N-(2-(7-fluoro-2-((6-(2-(hydroxymethyl)morpholino)pyridin-3-yl)amino)quinazolin-8-yl)pyridin-4-yl)acrylamide
(R)—N-(2-(7-fluoro-2-((6-(2-(hydroxymethyl)morpholino)pyridin-3-yl)amino)quinazolin-8-yl)pyridin-4-yl)acrylamide
(R)—N-(2-(2-((6-(2-(aminomethyl)morpholino)pyridin-3-yl)amino)-7-fluoroquinazolin-8-yl)pyridin-4-yl)acrylamide
(S)—N-(2-(2-((6-(2-(aminomethyl)morpholino)pyridin-3-yl)amino)-7-fluoroquinazolin-8-yl)pyridin-4-yl)acrylamide (R)—N-(2-(2-((6-(3-(aminomethyl)morpholino)pyridin-3-yl)amino)-7-fluoroquinazolin-8-yl)pyridin-4-yl)acrylamide
(S)—N-(2-(2-((6-(3-(aminomethyl)morpholino)pyridin-3-yl)amino)-7-fluoroquinazolin-8-yl)pyridin-4-yl)acrylamide
N-(2-(2-((6-morpholinopyridin-3-yl)amino)quinazolin-8-yl)pyridin-4-yl)acrylamide
N-(2-(2-((6-(piperazin-1-yl)pyridin-3-yl)amino)quinazolin-8-yl)pyridin-4-yl)acrylamide
N-(2-(2-((6-(4-methylpiperazin-1-yl)pyridin-3-yl)amino)quinazolin-8-yl)pyridin-4-yl)acrylamide
N-(2-(2-((6-(4-ethylpiperazin-1-yl)pyridin-3-yl)amino)quinazolin-8-yl)pyridin-4-yl)acrylamide
N-(2-(2-((6-(piperidin-1-yl)pyridin-3-yl)amino)quinazolin-8-yl)pyridin-4-yl)acrylamide
N-(2-(2-((6-(azetidin-3-ylamino)pyridin-3-yl)amino)quinazolin-8-yl)pyridin-4-yl)acrylamide
N-(2-(2-((6-((1-methylazetidin-3-yl)amino)pyridin-3-yl)amino)quinazolin-8-yl)pyridin-4-yl)acrylamide
tert-butyl 3-((5-((8-(4-acrylamidopyridin-2-yl)quinazolin-2-yl)amino)pyridin-2-yl)amino)azetidine-1-carboxylate
N-(2-(2-((6-((1-acetylazetidin-3-yl)amino)pyridin-3-yl)amino)quinazolin-8-yl)pyridin-4-yl)acrylamide
N-(2-(2-((6-((1-(2-fluoroethyl)azetidin-3-yl)amino)pyridin-3-yl)amino)quinazolin-8-yl)pyridin-4-yl)acrylamide
N-(2-(2-((6-(piperidin-4-ylamino)pyridin-3-yl)amino)quinazolin-8-yl)pyridin-4-yl)acrylamide
N-(2-(2-((6-((1-methylpiperidin-4-yl)amino)pyridin-3-yl)amino)quinazolin-8-yl)pyridin-4-yl)acrylamide
N-(2-(2-((6-(pyrrolidin-3-ylamino)pyridin-3-yl)amino)quinazolin-8-yl)pyridin-4-yl)acrylamide
(R)—N-(2-(2-((6-(pyrrolidin-3-ylamino)pyridin-3-yl)amino)quinazolin-8-yl)pyridin-4-yl)acrylamide
(S)—N-(2-(2-((6-(pyrrolidin-3-ylamino)pyridin-3-yl)amino)quinazolin-8-yl)pyridin-4-yl)acrylamide
(S)—N-(2-(2-((6-(2-(hydroxymethyl)morpholino)pyridin-3-yl)amino)quinazolin-8-yl)pyridin-4-yl)acrylamide
(R)—N-(2-(2-((6-(2-(hydroxymethyl)morpholino)pyridin-3-yl)amino)quinazolin-8-yl)pyridin-4-yl)acrylamide
(R)—N-(2-(2-((6-(2-(aminomethyl)morpholino)pyridin-3-yl)amino)quinazolin-8-yl)pyridin-4-yl)acrylamide
(S)—N-(2-(2-((6-(2-(aminomethyl)morpholino)pyridin-3-yl)amino)quinazolin-8-yl)pyridin-4-yl)acrylamide
(R)—N-(2-(2-((6-(3-(aminomethyl)morpholino)pyridin-3-yl)amino)quinazolin-8-yl)pyridin-4-yl)acrylamide
(S)—N-(2-(2-((6-(3-(aminomethyl)morpholino)pyridin-3-yl)amino)quinazolin-8-yl)pyridin-4-yl)acrylamide
(E)-4-(dimethylamino)-N-(3-(2-((4-morpholinophenyl)amino)pyrido[3,4-d]pyrimidin-8-yl)phenyl)but-2-enamide
(E)-4-(dimethylamino)-N-(3-(2-((4-(piperazin-1-yl)phenyl)amino)pyrido[3,4-d]pyrimidin-8-yl)phenyl)but-2-enamide
(E)-4-(dimethylamino)-N-(3-(2-((4-(4-methylpiperazin-1-yl)phenyl)amino)pyrido[3,4-d]pyrimidin-8-yl)phenyl)but-2-enamide
(E)-4-(dimethylamino)-N-(3-(2-((4-(4-methylpiperazin-1-yl)phenyl)amino)pyrido[3,2-d]pyrimidin-8-yl)phenyl)but-2-enamide
(E)-4-(dimethylamino)-N-(3-(2-((4-(4-methylpiperazin-1-yl)phenyl)amino)pyrido[4,3-d]pyrimidin-8-yl)phenyl)but-2-enamide
(E)-4-(dimethylamino)-N-(3-(2-((4-(piperidin-1-yl)phenyl)amino)pyrido[3,4-d]pyrimidin-8-yl)phenyl)but-2-enamide
(E)-N-(3-(2-((4-((1-acetylazetidin-3-yl)amino)phenyl)amino)pyrido[3,4-d]pyrimidin-8-yl)phenyl)-4-(dimethylamino)but-2-enamide
(E)-4-(dimethylamino)-N-(3-(2-((4-((1-(2-fluoroethyl)azetidin-3-yl)amino)phenyl)amino)pyrido[3,4-d]pyrimidin-8-yl)phenyl)but-2-enamide
(E)-4-(dimethylamino)-N-(3-(2-((4-((1-methylpiperidin-4-yl)amino)phenyl)amino)pyrido[3,4-d]pyrimidin-8-yl)phenyl)but-2-enamide
(E)-4-(dimethylamino)-N-(3-(2-((4-(pyrrolidin-3-ylamino)phenyl)amino)pyrido[3,4-d]pyrimidin-8-yl)phenyl)but-2-enamide
(E)-4-(dimethylamino)-N-(3-(2-((4-(2-(hydroxymethyl)morpholino)phenyl)amino)pyrido[3,4-d]pyrimidin-8-yl)phenyl)but-2-enamide
N-(3-(2-((4-morpholinophenyl)amino)pyrido[3,4-d]pyrimidin-8-yl)phenyl)propiolamide
N-(3-(2-((4-(piperazin-1-yl)phenyl)amino)pyrido[3,4-d]pyrimidin-8-yl)phenyl)propiolamide
N-(3-(2-((4-(4-methylpiperazin-1-yl)phenyl)amino)pyrido[3,4-d]pyrimidin-8-yl)phenyl)propiolamide
N-(3-(2-((4-((1-(2-fluoroethyl)azetidin-3-yl)amino)phenyl)amino)pyrido[3,4-d]pyrimidin-8-yl)phenyl)propiolamide
(E)-N-(3-(2-((4-morpholinophenyl)amino)pyrido[3,4-d]pyrimidin-8-yl)phenyl)but-2-enamide
(Z)—N-(3-(2-((4-morpholinophenyl)amino)pyrido[3,4-d]pyrimidin-8-yl)phenyl)but-2-enamide
(Z)-3-fluoro-N-(3-(2-((4-morpholinophenyl)amino)pyrido[3,4-d]pyrimidin-8-yl)phenyl)but-2-enamide
(E)-3-fluoro-N-(3-(2-((4-morpholinophenyl)amino)pyrido[3,4-d]pyrimidin-8-yl)phenyl)but-2-enamide
N-(3-(2-((4-morpholinophenyl)amino)pyrido[3,4-d]pyrimidin-8-yl)phenyl)methacrylamide
N-(3-(2-((4-morpholinophenyl)amino)pyrido[3,4-d]pyrimidin-8-yl)phenyl)ethenesulfonamide
(E)-N-(3-(2-((4-(4-methylpiperazin-1-yl)phenyl)amino)pyrido[3,4-d]pyrimidin-8-yl)phenyl)but-2-enamide
(Z)—N-(3-(2-((4-(4-methylpiperazin-1-yl)phenyl)amino)pyrido[3,4-d]pyrimidin-8-yl)phenyl)but-2-enamide
(Z)-3-fluoro-N-(3-(2-((4-(4-methylpiperazin-1-yl)phenyl)amino)pyrido[3,4-d]pyrimidin-8-yl)phenyl)but-2-enamide
(E)-3-fluoro-N-(3-(2-((4-(4-methylpiperazin-1-yl)phenyl)amino)pyrido[3,4-d]pyrimidin-8-yl)phenyl)but-2-enamide
N-(3-(2-((4-(4-methylpiperazin-1-yl)phenyl)amino)pyrido[3,4-d]pyrimidin-8-yl)phenyl)methacrylamide
N-(3-(2-((4-(4-methylpiperazin-1-yl)phenyl)amino)pyrido[3,4-d]pyrimidin-8-yl)phenyl)ethenesulfonamide
3,3-difluoro-N-(3-(2-((4-(4-methylpiperazin-1-yl)phenyl)amino)pyrido[3,4-d]pyrimidin-8-yl)phenyl)acrylamide
3-methyl-N-(3-(2-((4-(4-methylpiperazin-1-yl)phenyl)amino)pyrido[3,4-d]pyrimidin-8-yl)phenyl)but-2-enamide
(E)-4-(dimethylamino)-N-(3-(2-((4-morpholinophenyl)amino)quinazolin-8-yl)phenyl)but-2-enamide
(E)-4-(dimethylamino)-N-(3-(2-((4-(piperazin-1-yl)phenyl)amino)quinazolin-8-yl)phenyl)but-2-enamide
(E)-4-(dimethylamino)-N-(3-(2-((4-(4-methylpiperazin-1-yl)phenyl)amino)quinazolin-8-yl)phenyl)but-2-enamide
(E)-4-(dimethylamino)-N-(3-(2-((4-(piperidin-1-yl)phenyl)amino)quinazolin-8-yl)phenyl)but-2-enamide
(E)-N-(3-(2-((4-((1-acetylazetidin-3-yl)amino)phenyl)amino)quinazolin-8-yl)phenyl)-4-(dimethylamino)but-2-enamide (E)-4-(dimethylamino)-N-(3-(2-((4-((1-(2-fluoroethyl)azetidin-3-yl)amino)phenyl)amino)quinazolin-8-yl)phenyl)but-2-enamide
(E)-4-(dimethylamino)-N-(3-(2-((4-((1-methylpiperidin-4-yl)amino)phenyl)amino)quinazolin-8-yl)phenyl)but-2-enamide
(E)-4-(dimethylamino)-N-(3-(2-((4-(pyrrolidin-3-ylamino)phenyl)amino)quinazolin-8-yl)phenyl)but-2-enamide
(E)-4-(dimethylamino)-N-(3-(2-((4-(2-(hydroxymethyl)morpholino)phenyl)amino)quinazolin-8-yl)phenyl)but-2-enamide
N-(3-(2-((4-morpholinophenyl)amino)quinazolin-8-yl)phenyl)propiolamide
N-(3-(2-((4-(piperazin-1-yl)phenyl)amino)quinazolin-8-yl)phenyl)propiolamide
N-(3-(2-((4-(4-methylpiperazin-1-yl)phenyl)amino)quinazolin-8-yl)phenyl)propiolamide
N-(3-(2-((4-((1-(2-fluoroethyl)azetidin-3-yl)amino)phenyl)amino)quinazolin-8-yl)phenyl)propiolamide
(E)-N-(3-(2-((4-morpholinophenyl)amino)quinazolin-8-yl)phenyl)but-2-enamide
(Z)—N-(3-(2-((4-morpholinophenyl)amino)quinazolin-8-yl)phenyl)but-2-enamide
(Z)-3-fluoro-N-(3-(2-((4-morpholinophenyl)amino)quinazolin-8-yl)phenyl)but-2-enamide
(E)-3-fluoro-N-(3-(2-((4-morpholinophenyl)amino)quinazolin-8-yl)phenyl)but-2-enamide
N-(3-(2-((4-morpholinophenyl)amino)quinazolin-8-yl)phenyl)methacrylamide
N-(3-(2-((4-morpholinophenyl)amino)quinazolin-8-yl)phenyl)ethene sulfonamide
(E)-N-(3-(2-((4-(4-methylpiperazin-1-yl)phenyl)amino)quinazolin-8-yl)phenyl)but-2-enamide
(Z)—N-(3-(2-((4-(4-methylpiperazin-1-yl)phenyl)amino)quinazolin-8-yl)phenyl)but-2-enamide
(Z)-3-fluoro-N-(3-(2-((4-(4-methylpiperazin-1-yl)phenyl)amino)quinazolin-8-yl)phenyl)acrylamide
(E)-3-fluoro-N-(3-(2-((4-(4-methylpiperazin-1-yl)phenyl)amino)quinazolin-8-yl)phenyl)acrylamide
(Z)-3-fluoro-N-(3-(2-((4-(4-methylpiperazin-1-yl)phenyl)amino)quinazolin-8-yl)phenyl)but-2-enamide
N-(3-(2-((4-(4-methylpiperazin-1-yl)phenyl)amino)quinazolin-8-yl)phenyl)methacrylamide
3,3-difluoro-N-(3-(2-((4-(4-methylpiperazin-1-yl)phenyl)amino)quinazolin-8-yl)phenyl)acrylamide
3-methyl-N-(3-(2-((4-(4-methylpiperazin-1-yl)phenyl)amino)quinazolin-8-yl)phenyl)but-2-enamide
(E)-3-fluoro-N-(3-(2-((4-(4-methylpiperazin-1-yl)phenyl)amino)quinazolin-8-yl)phenyl)but-2-enamide
N-(3-(2-((4-(4-methylpiperazin-1-yl)phenyl)amino)quinazolin-8-yl)phenyl)ethenesulfonamide
(E)-4-(dimethylamino)-N-(2-(2-((6-morpholinopyridin-3-yl)amino)pyrido[3,4-d]pyrimidin-8-yl)pyridin-4-yl)but-2-enamide
(E)-4-(dimethylamino)-N-(2-(2-((6-(piperazin-1-yl)pyridin-3-yl)amino)pyrido[3,4-d]pyrimidin-8-yl)pyridin-4-yl)but-2-enamide
(E)-4-(dimethylamino)-N-(2-(2-((6-(4-methylpiperazin-1-yl)pyridin-3-yl)amino)pyrido[3,4-d]pyrimidin-8-yl)pyridin-4-yl)but-2-enamide
(E)-4-(dimethylamino)-N-(2-(2-((6-(4-methylpiperazin-1-yl)pyridin-3-yl)amino)pyrido[3,2-d]pyrimidin-8-yl)pyridin-4-yl)but-2-enamide
(E)-4-(dimethylamino)-N-(2-(2-((6-(4-methylpiperazin-1-yl)pyridin-3-yl)amino)pyrido[4,3-d]pyrimidin-8-yl)pyridin-4-yl)but-2-enamide
(E)-4-(dimethylamino)-N-(2-(2-((6-(piperidin-1-yl)pyridin-3-yl)amino)pyrido[3,4-d]pyrimidin-8-yl)pyridin-4-yl)but-2-enamide
(E)-N-(2-(2-((6-((1-acetylazetidin-3-yl)amino)pyridin-3-yl)amino)pyrido[3,4-d]pyrimidin-8-yl)pyridin-4-yl)-4-(dimethylamino)but-2-enamide
(E)-4-(dimethylamino)-N-(2-(2-((6-((1-(2-fluoroethyl)azetidin-3-yl)amino)pyridin-3-yl)amino)pyrido[3,4-d]pyrimidin-8-yl)pyridin-4-yl)but-2-enamide
(E)-4-(dimethylamino)-N-(2-(2-((6-((1-methylpiperidin-4-yl)amino)pyridin-3-yl)amino)pyrido[3,4-d]pyrimidin-8-yl)pyridin-4-yl)but-2-enamide
(E)-4-(dimethylamino)-N-(2-(2-((6-(pyrrolidin-3-ylamino)pyridin-3-yl)amino)pyrido[3,4-d]pyrimidin-8-yl)pyridin-4-yl)but-2-enamide
(E)-4-(dimethylamino)-N-(2-(2-((6-(2-(hydroxymethyl)morpholino)pyridin-3-yl)amino)pyrido[3,4-d]pyrimidin-8-yl)pyridin-4-yl)but-2-enamide
N-(2-(2-((6-morpholinopyridin-3-yl)amino)pyrido[3,4-d]pyrimidin-8-yl)pyridin-4-yl)propiolamide
N-(2-(2-((6-(piperazin-1-yl)pyridin-3-yl)amino)pyrido[3,4-d]pyrimidin-8-yl)pyridin-4-yl)propiolamide
N-(2-(2-((6-(4-methylpiperazin-1-yl)pyridin-3-yl)amino)pyrido[3,4-d]pyrimidin-8-yl)pyridin-4-yl)propiolamide
N-(2-(2-((6-((1-(2-fluoroethyl)azetidin-3-yl)amino)pyridin-3-yl)amino)pyrido[3,4-d]pyrimidin-8-yl)pyridin-4-yl)propiolamide
(E)-N-(2-(2-((6-morpholinopyridin-3-yl)amino)pyrido[3,4-d]pyrimidin-8-yl)pyridin-4-yl)but-2-enamide
(Z)—N-(2-(2-((6-morpholinopyridin-3-yl)amino)pyrido[3,4-d]pyrimidin-8-yl)pyridin-4-yl)but-2-enamide
(Z)-3-fluoro-N-(2-(2-((6-morpholinopyridin-3-yl)amino)pyrido[3,4-d]pyrimidin-8-yl)pyridin-4-yl)but-2-enamide
(E)-3-fluoro-N-(2-(2-((6-morpholinopyridin-3-yl)amino)pyrido[3,4-d]pyrimidin-8-yl)pyridin-4-yl)but-2-enamide
N-(2-(2-((6-morpholinopyridin-3-yl)amino)pyrido[3,4-d]pyrimidin-8-yl)pyridin-4-yl)methacrylamide
N-(2-(2-((6-morpholinopyridin-3-yl)amino)pyrido[3,4-d]pyrimidin-8-yl)pyridin-4-yl)ethenesulfonamide
(E)-N-(2-(2-((6-(4-methylpiperazin-1-yl)pyridin-3-yl)amino)pyrido[3,4-d]pyrimidin-8-yl)pyridin-4-yl)but-2-enamide
(Z)—N-(2-(2-((6-(4-methylpiperazin-1-yl)pyridin-3-yl)amino)pyrido[3,4-d]pyrimidin-8-yl)pyridin-4-yl)but-2-enamide
(Z)-3-fluoro-N-(2-(2-((6-(4-methylpiperazin-1-yl)pyridin-3-yl)amino)pyrido[3,4-d]pyrimidin-8-yl)pyridin-4-yl)but-2-enamide
(E)-3-fluoro-N-(2-(2-((6-(4-methylpiperazin-1-yl)pyridin-3-yl)amino)pyrido[3,4-d]pyrimidin-8-yl)pyridin-4-yl)but-2-enamide
N-(2-(2-((6-(4-methylpiperazin-1-yl)pyridin-3-yl)amino)pyrido[3,4-d]pyrimidin-8-yl)pyridin-4-yl)methacrylamide
N-(2-(2-((6-(4-methylpiperazin-1-yl)pyridin-3-yl)amino)pyrido[3,4-d]pyrimidin-8-yl)pyridin-4-yl)ethenesulfonamide
3,3-difluoro-N-(2-(2-((6-(4-methylpiperazin-1-yl)pyridin-3-yl)amino)pyrido[3,4-d]pyrimidin-8-yl)pyridin-4-yl)acrylamide
3-methyl-N-(2-(2-((6-(4-methylpiperazin-1-yl)pyridin-3-yl)amino)pyrido[3,4-d]pyrimidin-8-yl)pyridin-4-yl)but-2-enamide
(E)-4-(dimethylamino)-N-(2-(2-((4-morpholinophenyl)amino)pyrido[3,4-d]pyrimidin-8-yl)pyridin-4-yl)but-2-enamide (E)-4-(dimethylamino)-N-(2-(2-((4-(piperazin-1-yl)phenyl)amino)pyrido[3,4-d]pyrimidin-8-yl)pyridin-4-yl)but-2-enamide (E)-4-(dimethylamino)-N-(2-(2-((4-(4-methylpiperazin-1-yl)phenyl)amino)pyrido[3,4-d]pyrimidin-8-yl)pyridin-4-yl)but-2-enamide (E)-4-(dimethylamino)-N-(2-(2-((4-(4-methylpiperazin-1-yl)phenyl)amino)pyrido[3,2-d]pyrimidin-8-yl)pyridin-4-yl)but-2-enamide (E)-4-(dimethylamino)-N-(2-(2-((4-(4-methylpiperazin-1-yl)phenyl)amino)pyrido[4,3-d]pyrimidin-8-yl)pyridin-4-yl)but-2-enamide (E)-4-(dimethylamino)-N-(2-(2-((4-(piperidin-1-yl)phenyl)amino)pyrido[3,4-d]pyrimidin-8-yl)pyridin-4-yl)but-2-enamide (E)-N-(2-(2-((4-((1-acetylazetidin-3-yl)amino)phenyl)amino)pyrido[3,4-d]pyrimidin-8-yl)pyridin-4-yl)-4-(dimethylamino)but-2-enamide (E)-4-(dimethylamino)-N-(2-(2-((4-((1-(2-fluoroethyl)azetidin-3-yl)amino)phenyl)amino)pyrido[3,4-d]pyrimidin-8-yl)pyridin-4-yl)but-2-enamide (E)-4-(dimethylamino)-N-(2-(2-((4-((1-methylpiperidin-4-yl)amino)phenyl)amino)pyrido[3,4-d]pyrimidin-8-yl)pyridin-4-yl)but-2-enamide (E)-4-(dimethylamino)-N-(2-(2-((4-(pyrrolidin-3-ylamino)phenyl)amino)pyrido[3,4-d]pyrimidin-8-yl)pyridin-4-yl)but-2-enamide (E)-4-(dimethylamino)-N-(2-(2-((4-(2-(hydroxymethyl)morpholino)phenyl)amino)pyrido[3,4-d]pyrimidin-8-yl)pyridin-4-yl)but-2-enamide N-(2-(2-((4-morpholinophenyl)amino)pyrido[3,4-d]pyrimidin-8-yl)pyridin-4-yl)propiolamide N-(2-(2-((4-(piperazin-1-yl)phenyl)amino)pyrido[3,4-d]pyrimidin-8-yl)pyridin-4-yl)propiolamide N-(2-(2-((4-(4-methylpiperazin-1-yl)phenyl)amino)pyrido[3,4-d]pyrimidin-8-yl)pyridin-4-yl)propiolamide N-(2-(2-((4-((1-(2-fluoroethyl)azetidin-3-yl)amino)phenyl)amino)pyrido[3,4-d]pyrimidin-8-yl)pyridin-4-yl)propiolamide (E)-N-(2-(2-((4-morpholinophenyl)amino)pyrido[3,4-d]pyrimidin-8-yl)pyridin-4-yl)but-2-enamide (Z)—N-(2-(2-((4-morpholinophenyl)amino)pyrido[3,4-d]pyrimidin-8-yl)pyridin-4-yl)but-2-enamide (Z)-3-fluoro-N-(2-(2-((4-morpholinophenyl)amino)pyrido[3,4-d]pyrimidin-8-yl)pyridin-4-yl)but-2-enamide (E)-3-fluoro-N-(2-(2-((4-morpholinophenyl)amino)pyrido[3,4-d]pyrimidin-8-yl)pyridin-4-yl)but-2-enamide N-(2-(2-((4-morpholinophenyl)amino)pyrido[3,4-d]pyrimidin-8-yl)pyridin-4-yl)methacrylamide N-(2-(2-((4-morpholinophenyl)amino)pyrido[3,4-d]pyrimidin-8-yl)pyridin-4-yl)ethenesulfonamide (E)-N-(2-(2-((4-(4-methylpiperazin-1-yl)phenyl)amino)pyrido[3,4-d]pyrimidin-8-yl)pyridin-4-yl)but-2-enamide (Z)—N-(2-(2-((4-(4-methylpiperazin-1-yl)phenyl)amino)pyrido[3,4-d]pyrimidin-8-yl)pyridin-4-yl)but-2-enamide (Z)-3-fluoro-N-(2-(2-((4-(4-methylpiperazin-1-yl)phenyl)amino)pyrido[3,4-d]pyrimidin-8-yl)pyridin-4-yl)but-2-enamide (E)-3-fluoro-N-(2-(2-((4-(4-methylpiperazin-1-yl)phenyl)amino)pyrido[3,4-d]pyrimidin-8-yl)pyridin-4-yl)but-2-enamide N-(2-(2-((4-(4-methylpiperazin-1-yl)phenyl)amino)pyrido[3,4-d]pyrimidin-8-yl)pyridin-4-yl)methacrylamide N-(2-(2-((4-(4-methylpiperazin-1-yl)phenyl)amino)pyrido[3,4-d]pyrimidin-8-yl)pyridin-4-yl)ethenesulfonamide 3,3-difluoro-N-(2-(2-((4-(4-methylpiperazin-1-yl)phenyl)amino)pyrido[3,4-d]pyrimidin-8-yl)pyridin-4-yl)acrylamide 3-methyl-N-(2-(2-((4-(4-methylpiperazin-1-yl)phenyl)amino)pyrido[3,4-d]pyrimidin-8-yl)pyridin-4-yl)but-2-enamide (E)-4-(dimethylamino)-N-(3-(2-((6-morpholinopyridin-3-yl)amino)pyrido[3,4-d]pyrimidin-8-yl)phenyl)but-2-enamide (E)-4-(dimethylamino)-N-(3-(2-((6-(piperazin-1-yl)pyridin-3-yl)amino)pyrido[3,4-d]pyrimidin-8-yl)phenyl)but-2-enamide (E)-4-(dimethylamino)-N-(3-(2-((6-(4-methylpiperazin-1-yl)pyridin-3-yl)amino)pyrido[3,4-d]pyrimidin-8-yl)phenyl)but-2-enamide (E)-4-(dimethylamino)-N-(3-(2-((6-(4-methylpiperazin-1-yl)pyridin-3-yl)amino)pyrido[3,2-d]pyrimidin-8-yl)phenyl)but-2-enamide (E)-4-(dimethylamino)-N-(3-(2-((6-(4-methylpiperazin-1-yl)pyridin-3-yl)amino)pyrido[4,3-d]pyrimidin-8-yl)phenyl)but-2-enamide (E)-4-(dimethylamino)-N-(3-(2-((6-(piperidin-1-yl)pyridin-3-yl)amino)pyrido[3,4-d]pyrimidin-8-yl)phenyl)but-2-enamide (E)-N-(3-(2-((6-((1-acetylazetidin-3-yl)amino)pyridin-3-yl)amino)pyrido[3,4-d]pyrimidin-8-yl)phenyl)-4-(dimethylamino)but-2-enamide (E)-4-(dimethylamino)-N-(3-(2-((6-((1-(2-fluoroethyl)azetidin-3-yl)amino)pyridin-3-yl)amino)pyrido[3,4-d]pyrimidin-8-yl)phenyl)but-2-enamide (E)-4-(dimethylamino)-N-(3-(2-((6-((1-methylpiperidin-4-yl)amino)pyridin-3-yl)amino)pyrido[3,4-d]pyrimidin-8-yl)phenyl)but-2-enamide (E)-4-(dimethylamino)-N-(3-(2-((6-(pyrrolidin-3-ylamino)pyridin-3-yl)amino)pyrido[3,4-d]pyrimidin-8-yl)phenyl)but-2-enamide (E)-4-(dimethylamino)-N-(3-(2-((6-(2-(hydroxymethyl)morpholino)pyridin-3-yl)amino)pyrido[3,4-d]pyrimidin-8-yl)phenyl)but-2-enamide N-(3-(2-((6-morpholinopyridin-3-yl)amino)pyrido[3,4-d]pyrimidin-8-yl)phenyl)propiolamide N-(3-(2-((6-(piperazin-1-yl)pyridin-3-yl)amino)pyrido[3,4-d]pyrimidin-8-yl)phenyl)propiolamide N-(3-(2-((6-(4-methylpiperazin-1-yl)pyridin-3-yl)amino)pyrido[3,4-d]pyrimidin-8-yl)phenyl)propiolamide N-(3-(2-((6-((1-(2-fluoroethyl)azetidin-3-yl)amino)pyridin-3-yl)amino)pyrido[3,4-d]pyrimidin-8-yl)phenyl)propiolamide (E)-N-(3-(2-((6-morpholinopyridin-3-yl)amino)pyrido[3,4-d]pyrimidin-8-yl)phenyl)but-2-enamide (Z)—N-(3-(2-((6-morpholinopyridin-3-yl)amino)pyrido[3,4-d]pyrimidin-8-yl)phenyl)but-2-enamide (Z)-3-fluoro-N-(3-(2-((6-morpholinopyridin-3-yl)amino)pyrido[3,4-d]pyrimidin-8-yl)phenyl)but-2-enamide (E)-3-fluoro-N-(3-(2-((6-morpholinopyridin-3-yl)amino)pyrido[3,4-d]pyrimidin-8-yl)phenyl)but-2-enamide N-(3-(2-((6-morpholinopyridin-3-yl)amino)pyrido[3,4-d]pyrimidin-8-yl)phenyl)methacrylamide N-(3-(2-((6-morpholinopyridin-3-yl)amino)pyrido[3,4-d]pyrimidin-8-yl)phenyl)ethenesulfonamide (E)-N-(3-(2-((6-(4-methylpiperazin-1-yl)pyridin-3-yl)amino)pyrido[3,4-d]pyrimidin-8-yl)phenyl)but-2-enamide (Z)—N-(3-(2-((6-(4-methylpiperazin-1-yl)pyridin-3-yl)amino)pyrido[3,4-d]pyrimidin-8-yl)phenyl)but-2-enamide (Z)-3-fluoro-N-(3-(2-((6-(4-methylpiperazin-1-yl)pyridin-3-yl)amino)pyrido[3,4-d]pyrimidin-8-yl)phenyl)but-2-enamide (E)-3-fluoro-N-(3-(2-((6-(4-methylpiperazin-1-yl)pyridin-3-yl)amino)pyrido[3,4-d]pyrimidin-8-yl)phenyl)but-2-enamide N-(3-(2-((6-(4-methylpiperazin-1-yl)pyridin-3-yl)amino)pyrido[3,4-d]pyrimidin-8-yl)phenyl)methacrylamide N-(3-(2-((6-(4-methylpiperazin-1-yl)pyridin-3-yl)amino)pyrido[3,4-d]pyrimidin-8-yl)phenyl)ethenesulfonamide 3,3-difluoro-N-(3-(2-((6-(4-methylpiperazin-1-yl)pyridin-3-yl)amino)pyrido[3,4-d]pyrimidin-8-yl)phenyl)acrylamide 3-methyl-N-(3-(2-((6-(4-methylpiperazin-1-yl)pyridin-3-yl)amino)pyrido[3,4-d]pyrimidin-8-yl)phenyl)but-2-enamide (E)-4-(dimethylamino)-N-(2-(2-((6-morpholinopyridin-3-yl)amino)quinazolin-8-yl)pyridin-4-yl)but-2-enamide (E)-4-(dimethylamino)-N-(2-(2-((6-(piperazin-1-yl)pyridin-3-yl)amino)quinazolin-8-yl)pyridin-4-yl)but-2-enamide (E)-4-(dimethylamino)-N-(2-(2-((6-(4-methylpiperazin-1-yl)pyridin-3-yl)amino)quinazolin-8-yl)pyridin-4-yl)but-2-enamide (E)-4-(dimethylamino)-N-(2-(2-((6-(piperidin-1-yl)pyridin-3-yl)amino)quinazolin-8-yl)pyridin-4-yl)but-2-enamide (E)-N-(2-(2-((6-((1-acetylazetidin-3-yl)amino)pyridin-3-yl)amino)quinazolin-8-yl)pyridin-4-yl)-4-(dimethylamino)but-2-enamide (E)-4-(dimethylamino)-N-(2-(2-((6-((1-(2-fluoroethyl)azetidin-3-yl)amino)pyridin-3-yl)amino)quinazolin-8-yl)pyridin-4-yl)but-2-enamide (E)-4-(dimethylamino)-N-(2-(2-((6-((1-methylpiperidin-4-yl)amino)pyridin-3-yl)amino)quinazolin-8-yl)pyridin-4-yl)but-2-enamide (E)-4-(dimethylamino)-N-(2-(2-((6-(pyrrolidin-3-ylamino)pyridin-3-yl)amino)quinazolin-8-yl)pyridin-4-yl)but-2-enamide (E)-4-(dimethylamino)-N-(2-(2-((6-(2-(hydroxymethyl)morpholino)pyridin-3-yl)amino)quinazolin-8-yl)pyridin-4-yl)but-2-enamide N-(2-(2-((6-morpholinopyridin-3-yl)amino)quinazolin-8-yl)pyridin-4-yl)propiolamide N-(2-(2-((6-(piperazin-1-yl)pyridin-3-yl)amino)quinazolin-8-yl)pyridin-4-yl)propiolamide N-(2-(2-((6-(4-methylpiperazin-1-yl)pyridin-3-yl)amino)quinazolin-8-yl)pyridin-4-yl)propiolamide N-(2-(2-((6-((1-(2-fluoroethyl)azetidin-3-yl)amino)pyridin-3-yl)amino)quinazolin-8-yl)pyridin-4-yl)propiolamide (E)-N-(2-(2-((6-morpholinopyridin-3-yl)amino)quinazolin-8-yl)pyridin-4-yl)but-2-enamide (Z)—N-(2-(2-((6-morpholinopyridin-3-yl)amino)quinazolin-8-yl)pyridin-4-yl)but-2-enamide (Z)-3-fluoro-N-(2-(2-((6-morpholinopyridin-3-yl)amino)quinazolin-8-yl)pyridin-4-yl)but-2-enamide (E)-3-fluoro-N-(2-(2-((6-morpholinopyridin-3-yl)amino)quinazolin-8-yl)pyridin-4-yl)but-2-enamide N-(2-(2-((6-morpholinopyridin-3-yl)amino)quinazolin-8-yl)pyridin-4-yl)methacrylamide N-(2-(2-((6-morpholinopyridin-3-yl)amino)quinazolin-8-yl)pyridin-4-yl)ethenesulfonamide (E)-N-(2-(2-((6-(4-methylpiperazin-1-yl)pyridin-3-yl)amino)quinazolin-8-yl)pyridin-4-yl)but-2-enamide (Z)—N-(2-(2-((6-(4-methylpiperazin-1-yl)pyridin-3-yl)amino)quinazolin-8-yl)pyridin-4-yl)but-2-enamide (Z)-3-fluoro-N-(2-(2-((6-(4-methylpiperazin-1-yl)pyridin-3-yl)amino)quinazolin-8-yl)pyridin-4-yl)acrylamide (E)-3-fluoro-N-(2-(2-((6-(4-methylpiperazin-1-yl)pyridin-3-yl)amino)quinazolin-8-yl)pyridin-4-yl)acrylamide (Z)-3-fluoro-N-(2-(2-((6-(4-methylpiperazin-1-yl)pyridin-3-yl)amino)quinazolin-8-yl)pyridin-4-yl)but-2-enamide N-(2-(2-((6-(4-methylpiperazin-1-yl)pyridin-3-yl)amino)quinazolin-8-yl)pyridin-4-yl)methacrylamide 3,3-difluoro-N-(2-(2-((6-(4-methylpiperazin-1-yl)pyridin-3-yl)amino)quinazolin-8-yl)pyridin-4-yl)acrylamide 3-methyl-N-(2-(2-((6-(4-methylpiperazin-1-yl)pyridin-3-yl)amino)quinazolin-8-yl)pyridin-4-yl)but-2-enamide (E)-3-fluoro-N-(2-(2-((6-(4-methylpiperazin-1-yl)pyridin-3-yl)amino)quinazolin-8-yl)pyridin-4-yl)but-2-enamide N-(2-(2-((6-(4-methylpiperazin-1-yl)pyridin-3-yl)amino)quinazolin-8-yl)pyridin-4-yl)ethenesulfonamide (E)-4-(dimethylamino)-N-(2-(2-((4-morpholinophenyl)amino)quinazolin-8-yl)pyridin-4-yl)but-2-enamide (E)-4-(dimethylamino)-N-(2-(2-((4-(piperazin-1-yl)phenyl)amino)quinazolin-8-yl)pyridin-4-yl)but-2-enamide (E)-4-(dimethylamino)-N-(2-(2-((4-(4-methylpiperazin-1-yl)phenyl)amino)quinazolin-8-yl)pyridin-4-yl)but-2-enamide (E)-4-(dimethylamino)-N-(2-(2-((4-(piperidin-1-yl)phenyl)amino)quinazolin-8-yl)pyridin-4-yl)but-2-enamide (E)-N-(2-(2-((4-((1-acetylazetidin-3-yl)amino)phenyl)amino)quinazolin-8-yl)pyridin-4-yl)-4-(dimethylamino)but-2-enamide (E)-4-(dimethylamino)-N-(2-(2-((4-((1-(2-fluoroethyl)azetidin-3-yl)amino)phenyl)amino)quinazolin-8-yl)pyridin-4-yl)but-2-enamide (E)-4-(dimethylamino)-N-(2-(2-((4-((1-methylpiperidin-4-yl)amino)phenyl)amino)quinazolin-8-yl)pyridin-4-yl)but-2-enamide (E)-4-(dimethylamino)-N-(2-(2-((4-(pyrrolidin-3-ylamino)phenyl)amino)quinazolin-8-yl)pyridin-4-yl)but-2-enamide (E)-4-(dimethylamino)-N-(2-(2-((4-(2-(hydroxymethyl)morpholino)phenyl)amino)quinazolin-8-yl)pyridin-4-yl)but-2-enamide N-(2-(2-((4-morpholinophenyl)amino)quinazolin-8-yl)pyridin-4-yl)propiolamide N-(2-(2-((4-(piperazin-1-yl)phenyl)amino)quinazolin-8-yl)pyridin-4-yl)propiolamide N-(2-(2-((4-(4-methylpiperazin-1-yl)phenyl)amino)quinazolin-8-yl)pyridin-4-yl)propiolamide N-(2-(2-((4-((1-(2-fluoroethyl)azetidin-3-yl)amino)phenyl)amino)quinazolin-8-yl)pyridin-4-yl)propiolamide (E)-N-(2-(2-((4-morpholinophenyl)amino)quinazolin-8-yl)pyridin-4-yl)but-2-enamide (Z)—N-(2-(2-((4-morpholinophenyl)amino)quinazolin-8-yl)pyridin-4-yl)but-2-enamide (Z)-3-fluoro-N-(2-(2-((4-morpholinophenyl)amino)quinazolin-8-yl)pyridin-4-yl)but-2-enamide (E)-3-fluoro-N-(2-(2-((4-morpholinophenyl)amino)quinazolin-8-yl)pyridin-4-yl)but-2-enamide N-(2-(2-((4-morpholinophenyl)amino)quinazolin-8-yl)pyridin-4-yl)methacrylamide N-(2-(2-((4-morpholinophenyl)amino)quinazolin-8-yl)pyridin-4-yl)ethenesulfonamide (E)-N-(2-(2-((4-(4-methylpiperazin-1-yl)phenyl)amino)quinazolin-8-yl)pyridin-4-yl)but-2-enamide (Z)—N-(2-(2-((4-(4-methylpiperazin-1-yl)phenyl)amino)quinazolin-8-yl)pyridin-4-yl)but-2-enamide (Z)-3-fluoro-N-(2-(2-((4-(4-methylpiperazin-1-yl)phenyl)amino)quinazolin-8-yl)pyridin-4-yl)acrylamide (E)-3-fluoro-N-(2-(2-((4-(4-methylpiperazin-1-yl)phenyl)amino)quinazolin-8-yl)pyridin-4-yl)acrylamide (Z)-3-fluoro-N-(2-(2-((4-(4-methylpiperazin-1-yl)phenyl)
   amino)quinazolin-8-yl)pyridin-4-yl)but-2-enamide
N-(2-(2-((4-(4-methylpiperazin-1-yl)phenyl)amino)qui-
   nazolin-8-yl)pyridin-4-yl)methacrylamide
3,3-difluoro-N-(2-(2-((4-(4-methylpiperazin-1-yl)phenyl)
   amino)quinazolin-8-yl)pyridin-4-yl)acrylamide
3-methyl-N-(2-(2-((4-(4-methylpiperazin-1-yl)phenyl)
   amino)quinazolin-8-yl)pyridin-4-yl)but-2-enamide
(E)-3-fluoro-N-(2-(2-((4-(4-methylpiperazin-1-yl)phenyl)
   amino)quinazolin-8-yl)pyridin-4-yl)but-2-enamide
N-(2-(2-((4-(4-methylpiperazin-1-yl)phenyl)amino)qui-
   nazolin-8-yl)pyridin-4-yl)ethene sulfonamide
(E)-4-(dimethylamino)-N-(3-(2-((6-morpholinopyridin-3-
   yl)amino)quinazolin-8-yl)phenyl)but-2-enamide
(E)-4-(dimethylamino)-N-(3-(2-((6-(piperazin-1-yl)pyridin-
   3-yl)amino)quinazolin-8-yl)phenyl)but-2-enamide
(E)-4-(dimethylamino)-N-(3-(2-((6-(4-methylpiperazin-1-
   yl)pyridin-3-yl)amino)quinazolin-8-yl)phenyl)but-2-ena-
   mide
(E)-4-(dimethylamino)-N-(3-(2-((6-(piperidin-1-yl)pyridin-
   3-yl)amino)quinazolin-8-yl)phenyl)but-2-enamide
(E)-N-(3-(2-((6-((1-acetylazetidin-3-yl)amino)pyridin-3-yl)
   amino)quinazolin-8-yl)phenyl)-4-(dimethylamino)but-2-
   enamide
(E)-4-(dimethylamino)-N-(3-(2-((6-((1-(2-fluoroethyl)aze-
   tidin-3-yl)amino)pyridin-3-yl)amino)quinazolin-8-yl)
   phenyl)but-2-enamide
(E)-4-(dimethylamino)-N-(3-(2-((6-((1-methylpiperidin-4-
   yl)amino)pyridin-3-yl)amino)quinazolin-8-yl)phenyl)
   but-2-enamide
(E)-4-(dimethylamino)-N-(3-(2-((6-(pyrrolidin-3-ylamino)
   pyridin-3-yl)amino)quinazolin-8-yl)phenyl)but-2-enam-
   ide
(E)-4-(dimethylamino)-N-(3-(2-((6-(2-(hydroxymethyl)
   morpholino)pyridin-3-yl)amino)quinazolin-8-yl)phenyl)
   but-2-enamide
N-(3-(2-((6-morpholinopyridin-3-yl)amino)quinazolin-8-
   yl)phenyl)propiolamide
N-(3-(2-((6-(piperazin-1-yl)pyridin-3-yl)amino)quinazolin-
   8-yl)phenyl)propiolamide
N-(3-(2-((6-(4-methylpiperazin-1-yl)pyridin-3-yl)amino)
   quinazolin-8-yl)phenyl)propiolamide
N-(3-(2-((6-((1-(2-fluoroethyl)azetidin-3-yl)amino)pyridin-
   3-yl)amino)quinazolin-8-yl)phenyl)propiolamide
(E)-N-(3-(2-((6-morpholinopyridin-3-yl)amino)quinazolin-
   8-yl)phenyl)but-2-enamide
(Z)—N-(3-(2-((6-morpholinopyridin-3-yl)amino)quinazo-
   lin-8-yl)phenyl)but-2-enamide
(Z)-3-fluoro-N-(3-(2-((6-morpholinopyridin-3-yl)amino)
   quinazolin-8-yl)phenyl)but-2-enamide
(E)-3-fluoro-N-(3-(2-((6-morpholinopyridin-3-yl)amino)
   quinazolin-8-yl)phenyl)but-2-enamide
N-(3-(2-((6-morpholinopyridin-3-yl)amino)quinazolin-8-
   yl)phenyl)methacrylamide
N-(3-(2-((6-morpholinopyridin-3-yl)amino)quinazolin-8-
   yl)phenyl)ethenesulfonamide
(E)-N-(3-(2-((6-(4-methylpiperazin-1-yl)pyridin-3-yl)
   amino)quinazolin-8-yl)phenyl)but-2-enamide
(Z)—N-(3-(2-((6-(4-methylpiperazin-1-yl)pyridin-3-yl)
   amino)quinazolin-8-yl)phenyl)but-2-enamide
(Z)-3-fluoro-N-(3-(2-((6-(4-methylpiperazin-1-yl)pyridin-
   3-yl)amino)quinazolin-8-yl)phenyl)acrylamide
(E)-3-fluoro-N-(3-(2-((6-(4-methylpiperazin-1-yl)pyridin-
   3-yl)amino)quinazolin-8-yl)phenyl)acrylamide
(Z)-3-fluoro-N-(3-(2-((6-(4-methylpiperazin-1-yl)pyridin-
   3-yl)amino)quinazolin-8-yl)phenyl)but-2-enamide
N-(3-(2-((6-(4-methylpiperazin-1-yl)pyridin-3-yl)amino)
   quinazolin-8-yl)phenyl)methacrylamide
3,3-difluoro-N-(3-(2-((6-(4-methylpiperazin-1-yl)pyridin-
   3-yl)amino)quinazolin-8-yl)phenyl)acrylamide
3-methyl-N-(3-(2-((6-(4-methylpiperazin-1-yl)pyridin-3-yl)
   amino)quinazolin-8-yl)phenyl)but-2-enamide
(E)-3-fluoro-N-(3-(2-((6-(4-methylpiperazin-1-yl)pyridin-
   3-yl)amino)quinazolin-8-yl)phenyl)but-2-enamide
N-(3-(2-((6-(4-methylpiperazin-1-yl)pyridin-3-yl)amino)
   quinazolin-8-yl)phenyl)ethenesulfonamide
8-(4-(2-morpholinoethoxy)pyridin-2-yl)-N2-(6-morpholin-
   opyridin-3-yl)quinazoline-2,4-diamine
8-(4-(2-morpholinoethoxy)pyridin-2-yl)-N2-(6-(piperazin-
   1-yl)pyridin-3-yl)quinazoline-2,4-diamine
N2-(6-morpholinopyridin-3-yl)-8-(pyridin-2-yl)quinazo-
   line-2,4-diamine
8-(4-(2-(dimethylamino)ethoxy)pyridin-2-yl)-N2-(6-mor-
   pholinopyridin-3-yl)quinazoline-2,4-diamine
8-(5-(2-morpholinoethoxy)pyridin-2-yl)-N2-(6-morpholin-
   opyridin-3-yl)quinazoline-2,4-diamine
8-(5-(2-(dimethylamino)ethoxy)pyridin-2-yl)-N2-(6-mor-
   pholinopyridin-3-yl)quinazoline-2,4-diamine
N2-(6-(piperazin-1-yl)pyridin-3-yl)-8-(pyridin-2-yl)qui-
   nazoline-2,4-diamine
8-(2-fluorophenyl)-N2-(6-morpholinopyridin-3-yl)pyrido
   [3,4-d]pyrimidine-2,4-diamine
8-(5-chloro-2-fluorophenyl)-N2-(6-morpholinopyridin-3-
   yl)pyrido[3,4-d]pyrimidine-2,4-diamine
8-(5-chloro-2-fluorophenyl)-N2-(6-(piperazin-1-yl)pyridin-
   3-yl)pyrido[3,4-d]pyrimidine-2,4-diamine
8-(3-fluorophenyl)-N2-(6-morpholinopyridin-3-yl)pyrido
   [3,4-d]pyrimidine-2,4-diamine
8-(2,6-difluorophenyl)-N2-(6-morpholinopyridin-3-yl)
   pyrido[3,4-d]pyrimidine-2,4-diamine
8-(2,6-difluorophenyl)-N2-(6-(piperazin-1-yl)pyridin-3-yl)
   pyrido[3,4-d]pyrimidine-2,4-diamine
8-(2-fluoro-5-(2-morpholinoethoxy)phenyl)-N2-(6-mor-
   pholinopyridin-3-yl)pyrido[3,4-d]pyrimidine-2,4-di-
   amine
8-(5-(2-(dimethylamino)ethoxy)-2-fluorophenyl)-N2-(6-
   morpholinopyridin-3-yl)pyrido[3,4-d]pyrimidine-2,4-di-
   amine
8-(3-(2-morpholinoethoxy)phenyl)-N2-(6-morpholinopyri-
   din-3-yl)pyrido[3,4-d]pyrimidine-2,4-diamine
8-(3-(2-(dimethylamino)ethoxy)phenyl)-N2-(6-morpholin-
   opyridin-3-yl)pyrido[3,4-d]pyrimidine-2,4-diamine
8-(4-(2-morpholinoethoxy)phenyl)-N2-(6-morpholinopyri-
   din-3-yl)pyrido[3,4-d]pyrimidine-2,4-diamine
8-(4-(2-(dimethylamino)ethoxy)phenyl)-N2-(6-morpholin-
   opyridin-3-yl)pyrido[3,4-d]pyrimidine-2,4-diamine
8-(2-fluoro-4-(2-morpholinoethoxy)phenyl)-N2-(6-mor-
   pholinopyridin-3-yl)pyrido[3,4-d]pyrimidine-2,4-di-
   amine
8-(4-(2-(dimethylamino)ethoxy)-2-fluorophenyl)-N2-(6-
   morpholinopyridin-3-yl)pyrido[3,4-d]pyrimidine-2,4-di-
   amine
8-(2-fluorophenyl)-N2-(6-(piperazin-1-yl)pyridin-3-yl)
   pyrido[3,4-d]pyrimidine-2,4-diamine
N2-(6-(piperazin-1-yl)pyridin-3-yl)-8-(pyridin-2-yl)pyrido
   [3,4-d]pyrimidine-2,4-diamine
8-(2-fluoro-4-(2-morpholinoethoxy)phenyl)-N2-(6-(piper-
   azin-1-yl)pyridin-3-yl)pyrido[3,4-d]pyrimidine-2,4-di-
   amine
8-(4-(2-morpholinoethoxy)pyridin-2-yl)-N2-(4-mor-
   pholinophenyl)pyrido[3,4-d]pyrimidine-2,4-diamine
8-(4-(2-(dimethylamino)ethoxy)pyridin-2-yl)-N2-(4-mor-
   pholinophenyl)pyrido[3,4-d]pyrimidine-2,4-diamine 8-(5-(2-morpholinoethoxy)pyridin-2-yl)-N2-(4-morpholinophenyl)pyrido[3,4-d]pyrimidine-2,4-diamine 8-(5-(2-(dimethylamino)ethoxy)pyridin-2-yl)-N2-(4-morpholinophenyl)pyrido[3,4-d]pyrimidine-2,4-diamine N2-(4-(piperazin-1-yl)phenyl)-8-(pyridin-2-yl)pyrido[3,4-d]pyrimidine-2,4-diamine 8-(4-(2-morpholinoethoxy)pyridin-2-yl)-N2-(4-morpholinophenyl)quinazoline-2,4-diamine 8-(4-(2-(dimethylamino)ethoxy)pyridin-2-yl)-N2-(4-morpholinophenyl)quinazoline-2,4-diamine 8-(5-(2-morpholinoethoxy)pyridin-2-yl)-N2-(4-morpholinophenyl)quinazoline-2,4-diamine 8-(5-(2-(dimethylamino)ethoxy)pyridin-2-yl)-N2-(4-morpholinophenyl)quinazoline-2,4-diamine N2-(4-(piperazin-1-yl)phenyl)-8-(pyridin-2-yl)quinazoline-2,4-diamine 8-(2-fluorophenyl)-N2-(6-morpholinopyridin-3-yl)quinazoline-2,4-diamine 8-(5-chloro-2-fluorophenyl)-N2-(6-morpholinopyridin-3-yl)quinazoline-2,4-diamine 8-(3-fluorophenyl)-N2-(6-morpholinopyridin-3-yl)quinazoline-2,4-diamine 8-(3-fluorophenyl)-N2-(6-(piperazin-1-yl)pyridin-3-yl)quinazoline-2,4-diamine 8-(2,6-difluorophenyl)-N2-(6-morpholinopyridin-3-yl)quinazoline-2,4-diamine 8-(5-chloro-2-fluorophenyl)-N2-(6-(piperazin-1-yl)pyridin-3-yl)quinazoline-2,4-diamine 8-(2,6-difluorophenyl)-N2-(6-(piperazin-1-yl)pyridin-3-yl)quinazoline-2,4-diamine 8-(2-fluoro-5-(2-morpholinoethoxy)phenyl)-N2-(6-morpholinopyridin-3-yl)quinazoline-2,4-diamine 8-(2-fluoro-5-(2-morpholinoethoxy)phenyl)-N2-(6-(piperazin-1-yl)pyridin-3-yl)quinazoline-2,4-diamine 8-(5-(2-(dimethylamino)ethoxy)-2-fluorophenyl)-N2-(6-morpholinopyridin-3-yl)quinazoline-2,4-diamine 8-(5-(2-(dimethylamino)ethoxy)-2-fluorophenyl)-N2-(6-(piperazin-1-yl)pyridin-3-yl)quinazoline-2,4-diamine 8-(3-(2-morpholinoethoxy)phenyl)-N2-(6-morpholinopyridin-3-yl)quinazoline-2,4-diamine 8-(3-(2-(dimethylamino)ethoxy)phenyl)-N2-(6-morpholinopyridin-3-yl)quinazoline-2,4-diamine 8-(4-(2-morpholinoethoxy)phenyl)-N2-(6-morpholinopyridin-3-yl)quinazoline-2,4-diamine 8-(4-(2-(dimethylamino)ethoxy)phenyl)-N2-(6-morpholinopyridin-3-yl)quinazoline-2,4-diamine 8-(2-fluoro-4-(2-morpholinoethoxy)phenyl)-N2-(6-morpholinopyridin-3-yl)quinazoline-2,4-diamine 8-(4-(2-(dimethylamino)ethoxy)-2-fluorophenyl)-N2-(6-morpholinopyridin-3-yl)quinazoline-2,4-diamine 8-(2-fluorophenyl)-N2-(6-(piperazin-1-yl)pyridin-3-yl)quinazoline-2,4-diamine 8-(2-fluoro-4-(2-morpholinoethoxy)phenyl)-N2-(6-(piperazin-1-yl)pyridin-3-yl)quinazoline-2,4-diamine 8-(2-fluorophenyl)-N2-(4-morpholinophenyl)pyrido[3,4-d]pyrimidine-2,4-diamine 8-(5-chloro-2-fluorophenyl)-N2-(4-morpholinophenyl)pyrido[3,4-d]pyrimidine-2,4-diamine 8-(3-fluorophenyl)-N2-(4-morpholinophenyl)pyrido[3,4-d]pyrimidine-2,4-diamine 8-(2,6-difluorophenyl)-N2-(4-morpholinophenyl)pyrido[3,4-d]pyrimidine-2,4-diamine 8-(5-chloro-2-fluorophenyl)-N2-(4-(piperazin-1-yl)phenyl)pyrido[3,4-d]pyrimidine-2,4-diamine 8-(2,6-difluorophenyl)-N2-(4-(piperazin-1-yl)phenyl)pyrido[3,4-d]pyrimidine-2,4-diamine 8-(2-fluoro-5-(2-morpholinoethoxy)phenyl)-N2-(4-morpholinophenyl)pyrido[3,4-d]pyrimidine-2,4-diamine 8-(2-fluoro-5-(2-morpholinoethoxy)phenyl)-N2-(4-(piperazin-1-yl)phenyl)pyrido[3,4-d]pyrimidine-2,4-diamine 8-(5-(2-(dimethylamino)ethoxy)-2-fluorophenyl)-N2-(4-morpholinophenyl)pyrido[3,4-d]pyrimidine-2,4-diamine 8-(5-(2-(dimethylamino)ethoxy)-2-fluorophenyl)-N2-(4-(piperazin-1-yl)phenyl)pyrido[3,4-d]pyrimidine-2,4-diamine 8-(3-(2-morpholinoethoxy)phenyl)-N2-(4-morpholinophenyl)pyrido[3,4-d]pyrimidine-2,4-diamine 8-(3-(2-(dimethylamino)ethoxy)phenyl)-N2-(4-morpholinophenyl)pyrido[3,4-d]pyrimidine-2,4-diamine 8-(4-(2-morpholinoethoxy)phenyl)-N2-(4-morpholinophenyl)pyrido[3,4-d]pyrimidine-2,4-diamine 8-(4-(2-(dimethylamino)ethoxy)phenyl)-N2-(4-morpholinophenyl)pyrido[3,4-d]pyrimidine-2,4-diamine 8-(2-fluoro-4-(2-morpholinoethoxy)phenyl)-N2-(4-morpholinophenyl)pyrido[3,4-d]pyrimidine-2,4-diamine 8-(4-(2-(dimethylamino)ethoxy)-2-fluorophenyl)-N2-(4-morpholinophenyl)pyrido[3,4-d]pyrimidine-2,4-diamine 8-(2-fluorophenyl)-N2-(4-(piperazin-1-yl)phenyl)pyrido[3,4-d]pyrimidine-2,4-diamine 8-(2-fluoro-4-(2-morpholinoethoxy)phenyl)-N2-(4-(piperazin-1-yl)phenyl)pyrido[3,4-d]pyrimidine-2,4-diamine 8-(2-fluorophenyl)-N2-(4-morpholinophenyl)quinazoline-2,4-diamine 8-(2-fluorophenyl)-N2-(4-(piperazin-1-yl)phenyl)quinazoline-2,4-diamine 8-(5-chloro-2-fluorophenyl)-N2-(4-morpholinophenyl)quinazoline-2,4-diamine 8-(5-chloro-2-fluorophenyl)-N2-(4-(piperazin-1-yl)phenyl)quinazoline-2,4-diamine 8-(3-fluorophenyl)-N2-(4-morpholinophenyl)quinazoline-2,4-diamine 8-(2,6-difluorophenyl)-N2-(4-morpholinophenyl)quinazoline-2,4-diamine 8-(2,6-difluorophenyl)-N2-(4-(piperazin-1-yl)phenyl)quinazoline-2,4-diamine 8-(2-fluoro-5-(2-morpholinoethoxy)phenyl)-N2-(4-morpholinophenyl)quinazoline-2,4-diamine 8-(2-fluoro-5-(2-morpholinoethoxy)phenyl)-N2-(4-(piperazin-1-yl)phenyl)quinazoline-2,4-diamine 8-(5-(2-(dimethylamino)ethoxy)-2-fluorophenyl)-N2-(4-morpholinophenyl)quinazoline-2,4-diamine 8-(3-(2-morpholinoethoxy)phenyl)-N2-(4-morpholinophenyl)quinazoline-2,4-diamine 8-(3-(2-(dimethylamino)ethoxy)phenyl)-N2-(4-morpholinophenyl)quinazoline-2,4-diamine 8-(4-(2-morpholinoethoxy)phenyl)-N2-(4-morpholinophenyl)quinazoline-2,4-diamine 8-(4-(2-(dimethylamino)ethoxy)phenyl)-N2-(4-morpholinophenyl)quinazoline-2,4-diamine 8-(2-fluoro-4-(2-morpholinoethoxy)phenyl)-N2-(4-morpholinophenyl)quinazoline-2,4-diamine 8-(4-(2-(dimethylamino)ethoxy)-2-fluorophenyl)-N2-(4-morpholinophenyl)quinazoline-2,4-diamine 8-(2-fluoro-4-(2-morpholinoethoxy)phenyl)-N2-(4-(piperazin-1-yl)phenyl)quinazoline-2,4-diamine (E)-N-(3-(4-amino-2-((4-morpholinophenyl)amino)quinazolin-8-yl)phenyl)-4-(dimethylamino)but-2-enamide N-(3-(4-amino-2-((4-morpholinophenyl)amino)quinazolin-8-yl)phenyl)acrylamide N-(3-(4-amino-2-((4-(4-methylpiperazin-1-yl)phenyl)amino)quinazolin-8-yl)phenyl)acrylamide (E)-N-(3-(4-amino-2-((4-(4-methylpiperazin-1-yl)phenyl) amino)quinazolin-8-yl)phenyl)-4-(dimethylamino)but-2-enamide N-(3-(4-amino-2-((4-((1-(2-fluoroethyl)azetidin-3-yl) amino)phenyl)amino)quinazolin-8-yl)phenyl)acrylamide (E)-N-(3-(4-amino-2-((4-((1-(2-fluoroethyl)azetidin-3-yl) amino)phenyl)amino)quinazolin-8-yl)phenyl)-4-(dimethylamino)but-2-enamide N-(3-(4-amino-2-((4-morpholinophenyl)amino)quinazolin-8-yl)phenyl)propiolamide N-(3-(4-amino-2-((4-(4-methylpiperazin-1-yl)phenyl) amino)quinazolin-8-yl)phenyl)propiolamide N-(3-(4-amino-2-((4-(4-methylpiperazin-1-yl)phenyl) amino)quinazolin-8-yl)phenyl)ethenesulfonamide N-(3-(4-amino-2-((4-morpholinophenyl)amino)quinazolin-8-yl)phenyl)methacrylamide N-(3-(4-amino-2-((4-(4-methylpiperazin-1-yl)phenyl) amino)quinazolin-8-yl)phenyl)methacrylamide (E)-N-(2-(4-amino-2-((4-morpholinophenyl)amino)quinazolin-8-yl)pyridin-4-yl)-4-(dimethylamino)but-2-enamide N-(2-(4-amino-2-((4-morpholinophenyl)amino)quinazolin-8-yl)pyridin-4-yl)acrylamide N-(2-(4-amino-2-((4-(4-methylpiperazin-1-yl)phenyl) amino)quinazolin-8-yl)pyridin-4-yl)acrylamide (E)-N-(2-(4-amino-2-((4-(4-methylpiperazin-1-yl)phenyl) amino)quinazolin-8-yl)pyridin-4-yl)-4-(dimethylamino) but-2-enamide N-(2-(4-amino-2-((4-((1-(2-fluoroethyl)azetidin-3-yl) amino)phenyl)amino)quinazolin-8-yl)pyridin-4-yl)acrylamide (E)-N-(2-(4-amino-2-((4-((1-(2-fluoroethyl)azetidin-3-yl) amino)phenyl)amino)quinazolin-8-yl)pyridin-4-yl)-4-(dimethylamino)but-2-enamide N-(2-(4-amino-2-((4-morpholinophenyl)amino)quinazolin-8-yl)pyridin-4-yl)propiolamide N-(2-(4-amino-2-((4-(4-methylpiperazin-1-yl)phenyl) amino)quinazolin-8-yl)pyridin-4-yl)propiolamide N-(2-(4-amino-2-((4-(4-methylpiperazin-1-yl)phenyl) amino)quinazolin-8-yl)pyridin-4-yl)ethenesulfonamide (E)-N-(3-(4-amino-2-((6-morpholinopyridin-3-yl)amino) quinazolin-8-yl)phenyl)-4-(dimethylamino)but-2-enamide N-(3-(4-amino-2-((6-morpholinopyridin-3-yl)amino)quinazolin-8-yl)phenyl)acrylamide N-(3-(4-amino-2-((6-(4-methylpiperazin-1-yl)pyridin-3-yl) amino)quinazolin-8-yl)phenyl)acrylamide (E)-N-(3-(4-amino-2-((6-(4-methylpiperazin-1-yl)pyridin-3-yl)amino)quinazolin-8-yl)phenyl)-4-(dimethylamino) but-2-enamide N-(3-(4-amino-2-((6-((1-(2-fluoroethyl)azetidin-3-yl) amino)pyridin-3-yl)amino)quinazolin-8-yl)phenyl)acrylamide (E)-N-(3-(4-amino-2-((6-((1-(2-fluoroethyl)azetidin-3-yl) amino)pyridin-3-yl)amino)quinazolin-8-yl)phenyl)-4-(dimethylamino)but-2-enamide N-(3-(4-amino-2-((6-morpholinopyridin-3-yl)amino)quinazolin-8-yl)phenyl)propiolamide N-(3-(4-amino-2-((6-(4-methylpiperazin-1-yl)pyridin-3-yl) amino)quinazolin-8-yl)phenyl)propiolamide N-(3-(4-amino-2-((6-(4-methylpiperazin-1-yl)pyridin-3-yl) amino)quinazolin-8-yl)phenyl)ethenesulfonamide (E)-N-(3-(4-amino-2-((4-morpholinophenyl)amino)pyrido [3,4-d]pyrimidin-8-yl)phenyl)-4-(dimethylamino)but-2-enamide N-(3-(4-amino-2-((4-morpholinophenyl)amino)pyrido[3,4-d]pyrimidin-8-yl)phenyl)acrylamide N-(3-(4-amino-2-((4-(4-methylpiperazin-1-yl)phenyl) amino)pyrido[3,4-d]pyrimidin-8-yl)phenyl)acrylamide (E)-N-(3-(4-amino-2-((4-(4-methylpiperazin-1-yl)phenyl) amino)pyrido[3,4-d]pyrimidin-8-yl)phenyl)-4-(dimethylamino)but-2-enamide N-(3-(4-amino-2-((4-((1-(2-fluoroethyl)azetidin-3-yl) amino)phenyl)amino)pyrido[3,4-d]pyrimidin-8-yl)phenyl)acrylamide (E)-N-(3-(4-amino-2-((4-((1-(2-fluoroethyl)azetidin-3-yl) amino)phenyl)amino)pyrido[3,4-d]pyrimidin-8-yl)phenyl)-4-(dimethylamino)but-2-enamide N-(3-(4-amino-2-((4-morpholinophenyl)amino)pyrido[3,4-d]pyrimidin-8-yl)phenyl)propiolamide N-(3-(4-amino-2-((4-(4-methylpiperazin-1-yl)phenyl) amino)pyrido[3,4-d]pyrimidin-8-yl)phenyl)propiolamide N-(3-(4-amino-2-((4-(4-methylpiperazin-1-yl)phenyl) amino)pyrido[3,4-d]pyrimidin-8-yl)phenyl)ethenesulfonamide (E)-N-(2-(4-amino-2-((4-morpholinophenyl)amino)pyrido [3,4-d]pyrimidin-8-yl)pyridin-4-yl)-4-(dimethylamino) but-2-enamide N-(2-(4-amino-2-((4-morpholinophenyl)amino)pyrido[3,4-d]pyrimidin-8-yl)pyridin-4-yl)acrylamide N-(2-(4-amino-2-((4-(4-methylpiperazin-1-yl)phenyl) amino)pyrido[3,4-d]pyrimidin-8-yl)pyridin-4-yl)acrylamide (E)-N-(2-(4-amino-2-((4-(4-methylpiperazin-1-yl)phenyl) amino)pyrido[3,4-d]pyrimidin-8-yl)pyridin-4-yl)-4-(dimethylamino)but-2-enamide N-(2-(4-amino-2-((4-((1-(2-fluoroethyl)azetidin-3-yl) amino)phenyl)amino)pyrido[3,4-d]pyrimidin-8-yl)pyridin-4-yl)acrylamide (E)-N-(2-(4-amino-2-((4-((1-(2-fluoroethyl)azetidin-3-yl) amino)phenyl)amino)pyrido[3,4-d]pyrimidin-8-yl)pyridin-4-yl)-4-(dimethylamino)but-2-enamide N-(2-(4-amino-2-((4-morpholinophenyl)amino)pyrido[3,4-d]pyrimidin-8-yl)pyridin-4-yl)propiolamide N-(2-(4-amino-2-((4-(4-methylpiperazin-1-yl)phenyl) amino)pyrido[3,4-d]pyrimidin-8-yl)pyridin-4-yl)propiolamide N-(2-(4-amino-2-((4-(4-methylpiperazin-1-yl)phenyl) amino)pyrido[3,4-d]pyrimidin-8-yl)pyridin-4-yl)ethenesulfonamide (E)-N-(2-(4-amino-2-((6-morpholinopyridin-3-yl)amino) quinazolin-8-yl)pyridin-4-yl)-4-(dimethylamino)but-2-enamide N-(2-(4-amino-2-((6-morpholinopyridin-3-yl)amino)quinazolin-8-yl)pyridin-4-yl)acrylamide N-(2-(4-amino-2-((6-(4-methylpiperazin-1-yl)pyridin-3-yl) amino)quinazolin-8-yl)pyridin-4-yl)acrylamide (E)-N-(2-(4-amino-2-((6-(4-methylpiperazin-1-yl)pyridin-3-yl)amino)quinazolin-8-yl)pyridin-4-yl)-4-(dimethylamino)but-2-enamide N-(2-(4-amino-2-((6-((1-(2-fluoroethyl)azetidin-3-yl) amino)pyridin-3-yl)amino)quinazolin-8-yl)pyridin-4-yl) acrylamide (E)-N-(2-(4-amino-2-((6-((1-(2-fluoroethyl)azetidin-3-yl) amino)pyridin-3-yl)amino)quinazolin-8-yl)pyridin-4-yl)-4-(dimethylamino)but-2-enamide N-(2-(4-amino-2-((6-morpholinopyridin-3-yl)amino)quinazolin-8-yl)pyridin-4-yl)propiolamide N-(2-(4-amino-2-((6-(4-methylpiperazin-1-yl)pyridin-3-yl) amino)quinazolin-8-yl)pyridin-4-yl)propiolamide N-(2-(4-amino-2-((6-(4-methylpiperazin-1-yl)pyridin-3-yl) amino)quinazolin-8-yl)pyridin-4-yl)ethenesulfonamide (E)-N-(3-(4-amino-2-((6-morpholinopyridin-3-yl)amino) pyrido[3,4-d]pyrimidin-8-yl)phenyl)-4-(dimethylamino) but-2-enamide N-(3-(4-amino-2-((6-morpholinopyridin-3-yl)amino)pyrido [3,4-d]pyrimidin-8-yl)phenyl)acrylamide N-(3-(4-amino-2-((6-(4-methylpiperazin-1-yl)pyridin-3-yl) amino)pyrido[3,4-d]pyrimidin-8-yl)phenyl)acrylamide N-(2-(4-amino-2-((6-(4-methylpiperazin-1-yl)pyridin-3-yl) amino)pyrido[3,4-d]pyrimidin-8-yl)pyridin-4-yl)acrylamide (E)-N-(3-(4-amino-2-((6-(4-methylpiperazin-1-yl)pyridin-3-yl)amino)pyrido[3,4-d]pyrimidin-8-yl)phenyl)-4-(dimethylamino)but-2-enamide N-(3-(4-amino-2-((6-((1-(2-fluoroethyl)azetidin-3-yl) amino)pyridin-3-yl)amino)pyrido[3,4-d]pyrimidin-8-yl) phenyl)acrylamide (E)-N-(3-(4-amino-2-((6-((1-(2-fluoroethyl)azetidin-3-yl) amino)pyridin-3-yl)amino)pyrido[3,4-d]pyrimidin-8-yl) phenyl)-4-(dimethylamino)but-2-enamide N-(3-(4-amino-2-((6-morpholinopyridin-3-yl)amino)pyrido [3,4-d]pyrimidin-8-yl)phenyl)propiolamide N-(3-(4-amino-2-((6-(4-methylpiperazin-1-yl)pyridin-3-yl) amino)pyrido[3,4-d]pyrimidin-8-yl)phenyl)propiolamide N-(3-(4-amino-2-((6-(4-methylpiperazin-1-yl)pyridin-3-yl) amino)pyrido[3,4-d]pyrimidin-8-yl)phenyl)ethenesulfonamide tert-butyl 4-(4-((8-(3-acrylamidophenyl)quinazolin-2-yl)amino)-3-methoxyphenyl)piperazine-1-carboxylate N-(3-(2-((4-(4-acetylpiperazin-1-yl)phenyl)amino)pyrido [3,2-d]pyrimidin-8-yl)phenyl)acrylamide N-(3-(2-((4-(4-acetylpiperazin-1-yl)phenyl)amino)pyrido [3,4-d]pyrimidin-8-yl)phenyl)acrylamide N-(3-(2-((4-(4-acetylpiperazin-1-yl)-2-methoxyphenyl) amino)pyrido[4,3-d]pyrimidin-8-yl)phenyl)acrylamide N-(3-(2-((4-(4-acetylpiperazin-1-yl)-2-methoxyphenyl) amino)pyrido[3,4-d]pyrimidin-8-yl)phenyl)acrylamide N-(3-(2-((4-(4-acetylpiperazin-1-yl)-2-methoxyphenyl) amino)pyrido[3,2-d]pyrimidin-8-yl)phenyl)acrylamide N-(3-(2-((4-(4-acetylpiperazin-1-yl)-2-methoxyphenyl) amino)quinazolin-8-yl)phenyl)acrylamide N-(3-(7-(hydroxymethyl)-2-((4-(4-methylpiperazin-1-yl) phenyl)amino)quinazolin-8-yl)phenyl)acrylamide 8-(3-acrylamidophenyl)-2-((4-(4-methylpiperazin-1-yl)phenyl)amino)quinazoline-7-carboxamide N-(3-(7-(2-amino-2-oxoethyl)-2-((4-(4-methylpiperazin-1-yl)phenyl)amino)quinazolin-8-yl)phenyl)acrylamide N-(3-(7-acetamido-2-((4-(4-methylpiperazin-1-yl)phenyl) amino)quinazolin-8-yl)phenyl)acrylamide N-(3-(2-((4-(4-acetylpiperazin-1-yl)phenyl)amino)-7-fluoroquinazolin-8-yl)phenyl)acrylamide N-(3-(2-((4-(4-acetylpiperazin-1-yl)phenyl)amino)-7-chloroquinazolin-8-yl)phenyl)acrylamide N-(3-(2-((4-(4-acetylpiperazin-1-yl)phenyl)amino)-7-(hydroxymethyl)quinazolin-8-yl)phenyl)acrylamide N-(3-(2-((4-(4-acetylpiperazin-1-yl)phenyl)amino)-7-(2-amino-2-oxoethyl)quinazolin-8-yl)phenyl)acrylamide 2-((4-(4-acetylpiperazin-1-yl)phenyl)amino)-8-(3-acrylamidophenyl)quinazoline-7-carboxamide N-(3-(7-acetamido-2-((4-(4-acetylpiperazin-1-yl)phenyl) amino)quinazolin-8-yl)phenyl)acrylamide N-(3-(2-((4-(4-acetylpiperazin-1-yl)phenyl)amino)quinazolin-8-yl)phenyl)acrylamide N-(3-(2-((2-fluoro-4-(4-methylpiperazin-1-yl)phenyl) amino)quinazolin-8-yl)phenyl)acrylamide N-(3-(2-((2-chloro-4-(4-methylpiperazin-1-yl)phenyl) amino)quinazolin-8-yl)phenyl)acrylamide 2-((8-(3-acrylamidophenyl)quinazolin-2-yl)amino)-5-(4-methylpiperazin-1-yl)benzamide N-(3-(2-((2-(hydroxymethyl)-4-(4-methylpiperazin-1-yl) phenyl)amino)quinazolin-8-yl)phenyl)acrylamide N-(3-(2-((4-(4-acetylpiperazin-1-yl)-2-fluorophenyl)amino) quinazolin-8-yl)phenyl)acrylamide N-(3-(2-((4-(4-acetylpiperazin-1-yl)-2-chlorophenyl) amino)quinazolin-8-yl)phenyl)acrylamide 5-(4-acetylpiperazin-1-yl)-2-((8-(3-acrylamidophenyl)quinazolin-2-yl)amino)benzamide N-(3-(2-((4-(4-acetylpiperazin-1-yl)-2-(hydroxymethyl) phenyl)amino)quinazolin-8-yl)phenyl)acrylamide N-(2-fluoro-3-(2-((4-(4-methylpiperazin-1-yl)phenyl) amino)quinazolin-8-yl)phenyl)acrylamide N-(2-chloro-3-(2-((4-(4-methylpiperazin-1-yl)phenyl) amino)quinazolin-8-yl)phenyl)acrylamide N-(2-(hydroxymethyl)-3-(2-((4-(4-methylpiperazin-1-yl) phenyl)amino)quinazolin-8-yl)phenyl)acrylamide N-(2-methoxy-3-(2-((4-(4-methylpiperazin-1-yl)phenyl) amino)quinazolin-8-yl)phenyl)acrylamide N-(2-(fluoromethyl)-3-(2-((4-(4-methylpiperazin-1-yl)phenyl)amino)quinazolin-8-yl)phenyl)acrylamide N-(3-(2-((4-(4-acetylpiperazin-1-yl)phenyl)amino)quinazolin-8-yl)-2-fluorophenyl)acrylamide N-(3-(2-((4-(4-acetylpiperazin-1-yl)phenyl)amino)quinazolin-8-yl)-2-chlorophenyl)acrylamide N-(3-(2-((4-(4-acetylpiperazin-1-yl)phenyl)amino)quinazolin-8-yl)-2-(hydroxymethyl)phenyl)acrylamide N-(3-(2-((4-(4-acetylpiperazin-1-yl)phenyl)amino)quinazolin-8-yl)-2-(fluoromethyl)phenyl)acrylamide N-(3-(2-((4-(4-acetylpiperazin-1-yl)phenyl)amino)quinazolin-8-yl)-2-methoxyphenyl)acrylamide N-(6-(2-((4-morpholinophenyl)amino)quinazolin-8-yl)pyridin-2-yl)acrylamide N-(6-(2-((4-(piperazin-1-yl)phenyl)amino)quinazolin-8-yl) pyridin-2-yl)acrylamide N-(6-(2-((4-(4-methylpiperazin-1-yl)phenyl)amino)quinazolin-8-yl)pyridin-2-yl)acrylamide N-(6-(2-((4-(4-acetylpiperazin-1-yl)phenyl)amino)quinazolin-8-yl)pyridin-2-yl)acrylamide N-(4-(2-((4-morpholinophenyl)amino)quinazolin-8-yl)pyridin-2-yl)acrylamide N-(4-(2-((4-(piperazin-1-yl)phenyl)amino)quinazolin-8-yl) pyridin-2-yl)acrylamide N-(4-(2-((4-(4-methylpiperazin-1-yl)phenyl)amino)quinazolin-8-yl)pyridin-2-yl)acrylamide N-(4-(2-((4-(4-acetylpiperazin-1-yl)phenyl)amino)quinazolin-8-yl)pyridin-2-yl)acrylamide N-(5-(2-((4-morpholinophenyl)amino)quinazolin-8-yl)pyridin-3-yl)acrylamide N-(5-(2-((4-(piperazin-1-yl)phenyl)amino)quinazolin-8-yl) pyridin-3-yl)acrylamide N-(5-(2-((4-(4-methylpiperazin-1-yl)phenyl)amino)quinazolin-8-yl)pyridin-3-yl)acrylamide N-(5-(2-((4-(4-acetylpiperazin-1-yl)phenyl)amino)quinazolin-8-yl)pyridin-3-yl)acrylamide N-(2-(2-((2-chloro-4-morpholinophenyl)amino)quinazolin-8-yl)pyridin-4-yl)acrylamide N-(2-(2-((2-chloro-4-(piperazin-1-yl)phenyl)amino)quinazolin-8-yl)pyridin-4-yl)acrylamide N-(2-(2-((2-chloro-4-(4-methylpiperazin-1-yl)phenyl) amino)quinazolin-8-yl)pyridin-4-yl)acrylamide N-(2-(2-((4-(4-acetylpiperazin-1-yl)-2-chlorophenyl) amino)quinazolin-8-yl)pyridin-4-yl)acrylamide N-(2-(2-((2-fluoro-4-morpholinophenyl)amino)quinazolin-8-yl)pyridin-4-yl)acrylamide N-(2-(2-((2-fluoro-4-(piperazin-1-yl)phenyl)amino)quinazolin-8-yl)pyridin-4-yl)acrylamide
N-(2-(2-((2-fluoro-4-(4-methylpiperazin-1-yl)phenyl)amino)quinazolin-8-yl)pyridin-4-yl)acrylamide
N-(2-(2-((4-(4-acetylpiperazin-1-yl)-2-fluorophenyl)amino)quinazolin-8-yl)pyridin-4-yl)acrylamide
2-((8-(4-acrylamidopyridin-2-yl)quinazolin-2-yl)amino)-5-morpholinobenzamide
2-((8-(4-acrylamidopyridin-2-yl)quinazolin-2-yl)amino)-5-(piperazin-1-yl)benzamide
2-((8-(4-acrylamidopyridin-2-yl)quinazolin-2-yl)amino)-5-(4-methylpiperazin-1-yl)benzamide
5-(4-acetylpiperazin-1-yl)-2-((8-(4-acrylamidopyridin-2-yl)quinazolin-2-yl)amino)benzamide
N-(2-(2-((2-(hydroxymethyl)-4-morpholinophenyl)amino)quinazolin-8-yl)pyridin-4-yl)acrylamide
N-(2-(2-((2-(hydroxymethyl)-4-(piperazin-1-yl)phenyl)amino)quinazolin-8-yl)pyridin-4-yl)acrylamide
N-(2-(2-((2-(hydroxymethyl)-4-(4-methylpiperazin-1-yl)phenyl)amino)quinazolin-8-yl)pyridin-4-yl)acrylamide
N-(2-(2-((4-(4-acetylpiperazin-1-yl)-2-(hydroxymethyl)phenyl)amino)quinazolin-8-yl)pyridin-4-yl)acrylamide
N-(2-(2-((2-chloro-4-(4-methylpiperazin-1-yl)phenyl)amino)-7-fluoroquinazolin-8-yl)pyridin-4-yl)acrylamide
N-(2-(7-chloro-2-((2-fluoro-4-(4-methylpiperazin-1-yl)phenyl)amino)quinazolin-8-yl)pyridin-4-yl)acrylamide
N-(2-(7-fluoro-2-((2-fluoro-4-(4-methylpiperazin-1-yl)phenyl)amino)quinazolin-8-yl)pyridin-4-yl)acrylamide
N-(3-(2-((2-chloro-4-(4-methylpiperazin-1-yl)phenyl)amino)-7-fluoroquinazolin-8-yl)phenyl)acrylamide
N-(3-(7-chloro-2-((2-fluoro-4-(4-methylpiperazin-1-yl)phenyl)amino)quinazolin-8-yl)phenyl)acrylamide
N-(2-(7-(2-amino-2-oxoethyl)-2-((2-chloro-4-(4-methylpiperazin-1-yl)phenyl)amino)quinazolin-8-yl)pyridin-4-yl)acrylamide
N-(2-(7-(2-amino-2-oxoethyl)-2-((2-fluoro-4-(4-methylpiperazin-1-yl)phenyl)amino)quinazolin-8-yl)pyridin-4-yl)acrylamide
N-(2-(2-((2-chloro-4-(4-methylpiperazin-1-yl)phenyl)amino)-7-(hydroxymethyl)quinazolin-8-yl)pyridin-4-yl)acrylamide
N-(2-(2-((2-fluoro-4-(4-methylpiperazin-1-yl)phenyl)amino)-7-(hydroxymethyl)quinazolin-8-yl)pyridin-4-yl)acrylamide
8-(4-acrylamidopyridin-2-yl)-2-((2-chloro-4-(4-methylpiperazin-1-yl)phenyl)amino)quinazoline-7-carboxamide
8-(4-acrylamidopyridin-2-yl)-2-((2-fluoro-4-(4-methylpiperazin-1-yl)phenyl)amino)quinazoline-7-carboxamide
N-(3-(7-fluoro-2-((2-fluoro-4-(4-methylpiperazin-1-yl)phenyl)amino)quinazolin-8-yl)phenyl)acrylamide
N-(3-(7-(2-amino-2-oxoethyl)-2-((2-chloro-4-(4-methylpiperazin-1-yl)phenyl)amino)quinazolin-8-yl)phenyl)acrylamide
N-(3-(7-(2-amino-2-oxoethyl)-2-((2-fluoro-4-(4-methylpiperazin-1-yl)phenyl)amino)quinazolin-8-yl)phenyl)acrylamide
N-(3-(2-((2-chloro-4-(4-methylpiperazin-1-yl)phenyl)amino)-7-(hydroxymethyl)quinazolin-8-yl)phenyl)acrylamide
N-(3-(2-((2-fluoro-4-(4-methylpiperazin-1-yl)phenyl)amino)-7-(hydroxymethyl)quinazolin-8-yl)phenyl)acrylamide
8-(3-acrylamidophenyl)-2-((2-chloro-4-(4-methylpiperazin-1-yl)phenyl)amino)quinazoline-7-carboxamide
8-(3-acrylamidophenyl)-2-((2-fluoro-4-(4-methylpiperazin-1-yl)phenyl)amino)quinazoline-7-carboxamide
N-(3-(2-((4-(4-methylpiperazin-1-yl)oxazol-2-yl)amino)quinazolin-8-yl)phenyl)acrylamide
N-(3-(2-((4-(4-methylpiperazin-1-yl)thiazol-2-yl)amino)quinazolin-8-yl)phenyl)acrylamide
N-(3-(2-((4-(4-methylpiperazin-1-yl)thiophen-2-yl)amino)quinazolin-8-yl)phenyl)acrylamide
N-(3-(2-((4-(4-methylpiperazin-1-yl)-1H-imidazol-2-yl)amino)quinazolin-8-yl)phenyl)acrylamide
N-(3-(2-((2-(4-methylpiperazin-1-yl)-1H-imidazol-5-yl)amino)quinazolin-8-yl)phenyl)acrylamide
N-(3-(2-((4-methoxy-3-(4-methylpiperazin-1-yl)-1H-pyrazol-5-yl)amino)quinazolin-8-yl)phenyl)acrylamide
N-(3-(2-((3-(4-methylpiperazin-1-yl)isoxazol-5-yl)amino)quinazolin-8-yl)phenyl)acrylamide
N-(3-(2-((5-(4-methylpiperazin-1-yl)pyrimidin-2-yl)amino)quinazolin-8-yl)phenyl)acrylamide
N-(3-(2-((2-(4-methylpiperazin-1-yl)pyrimidin-5-yl)amino)quinazolin-8-yl)phenyl)acrylamide
N-(3-(2-((2-(4-methylpiperazin-1-yl)thiazol-5-yl)amino)quinazolin-8-yl)phenyl)acrylamide
N-(3-(2-((5-(4-methylpiperazin-1-yl)thiophen-2-yl)amino)quinazolin-8-yl)phenyl)acrylamide
N-(5-(2-((4-(4-methylpiperazin-1-yl)phenyl)amino)quinazolin-8-yl)oxazol-2-yl)acrylamide
N-(4-(2-((4-(4-methylpiperazin-1-yl)phenyl)amino)quinazolin-8-yl)-1H-imidazol-2-yl)acrylamide
N-(1-methyl-5-(2-((4-(4-methylpiperazin-1-yl)phenyl)amino)quinazolin-8-yl)-1H-imidazol-2-yl)acrylamide
N-(2-(2-(4-(4-methylpiperazin-1-yl)phenylamino)quinazolin-8-yl)pyrimidin-4-yl)acrylamide
N-(6-(2-((4-(4-methylpiperazin-1-yl)phenyl)amino)quinazolin-8-yl)pyrimidin-4-yl)acrylamide
N-(5-(2-((4-(4-methylpiperazin-1-yl)phenyl)amino)quinazolin-8-yl)isoxazol-3-yl)acrylamide
N-(3-(2-((4-(4-methylpiperazin-1-yl)phenyl)amino)quinazolin-8-yl)-1H-pyrazol-5-yl)acrylamide
N-(2-(2-((4-(4-methylpiperazin-1-yl)phenyl)amino)quinazolin-8-yl)thiazol-5-yl)acrylamide
N-(5-(2-((4-(4-methylpiperazin-1-yl)phenyl)amino)quinazolin-8-yl)thiazol-2-yl)acrylamide
N-(5-(2-((4-(4-methylpiperazin-1-yl)phenyl)amino)quinazolin-8-yl)thiophen-2-yl)acrylamide
N-(4-(2-((4-(4-methylpiperazin-1-yl)phenyl)amino)quinazolin-8-yl)thiophen-2-yl)acrylamide
1-(2-(2-((4-(4-methylpiperazin-1-yl)phenyl)amino)quinazolin-8-yl)morpholino)prop-2-en-1-one
(R)-1-(2-(2-((4-(4-methylpiperazin-1-yl)phenyl)amino)quinazolin-8-yl)morpholino)prop-2-en-1-one
(S)-1-(2-(2-((4-(4-methylpiperazin-1-yl)phenyl)amino)quinazolin-8-yl)morpholino)prop-2-en-1-one
1-(2-(2-((6-(4-methylpiperazin-1-yl)pyridin-3-yl)amino)quinazolin-8-yl)morpholino)prop-2-en-1-one
1-(3-(2-((4-(4-methylpiperazin-1-yl)phenyl)amino)quinazolin-8-yl)piperidin-1-yl)prop-2-en-1-one
(R)-1-(3-(2-((4-(4-methylpiperazin-1-yl)phenyl)amino)quinazolin-8-yl)piperidin-1-yl)prop-2-en-1-one
(S)-1-(3-(2-((4-(4-methylpiperazin-1-yl)phenyl)amino)quinazolin-8-yl)piperidin-1-yl)prop-2-en-1-one
1-(3-(2-((6-(4-methylpiperazin-1-yl)pyridin-3-yl)amino)quinazolin-8-yl)piperidin-1-yl)prop-2-en-1-one
(R)-1-(3-(2-((6-(4-methylpiperazin-1-yl)pyridin-3-yl)amino)quinazolin-8-yl)piperidin-1-yl)prop-2-en-1-one
(S)-1-(3-(2-((6-(4-methylpiperazin-1-yl)pyridin-3-yl)amino)quinazolin-8-yl)piperidin-1-yl)prop-2-en-1-one
1-(4-(2-((4-(4-methylpiperazin-1-yl)phenyl)amino)quinazolin-8-yl)piperidin-1-yl)prop-2-en-1-one N-(1-(2-((4-(4-methylpiperazin-1-yl)phenyl)amino)quinazolin-8-yl)piperidin-4-yl)acrylamide
1-(3-(2-((4-(4-methylpiperazin-1-yl)phenyl)amino)quinazolin-8-yl)pyrrolidin-1-yl)prop-2-en-1-one
(R)-1-(3-(2-((4-(4-methylpiperazin-1-yl)phenyl)amino)quinazolin-8-yl)pyrrolidin-1-yl)prop-2-en-1-one
(S)-1-(3-(2-((4-(4-methylpiperazin-1-yl)phenyl)amino)quinazolin-8-yl)pyrrolidin-1-yl)prop-2-en-1-one
1-(3-(2-((6-(4-methylpiperazin-1-yl)pyridin-3-yl)amino)quinazolin-8-yl)pyrrolidin-1-yl)prop-2-en-1-one
(S)-1-(3-(2-((6-(4-methylpiperazin-1-yl)pyridin-3-yl)amino)quinazolin-8-yl)pyrrolidin-1-yl)prop-2-en-1-one
(R)-1-(3-(2-((6-(4-methylpiperazin-1-yl)pyridin-3-yl)amino)quinazolin-8-yl)pyrrolidin-1-yl)prop-2-en-1-one
N-(1-(2-((4-(4-methylpiperazin-1-yl)phenyl)amino)quinazolin-8-yl)pyrrolidin-3-yl)acrylamide
N-(1-(2-((4-(4-methylpiperazin-1-yl)phenyl)amino)quinazolin-8-yl)piperidin-3-yl)acrylamide
N-(1-(2-((6-(4-methylpiperazin-1-yl)pyridin-3-yl)amino)quinazolin-8-yl)piperidin-3-yl)acrylamide
1-(4-(2-((4-(4-methylpiperazin-1-yl)phenyl)amino)quinazolin-8-yl)piperazin-1-yl)prop-2-en-1-one
N-(4-(2-((4-(4-methylpiperazin-1-yl)phenyl)amino)quinazolin-8-yl)pyrimidin-2-yl)acrylamide
N-(6-(2-((4-(4-methylpiperazin-1-yl)phenyl)amino)quinazolin-8-yl)pyrazin-2-yl)acrylamide
N-(3-(2-((5-(4-methylpiperazin-1-yl)pyridin-2-yl)amino)quinazolin-8-yl)phenyl)acrylamide
N-(2-fluoro-3-(2-((6-(4-methylpiperazin-1-yl)pyridin-3-yl)amino)quinazolin-8-yl)phenyl)acrylamide
N-(2-chloro-3-(2-((6-(4-methylpiperazin-1-yl)pyridin-3-yl)amino)quinazolin-8-yl)phenyl)acrylamide
N-(6-(2-((6-(4-methylpiperazin-1-yl)pyridin-3-yl)amino)quinazolin-8-yl)pyridin-2-yl)acrylamide
N-(4-(2-((6-(4-methylpiperazin-1-yl)pyridin-3-yl)amino)quinazolin-8-yl)pyridin-2-yl)acrylamide
N-(5-(2-((6-(4-methylpiperazin-1-yl)pyridin-3-yl)amino)quinazolin-8-yl)pyridin-3-yl)acrylamide
tert-butyl 4-(4-((8-(2-fluorophenyl)quinazolin-2-yl)amino)phenyl)piperazine-1-carboxylate
tert-butyl 4-(4-((8-(2-chlorophenyl)quinazolin-2-yl)amino)phenyl)piperazine-1-carboxylate
tert-butyl 4-(4-((8-(3-fluorophenyl)quinazolin-2-yl)amino)phenyl)piperazine-1-carboxylate
tert-butyl 4-(4-((8-(5-chloro-2-fluorophenyl)quinazolin-2-yl)amino)phenyl)piperazine-1-carboxylate
tert-butyl 4-(4-((8-(3-chlorophenyl)quinazolin-2-yl)amino)phenyl)piperazine-1-carboxylate
tert-butyl 4-(4-((8-phenylquinazolin-2-yl)amino)phenyl)piperazine-1-carboxylate
tert-butyl 4-(4-((8-(2-fluoro-5-(2-morpholinoethoxy)phenyl)quinazolin-2-yl)amino)phenyl)piperazine-1-carboxylate
N-(3-(2-((4-(4-methylpiperazin-1-yl)phenyl)amino)quinazolin-8-yl)phenyl)propionamide
N-(3-(2-((4-(4-acetylpiperazin-1-yl)phenyl)amino)-7-methylquinazolin-8-yl)phenyl)acrylamide
N-(3-(2-((6-(4-acetylpiperazin-1-yl)pyridin-3-yl)amino)quinazolin-8-yl)phenyl)acrylamide
N-(3-(2-((4-(4-ethylpiperazin-1-yl)phenyl)amino)quinazolin-8-yl)-2-fluorophenyl)acrylamide
N-(3-(7-methyl-2-((4-(4-methylpiperazin-1-yl)phenyl)amino)quinazolin-8-yl)phenyl)propionamide
(E)-N-(3-(2-((4-(4-acetylpiperazin-1-yl)phenyl)amino)quinazolin-8-yl)phenyl)-4-(dimethylamino)but-2-enamide
N-(3-(2-((4-(4-fluoroethyl)piperazin-1-yl)phenyl)amino)quinazolin-8-yl)phenyl)acrylamide
N-(3-(2-((4-(4-(2,2-difluoroethyl)piperazin-1-yl)phenyl)amino)quinazolin-8-yl)phenyl)acrylamide
N-(5-(2-((4-(4-(2-fluoroethyl)piperazin-1-yl)phenyl)amino)quinazolin-8-yl)pyridin-3-yl)acrylamide
N-(3-(2-((4-(4-(2-hydroxyethyl)piperazin-1-yl)phenyl)amino)quinazolin-8-yl)phenyl) acrylamide
(E)-N-(3-(2-((4-(4-acetylpiperazin-1-yl)phenyl)amino)quinazolin-8-yl)-2-chlorophenyl)-4-(dimethylamino)but-2-enamide
N-(2-fluoro-3-(2-((4-(4-(2-fluoroethyl)piperazin-1-yl)phenyl)amino)quinazolin-8-yl)phenyl)acrylamide
(E)-4-(dimethylamino)-N-(2-fluoro-3-(2-((4-(4-methylpiperazin-1-yl)phenyl)amino)quinazolin-8-yl)phenyl)but-2-enamide
N-(3-(2-((4-((2-fluoroethyl)(methyl)amino)phenyl)amino)quinazolin-8-yl)phenyl)acrylamide
N-(2-fluoro-3-(2-((4-((2-fluoroethyl)(methyl)amino)phenyl)amino)quinazolin-8-yl)phenyl)acrylamide
N-(3-(2-((4-((2-hydroxyethyl)amino)phenyl)amino)quinazolin-8-yl)phenyl)acrylamide
N-(4-fluoro-3-(2-((4-(4-methylpiperazin-1-yl)phenyl)amino)quinazolin-8-yl)phenyl)acrylamide
N-(2-cyano-3-(2-((4-(4-methylpiperazin-1-yl)phenyl)amino)quinazolin-8-yl)phenyl)acrylamide
N-(3-(2-((3-fluoro-4-(4-methylpiperazin-1-yl)phenyl)amino)quinazolin-8-yl)phenyl)acrylamide
1-(3-(2-((4-(4-methylpiperazin-1-yl)phenyl)amino)quinazolin-8-yl)-5,6-dihydropyridin-1(2H)-yl)prop-2-en-1-one
N-(3-(2-((3-chloro-4-(4-methylpiperazin-1-yl)phenyl)amino)quinazolin-8-yl)phenyl)acrylamide
N-(4-chloro-3-(2-((4-(4-methylpiperazin-1-yl)phenyl)amino)quinazolin-8-yl)phenyl)acrylamide
N-(3-(2-((3-cyano-4-(4-methylpiperazin-1-yl)phenyl)amino)quinazolin-8-yl)phenyl)acrylamide
N-(3-(2-((3-methoxy-4-(4-methylpiperazin-1-yl)phenyl)amino)quinazolin-8-yl)phenyl)acrylamide
methyl 4-(4-((8-(3-acrylamidophenyl)quinazolin-2-yl)amino)phenyl)piperazine-1-carboxylate
N-(3-(2-((4-(3-(hydroxymethyl)-4-methylpiperazin-1-yl)phenyl)amino)quinazolin-8-yl)phenyl)acrylamide
N-(3-(2-((4-((1-(2-fluoroethyl)azetidin-3-yl)oxy)phenyl)amino)quinazolin-8-yl)phenyl)acrylamide
N-(3-(2-((4-((3-fluoro-1-methylpiperidin-4-yl)oxy)phenyl)amino)quinazolin-8-yl)phenyl)acrylamide
N-(2-fluoro-3-(2-((4-((3-fluoro-1-methylpiperidin-4-yl)oxy)phenyl)amino)quinazolin-8-yl)phenyl)acrylamide
N-(3-(2-((5-chloro-6-(4-methylpiperazin-1-yl)pyridin-3-yl)amino)quinazolin-8-yl)phenyl)acrylamide
N-(3-(2-((4-(4-(2-hydroxyacetyl)piperazin-1-yl)phenyl)amino)quinazolin-8-yl)phenyl)acrylamide
4-(4-((8-(3-acrylamidophenyl)quinazolin-2-yl)amino)phenyl)-N-methylpiperazine-1-carboxamide
N-(3-(2-((4-(4-propionylpiperazin-1-yl)phenyl)amino)quinazolin-8-yl)phenyl)acrylamide
5-((8-(3-acrylamidophenyl)quinazolin-2-yl)amino)-2-(4-methylpiperazin-1-yl)benzamide
N-(3-(2-((5-cyano-6-(4-methylpiperazin-1-yl)pyridin-3-yl)amino)quinazolin-8-yl)phenyl)acrylamide
N-(3-(7-fluoro-2-((4-(4-(2-fluoroethyl)piperazin-1-yl)phenyl)amino)quinazolin-8-yl)phenyl)acrylamide
methyl 4-(4-((8-(3-acrylamidophenyl)quinazolin-2-yl)amino)phenyl)-1-methylpiperazine-2-carboxylate
4-(4-((8-(3-acrylamidophenyl)quinazolin-2-yl)amino)phenyl)-1-methylpiperazine-2-carboxylic acid
N-(3-(2-((4-(2-oxooxazolidin-3-yl)phenyl)amino)quinazolin-8-yl)phenyl)acrylamide N-(3-(2-((4-(4-(methylsulfonyl)piperazin-1-yl)phenyl) amino)quinazolin-8-yl)phenyl)acrylamide
4-(4-((8-(3-acrylamidophenyl)quinazolin-2-yl)amino)phenyl)-1-methylpiperazine-2-carboxamide
N-(3-(2-((4-(1H-imidazol-1-yl)phenyl)amino)quinazolin-8-yl)phenyl)acrylamide
N-(3-(2-((4-(3-oxomorpholino)phenyl)amino)quinazolin-8-yl)phenyl)acrylamide
N-(3-(2-((4-(2-oxopyrrolidin-1-yl)phenyl)amino)quinazolin-8-yl)phenyl)acrylamide
N-(3-(2-((4-(2-oxoimidazolidin-1-yl)phenyl)amino)quinazolin-8-yl)phenyl)acrylamide
N-(3-(2-((4-(3-hydroxypyrrolidin-1-yl)phenyl)amino)quinazolin-8-yl)phenyl)acrylamide
N-(3-(2-((4-((1-(2-hydroxyethyl)azetidin-3-yl)amino)phenyl)amino)quinazolin-8-yl)phenyl)acrylamide
N-(4-cyano-3-(2-((4-(4-methylpiperazin-1-yl)phenyl) amino)quinazolin-8-yl)phenyl)acrylamide
methyl 2-acrylamido-6-(2-((4-(4-methylpiperazin-1-yl)phenyl)amino)quinazolin-8-yl)benzoate
N-(3-(2-((4-(1,4-oxazepan-4-yl)phenyl)amino)quinazolin-8-yl)phenyl)acrylamide
methyl 2-((8-(3-acrylamidophenyl)quinazolin-2-yl)amino)-5-(4-methylpiperazin-1-yl)benzoate
N-(3-(2-((4-((3-fluoro-1-methylpiperidin-4-yl)amino)phenyl)amino)quinazolin-8-yl)phenyl)acrylamide
N-(3-(2-((4-(4-methyl-2-oxopiperazin-1-yl)phenyl)amino) quinazolin-8-yl)phenyl)acrylamide
N-(3-(2-((4-(2-methoxyethoxy)phenyl)amino)quinazolin-8-yl)phenyl)acrylamide
N-(3-(2-((4-(2-hydroxyethoxy)phenyl)amino)quinazolin-8-yl)phenyl)acrylamide
N-(3-(2-((4-(2-(azetidin-1-yl)ethoxy)phenyl)amino)quinazolin-8-yl)phenyl)acrylamide
N-(3-(2-((4-(2-(dimethylamino)ethoxy)phenyl)amino)quinazolin-8-yl)phenyl)acrylamide
N-(3-(2-((4-((tetrahydro-2H-pyran-4-yl)amino)phenyl) amino)quinazolin-8-yl)phenyl)acrylamide
N-(3-(2-((4-((tetrahydro-2H-pyran-4-yl)oxy)phenyl)amino) quinazolin-8-yl)phenyl)acrylamide
(S)—N-(3-(2-((4-((tetrahydrofuran-3-yl)oxy)phenyl)amino) quinazolin-8-yl)phenyl)acrylamide
(S)—N-(3-(2-((4-((tetrahydrofuran-3-yl)amino)phenyl) amino)quinazolin-8-yl)phenyl)acrylamide
(R)—N-(3-(2-((4-((tetrahydrofuran-3-yl)amino)phenyl) amino)quinazolin-8-yl)phenyl)acrylamide
N-(3-(2-((4-(4-methyl-3-oxopiperazin-1-yl)phenyl)amino) quinazolin-8-yl)phenyl)acrylamide
N-(3-(2-((4-(3-oxopiperazin-1-yl)phenyl)amino)quinazolin-8-yl)phenyl)acrylamide
(R)—N-(3-(2-((4-((tetrahydrofuran-3-yl)oxy)phenyl) amino)quinazolin-8-yl)phenyl)acrylamide
N-(3-(2-((4-((1-acetylpiperidin-4-yl)amino)phenyl)amino) quinazolin-8-yl)phenyl)acrylamide
(S)—N-(3-(2-((4-((1-methylpyrrolidin-3-yl)oxy)phenyl) amino)quinazolin-8-yl)phenyl)acrylamide
N-(3-(2-((4-((1-acetylazetidin-3-yl)oxy)phenyl)amino)quinazolin-8-yl)phenyl)acrylamide
(R)—N-(3-(2-((4-((1-methylpyrrolidin-3-yl)oxy)phenyl) amino)quinazolin-8-yl)phenyl)acrylamide
N-(3-(2-((4-((1-acetylpiperidin-4-yl)oxy)phenyl)amino)quinazolin-8-yl)phenyl)acrylamide
N-(3-(2-((4-((1-methylpiperidin-4-yl)oxy)phenyl)amino) quinazolin-8-yl)phenyl)acrylamide
(S)—N-(3-(2-((4-((1-methylpyrrolidin-3-yl)amino)phenyl) amino)quinazolin-8-yl)phenyl)acrylamide
(S)—N-(3-(2-((4-((1-acetylpyrrolidin-3-yl)amino)phenyl) amino)quinazolin-8-yl)phenyl) acrylamide
(R)—N-(3-(2-((4-((1-methylpyrrolidin-3-yl)amino)phenyl) amino)quinazolin-8-yl)phenyl)acrylamide
(R)—N-(3-(2-((4-((1-acetylpyrrolidin-3-yl)amino)phenyl) amino) quinazolin-8-yl)phenyl) acrylamide
(S)—N-(3-(2-((4-((1-acetylpyrrolidin-3-yl)oxy)phenyl) amino)quinazolin-8-yl)phenyl)acrylamide
(R)—N-(3-(2-((4-((1-acetylpyrrolidin-3-yl)oxy)phenyl) amino)quinazolin-8-yl)phenyl)acrylamide
N-(3-(2-((4-((2-fluoroethyl)amino)phenyl)amino)quinazolin-8-yl)phenyl)acrylamide
N-(3-(2-((4-((2,2-difluoroethyl)amino)phenyl)amino)quinazolin-8-yl)phenyl)acrylamide
N-(3-(2-((4-((1-(2-fluoroethyl)piperidin-4-yl)oxy)phenyl) amino)quinazolin-8-yl)phenyl)acrylamide
N-(3-(2-((4-((1-(2-hydroxyethyl)piperidin-4-yl)oxy)phenyl) amino)quinazolin-8-yl)phenyl)acrylamide
N-(3-(2-((4-((1-(2-fluoroethyl)piperidin-4-yl)amino)phenyl)amino)quinazolin-8-yl)phenyl)acrylamide
N-(3-(2-((4-((1-(2-hydroxyethyl)piperidin-4-yl)amino)phenyl)amino)quinazolin-8-yl)phenyl)acrylamide
N-(3-(2-((2-fluoro-4-((1-methylpiperidin-4-yl)amino)phenyl)amino)quinazolin-8-yl)phenyl)acrylamide
N-(3-(2-((2-fluoro-4-((1-methylpiperidin-4-yl)oxy)phenyl) amino)quinazolin-8-yl)phenyl)acrylamide
N-(3-(2-((2,3-difluoro-4-(4-(2-hydroxyethyl)piperazin-1-yl)phenyl)amino)quinazolin-8-yl)phenyl)acrylamide
N-(3-(2-((3,5-difluoro-4-(4-(2-hydroxyethyl)piperazin-1-yl)phenyl)amino)quinazolin-8-yl)phenyl)acrylamide
N-(3-(2-((2,6-difluoro-4-(4-(2-hydroxyethyl)piperazin-1-yl)phenyl)amino)quinazolin-8-yl)phenyl)acrylamide
N-(3-(2-((2,3-difluoro-4-(4-methylpiperazin-1-yl)phenyl) amino)quinazolin-8-yl)phenyl)acrylamide
N-(3-(2-((3,5-difluoro-4-(4-methylpiperazin-1-yl)phenyl) amino)quinazolin-8-yl)phenyl)acrylamide
N-(3-(2-((2,6-difluoro-4-(4-methylpiperazin-1-yl)phenyl) amino)quinazolin-8-yl)phenyl)acrylamide
N-(3-(2-((3,5-difluoro-4-(4-(2-fluoroethyl)piperazin-1-yl) phenyl)amino)quinazolin-8-yl)phenyl)acrylamide
N-(3-(2-((2,3-difluoro-4-(4-(2-fluoroethyl)piperazin-1-yl) phenyl)amino)quinazolin-8-yl)phenyl)acrylamide
N-(3-(2-((2,6-difluoro-4-(4-(2-fluoroethyl)piperazin-1-yl) phenyl)amino)quinazolin-8-yl)phenyl)acrylamide
N-(3-(2-((2-fluoro-4-(4-(2-hydroxyethyl)piperazin-1-yl) phenyl)amino)quinazolin-8-yl)phenyl)acrylamide
N-(3-(2-((2-chloro-4-(4-(2-hydroxyethyl)piperazin-1-yl) phenyl)amino)quinazolin-8-yl)phenyl)acrylamide
N-(3-(2-((2-cyano-4-(4-(2-hydroxyethyl)piperazin-1-yl) phenyl)amino)quinazolin-8-yl)phenyl)acrylamide
N-(3-(2-((4-(4-(2-hydroxyethyl)piperazin-1-yl)-2-methoxyphenyl)amino)quinazolin-8-yl)phenyl)acrylamide
N-(3-(2-((4-(4-(2-hydroxyethyl)piperazin-1-yl)-2-(hydroxymethyl)phenyl)amino)quinazolin-8-yl)phenyl)acrylamide
2-((8-(3-acrylamidophenyl)quinazolin-2-yl)amino)-5-(4-(2-hydroxyethyl)piperazin-1-yl)benzamide
N-(3-(2-((2-fluoro-4-(4-(2-fluoroethyl)piperazin-1-yl)phenyl)amino)quinazolin-8-yl)phenyl)acrylamide
N-(3-(2-((2-chloro-4-(4-(2-fluoroethyl)piperazin-1-yl)phenyl)amino)quinazolin-8-yl)phenyl)acrylamide
N-(3-(2-((4-(4-(2-fluoroethyl)piperazin-1-yl)-2-methoxyphenyl)amino)quinazolin-8-yl)phenyl)acrylamide
N-(3-(2-((2-cyano-4-(4-(2-fluoroethyl)piperazin-1-yl)phenyl)amino)quinazolin-8-yl)phenyl)acrylamide
N-(3-(2-((4-(4-(2-fluoroethyl)piperazin-1-yl)-2-(hydroxymethyl)phenyl)amino)quinazolin-8-yl)phenyl)acrylamide 2-((8-(3-acrylamidophenyl)quinazolin-2-yl)amino)-5-(4-(2-fluoroethyl)piperazin-1-yl)benzamide
N-(3-(2-((2-fluoro-4-(4-(2-hydroxy-2-methylpropyl)piperazin-1-yl)phenyl)amino)quinazolin-8-yl)phenyl)acrylamide
N-(3-(2-((2-chloro-4-(4-(2-hydroxy-2-methylpropyl)piperazin-1-yl)phenyl)amino)quinazolin-8-yl)phenyl)acrylamide
N-(3-(2-((2-cyano-4-(4-(2-hydroxy-2-methylpropyl)piperazin-1-yl)phenyl)amino)quinazolin-8-yl)phenyl)acrylamide
N-(3-(2-((4-(4-(2-hydroxy-2-methylpropyl)piperazin-1-yl)-2-methoxyphenyl)amino)quinazolin-8-yl)phenyl)acrylamide
2-((8-(3-acrylamidophenyl)quinazolin-2-yl)amino)-5-(4-(2-hydroxy-2-methylpropyl)piperazin-1-yl)benzamide
N-(3-(2-((4-(4-(2-hydroxy-2-methylpropyl)piperazin-1-yl)-2-(hydroxymethyl)phenyl)amino)quinazolin-8-yl)phenyl)acrylamide
N-(3-(2-((2-fluoro-4-(4-(2-hydroxypropyl)piperazin-1-yl)phenyl)amino)quinazolin-8-yl)phenyl)acrylamide
N-(3-(2-((2-chloro-4-(4-(2-hydroxypropyl)piperazin-1-yl)phenyl)amino)quinazolin-8-yl)phenyl)acrylamide
N-(3-(2-((2-cyano-4-(4-(2-hydroxypropyl)piperazin-1-yl)phenyl)amino)quinazolin-8-yl)phenyl)acrylamide
2-((8-(3-acrylamidophenyl)quinazolin-2-yl)amino)-5-(4-(2-hydroxypropyl)piperazin-1-yl)benzamide
N-(3-(2-((4-(4-(2-hydroxypropyl)piperazin-1-yl)-2-methoxyphenyl)amino)quinazolin-8-yl)phenyl)acrylamide
N-(3-(2-((2-(hydroxymethyl)-4-(4-(2-hydroxypropyl)piperazin-1-yl)phenyl)amino)quinazolin-8-yl)phenyl)acrylamide
N-(3-(2-((3-(hydroxymethyl)-4-(4-methylpiperazin-1-yl)phenyl)amino)quinazolin-8-yl)phenyl)acrylamide
N-(3-(2-((3-fluoro-4-(4-(2-hydroxyethyl)piperazin-1-yl)phenyl)amino)quinazolin-8-yl)phenyl)acrylamide
N-(3-(2-((3-chloro-4-(4-(2-hydroxyethyl)piperazin-1-yl)phenyl)amino)quinazolin-8-yl)phenyl)acrylamide
N-(3-(2-((3-cyano-4-(4-(2-hydroxyethyl)piperazin-1-yl)phenyl)amino)quinazolin-8-yl)phenyl)acrylamide
5-((8-(3-acrylamidophenyl)quinazolin-2-yl)amino)-2-(4-(2-hydroxyethyl)piperazin-1-yl)benzamide
N-(3-(2-((4-(4-(2-hydroxyethyl)piperazin-1-yl)-3-(hydroxymethyl)phenyl)amino)quinazolin-8-yl)phenyl)acrylamide
N-(3-(2-((3-fluoro-4-(4-(2-fluoroethyl)piperazin-1-yl)phenyl)amino)quinazolin-8-yl)phenyl)acrylamide
N-(3-(2-((3-chloro-4-(4-(2-fluoroethyl)piperazin-1-yl)phenyl)amino)quinazolin-8-yl)phenyl)acrylamide
N-(3-(2-((3-cyano-4-(4-(2-fluoroethyl)piperazin-1-yl)phenyl)amino)quinazolin-8-yl)phenyl)acrylamide
5-((8-(3-acrylamidophenyl)quinazolin-2-yl)amino)-2-(4-(2-fluoroethyl)piperazin-1-yl)benzamide
N-(3-(2-((4-(4-(2-fluoroethyl)piperazin-1-yl)-3-(hydroxymethyl)phenyl)amino)quinazolin-8-yl)phenyl)acrylamide
N-(3-(2-((3-fluoro-4-(4-(2-hydroxy-2-methylpropyl)piperazin-1-yl)phenyl)amino)quinazolin-8-yl)phenyl)acrylamide
N-(3-(2-((3-chloro-4-(4-(2-hydroxy-2-methylpropyl)piperazin-1-yl)phenyl)amino)quinazolin-8-yl)phenyl)acrylamide
N-(3-(2-((3-cyano-4-(4-(2-hydroxy-2-methylpropyl)piperazin-1-yl)phenyl)amino)quinazolin-8-yl)phenyl)acrylamide
5-((8-(3-acrylamidophenyl)quinazolin-2-yl)amino)-2-(4-(2-hydroxy-2-methylpropyl)piperazin-1-yl)benzamide
N-(3-(2-((4-(4-(2-hydroxy-2-methylpropyl)piperazin-1-yl)-3-(hydroxymethyl)phenyl)amino)quinazolin-8-yl)phenyl)acrylamide
N-(3-(2-((3-fluoro-4-(4-(2-hydroxypropyl)piperazin-1-yl)phenyl)amino)quinazolin-8-yl)phenyl)acrylamide
N-(3-(2-((3-chloro-4-(4-(2-hydroxypropyl)piperazin-1-yl)phenyl)amino)quinazolin-8-yl)phenyl)acrylamide
N-(3-(2-((3-cyano-4-(4-(2-hydroxypropyl)piperazin-1-yl)phenyl)amino)quinazolin-8-yl)phenyl)acrylamide
5-((8-(3-acrylamidophenyl)quinazolin-2-yl)amino)-2-(4-(2-hydroxypropyl)piperazin-1-yl)benzamide
N-(3-(2-((3-(hydroxymethyl)-4-(4-(2-hydroxypropyl)piperazin-1-yl)phenyl)amino)quinazolin-8-yl)phenyl)acrylamide
(S)—N-(3-(2-((3-fluoro-4-(4-(2-hydroxypropyl)piperazin-1-yl)phenyl)amino)quinazolin-8-yl)phenyl)acrylamide
(R)—N-(3-(2-((3-fluoro-4-(4-(2-hydroxypropyl)piperazin-1-yl)phenyl)amino)quinazolin-8-yl)phenyl)acrylamide
N-(3-(2-((3-fluoro-4-((1-methylpiperidin-4-yl)oxy)phenyl)amino)quinazolin-8-yl)phenyl)acrylamide
N-(3-(2-((3-fluoro-4-((1-methylpiperidin-4-yl)amino)phenyl)amino)quinazolin-8-yl)phenyl)acrylamide
N-(3-(2-((2-fluoro-4-((1-(2-hydroxyethyl)piperidin-4-yl)oxy)phenyl)amino)quinazolin-8-yl)phenyl)acrylamide
N-(3-(2-((2-fluoro-4-((1-(2-fluoroethyl)piperidin-4-yl)oxy)phenyl)amino)quinazolin-8-yl)phenyl)acrylamide
N-(3-(2-((3-fluoro-4-((1-(2-hydroxyethyl)piperidin-4-yl)amino)phenyl)amino)quinazolin-8-yl)phenyl)acrylamide
N-(3-(2-((3-fluoro-4-((1-(2-fluoroethyl)piperidin-4-yl)amino)phenyl)amino)quinazolin-8-yl)phenyl)acrylamide
N-(3-(2-((4-(((3R,4S)-3-fluoro-1-methylpiperidin-4-yl)oxy)phenyl)amino)quinazolin-8-yl)phenyl)acrylamide
N-(3-(2-((4-(((3 S,4S)-3-fluoro-1-methylpiperidin-4-yl)oxy)phenyl)amino)quinazolin-8-yl)phenyl)acrylamide
N-(3-(2-((4-(((3 S,4R)-3-fluoro-1-methylpiperidin-4-yl)oxy)phenyl)amino)quinazolin-8-yl)phenyl)acrylamide
N-(3-(2-((4-(((3R,4R)-3-fluoro-1-methylpiperidin-4-yl)oxy)phenyl)amino)quinazolin-8-yl)phenyl)acrylamide
N-(3-(2-((4-(((3R,4S)-3-fluoro-1-methylpiperidin-4-yl)amino)phenyl)amino)quinazolin-8-yl)phenyl)acrylamide
N-(3-(2-((4-(((3 S,4S)-3-fluoro-1-methylpiperidin-4-yl)amino)phenyl)amino)quinazolin-8-yl)phenyl)acrylamide
N-(3-(2-((4-(((3 S,4R)-3-fluoro-1-methylpiperidin-4-yl)amino)phenyl)amino)quinazolin-8-yl)phenyl)acrylamide
N-(3-(2-((4-(((3R,4R)-3-fluoro-1-methylpiperidin-4-yl)amino)phenyl)amino)quinazolin-8-yl)phenyl)acrylamide
N-(3-(2-((6-(4-(2-hydroxyethyl)piperazin-1-yl)pyridin-3-yl)amino)quinazolin-8-yl)phenyl)acrylamide
N-(3-(2-((5-(4-(2-hydroxyethyl)piperazin-1-yl)pyridin-2-yl)amino)quinazolin-8-yl)phenyl)acrylamide
N-(4-(2-((4-(4-(2-hydroxyethyl)piperazin-1-yl)phenyl)amino)quinazolin-8-yl)pyridin-2-yl)acrylamide
N-(5-(2-((4-(4-(2-hydroxyethyl)piperazin-1-yl)phenyl)amino)quinazolin-8-yl)pyridin-3-yl)acrylamide
N-(2-(2-((4-(4-(2-hydroxyethyl)piperazin-1-yl)phenyl)amino)quinazolin-8-yl)pyridin-4-yl)acrylamide
N-(6-(2-((4-(4-(2-hydroxyethyl)piperazin-1-yl)phenyl)amino)quinazolin-8-yl)pyridin-2-yl)acrylamide
N-(4-fluoro-3-(2-((4-(4-(2-hydroxyethyl)piperazin-1-yl)phenyl)amino)quinazolin-8-yl)phenyl)acrylamide
N-(2-fluoro-3-(2-((4-(4-(2-hydroxyethyl)piperazin-1-yl)phenyl)amino)quinazolin-8-yl)phenyl)acrylamide
N-(4-fluoro-3-(2-((6-(4-(2-hydroxyethyl)piperazin-1-yl)pyridin-3-yl)amino)quinazolin-8-yl)phenyl)acrylamide
N-(5-(2-((6-(4-(2-hydroxyethyl)piperazin-1-yl)pyridin-3-yl)amino)quinazolin-8-yl)pyridin-3-yl)acrylamide N-(4-(2-((6-(4-(2-hydroxyethyl)piperazin-1-yl)pyridin-3-yl)amino)quinazolin-8-yl)pyridin-2-yl)acrylamide
N-(4-(2-((2-fluoro-4-(4-(2-hydroxyethyl)piperazin-1-yl)phenyl)amino)quinazolin-8-yl)pyridin-2-yl)acrylamide
N-(4-(2-((3-fluoro-4-(4-(2-hydroxyethyl)piperazin-1-yl)phenyl)amino)quinazolin-8-yl)pyridin-2-yl)acrylamide
N-(5-(2-((2-fluoro-4-(4-(2-hydroxyethyl)piperazin-1-yl)phenyl)amino)quinazolin-8-yl)pyridin-3-yl)acrylamide
N-(5-(2-((3-fluoro-4-(4-(2-hydroxyethyl)piperazin-1-yl)phenyl)amino)quinazolin-8-yl)pyridin-3-yl)acrylamide
N-(4-fluoro-3-(2-((6-(4-methylpiperazin-1-yl)pyridin-3-yl)amino)quinazolin-8-yl)phenyl)acrylamide
N-(4-(2-((2-fluoro-4-(4-methylpiperazin-1-yl)phenyl)amino)quinazolin-8-yl)pyridin-2-yl)acrylamide
N-(4-(2-((3-fluoro-4-(4-methylpiperazin-1-yl)phenyl)amino)quinazolin-8-yl)pyridin-2-yl)acrylamide
N-(5-(2-((2-fluoro-4-(4-methylpiperazin-1-yl)phenyl)amino)quinazolin-8-yl)pyridin-3-yl)acrylamide
N-(5-(2-((3-fluoro-4-(4-methylpiperazin-1-yl)phenyl)amino)quinazolin-8-yl)pyridin-3-yl)acrylamide
N-(3-(2-((6-(4-(2-fluoroethyl)piperazin-1-yl)pyridin-3-yl)amino)quinazolin-8-yl)phenyl)acrylamide
N-(3-(2-((5-(4-(2-fluoroethyl)piperazin-1-yl)pyridin-2-yl)amino)quinazolin-8-yl)phenyl)acrylamide
N-(4-(2-((4-(4-(2-fluoroethyl)piperazin-1-yl)phenyl)amino)quinazolin-8-yl)pyridin-2-yl)acrylamide
N-(2-(2-((4-(4-(2-fluoroethyl)piperazin-1-yl)phenyl)amino)quinazolin-8-yl)pyridin-4-yl)acrylamide
N-(6-(2-((4-(4-(2-fluoroethyl)piperazin-1-yl)phenyl)amino)quinazolin-8-yl)pyridin-2-yl)acrylamide
N-(4-fluoro-3-(2-((4-(4-(2-fluoroethyl)piperazin-1-yl)phenyl)amino)quinazolin-8-yl)phenyl)acrylamide
N-(4-fluoro-3-(2-((6-(4-(2-fluoroethyl)piperazin-1-yl)pyridin-3-yl)amino)quinazolin-8-yl)phenyl)acrylamide
N-(5-(2-((6-(4-(2-fluoroethyl)piperazin-1-yl)pyridin-3-yl)amino)quinazolin-8-yl)pyridin-3-yl) acrylamide
N-(4-(2-((6-(4-(2-fluoroethyl)piperazin-1-yl)pyridin-3-yl)amino)quinazolin-8-yl)pyridin-2-yl)acrylamide
N-(4-(2-((2-fluoro-4-(4-(2-fluoroethyl)piperazin-1-yl)phenyl)amino)quinazolin-8-yl)pyridin-2-yl)acrylamide
N-(4-(2-((3-fluoro-4-(4-(2-fluoroethyl)piperazin-1-yl)phenyl)amino)quinazolin-8-yl)pyridin-2-yl)acrylamide
N-(5-(2-((2-fluoro-4-(4-(2-fluoroethyl)piperazin-1-yl)phenyl)amino)quinazolin-8-yl)pyridin-3-yl)acrylamide
N-(5-(2-((3-fluoro-4-(4-(2-fluoroethyl)piperazin-1-yl)phenyl)amino)quinazolin-8-yl)pyridin-3-yl)acrylamide
N-(3-(2-((6-(4-(2-hydroxy-2-methylpropyl)piperazin-1-yl)pyridin-3-yl)amino)quinazolin-8-yl)phenyl)acrylamide
N-(3-(2-((5-(4-(2-hydroxy-2-methylpropyl)piperazin-1-yl)pyridin-2-yl)amino)quinazolin-8-yl)phenyl)acrylamide
N-(4-(2-((4-(4-(2-hydroxy-2-methylpropyl)piperazin-1-yl)phenyl)amino)quinazolin-8-yl)pyridin-2-yl)acrylamide
N-(5-(2-((4-(4-(2-hydroxy-2-methylpropyl)piperazin-1-yl)phenyl)amino)quinazolin-8-yl)pyridin-3-yl)acrylamide
N-(2-(2-((4-(4-(2-hydroxy-2-methylpropyl)piperazin-1-yl)phenyl)amino)quinazolin-8-yl)pyridin-4-yl)acrylamide
N-(6-(2-((4-(4-(2-hydroxy-2-methylpropyl)piperazin-1-yl)phenyl)amino)quinazolin-8-yl)pyridin-2-yl)acrylamide
N-(4-fluoro-3-(2-((4-(4-(2-hydroxy-2-methylpropyl)piperazin-1-yl)phenyl)amino)quinazolin-8-yl)phenyl)acrylamide
N-(2-fluoro-3-(2-((4-(4-(2-hydroxy-2-methylpropyl)piperazin-1-yl)phenyl)amino)quinazolin-8-yl)phenyl)acrylamide
N-(4-fluoro-3-(2-((6-(4-(2-hydroxy-2-methylpropyl)piperazin-1-yl)pyridin-3-yl)amino)quinazolin-8-yl)phenyl)acrylamide
N-(5-(2-((6-(4-(2-hydroxy-2-methylpropyl)piperazin-1-yl)pyridin-3-yl)amino)quinazolin-8-yl)pyridin-3-yl)acrylamide
N-(4-(2-((6-(4-(2-hydroxy-2-methylpropyl)piperazin-1-yl)pyridin-3-yl)amino)quinazolin-8-yl)pyridin-2-yl)acrylamide
N-(4-(2-((2-fluoro-4-(4-(2-hydroxy-2-methylpropyl)piperazin-1-yl)phenyl)amino)quinazolin-8-yl)pyridin-2-yl)acrylamide
N-(4-(2-((3-fluoro-4-(4-(2-hydroxy-2-methylpropyl)piperazin-1-yl)phenyl)amino)quinazolin-8-yl)pyridin-2-yl)acrylamide
N-(5-(2-((2-fluoro-4-(4-(2-hydroxy-2-methylpropyl)piperazin-1-yl)phenyl)amino)quinazolin-8-yl)pyridin-3-yl)acrylamide
N-(5-(2-((3-fluoro-4-(4-(2-hydroxy-2-methylpropyl)piperazin-1-yl)phenyl)amino)quinazolin-8-yl)pyridin-3-yl)acrylamide
N-(3-(2-((6-(4-(2-hydroxypropyl)piperazin-1-yl)pyridin-3-yl)amino)quinazolin-8-yl)phenyl)acrylamide
N-(3-(2-((5-(4-(2-hydroxypropyl)piperazin-1-yl)pyridin-2-yl)amino)quinazolin-8-yl)phenyl)acrylamide
N-(4-(2-((4-(4-(2-hydroxypropyl)piperazin-1-yl)phenyl)amino)quinazolin-8-yl)pyridin-2-yl)acrylamide
N-(5-(2-((4-(4-(2-hydroxypropyl)piperazin-1-yl)phenyl)amino)quinazolin-8-yl)pyridin-3-yl)acrylamide
N-(2-(2-((4-(4-(2-hydroxypropyl)piperazin-1-yl)phenyl)amino)quinazolin-8-yl)pyridin-4-yl)acrylamide
N-(6-(2-((4-(4-(2-hydroxypropyl)piperazin-1-yl)phenyl)amino)quinazolin-8-yl)pyridin-2-yl)acrylamide
N-(4-fluoro-3-(2-((4-(4-(2-hydroxypropyl)piperazin-1-yl)phenyl)amino)quinazolin-8-yl)phenyl)acrylamide
N-(2-fluoro-3-(2-((4-(4-(2-hydroxypropyl)piperazin-1-yl)phenyl)amino)quinazolin-8-yl)phenyl)acrylamide
N-(4-fluoro-3-(2-((6-(4-(2-hydroxypropyl)piperazin-1-yl)pyridin-3-yl)amino)quinazolin-8-yl)phenyl)acrylamide
N-(5-(2-((6-(4-(2-hydroxypropyl)piperazin-1-yl)pyridin-3-yl)amino)quinazolin-8-yl)pyridin-3-yl)acrylamide
N-(4-(2-((6-(4-(2-hydroxypropyl)piperazin-1-yl)pyridin-3-yl)amino)quinazolin-8-yl)pyridin-2-yl)acrylamide
N-(4-(2-((2-fluoro-4-(4-(2-hydroxypropyl)piperazin-1-yl)phenyl)amino)quinazolin-8-yl)pyridin-2-yl)acrylamide
N-(4-(2-((3-fluoro-4-(4-(2-hydroxypropyl)piperazin-1-yl)phenyl)amino)quinazolin-8-yl)pyridin-2-yl)acrylamide
N-(5-(2-((2-fluoro-4-(4-(2-hydroxypropyl)piperazin-1-yl)phenyl)amino)quinazolin-8-yl)pyridin-3-yl)acrylamide
N-(5-(2-((3-fluoro-4-(4-(2-hydroxypropyl)piperazin-1-yl)phenyl)amino)quinazolin-8-yl)pyridin-3-yl)acrylamide
N-(3-(2-((4-(4-(2-hydroxyethyl)piperazin-1-yl)phenyl)amino)-7-methylquinazolin-8-yl)phenyl)acrylamide
N-(3-(7-fluoro-2-((4-(4-(2-hydroxyethyl)piperazin-1-yl)phenyl)amino)quinazolin-8-yl)phenyl)acrylamide
N-(3-(2-((4-(4-(2-hydroxyethyl)piperazin-1-yl)phenyl)amino)-7-(hydroxymethyl)quinazolin-8-yl)phenyl)acrylamide
N-(3-(2-((4-(4-(2-hydroxyethyl)piperazin-1-yl)phenyl)amino)pyrido[3,4-d]pyrimidin-8-yl)phenyl)acrylamide
N-(3-(2-((4-(4-(2-fluoroethyl)piperazin-1-yl)phenyl)amino)-7-methylquinazolin-8-yl)phenyl)acrylamide
N-(3-(2-((4-(4-(2-fluoroethyl)piperazin-1-yl)phenyl)amino)-7-(hydroxymethyl)quinazolin-8-yl)phenyl)acrylamide
N-(3-(2-((4-(4-(2-fluoroethyl)piperazin-1-yl)phenyl)amino)pyrido[3,4-d]pyrimidin-8-yl)phenyl)acrylamide
N-(3-(2-((4-(4-(2-hydroxy-2-methylpropyl)piperazin-1-yl)phenyl)amino)-7-methylquinazolin-8-yl)phenyl)acrylamide N-(3-(7-fluoro-2-((4-(4-(2-hydroxy-2-methylpropyl)piperazin-1-yl)phenyl)amino) quinazolin-8-yl)phenyl)acrylamide N-(3-(2-((4-(4-(2-hydroxy-2-methylpropyl)piperazin-1-yl)phenyl)amino)-7-(hydroxymethyl)quinazolin-8-yl)phenyl)acrylamide N-(3-(2-((4-(4-(2-hydroxy-2-methylpropyl)piperazin-1-yl)phenyl)amino)pyrido[3,4-d]pyrimidin-8-yl)phenyl)acrylamide N-(3-(2-((4-(4-(2-hydroxypropyl)piperazin-1-yl)phenyl)amino)-7-methylquinazolin-8-yl)phenyl)acrylamide N-(3-(7-fluoro-2-((4-(4-(2-hydroxypropyl)piperazin-1-yl)phenyl)amino)quinazolin-8-yl)phenyl)acrylamide N-(3-(7-(hydroxymethyl)-2-((4-(4-(2-hydroxypropyl)piperazin-1-yl)phenyl)amino)quinazolin-8-yl)phenyl)acrylamide N-(3-(2-((4-(4-(2-hydroxypropyl)piperazin-1-yl)phenyl)amino)pyrido[3,4-d]pyrimidin-8-yl)phenyl)acrylamide N-(4-(7-fluoro-2-((3-fluoro-4-(4-(2-hydroxyethyl)piperazin-1-yl)phenyl)amino)quinazolin-8-yl)pyridin-2-yl)acrylamide N-(4-(7-fluoro-2-((3-fluoro-4-(4-(2-fluoroethyl)piperazin-1-yl)phenyl)amino)quinazolin-8-yl)pyridin-2-yl)acrylamide N-(4-(7-fluoro-2-((3-fluoro-4-(4-(2-hydroxypropyl)piperazin-1-yl)phenyl)amino)quinazolin-8-yl)pyridin-2-yl)acrylamide N-(4-(7-fluoro-2-((3-fluoro-4-(4-(2-hydroxy-2-methylpropyl)piperazin-1-yl)phenyl)amino)quinazolin-8-yl)pyridin-2-yl)acrylamide N-(4-(7-fluoro-2-((3-fluoro-4-(4-methylpiperazin-1-yl)phenyl)amino)quinazolin-8-yl)pyridin-2-yl)acrylamide N-(4-(7-fluoro-2-((2-fluoro-4-(4-(2-hydroxyethyl)piperazin-1-yl)phenyl)amino)quinazolin-8-yl)pyridin-2-yl)acrylamide N-(4-(7-fluoro-2-((2-fluoro-4-(4-(2-fluoroethyl)piperazin-1-yl)phenyl)amino)quinazolin-8-yl)pyridin-2-yl)acrylamide N-(4-(7-fluoro-2-((2-fluoro-4-(4-(2-hydroxypropyl)piperazin-1-yl)phenyl)amino)quinazolin-8-yl)pyridin-2-yl)acrylamide N-(4-(7-fluoro-2-((2-fluoro-4-(4-(2-hydroxy-2-methylpropyl)piperazin-1-yl)phenyl)amino)quinazolin-8-yl)pyridin-2-yl)acrylamide N-(4-(7-fluoro-2-((2-fluoro-4-(4-methylpiperazin-1-yl)phenyl)amino)quinazolin-8-yl)pyridin-2-yl)acrylamide N-(3-(7-fluoro-2-((3-fluoro-4-(4-(2-hydroxyethyl)piperazin-1-yl)phenyl)amino)quinazolin-8-yl)phenyl)acrylamide N-(3-(7-fluoro-2-((3-fluoro-4-(4-(2-fluoroethyl)piperazin-1-yl)phenyl)amino)quinazolin-8-yl)phenyl)acrylamide N-(3-(7-fluoro-2-((3-fluoro-4-(4-(2-hydroxypropyl)piperazin-1-yl)phenyl)amino)quinazolin-8-yl)phenyl)acrylamide N-(3-(7-fluoro-2-((3-fluoro-4-(4-(2-hydroxy-2-methylpropyl)piperazin-1-yl)phenyl)amino)quinazolin-8-yl)phenyl)acrylamide N-(3-(7-fluoro-2-((3-fluoro-4-(4-methylpiperazin-1-yl)phenyl)amino)quinazolin-8-yl)phenyl)acrylamide N-(3-(7-fluoro-2-((2-fluoro-4-(4-(2-hydroxyethyl)piperazin-1-yl)phenyl)amino)quinazolin-8-yl)phenyl)acrylamide N-(3-(7-fluoro-2-((2-fluoro-4-(4-(2-fluoroethyl)piperazin-1-yl)phenyl)amino)quinazolin-8-yl)phenyl)acrylamide N-(3-(7-fluoro-2-((2-fluoro-4-(4-(2-hydroxypropyl)piperazin-1-yl)phenyl)amino)quinazolin-8-yl)phenyl)acrylamide N-(3-(7-fluoro-2-((2-fluoro-4-(4-(2-hydroxy-2-methylpropyl)piperazin-1-yl)phenyl)amino)quinazolin-8-yl)phenyl)acrylamide N-(3-(2-((2,3-difluoro-4-(4-(2-hydroxy-2-methylpropyl)piperazin-1-yl)phenyl)amino)quinazolin-8-yl)phenyl)acrylamide N-(3-(2-((2,3-difluoro-4-(4-(2-methoxyethyl)piperazin-1-yl)phenyl)amino)quinazolin-8-yl)phenyl)acrylamide (R)—N-(3-(2-((2,3-difluoro-4-(4-(2-hydroxypropyl)piperazin-1-yl)phenyl)amino)quinazolin-8-yl)phenyl)acrylamide (S)—N-(3-(2-((2,3-difluoro-4-(4-(2-hydroxypropyl)piperazin-1-yl)phenyl)amino)quinazolin-8-yl)phenyl)acrylamide N-(3-(2-((2,3-difluoro-4-(4-(2-hydroxypropyl)piperazin-1-yl)phenyl)amino)quinazolin-8-yl)phenyl)acrylamide N-(3-(2-((3,5-difluoro-4-(4-(2-hydroxy-2-methylpropyl)piperazin-1-yl)phenyl)amino)quinazolin-8-yl)phenyl)acrylamide N-(3-(2-((2,6-difluoro-4-(4-(2-hydroxy-2-methylpropyl)piperazin-1-yl)phenyl)amino)quinazolin-8-yl)phenyl)acrylamide N-(3-(2-((2,6-difluoro-4-(4-(2-methoxyethyl)piperazin-1-yl)phenyl)amino)quinazolin-8-yl)phenyl)acrylamide N-(3-(2-((3,5-difluoro-4-(4-(2-methoxyethyl)piperazin-1-yl)phenyl)amino)quinazolin-8-yl)phenyl)acrylamide N-(3-(2-((2,5-difluoro-4-(4-(2-fluoroethyl)piperazin-1-yl)phenyl)amino)quinazolin-8-yl)phenyl)acrylamide N-(3-(2-((2-fluoro-4-(4-(2-methoxyethyl)piperazin-1-yl)phenyl)amino)quinazolin-8-yl)phenyl)acrylamide N-(3-(2-((2-chloro-4-(4-(2-methoxyethyl)piperazin-1-yl)phenyl)amino)quinazolin-8-yl)phenyl)acrylamide N-(3-(2-((2-cyano-4-(4-(2-methoxyethyl)piperazin-1-yl)phenyl)amino)quinazolin-8-yl)phenyl)acrylamide N-(3-(2-((2-methoxy-4-(4-(2-methoxyethyl)piperazin-1-yl)phenyl)amino)quinazolin-8-yl)phenyl)acrylamide N-(3-(2-((2-(hydroxymethyl)-4-(4-(2-methoxyethyl)piperazin-1-yl)phenyl)amino)quinazolin-8-yl)phenyl)acrylamide 2-((8-(3-acrylamidophenyl)quinazolin-2-yl)amino)-5-(4-(2-methoxyethyl)piperazin-1-yl)benzamide N-(3-(2-((3-fluoro-4-(4-(2-methoxyethyl)piperazin-1-yl)phenyl)amino)quinazolin-8-yl)phenyl)acrylamide N-(3-(2-((3-chloro-4-(4-(2-methoxyethyl)piperazin-1-yl)phenyl)amino)quinazolin-8-yl)phenyl)acrylamide N-(3-(2-((3-cyano-4-(4-(2-methoxyethyl)piperazin-1-yl)phenyl)amino)quinazolin-8-yl)phenyl)acrylamide 5-((8-(3-acrylamidophenyl)quinazolin-2-yl)amino)-2-(4-(2-methoxyethyl)piperazin-1-yl)benzamide N-(3-(2-((3-(hydroxymethyl)-4-(4-(2-methoxyethyl)piperazin-1-yl)phenyl)amino)quinazolin-8-yl)phenyl)acrylamide N-(3-(2-((6-(4-(2-methoxyethyl)piperazin-1-yl)pyridin-3-yl)amino)quinazolin-8-yl)phenyl)acrylamide N-(3-(2-((5-(4-(2-methoxyethyl)piperazin-1-yl)pyridin-2-yl)amino)quinazolin-8-yl)phenyl)acrylamide N-(4-(2-((4-(4-(2-methoxyethyl)piperazin-1-yl)phenyl)amino)quinazolin-8-yl)pyridin-2-yl)acrylamide N-(5-(2-((4-(4-(2-methoxyethyl)piperazin-1-yl)phenyl)amino)quinazolin-8-yl)pyridin-3-yl)acrylamide N-(2-(2-((4-(4-(2-methoxyethyl)piperazin-1-yl)phenyl)amino)quinazolin-8-yl)pyridin-4-yl)acrylamide N-(6-(2-((4-(4-(2-methoxyethyl)piperazin-1-yl)phenyl)amino)quinazolin-8-yl)pyridin-2-yl)acrylamide N-(4-fluoro-3-(2-((4-(4-(2-methoxyethyl)piperazin-1-yl)phenyl)amino)quinazolin-8-yl)phenyl)acrylamide N-(2-fluoro-3-(2-((4-(4-(2-methoxyethyl)piperazin-1-yl)phenyl)amino)quinazolin-8-yl)phenyl)acrylamide
N-(4-fluoro-3-(2-((6-(4-(2-methoxyethyl)piperazin-1-yl)pyridin-3-yl)amino)quinazolin-8-yl)phenyl)acrylamide
N-(5-(2-((6-(4-(2-methoxyethyl)piperazin-1-yl)pyridin-3-yl)amino)quinazolin-8-yl)pyridin-3-yl)acrylamide
N-(4-(2-((6-(4-(2-methoxyethyl)piperazin-1-yl)pyridin-3-yl)amino)quinazolin-8-yl)pyridin-2-yl)acrylamide
N-(4-(2-((2-fluoro-4-(4-(2-methoxyethyl)piperazin-1-yl)phenyl)amino)quinazolin-8-yl)pyridin-2-yl)acrylamide
N-(4-(2-((3-fluoro-4-(4-(2-methoxyethyl)piperazin-1-yl)phenyl)amino)quinazolin-8-yl)pyridin-2-yl)acrylamide
N-(5-(2-((2-fluoro-4-(4-(2-methoxyethyl)piperazin-1-yl)phenyl)amino)quinazolin-8-yl)pyridin-3-yl)acrylamide
N-(5-(2-((3-fluoro-4-(4-(2-methoxyethyl)piperazin-1-yl)phenyl)amino)quinazolin-8-yl)pyridin-3-yl)acrylamide
N-(4-(2-((2,3-difluoro-4-(4-(2-hydroxyethyl)piperazin-1-yl)phenyl)amino)quinazolin-8-yl)pyridin-2-yl)acrylamide
N-(5-(2-((2,3-difluoro-4-(4-(2-hydroxyethyl)piperazin-1-yl)phenyl)amino)quinazolin-8-yl)pyridin-3-yl)acrylamide
N-(2-(2-((2,3-difluoro-4-(4-(2-hydroxyethyl)piperazin-1-yl)phenyl)amino)quinazolin-8-yl)pyridin-4-yl)acrylamide
N-(6-(2-((2,3-difluoro-4-(4-(2-hydroxyethyl)piperazin-1-yl)phenyl)amino)quinazolin-8-yl)pyridin-2-yl)acrylamide
N-(3-(2-((2,3-difluoro-4-(4-(2-hydroxyethyl)piperazin-1-yl)phenyl)amino)quinazolin-8-yl)-4-fluorophenyl)acrylamide
N-(3-(2-((2,3-difluoro-4-(4-(2-hydroxyethyl)piperazin-1-yl)phenyl)amino)quinazolin-8-yl)-2-fluorophenyl)acrylamide
N-(3-(2-((2,3-difluoro-4-(4-(2-hydroxyethyl)piperazin-1-yl)phenyl)amino)quinazolin-8-yl)-5-fluorophenyl)acrylamide
N-(5-(2-((2,3-difluoro-4-(4-(2-hydroxyethyl)piperazin-1-yl)phenyl)amino)quinazolin-8-yl)-2-fluorophenyl)acrylamide
N-(4-(2-((2,3-difluoro-4-(4-methylpiperazin-1-yl)phenyl)amino)quinazolin-8-yl)pyridin-2-yl)acrylamide
N-(5-(2-((2,3-difluoro-4-(4-methylpiperazin-1-yl)phenyl)amino)quinazolin-8-yl)pyridin-3-yl)acrylamide
N-(2-(2-((2,3-difluoro-4-(4-methylpiperazin-1-yl)phenyl)amino)quinazolin-8-yl)pyridin-4-yl)acrylamide
N-(6-(2-((2,3-difluoro-4-(4-methylpiperazin-1-yl)phenyl)amino)quinazolin-8-yl)pyridin-2-yl)acrylamide
N-(3-(2-((2,3-difluoro-4-(4-methylpiperazin-1-yl)phenyl)amino)quinazolin-8-yl)-4-fluorophenyl)acrylamide
N-(3-(2-((2,3-difluoro-4-(4-methylpiperazin-1-yl)phenyl)amino)quinazolin-8-yl)-2-fluorophenyl)acrylamide
N-(3-(2-((2,3-difluoro-4-(4-methylpiperazin-1-yl)phenyl)amino)quinazolin-8-yl)-5-fluorophenyl)acrylamide
N-(5-(2-((2,3-difluoro-4-(4-methylpiperazin-1-yl)phenyl)amino)quinazolin-8-yl)-2-fluorophenyl)acrylamide
N-(4-(2-((2,3-difluoro-4-(4-(2-methoxyethyl)piperazin-1-yl)phenyl)amino)quinazolin-8-yl)pyridin-2-yl)acrylamide
N-(5-(2-((2,3-difluoro-4-(4-(2-methoxyethyl)piperazin-1-yl)phenyl)amino)quinazolin-8-yl)pyridin-3-yl)acrylamide
N-(2-(2-((2,3-difluoro-4-(4-(2-methoxyethyl)piperazin-1-yl)phenyl)amino)quinazolin-8-yl)pyridin-4-yl)acrylamide
N-(6-(2-((2,3-difluoro-4-(4-(2-methoxyethyl)piperazin-1-yl)phenyl)amino)quinazolin-8-yl)pyridin-2-yl)acrylamide
N-(3-(2-((2,3-difluoro-4-(4-(2-methoxyethyl)piperazin-1-yl)phenyl)amino)quinazolin-8-yl)-4-fluorophenyl)acrylamide
N-(3-(2-((2,3-difluoro-4-(4-(2-methoxyethyl)piperazin-1-yl)phenyl)amino)quinazolin-8-yl)-2-fluorophenyl)acrylamide
N-(4-(2-((2,3-difluoro-4-(4-(2-hydroxy-2-methylpropyl)piperazin-1-yl)phenyl)amino)quinazolin-8-yl)pyridin-2-yl)acrylamide
N-(5-(2-((2,3-difluoro-4-(4-(2-hydroxy-2-methylpropyl)piperazin-1-yl)phenyl)amino)quinazolin-8-yl)pyridin-3-yl)acrylamide
N-(2-(2-((2,3-difluoro-4-(4-(2-hydroxy-2-methylpropyl)piperazin-1-yl)phenyl)amino)quinazolin-8-yl)pyridin-4-yl)acrylamide
N-(6-(2-((2,3-difluoro-4-(4-(2-hydroxy-2-methylpropyl)piperazin-1-yl)phenyl)amino)quinazolin-8-yl)pyridin-2-yl)acrylamide
N-(3-(2-((2,3-difluoro-4-(4-(2-hydroxy-2-methylpropyl)piperazin-1-yl)phenyl)amino)quinazolin-8-yl)-4-fluorophenyl)acrylamide
N-(3-(2-((2,3-difluoro-4-(4-(2-hydroxy-2-methylpropyl)piperazin-1-yl)phenyl)amino)quinazolin-8-yl)-2-fluorophenyl)acrylamide
N-(4-(2-((2,3-difluoro-4-(4-(2-hydroxypropyl)piperazin-1-yl)phenyl)amino)quinazolin-8-yl)pyridin-2-yl)acrylamide
N-(5-(2-((2,3-difluoro-4-(4-(2-hydroxypropyl)piperazin-1-yl)phenyl)amino)quinazolin-8-yl)pyridin-3-yl)acrylamide
N-(2-(2-((2,3-difluoro-4-(4-(2-hydroxypropyl)piperazin-1-yl)phenyl)amino)quinazolin-8-yl)pyridin-4-yl)acrylamide
N-(6-(2-((2,3-difluoro-4-(4-(2-hydroxypropyl)piperazin-1-yl)phenyl)amino)quinazolin-8-yl)pyridin-2-yl)acrylamide
N-(3-(2-((2,3-difluoro-4-(4-(2-hydroxypropyl)piperazin-1-yl)phenyl)amino)quinazolin-8-yl)-4-fluorophenyl)acrylamide
N-(3-(2-((2,3-difluoro-4-(4-(2-hydroxypropyl)piperazin-1-yl)phenyl)amino)quinazolin-8-yl)-2-fluorophenyl)acrylamide
N-(4-(2-((2,3-difluoro-4-(4-(2-fluoroethyl)piperazin-1-yl)phenyl)amino)quinazolin-8-yl)pyridin-2-yl)acrylamide
N-(5-(2-((2,3-difluoro-4-(4-(2-fluoroethyl)piperazin-1-yl)phenyl)amino)quinazolin-8-yl)pyridin-3-yl)acrylamide
N-(2-(2-((2,3-difluoro-4-(4-(2-fluoroethyl)piperazin-1-yl)phenyl)amino)quinazolin-8-yl)pyridin-4-yl)acrylamide
N-(6-(2-((2,3-difluoro-4-(4-(2-fluoroethyl)piperazin-1-yl)phenyl)amino)quinazolin-8-yl)pyridin-2-yl)acrylamide
N-(3-(2-((2,3-difluoro-4-(4-(2-fluoroethyl)piperazin-1-yl)phenyl)amino)quinazolin-8-yl)-4-fluorophenyl)acrylamide
N-(3-(2-((2,3-difluoro-4-(4-(2-fluoroethyl)piperazin-1-yl)phenyl)amino)quinazolin-8-yl)-2-fluorophenyl)acrylamide
N-(3-(2-((4-(4-(2-methoxyethyl)piperazin-1-yl)phenyl)amino)-7-methylquinazolin-8-yl)phenyl)acrylamide
N-(3-(7-fluoro-2-((4-(4-(2-methoxyethyl)piperazin-1-yl)phenyl)amino)quinazolin-8-yl)phenyl)acrylamide
N-(3-(7-(hydroxymethyl)-2-((4-(4-(2-methoxyethyl)piperazin-1-yl)phenyl)amino)quinazolin-8-yl)phenyl)acrylamide N-(3-(2-((4-(4-(2-methoxyethyl)piperazin-1-yl)phenyl) amino)pyrido[3,4-d]pyrimidin-8-yl)phenyl)acrylamide N-(4-(7-fluoro-2-((4-(4-(2-methoxyethyl)piperazin-1-yl)phenyl)amino)quinazolin-8-yl)pyridin-2-yl)acrylamide N-(4-(7-fluoro-2-((3-fluoro-4-(4-(2-methoxyethyl)piperazin-1-yl)phenyl)amino)quinazolin-8-yl)pyridin-2-yl)acrylamide N-(4-(7-fluoro-2-((2-fluoro-4-(4-(2-methoxyethyl)piperazin-1-yl)phenyl)amino)quinazolin-8-yl)pyridin-2-yl)acrylamide N-(3-(7-fluoro-2-((3-fluoro-4-(4-(2-methoxyethyl)piperazin-1-yl)phenyl)amino)quinazolin-8-yl)phenyl)acrylamide N-(3-(7-fluoro-2-((2-fluoro-4-(4-(2-methoxyethyl)piperazin-1-yl)phenyl)amino)quinazolin-8-yl)phenyl)acrylamide N-(3-(2-((4-(2,3-difluoro-4-(2-hydroxyethyl)piperazin-1-yl)phenyl)amino)-7-methylquinazolin-8-yl)phenyl)acrylamide N-(3-(2-((4-(2,3-difluoro-4-(2-hydroxyethyl)piperazin-1-yl)phenyl)amino)-7-fluoroquinazolin-8-yl)phenyl)acrylamide N-(3-(2-((4-(2,3-difluoro-4-(2-hydroxyethyl)piperazin-1-yl)phenyl)amino)-7-(hydroxymethyl)quinazolin-8-yl)phenyl)acrylamide N-(3-(2-((4-(2,3-difluoro-4-(2-hydroxyethyl)piperazin-1-yl)phenyl)amino)pyrido[3,4-d]pyrimidin-8-yl)phenyl)acrylamide N-(4-(2-((4-(2,3-difluoro-4-(2-hydroxyethyl)piperazin-1-yl)phenyl)amino)-7-fluoroquinazolin-8-yl)pyridin-2-yl)acrylamide N-(3-(2-((4-(2,3-difluoro-4-(2-hydroxypropyl)piperazin-1-yl)phenyl)amino)-7-methylquinazolin-8-yl)phenyl)acrylamide N-(3-(2-((4-(2,3-difluoro-4-(2-hydroxypropyl)piperazin-1-yl)phenyl)amino)-7-fluoroquinazolin-8-yl)phenyl)acrylamide N-(3-(2-((4-(2,3-difluoro-4-(2-hydroxypropyl)piperazin-1-yl)phenyl)amino)-7-(hydroxymethyl)quinazolin-8-yl)phenyl)acrylamide N-(3-(2-((4-(2,3-difluoro-4-(2-hydroxypropyl)piperazin-1-yl)phenyl)amino)pyrido[3,4-d]pyrimidin-8-yl)phenyl)acrylamide N-(4-(2-((4-(2,3-difluoro-4-(2-hydroxypropyl)piperazin-1-yl)phenyl)amino)-7-fluoroquinazolin-8-yl)pyridin-2-yl)acrylamide N-(3-(2-((4-(2,3-difluoro-4-(2-hydroxy-2-methylpropyl)piperazin-1-yl)phenyl)amino)-7-methylquinazolin-8-yl)phenyl)acrylamide N-(3-(2-((4-(2,3-difluoro-4-(2-hydroxy-2-methylpropyl)piperazin-1-yl)phenyl)amino)-7-fluoroquinazolin-8-yl)phenyl)acrylamide N-(3-(2-((4-(2,3-difluoro-4-(2-hydroxy-2-methylpropyl)piperazin-1-yl)phenyl)amino)-7-(hydroxymethyl)quinazolin-8-yl)phenyl)acrylamide N-(3-(2-((4-(2,3-difluoro-4-(2-hydroxy-2-methylpropyl)piperazin-1-yl)phenyl)amino)pyrido[3,4-d]pyrimidin-8-yl)phenyl)acrylamide N-(4-(2-((4-(2,3-difluoro-4-(2-hydroxy-2-methylpropyl)piperazin-1-yl)phenyl)amino)-7-fluoroquinazolin-8-yl)pyridin-2-yl)acrylamide N-(3-(2-((4-(2,3-difluoro-4-(2-fluoroethyl)piperazin-1-yl)phenyl)amino)-7-methylquinazolin-8-yl)phenyl)acrylamide N-(3-(2-((4-(2,3-difluoro-4-(2-fluoroethyl)piperazin-1-yl)phenyl)amino)-7-fluoroquinazolin-8-yl)phenyl)acrylamide N-(3-(2-((4-(2,3-difluoro-4-(2-fluoroethyl)piperazin-1-yl)phenyl)amino)-7-(hydroxymethyl)quinazolin-8-yl)phenyl)acrylamide N-(3-(2-((4-(2,3-difluoro-4-(2-fluoroethyl)piperazin-1-yl)phenyl)amino)pyrido[3,4-d]pyrimidin-8-yl)phenyl)acrylamide N-(4-(2-((4-(2,3-difluoro-4-(2-fluoroethyl)piperazin-1-yl)phenyl)amino)-7-fluoroquinazolin-8-yl)pyridin-2-yl)acrylamide N-(3-(2-((4-(2,3-difluoro-4-(2-methoxyethyl)piperazin-1-yl)phenyl)amino)-7-methylquinazolin-8-yl)phenyl)acrylamide N-(3-(2-((4-(2,3-difluoro-4-(2-methoxyethyl)piperazin-1-yl)phenyl)amino)-7-fluoroquinazolin-8-yl)phenyl)acrylamide N-(3-(2-((4-(2,3-difluoro-4-(2-methoxyethyl)piperazin-1-yl)phenyl)amino)-7-(hydroxymethyl)quinazolin-8-yl) phenyl)acrylamide N-(3-(2-((4-(2,3-difluoro-4-(2-methoxyethyl)piperazin-1-yl)phenyl)amino)pyrido[3,4-d]pyrimidin-8-yl)phenyl)acrylamide N-(4-(2-((4-(2,3-difluoro-4-(2-methoxyethyl)piperazin-1-yl)phenyl)amino)-7-fluoroquinazolin-8-yl)pyridin-2-yl)acrylamide N-(3-(2-((2,3-difluoro-4-(4-(2-hydroxy-2-methylpropyl)piperazin-1-yl)phenyl)amino)quinazolin-8-yl)-5-fluorophenyl)acrylamide N-(5-(2-((2,3-difluoro-4-(4-(2-hydroxy-2-methylpropyl)piperazin-1-yl)phenyl)amino)quinazolin-8-yl)-2-fluorophenyl)acrylamide N-(2-fluoro-5-(2-(((6-(4-(2-methoxyethyl)piperazin-1-yl)pyridin-3-yl)amino)quinazolin-8-yl)phenyl)acrylamide N-(3-fluoro-5-(2-(((6-(4-(2-methoxyethyl)piperazin-1-yl)pyridin-3-yl)amino)quinazolin-8-yl)phenyl)acrylamide N-(3-(2-((4-(4-(2-hydroxy-2-methylpropyl)piperazin-1-yl)phenyl)amino)quinazolin-8-yl)phenyl)acrylamide N-(3-(2-((4-(4-(2-amino-2-oxoethyl)piperazin-1-yl)phenyl)amino)quinazolin-8-yl)phenyl)acrylamide N-(3-(2-((4-(4-(2-methoxyethyl)piperazin-1-yl)phenyl)amino)quinazolin-8-yl)phenyl)acrylamide N-(3-(2-((4-(4-(2-amino-2-oxoethyl)piperazin-1-yl)-2-fluorophenyl)amino)quinazolin-8-yl)phenyl)acrylamide N-(3-(2-((4-(1H-pyrazol-1-yl)phenyl)amino)quinazolin-8-yl)phenyl)acrylamide N-(3-(2-((4-(1H-pyrazol-4-yl)phenyl)amino)quinazolin-8-yl)phenyl)acrylamide N-(3-(2-((2,5-difluoro-4-(4-methylpiperazin-1-yl)phenyl)amino)quinazolin-8-yl)phenyl)acrylamide N-(3-(2-((2,5-difluoro-4-(4-(2-methoxyethyl)piperazin-1-yl)phenyl)amino)quinazolin-8-yl)phenyl)acrylamide N-(3-(2-((2,5-difluoro-4-(4-(2-hydroxyethyl)piperazin-1-yl)phenyl)amino)quinazolin-8-yl)phenyl)acrylamide N-(3-(2-((2,5-difluoro-4-(4-(2-hydroxy-2-methylpropyl)piperazin-1-yl)phenyl)amino)quinazolin-8-yl)phenyl)acrylamide and N-(3-(2-((4-(4-(2-amino-2-oxoethyl)piperazin-1-yl)-3-fluorophenyl)amino)quinazolin-8-yl)phenyl)acrylamide.

In yet another aspect, the present disclosure provides a compound chosen from the compounds set forth in Table 1 below and pharmaceutically acceptable salts thereof.

TABLE 1

Illustrative Compounds of the Present Invention

| Compound No. | Chemical Name |
|---|---|
| C001 | N-(3-(2-((4-morpholinophenyl)amino)quinazolin-8-yl)phenyl)acrylamide |
| C002 | N-(3-(2-((2-methoxy-4-morpholinophenyl)amino)quinazolin-8-yl)phenyl)acrylamide |
| C003 | N-(3-(2-((2-methoxy-4-(4-methylpiperazin-1-yl)phenyl)amino)quinazolin-8-yl)phenyl)acrylamide |
| C004 | N-(4-morpholinophenyl)-8-phenylquinazolin-2-amine |
| C005 | N-(3-(4-amino-2-((4-morpholinophenyl)amino)pyrido[3,4-d]pyrimidin-8-yl)phenyl)acrylamide |
| C006 | tert-butyl 4-(4-((8-(3-acrylamidophenyl)quinazolin-2-yl)amino)-3-methoxyphenyl)piperazine-1-carboxylate |
| C007 | 8-(5-chloro-2-fluorophenyl)-N-(4-morpholinophenyl)quinazolin-2-amine |
| C008 | 8-(3-chlorophenyl)-N-(4-morpholinophenyl)quinazolin-2-amine |
| C009 | 8-(3-fluorophenyl)-N-(4-morpholinophenyl)quinazolin-2-amine |
| C010 | 8-(2-fluorophenyl)-N-(4-morpholinophenyl)quinazolin-2-amine |
| C011 | 8-(2-chlorophenyl)-N-(4-morpholinophenyl)quinazolin-2-amine |
| C012 | N-(3-(2-((4-morpholinophenyl)amino)pyrido[3,4-d]pyrimidin-8-yl)phenyl)acrylamide |
| C013 | tert-butyl 4-(4-((8-(2-fluorophenyl)quinazolin-2-yl)amino)phenyl)piperazine-1-carboxylate |
| C014 | tert-butyl 4-(4-((8-(2-chlorophenyl)quinazolin-2-yl)amino)phenyl)piperazine-1-carboxylate |
| C015 | tert-butyl 4-(4-((8-(3-fluorophenyl)quinazolin-2-yl)amino)phenyl)piperazine-1-carboxylate |
| C016 | tert-butyl 4-(4-((8-(5-chloro-2-fluorophenyl)quinazolin-2-yl)amino)phenyl)piperazine-1-carboxylate |
| C017 | tert-butyl 4-(4-((8-(3-chlorophenyl)quinazolin-2-yl)amino)phenyl)piperazine-1-carboxylate |
| C018 | tert-butyl 4-(4-((8-phenylquinazolin-2-yl)amino)phenyl)piperazine-1-carboxylate |
| C019 | tert-butyl 4-(4-((8-(2-fluoro-5-(2-morpholinoethoxy)phenyl)quinazolin-2-yl)amino)phenyl)piperazine-1-carboxylate |
| C020 | N-(3-(2-((4-(4-methylpiperazin-1-yl)phenyl)amino)quinazolin-8-yl)phenyl)propionamide |
| C021 | N-(3-(2-((4-(4-methylpiperazin-1-yl)phenyl)amino)quinazolin-8-yl)phenyl)acrylamide |
| C022 | N-(3-(2-((4-(4-methylpiperazin-1-yl)phenyl)amino)quinazolin-8-yl)phenyl)acetamide |
| C023 | 8-(2-fluoro-5-(2-morpholinoethoxy)phenyl)-N-(4-morpholinophenyl)quinazolin-2-amine |
| C024 | 8-(5-chloro-2-fluorophenyl)-N-(4-(piperazin-1-yl)phenyl)quinazolin-2-amine |
| C025 | 8-(3-chlorophenyl)-N-(4-(piperazin-1-yl)phenyl)quinazolin-2-amine |
| C026 | 8-(2-chlorophenyl)-N-(4-(piperazin-1-yl)phenyl)quinazolin-2-amine |
| C027 | 8-(3-fluorophenyl)-N-(4-(piperazin-1-yl)phenyl)quinazolin-2-amine |
| C028 | 8-(2-fluoro-5-(2-morpholinoethoxy)phenyl)-N-(4-(piperazin-1-yl)phenyl)quinazolin-2-amine |
| C029 | N-(3-(2-((4-(4-ethylpiperazin-1-yl)phenyl)amino)quinazolin-8-yl)phenyl)acrylamide |
| C030 | 8-phenyl-N-(4-(piperazin-1-yl)phenyl)quinazolin-2-amine |
| C031 | 8-(2-fluorophenyl)-N-(4-(piperazin-1-yl)phenyl)quinazolin-2-amine |
| C032 | N-(3-(2-((4-(4-acetylpiperazin-1-yl)phenyl)amino)quinazolin-8-yl)phenyl)acrylamide |
| C033 | N-(3-(7-methyl-2-((4-morpholinophenyl)amino)quinazolin-8-yl)phenyl)acrylamide |
| C034 | N-(3-(7-methyl-2-((4-(4-methylpiperazin-1-yl)phenyl)amino)quinazolin-8-yl)phenyl)acrylamide |
| C035 | N-(3-(2-((4-(4-acetylpiperazin-1-yl)phenyl)amino)-7-methylquinazolin-8-yl)phenyl)acrylamide |
| C036 | N-(3-(2-((6-(4-acetylpiperazin-1-yl)pyridin-3-yl)amino)quinazolin-8-yl)phenyl)acrylamide |
| C037 | N-(3-(7-(hydroxymethyl)-2-((4-(4-methylpiperazin-1-yl)phenyl)amino)quinazolin-8-yl)phenyl)acrylamide |
| C038 | N-(3-(2-((4-(4-ethylpiperazin-1-yl)phenyl)amino)quinazolin-8-yl)-2-fluorophenyl)acrylamide |
| C039 | N-(5-(2-((4-(4-acetylpiperazin-1-yl)phenyl)amino)quinazolin-8-yl)pyridin-3-yl)acrylamide |
| C040 | N-(5-(2-((4-(4-methylpiperazin-1-yl)phenyl)amino)quinazolin-8-yl)pyridin-3-yl)acrylamide |
| C041 | N-(3-(2-((6-(4-methylpiperazin-1-yl)pyridin-3-yl)amino)quinazolin-8-yl)phenyl)acrylamide |
| C042 | N-(3-(7-methyl-2-((4-(4-methylpiperazin-1-yl)phenyl)amino)quinazolin-8-yl)phenyl)propionamide |
| C043 | N-(3-(2-((2-chloro-4-(4-methylpiperazin-1-yl)phenyl)amino)quinazolin-8-yl)phenyl)acrylamide |
| C044 | N-(3-(2-((2-fluoro-4-(4-methylpiperazin-1-yl)phenyl)amino)quinazolin-8-yl)phenyl)acrylamide |

TABLE 1-continued

Illustrative Compounds of the Present Invention

| Compound No. | Chemical Name |
|---|---|
| C045 | N-(2-fluoro-3-(2-((4-(4-methylpiperazin-1-yl)phenyl)amino)quinazolin-8-yl)phenyl)acrylamide |
| C046 | N-(3-(2-((2-(4-methylpiperazin-1-yl)pyrimidin-5-yl)amino)quinazolin-8-yl)phenyl)acrylamide |
| C047 | N-(5-(2-((6-(4-methylpiperazin-1-yl)pyridin-3-yl)amino)quinazolin-8-yl)pyridin-3-yl)acrylamide |
| C048 | N-(2-fluoro-3-(2-((6-(4-methylpiperazin-1-yl)pyridin-3-yl)amino)quinazolin-8-yl)phenyl)acrylamide |
| C049 | N-(3-(2-((4-(4-acetylpiperazin-1-yl)phenyl)amino)quinazolin-8-yl)-2-fluorophenyl)acrylamide |
| C050 | (E)-N-(3-(2-((4-(4-acetylpiperazin-1-yl)phenyl)amino)quinazolin-8-yl)phenyl)-4-(dimethylamino)but-2-enamide |
| C051 | N-(3-(2-((4-(4-acetylpiperazin-1-yl)phenyl)amino)quinazolin-8-yl)-2-chlorophenyl)acrylamide |
| C052 | (E)-4-(dimethylamino)-N-(3-(2-((4-(4-methylpiperazin-1-yl)phenyl)amino)quinazolin-8-yl)phenyl)but-2-enamide |
| C053 | N-(3-(2-((4-(4-(2-fluoroethyl)piperazin-1-yl)phenyl)amino)quinazolin-8-yl)phenyl)acrylamide |
| C054 | N-(2-chloro-3-(2-((4-(4-methylpiperazin-1-yl)phenyl)amino)quinazolin-8-yl)phenyl)acrylamide |
| C055 | N-(3-(2-((2-methoxy-6-(4-methylpiperazin-1-yl)pyridin-3-yl)amino)quinazolin-8-yl)phenyl)acrylamide |
| C056 | N-(3-(2-((4-(4-(2,2-difluoroethyl)piperazin-1-yl)phenyl)amino)quinazolin-8-yl)phenyl)acrylamide |
| C057 | N-(4-(2-((4-(4-methylpiperazin-1-yl)phenyl)amino)quinazolin-8-yl)pyridin-2-yl)acrylamide |
| C058 | N-(5-(2-((4-(4-(2-fluoroethyl)piperazin-1-yl)phenyl)amino)quinazolin-8-yl)pyridin-3-yl)acrylamide |
| C059 | N-(3-(2-((4-(4-(2-hydroxyethyl)piperazin-1-yl)phenyl)amino)quinazolin-8-yl)phenyl)acrylamide |
| C060 | (E)-N-(3-(2-((4-(4-acetylpiperazin-1-yl)phenyl)amino)quinazolin-8-yl)-2-chlorophenyl)-4-(dimethylamino)but-2-enamide |
| C061 | N-(2-fluoro-3-(2-((4-(4-(2-fluoroethyl)piperazin-1-yl)phenyl)amino)quinazolin-8-yl)phenyl)acrylamide |
| C062 | (E)-4-(dimethylamino)-N-(2-fluoro-3-(2-((4-(4-methylpiperazin-1-yl)phenyl)amino)quinazolin-8-yl)phenyl)but-2-enamide |
| C063 | N-(2-methoxy-3-(2-((4-(4-methylpiperazin-1-yl)phenyl)amino)quinazolin-8-yl)phenyl)acrylamide |
| C064 | N-(3-(2-((4-((2-fluoroethyl)(methyl)amino)phenyl)amino)quinazolin-8-yl)phenyl)acrylamide |
| C065 | N-(2-fluoro-3-(2-((4-((2-fluoroethyl)(methyl)amino)phenyl)amino)quinazolin-8-yl)phenyl)acrylamide |
| C066 | N-(3-(2-((4-((2-hydroxyethyl)amino)phenyl)amino)quinazolin-8-yl)phenyl)acrylamide |
| C067 | N-(4-fluoro-3-(2-((4-(4-methylpiperazin-1-yl)phenyl)amino)quinazolin-8-yl)phenyl)acrylamide |
| C068 | N-(2-cyano-3-(2-((4-(4-methylpiperazin-1-yl)phenyl)amino)quinazolin-8-yl)phenyl)acrylamide |
| C069 | N-(3-(2-((3-fluoro-4-(4-methylpiperazin-1-yl)phenyl)amino)quinazolin-8-yl)phenyl)acrylamide |
| C070 | 1-(4-(2-((4-(4-methylpiperazin-1-yl)phenyl)amino)quinazolin-8-yl)piperazin-1-yl)prop-2-en-1-one |
| C071 | 1-(3-(2-((4-(4-methylpiperazin-1-yl)phenyl)amino)quinazolin-8-yl)-5,6-dihydropyridin-1(2H)-yl)prop-2-en-1-one |
| C072 | N-(3-(2-((3-chloro-4-(4-methylpiperazin-1-yl)phenyl)amino)quinazolin-8-yl)phenyl)acrylamide |
| C073 | N-(4-chloro-3-(2-((4-(4-methylpiperazin-1-yl)phenyl)amino)quinazolin-8-yl)phenyl)acrylamide |
| C074 | N-(3-(2-((3-cyano-4-(4-methylpiperazin-1-yl)phenyl)amino)quinazolin-8-yl)phenyl)acrylamide |
| C075 | N-(3-(2-((3-methoxy-4-(4-methylpiperazin-1-yl)phenyl)amino)quinazolin-8-yl)phenyl)acrylamide |
| C076 | methyl 4-(4-((8-(3-acrylamidophenyl)quinazolin-2-yl)amino)phenyl)piperazine-1-carboxylate |
| C077 | N-(3-(2-((4-(3-(hydroxymethyl)-4-methylpiperazin-1-yl)phenyl)amino)quinazolin-8-yl)phenyl)acrylamide |
| C078 | N-(3-(2-((4-((1-(2-fluoroethyl)azetidin-3-yl)oxy)phenyl)amino)quinazolin-8-yl)phenyl)acrylamide |
| C079 | N-(3-(2-((4-((3-fluoro-1-methylpiperidin-4-yl)oxy)phenyl)amino)quinazolin-8-yl)phenyl)acrylamide |
| C080 | N-(2-fluoro-3-(2-((4-((3-fluoro-1-methylpiperidin-4-yl)oxy)phenyl)amino)quinazolin-8-yl)phenyl)acrylamide |
| C081 | N-(3-(2-((5-chloro-6-(4-methylpiperazin-1-yl)pyridin-3-yl)amino)quinazolin-8-yl)phenyl)acrylamide |
| C082 | N-(3-(2-((4-(4-(2-hydroxyacetyl)piperazin-1-yl)phenyl)amino)quinazolin-8-yl)phenyl)acrylamide |

TABLE 1-continued

Illustrative Compounds of the Present Invention

| Compound No. | Chemical Name |
|---|---|
| C083 | 4-(4-((8-(3-acrylamidophenyl)quinazolin-2-yl)amino)phenyl)-N-methylpiperazine-1-carboxamide |
| C084 | N-(3-(2-((4-(4-propionylpiperazin-1-yl)phenyl)amino)quinazolin-8-yl)phenyl)acrylamide |
| C085 | 5-((8-(3-acrylamidophenyl)quinazolin-2-yl)amino)-2-(4-methylpiperazin-1-yl)benzamide |
| C086 | N-(3-(2-((5-cyano-6-(4-methylpiperazin-1-yl)pyridin-3-yl)amino)quinazolin-8-yl)phenyl)acrylamide |
| C087 | N-(3-(7-fluoro-2-((4-(4-methylpiperazin-1-yl)phenyl)amino)quinazolin-8-yl)phenyl)acrylamide |
| C088 | N-(3-(7-fluoro-2-((4-(4-(2-fluoroethyl)piperazin-1-yl)phenyl)amino)quinazolin-8-yl)phenyl)acrylamide |
| C089 | methyl 4-(4-((8-(3-acrylamidophenyl)quinazolin-2-yl)amino)phenyl)-1-methylpiperazine-2-carboxylate |
| C090 | 4-(4-((8-(3-acrylamidophenyl)quinazolin-2-yl)amino)phenyl)-1-methylpiperazine-2-carboxylic acid |
| C091 | N-(3-(2-((4-(2-oxooxazolidin-3-yl)phenyl)amino)quinazolin-8-yl)phenyl)acrylamide |
| C092 | N-(3-(2-((4-(4-(methylsulfonyl)piperazin-1-yl)phenyl)amino)quinazolin-8-yl)phenyl)acrylamide |
| C093 | 4-(4-((8-(3-acrylamidophenyl)quinazolin-2-yl)amino)phenyl)-1-methylpiperazine-2-carboxamide |
| C094 | N-(3-(2-((4-(1H-imidazol-1-yl)phenyl)amino)quinazolin-8-yl)phenyl)acrylamide |
| C095 | N-(3-(2-((4-(3-oxomorpholino)phenyl)amino)quinazolin-8-yl)phenyl)acrylamide |
| C096 | N-(3-(2-((4-(2-oxopyrrolidin-1-yl)phenyl)amino)quinazolin-8-yl)phenyl)acrylamide |
| C097 | N-(3-(2-((4-(2-oxoimidazolidin-1-yl)phenyl)amino)quinazolin-8-yl)phenyl)acrylamide |
| C098 | N-(3-(2-((4-(3-hydroxypyrrolidin-1-yl)phenyl)amino)quinazolin-8-yl)phenyl)acrylamide |
| C099 | N-(3-(2-((4-((1-(2-hydroxyethyl)azetidin-3-yl)amino)phenyl)amino)quinazolin-8-yl)phenyl)acrylamide |
| C100 | N-(4-cyano-3-(2-((4-(4-methylpiperazin-1-yl)phenyl)amino)quinazolin-8-yl)phenyl)acrylamide |
| C101 | methyl 2-acrylamido-6-(2-((4-(4-methylpiperazin-1-yl)phenyl)amino)quinazolin-8-yl)benzoate |
| C102 | N-(3-(2-((4-(1,4-oxazepan-4-yl)phenyl)amino)quinazolin-8-yl)phenyl)acrylamide |
| C103 | N-(3-(2-((4-((1-(2-fluoroethyl)azetidin-3-yl)amino)phenyl)amino)quinazolin-8-yl)phenyl)acrylamide |
| C104 | methyl 2-((8-(3-acrylamidophenyl)quinazolin-2-yl)amino)-5-(4-methylpiperazin-1-yl)benzoate |
| C105 | N-(3-(2-((4-((3-fluoro-1-methylpiperidin-4-yl)amino)phenyl)amino)quinazolin-8-yl)phenyl)acrylamide |
| C106 | N-(3-(2-((4-(4-methyl-2-oxopiperazin-1-yl)phenyl)amino)quinazolin-8-yl)phenyl)acrylamide |
| C107 | N-(3-(2-((4-(2-methoxyethoxy)phenyl)amino)quinazolin-8-yl)phenyl)acrylamide |
| C108 | N-(3-(2-((4-(2-hydroxyethoxy)phenyl)amino)quinazolin-8-yl)phenyl)acrylamide |
| C109 | N-(3-(2-((4-(2-(azetidin-1-yl)ethoxy)phenyl)amino)quinazolin-8-yl)phenyl)acrylamide |
| C110 | N-(3-(2-((4-(2-(dimethylamino)ethoxy)phenyl)amino)quinazolin-8-yl)phenyl)acrylamide |
| C111 | N-(3-(2-((4-((tetrahydro-2H-pyran-4-yl)amino)phenyl)amino)quinazolin-8-yl)phenyl)acrylamide |
| C112 | N-(3-(2-((4-((tetrahydro-2H-pyran-4-yl)oxy)phenyl)amino)quinazolin-8-yl)phenyl)acrylamide |
| C113 | (S)-N-(3-(2-((4-((tetrahydrofuran-3-yl)oxy)phenyl)amino)quinazolin-8-yl)phenyl)acrylamide |
| C114 | (S)-N-(3-(2-((4-((tetrahydrofuran-3-yl)amino)phenyl)amino)quinazolin-8-yl)phenyl)acrylamide |
| C115 | (R)-N-(3-(2-((4-((tetrahydrofuran-3-yl)amino)phenyl)amino)quinazolin-8-yl)phenyl)acrylamide |
| C116 | N-(3-(2-((4-(4-methyl-3-oxopiperazin-1-yl)phenyl)amino)quinazolin-8-yl)phenyl)acrylamide |
| C117 | N-(3-(2-((4-(3-oxopiperazin-1-yl)phenyl)amino)quinazolin-8-yl)phenyl)acrylamide |
| C118 | N-(3-(2-((4-((1-methylpiperidin-4-yl)amino)phenyl)amino)quinazolin-8-yl)phenyl)acrylamide |
| C119 | (R)-N-(3-(2-((4-((tetrahydrofuran-3-yl)oxy)phenyl)amino)quinazolin-8-yl)phenyl)acrylamide |
| C120 | N-(3-(2-((4-((1-acetylpiperidin-4-yl)amino)phenyl)amino)quinazolin-8-yl)phenyl)acrylamide |

TABLE 1-continued

Illustrative Compounds of the Present Invention

| Compound No. | Chemical Name |
|---|---|
| C121 | (S)-N-(3-(2-((4-((1-methylpyrrolidin-3-yl)oxy)phenyl)amino)quinazolin-8-yl)phenyl)acrylamide |
| C122 | N-(3-(2-((4-((1-acetylazetidin-3-yl)oxy)phenyl)amino)quinazolin-8-yl)phenyl)acrylamide |
| C123 | (R)-N-(3-(2-((4-((1-methylpyrrolidin-3-yl)oxy)phenyl)amino)quinazolin-8-yl)phenyl)acrylamide |
| C124 | N-(3-(2-((4-((1-acetylazetidin-3-yl)amino)phenyl)amino)quinazolin-8-yl)phenyl)acrylamide |
| C125 | N-(3-(2-((4-((1-acetylpiperidin-4-yl)oxy)phenyl)amino)quinazolin-8-yl)phenyl)acrylamide |
| C126 | N-(3-(2-((4-((1-methylpiperidin-4-yl)oxy)phenyl)amino)quinazolin-8-yl)phenyl)acrylamide |
| C127 | (S)-N-(3-(2-((4-((1-methylpyrrolidin-3-yl)amino)phenyl)amino)quinazolin-8-yl)phenyl)acrylamide |
| C128 | (S)-N-(3-(2-((4-((1-acetylpyrrolidin-3-yl)amino)phenyl)amino)quinazolin-8-yl)phenyl)acrylamide |
| C129 | (R)-N-(3-(2-((4-((1-methylpyrrolidin-3-yl)amino)phenyl)amino)quinazolin-8-yl)phenyl)acrylamide |
| C130 | (R)-N-(3-(2-((4-((1-acetylpyrrolidin-3-yl)amino)phenyl)amino)quinazolin-8-yl)phenyl)acrylamide |
| C131 | (S)-N-(3-(2-((4-((1-acetylpyrrolidin-3-yl)oxy)phenyl)amino)quinazolin-8-yl)phenyl)acrylamide |
| C132 | N-(3-(2-((4-(4-methylpiperazin-1-yl)phenyl)amino)quinazolin-8-yl)-1H-pyrazol-5-yl)acrylamide |
| C133 | (R)-N-(3-(2-((4-((1-acetylpyrrolidin-3-yl)oxy)phenyl)amino)quinazolin-8-yl)phenyl)acrylamide |
| C134 | N-(3-(2-((4-((2-fluoroethyl)amino)phenyl)amino)quinazolin-8-yl)phenyl)acrylamide |
| C135 | N-(3-(2-((4-((2,2-difluoroethyl)amino)phenyl)amino)quinazolin-8-yl)phenyl)acrylamide |
| C136 | N-(3-(2-((4-((1-(2-fluoroethyl)piperidin-4-yl)oxy)phenyl)amino)quinazolin-8-yl)phenyl)acrylamide |
| C137 | N-(3-(2-((4-((1-(2-hydroxyethyl)piperidin-4-yl)oxy)phenyl)amino)quinazolin-8-yl)phenyl)acrylamide |
| C138 | N-(3-(2-((4-((1-(2-fluoroethyl)piperidin-4-yl)amino)phenyl)amino)quinazolin-8-yl)phenyl)acrylamide |
| C139 | N-(3-(2-((4-((1-(2-hydroxyethyl)piperidin-4-yl)amino)phenyl)amino)quinazolin-8-yl)phenyl)acrylamide |
| C140 | N-(3-(2-((2-fluoro-4-((1-methylpiperidin-4-yl)amino)phenyl)amino)quinazolin-8-yl)phenyl)acrylamide |
| C141 | N-(3-(2-((2-fluoro-4-((1-methylpiperidin-4-yl)oxy)phenyl)amino)quinazolin-8-yl)phenyl)acrylamide |
| C142 | N-(3-(2-((3-fluoro-4-(4-(2-hydroxyethyl)piperazin-1-yl)phenyl)amino)quinazolin-8-yl)phenyl)acrylamide |
| C143 | N-(3-(2-((3-fluoro-4-(4-(2-hydroxy-2-methylpropyl)piperazin-1-yl)phenyl)amino)quinazolin-8-yl)phenyl)acrylamide |
| C144 | N-(3-(2-((2-fluoro-4-((1-(2-hydroxyethyl)piperidin-4-yl)oxy)phenyl)amino)quinazolin-8-yl)phenyl)acrylamide |
| C145 | N-(3-(2-((4-(4-(2-hydroxy-2-methylpropyl)piperazin-1-yl)phenyl)amino)quinazolin-8-yl)phenyl)acrylamide |
| C146 | N-(3-(2-((3,5-difluoro-4-(4-methylpiperazin-1-yl)phenyl)amino)quinazolin-8-yl)phenyl)acrylamide |
| C147 | N-(3-(2-((2-fluoro-4-(4-(2-hydroxyethyl)piperazin-1-yl)phenyl)amino)quinazolin-8-yl)phenyl)acrylamide |
| C148 | N-(3-(2-((2,6-difluoro-4-(4-methylpiperazin-1-yl)phenyl)amino)quinazolin-8-yl)phenyl)acrylamide |
| C149 | N-(3-(2-((2-fluoro-4-(4-(2-hydroxy-2-methylpropyl)piperazin-1-yl)phenyl)amino)quinazolin-8-yl)phenyl)acrylamide |
| C150 | N-(3-(2-((4-(4-(2-amino-2-oxoethyl)piperazin-1-yl)phenyl)amino)quinazolin-8-yl)phenyl)acrylamide |
| C151 | N-(3-(2-((2,3-difluoro-4-(4-(2-hydroxyethyl)piperazin-1-yl)phenyl)amino)quinazolin-8-yl)phenyl)acrylamide |
| C152 | N-(3-(2-((4-(4-(2-methoxyethyl)piperazin-1-yl)phenyl)amino)quinazolin-8-yl)phenyl)acrylamide |
| C153 | N-(3-(2-((2-fluoro-4-(4-(2-methoxyethyl)piperazin-1-yl)phenyl)amino)quinazolin-8-yl)phenyl)acrylamide |
| C154 | N-(3-(2-((4-(4-(2-amino-2-oxoethyl)piperazin-1-yl)-2-fluorophenyl)amino)quinazolin-8-yl)phenyl)acrylamide |
| C155 | N-(3-(2-((3-fluoro-4-(4-(2-methoxyethyl)piperazin-1-yl)phenyl)amino)quinazolin-8-yl)phenyl)acrylamide |
| C156 | N-(3-(2-((2,3-difluoro-4-(4-methylpiperazin-1-yl)phenyl)amino)quinazolin-8-yl)phenyl)acrylamide |
| C157 | N-(3-(2-((2-fluoro-4-((1-(2-fluoroethyl)piperidin-4-yl)oxy)phenyl)amino)quinazolin-8-yl)phenyl)acrylamide |
| C158 | N-(3-(2-((4-(1H-pyrazol-1-yl)phenyl)amino)quinazolin-8-yl)phenyl)acrylamide |

TABLE 1-continued

Illustrative Compounds of the Present Invention

| Compound No. | Chemical Name |
|---|---|
| C159 | N-(3-(2-((4-(1H-pyrazol-4-yl)phenyl)amino)quinazolin-8-yl)phenyl)acrylamide |
| C160 | N-(3-(2-((2,5-difluoro-4-(4-methylpiperazin-1-yl)phenyl)amino)quinazolin-8-yl)phenyl)acrylamide |
| C161 | N-(3-(2-((2,5-difluoro-4-(4-(2-methoxyethyl)piperazin-1-yl)phenyl)amino)quinazolin-8-yl)phenyl)acrylamide |
| C162 | N-(3-(2-((2,5-difluoro-4-(4-(2-hydroxyethyl)piperazin-1-yl)phenyl)amino)quinazolin-8-yl)phenyl)acrylamide |
| C163 | N-(3-(2-((2,5-difluoro-4-(4-(2-hydroxy-2-methylpropyl)piperazin-1-yl)phenyl)amino)quinazolin-8-yl)phenyl)acrylamide |
| C164 | N-(3-(2-((4-(4-(2-amino-2-oxoethyl)piperazin-1-yl)-3-fluorophenyl)amino)quinazolin-8-yl)phenyl)acrylamide |
| C165 | N-(3-(2-((2,3-difluoro-4-(4-(2-hydroxy-2-methylpropyl)piperazin-1-yl)phenyl)amino)quinazolin-8-yl)phenyl)acrylamide |
| C166 | N-(3-(2-((2,3-difluoro-4-(4-(2-methoxyethyl)piperazin-1-yl)phenyl)amino)quinazolin-8-yl)phenyl)acrylamide |

In some embodiments, a compound of Formula I binds to a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAP-KAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I binds to a kinase selected from the group consisting of EGFR, HER2, HER4, KDR, ALK, ARK5, BLK, BTK, FMS, ITK, JAK1, JAK2, JAK3, PLK1, PLK2, PLK3, PLK4, FAK, and SNARK In some embodiments, the compound of Formula I binds to a kinase selected from the group consisting of EGFR mutants such as EGFR del E746-A750, EGFR del E747-E749/A750P, EGFR del E747-S752/P753S, EGFR del E747-T751/Sins/A750P, EGFR del S752-I759, EGFR G719S, EGFR G719C, EGFR L861Q, EGFR L858R, EGFR T790M, EGFR L858R/T790M. For example, the compound of Formula I binds to a kinase which is EGFR L858R, EGFR T790M or EGFR L858R/T790M mutant. In some embodiments, a compound of Formula I binds to a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAP-KAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof, with a Kd which is lower than 50 µM, 25 µM, 10 µM, 5 µM, or 1 µM as measured in an in vitro assay. For example, the compound of Formula I binds to a kinase selected from the group consisting of EGFR, EGFR L858R, EGFR T790M, EGFR del E746-A750, or EGFR L858R/T790M mutant, Her2, Her4, Fak, FGFR1, FGFR2, FGFR3, FGFR4, Btk, Met, Pim1, Pim2, Pim3, Pyk2, KDR, Src and Ret, and any mutated versions thereof with a Kd which is lower than 50 µM, 25 µM, 10 µM, 5 µM, or 1 µM as measured in an in vitro assay. In some embodiments, the compound of Formula I binds to a kinase selected from the group consisting of Btk, KDR, EGFR, EGFR L858R, EGFR T790M or EGFR L858R/T790M mutant with a Kd which is lower than 50 µM, 25 µM, 10 µM, 5 µM, or 1 µM as measured in an in vitro assay. For example, the compound of Formula I binds to a kinase which is EGFR, EGFR L858R, EGFR T790M, EGFR del E746-A750, EGFR L858R/T790M mutant with a Kd which is lower than 50 µM, 25 µM, 10 µM, 5 µM, or 1 µM as measured in an in vitro assay.

In some embodiments, a compound of Formula I inhibits a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAP-KAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I inhibits a kinase selected from the group consisting of EGFR, Btk, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof. In some embodiments, the compound of Formula I inhibits a kinase selected from the group consisting of EGFR, EGFR L858R, EGFR del E746-A750, EGFR T790M or EGFR L858R/T790M mutant. For example, the compound of Formula I inhibits a kinase which is EGFR or EGFR L858R/T790M mutant. In some embodiments, a compound of Formula I inhibits a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDG- FRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof with an $IC_{50}$ in an in vitro assay of 10 µM, 5 µM, 2 µM, 1 µM, 500 nM, 200 nM, 100 nM or less as ascertained in an in vitro kinase assay. For example, the compound of Formula I inhibits a kinase selected from the group consisting of EGFR., HER2, HER3, HER4, KDR, ALK, ARK5, BLK, BTK, FGFR1, FGFR2, FGFR3, FMS, ITK, JAK1, JAK2, JAK3, PLK1, PLK2, PLK3, PLK4, FAK, and SNARK, Src and Ret, and any mutated versions thereof with an $IC_{50}$ in an in vitro assay of 10 µM, 5 µM, 2 µM, 1 µM, 500 nM, 200 nM, 100 nM or less as ascertained in an in vitro kinase assay. In some embodiments, the compound of Formula I inhibits a kinase selected from the group consisting of EGFR, EGFR L858R, EGFR del E746-A750, EGFR T790M or EGFR L858R/T790M mutant with an $IC_{50}$ in an in vitro assay of 10 µM, 5 µM, 2 µM, 1 µM, 500 nM, 200 nM, 100 nM or less as ascertained in an in vitro kinase assay. For example, the compound of Formula I inhibits a kinase which is EGFR or EGFR L858R/T790M mutant with an $IC_{50}$ in an in vitro assay of 10 µM, 5 µM, 2 µM, 1 µM, 500 nM, 200 nM, 100 nM or less as ascertained in an in vitro kinase assay.

In some embodiments, the compound of Formula I inhibits the activity of one or more kinases selected from the group consisting of EGFR, EGFR L858R, EGFR T790M or EGFR L858R/T790M with an $IC_{50}$ in an in vitro assay of 1 µM, 500 nM, 200 nM, 100 nM, 50 nM, 25 nM or less as ascertained in an in vitro kinase assay.

In some embodiments, the compound of Formula I selectively inhibits the activity of one or more kinases selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I selectively inhibits the activity of one or more kinases selected from the group consisting of EGFR, EGFR L858R, EGFR T790M, EGFR del E746-A750 or EGFR L858R/T790M, HER2, HER3, HER4, KDR, ALK, ARK5, BLK, BTK, FGFR1, FGFR2, FGFR3, FMS, ITK, JAK1, JAK2, JAK3, PLK1, PLK2, PLK3, PLK4, FAK, and SNARK, Src and Ret, In some embodiments, the compound of Formula I selectively inhibits the activity of one or more kinases selected from the group consisting of EGFR, EGFR L858R, EGFR T790M, EGFR del E746-A750 or EGFR L858R/T790M mutant.

In some embodiments, the compound of Formula I selectively inhibits the activity of, EGFR L858R, EGFR T790M, EGFR del E746-A750, or EGFR L858R/T790M mutant relative to one or more kinases selected from the group consisting of ABL1, AKT1 (PKB alpha), AURKB (Aurora B), BLK, BTK, CDK1/cyclin B, CHEK1 (CHK1), CSF1R (FMS), CSNK1G2 (CK1 gamma 2), EGFR (ErbB1), FGFR1, FGFR2, FGFR3, FGR, FLT3, FRAP1 (mTOR), FYN, IGF1R, IKBKB (IKK beta), INSR, JAK1, JAK2, JAK3, KDR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES 1. In some embodiments, the compound of Formula I selectively inhibits the activity of one or more kinases selected from the group consisting of EGFR L858R, EGFR T790M EGFR del E746-A750, or EGFR L858R/ T790M with an $IC_{50}$ which is $\frac{1}{2}$, $\frac{1}{3}^{rd}$, $\frac{1}{4}^{th}$, $\frac{1}{5}^{th}$, $\frac{1}{7}^{th}$, $\frac{1}{10}^{th}$, $\frac{1}{15}^{th}$, $\frac{1}{20}^{th}$, $\frac{1}{25}^{th}$, $\frac{1}{30}^{th}$, $\frac{1}{40}^{th}$, $\frac{1}{50}^{th}$, $\frac{1}{100}^{th}$, $\frac{1}{150}^{th}$, $\frac{1}{200}^{th}$, $\frac{1}{300}^{th}$, $\frac{1}{400}^{th}$, $\frac{1}{500}^{th}$, $\frac{1}{1000}^{th}$, $\frac{1}{2000}^{th}$ or less than the $IC_{50}$ for a kinase selected from the group consisting of ABL1, AKT1 (PKB alpha), AURKB (Aurora B), BLK, BTK, CDK1/cyclin B, CHEK1 (CHK1), CSNK1G2 (CK1 gamma 2), EGFR (ErbB1), FGFR1, FGFR2, FGFR3, FGR, FLT3, FRAP1 (mTOR), FYN, IGF1R, IKBKB (IKK beta), INSR, JAK1, JAK2, JAK3, KDR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES 1.

In some embodiments, one or more compounds of Formula I are capable of inhibiting cellular proliferation. For example, In some embodiments, one or more compounds of Formula I inhibit proliferation of tumor cells or tumor cell lines. For example, such cell lines express a kinase which is EGFR L858R, EGFR T790M, EGFR del E746-A750, or EGFR L858R/T790M mutant. In some embodiments, the compounds of Formula I inhibit A549, A431, HCC827 or H1975 cell proliferation in vitro or in an in vivo model such as a xenograft mouse model. In some embodiments, in vitro cultured HCC827 or H1975 cell proliferation may be inhibited with an $IC_{50}$ of less than 100 µM, 75 µM, 50 µM, 25 µM, 15 µM, 10 µM, 5 µM, 3 µM, 2 µM, 1 µM or less by one or more compounds of Formula I.

B. Methods of Making

Compounds disclosed herein may be prepared by the routes described below. Materials used herein are either commercially available or prepared by synthetic methods generally known in the art. These schemes are not limited to the compounds listed or by any particular substituents, which are employed for illustrative purposes. Although various steps of are described and depicted in Scheme A, the steps in some cases may be performed in a different order than the order shown in Scheme A. Various modifications to these synthetic reaction schemes may be made and will be suggested to one skilled in the art having referred to the disclosure contained in this Application. Numbering does not necessarily correspond to that of claims or other tables.

Scheme A

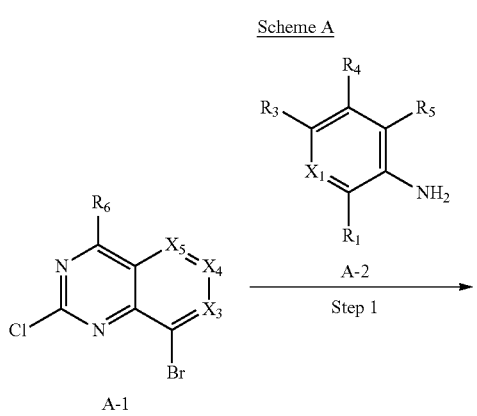

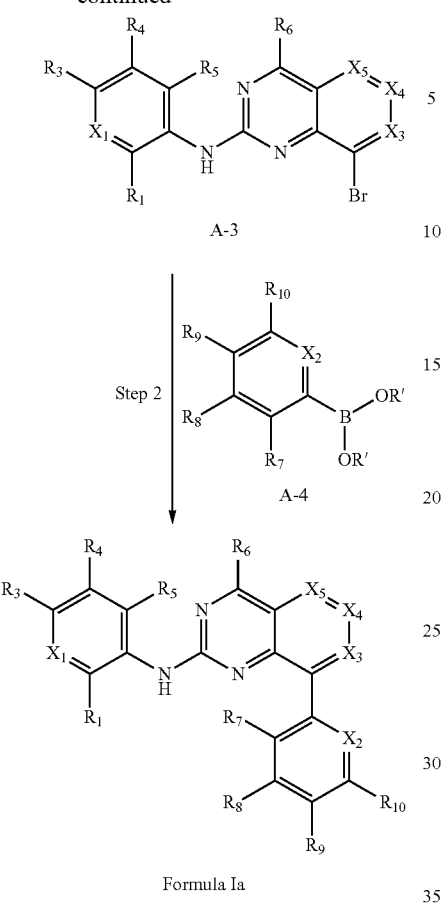

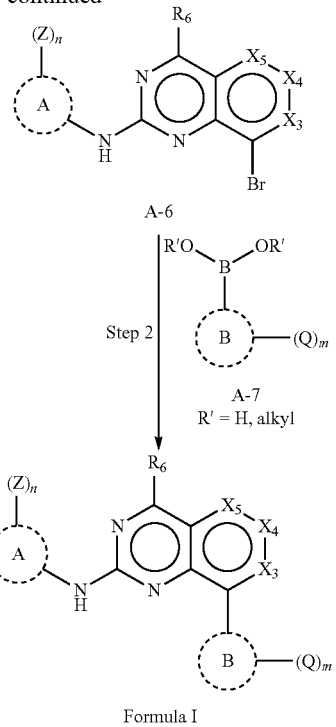

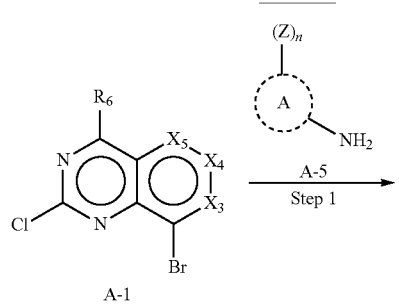

In Scheme A, A-1 is reacted with A-2 in the presence of a base. Suitable bases include Cs$_2$CO$_3$, NaH, KH, t-BuOK, LiH, and CaH$_2$. Suitable solvents include, but are not limited to, DMF, DMSO, DMA, and N-methyl piperidone. The reaction are generally carried out at a temperature ranging from 25 to 240° C. Suzuki cross-coupling reaction of A-3 with boronic acid or ester A-4 in the presence of a base, such as Na$_2$CO$_3$, K$_2$CO$_3$, Cs$_2$CO$_3$, and a Pd catalyst, gives compounds of Formula Ia. The reaction is generally carried out at a temperature ranging from 25 to 180° C. in a suitable solvent such as 1,4-dioxane, water, tetrahydrofuran, or a mixture thereof.

In Scheme B, A-1 is reacted with A-5 in the presence of a base. Suitable bases include Cs$_2$CO$_3$, NaH, KH, t-BuOK, LiH, and CaH$_2$. Suitable solvents include, but are not limited to, DMF, DMSO, DMA, and N-methyl piperidone. The reaction are generally carried out at a temperature ranging from 25 to 240° C. Suzuki cross-coupling reaction of A-6 with boronic acid or ester A-7 in the presence of a base, such as Na$_2$CO$_3$, K$_2$CO$_3$, Cs$_2$CO$_3$, and a Pd catalyst, gives compounds of Formula I. The reaction is generally carried out at a temperature ranging from 25 to 180° C. in a suitable solvent such as 1,4-dioxane, water, tetrahydrofuran, or a mixture thereof.

C. Pharmaceutical Compositions and Formulations

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising a compound of Formula I, and a pharmaceutically acceptable diluent(s), excipient(s), or carrier(s). In certain embodiments, the compounds described are administered as pharmaceutical compositions in which compounds of Formula I, are mixed with other active ingredients, as in combination therapy. Encompassed herein are all combinations of actives set forth in the combination therapies section below and throughout this disclosure. In specific embodiments, the pharmaceutical compositions include one or more compounds of Formula I.

A pharmaceutical composition, as used herein, refers to a mixture of a compound of Formula I, with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Formula I, provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of Formula I, is formulated in an aqueous solution. In specific embodiments, the aqueous solution is selected from, by way of example only, a physiologically compatible buffer, such as Hank's solution, Ringer's solution, or physiological saline buffer. In other embodiments, one or more compound of Formula I, is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including compounds of Formula I, are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a compound of Formula I is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Formula I are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula I are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula I, is accomplished by means of iontophoretic patches and the like. In certain embodiments, transdermal patches provide controlled delivery of the compounds of Formula I. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Formula I, are formulated for administration by inhalation. Various forms suitable for administration by inhalation include, but are not limited to, aerosols, mists or powders. Pharmaceutical compositions of Formula I, are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of Formula I, are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Formula I, are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula I, described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising at least one compound of Formula I, illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Formula I. The term "solubilizing agent"

generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

D. Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

E. Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, Ccompositions containing a compound provided herein formulated in a compatible pharmaceutical carrier are prepared, placed in an appropriate container, and labeled for treatment of an indicated condition.

F. Methods of Use

The chemical entities described herein are useful in the treatment, or in the preparation of a medicament for the treatment of various disorders. For example, compounds of Formula I are useful as inhibitors of protein kinases. In some embodiments, the chemical entities described herein are inhibitors of one or more kinases. For example, compounds of Formula I are inhibitors of EGFR and of mutants of such kinase, including the EGFR del E746-A750, EGFR del E747-E749/A750P, EGFR del E747-5752/P753S, EGFR del E747-T751/Sins/A750P, EGFR del S752-1759, EGFR G719S, EGFR G719C, EGFR L861Q, EGFR L858R, EGFR T790M or EGFR L858R/T790M mutant. Thus, without wishing to be bound by any particular theory, the compounds of Formula I are particularly useful for treating or lessening the severity of a disease, condition, or disorder where activation of one or more kinases, such as EGFR, which is implicated in the disease, condition, or disorder. When activation of EGFR kinase is implicated in a particular disease, condition, or disorder, the disease, condition, or disorder may also be referred to as "EGFR-mediated disease" or disease symptom. Accordingly, in another aspect, the present invention provides a method for treating or lessening the severity of a disease, condition, or disorder where activation of EGFR and/or other kinases is implicated in the disease state.

The inhibition of kinases may be assayed in vitro, in vivo or in a cell line. In vitro assays include assays that determine inhibition of either the phosphorylation activity or ATPase activity of activated kinase. Alternate in vitro assays quantitate the ability of the inhibitor to bind to kinase. Inhibitor binding may be measured by radiolabelling the inhibitor prior to binding, isolating the inhibitor, complex and determining the amount of radiolabel bound. Alternatively, inhibitor binding may be determined by running a competition experiment where new inhibitors are incubated with kinase bound to known radioligands. At 1 micro-molar concentration, one or more compounds of the present invention exhibits at least about 50%, 60%, 70, 80%, 90% or even higher inhibition of kinases including EGFR, EGFR L858R, EGFR del E746-A750, EGFR T790M or EGFR L858R/T790M.

The chemical entities described herein may be prepared in substantially pure form, typically by standard chromatographic methods, prior to formulation in a pharmaceutically acceptable form.

The chemical entities described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the chemical entities described herein are used for the treatment of cancers of the
  i. digestive system including, without limitation, the esophagus, stomach, small intestine, colon (including colorectal), liver & intrahepatic bile duct, gallbladder & other biliary, pancreas, and other digestive organs;
  ii. respiratory system, including without limitation, larynx, lung & bronchus, and other respiratory organs;
  iii. skin;
  iv. thyroid;
  v. breast;
  vi. genital system, including without limitation, uterine cervix, ovary, and prostate;
  vii. urinary system, including without limitation, urinary bladder and kidney and renal pelvis; and
  viii. oral cavity & pharynx, including without limitation, tongue, mouth, pharynx, and other oral cavity.

In some embodiments, the chemical entities described herein are used for the treatment of colon cancer, liver cancer, lung cancer, melanoma, thyroid cancer, breast cancer, ovarian cancer, and oral cancer.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3 methylenedioxyanilino)-7-[2-(4-methylpiperazin-1-yl)ethoxy]-5-tetrahydropyran-4yloxy-quinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chem., 2004, 47, 66586661) and bosutinib (SK1-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-{4-fluoro-2-methylindol-5-yloxy)-6-methoxy-7-(3pyrrolidin-1-ylpropoxy) quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

In certain embodiments, the at least one chemical entity is administered in combination with one or more agents chosen from pacliataxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

When a chemical entity described herein is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one chemical entity is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the chemical entity, such as including, e.g., from about 1 mg to about 1000 mg. The quantity of the at least one chemical entity in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one chemical entity described herein is not the sole active ingredient, it may be possible to administer lesser amounts of the at least one chemical entity and still have therapeutic or prophylactic effect.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The amount and frequency of administration of the at least one chemical entities described herein, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one chemical entities described herein need not be administered in the same pharmaceutical composition as a chemotherapeutic agent, and may, because of different physical and chemical characteristics, be administered by a different route. For example, the chemical entities/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemical entity (and where appropriate, chemotherapeutic agent and/or radiation) will depend upon the diagnosis of the attending physicians and their judgment of the condition of the subject and the appropriate treatment protocol.

The chemical entities described herein (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the chemical entity/composition.

In combinational applications and uses, the chemical entity/composition and the chemotherapeutic agent and/or radiation need not be administered simultaneously or essentially simultaneously, and the initial order of administration of the chemical entity/composition, and the chemotherapeutic agent and/or radiation, may not be important. Thus, the at least one chemical entity described herein may be administered first followed by the administration of the chemotherapeutic agent and/or radiation; or the chemotherapeutic agent and/or radiation may be administered first followed by the administration of the at least one chemical entity described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one chemical entity described herein followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that references to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Example 1: Preparation of N-(3-(2-((2-methoxy-4-morpholinophenyl)amino)quinazolin-8-yl)phenyl)acrylamide

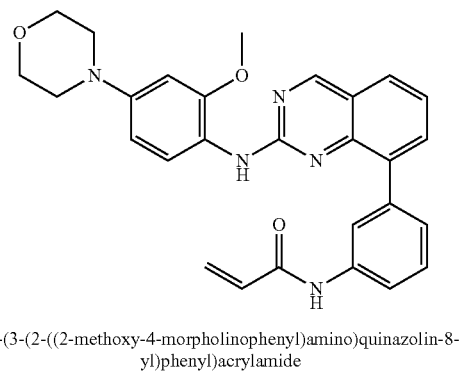

N-(3-(2-((2-methoxy-4-morpholinophenyl)amino)quinazolin-8-yl)phenyl)acrylamide

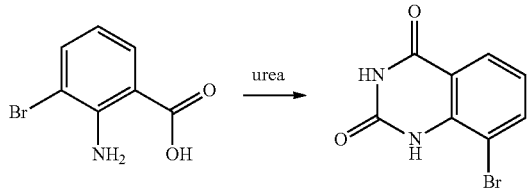

A mixture of 2-amino-3-bromobenzoic acid (10.8 g, 50 mmol, 1 eq.) and urea (15 g, 250 mmol, 5 eq.) was stirred at 200° C. for 3 h, then cooled and poured into ice-water. The solid was collected by filtration, washed with H$_2$O for three times, and dried in vacuo to afford 8-bromoquinazoline-2,4(1H,3H)-dione as a yellow solid (12.1 g, ca. 100% yield).

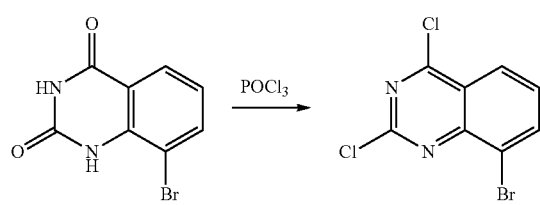

To a mixture of 8-bromoquinazoline-2,4(1H,3H)-dione (12.1 g, 50 mmol, 1 eq.) in POCl$_3$ (130 mL) was added DMF (0.5 mL). The mixture was stirred at 130° C. for 12 h, then cooled to r.t. and concentrated. The resulting residue was dissolved in EA (100 mL) and poured into ice-water with vigorous stirring. The organic phase was separated and washed with brine, dried over anhydrous Na$_2$SO$_4$ and concentrated. The resulting residue was purified via column chromatography (PE/EA==10:1, v/v) to afford 8-bromo-2,4-dichloroquinazoline as a yellow solid (9.1 g, 60% yield).

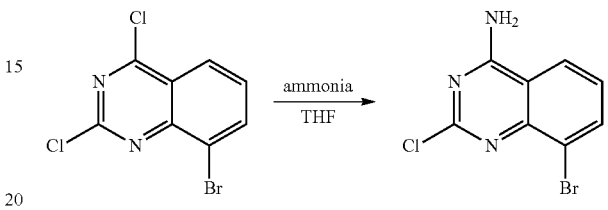

To a solution of ammonia hydroxide (25 mL, 330 mmol, 10 eq.) in THF (50 mL) cooled to 0° C. was added a solution of 8-bromo-2,4-dichloroquinazoline (9.1 g, 32.7 mmol, 1 eq.) in THF (50 mL). The mixture was stirred at 0° C. for 30 min, then diluted with EA (100 mL), washed with brine, dried over anhydrous Na$_2$SO$_4$ and concentrated. The resulting residue was purified via column chromatography (PE/EA=10:1, v/v) to afford 8-bromo-2-chloroquinazolin-4-amine as a yellow solid (7.1 g, 83.5% yield).

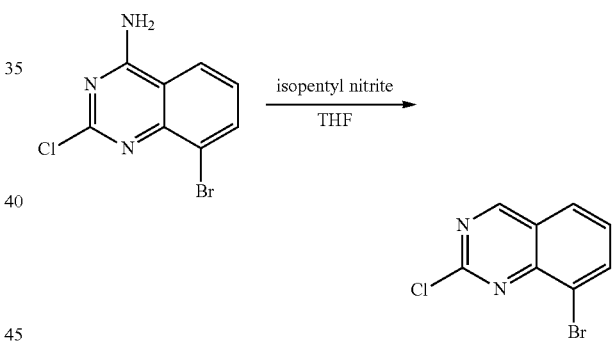

To a solution of 8-bromo-2-chloroquinazolin-4-amine (7.1 g, 27 mmol, 1 eq.) in THF (80 mL) at 70° C. was added isopentyl nitrite (14 mL, 108 mmol, 4 eq.) dropwise. The resulting mixture was stirred at 70° C. for 12 h, then cooled to r.t. and concentrated. The resulting residue was purified via column chromatography (PE/EA=5:1, v/v) to afford 8-bromo-2-chloroquinazoline as a yellow solid (1.5 g, 23% yield).

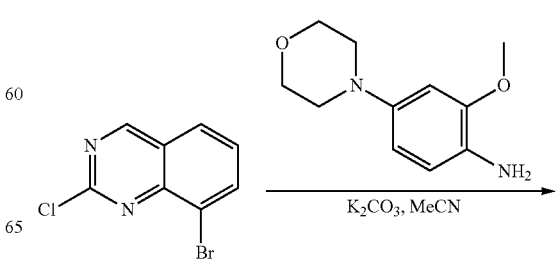

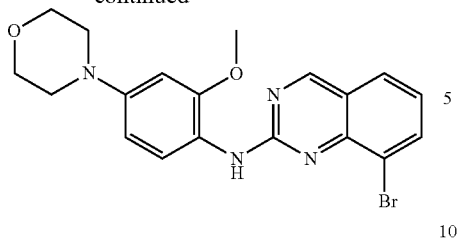

To a solution of 2-methoxy-4-morpholinoaniline (104 mg, 0.5 mmol, 1 eq.) and 8-bromo-2-chloroquinazoline (121 mg, 0.5 mmol, 1 eq.) in MeCN (10 mL) was added K$_2$CO$_3$ (138 mg, 1 mmol, 2 eq.). The mixture was stirred at 120° C. for 12 h, then cooled to r.t. and concentrated. The resulting residue was purified via column chromatography (PE/EA=3:1, v/v) to afford 8-bromo-N-(2-methoxy-4-morpholinophenyl)quinazolin-2-amine as a yellow solid (29 mg, 29% yield).

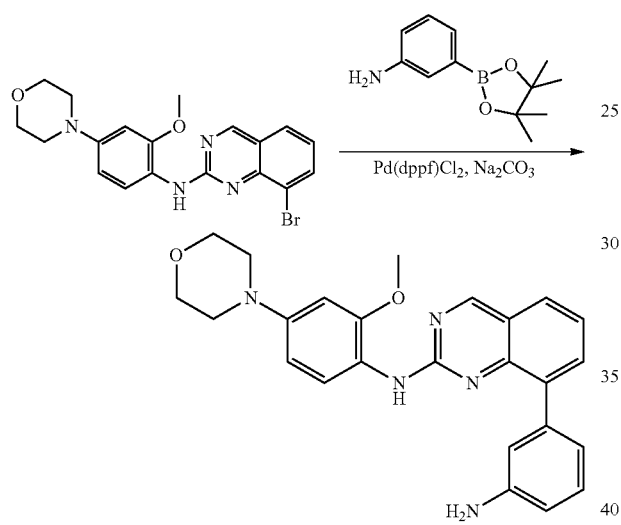

To a solution of 8-bromo-N-(2-methoxy-4-morpholinophenyl)quinazolin-2-amine (60 mg, 0.15 mmol, 1 eq.) and 3-(4,4,5,5-tetramethyl-1,3,2-dioxaborolan-2-yl)aniline (50 mg, 0.23 mmol, 1.5 eq.) in dioxane (4 mL) was added Na$_2$CO$_3$ (31.8 mg, 0.3 mmol, 2 eq.), followed by Pd(dppf)Cl$_2$ (6 mg, 0.007 mmol, 0.05 eq.) under N$_2$ protection. The mixture was stirred at 90° C. for 12 h, then cooled to r.t., diluted with EA (40 mL) and filtered. The filtrate was concentrated. The resulting residue was purified via column chromatography (PE/EA=1/3, v/v) to afford 8-(3-aminophenyl)-N-(2-methoxy-4-morpholinophenyl)quinazolin-2-amine as a yellow solid (41 mg, 64% yield).

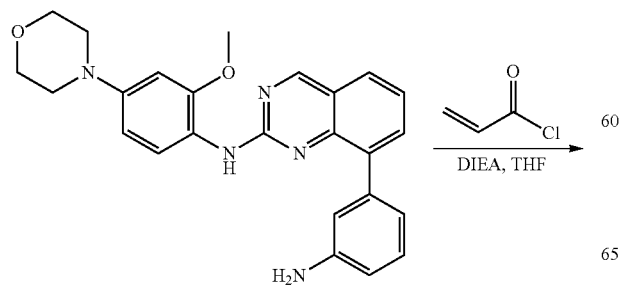

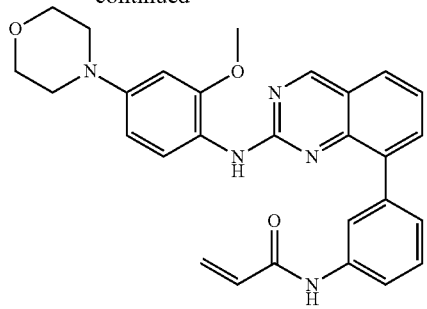

To a solution of 8-(3-aminophenyl)-N-(2-methoxy-4-morpholinophenyl)quinazolin-2-amine (41 mg, 0.1 mmol, 1 eq.) in THF (50 mL) was added DIEA (0.06 mL, 0.3 mmol, 3 eq.), followed by acryloyl chloride (0.01 mL, 0.12 mmol, 1.2 eq.). The resulting mixture was stirred at r.t. for 1 h, then diluted with EA (10 mL), washed with brine, dried over anhydrous Na$_2$SO$_4$ and concentrated. The resulting residue was purified via column chromatography (PE/EA=1:3, v/v) to afford N-(3-(2-((2-methoxy-4-morpholinophenyl)amino)quinazolin-8-yl)phenyl)acrylamide as a yellow solid (17.3 mg, 36% yield). LRMS (M+H$^+$) m/z calculated 482.2, found 482.1. $^1$H NMR (CDCl$_3$, 400 MHz) δ 9.07 (s, 1H), 8.58 (d, 1H), 8.09-8.11 (m, 1H), 7.81-7.84 (m, 3H), 7.71 (dd, 1H), 7.51-7.55 (m, 2H), 7.33-7.39 (m, 2H), 3.90 (s, 3H). 3.85 (t, 4H), 3.07 (t, 4H).

Example 2: Preparation of N-(3-(2-((4-morpholinophenyl)amino)quinazolin-8-yl)phenyl)acrylamide

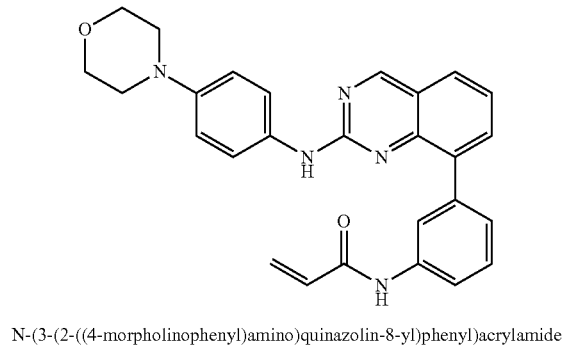

N-(3-(2-((4-morpholinophenyl)amino)quinazolin-8-yl)phenyl)acrylamide

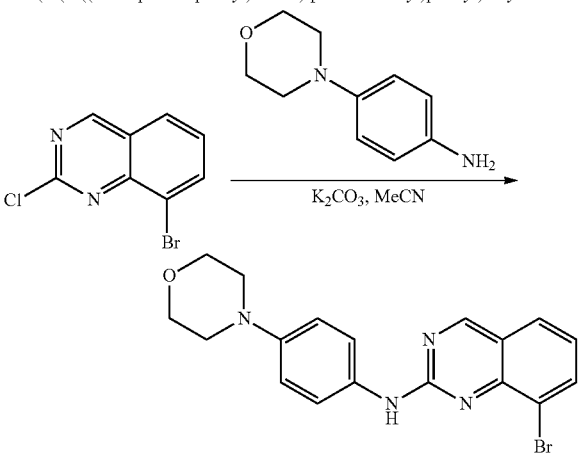

To a solution of 4-morpholinoaniline (154 mg, 0.86 mmol, 1 eq.) and 8-bromo-2-chloroquinazoline (210 mg, 0.86 mmol, 1 eq.) in MeCN (10 mL) was added K₂CO₃ (138 mg, 1 mmol, 2 eq.), and the mixture was stirred at 120° C. for 12 h. The mixture was cooled to r.t. and filtered. The filtrate was concentrated. The resulting residue was purified via column chromatography (PE/EA=1:1, v/v) to afford 8-bromo-N-(4-morpholinophenyl)quinazolin-2-amine as a brown solid (170 mg, 51.5% yield).

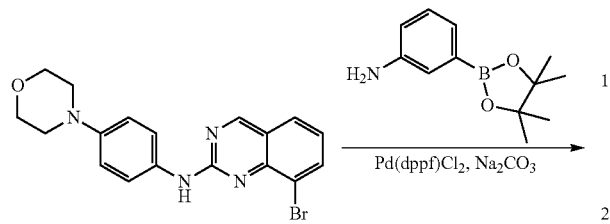

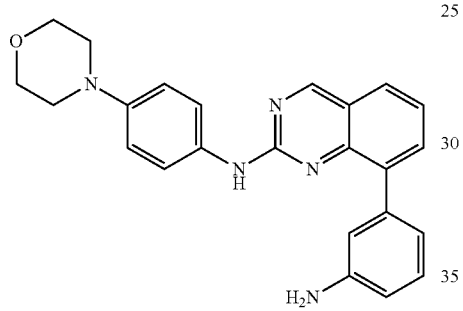

To a solution of 8-bromo-N-(4-morpholinophenyl)quinazolin-2-amine (77 mg, 0.2 mmol, 1 eq.) and 3-(4,4,5,5-tetramethyl-1,3,2-dioxaborolan-2-yl)aniline (66 mg, 0.3 mmol, 1.5 eq.) in dioxane (5 mL) and H₂O (1 mL) was added Na₂CO₃ (63 mg, 0.6 mmol, 3 eq.), followed by Pd(dppf)Cl₂ (16 mg, 0.006 mmol, 0.1 eq.) under N₂ protection. The mixture was stirred at 90° C. for 12 h, then cooled to r.t., diluted with EA (30 mL) and filtered. The filtrate was concentrated and the resulting residue was purified via column chromatography (PE/EA=1:2, v/v) to afford 8-(3-aminophenyl)-N-(4-morpholinophenyl)quinazolin-2-amine as a yellow solid (61 mg, 76.8% yield).

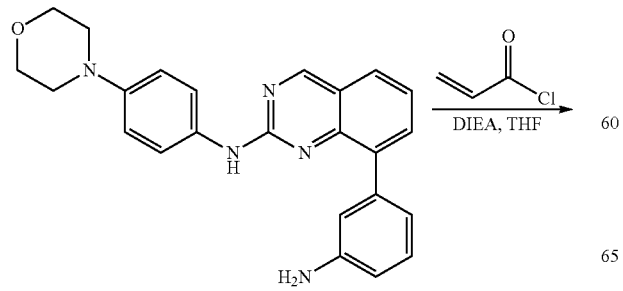

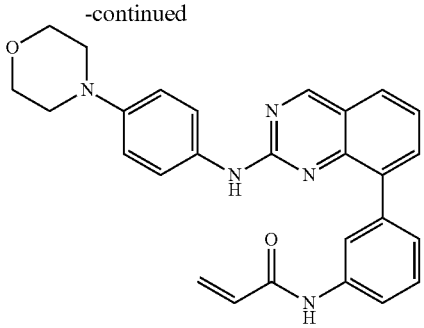

To a solution of 8-(3-aminophenyl)-N-(4-morpholinophenyl)quinazolin-2-amine (61 mg, 0.15 mmol, 1 eq.) in THF (5 mL) was added DIEA (0.12 mL, 0.6 mmol, 4 eq.), followed by acryloyl chloride (27 mg, 0.3 mmol, 2 eq.). The resulting mixture was stirred at r.t. for 1 h, then washed with brine, dried, concentrated and purified by column chromatography (PE/EA=1:2, v/v) to afford N-(3-(2-((4-morpholinophenyl)amino)quinazolin-8-yl)phenyl)acrylamide as a yellow solid (25.1 mg, 38.7% yield) LRMS (M+H+) m/z calculated 452.2, found 452.3. ¹H NMR (CDCl₃, 400 MHz) δ 9.08 (s, 1H), 8.02-8.05 (m, 1H), 7.82-7.84 (m, 2H), 7.65-7.73 (m, 3H), 7.50-7.53 (m, 2H), 7.38 (t, 1H), 7.26-7.28 (m, 1H), 7.21 (s, 1H), 6.77-6.81 (m, 2H), 6.45 (dd, 1H), 6.20-6.26 (m, 1H), 5.77 (dd, 1H), 3.85 (t, 4H), 3.07 (t, 4H).

Example 3: Preparation of N-(3-(2-((2-methoxy-4-(4-methylpiperazin-1-yl)phenyl)amino)quinazolin-8-yl)phenyl)acrylamide

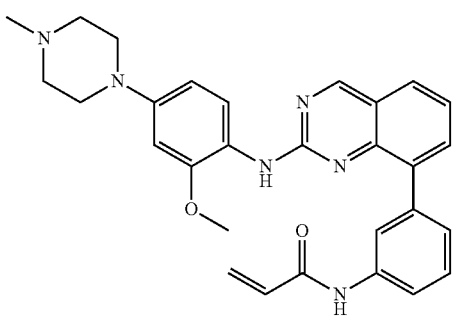

N-(3-(2-((2-methoxy-4-(4-methylpiperazin-1-yl)phenyl)amino)quinazolin-8-yl)phenyl)acrylamide

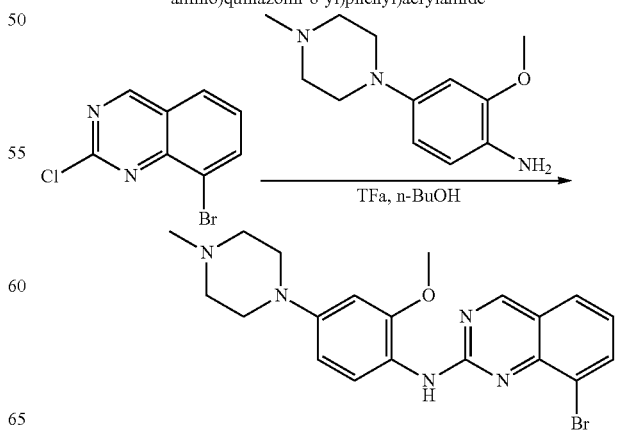

To a solution of 2-methoxy-4-(4-methylpiperazin-1-yl)aniline (331 mg, 1.5 mmol, 1 eq.) and 8-bromo-2-chloroquinazoline (363 mg, 1.5 mmol, 1 eq.) in n-BuOH (10 mL) was added TFA (0.14 mL, 1.8 mmol, 1.2 eq.). The mixture was stirred at 110° C. for 12 h. The solution was then cooled to r.t. and concentrated. The resulting residue was dissolved in EA (20 mL), washed with aqueous $Na_2CO_3$ solution, dried over anhydrous $Na_2SO_4$ and concentrated. The resulting residue was purified via column chromatography (EA/MeOH=5:1, v/v) to afford 8-bromo-N-(2-methoxy-4-(4-methylpiperazin-1-yl)phenyl)quinazolin-2-amine (140 mg, 22% yield).

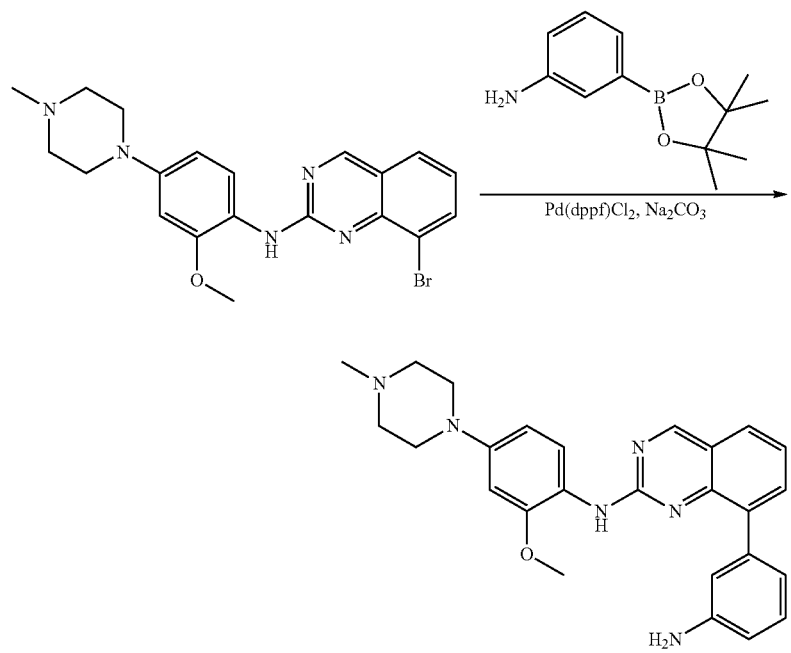

To a solution of 8-bromo-N-(2-methoxy-4-(4-methylpiperazin-1-yl)phenyl)quinazolin-2-amine (140 mg, 0.33 mmol, 1 eq.) and 3-(4,4,5,5-tetramethyl-1,3,2-dioxaborolan-2-yl)aniline (110 mg, 0.5 mmol, 1.5 eq.) in dioxane (10 mL) and $H_2O$ (2 mL) was added $Na_2CO_3$ (70 mg, 0.6 mmol, 3 eq.), followed by $Pd(dppf)Cl_2$ (25 mg, 0.03 mmol 0.1 eq.) under $N_2$ protection. The mixture was stirred at 90° C. under $N_2$ protection for 12 h, then cooled to r.t., diluted with EA (10 mL) and filtered. The filtrate was concentrated and the resulting residue was purified via column chromatography (EA/MeOH=5:1, v/v) to afford 8-(3-aminophenyl)-N-(2-methoxy-4-(4-methylpiperazin-1-yl)phenyl)quinazolin-2-amine (110 mg, 75.8% yield).

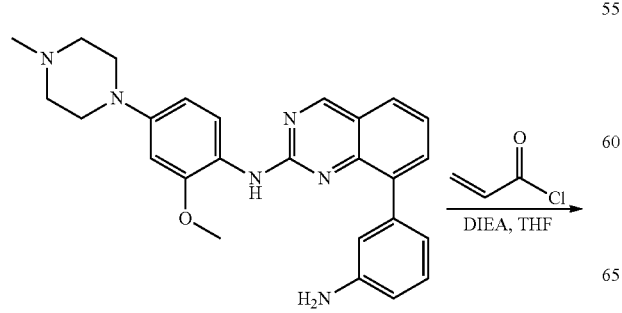

-continued

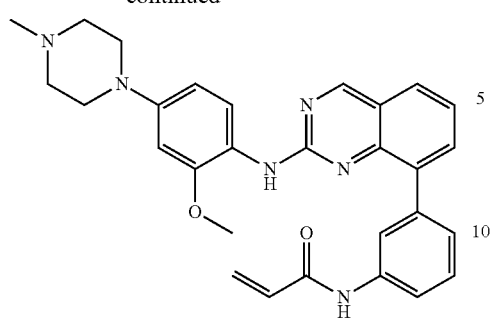

To a solution of 8-(3-aminophenyl)-N-(2-methoxy-4-(4-methylpiperazin-1-yl)phenyl)quinazolin-2-amine (110 mg, 0.25 mmol, 1 eq.) in THF (5 mL) was added DIEA (0.13 mL, 0.75 mmol, 3 eq.) followed by acryloyl chloride (27 mg, 0.3 mmol, 2 eq.). The resulting mixture was stirred at r.t. for 1 h, then diluted with EA (10 mL), washed with brine, dried over anhydrous Na$_2$SO$_4$ and concentrated. The resulting residue was re-crystallized from EA to afford 8-(3-aminophenyl)-N-(2-methoxy-4-(4-methylpiperazin-1-yl)phenyl)quinazolin-2-amine as a yellow solid (32.7 mg, 26.4% yield) LRMS (M+H$^+$) m/z calculated 495.2, found 495.3. $^1$H NMR (CDCl$_3$, 300 MHz) δ 9.08 (s, 1H), 8.57 (d, 2H), 8.19 (s, 1H), 8.10 (s, 1H), 7.82-7.87 (m, 3H), 7.71 (dd, 1H), 7.52-7.54 (m, 2H), 7.35-7.42 (m, 2H), 6.43-6.54 (m, 2H), 6.26-6.37 (m, 2H), 5.78 (dd, 1H), 3.91 (s, 3H), 3.16 (t, 4H), 2.64 (t, 4H), 2.40 (s, 3H).

Example 4: Preparation of N-(3-(2-((4-(4-methylpiperazin-1-yl)phenyl)amino)quinazolin-8-yl)phenyl)propionamide

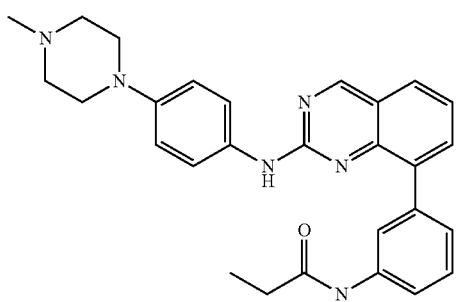

N-(3-(2-((4-(4-methylpiperazin-1-yl)phenyl)amino)quinazolin-8-yl)phenyl)propionamide N-(3-(2-((4-(4-methylpiperazin-1-yl)phenyl)amino)quinazolin-8-yl)phenyl)propionamide (20 mg) was prepared as described for N-(3-(2-((2-methoxy-4-(4-methylpiperazin-1-yl)phenyl)amino)quinazolin-8-yl)phenyl)acrylamide.
LRMS (M+H$^+$) m/z calculated 467.2, found 467.2. $^1$H NMR (CDCl$_3$, 300 MHz) δ 9.05 (s, 1H), 7.62-7.90 (m, 6H), 7.28-7.49 (m, 5H), 6.81 (d, 2H), 3.15 (t, 4H), 2.61 (t, 4H), 2.32-2.43 (m, 5H), 1.12 (t, 3H).

Example 5: Preparation of N-(3-(2-((4-(4-methylpiperazin-1-yl)phenyl)amino)quinazolin-8-yl)phenyl)acrylamide

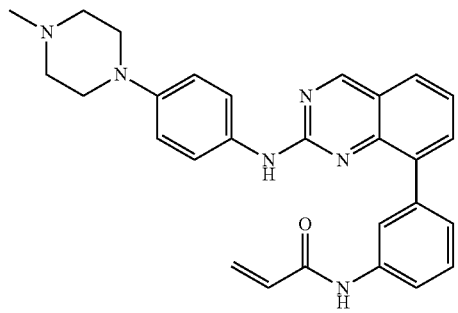

N-(3-(2-((4-(4-methylpiperazin-1-yl)phenyl)amino)quinazolin-8-yl)phenyl)acrylamide

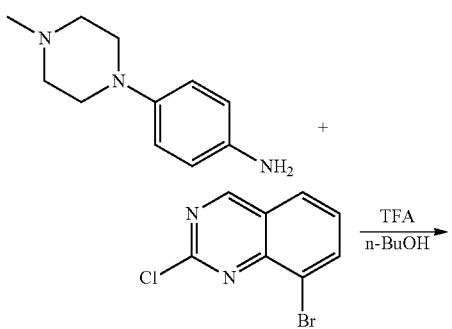

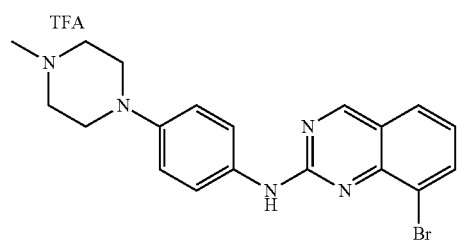

To a suspension of 4-(4-methylpiperazin-1-yl)aniline (9.55 g, 50 mmol, 1 eq.) and 8-bromo-2-chloroquinazoline (12.1 g, 50 mmol, 1 eq.) in n-BuOH (200 mL) was added TFA (7.6 mL, 100 mmol, 2 eq.). The mixture was stirred at 90° C. for 12 h. The solution was cooled to r.t. and the precipitate was collected by filtration, washed with EA, dried in vacuo to afford 8-bromo-N-(4-(4-methylpiperazin-1-yl)phenyl)quinazolin-2-amine as a green solid (17.2 g, 67%).

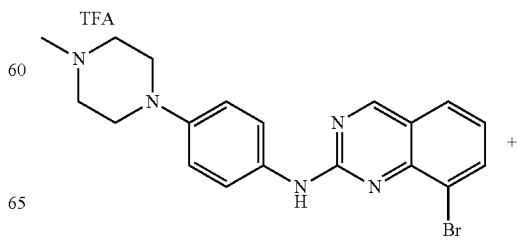

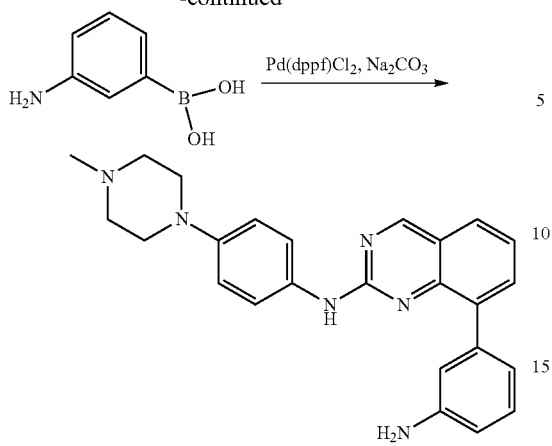

To a solution of 8-bromo-N-(4-(4-methylpiperazin-1-yl)phenyl)quinazolin-2-amine (17.2 g, 33.6 mmol, 1 eq.) and (3-aminophenyl)boronic acid (5.52 g, 40.3 mmol, 1.2 eq.) in dioxane (200 mL) and H$_2$O (40 mL) was added Na$_2$CO$_3$ (14.2 g, 134.4 mmol, 4 eq.), followed by Pd(dppf)Cl$_2$ (1.4 g, 1.7 mmol, 0.05 eq.) under N$_2$ protection. The mixture was stirred at 90° C. for 12 h, then cooled to r.t., diluted with EA (30 mL) and filtered. The filtrate was concentrated and the resulting residue was purified via column chromatography (DCM/MeOH=20:1, v/v) to afford 8-(3-aminophenyl)-N-(4-(4-methylpiperazin-1-yl)phenyl)quinazolin-2-amine as a yellow solid (13.3 g, 96% yield).

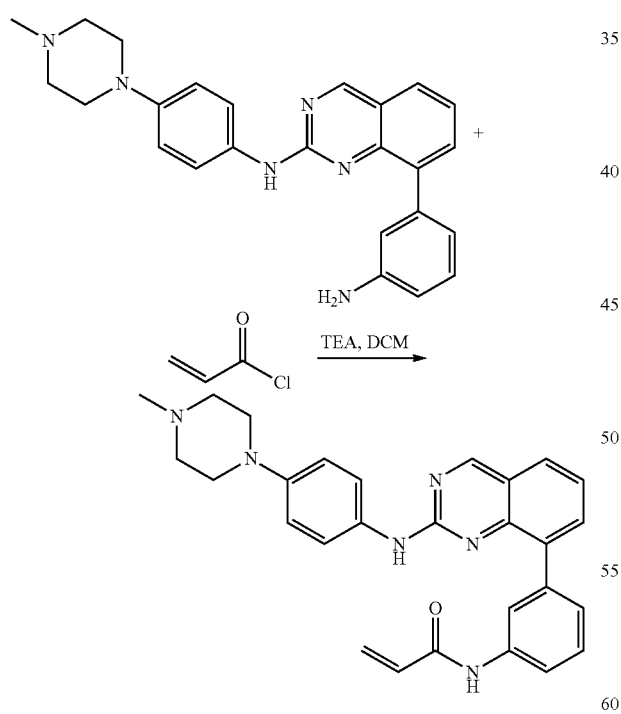

To a solution of 8-(3-aminophenyl)-N-(4-(4-methylpiperazin-1-yl)phenyl)quinazolin-2-amine (13.3 g, 32.4 mmol, 1 eq.) in DCM (400 mL) cooled in ice-bath was added TEA (9 mL, 64.8 mmol, 2 eq.) was added acryloyl chloride (3.1 mL, 39 mmol, 1.2 eq.) dropwise. The resulting mixture was stirred at r.t. for 1 h, washed with brine, dried over anhydrous N$_2$SO$_4$, concentrated and the resulting residue was purified via column chromatography (DCM/MeOH=10:1, v/v) to afford N-(3-(2-((4-(4-methylpiperazin-1-yl)phenyl)amino)quinazolin-8-yl)phenyl)acrylamide as a yellow solid (11 g, 73% yield).

LRMS (M+H$^+$) m/z calculated 465.2, found 465.1. $^1$H NMR (CDCl$_3$, 300 MHz) δ 9.06 (s, 1H), 8.00 (s, 1H), 7.49-7.97 (m, 8H), 7.34-7.39 (m, 2H), 6.81 (d, 2H), 6.42-6.48 (m, 1H), 6.22-6.31 (m, 1H), 5.76 (dd, 1H), 3.16 (t, 4H), 2.64 (t, 4H), 2.41 (s, 3H).

Example 6: Preparation of N-(3-(2-((4-(4-methylpiperazin-1-yl)phenyl)amino)quinazolin-8-yl)phenyl)acetamide

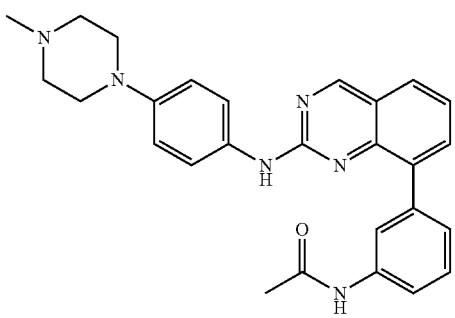

N-(3-(2-((4-(4-methylpiperazin-1-yl)phenyl)amino)quinazolin-8-yl)phenyl)acetamide N-(3-(2-((4-(4-methylpiperazin-1-yl)phenyl)amino)quinazolin-8-yl)phenyl)actamide (20 mg) was prepared as described for N-(3-(2-((2-methoxy-4-(4-methylpiperazin-1-yl)phenyl)amino)quinazolin-8-yl)phenyl)acrylamide.

LRMS (M+H$^+$) m/z calculated 453.2, found 453.2. $^1$H NMR (CDCl$_3$, 300 MHz) δ 9.08 (s, 1H), 7.63-7.90 (m, 6H), 7.50 (d, 2H), 7.38 (t, 1H), 7.23 (s, 2H), 6.83 (d, 2H), 3.17 (t, 4H), 2.61 (t, 4H), 2.34 (s, 3H), 2.19 (s, 3H).

Example 7: Preparation of N-(3-(2-((4-(4-ethylpiperazin-1-yl)phenyl)amino)quinazolin-8-yl)phenyl)acrylamide

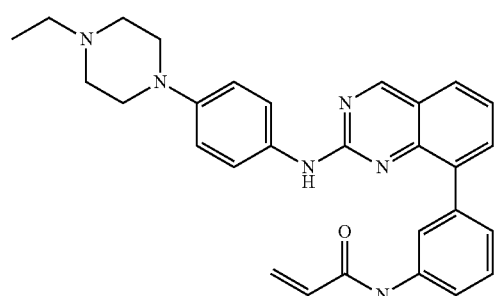

N-(3-(2-((4-(4-ethylpiperazin-1-yl)phenyl)amino)quinazolin-8-yl)phenyl)acrylamide N-(3-(2-((4-(4-ethylpiperazin-1-yl)phenyl)amino)quinazolin-8-yl)phenyl)acrylamide (44.2 mg) was prepared as described for N-(3-(2-((2-methoxy-4-(4-methylpiperazin-1-yl)phenyl)amino)quinazolin-8-yl)phenyl)acrylamide.

LRMS (M+H⁺) m/z calculated 479.2, found 479.2. ¹H NMR (CDCl₃, 400 MHz) δ 9.07 (s, 1H), 7.47-7.92 (m, 9H), 7.38 (t, 1H), 7.22 (s, 1H), 6.81 (d, 2H), 6.42-6.46 (m, 2H), 5.77 (d, 1H), 3.21-3.24 (m, 4H), 2.75-2.81 (m, 4H), 2.63-2.65 (m, 2H), 1.22-1.29 (m, 3H).

Example 8: Preparation of N-(3-(2-((4-(4-acetylpiperazin-1-yl)phenyl)amino)quinazolin-8-yl)phenyl)acrylamide

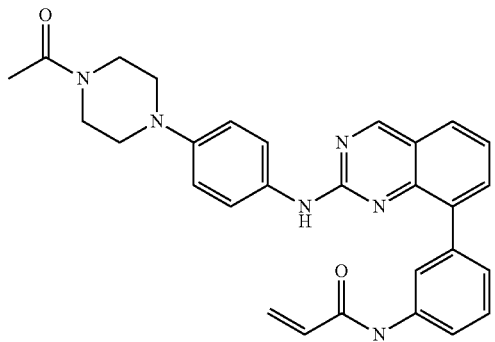

N-(3-(2-((4-(4-acetylpiperazin-1-yl)phenyl)amino)quinazolin-8-yl)phenyl)acrylamide N-(3-(2-((4-(4-acetylpiperazin-1-yl)phenyl)amino)quinazolin-8-yl)phenyl)acrylamide (653 mg) was prepared as described for N-(3-(2-((2-methoxy-4-(4-methylpiperazin-1-yl)phenyl)amino)quinazolin-8-yl)phenyl)acrylamide.
LRMS (M+H⁺) m/z calculated 493.2, found 493.1. ¹H NMR (DMSO-d6, 300 MHz) δ 10.29 (s, 1H), 9.70 (s, 1H), 9.30 (s, 1H), 7.75-8.01 (m, 6H), 7.32-7.51 (m, 3H), 6.73 (d, 2H), 6.44-6.53 (m, 1H), 6.24-6.53 (m, 1H), 5.75-5.79 (m, 1H), 3.54-3.56 (m, 4H), 2.90-3.00 (m, 4H), 2.04 (s, 3H).

Example 9: Preparation of N-(3-(2-((6-(4-acetylpiperazin-1-yl)pyridin-3-yl)amino)quinazolin-8-yl)phenyl)acrylamide

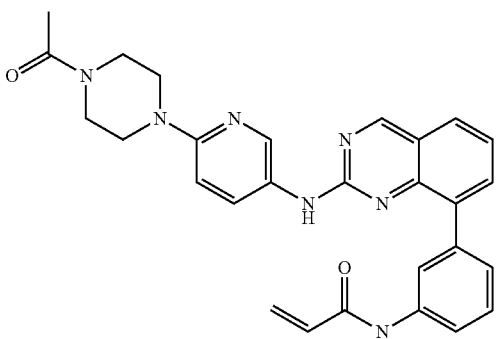

N-(3-(2-((6-(4-acetylpiperazin-1-yl)pyridin-3-yl)amino)quinazolin-8-yl)phenyl)acrylamide N-(3-(2-((6-(4-acetylpiperazin-1-yl)pyridin-3-yl)amino)quinazolin-8-yl)phenyl)acrylamide (10.4 mg) was prepared as described for N-(3-(2-((2-methoxy-4-(4-methylpiperazin-1-yl)phenyl)amino)quinazolin-8-yl)phenyl)acrylamide.
LRMS (M+H⁺) m/z calculated 494.2, found 494.1. ¹H NMR (CDCl₃, 300 MHz) δ 9.10 (s, 1H), 8.51 (s, 1H), 8.11-8.13 (m, 1H), 7.32-7.89 (m, 9H), 6.26-6.58 (m, 3H), 5.78 (d, 1H), 3.40-3.77 (m, 8H), 2.16 (s, 3H).

Example 10: Preparation of N-(3-(2-((6-(4-acetylpiperazin-1-yl)pyridin-3-yl)amino)quinazolin-8-yl)phenyl)acrylamide

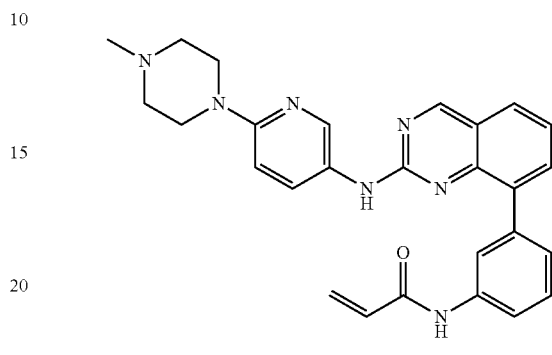

N-(3-(2-((6-(4-methylpiperazin-1-yl)pyridin-3-yl)amino)quinazolin-8-yl)phenyl)acrylamide N-(3-(2-((6-(4-methylpiperazin-1-yl)pyridin-3-yl)amino)quinazolin-8-yl)phenyl)acrylamide (22 mg) was prepared as described for N-(3-(2-((2-methoxy-4-(4-methylpiperazin-1-yl)phenyl)amino)quinazolin-8-yl)phenyl)acrylamide.
LRMS (M+H+) m/z calculated 466.2, found 465.9. 1H NMR (CD₃OD, 300 MHz) δ 9.18 (s, 1H), 8.33-8.42 (m, 2H), 7.82-7.93 (m, 4H), 7.39-7.49 (m, 3H), 6.40-6.63 (m, 3H), 5.80 (dd, 1H), 3.52-3.54 (m, 4H), 2.91-2.94 (m, 4H), 2.63 (s, 3H).

Example 11: Preparation of N-(3-(2-((4-(4-ethylpiperazin-1-yl)phenyl)amino)quinazolin-8-yl)-2-fluorophenyl)acrylamide

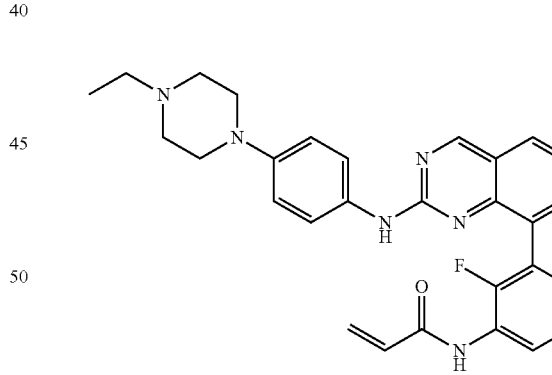

N-(3-(2-((4-(4-ethylpiperazin-1-yl)phenyl)amino)quinazolin-8-yl)2-fluorophenyl)acrylamide N-(3-(2-((4-(4-ethylpiperazin-1-yl)phenyl)amino)quinazolin-8-yl)-2-fluorophenyl)acrylamide (9.1 mg) was prepared as described for N-(3-(2-((2-methoxy-4-(4-methylpiperazin-1-yl)phenyl)amino)quinazolin-8-yl)phenyl)acrylamide. LRMS (M+H⁺) m/z calculated 497.2, found 497.2. ¹H NMR (CDCl₃, 300 MHz) δ 9.09 (s, 1H), 8.54 (t, 1H), 7.78-7.80 (m, 3H), 7.53 (d, 2H), 7.23-7.43 (m, 4H), 7.10 (t, 1H), 6.71 (d, 2H), 6.30-6.50 (m, 2H), 5.84 (d, 1H), 4.64 (d, 2H), 3.35-3.38 (m, 4H), 3.00-3.13 (m, 4H), 2.84-2.89 (m, 2H), 1.34-1.43 (m, 3H).

Example 12: Preparation of N-(5-(2-((4-(4-acetylpiperazin-1-yl)phenyl)amino)quinazolin-8-yl)pyridin-3-yl)acrylamide

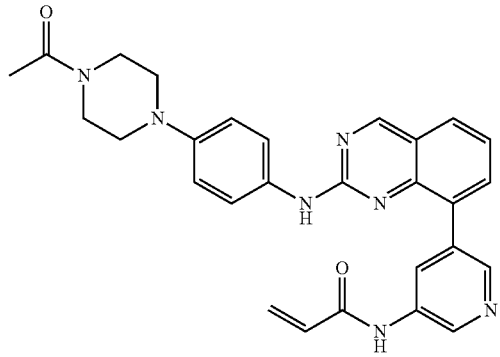

N-(5-(2-((4-(4-acetylpiperazin-1-yl)phenyl)amino)quinazolin-8-yl)pyridin-3-yl)acrylamide N-(5-(2-((4-(4-acetylpiperazin-1-yl)phenyl)amino)quinazolin-8-yl)pyridin-3-yl)acrylamide (23.7 mg) was prepared as described for N-(3-(2-((2-methoxy-4-(4-methylpiperazin-1-yl)phenyl)amino)quinazolin-8-yl)phenyl)acrylamide. LRMS (M+H$^+$) m/z calculated 494.2, found 494.2. $^1$H NMR (DMSO-d6, 300 MHz) δ 10.52 (s, 1H), 9.75 (s, 1H), 9.32 (s, 1H), 9.01 (s, 1H), 8.48-8.50 (m, 2H), 7.95 (dd, 2H), 7.70 (d, 2H), 7.45 (t, 1H), 6.72 (d, 2H), 6.28-6.55 (m, 2H), 5.82 (d, 1H), 3.50-3.56 (m, 4H), 2.90-3.02 (m, 4H), 2.05 (s, 3H).

Example 13: Preparation of N-(5-(2-((4-(4-methylpiperazin-1-yl)phenyl)amino)quinazolin-8-yl)pyridin-3-yl)acrylamide

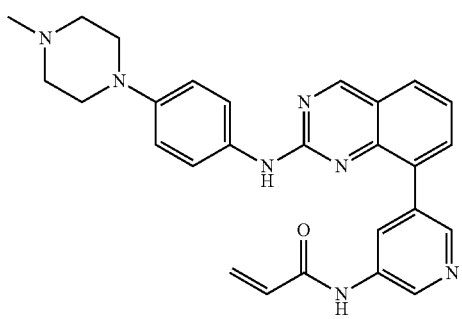

N-(5-(2-((4-(4-methylpiperazin-1-yl)phenyl)amino)quinazolin-8-yl)pyridin-3-yl)acrylamide N-(5-(2-((4-(4-methylpiperazin-1-yl)phenyl)amino)quinazolin-8-yl)pyridin-3-yl)acrylamide (24.2 mg) was prepared as described for N-(3-(2-((2-methoxy-4-(4-methylpiperazin-1-yl)phenyl)amino)quinazolin-8-yl)phenyl)acrylamide. LRMS (M+H$^+$) m/z calculated 466.2, found 465.9. $^1$H NMR (CD$_3$OD, 300 MHz) δ 9.16 (s, 1H), 9.08 (s, 1H), 8.57 (s, 1H), 8.47-8.48 (s, 1H), 7.85-7.89 (m, 2H), 7.65 (d, 2H), 7.43 (t, 1H), 6.81 (d, 2H), 6.45-6.49 (m, 2H), 5.86 (dd, 1H), 3.17-3.20 (m, 4H), 2.90-2.93 (m, 4H), 2.59 (s, 3H).

Example 14: Preparation of tert-butyl 4-(4-((8-(3-acrylamidophenyl)quinazolin-2-yl)amino)-3-methoxyphenyl)piperazine-1-carboxylate

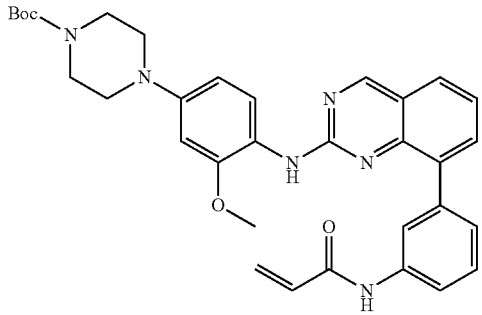

tert-butyl 4-(4-((8-(3-acrylamidophenyl)quinazolin-2-yl)amino)-3-methoxyphenyl)piperazine-1-carboxylate

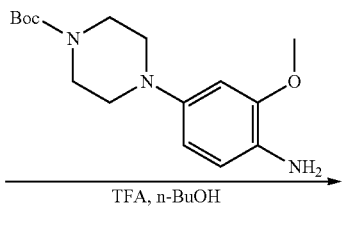

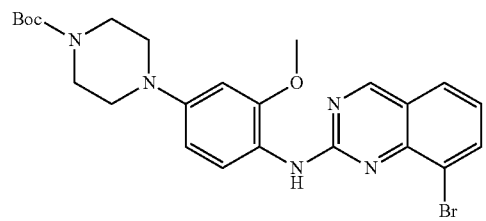

To a solution of tert-butyl 4-(4-amino-3-methoxyphenyl)piperazine-1-carboxylate (450 mg, 1.5 mmol, 1 eq.) and 8-bromo-2-chloroquinazoline (363 mg, 1.5 mmol, 1 eq.) in n-BuOH (10 mL) was added TFA (0.14 mL, 1.8 mmol, 1.2 eq.). The mixture was stirred at 110° C. for 12 h, then cooled to r.t. and concentrated. The resulting residue was dissolved in EA, washed with aqueous Na$_2$CO$_3$ solution, dried over anhydrous Na$_2$SO$_4$ and concentrated. The resulting residue was purified via column chromatography (PE/EA=1:1, v/v) to afford tert-butyl 4-(4-((8-bromoquinazolin-2-yl)amino)-3-methoxyphenyl)piperazine-1-carboxylate as a yellow solid (110 mg, 13%).

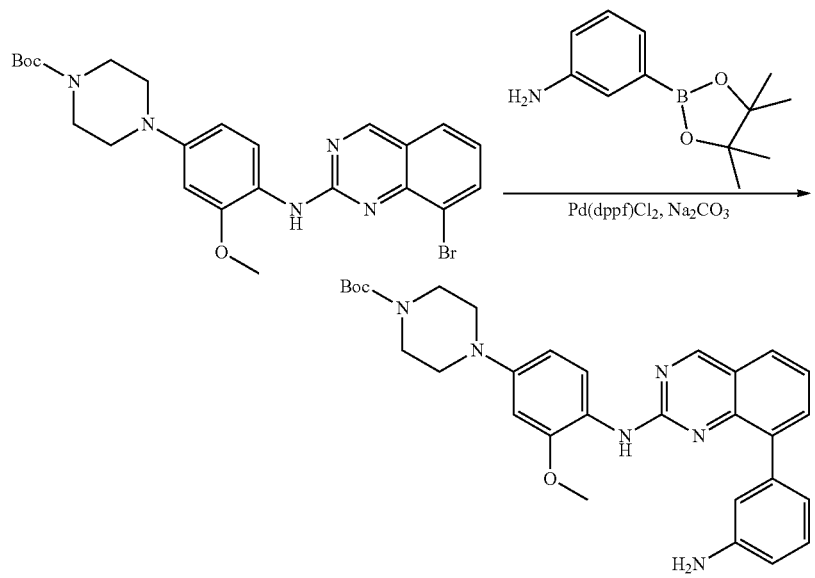

To a solution of tert-butyl 4-(4-((8-bromoquinazolin-2-yl)amino)-3-methoxyphenyl)piperazine-1-carboxylate (110 mg, 0.2 mmol, 1 eq.) and 3-(4,4,5,5-tetramethyl-1,3,2-dioxaborolan-2-yl)aniline (66 mg, 0.3 mmol, 1.5 eq.) in dioxane (10 mL) and H$_2$O (2 mL) was added Na$_2$CO$_3$ (43 mg, 0.4 mmol, 2 eq.), followed by Pd(dppf)Cl$_2$ (20 mg, 0.02 mmol, 0.1 eq.) under N$_2$ protection. The mixture was stirred at 90° C. under N$_2$ protection for 12 h, then cooled to r.t., diluted with EA (20 mL) and filtered. The filtrate was concentrated and the resulting residue was purified via column chromatography (PE/EA=1:1, v/v) to afford tert-butyl 4-(4-((8-(3-aminophenyl)quinazolin-2-yl)amino)-3-methoxyphenyl)piperazine-1-carboxylate (82 mg, 72% yield).

added DIEA (0.1 mL, 0.48 mmol, 3 eq.) followed by acryloyl chloride (30 mg, 0.32 mmol, 2 eq.). The resulting mixture was stirred at r.t. for 1 h, then washed with brine, dried over anhydrous Na$_2$SO$_4$ and concentrated. The resulting residue was purified via column chromatography (PE/EA=2:3, v/v) to afford tert-butyl 4-(4-((8-(3-acrylamidophenyl)quinazolin-2-yl)amino)-3-methoxyphenyl)piperazine-1-carboxylate as a yellow solid (19.7 mg, 22% yield). LRMS (M+H$^+$) m/z calculated 581.3, found 581.2. $^1$H NMR (CDCl$_3$, 300 MHz) δ 9.09 (s, 1H), 8.58 (d, 2H), 8.11 (d, 1H), 7.82-7.87 (m, 3H), 7.73 (d, 1H), 7.52-7.54 (m, 1H), 7.36-7.41 (m, 2H), 6.45-6.55 (m, 2H), 6.21-6.35 (m, 2H), 5.78 (dd, 1H), 3.91 (s, 3H), 3.58 (t, 4H), 3.04 (t, 4H), 1.48 (s, 9H).

Example 15: Preparation of N-(4-morpholinophenyl)-8-phenylquinazolin-2-amine

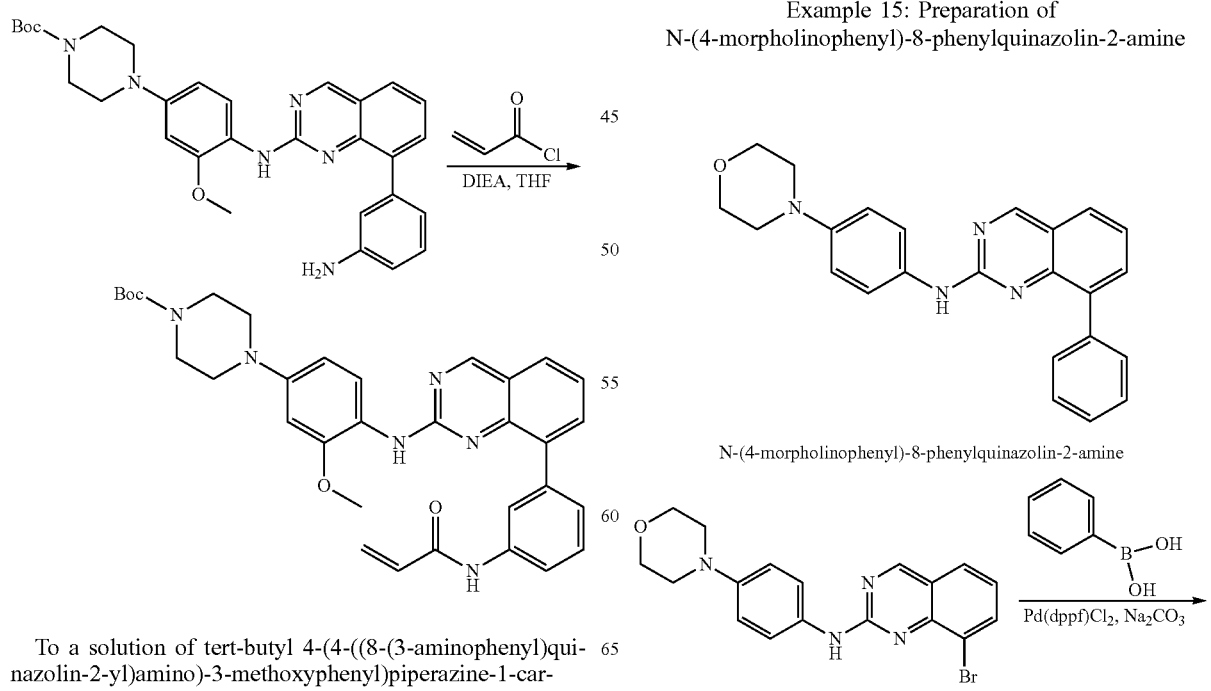

To a solution of tert-butyl 4-(4-((8-(3-aminophenyl)quinazolin-2-yl)amino)-3-methoxyphenyl)piperazine-1-carboxylate (82 mg, 0.16 mmol, 1 eq.) in THF (5 mL) was -continued

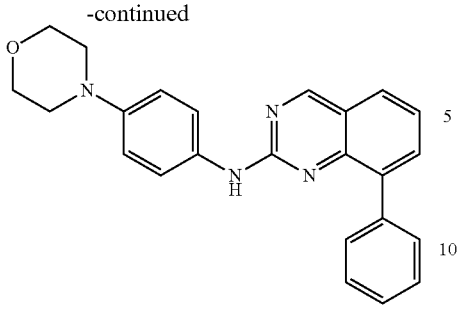

To a solution of 8-bromo-N-(4-morpholinophenyl)quinazolin-2-amine (77 mg, 0.2 mmol, 1 eq.) and phenylboronic acid (37 mg, 0.3 mmol, 1.5 eq.) in dioxane (5 mL) and H$_2$O (1 mL) was added Na$_2$CO$_3$ (63 mg, 0.6 mmol, 3 eq.), followed by Pd(dppf)Cl$_2$ (16 mg, 0.006 mmol, 0.1 eq.) under N$_2$ protection. The mixture was stirred at 90° C. under N$_2$ protection for 12 h, then cooled to r.t., diluted with EA (15 mL) and filtered. The filtrate was concentrated and the resulting residue was purified via column chromatography (PE/EA=1:1, v/v) to afford N-(4-morpholinophenyl)-8-phenylquinazolin-2-amine. (30.3 mg, 39.4% yield) LRMS (M+H$^+$) m/z calculated 383.2, found 383.1. $^1$H NMR (CDCl$_3$, 400 MHz) δ 9.08 (s, 1H), 7.63-7.81 (m, 6H), 7.38-7.53 (m, 4H), 7.21 (s, 1H), 6.81 (d, 2H), 3.88 (t, 4H), 3.10 (t, 4H).

Example 16: Preparation of 8-(5-chloro-2-fluorophenyl)-N-(4-morpholinophenyl) quinazolin-2-amine

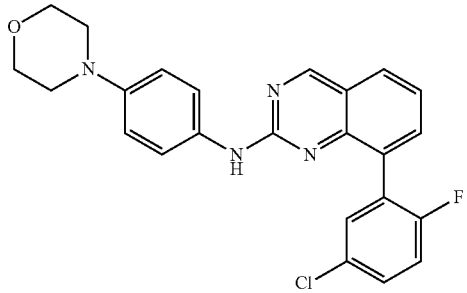

8-(5-chloro-2-fluorophenyl)-N-(4-morpholinophenyl) quinazolin-2-amine 8-(5-Chloro-2-fluorophenyl)-N-(4-morpholinophenyl) quinazolin-2-amine (80 mg) was prepared as described for N-(4-morpholinophenyl)-8-phenylquinazolin-2-amine LRMS (M+H$^+$) m/z calculated 435.1, found 435.1. $^1$H NMR (CDCl$_3$, 400 MHz) δ 9.08 (s, 1H), 7.76-7.79 (m, 2H), 7.61-7.64 (m, 1H), 7.54-7.56 (m, 2H), 7.24 (s, 1H), 7.15 (t, 1H), 6.82-6.85 (m, 2H), 3.88 (t, 4H), 3.10 (t, 4H).

Example 17: Preparation of 8-(3-chlorophenyl)-N-(4-morpholinophenyl) quinazolin-2-amine

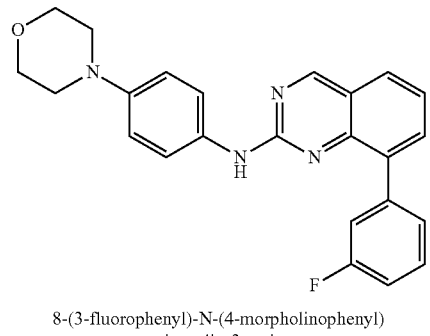

8-(3-chlorophenyl)-N-(4-morpholinophenyl) quinazolin-2-amine 8-(3-Chlorophenyl)-N-(4-morpholinophenyl)quinazolin-2-amine (50.4 mg) was prepared as described for N-(4-morpholinophenyl)-8-phenylquinazolin-2-amine. LRMS (M+H$^+$) m/z calculated 417.1, found 417.1. $^1$H NMR (CDCl$_3$, 300 MHz) δ 9.09 (s, 1H), 7.88 (s, 1H), 7.74-7.81 (m, 2H), 7.60-7.67 (m, 3H), 7.37-7.45 (m, 3H), 7.30 (s, 1H), 7.15 (t, 1H), 6.90 (d, 2H), 3.90 (t, 4H), 3.13 (t, 4H).

Example 18: Preparation of 8-(3-fluorophenyl)-N-(4-morpholinophenyl) quinazolin-2-amine 8-(3-fluorophenyl)-N-(4-morpholinophenyl) quinazolin-2-amine 8-(3-Fluorophenyl)-N-(4-morpholinophenyl)quinazolin-2-amine (58.6 mg) was prepared as described for N-(4-morpholinophenyl)-8-phenylquinazolin-2-amine. LRMS (M+H$^+$) m/z calculated 401.2, found 401.2. $^1$H NMR (CDCl$_3$, 300 MHz) δ 9.10 (s, 1H), 7.59-7.83 (m, 5H), 7.37-7.57 (m, 3H), 7.31 (s, 1H), 7.13-7.19 (m, 1H), 6.86 (d, 2H), 3.90 (t, 4H), 3.13 (t, 4H).

Example 19: Preparation of 8-(2-fluorophenyl)-N-(4-morpholinophenyl) quinazolin-2-amine

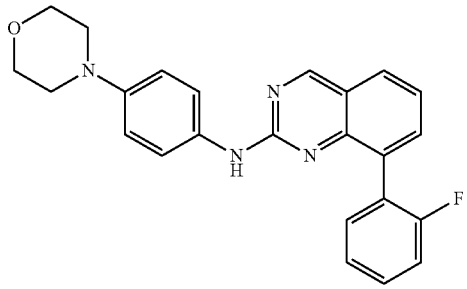

8-(2-fluorophenyl)-N-(4-morpholinophenyl) quinazolin-2-amine 8-(2-Fluorophenyl)-N-(4-morpholinophenyl)quinazolin-2-amine (40.2 mg) was prepared as described for N-(4-morpholinophenyl)-8-phenylquinazolin-2-amine. LRMS (M+H$^+$) m/z calculated 401.2, found 401.2. $^1$H NMR (CDCl$_3$, 300 MHz) δ 9.10 (s, 1H), 7.76-7.83 (m, 2H), 7.55-7.60 (m, 3H), 7.23-7.42 (m, 5H), 6.78 (d, 2H), 3.89 (t, 4H), 3.10 (t, 4H).

Example 20: Preparation of 8-(2-chlorophenyl)-N-(4-morpholinophenyl)quinazolin-2-amine

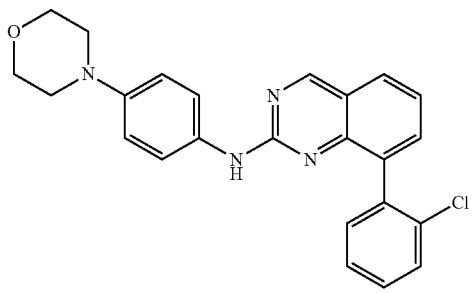

8-(2-chlorophenyl)-N-(4-morpholinophenyl) quinazolin-2-amine 8-(2-Chlorophenyl)-N-(4-morpholinophenyl)quinazolin-2-amine (19.4 mg) was prepared as described for N-(4-morpholinophenyl)-8-phenylquinazolin-2-amine. LRMS (M+H$^+$) m/z calculated 417.1, found 417.1. $^1$H NMR (CDCl$_3$, 300 MHz) δ 9.10 (s, 1H), 7.75-7.80 (m, 3H), 7.59-7.62 (m, 1H), 7.38-7.451 (m, 6H), 7.18 (s, 1H), 6.73 (d, 2H), 3.87 (t, 4H), 3.09 (t, 4H).

Example 21: Preparation of tert-butyl 4-(4-((8-(2-fluorophenyl)quinazolin-2-yl)amino)phenyl)piperazine-1-carboxylate

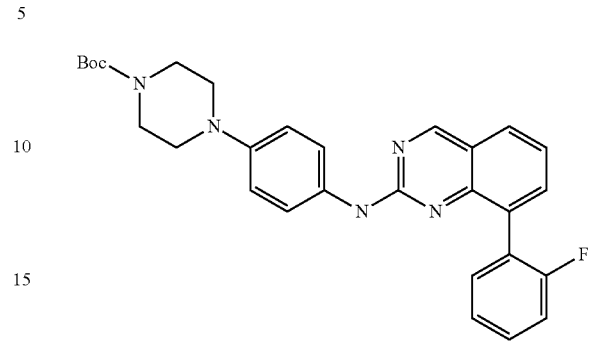

tert-butyl 4-(4-((8-(2-fluorophenyl)quinazolin-2-yl) amino)phenyl)piperazine-1-carboxylate Tert-butyl 4-(4-((8-(2-fluorophenyl)quinazolin-2-yl)amino)phenyl)piperazine-1-carboxylate (7.7 mg) was prepared as described for N-(4-morpholinophenyl)-8-phenylquinazolin-2-amine. LRMS (M+H$^+$) m/z calculated 500.2, found 500.1. $^1$H NMR (CDCl$_3$, 300 MHz) δ 9.10 (s, 1H), 7.76-7.82 (m, 2H), 7.54-7.57 (m, 3H), 7.38-7.43 (m, 1H), 7.29-7.33 (m, 2H), 7.19-7.26 (m, 2H), 6.76-6.81 (m, 2H), 3.61 (t, 4H), 3.04 (t, 4H), 1.51 (s, 9H).

Example 22: Preparation of tert-butyl 4-(4-((8-(2-chlorophenyl)quinazolin-2-yl)amino)phenyl)piperazine-1-carboxylate

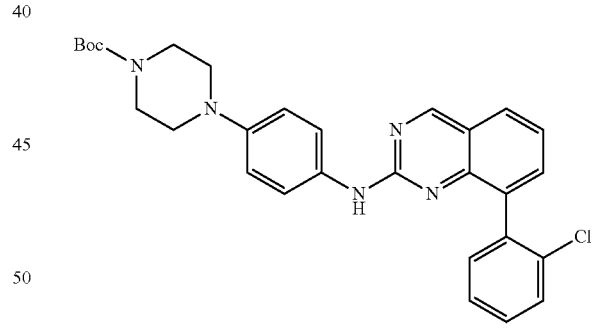

tert-butyl 4-(4-((8-(2-chlorophenyl)quinazolin-2-yl) amino)phenyl)piperazine-1-carboxylate Tert-butyl 4-(4-((8-(2-chlorophenyl)quinazolin-2-yl)amino)phenyl)piperazine-1-carboxylate (5.2 mg) was prepared as described for N-(4-morpholinophenyl)-8-phenylquinazolin-2-amine. LRMS (M+H$^+$) m/z calculated 515.2, found 516.1. $^1$H NMR (CDCl$_3$, 300 MHz) δ 9.10 (s, 1H), 7.78 (t, 2H), 7.59 (d, 1H), 7.38-7.50 (m, 6H), 7.18 (s, 1H), 6.73 (d, 2H), 3.60 (m, 4H), 3.04 (m, 4H).

Example 23: Preparation of tert-butyl 4-(4-((8-(3-fluorophenyl)quinazolin-2-yl)amino)phenyl)piperazine-1-carboxylate

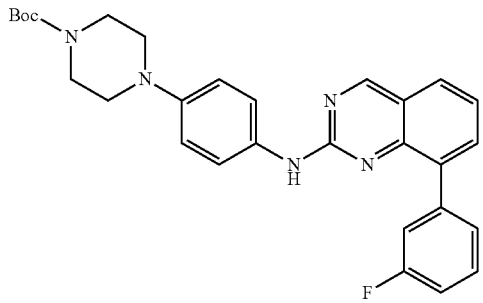

tert-butyl 4-(4-((8-(3-fluorophenyl)quinazolin-2-yl)amino)phenyl)piperazine-1-carboxylate Tert-butyl 4-(4-((8-(3-fluorophenyl)quinazolin-2-yl)amino)phenyl)piperazine-1-carboxylate (7.3 mg) was prepared as described for N-(4-morpholinophenyl)-8-phenylquinazolin-2-amine. LRMS (M+H$^+$) m/z calculated 500.2, found 500.1. $^1$H NMR (CDCl$_3$, 300 MHz) δ 9.10 (s, 1H), 7.37-7.83 (m, 8H), 7.22-7.27 (m, 2H), 6.87 (d, 2H), 3.60-3.63 (m, 4H), 3.06-3.09 (m, 4H), 1.51 (s, 9H).

Example 24: Preparation of tert-butyl 4-(4-((8-(5-chloro-2-fluorophenyl)quinazolin-2-yl)amino)phenyl)piperazine-1-carboxylate

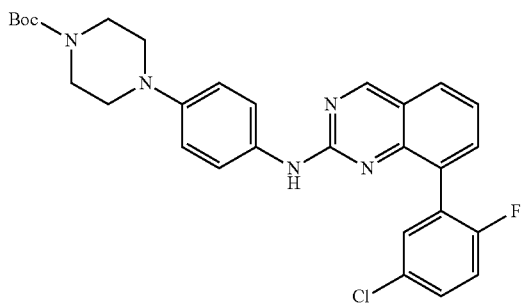

tert-butyl 4-(4-((8-(5-chloro-2-fluorophenyl)quinazolin-2-yl)amino)phenyl)piperazine-1-carboxylate Tert-butyl 4-(4-((8-(5-chloro-2-fluorophenyl)quinazolin-2-yl)amino)phenyl)piperazine-1-carboxylate (3.2 mg) was prepared as described for N-(4-morpholinophenyl)-8-phenylquinazolin-2-amine. LRMS (M+H$^+$) m/z calculated 500.2, found 500.1. $^1$H NMR (CDCl$_3$, 300 MHz) δ 9.10 (s, 1H), 7.37-7.83 (m, 8H), 7.22-7.27 (m, 2H), 6.87 (d, 2H), 3.60-3.63 (m, 4H), 3.06-3.09 (m, 4H), 1.51 (s, 9H).

Example 25: Preparation of tert-butyl 4-(4-((8-(3-chlorophenyl)quinazolin-2-yl)amino)phenyl)piperazine-1-carboxylate

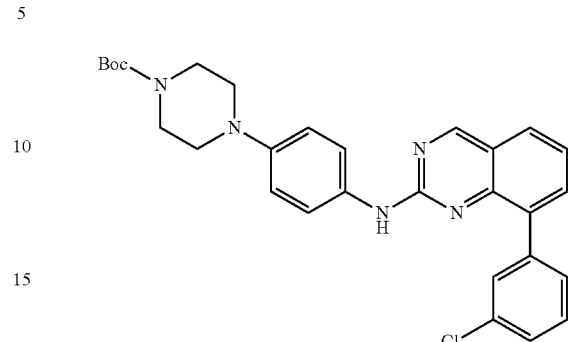

tert-butyl 4-(4-((8-(3-chlorophenyl)quinazolin-2-yl)amino)phenyl)piperazine-1-carboxylate Tert-butyl 4-(4-((8-(3-chlorophenyl)quinazolin-2-yl)amino)phenyl)piperazine-1-carboxylate (6.1 mg) was prepared as described for N-(4-morpholinophenyl)-8-phenylquinazolin-2-amine. LRMS (M+H$^+$) m/z calculated 516.2, found 516.2. $^1$H NMR (CDCl$_3$, 300 MHz) δ 9.10 (s, 1H), 7.37-7.88 (m, 9H), 7.23 (s, 1H), 6.91 (d, 2H), 3.60-3.63 (m, 4H), 3.06-3.09 (m, 4H), 1.51 (s, 9H).

Example 26: Preparation of tert-butyl 4-(4-((8-phenylquinazolin-2-yl)amino)phenyl)piperazine-1-carboxylate

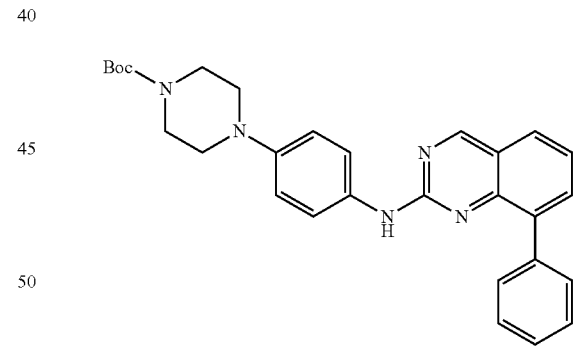

tert-butyl 4-(4-((8-phenylquinazolin-2-yl)amino)phenyl)piperazine-1-carboxylate

Tert-butyl 4-(4-((8-phenylquinazolin-2-yl)amino)phenyl)piperazine-1-carboxylate (7.6 mg) was prepared as described for N-(4-morpholinophenyl)-8-phenylquinazolin-2-amine. LRMS (M+H$^+$) m/z calculated 482.2, found 482.2. $^1$H NMR (CDCl$_3$, 300 MHz) δ 9.10 (s, 1H), 7.40-7.81 (m, 9H), 7.21 (s, 1H), 6.84 (d, 2H), 3.60-3.63 (m, 4H), 3.05-3.09 (m, 4H), 1.51 (s, 9H).

Example 27: Preparation of 8-(5-chloro-2-fluorophenyl)-N-(4-(piperazin-1-yl)phenyl)quinazolin-2-amine

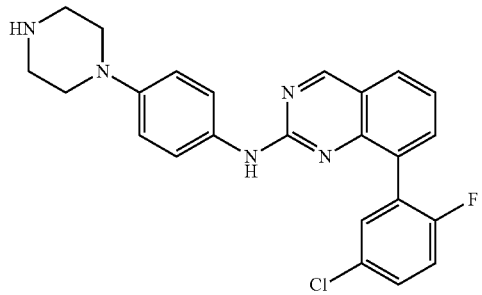

8-(5-chloro-2-fluorophenyl)-N-(4-(piperazin-1-yl)phenyl)quinazolin-2-amine 8-(5-Chloro-2-fluorophenyl)-N-(4-(piperazin-1-yl)phenyl)quinazolin-2-amine (13.5 mg) was prepared as described for N-(4-morpholinophenyl)-8-phenylquinazolin-2-amine. LRMS (M+H$^+$) m/z calculated 434.1, found 434.2. $^1$H NMR (CDCl$_3$, 400 MHz) δ 9.07 (s, 1H), 7.37-7.79 (m, 8H), 6.85 (d, 2H), 3.12-3.15 (m, 8H).

Example 28: Preparation of 8-(3-chlorophenyl)-N-(4-(piperazin-1-yl)phenyl)quinazolin-2-amine

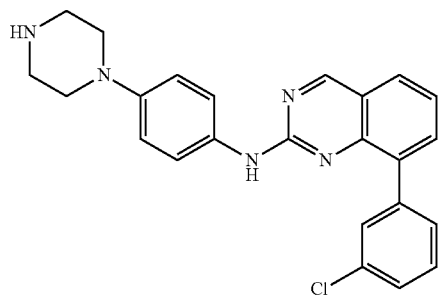

8-(3-chlorophenyl)-N-(4-(piperazin-1-yl)phenyl)quinazolin-2-amine 8-(3-Chlorophenyl)-N-(4-(piperazin-1-yl)phenyl)quinazolin-2-amine (20.1 mg) was prepared as described for N-(4-morpholinophenyl)-8-phenylquinazolin-2-amine. LRMS (M+H$^+$) m/z calculated 416.2, found 416.2. $^1$H NMR (CDCl$_3$, 400 MHz) δ 9.07 (s, 1H), 7.30-7.85 (m, 10H), 6.89 (d, 2H), 3.12-3.15 (m, 8H).

Example 29: Preparation of 8-(2-chlorophenyl)-N-(4-(piperazin-1-yl)phenyl)quinazolin-2-amine

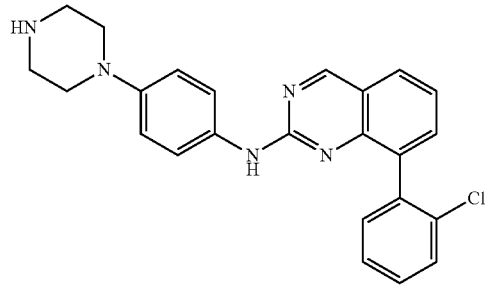

8-(2-chlorophenyl)-N-(4-(piperazin-1-yl)phenyl)quinazolin-2-amine 8-(2-Chlorophenyl)-N-(4-(piperazin-1-yl)phenyl)quinazolin-2-amine (24.5 mg) was prepared as described for N-(4-morpholinophenyl)-8-phenylquinazolin-2-amine. LRMS (M+H+) m/z calculated 416.2, found 416.2. $^1$H NMR (CDCl$_3$, 400 MHz) δ 9.07 (s, 1H), 7.28-7.78 (m, 10H), 6.72 (d, 2H), 3.10 (m, 8H).

Example 30: Preparation of 8-(3-fluorophenyl)-N-(4-(piperazin-1-yl)phenyl)quinazolin-2-amine

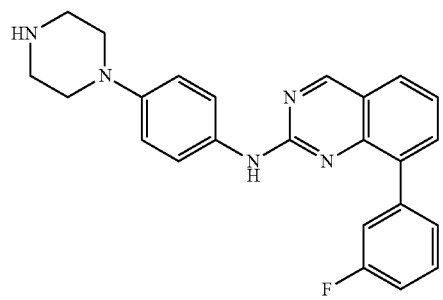

8-(3-fluorophenyl)-N-(4-(piperazin-1-yl)phenyl)quinazolin-2-amine 8-(3-Fluorophenyl)-N-(4-(piperazin-1-yl)phenyl)quinazolin-2-amine (7.6 mg) was prepared as described for N-(4-morpholinophenyl)-8-phenylquinazolin-2-amine. LRMS (M+H$^+$) m/z calculated 400.2, found 400.1. $^1$H NMR (CDCl$_3$, 300 MHz) δ 9.07 (s, 1H), 7.29-7.80 (m, 9H), 7.15 (t, 1H), 6.86 (d, 2H), 3.06-3.11 (m, 8H).

Example 31: Preparation of 8-phenyl-N-(4-(piperazin-1-yl)phenyl)quinazolin-2-amine

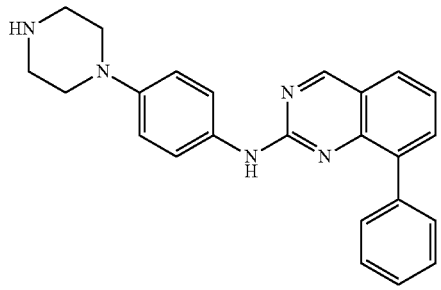

8-phenyl-N-(4-(piperazin-1-yl)phenyl)quinazolin-2-amine

8-Phenyl-N-(4-(piperazin-1-yl)phenyl)quinazolin-2-amine (14.6 mg) was prepared as described for N-(4-morpholinophenyl)-8-phenylquinazolin-2-amine. LRMS (M+H$^+$) m/z calculated 382.2, found 382.2. $^1$H NMR (CD3Cl3, 400 MHz) δ 9.07 (s, 1H), 7.33-7.81 (m, 11H), 6.82 (d, 2H), 3.10 (m, 8H).

Example 32: Preparation of 8-(2-fluorophenyl)-N-(4-(piperazin-1-yl)phenyl)quinazolin-2-amine

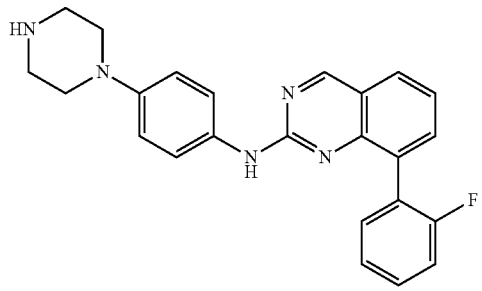

8-(2-fluorophenyl)-N-(4-(piperazin-1-yl)phenyl)quinazolin-2-amine 8-(2-Fluorophenyl)-N-(4-(piperazin-1-yl)phenyl)quinazolin-2-amine (41.6 mg) was prepared as described for N-(4-morpholinophenyl)-8-phenylquinazolin-2-amine. LRMS (M+H$^+$) m/z calculated 400.2, found 400.2. $^1$H NMR (CDCl$_3$, 400 MHz) δ 9.07 (s, 1H), 7.18-7.79 (m, 10H), 6.78 (d, 2H), 3.04-3.06 (m, 8H).

Example 33: Preparation of tert-butyl 4-(4-((8-(2-fluoro-5-(2-morpholinoethoxy)phenyl)quinazolin-2-yl)amino)phenyl)piperazine-1-carboxylate

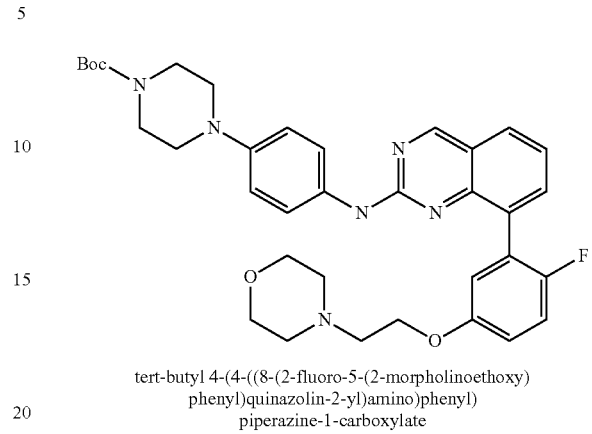

tert-butyl 4-(4-((8-(2-fluoro-5-(2-morpholinoethoxy)phenyl)quinazolin-2-yl)amino)phenyl)piperazine-1-carboxylate Tert-butyl 4-(4-((8-(2-fluoro-5-(2-morpholinoethoxy)phenyl)quinazolin-2-yl)amino)phenyl)piperazine-1-carboxylate (12.6 mg) was prepared as described for N-(4-morpholinophenyl)-8-phenylquinazolin-2-amine. LRMS (M+H) m/z calculated 629.3, found 629.2. $^1$H NMR (CDCl$_3$, 300 MHz) δ 9.08 (s, 1H), 7.79 (t, 2H), 7.58-7.75 (m, 3H), 7.40 (t, 1H), 7.00-7.20 (m, 3H), 6.80 (d, 2H), 4.10 (t, 2H), 3.59-3.73 (m, 8H), 3.04-3.07 (m, 4H), 2.78 (t, 2H), 2.54-2.58 (m, 4H), 1.51 (s, 1H).

Example 34: Preparation of 8-(2-fluoro-5-(2-morpholinoethoxy)phenyl)-N-(4-morpholinophenyl)quinazolin-2-amine

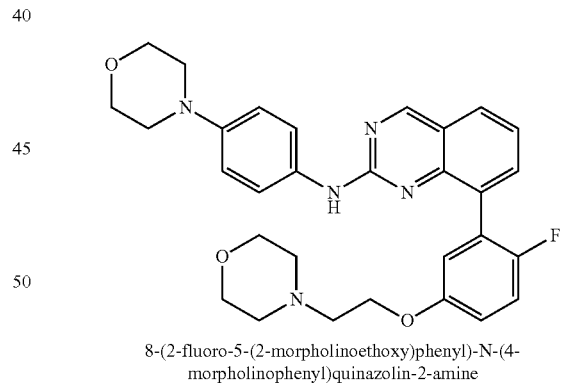

8-(2-fluoro-5-(2-morpholinoethoxy)phenyl)-N-(4-morpholinophenyl)quinazolin-2-amine 8-(2-Fluoro-5-(2-morpholinoethoxy)phenyl)-N-(4-morpholinophenyl)quinazolin-2-amine (11 mg) was prepared as described for N-(4-morpholinophenyl)-8-phenylquinazolin-2-amine. LRMS (M+H$^+$) m/z calculated 530.2, found 530.3. $^1$H NMR (CDCl$_3$, 300 MHz) δ 9.07 (s, 1H), 7.77 (t, 2H), 7.57 (d, 2H), 7.30-7.40 (m, 2H), 7.07-7.17 (m, 2H), 6.97-7.00 (m, 1H), 6.77 (d, 2H), 4.09 (t, 2H), 3.87 (t, 4H), 3.70 (t, 4H), 3.08 (t, 4H), 2.79 (t, 2H), 2.55 (t, 4H), 2.34 (s, 3H), 2.19 (s, 3H).

Example 35: Preparation of 8-(2-fluoro-5-(2-morpholinoethoxy)phenyl)-N-(4-(piperazin-1-yl)phenyl)quinazolin-2-amine

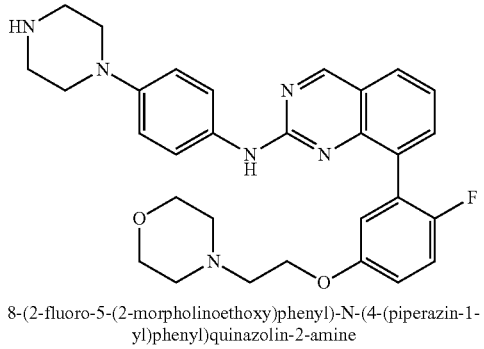 [SMILES: Fc1ccc(OCCN2CCOCC2)cc1-c1cccc2cnc(Nc3ccc(N4CCNCC4)cc3)nc12]

8-(2-fluoro-5-(2-morpholinoethoxy)phenyl)-N-(4-(piperazin-1-yl)phenyl)quinazolin-2-amine 8-(2-Fluoro-5-(2-morpholinoethoxy)phenyl)-N-(4-(piperazin-1-yl)phenyl)quinazolin-2-amine (53.4 mg) was prepared as described for N-(4-morpholinophenyl)-8-phenylquinazolin-2-amine. LRMS (M+H$^+$) m/z calculated 529.3, found 529.3. $^1$H NMR (CDCl$_3$, 400 MHz) δ 9.08 (s, 1H), 7.78 (t, 2H), 7.57 (d, 2H), 7.39 (t, 1H), 7.25 (s, 1H), 7.16 (t, 1H), 7.06-7.14 (m, 3H), 6.79 (d, 2H), 4.091 (t, 2H), 3.69 (t, 4H), 3.20 (m, 8H), 2.78 (t, 2H), 2.54 (m, 4H).

Example 36: Preparation of N-(3-(4-amino-2-((4-morpholinophenyl)amino)pyrido[3,4-d]pyrimidin-8-yl)phenyl)acrylamide

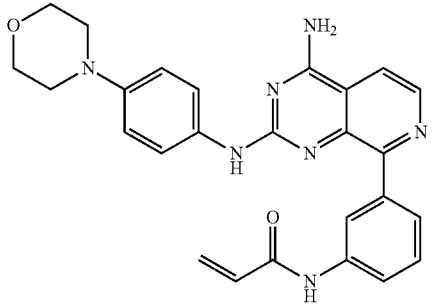

N-(3-(4-amino-2-((4-morpholinophenyl)amino)pyrido[3,4-d]pyrimidin-8-yl)phenyl)acrylamide

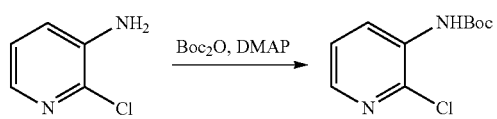

To a solution of 2-chloropyridin-3-amine (12.9 g, 0.1 mol, 1 eq.) and DMAP (13.4 g, 0.11 mmol, 1.1 eq.) in DCM (150 mL) was added Boc$_2$O (24.0 g, 0.11 mmol, 1.1 eq.) dropwise at r.t. The resulting mixture was stirred at r.t. for 3 h, then concentrated. The resulting residue was purified via flash column chromatography (EA/PE=1/30, v/v) to afford tert-butyl (2-chloropyridin-3-yl)carbamate (16.99 g, 74.2% yield).

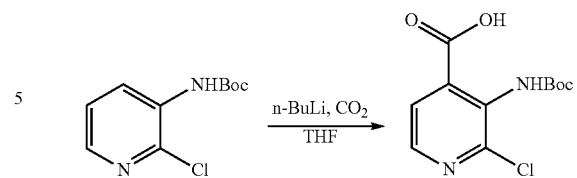

To a mixture of tert-butyl (2-chloropyridin-3-yl)carbamate (2.29 g, 10 mmol, 1 eq.) in THF (50 mL) was added n-BuLi (12 mL, 2.5M, 30 mmol, 3 eq.) dropwise at −78 OC under N$_2$. The mixture was stirred at −78 OC for 1 h, then bubbled with CO$_2$ for 30 min, concentrated, washed by sat. Na$_2$CO$_3$ solution, and extracted by EA (100 mL×2). The water phase was acidified with conc. HCl to pH 4-5, extracted with EA (100 mL×2). The combined organic phases were washed with brine, dried over anhydrous Na$_2$SO$_4$ and concentrated to afford 3-((tert-butoxycarbonyl)amino)-2-chloroisonicotinic acid (2.1 g, 76.9% yield).

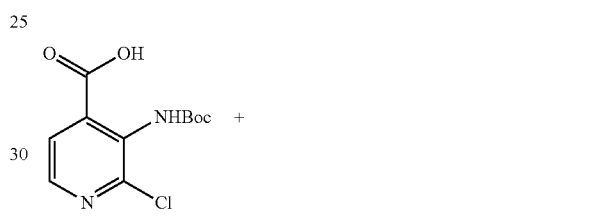

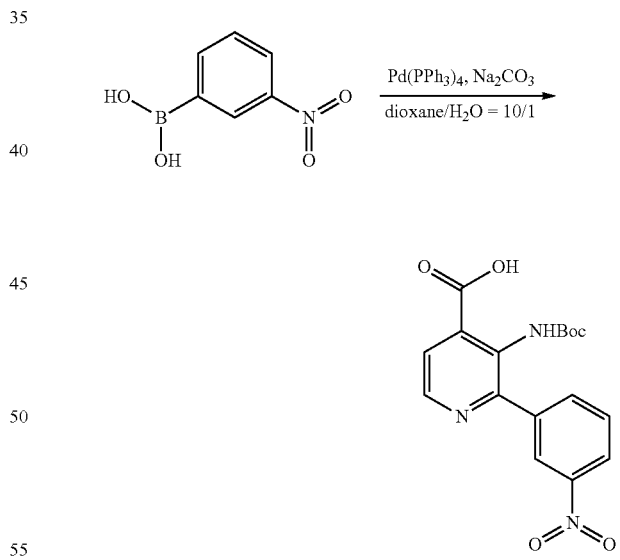

A mixture of 3-((tert-butoxycarbonyl)amino)-2-chloroisonicotinic acid (7.26 g, 27 mmol, 1 eq.), (3-nitrophenyl)boronic acid (4.9 g, 29 mmol, 1.1 eq.), Na$_2$CO$_3$ (11.45 g, 110 mmol, 4 eq.) and Pd(PPh$_3$)$_4$ (1.54 g, 2.7 mmol, 0.1 eq.) in dioxane (100 mL) and water (10 mL) was heated at 100° C. overnight, then cooled and concentrated. The resulting residue was dissolved in DCM (30 mL) and filtered. The filtrate was concentrated to afford crude 3-((tert-butoxycarbonyl)amino)-2-(3-nitrophenyl)isonicotinic acid, which was used in next step without further purification.

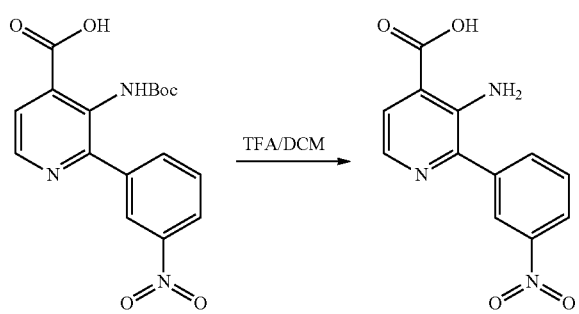 [SMILES: CC(C)(C)OC(=O)Nc1c(C(=O)O)ccnc1-c1cccc([N+](=O)[O-])c1 ; Nc1c(C(=O)O)ccnc1-c1cccc([N+](=O)[O-])c1]

To a solution of crude 3-((tert-butoxycarbonyl)amino)-2-(3-nitrophenyl)isonicotinic acid (6.8 g, 19 mmol, 1 eq.) in DCM (50 mL) at r.t. was added TFA (10 mL, 108 mmol, 4 eq.) dropwise. The resulting mixture was stirred at r.t. overnight, then concentrated. The residue was purified via RP-HPLC to afford 3-amino-2-(3-nitrophenyl)isonicotinic acid as yellow solid (4.7 g, 96% yield).

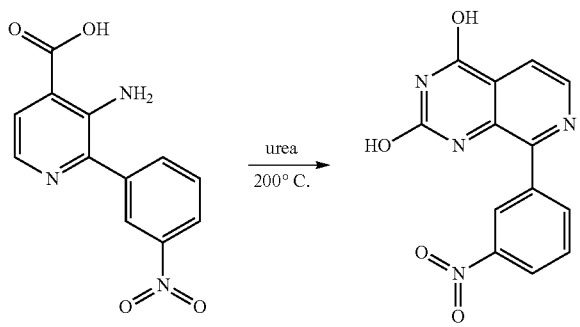 [SMILES: Nc1c(C(=O)O)ccnc1-c1cccc([N+](=O)[O-])c1 ; O=[N+]([O-])c1cccc(-c2nccc3c(O)nc(O)nc23)c1]

A mixture of 3-amino-2-(3-nitrophenyl)isonicotinic acid (4.7 g, 18 mmol, 1 eq.) and urea (10.9 g, 180 mmol, 50 eq.) was stirred at 200° C. for 6 h, then cooled and poured into ice-water. The solid was collected by filtration, then suspended in 5% aq. NaOH and stirred at r.t. overnight. The solid was collected by filtration, washed with $H_2O$ (100 mL×3) and dried in vacuo to afford 8-(3-nitrophenyl)pyrido[3,4-d]pyrimidine-2,4-diol (3.7 g, 71.8% yield).

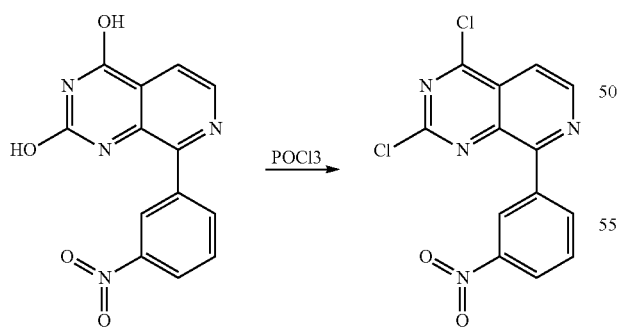

To a mixture of 8-(3-nitrophenyl)pyrido[3,4-d]pyrimidine-2,4-diol (3.7 g, 13 mmol, 1 eq.) in $POCl_3$ (40 mL) was added DMF (0.5 mL). The mixture was stirred at 130° C. for 12 h, then cooled to r.t. and concentrated. The residue was dissolved in EA (40 mL) and slowly poured into ice-water with vigorous stirring. The organic phase was separated, washed with brine, dried over anhydrous $Na_2SO_4$ and concentrated. The resulting residue was purified via flash column chromography (PE/EA=4/1, v/v) to afford 2,4-dichloro-8-(3-nitrophenyl)pyrido[3,4-d]pyrimidine (1.25 g, 30% yield).

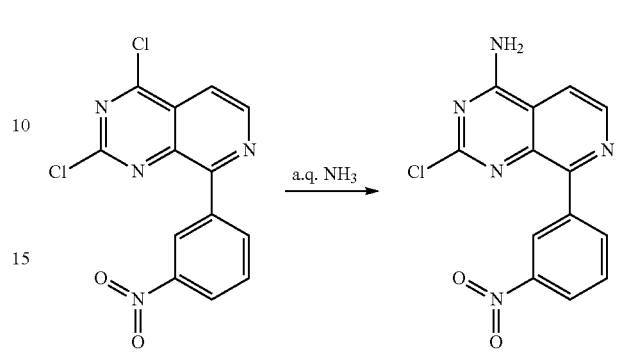

To a solution of ammonia hydroxide (2.97 mL, 38.9 mmol, 10 eq.) in THF (5 mL) at 0° C. was added a solution of 2,4-dichloro-8-(3-nitrophenyl)pyrido[3,4-d]pyrimidine (1.25 g, 3.89 mmol, 1 eq.) in THF (25 mL). The mixture was stirred at 0° C. for 30 min, then diluted with EA (50 mL), washed with brine, dried over anhydrous $Na_2SO_4$ and concentrated. The resulting residue was purified via flash column chromography (DCM/MeOH=10:1, v:v) to afford 2-chloro-8-(3-nitrophenyl)pyrido[3,4-d]pyrimidin-4-amine (0.517 g, 44% yield).

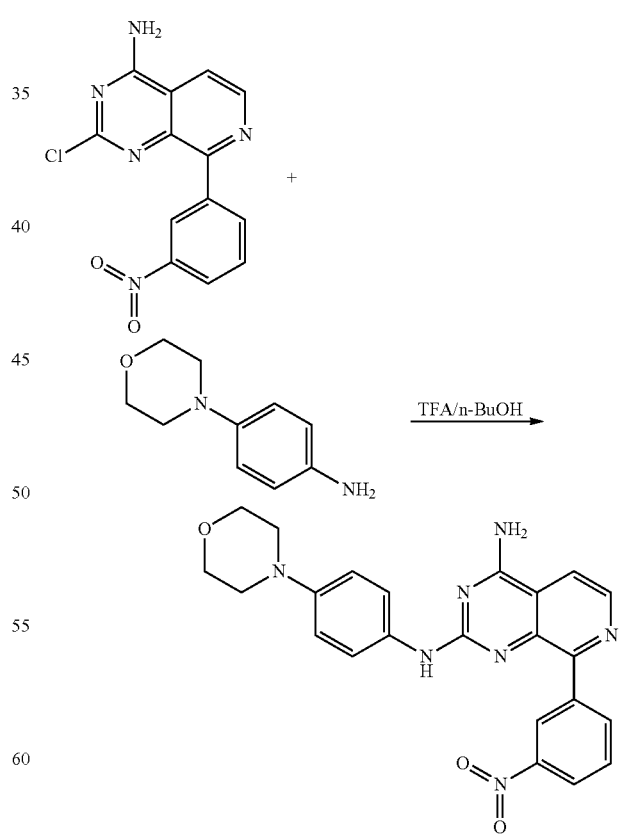

To a solution of 4-morpholinoaniline (65 mg, 0.36 mmol, 1.1 eq.) and 2-chloro-8-(3-nitrophenyl)pyrido[3,4-d]pyrimidin-4-amine (100 mg, 0.33 mmol, 1 eq.) in n-BuOH (20 mL)

was added TFA (75 mg, 0.66 mmol, 2 eq.). The mixture was stirred at 100° C. for 12 h, then cooled to r.t. The precipitate was collected by filtration, washed with MeOH (10 mL×2) and dried in vacuo to afford N²-(4-morpholinophenyl)-8-(3-nitrophenyl)pyrido[3,4-d]pyrimidine-2,4-diamine (95 mg, 65% yield).

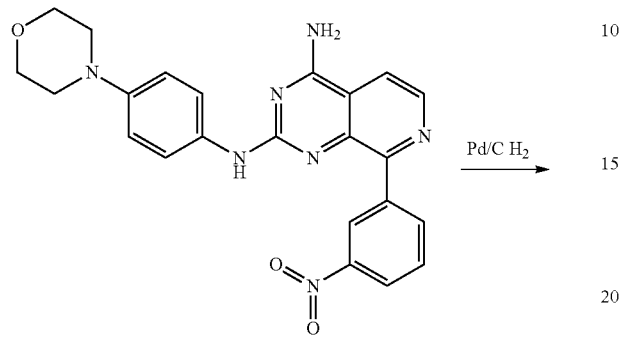

To a solution of N²-(4-morpholinophenyl)-8-(3-nitrophenyl)pyrido[3,4-d]pyrimidine-2,4-diamine (55 mg, 0.12 mmol, 1 eq.) and DIEA (32 mg, 0.24 mmol, 2 eq.) in EA (10 mL) was added Pd/C (5.5 mg, w/w>50%). The mixture was stirred at r.t. under H₂ atmosphere (1 atm) overnight, then filtered and concentrated. The residue was purified via flash column chromography (DCM/MeOH=10:1, v:v) to afford 8-(3-aminophenyl)-N²-(4-morpholinophenyl)pyrido[3,4-d]pyrimidine-2,4-diamine (32 mg, 65% yield).

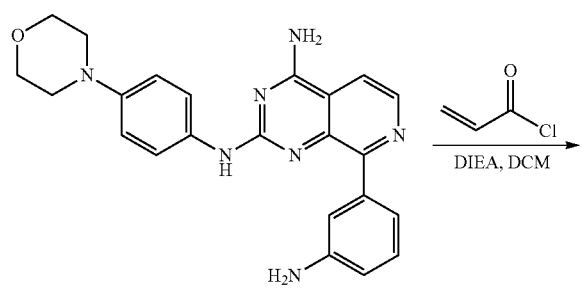

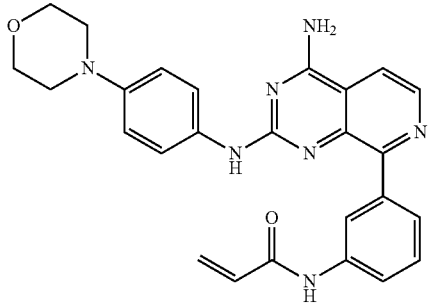

To a solution of 8-(3-aminophenyl)-N²-(4-morpholinophenyl)pyrido[3,4-d]pyrimidine-2,4-diamine (26 mg, 0.06 mmol, 1 eq.) in DCM (10 mL) was added DIEA (0.04 mL, 0.18 mmol, 3 eq.), followed by acryloyl chloride (0.006 mL, 0.12 mmol, 1.2 eq.). The resulting mixture was stirred at r.t. for 1 h, then washed with brine, dried over anhydrous Na₂SO₄ and concentrated. The resulting residue was purified via RP-HPLC to afford N-(3-(4-amino-2-((4-morpholinophenyl)amino)pyrido[3,4-d]pyrimidin-8-yl)phenyl)acrylamide as yellow solid (8.3 mg, 30% yield). LRMS (M+H⁺) m/z calculated 468.2, found 468.2. ¹H NMR (CD₃OD, 300 MHz) δ 8.60 (d, 1H), 8.15 (m, 1H), 8.05 (d, 1H), 7.74 (d, 1H), 7.60 (t, 1H), 7.45-7.48 (m, 3H), 7.03 (d, 2H), 6.43-6.49 (m, 2H), 5.85 (dd, 1H), 3.85-3.87 (m, 4H), 3.85-3.87 (m, 4H).

Example 37: Preparation of N-(3-(2-((4-morpholinophenyl)amino)pyrido[3,4-d]pyrimidin-8-yl)phenyl)acrylamide

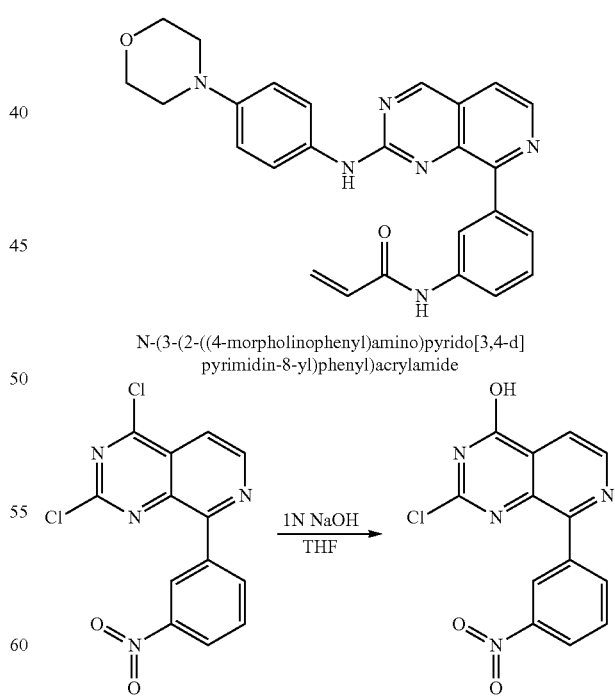

N-(3-(2-((4-morpholinophenyl)amino)pyrido[3,4-d]pyrimidin-8-yl)phenyl)acrylamide To a solution of 2,4-dichloro-8-(3-nitrophenyl)pyrido[3,4-d]pyrimidine (455 mg, 1.42 mmol, 1 eq.) in THF (10 mL) was added NaOH (1N, 5 mL, 5 mmol, 3.52 eq.). The mixture was stirred at r.t. for 2 h, then diluted with EA (50 mL), washed with brine, dried over anhydrous Na$_2$SO$_4$ and concentrated. The resulting residue was purified via flash column chromatography (DCM/MeOH=10:1, v:v) to afford 2-chloro-8-(3-nitrophenyl)pyrido[3,4-d]pyrimidin-4-ol (395 mg, 92.7% yield).

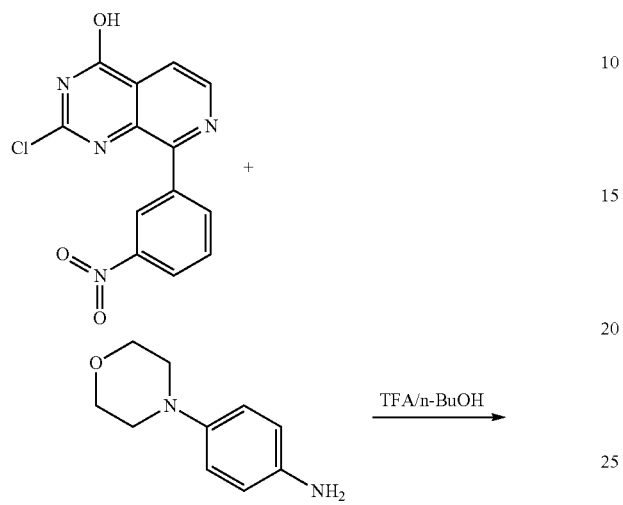

To a solution of 4-morpholinoaniline (258 mg, 1.45 mmol, 1.1 eq.) and 2-chloro-8-(3-nitrophenyl)pyrido[3,4-d]pyrimidin-4-ol (395 mg, 1.32 mmol, 1 eq.) in n-BuOH (20 mL) was added TFA (266 mg, 2.64 mmol, 2 eq.). The mixture was stirred at 100° C. for 12 h, then cooled to r.t. The precipitate was collected by filtration, washed with MeOH (10 mL×2) and dried in vacuo to afford 2-((4-morpholinophenyl)amino)-8-(3-nitrophenyl)pyrido[3,4-d]pyrimidin-4-ol (350 mg, 65% yield).

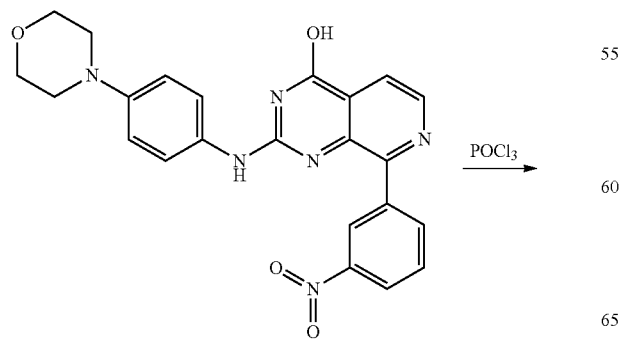

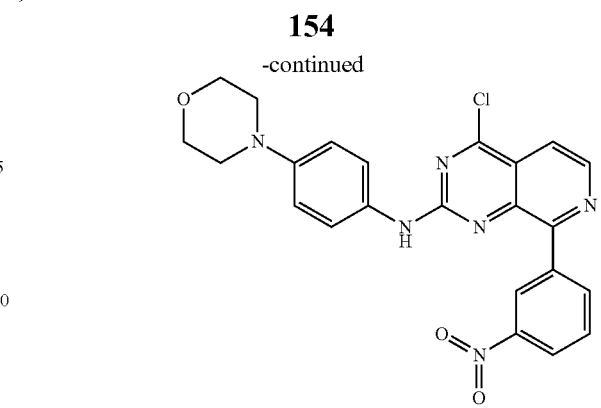

A mixture of 2-((4-morpholinophenyl)amino)-8-(3-nitrophenyl)pyrido[3,4-d]pyrimidin-4-ol (350 mg, 0.79 mmol, 1 eq.) in POCl$_3$ (15 mL) was heated to 140° C. for 2 h, then cooled to r.t. and concentrated. The residue was dissolved in EA (50 mL) and slowly poured into ice-water. The organic phase was separated, washed with brine, dried over anhydrous Na$_2$SO$_4$, and concentrated to afford 4-chloro-N-(4-morpholinophenyl)-8-(3-nitrophenyl)pyrido[3,4-d]pyrimidin-2-amine (305 mg, 83.8% yield).

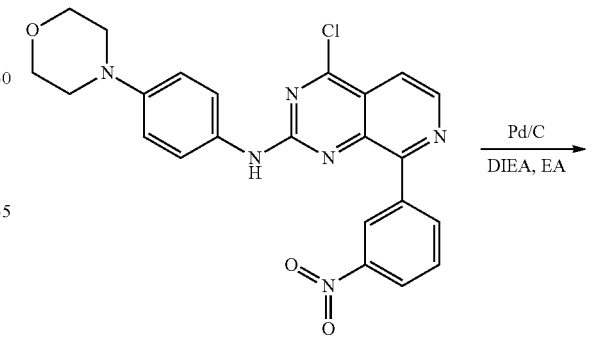

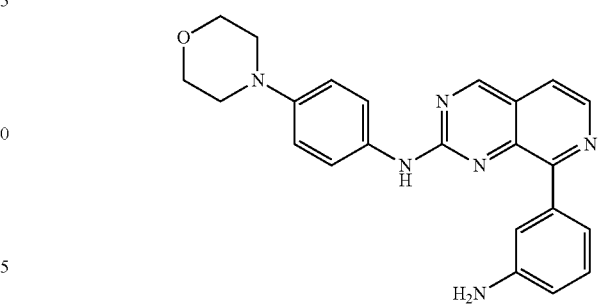

To a solution of 4-chloro-N-(4-morpholinophenyl)-8-(3-nitrophenyl)pyrido[3,4-d]pyrimidin-2-amine (305 mg, 0.66 mmol, 1 eq.) and DIEA (235 mg, 1.82 mmol, 2.76 eq.) in EA (15 mL) was added Pd/C (30 mg, w/w>50%). The mixture was stirred at r.t. under H$_2$ atmosphere (1 atm) overnight, then filtered and concentrated. The resulting residue was purified via flash column chromatography (PE/EA=¼, v:v) to afford 8-(3-aminophenyl)-N-(4-morpholinophenyl)pyrido[3,4-d]pyrimidin-2-amine.

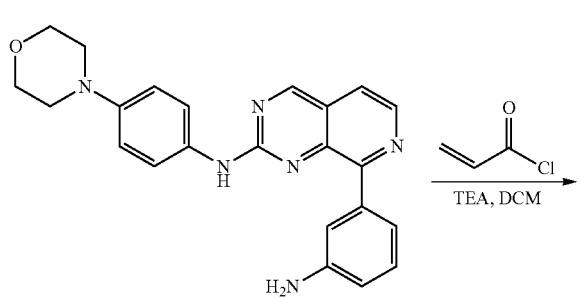

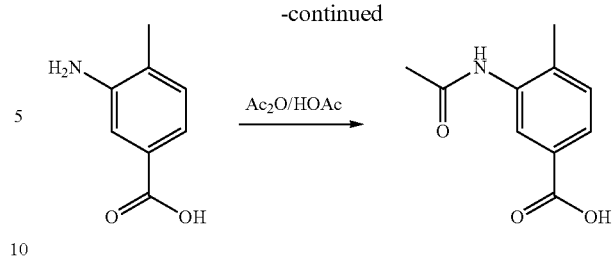

To a solution of 3-amino-4-methylbenzoic acid (100 g, 0.66 mol, 1.0 eq.) in AcOH (1.34 L) was added Ac₂O (412 g, 4.04 mol, 6 eq.) dropwise at r.t. over 1 h. The mixture was stirred overnight. The solid was collected by filtration, washed with EA (200 mL×3) and dried in vacuo to afford 3-acetamido-4-methylbenzoic acid (123 g, 96.2% yield).

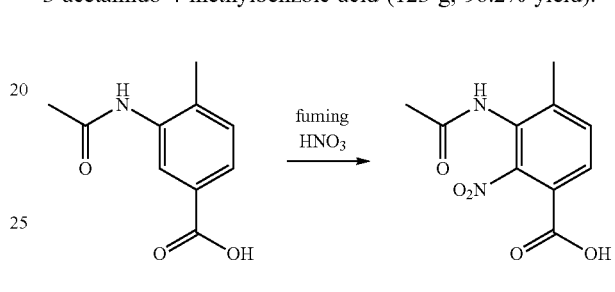

To a solution of 8-(3-aminophenyl)-N-(4-morpholinophenyl)pyrido[3,4-d]pyrimidin-2-amine (50 mg, 0.13 mmol, 1 eq.) in DCM (10 mL) was added TEA (35 mg, 0.35 mmol, 2.7 eq.), followed by acryloyl chloride (0.008 mL, 0.16 mmol, 1.2 eq.). The resulting mixture was stirred at r.t. for 1 h, then washed with brine, dried over anhydrous Na₂SO₄ and concentrated. The residue was purified via RP-HPLC to afford N-(3-(2-((4-morpholinophenyl)amino)pyrido[3,4-d]pyrimidin-8-yl)phenyl)acrylamide (4.1 mg, 6.9% yield). LRMS (M+H⁺) m/z calculated 453.2, found 453.1. ¹H NMR (CD₃OD, 300 MHz) δ 9.44 (s, 1H), 8.53-8.55 (m, 2H), 7.90-8.34 (m, 3H), 7.56-7.75 (m, 3H), 7.05-7.28 (m, 2H), 6.43-6.49 (m, 2H), 5.81-5.87 (m, 1H), 3.84-3.96 (m, 4H), 3.18-3.38 (m, 4H).

To a solution of fuming HNO₃ (500 mL) at 0-5° C. was added 3-acetamido-4-methylbenzoic acid (123 g, 0.637 mol, 1 eq.) in portions over 1 h. The mixture was stirred for 1.5 h, then ice was added. The mixture was stirred for a further 30 min. The solid was collected by filtration, and dried in vacuo to afford 3-acetamido-4-methyl-2-nitrobenzoic acid (82 g, 54% yield).

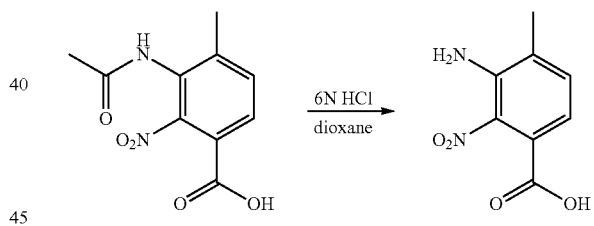

To a solution of 3-acetamido-4-methyl-2-nitrobenzoic acid (79 g, 0.33 mol, 1.0 eq.) in dioxane (400 mL) was added HCl (6 N, 200 mL) dropwise. The mixture was heated under reflux overnight, then extracted with EA (200 mL×3). The combined organic phases were dried over Na₂SO₄ and concentrated. The solid was triturated with the mixed solvent (PE/EA=10/1, v/v) and filtered to afford 3-amino-4-methyl-2-nitrobenzoic acid (60 g, 92.7% yield).

Example 38: Preparation of N-(3-(7-methyl-2-((4-morpholinophenyl)amino)quinazolin-8-yl)phenyl)acrylamide

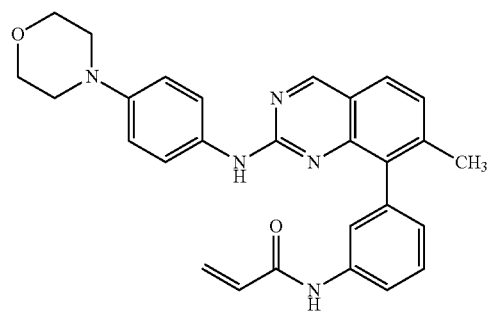

N-(3-(7-methyl-2-((4-morpholinophenyl)amino)quinazolin-8-yl)phenyl)acrylamide

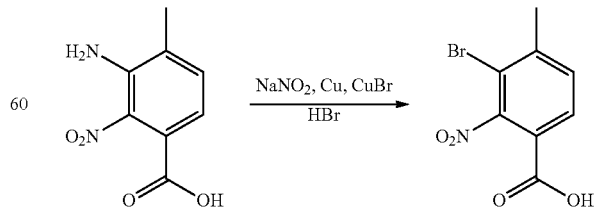

To a solution of 3-amino-4-methyl-2-nitrobenzoic acid (48.5 g, 0.25 mol, 1.0 eq.) in HBr (500 mL) at 0° C. was added NaNO$_2$ (30.7 g, 0.44 mol, 1.8 eq.) in water (100 mL) dropwise. After 15 min, Cu powder (2.91 g, 0.045 mol, 0.18 eq.) was added in portions. After 30 min, the mixture was heated at 60° C. for 1 h, then cooled and added ice-water until a yellow precipitate formed. The precipitate was filtered, washed with water and dried in vacuo to afford 3-bromo-4-methyl-2-nitrobenzoic acid (56.7 g, 86.5% yield).

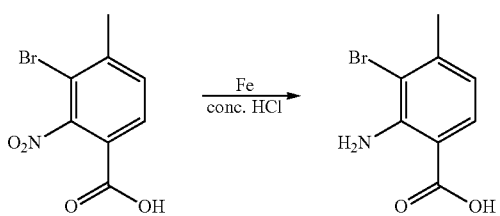

To a solution of 3-bromo-4-methyl-2-nitrobenzoic acid (56.7 g, 0.22 mol, 1.0 eq.) and conc. HCl (50 mL) in EtOH (700 mL) was added Fe (36.8 g, 0.66 mol, 3 eq.) in portions. The mixture was heated under reflux overnight, then concentrated and adjusted to to pH 8-9 with NaOH (1N) and filtered. The filtrate was neutralized to pH-6, the resulting precipitate was filtered and dried in vacuo to afford 2-amino-3-bromo-4-methylbenzoic acid (49.5 g, 97.8% yield).

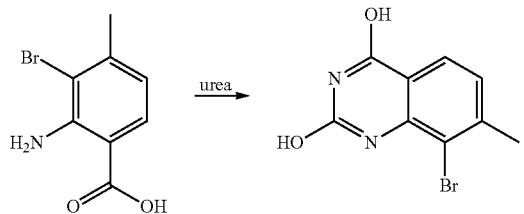

A mixture of 2-amino-3-bromo-4-methylbenzoic acid (2.29 g, 10 mmol, 1 eq.) and urea (8.9 g, 150 mmol, 15 eq.) was stirred at 200° C. for 3 h, then poured into ice-water. The solid was collected by filtration, washed with H$_2$O for three times, and dried in vacuo to afford 8-bromo-7-methylquinazoline-2,4-diol (1.6 g, 64% yield).

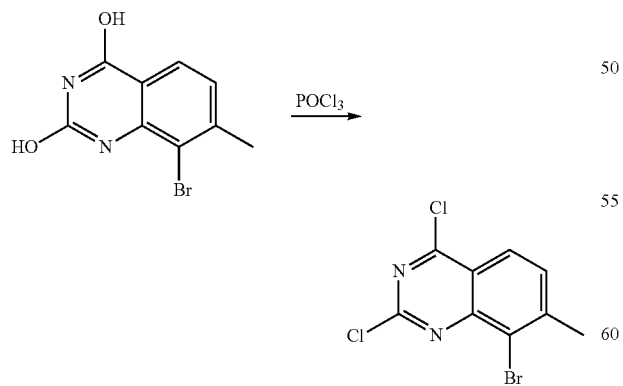

To a mixture of 8-bromo-7-methylquinazoline-2,4-diol (1.6 g, 6.2 mmol, 1 eq.) in POCl$_3$ (20 mL) was added DMF (0.5 mL). The mixture was stirred at 130° C. for 12 h, then cooled to r.t., and concentrated. The resulting residue was dissolved in EA (50 mL) and poured into ice-water with vigorous stirring. The organic phase was separated and washed with brine, dried over anhydrous Na$_2$SO$_4$ and concentrated. The resulting residue was purified via column chromatography (PE/EA==10:1, v/v) to afford 8-bromo-2,4-dichloro-7-methylquinazoline as a white solid (1.2 g, 66.7% yield).

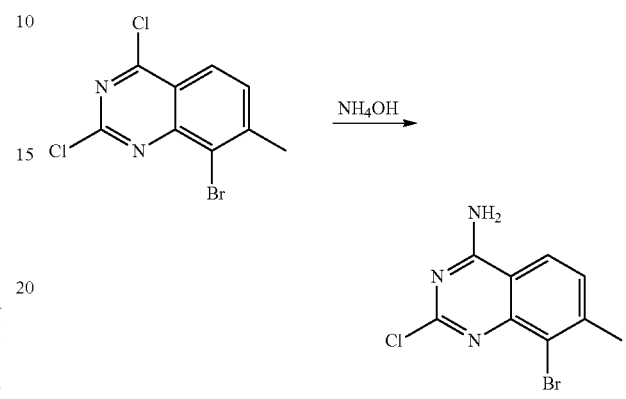

To a solution of ammonia hydroxide (3 mL, 41 mmol, 10 eq.) in THF (25 mL) cooled to 0° C. was added a solution of 8-bromo-2,4-dichloro-7-methylquinazoline (1.2 g, 4.1 mmol, 1 eq.) in THF (25 mL). The mixture was stirred at 0° C. for 30 min, then diluted with EA (50 mL), washed with brine, dried over anhydrous Na$_2$SO$_4$ and concentrated. The resulting residue was purified via column chromatography (PE/EA=10:1, v/v) to afford 8-bromo-2-chloro-7-methylquinazolin-4-amine as a white solid (1.0 g, 90.9% yield).

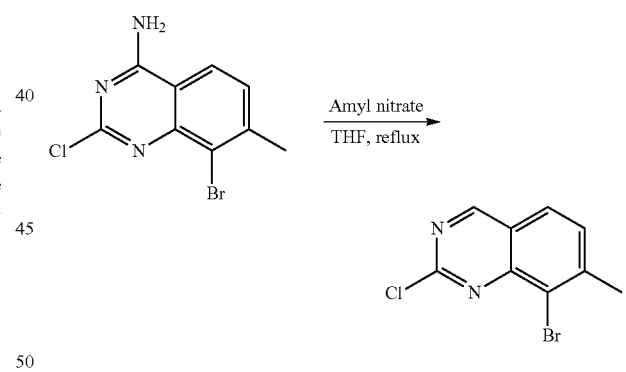

To a solution of 8-bromo-2-chloro-7-methylquinazolin-4-amine (1.0 g, 3.7 mmol, 1 eq.) in THF (20 mL) at 70° C. was added isopentyl nitrite (1.9 mL, 14.8 mmol, 4 eq.) dropwise. The resulting mixture was stirred at 70° C. for 12 h, then cooled to r.t. and concentrated. The resulting residue was purified via column chromatography (PE/EA=8:1, v/v) to afford 8-bromo-2-chloro-7-methylquinazoline as a yellow solid (540 mg, 56.8% yield).

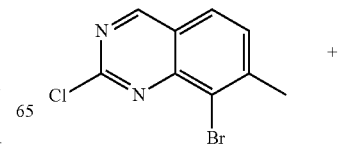

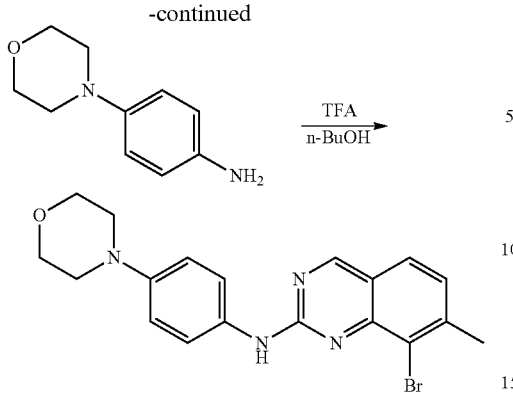

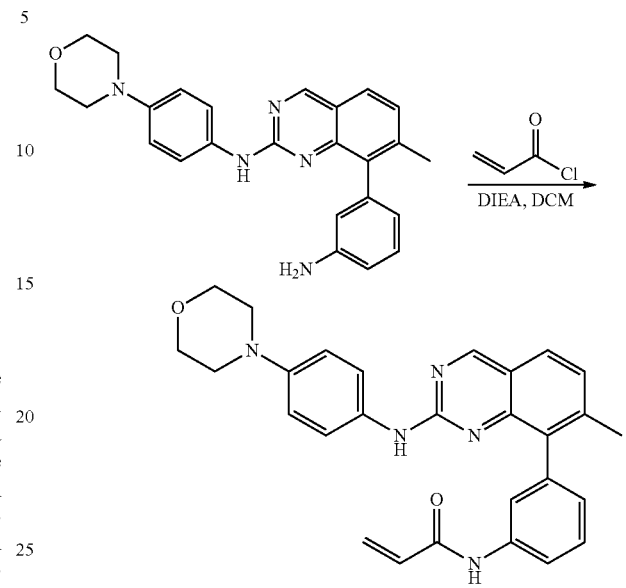

To a solution of 4-morpholinoaniline (186 mg, 1.05 mmol, 1 eq.) and 8-bromo-2-chloro-7-methylquinazoline (270 mg, 1.05 mmol, 1 eq.) in n-BuOH (10 mL) was added TFA (0.09 mL, 1.2 mmol, 1.2 eq). The mixture was stirred at 80° C. for 12 h, cooled to r.t. and concentrated. The resulting residue was dissolved in EA (10 mL), washed with Na$_2$CO$_3$ solution, dried over anhydrous Na$_2$SO$_4$ and concentrated. The resulting residue was purified via column chromatography (PE/EA=3:1, v/v) to afford 8-bromo-7-methyl-N-(4-morpholinophenyl)quinazolin-2-amine as a yellow solid (311 mg, 74.6% yield).

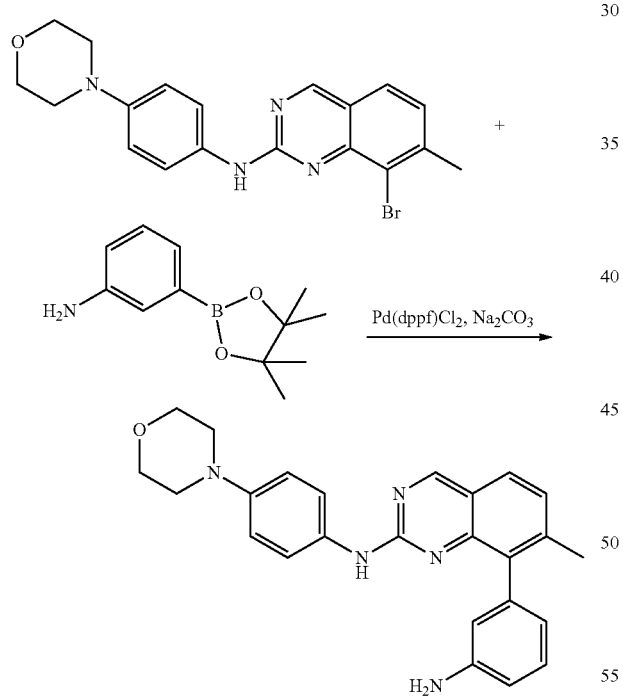

To a solution of 8-bromo-7-methyl-N-(4-morpholinophenyl)quinazolin-2-amine (311 mg, 0.78 mmol, 1 eq.) and 3-(4,4,5,5-tetramethyl-1,3,2-dioxaborolan-2-yl)aniline (213.7 mg, 1.56 mmol, 2 eq.) in dioxane (16 mL) and water (4 mL) was added Na$_2$CO$_3$ (330 mg, 3.12 mmol, 4 eq.), followed by Pd(dppf)Cl$_2$ (65 mg, 0.08 mmol, 0.1 eq.) under N$_2$ protection. The mixture was stirred at 90° C. for 12 h under N$_2$ protection, cooled to r.t., diluted with EA (40 mL) and filtered. The filtrate was concentrated and the resulting residue was purified by column chromatography (PE/EA=1/2, v/v) to afford 8-(3-aminophenyl)-7-methyl-N-(4-morpholinophenyl)quinazolin-2-amine (274 mg, 85.4% yield).

To a solution of 8-(3-aminophenyl)-7-methyl-N-(4-morpholinophenyl)quinazolin-2-amine (70 mg, 0.117 mmol, 1 eq.) in DCM (10 mL) was added DIEA (0.10 mL, 0.51 mmol, 3 eq.), followed by acryloyl chloride (0.017 mL, 0.20 mmol, 1.2 eq.). The resulting mixture was stirred at r.t. for 1 h, diluted with EA, washed with brine, dried over anhydrous Na$_2$SO$_4$, and concentrated. The resulting residue was purified via column chromatography (PE/EA=1:3, v/v) to afford N-(3-(7-methyl-2-((4-morpholinophenyl)amino)quinazolin-8-yl)phenyl)acrylamide (22 mg, 27.8% yield). LRMS (M+H$^+$) m/z calculated 466.2, found 466.2. $^1$H NMR (CDCl$_3$, 300 MHz) δ 9.06 (s, 1H), 8.07-8.11 (m, 1H), 7.14-7.66 (m, 9H), 6.69-6.76 (m, 2H), 6.18-6.47 (m, 2H), 5.75-5.79 (m, 1H), 3.85-3.90 (m, 4H), 3.03-3.10 (m, 4H), 2.41 (t, 4H), 2.41 (s, 3H).

Example 39: Preparation of N-(3-(7-methyl-2-((4-(4-methylpiperazin-1-yl)phenyl)amino)quinazolin-8-yl)phenyl)acrylamide

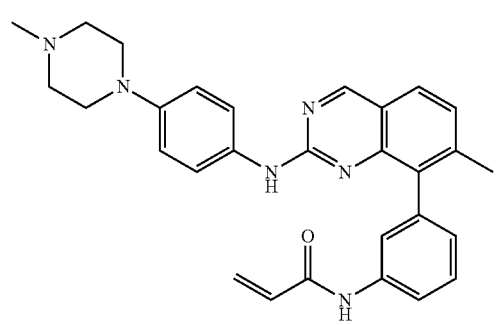

N-(3-(7-methyl-2-((4-(4-methylpiperazin-1-yl)phenyl)amino)quinazolin-8-yl)phenyl)acrylamide N-(3-(7-methyl-2-((4-(4-methylpiperazin-1-yl)phenyl)amino)quinazolin-8-yl)phenyl)acrylamide (18.7 mg) was prepared as described for N-(3-(7-methyl-2-((4-morpholinophenyl)amino)quinazolin-8-yl)phenyl)acrylamide. LRMS (M+H⁺) m/z calculated 479.2, found 479.2. ¹H NMR (DMSO-d6, 300 MHz) δ 10.32 (s, 1H), 9.65 (s, 1H), 9.20 (s, 1H), 7.96-7.99 (m, 1H), 7.81 (d, 1H), 7.31-7.56 (m, 5H), 7.00 (d, 1H), 6.63 (d, 2H), 6.09-6.52 (m, 2H), 5.73 (d, 1H), 2.90-2.95 (m, 8H), 2.55-2.59 (m, 3H), 2.38 (s, 3H).

Example 40: Preparation of N-(3-(2-((4-(4-acetylpiperazin-1-yl)phenyl)amino)-7-methylquinazolin-8-yl)phenyl)acrylamide

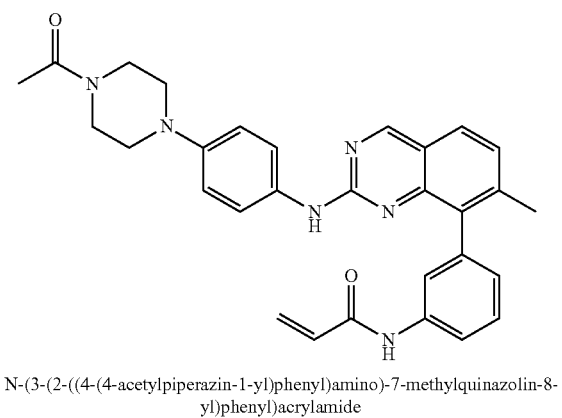 [SMILES: C=CC(=O)Nc1cccc(-c2c(C)ccc3cnc(Nc4ccc(N5CCN(C(C)=O)CC5)cc4)nc23)c1]

N-(3-(2-((4-(4-acetylpiperazin-1-yl)phenyl)amino)-7-methylquinazolin-8-yl)phenyl)acrylamide N-(3-(2-((4-(4-acetylpiperazin-1-yl)phenyl)amino)-7-methylquinazolin-8-yl)phenyl)acrylamide (14.1 mg) was prepared as described for N-(3-(7-methyl-2-((4-morpholinophenyl)amino)quinazolin-8-yl)phenyl)acrylamide. LRMS (M+H⁺) m/z calculated 507.2, found 507.2. ¹H NMR (CD₃OD, 300 MHz) δ 9.05 (s, 1H), 8.06 (d, 1H), 7.74 (d, 1H), 7.50-7.53 (m, 4H), 7.31 (d, 1H), 7.07 (d, 1H), 6.72 (d, 2H), 6.39-6.45 (m, 2H), 5.77 (dd, 1H), 3.66-3.74 (m, 4H), 2.98-3.06 (m, 4H), 2.38 (s, 3H), 2.02 (s, 3H).

Example 41: Preparation of N-(3-(7-methyl-2-((4-(4-methylpiperazin-1-yl)phenyl)amino)quinazolin-8-yl)phenyl)propionamide

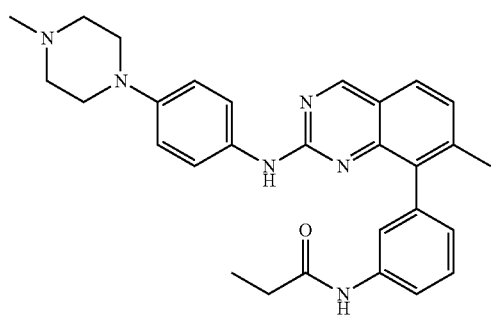

N-(3-(7-methyl-2-((4-(4-methylpiperazin-1-yl)phenyl)amino)quinazolin-8-yl)phenyl)propionamide N-(3-(7-methyl-2-((4-(4-methylpiperazin-1-yl)phenyl)amino)quinazolin-8-yl)phenyl)propionamide (40.8 mg) was prepared as described for N-(3-(7-methyl-2-((4-morpholinophenyl)amino)quinazolin-8-yl)phenyl)acrylamide. LRMS (M+H+) m/z calculated 481.3, found 481.0. 1H NMR ((DMSO-d6, 300 MHz) δ 10.00 (s, 1H), 9.60 (s, 1H), 9.19 (s, 1H), 7.79-7.86 (m, 2H), 7.31-7.57 (m, 5H), 6.96 (d, 1H), 6.66 (d, 2H), 3.15-3.28 (m, 6H), 2.73-2.89 (m, 4H), 2.28-2.33 (m, 6H), 1.05 (t, 3H).

Example 42: Preparation of N-(3-(7-(hydroxymethyl)-2-((4-(4-methylpiperazin-1-yl)phenyl)amino)quinazolin-8-yl)phenyl)acrylamide

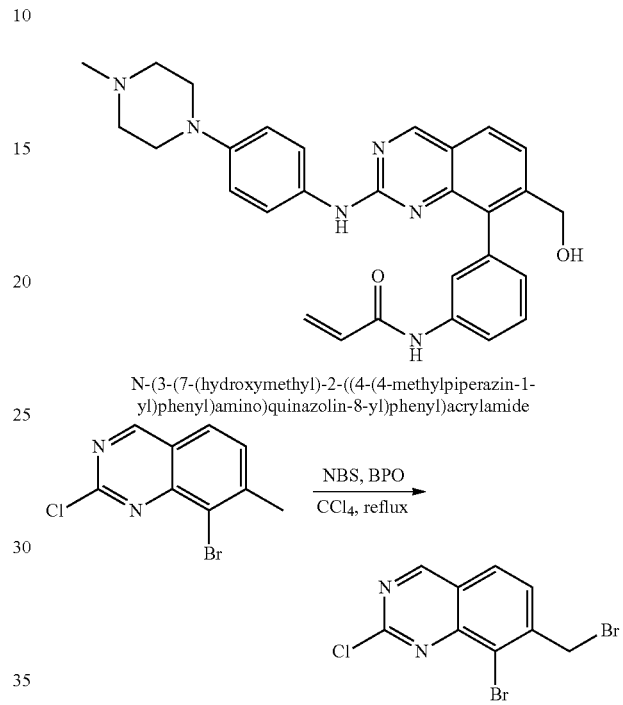

N-(3-(7-(hydroxymethyl)-2-((4-(4-methylpiperazin-1-yl)phenyl)amino)quinazolin-8-yl)phenyl)acrylamide To a solution of 8-bromo-2-chloro-7-methylquinazoline (2.7 g, 10.5 mmol, 1 eq.) and NBS (2.2 g, 12.6 mmol, 1.2 eq.) in CCl₄ (30 mL) was added BPO (254 mg, 1.05 mmol, 0.1 eq.). The mixture was heated at 100° C. overnight, cooled to r.t., washed with sat. NaHCO₃ solution, dried over anhydrous Na₂SO₄ and concentrated. The resulting residue was purified via column chromatography (PE/EA=10/1, v/v) to afford 8-bromo-7-(bromomethyl)-2-chloroquinazoline as a yellow solid (2.0 g, 57.1% yield).

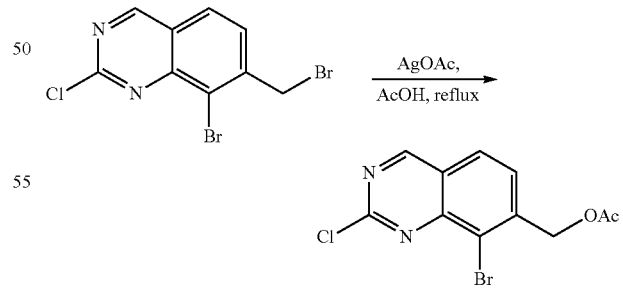

To a solution of 8-bromo-7-(bromomethyl)-2-chloroquinazoline (1 g, 3.0 mmol, 1 eq.) in AcOH (50 mL) was added AgOAc (1 g, 6.0 mmol, 2 eq.). The mixture was heated at 100° C. for 1.5 h, cooled and concentrated. The resulting residue was purified via column chromatography (PE/EA=5/1, v/v) to afford (8-bromo-2-chloroquinazolin-7-yl)methyl acetated (756 mg, 80% yield).

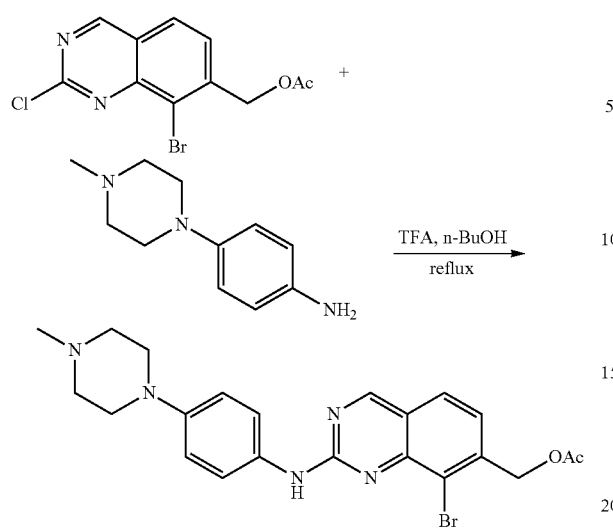

To a solution of 4-(4-methylpiperazin-1-yl)aniline (56 mg, 0.291 mmol, 1.1 eq.) and (8-bromo-2-chloroquinazolin-7-yl)methyl acetate (84 mg, 0.265 mmol, 1 eq.) in n-BuOH (10 mL) was added TFA (30 mg, 0.265 mmol, 1 eq.). The mixture was stirred at 80° C. for 12 h, cooled and concentrated. The resulting residue was dissolved in EA (40 mL), washed with Na$_2$CO$_3$ solution, dried over anhydrous Na$_2$SO$_4$ and concentrated. The resulting residue was purified via column chromatography (DCM/MeOH=20:1, v/v) to afford (8-bromo-2-((4-(4-methylpiperazin-1-yl)phenyl)amino)quinazolin-7-yl)methyl acetate (52 mg, 42% yield).

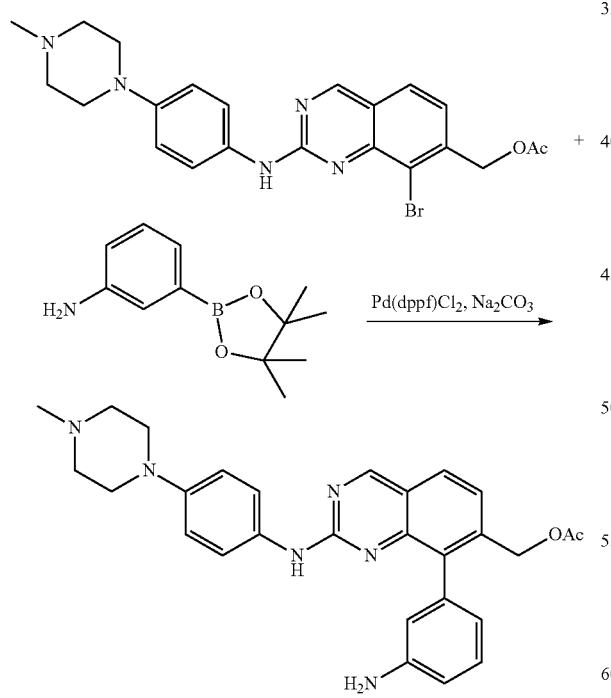

To a solution of (8-bromo-2-((4-(4-methylpiperazin-1-yl)phenyl)amino)quinazolin-7-yl)methyl acetate (52 mg, 0.11 mmol, 1 eq.) and 3-(4,4,5,5-tetramethyl-1,3,2-dioxaborolan-2-yl)aniline (18 mg, 0.132 mmol, 1.2 eq.) in dioxane (10 mL) and water (1 mL) was added Na$_2$CO$_3$ (23 mg, 0.22 mmol, 2 eq.), followed by Pd(dppf)Cl$_2$ (9 mg, 0.011 mmol, 0.1 eq.) under N$_2$. The mixture was stirred at 90° C. for 12 h under N$_2$. The solution was cooled, diluted with EA and filtered. The filtrate was concentrated and the resulting residue was purified via column chromatography (DCM/MeOH=20:1, v/v) to afford (8-(3-aminophenyl)-2-((4-(4-methylpiperazin-1-yl)phenyl)amino)quinazolin-7-yl)methyl acetate (35.5 mg, 67% yield).

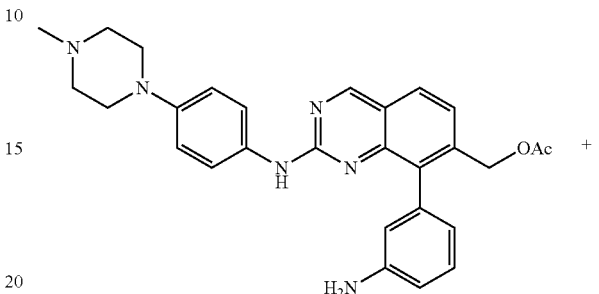

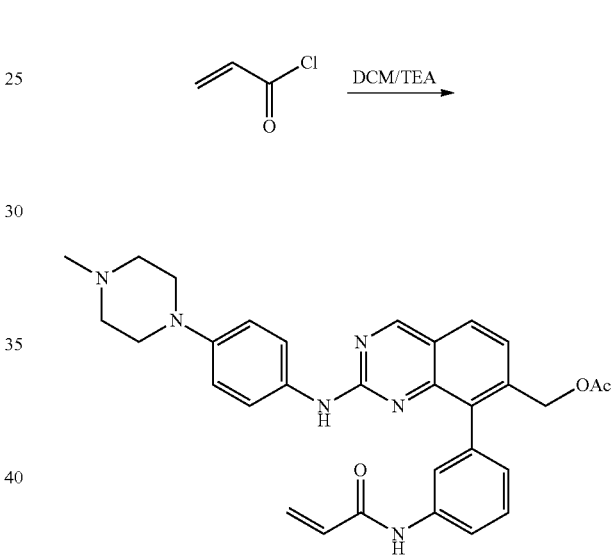

To a solution of (8-(3-aminophenyl)-2-((4-(4-methylpiperazin-1-yl)phenyl)amino)quinazolin-7-yl)methyl acetate (35.5 mg, 0.07 mmol, 1 eq.) in DCM (10 mL) was added DIEA (28 mg, 0.22 mmol, 3 eq.), followed by acryloyl chloride (7.24 mg, 0.08 mmol, 1.2 eq.). The resulting mixture was stirred at r.t. for 1 h, diluted with EA (30 mL), washed with brine, dried over anhydrous Na$_2$SO$_4$ and concentrated. The resulting residue was purified v a column chromatography (DCM/MeOH=20:1, v/v) to afford (8-(3-acrylamidophenyl)-2-((4-(4-methylpiperazin-1-yl)phenyl)amino)quinazolin-7-yl)methyl acetate (23 mg, 27.8% yield).

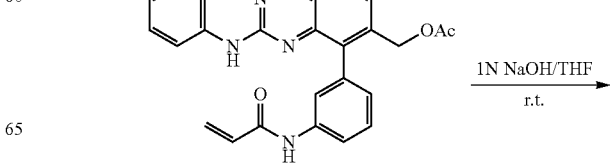

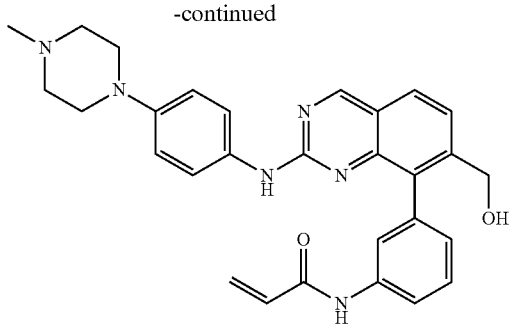

To a solution of (8-(3-acrylamidophenyl)-2-((4-(4-methylpiperazin-1-yl)phenyl)amino)quinazolin-7-yl)methyl acetate (23 mg, 0.04 mmol, 1 eq.) in THF (8 mL) was added NaOH (1N, 2 mL, 2 mmol, 50 eq.). The resulting mixture was stirred at r.t. for 1 h, diluted with EA (10 mL), washed via RP-HPLC to afford N-(3-(7-(hydroxymethyl)-2-((4-(4-methylpiperazin-1-yl)phenyl)amino)quinazolin-8-yl)phenyl)acrylamide (13.5 mg, 68.2% yield). LRMS (M+H$^+$) m/z calculated 494.2, found 494.9. $^1$H NMR (CD$_3$OD, 300 MHz) δ 9.10 (s, 1H), 8.05 (d, 1H), 7.86 (d, 1H), 7.64 (d, 1H), 7.48-7.54 (m, 4H), 7.10 (t, 1H), 6.71 (d, 2H), 6.39-6.46 (m, 2H), 5.77 (d, 1H), 4.64 (d, 2H), 3.27-3.29 (m, 4H), 3.13-3.17 (m, 4H), 2.52 (s, 3H).

Example 43: Preparation of (S)—N-(3-(2-((4-((1-acetylpyrrolidin-3-yl)oxy)phenyl)amino)quinazolin-8-yl)phenyl)acrylamide

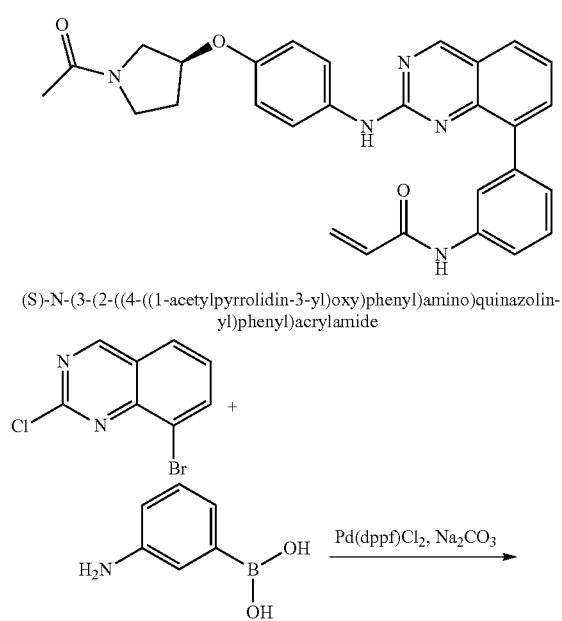

(S)-N-(3-(2-((4-((1-acetylpyrrolidin-3-yl)oxy)phenyl)amino)quinazolin-8-yl)phenyl)acrylamide To a solution of 8-bromo-2-chloroquinazoline (15.4 g, 63.6 mmol, 1 eq.) and (3-aminophenyl)boronic acid (8.7 g, 63.6 mmol, 1 eq.) in dioxane/H$_2$O (200 mL/20 mL) was added Na$_2$CO$_3$ (13.5 g, 127.2 mmol, 2 eq.), followed by Pd(dppf)Cl$_2$ (2.6 g, 3.2 mmol, 0.05 eq.) under N$_2$, then the mixture was stirred at 80° C. for 12 h. Then the solution was cooled to r.t., concentrated and the residue was purified via column chromatography (PE/EA=3:2, v/v) to afford 3-(2-chloroquinazolin-8-yl)aniline as yellow solid (8.7 g, 53.7% yield).

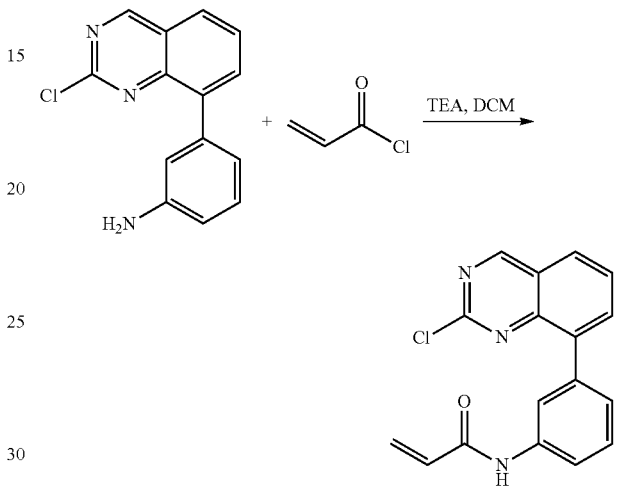

To a solution of 3-(2-chloroquinazolin-8-yl)aniline (8.7 g, 34 mmol, 1 eq.) in DCM (200 mL) cooled in ice-bath was added TEA (9.5 mL, 68 mmol, 2 eq.), followed by acryloyl chloride (4.1 mL, 51 mmol, 1.5 eq.) dropwise. The resulting mixture was stirred at r.t. for 1 h, then washed with brine, dried over anhydrous N$_2$SO$_4$, concentrated and the residue was purified via column chromatography (PE/EA=1:1, v:v) to afford N-(3-(2-chloroquinazolin-8-yl)phenyl)acrylamide as yellow solid (6.6 g, 65% yield).

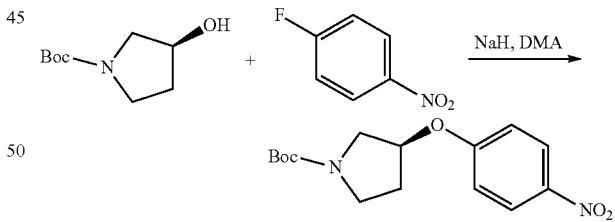

To a solution of (S)-tert-butyl 3-hydroxypyrrolidine-1-carboxylate (1.87 g, 10 mmol, 1 eq.) in DMA (20 mL) cooled in ice-bath was added NaH (480 mg, 12 mmol, 1.2 eq.) and the mixture was stirred at 0° C. for 30 min, then 1-fluoro-4-nitrobenzene (1.41 g, 10 mmol, 1 eq) was added. The resulting mixture was stirred at r.t. overnight, then poured into ice-water (200 mL). The precipitate was collected by filtration, washed with water and dried in vacuo to afford (S)-tert-butyl 3-(4-nitrophenoxy)pyrrolidine-1-carboxylate as yellow solid (3.08 g, 100% yield).

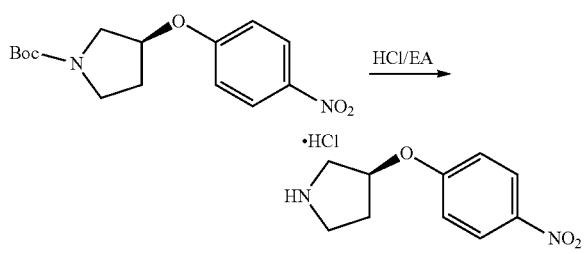

To a solution of (S)-tert-butyl 3-(4-nitrophenoxy)pyrrolidine-1-carboxylate (3.08 g, 10 mmol, 1 eq.) in EA (10 mL) was added HCl/EA (6N, 30 mL) and the mixture was stirred at r.t. for 1 h. Then the mixture was concentrated to afford (S)-3-(4-nitrophenoxy)pyrrolidine hydrochloride as yellow solid (2.44 g, 100% yield).

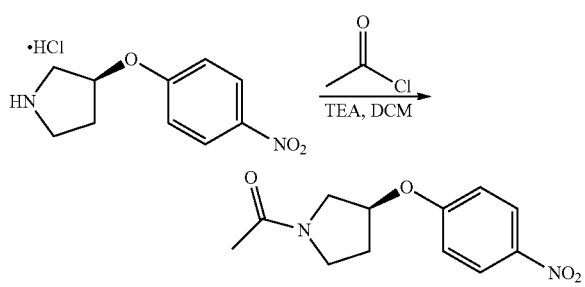

To a solution of (S)-3-(4-nitrophenoxy)pyrrolidine hydrochloride (2.44 g, 10 mmol, 1 eq.) in DCM (40 mL) cooled in ice-bath was added TEA (4.0 g, 40 mmol, 4 eq.) followed by acetyl chloride (1.57 g, 20 mmol, 2 eq.) dropwise. The resulting mixture was stirred at r.t. for 1 h, then washed with brine, dried over anhydrous NaSO$_4$ and concentrated to afford (S)-1-(3-(4-nitrophenoxy)pyrrolidin-1-yl)ethanone as brown oil (2.2 g, 88% yield).

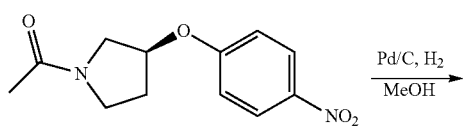

To a solution of (S)-1-(3-(4-nitrophenoxy)pyrrolidin-1-yl)ethanone (2.2 g, 8.8 mmol, 1 eq.) in MeOH (20 mL) was added Pd/C (400 mg) and the resulting mixture was stirred at hydrogen atmosphere at r.t. overnight. Then the catalyst was removed by filtration and the filtrate was concentrated to afford (S)-1-(3-(4-aminophenoxy)pyrrolidin-1-yl)ethanone as brown solid (1.7 g, 88% yield).

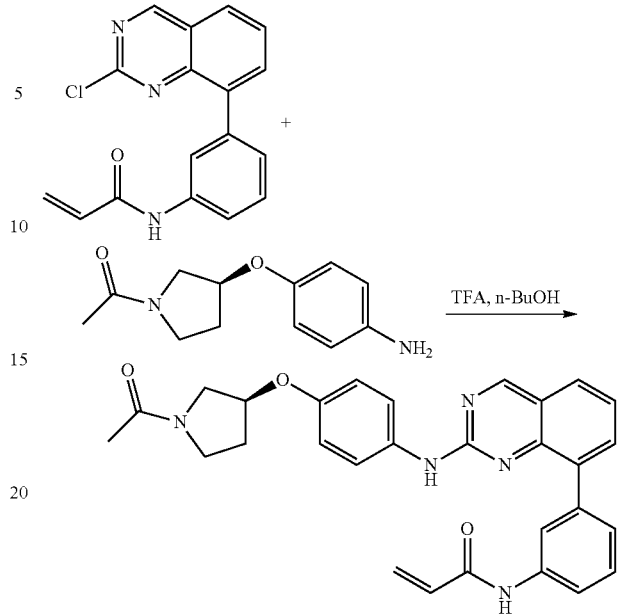

To a solution of N-(3-(2-chloroquinazolin-8-yl)phenyl)acrylamide (154 mg, 0.5 mmol, 1 eq.) and (S)-1-(3-(4-aminophenoxy)pyrrolidin-1-yl)ethanone (110 mg, 0.5 mmol, 1 eq.) in n-BuOH (10 mL) was added TFA (286 mg, 2.5 mmol, 5 eq.) and the resulting mixture was stirred at 80° C. overnight. The mixture was concentrated and the residue was dissolved in DCM, washed with Na$_2$CO$_3$ solution, dried over anhydrous Na$_2$SO$_4$, then purified via column chromatography (DCM/MeOH=10/1) to afford (S)—N-(3-(2-((4-((1-acetylpyrrolidin-3-yl)oxy)phenyl)amino)quinazolin-8-yl)phenyl)acrylamide as yellow solid (35.2 mg, 14.7% yield). LRMS (M+H$^+$) m/z calculated 494.2, found 494.2. $^1$H NMR (DMSO-d6, 400 MHz) δ 10.30 (s, 1H), 9.80 (s, 1H), 9.32 (s, 1H), 8.04 (s, 1H), 7.80-7.93 (m, 5H), 7.35-7.51 (m, 3H), 6.71 (t, 2H), 6.44-6.51 (m, 1H), 6.26 (d, 1H), 5.76 (dd, 1H), 4.86-4.94 (m, 1H), 3.48-3.76 (m, 3H), 3.28-3.31 (m, 1H), 1.93-2.16 (m, 5H).

Example 44: Preparation of N-(3-(2-((2-chloro-4-(4-methylpiperazin-1-yl)phenyl)amino)quinazolin-8-yl)phenyl)acrylamide

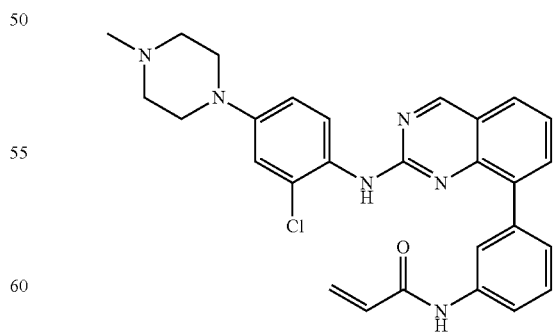

N-(3-(2-((2-chloro-4-(4-methylpiperazin-1-yl)phenyl)amino)quinazolin-8-yl)phenyl)acrylamide N-(3-(2-((2-chloro-4-(4-methylpiperazin-1-yl)phenyl)amino)quinazolin-8-yl)phenyl)acrylamide (25.1 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 499.2.1, found 498.9. ¹H NMR (CD₃OD, 300 MHz) δ 9.22 (s, 1H), 8.48 (d, 1H), 7.85-7.94 (m, 4H), 7.38-7.50 (m, 3H), 7.03 (s, 1H), 6.66 (d, 1H), 6.40-6.46 (m, 2H), 5.78-5.82 (m, 1H), 3.18-3.23 (m, 4H), 2.93-2.96 (m, 4H), 2.62 (s, 3H).

Example 45: Preparation of N-(3-(2-((2-fluoro-4-(4-methylpiperazin-1-yl)phenyl)amino)quinazolin-8-yl)phenyl)acrylamide

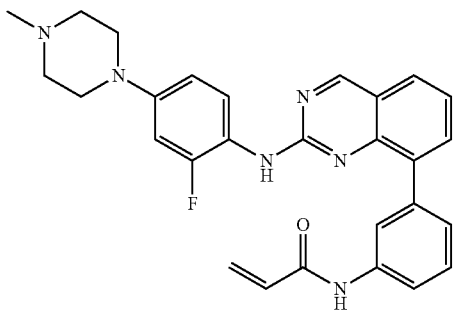

N-(3-(2-((2-fluoro-4-(4-methylpiperazin-1-yl)phenyl)amino)quinazolin-8-yl)phenyl)acrylamide N-(3-(2-((2-fluoro-4-(4-methylpiperazin-1-yl)phenyl)amino)quinazolin-8-yl)phenyl)acrylamide (59 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 483.6, found 483.9. ¹H NMR (CD₃OD, 300 MHz) δ 9.21 (s, 1H), 8.37 (t, 1H), 7.85-7.97 (m, 4H), 7.40-7.51 (m, 3H), 6.83 (dd, 1H), 6.41-6.54 (m, 3H), 5.79-5.83 (m, 1H), 3.17-3.32 (m, 8H) 2.81 (s, 3H).

Example 46: Preparation of N-(5-(2-((6-(4-methylpiperazin-1-yl)pyridin-3-yl)amino)quinazolin-8-yl)pyridin-3-yl)acrylamide

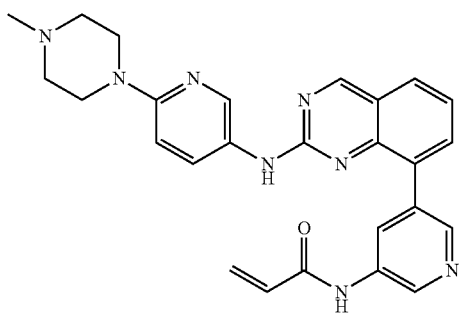

N-(5-(2-((6-(4-methylpiperazin-1-yl)pyridin-3-yl)amino)quinazolin-8-yl)pyridin-3-yl)acrylamide N-(5-(2-((6-(4-methylpiperazin-1-yl)pyridin-3-yl)amino)quinazolin-8-yl)pyridin-3-yl)acrylamide (43.3 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 467.2, found 466.9. ¹H NMR (CD₃OD, 300 MHz) δ 9.20 (s, 1H), 9.02 (s, 1H), 8.53 (s, 2H), 8.18-8.31 (m, 2H), 7.90 (t, 2H), 7.47 (t, 1H), 6.39-6.64 (m, 3H), 5.84 (d, 1H) 3.40-3.45 (m, 4H), 2.55-2.620 (m, 4H), 2.34 (s, 3H).

Example 47: Preparation of N-(2-fluoro-3-(2-((4-(4-methylpiperazin-1-yl)phenyl)amino)quinazolin-8-yl)phenyl)acrylamide

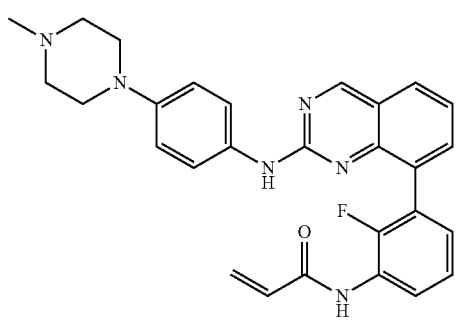

N-(2-fluoro-3-(2-((4-(4-methylpiperazin-1-yl)phenyl)amino)quinazolin-8-yl)phenyl)acrylamide N-(2-fluoro-3-(2-((4-(4-methylpiperazin-1-yl)phenyl)amino)quinazolin-8-yl)phenyl)acrylamide (37.1 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 483.2, found 482.9. ¹H NMR (CD₃OD, 300 MHz) δ 9.16 (s, 1H), 8.35 (t, 1H), 7.91 (d, 1H), 7.88 (d, 1H), 7.61 (d, 2H), 7.23-7.46 (m, 3H), 6.42-6.77 (m, 4H), 5.84 (d, 1H) 3.13-3.16 (m, 4H), 2.82-2.84 (m, 4H), 2.51 (s, 3H).

Example 48: Preparation of N-(2-fluoro-3-(2-((6-(4-methylpiperazin-1-yl)pyridin-3-yl)amino)quinazolin-8-yl)phenyl)acrylamide

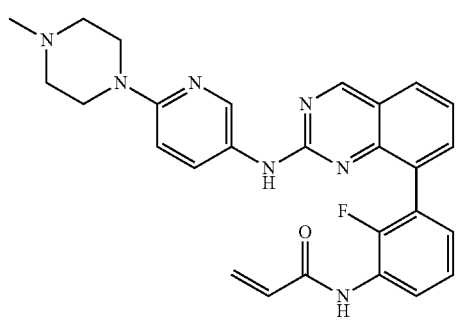

N-(2-fluoro-3-(2-((6-(4-methylpiperazin-1-yl)pyridin-3-yl)amino)quiazolin-8-yl)phenyl)acrylamide N-(2-fluoro-3-(2-((6-(4-methylpiperazin-1-yl)pyridin-3-yl)amino)quinazolin-8-yl)phenyl)acrylamide (135.5 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 484.2, found 483.9. ¹H NMR (DMSO-d6, 300 MHz) δ 10.02 (s, 1H), 9.75 (s, 1H), 9.31 (s, 1H), 8.25-8.31 (m, 2H), 8.12 (d, 1H), 7.97 (d, 1H), 7.82 (d, 1H), 7.45 (t, 1H), 7.29 (t, 1H), 7.17 (t, 1H), 6.67-6.76 (m, 1H), 6.29-6.46 (m, 2H), 5.81 (d, 1H), 3.26-3.37 (m, 4H), 2.41-2.49 (m, 4H), 2.24 (s, 3H).

Example 49: Preparation of N-(3-(2-((2-(4-methyl-piperazin-1-yl)pyrimidin-5-yl)amino)quinazolin-8-yl)phenyl)acrylamide

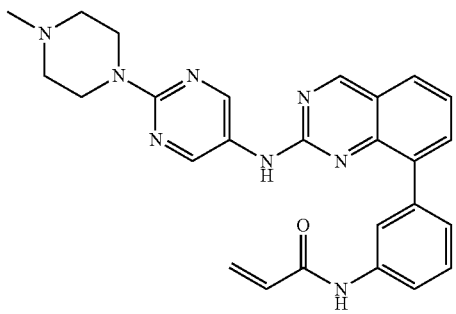

N-(3-(2-((2-(4-methylpiperazin-1-yl)pyrimidin-5-yl)amino)quinazolin-8-yl)phenyl)acrylamide N-(3-(2-((2-(4-methylpiperazin-1-yl)pyrimidin-5-yl)amino)quinazolin-8-yl)phenyl)acrylamide (31.9 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 467.2, found 466.9. $^1$H NMR (DMSO-d6, 300 MHz) δ 10.18 (s, 1H), 9.66 (s, 1H), 9.33 (s, 1H), 8.75 (s, 2H), 7.80-8.04 (m, 4H), 7.32-7.47 (m, 3H), 6.19-6.46 (m, 2H), 5.74 (d, 1H), 3.55-3.61 (m, 4H), 2.39-2.42 (m, 4H), 2.32 (s, 3H).

Example 50: Preparation of N-(3-(2-((4-(4-acetylpiperazin-1-yl)phenyl)amino)quinazolin-8-yl)-2-fluorophenyl)acrylamide

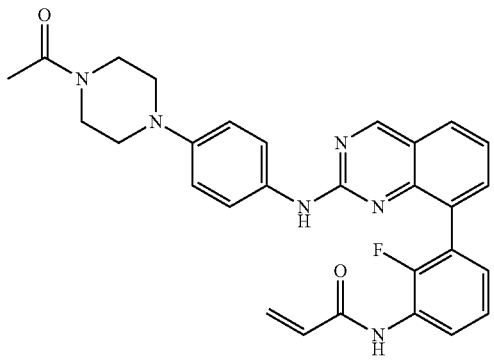

N-(3-(2-((4-(4-acetylpiperazin-1-yl)phenyl)amino)quinazolin-8-yl)-2-fluorophenyl)acrylamide N-(3-(2-((4-(4-acetylpiperazin-1-yl)phenyl)amino)quinazolin-8-yl)-2-fluorophenyl)acrylamide (50.7 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 511.2, found 510.9. $^1$H NMR (DMSO-d6, 300 MHz) δ 10.05 (s, 1H), 9.72 (s, 1H), 9.31 (s, 1H), 8.33 (t, 1H), 7.96 (d, 1H), 7.82 (d, 1H), 7.61 (d, 2H), 7.42 (t, 1H), 7.32 (t, 1H), 7.20 (t, 1H), 6.66-6.77 (m, 3H), 6.30-6.37 (m, 1H), 5.81 (d, 1H), 3.52-3.54 (m, 4H), 2.87-2.97 (m, 4H), 2.04 (s, 3H).

Example 51: Preparation of (E)-N-(3-(2-((4-(4-acetylpiperazin-1-yl)phenyl)amino)quinazolin-8-yl)phenyl)-4-(dimethylamino)but-2-enamide

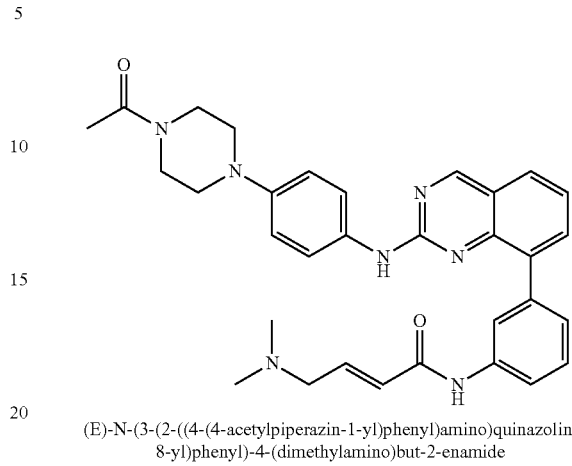

(E)-N-(3-(2-((4-(4-acetylpiperazin-1-yl)phenyl)amino)quinazolin-8-yl)phenyl)-4-(dimethylamino)but-2-enamide (E)-N-(3-(2-((4-(4-acetylpiperazin-1-yl)phenyl)amino)quinazolin-8-yl)phenyl)-4-(dimethylamino)but-2-enamide (46.9 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 550.3, found 549.9. $^1$H NMR (CD$_3$OD, 400 MHz) δ 9.17 (s, 1H), 7.76-7.99 (m, 6H), 7.42-7.53 (m, 3H), 6.81-6.97 (m, 3H), 6.31 (d, 1H), 3.68-3.75 (m, 4H), 3.19 (d, 2H), 3.02-3.10 (m, 4H) 2.30 (s, 6H), 2.18 (s, 3H).

Example 52: Preparation of N-(3-(2-((4-(4-acetylpiperazin-1-yl)phenyl)amino)quinazolin-8-yl)-2-chlorophenyl)acrylamide

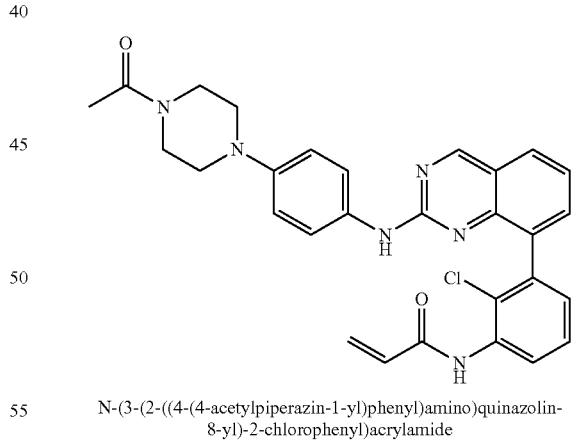

N-(3-(2-((4-(4-acetylpiperazin-1-yl)phenyl)amino)quinazolin-8-yl)-2-chlorophenyl)acrylamide N-(3-(2-((4-(4-acetylpiperazin-1-yl)phenyl)amino)quinazolin-8-yl)-2-chlorophenyl)acrylamide (60.6 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 527.2, found 527.2. $^1$H NMR (CD$_3$OD, 400 MHz) δ 9.16 (s, 1H), 8.20 (d, 1H), 7.91 (d, 1H), 7.74 (d, 1H), 7.42-7.55 (m, 4H), 7.25 (d, 1H), 6.76 (d, 2H), 6.63-6.69 (m, 1H) 6.46-6.50 (m, 1H), 5.86 (d, 1H), 3.68-3.75 (m, 4H), 3.02-3.09 (m, 4H), 2.18 (s, 3H).

Example 53: Preparation of (E)-4-(dimethylamino)-N-(3-(2-((4-(4-methylpiperazin-1-yl)phenyl)amino)quinazolin-8-yl)phenyl)but-2-enamide

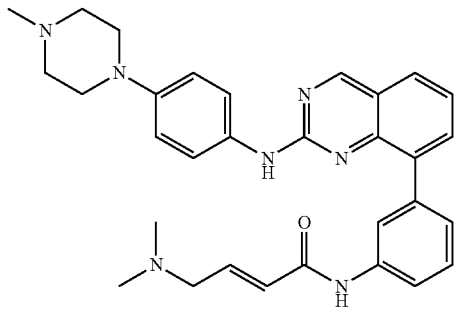

(E)-4-(dimethylamino)-N-(3-(2-((4-(4-methylpiperazin-1-yl)phenyl)amino)quinazolin-8-yl)phenyl)but-2-enamide (E)-4-(dimethylamino)-N-(3-(2-((4-(4-methylpiperazin-1-yl)phenyl)amino)quinazolin-8-yl)phenyl)but-2-enamide (139.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 522.3, found 522.3. $^1$H NMR (CD$_3$OD, 400 MHz) δ 9.02 (s, 1H), 7.86 (s, 1H), 7.76 (d, 1H), 7.69 (d, 2H), 7.61 (d, 2H), 7.26-7.37 (m, 3H), 6.77-6.81 (m, 1H), 6.67 (d, 2H), 6.19 (d, 1H), 3.10 (d, 1H), 2.97-2.99 (m, 4H), 2.53-2.55 (m, 4H), 2.28 (s, 3H), 2.20 (s, 3H).

Example 54: Preparation of N-(3-(2-((4-(4-(2-fluoroethyl)piperazin-1-yl)phenyl)amino)quinazolin-8-yl)phenyl)acrylamide

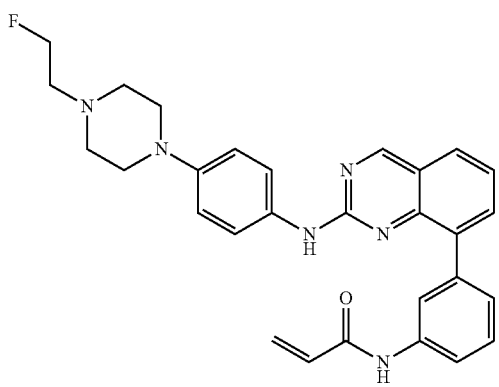

N(3-(2-((4-(4-(2-fluoroethyl)piperazin-1-yl)phenyl)amino)quinazolin-8-yl)phenyl)acrylamine N-(3-(2-((4-(4-(2-fluoroethyl)piperazin-1-yl)phenyl)amino)quinazolin-8-yl)phenyl)acrylamide (43.1 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 497.2, found 497.2. $^1$H NMR (CD$_3$OD, 300 MHz) δ 9.14 (s, 1H), 8.00 (s, 1H), 7.93 (d, 1H), 7.82 (d, 2H), 7.73 (m, 2H), 7.38-7.52 (m, 3H), 6.79 (d, 2H), 6.36-6.47 (m, 2H) 5.77 (d, 1H), 4.72 (t, 1H), 4.56 (t, 1H), 3.10-3.13 (m, 4H), 2.73-2.87 (m, 6H).

Example 55: Preparation of N-(2-chloro-3-(2-((4-(4-methylpiperazin-1-yl)phenyl)amino)quinazolin-8-yl)phenyl)acrylamide

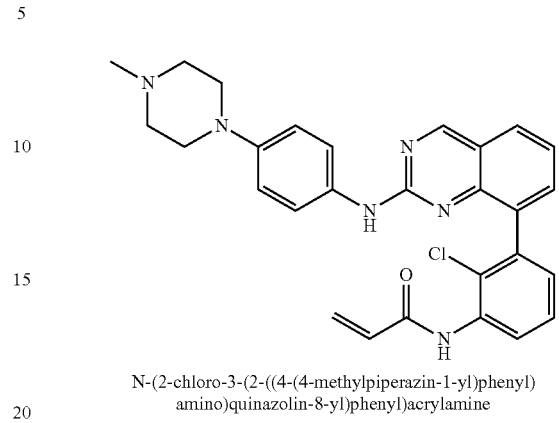

N-(2-chloro-3-(2-((4-(4-methylpiperazin-1-yl)phenyl)amino)quinazolin-8-yl)phenyl)acrylamine N-(2-chloro-3-(2-((4-(4-methylpiperazin-1-yl)phenyl)amino)quinazolin-8-yl)phenyl)acrylamide (23.1 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 499.2, found 499.2. $^1$H NMR (CD$_3$OD, 300 MHz) δ 9.03 (s, 1H), 8.05 (d, 1H), 7.76 (d, 1H), 7.60 (d, 1H), 7.28-7.41 (m, 4H), 7.11 (d, 1H), 6.51-6.63 (m, 3H), 6.32-6.36 (m, 1H), 2.97-2.98 (m, 4H), 2.51-2.53 (m, 4H), 2.26 (s, 3H).

Example 56: Preparation of N-(3-(2-((2-methoxy-6-(4-methylpiperazin-1-yl)pyridin-3-yl)amino)quinazolin-8-yl)phenyl)acrylamide

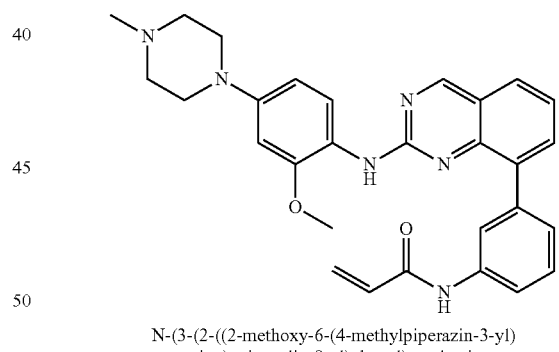

N-(3-(2-((2-methoxy-6-(4-methylpiperazin-3-yl)amino)quinazolin-8-yl)phenyl)acrylamine N-(3-(2-((2-methoxy-6-(4-methylpiperazin-1-yl)pyridin-3-yl)amino)quinazolin-8-yl)phenyl)acrylamide (30.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 496.2, found 496.2. $^1$H NMR (CD$_3$OD, 300 MHz) δ 9.16 (s, 1H), 8.65 (d, 1H), 7.84-7.95 (m, 4H), 7.38-7.50 (m, 3 H), 6.40-6.46 (m, 2H), 6.04 (d, 1H), 5.80 (d, 1H), 3.97 (s, 3H), 3.51-3.55 (m, 4H), 2.86-2.87 (m, 4H), 2.59 (s, 3H).

Example 57: Preparation of (E)-N-(3-(2-((4-(4-acetylpiperazin-1-yl)phenyl)amino)quinazolin-8-yl)-2-chlorophenyl)-4-(dimethylamino)but-2-enamide

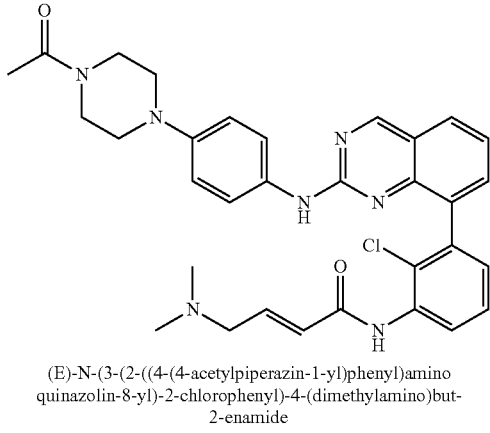 [SMILES: CC(=O)N1CCN(c2ccc(Nc3ncc4cccc(-c5cccc(NC(=O)/C=C/CN(C)C)c5Cl)c4n3)cc2)CC1]

(E)-N-(3-(2-((4-(4-acetylpiperazin-1-yl)phenyl)amino quinazolin-8-yl)-2-chlorophenyl)-4-(dimethylamino)but-2-enamide (E)-N-(3-(2-((4-(4-acetylpiperazin-1-yl)phenyl)amino)quinazolin-8-yl)-2-chlorophenyl)-4-(dimethylamino)but-2-enamide (10.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 584.2, found 584.2. $^1$H NMR (CDCl$_3$, 300 MHz) δ 9.10 (s, 1H), 8.65 (d, 1H), 7.94 (s, 1H), 7.73-7.81 (m, 2H), 7.39-7.48 (m, 4H), 7.18-7.28 (m, 2H), 7.01-7.06 (m, 1H), 6.70 (d, 2H), 6.20 (d, 1H), 3.74-3.78 (m, 2H), 3.60-3.64 (m, 2H), 3.16 (d, 2H), 3.02-3.08 (m, 4H), 2.31 (s, 6H), 2.16 (s, 3H).

Example 58: Preparation of N-(3-(2-((4-(4-(2,2-difluoroethyl)piperazin-1-yl)phenyl)amino)quinazolin-8-yl)phenyl)acrylamide

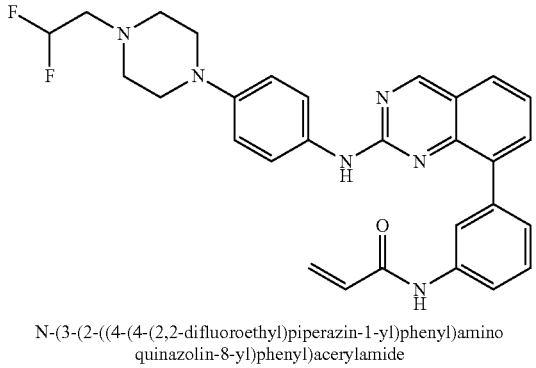 [SMILES: C=CC(=O)Nc1cccc(-c2cccc3cnc(Nc4ccc(N5CCN(CC(F)F)CC5)cc4)nc23)c1]

N-(3-(2-((4-(4-(2,2-difluoroethyl)piperazin-1-yl)phenyl)amino quinazolin-8-yl)phenyl)acerylamide N-(3-(2-((4-(4-(2,2-difluoroethyl)piperazin-1-yl)phenyl)amino)quinazolin-8-yl)phenyl)acrylamide (74.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 515.2, found 515.2. $^1$H NMR (CD$_3$OD, 300 MHz) δ 9.15 (s, 1H), 7.52-7.99 (m, 6H), 7.39-7.50 (m, 3H), 6.80 (d, 2H), 6.41-6.52 (m, 2H), 6.02 (t, 1H), 5.77-5.84 (m, 1H), 3.03-3.12 (m, 4H), 2.74-2.88 (m, 6H).

Example 59: Preparation of N-(5-(2-((4-(4-(2-fluoroethyl)piperazin-1-yl)phenyl)amino)quinazolin-8-yl)pyridin-3-yl)acrylamide

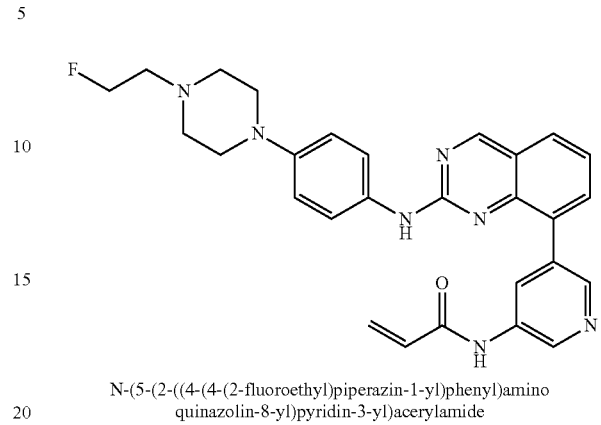

N-(5-(2-((4-(4-(2-fluoroethyl)piperazin-1-yl)phenyl)amino quinazolin-8-yl)pyridin-3-yl)acerylamide N-(5-(2-((4-(4-(2-fluoroethyl)piperazin-1-yl)phenyl)amino)quinazolin-8-yl)pyridin-3-yl)acrylamide (36.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 498.2, found 498.2. $^1$H NMR (CD$_3$OD, 300 MHz) δ 9.18 (s, 1H), 9.06 (s, 1H), 8.53-8.57 (m, 2H), 7.817-7.91 (m, 2H), 7.65 (d, 2H), 7.45 (t, 1H), 6.82 (d, 2H), 6.45-6.49 (m, 2H), 5.84-5.88 (m, 1H), 4.72 (t, 1H), 4.55 (t, 1H), 3.10-3.13 (m, 4H), 2.71-2.85 (m, 6H).

Example 60: Preparation of N-(4-(2-((4-(4-methylpiperazin-1-yl)phenyl)amino)quinazolin-8-yl)pyridin-2-yl)acrylamide

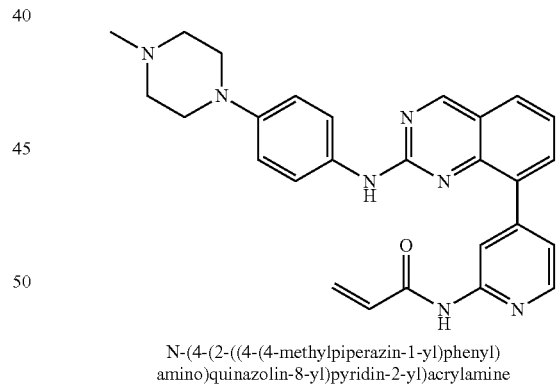

N-(4-(2-((4-(4-methylpiperazin-1-yl)phenyl)amino)quinazolin-8-yl)pyridin-2-yl)acrylamine N-(4-(2-((4-(4-methylpiperazin-1-yl)phenyl)amino)quinazolin-8-yl)pyridin-2-yl)acrylamide (10.9 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 466.2, found 466.2. $^1$H NMR (DMSO-d6, 300 MHz) δ 10.90 (s, 1H), 9.73 (s, 1H), 9.32 (s, 1H), 8.60 (s, 1H), 8.46 (d, 1H), 7.97 (d, 1H), 7.87 (d, 1H), 7.66 (d, 2H), 7.39-7.48 (m, 2H), 6.63-6.74 (m, 3H), 6.22-6.28 (m, 1H), 5.77 (d, 1H), 3.03 (m, 4H), 2.51 (m, 4H), 2.25 (s, 3H).

Example 61: Preparation of N-(3-(2-((4-(4-(2-hydroxyethyl)piperazin-1-yl)phenyl)amino)quinazolin-8-yl)phenyl)acrylamide

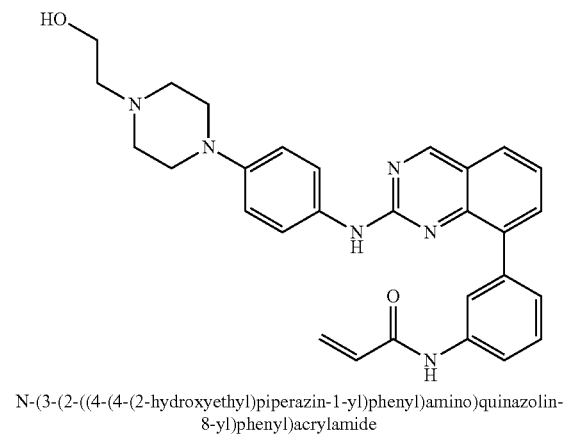

N-(3-(2-((4-(4-(2-hydroxyethyl)piperazin-1-yl)phenyl)amino)quinazolin-8-yl)phenyl)acrylamide

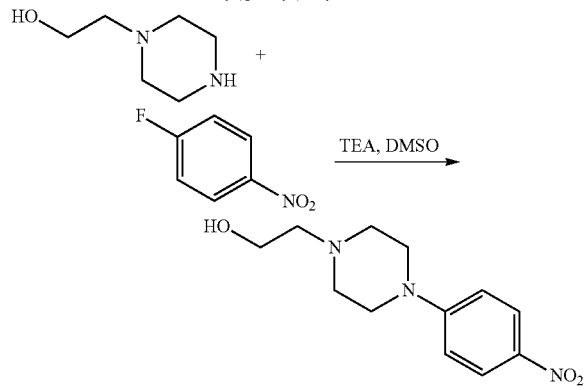

To a solution of 1-fluoro-4-nitrobenzene (4.23 g, 30 mmol, 1.0 eq.) in DMSO (40 mL) was added TEA (9.1 g, 90 mmol, 3.0 eq.) followed by 2-(piperazin-1-yl)ethanol (3.9 g, 30 mmol, 1.0 eq.) and the mixture was stirred at 90° C. overnight. The mixture was poured into ice-water (400 mL), filtered and dried in vacuum to afford 2-(4-(4-nitrophenyl)piperazin-1-yl)ethanol as a yellow solid (7.2 g, 95.6%).

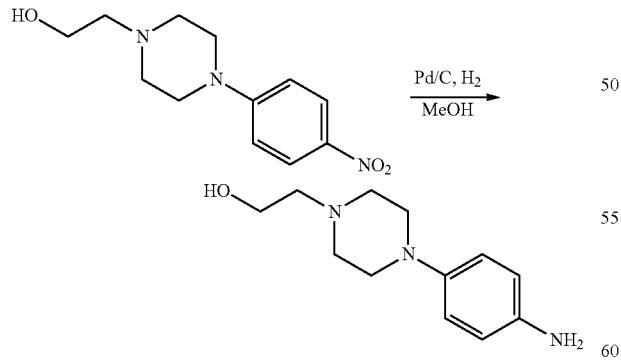

To a solution of 2-(4-(4-nitrophenyl)piperazin-1-yl)ethanol (3.6 g, 14.3 mmol) in MeOH (40 mL) was added Pd/C (700 mg) and the resulting mixture was stirred at r.t. overnight. The mixture was filtered, and the filtrate was concentrated to afford 2-(4-(4-aminophenyl)piperazin-1-yl)ethanol (2.8 g, 88% yield) as yellow solid.

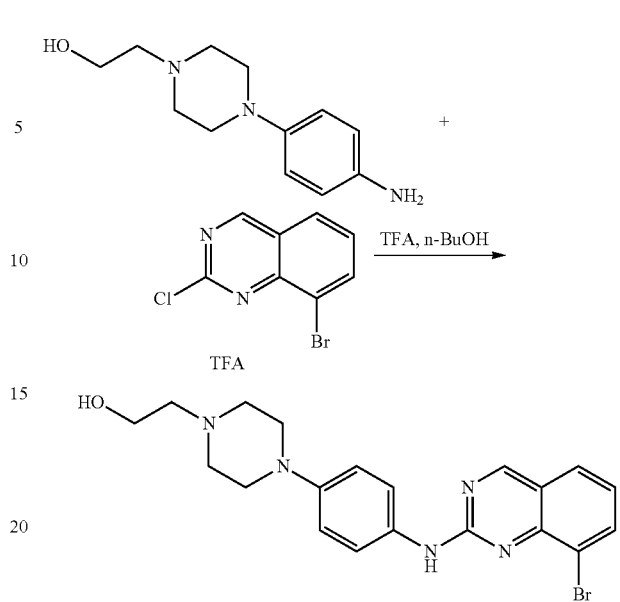

To a suspension of 2-(4-(4-aminophenyl)piperazin-1-yl)ethanol (221 mg, 1 mmol, 1 eq.) and 8-bromo-2-chloroquinazoline (243 mg, 1 mmol, 1 eq.) in n-BuOH (10 mL) was added TFA (570 mg, 5 mmol, 5 eq.) and the resulting mixture was stirred at 90° C. overnight. The solution was then cooled to r.t. and the precipitate was collected by filtration, washed with EA, dried in vacuo to afford 2-(4-(4-((8-bromoquinazolin-2-yl)amino)phenyl)piperazin-1-yl)ethanol as yellow solid (340 mg, 79%).

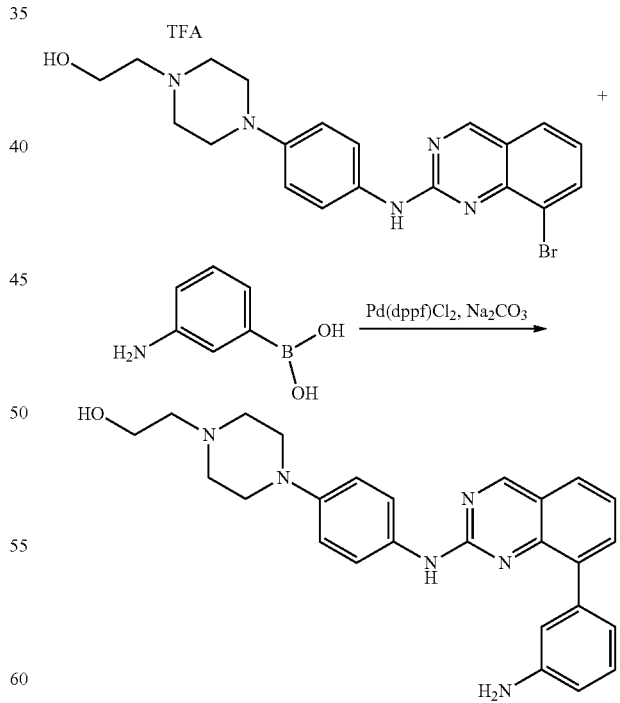

To a solution of 2-(4-(4-((8-bromoquinazolin-2-yl)amino)phenyl)piperazin-1-yl)ethanol (200 mg, 0.47 mmol, 1.0 eq.) and (3-aminophenyl)boronic acid (97 mg, 0.71 mmol, 1.5 eq.) in dioxane/H$_2$O (10 mL/1 mL) was added Na$_2$CO$_3$ (100 mg, 0.94 mmol, 2.0 eq.), followed by Pd(dppf)Cl$_2$ (38 mg, 0.05 mmol, 0.1 eq.) under N₂. The mixture was stirred at 90° C. for 12 h. The mixture was cooled to r.t., and concentrated. The resulting residue was purified via column chromatography (DCM/MeOH=30:1, v/v) to afford 2-(4-(4-((8-(3-aminophenyl)quinazolin-2-yl)amino)phenyl)piperazin-1-yl) ethanol as a yellow solid (100 mg, 48% yield).

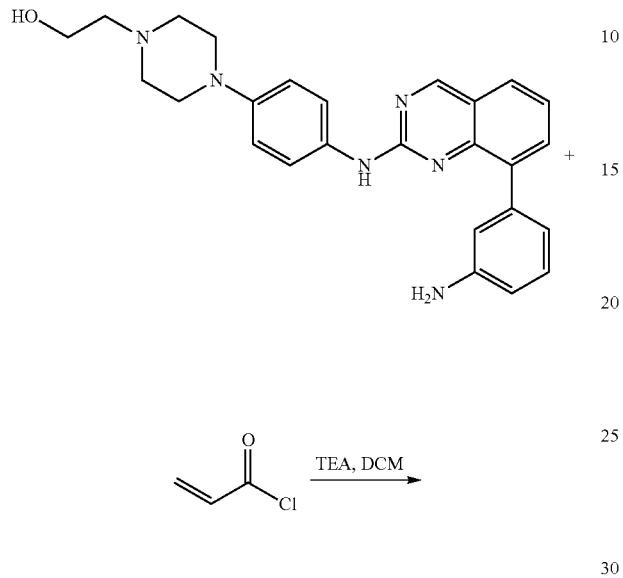

To a solution of 2-(4-(4-((8-(3-aminophenyl)quinazolin-2-yl)amino)phenyl)piperazin-1-yl)ethanol (100 mg, 0.23 mmol, 1.0 eq.) in DCM (5 mL) cooled in ice-bath was added TEA (46 mg, 0.46 mmol, 2.0 eq.) followed by acryloyl chloride (62.1 mg, 0.69 mmol, 3.0 eq.) dropwise. The resulting mixture was stirred at r.t. for 1 h, then washed with brine, dried over anhydrous Na₂SO₄ and concentrated to afford 2-(4-(4-((8-(3-acrylamidophenyl)quinazolin-2-yl) amino)phenyl)piperazin-1-yl)ethyl acrylate as a yellow solid (100 mg, 79.4% yield).

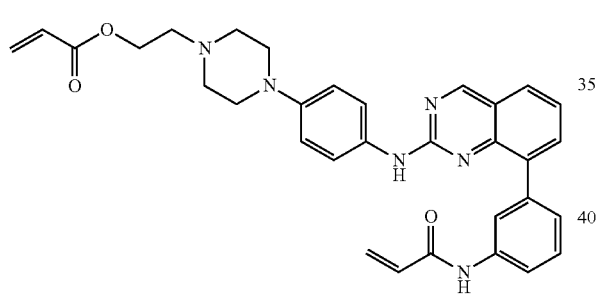

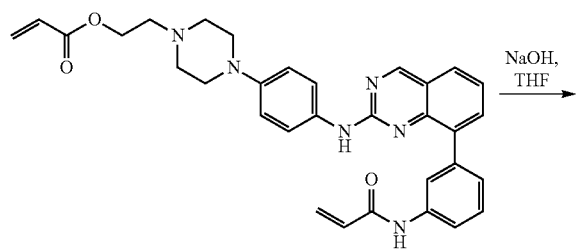

To a solution of 2-(4-(4-((8-(3-acrylamidophenyl)quinazolin-2-yl)amino)phenyl)piperazin-1-yl)ethyl acrylate (100 mg, 0.2 mmol, 1 eq.) in THF (2 mL) was added 1N NaOH (0.4 mL, 0.4 mmol, 2 eq.). The resulting mixture was stirred at r.t. overnight, then washed with brine, dried over anhydrous Na₂SO₄, and concentrated. The resulting residue was purified via column chromatography (DCM/MeOH=30: 1, v/v) to afford N-(3-(2-((4-(4-(2-hydroxyethyl)piperazin-1-yl)phenyl)amino)quinazolin-8-yl)phenyl)acrylamide (21 mg, 25.5% yield). LRMS (M+H⁺) m/z calculated 495.2, found 495.2. ¹H NMR (DMSO-d6, 300 MHz) δ 9.14 (s, 1H), 7.72-7.97 (m, 6H), 7.38-7.49 (m, 3H), 6.80 (d, 2H), 6.41-6.47 (m, 2H), 5.78 (d, 1H), 3.78 (t, 3H), 3.13-3.17 (m, 4H), 2.75-2.88 (m, 6H).

Example 62: Preparation of (E)-4-(dimethylamino)-N-(2-fluoro-3-(2-((4-(4-methylpiperazin-1-yl)phenyl)amino)quinazolin-8-yl)phenyl)but-2-enamide

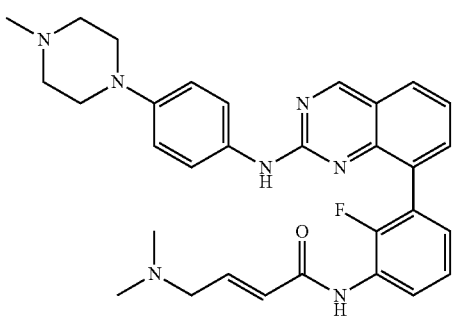

(E)-4-(dimethylamino)-N-(2-fluoro-3-(2-((4-(4-methylpiperazin-1-yl)phenyl)amino)quinazolin-8-yl)phenyl)but-2-enamide (E)-4-(dimethylamino)-N-(2-fluoro-3-(2-((4-(4-methylpiperazin-1-yl)phenyl)amino)quinazolin-8-yl)phenyl)but-2-enamide (45.5 mg) was prepared as described for (S)—N-(3-(2-((4-((1-acetylpyrrolidin-3-yl)oxy)phenyl)amino) quinazolin-8-yl)phenyl)acrylamide. LRMS (M+H⁺) m/z calculated 540.3, found 540.3. ¹H NMR (CD₃OD, 400 MHz) δ 9.17 (s, 1H), 8.34 (t, 1H), 7.90 (d, 1H), 7.81 (d, 1H), 7.60 (d, 2H), 7.45 (t, 1H), 7.23-7.42 (m, 2H), 6.97-7.01 (m, 1H), 6.76 (d, 2H), 6.47 (d, 1H), 3.23 (d, 2H), 3.11 (m, 4H), 2.65-2.67 (m, 4H), 2.40 (s, 3H), 2.33 (s, 6H).

Example 63: Preparation of N-(2-fluoro-3-(2-((4-(4-(2-fluoroethyl)piperazin-1-yl)phenyl)amino)quinazolin-8-yl)phenyl)acrylamide

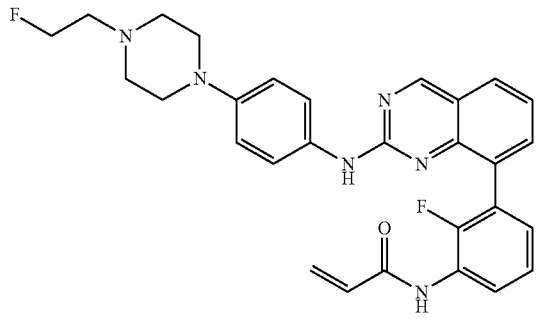

N-(2-fluoro-3-(2-((4-(4-(2-fluoroethyl)piperazin-1-yl)phenyl)amino quinazolin-8-yl)phenyl)acerylamide N-(2-fluoro-3-(2-((4-(4-(2-fluoroethyl)piperazin-1-yl)phenyl)amino)quinazolin-8-yl)phenyl)acrylamide (35.6 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 515.2, found 515.2. $^1$H NMR (CD$_3$OD, 400 MHz) δ 9.17 (s, 1H), 8.37 (t, 1H), 7.89 (d, 1H), 7.81 (d, 1H), 7.60 (d, 2H), 7.44 (t, 1H), 7.22-7.34 (m, 2H), 6.77 (d, 2H), 6.61-6.67 (m, 1H), 6.46 (dd, 1H), 5.84 (dd, 1H), 4.71 (t, 1H), 4.59 (t, 1H), 3.11 (t, 4H), 2.72-2.84 (m, 6H).

Example 64: Preparation of 1-(3-(2-((4-(4-methylpiperazin-1-yl)phenyl)amino)quinazolin-8-yl)-5,6-dihydropyridin-1(2H)-yl)prop-2-en-1-one

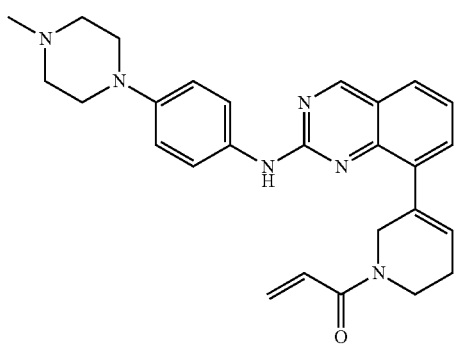

1-(3-(2-((4-(4-methylpiperazin-1-yl)phenyl(amino) quinazolin-8-yl)-5,6-dihydropyridin-1-(2H)-yl)prop-2-en-1-one 1-(3-(2-((4-(4-Methylpiperazin-1-yl)phenyl)amino)quinazolin-8-yl)-5,6-dihydropyridin-1(2H)-yl)prop-2-en-1-one (14.9 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 455.2, found 455.2. $^1$H NMR (CDCl$_3$, 400 MHz) δ 8.96 (d, 1H), 7.52-7.60 (m, 4H), 7.19-7.36 (m, 2H), 6.81 (d, 2H), 6.14-6.75 (m, 2H), 5.99 (s, 1H), 5.48-5.52 (m, 1H), 4.52-4.62 (m, 2H), 3.74-3.87 (m, 2H), 3.20-3.25 (m, 4H), 2.76-2.80 (m, 4H), 2.39-2.47 (m, 5H).

Example 65: Preparation of N-(2-cyano-3-(2-((4-(4-methylpiperazin-1-yl)phenyl)amino)quinazolin-8-yl)phenyl)acrylamide

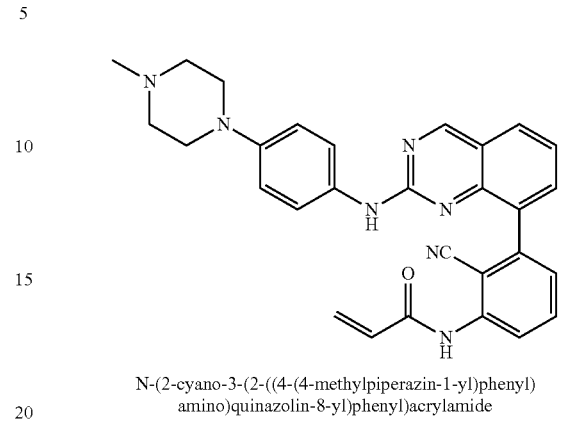

N-(2-cyano-3-(2-((4-(4-methylpiperazin-1-yl)phenyl) amino)quinazolin-8-yl)phenyl)acrylamide N-(2-cyano-3-(2-((4-(4-methylpiperazin-1-yl)phenyl)amino)quinazolin-8-yl)phenyl)acrylamide (41.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 490.2, found 490.2. $^1$H NMR (CD$_3$OD, 400 MHz) δ 9.08 (s, 1H), 7.93 (d, 1H), 7.83 (d, 1H), 7.67-7.73 (m, 2H), 7.43 (d, 2H), 7.31-7.36 (m, 2H), 6.66 (d, 2H), 6.34-6.51 (m, 2H), 5.76-5.79 (m, 1H), 3.08-3.09 (m, 4H), 2.80-2.82 (m, 4H), 2.48 (s, 3H).

Example 66: Preparation of N-(3-(2-((3-fluoro-4-(4-methylpiperazin-1-yl)phenyl)amino)quinazolin-8-yl)phenyl)acrylamide

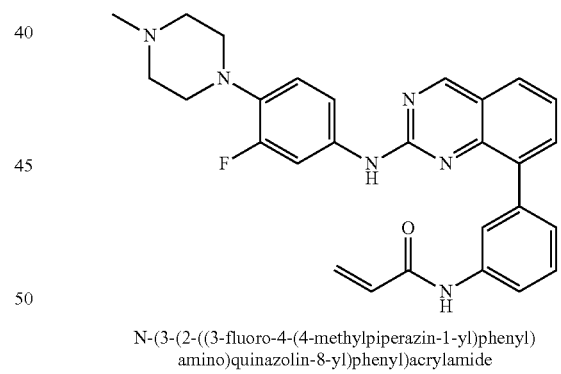

N-(3-(2-((3-fluoro-4-(4-methylpiperazin-1-yl)phenyl) amino)quinazolin-8-yl)phenyl)acrylamide N-(3-(2-((3-fluoro-4-(4-methylpiperazin-1-yl)phenyl)amino)quinazolin-8-yl)phenyl)acrylamide (33.7 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 483.2, found 483.2. $^1$H NMR (CD$_3$OD, 400 MHz) δ 9.07 (s, 1H), 7.92 (s, 1H), 7.72-7.77 (m, 4H), 7.29-7.41 (m, 4H), 6.73 (t, 1H), 6.20-6.35 (m, 2H), 5.64-5.67 (m, 1H), 2.60-2.65 (m, 4H), 2.30-2.34 (m, 4H), 2.05 (s, 3H).

Example 67: Preparation of N-(3-(2-((3-chloro-4-(4-methylpiperazin-1-yl)phenyl)amino)quinazolin-8-yl)phenyl)acrylamide

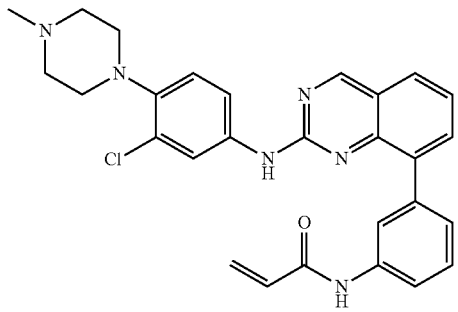

N-(3-(2-((3-chloro-4-(4-methylpiperazin-1-yl)phenyl)amino)quinazolin-8-yl)phenyl)acrylamide N-(3-(2-((3-chloro-4-(4-methylpiperazin-1-yl)phenyl)amino)quinazolin-8-yl)phenyl)acrylamide (33.7 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 499.2, found 499.1. $^1$H NMR (CD$_3$OD, 400 MHz) δ 9.21 (s, 1H), 8.04 (s, 1H), 7.71-7.93 (m, 5H), 7.44-7.54 (m, 3H), 6.93 (d, 1H), 6.34-6.48 (m, 2H), 5.76-5.79 (m, 1H), 2.99-3.01 (m, 4H), 2.62-2.65 (m, 4H), 2.37 (s, 3H).

Example 68: Preparation of N-(3-(2-((3-methoxy-4-(4-methylpiperazin-1-yl)phenyl)amino)quinazolin-8-yl)phenyl)acrylamide

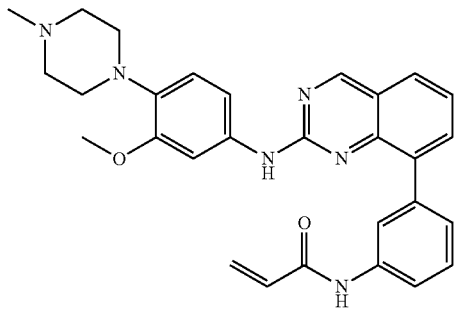

N-(3-(2-((3-methoxy-4-(4-methylpiperazin-1-yl)phenyl)amino)quinazolin-8-yl)phenyl)acrylamide N-(3-(2-((3-methoxy-4-(4-methylpiperazin-1-yl)phenyl)amino)quinazolin-8-yl)phenyl)acrylamide (122.7 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 495.2, found 495.2. $^1$H NMR (CD$_3$OD, 400 MHz) δ 9.10 (s, 1H), 7.88 (d, 1H), 7.69-7.76 (m, 3H), 7.32-7.38 (m, 5H), 6.65 (d, 1H), 6.25-6.33 (m, 2H), 5.66-5.69 (m, 1H), 3.31-3.34 (m, 5H), 3.10-3.15 (m, 2H), 2.83-2.85 (m, 5H).

Example 69: Preparation of N-(3-(2-((3-cyano-4-(4-methylpiperazin-1-yl)phenyl)amino)quinazolin-8-yl)phenyl)acrylamide

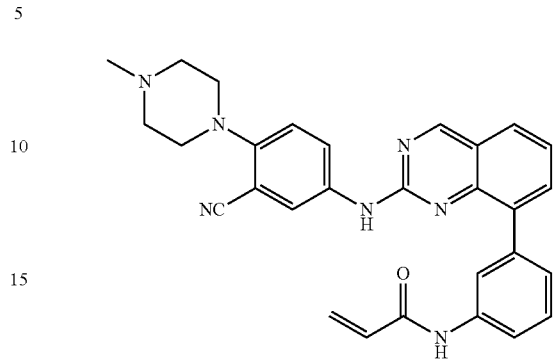

N-(3-(2-((3-cyano-4-(4-methylpiperazin-1-yl)phenyl)amino)quinazolin-8-yl)phenyl)acrylamide N-(3-(2-((3-cyano-4-(4-methylpiperazin-1-yl)phenyl)amino)quinazolin-8-yl)phenyl)acrylamide (35.9 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 490.2, found 490.2. $^1$H NMR (CD$_3$OD, 400 MHz) δ 9.11 (s, 1H), 8.05 (d, 1H), 7.72-7.96 (m, 5H), 7.33-7.46 (m, 3H), 6.90 (d, 1H), 6.22-6.40 (m, 2H), 5.66-5.68 (m, 1H), 3.07-3.21 (m, 8H), 2.70 (s, 3H).

Example 70: Preparation of N-(4-chloro-3-(2-((4-(4-methylpiperazin-1-yl)phenyl)amino)quinazolin-8-yl)phenyl)acrylamide

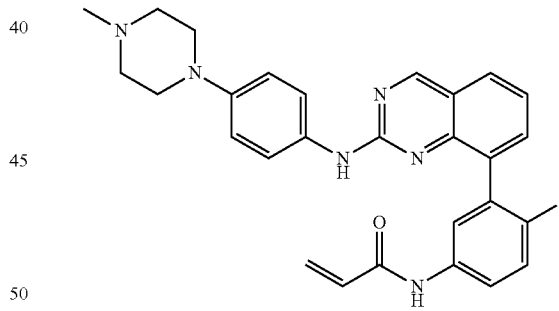

N-(4-chloro-3-(2-((4-(4-methylpiperazin-1-yl)phenyl)amino)quinazolin-8-yl)phenyl)acrylamide N-(4-chloro-3-(2-((4-(4-methylpiperazin-1-yl)phenyl)amino)quinazolin-8-yl)phenyl)acrylamide (43.4 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 499.2, found 499.2. $^1$H NMR (CD$_3$OD, 400 MHz) δ 9.18 (s, 1H), 8.05 (d, 1H), 7.90 (d, 1H), 7.78 (d, 1H), 7.57-7.7.62 (m, 4H), 7.44 (t, 1H), 6.72 (d, 2H), 6.36-6.49 (m, 2H), 5.80 (d, 1H), 3.22-3.28 (m, 4H), 3.08-3.09 (m, 4H), 2.72 (s, 3H).

Example 71: Preparation of methyl 4-(4-((8-(3-acrylamidophenyl)quinazolin-2-yl)amino)phenyl)piperazine-1-carboxylate

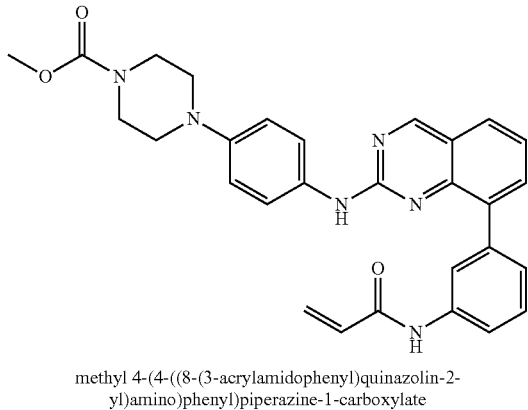 [SMILES: C=CC(=O)Nc1cccc(-c2cccc3cnc(Nc4ccc(N5CCN(C(=O)OC)CC5)cc4)nc23)c1]

methyl 4-(4-((8-(3-acrylamidophenyl)quinazolin-2-yl)amino)phenyl)piperazine-1-carboxylate Methyl 4-(4-((8-(3-acrylamidophenyl)quinazolin-2-yl)amino)phenyl)piperazine-1-carboxylate (31.4 mg) was prepared as described for (S)—N-(3-(2-((4-((1-acetylpyrrolidin-3-yl)oxy)phenyl)amino)quinazolin-8-yl)phenyl)acrylamide. LRMS (M+H+) m/z calculated 509.2, found 509.2. $^1$H NMR (CDCl3, 400 MHz) δ 9.08 (s, 1H), 8.01-8.02 (m, 1H), 7.83 (d, 2H), 7.72 (d, 2H), 7.67 (d, 3H), 7.50-7.52 (m, 2H), 7.34-7.40 (m, 2H), 6.81 (d, 2H), 6.46 (d 1H), 6.24-6.26 (m, 1H), 5.77 (d, 1H), 3.74 (s, 3H), 3.49-3.62 (m, 4H), 3.03-3.24 (m, 4H).

Example 72: Preparation of N-(3-(2-((4-(3-(hydroxymethyl)-4-methylpiperazin-1-yl)phenyl)amino)quinazolin-8-yl)phenyl)acrylamide

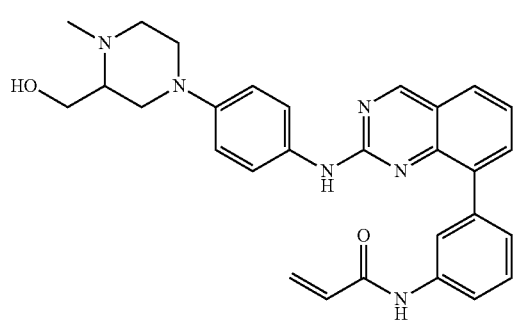

N-(3-(2-((4-(3-(hydroxymethyl)-4-methylpiperazin-1-yl)phenyl)amino)quinazolin-8-yl)phenyl)acrylamide N-(3-(2-((4-(3-(hydroxymethyl)-4-methylpiperazin-1-yl)phenyl)amino)quinazolin-8-yl)phenyl)acrylamide (41.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 495.2, found 495.2. $^1$H NMR (CD$_3$OD, 400 MHz) δ 9.01 (s, 1H), 7.80-7.86 (m, 2H), 7.68 (d, 2H), 7.62 (d, 2H), 7.35-7.38 (m, 1H), 7.25-7.30 (m, 2H), 6.68 (d, 2H), 6.25-6.39 (m, 2H), 5.68 (d, 1H), 3.66-3.67 (m, 2H), 3.45 (d, 1H), 3.33 (d, 1H), 2.99 (d, 1H), 2.56-2.71 (m, 1H), 2.46 (s, 1H)

Example 73: Preparation of N-(3-(2-((5-chloro-6-(4-methylpiperazin-1-yl)pyridin-3-yl)amino)quinazolin-8-yl)phenyl)acrylamide

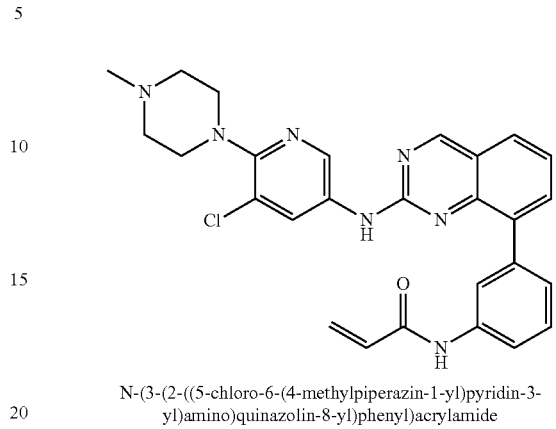

N-(3-(2-((5-chloro-6-(4-methylpiperazin-1-yl)pyridin-3-yl)amino)quinazolin-8-yl)phenyl)acrylamide N-(3-(2-((5-chloro-6-(4-methylpiperazin-1-yl)pyridin-3-yl)amino)quinazolin-8-yl)phenyl)acrylamide (41.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 500.2, found 500.2. $^1$H NMR (CDCl$_3$, 400 MHz) δ 9.08 (s, 1H), 8.32 (d, 1H), 8.03 (s, 1H), 7.63-7.84 (m, 4H), 7.26-7.51 (m, 4H), 6.30-6.44 (m, 2H), 5.74 (d, 1H), 3.31-3.33 (m, 4H), 2.70-2.74 (m, 4H), 2.45 (s, 3H).

Example 74: Preparation of N-(3-(2-((4-(4-(2-hydroxyacetyl)piperazin-1-yl)phenyl)amino)quinazolin-8-yl)phenyl)acrylamide

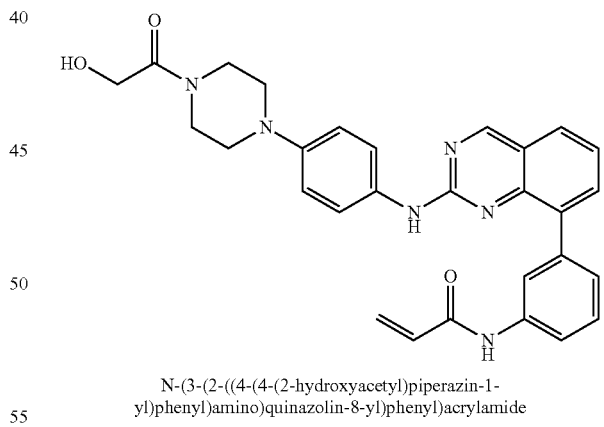

N-(3-(2-((4-(4-(2-hydroxyacetyl)piperazin-1-yl)phenyl)amino)quinazolin-8-yl)phenyl)acrylamide N-(3-(2-((4-(4-(2-hydroxyacetyl)piperazin-1-yl)phenyl)amino)quinazolin-8-yl)phenyl)acrylamide (27.5 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 509.2, found 509.2. $^1$H NMR (DMSO-d6, 300 MHz) δ 10.41 (s, 1H), 9.74 (s, 1H), 9.30 (s, 1H), 8.03 (s, 1H), 7.78-7.92 (m, 5H), 7.32-7.47 (m, 3H), 6.73 (d, 2H), 6.29-6.52 (m, 2H), 5.74-5.78 (m, 1H), 4.68 (t, 1H), 4.13 (d, 2H), 3.45-3.60 (m, 4H), 2.93-2.99 (m, 4H).

Example 75: Preparation of 4-(4-((8-(3-acrylamidophenyl)quinazolin-2-yl)amino)phenyl)-N-methylpiperazine-1-carboxamide

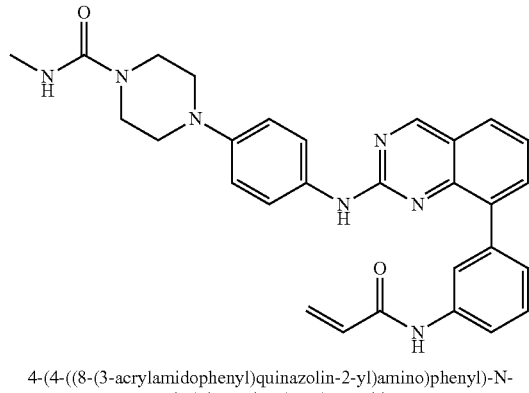

4-(4-((8-(3-acrylamidophenyl)quinazolin-2-yl)amino)phenyl)-N-methylpiperazine-1-carboxamide 4-(4-((8-(3-Acrylamidophenyl)quinazolin-2-yl)amino)phenyl)-N-methylpiperazine-1-carboxamide (71.0 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 508.2, found 508.2. $^1$H NMR (DMSO-d6, 300 MHz) δ 10.30 (s, 1H), 9.70 (d, 1H), 9.29 (s, 1H), 8.01 (s, 1H), 7.74-7.91 (m, 5H), 7.31-7.507 (m, 3H), 6.72 (d, 2H), 6.31-6.53 (m, 3H), 5.75-5.78 (m, 1H), 3.43 (s, 3H), 2.90-2.97 (m, 4H), 2.45-2.59 (m, 4H).

Example 76: Preparation of N-(3-(2-((4-(4-propionylpiperazin-1-yl)phenyl)amino)quinazolin-8-yl)phenyl)acrylamide

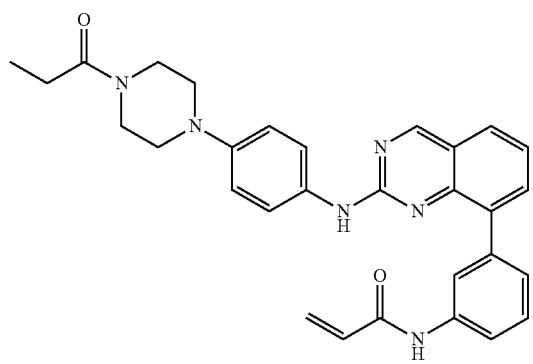

N-(3-(2-((4-(4-propionylpiperazin-1-yl)phenyl)amino)quinazolin-8-yl)phenyl)acrylamide N-(3-(2-((4-(4-propionylpiperazin-1-yl)phenyl)amino)quinazolin-8-yl)phenyl)acrylamide (39.6 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 507.2, found 507.2. $^1$H NMR (CDCl$_3$, 400 MHz) δ 9.07 (s, 1H), 8.03 (brs, 1H), 7.81-7.83 (m, 2H), 7.65-7.72 (m, 3 H), 7.49-7.53 (m, 3H), 7.33-7.39 (m, 2H), 6.79 (d, 3H), 6.45 (d, 1H), 6.23-6.28 (m, 1H), 5.76 (d, 1H), 3.76 (t, 2H), 3.59 (t, 2H), 3.01-3.05 (m, 4H), 2.39 (q, 2H), 1.18 (t, 3H).

Example 77: Preparation of N-(3-(2-((5-cyano-6-(4-methylpiperazin-1-yl)pyridin-3-yl)amino)quinazolin-8-yl)phenyl)acrylamide

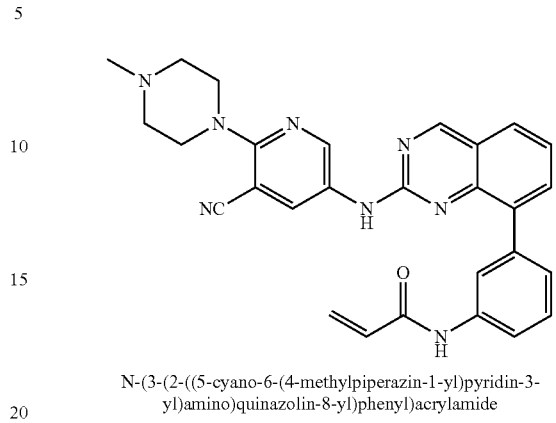

N-(3-(2-((5-cyano-6-(4-methylpiperazin-1-yl)pyridin-3-yl)amino)quinazolin-8-yl)phenyl)acrylamide N-(3-(2-((5-cyano-6-(4-methylpiperazin-1-yl)pyridin-3-yl)amino)quinazolin-8-yl)phenyl)acrylamide (55.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 491.2, found 491.2. $^1$H NMR (CDCl3, 400 MHz) δ 9.05 (s, 1H), 8.64 (brs, 1H), 8.39 (s, 1H), 8.28 (s, 1H), 7.73-7.85 (m, 3H), 7.28-7.54 (m, 5H), 6.28-6.43 (m, 2H), 5.74 (d, 1H), 3.56 (t, 4H), 2.68 (t, 4H), 2.43 (s, 3H).

Example 78: Preparation of 5-((8-(3-acrylamidophenyl)quinazolin-2-yl)amino)-2-(4-methylpiperazin-1-yl)benzamide

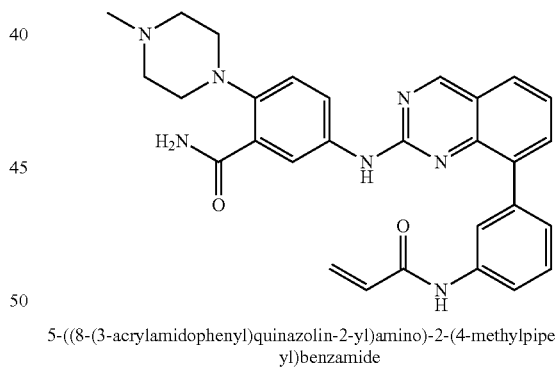

5-((8-(3-acrylamidophenyl)quinazolin-2-yl)amino)-2-(4-methylpiperazin-1-yl)benzamide 5-((8-(3-Acrylamidophenyl)quinazolin-2-yl)amino)-2-(4-methylpiperazin-1-yl)benzamide (50.0 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 508.2, found 508.2. $^1$H NMR (CD$_3$OD, 400 MHz) δ 9.07 (s, 1H), 8.35 (dd, 1H), 7.88 (s, 1H), 7.71-7.78 (m, 4H), 7.31-7.40 (m, 3H), 6.88 (d, 1H), 6.29-6.37 (m, 2H), 5.67 (dd, 2H), 2.89 (t, 4H), 2.66 (brs, 4H), 2.37 (s, 3H).

Example 79: Preparation of N-(3-(7-fluoro-2-((4-(4-methylpiperazin-1-yl)phenyl)amino)quinazolin-8-yl)phenyl)acrylamide

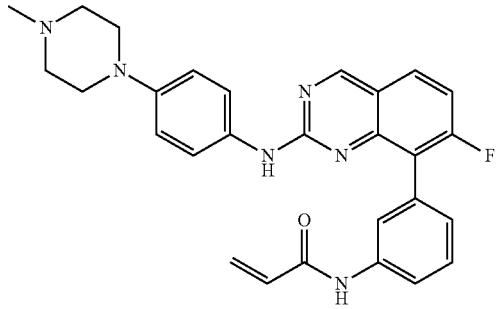

N-(3-(7-fluoro-2-((4-(4-methylpiperazin-1-yl)phenyl)amino)quinazolin-8-yl)phenyl)acrylamide N-(3-(7-fluoro-2-((4-(4-methylpiperazin-1-yl)phenyl)amino)quinazolin-8-yl)phenyl)acrylamide (45.1 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 483.2, found 483.2. $^1$H NMR (CD$_3$OD, 400 MHz) δ 9.10 (s, 1H), 8.02 (d, 1H), 7.88 (q, 1H), 7.80 (s, 1H), 7.65 (d, 2H), 7.51 (t, 1H), 7.20-7.30 (m, 2H), 6.76 (d, 2H), 6.37-6.47 (m, 2H), 5.79 (dd, 1H), 3.13 (t, 4H), 2.75 (t, 4H), 2.47 (s, 3H).

Example 80: Preparation of methyl 4-(4-((8-(3-acrylamidophenyl)quinazolin-2-yl)amino)phenyl)-1-methylpiperazine-2-carboxylate

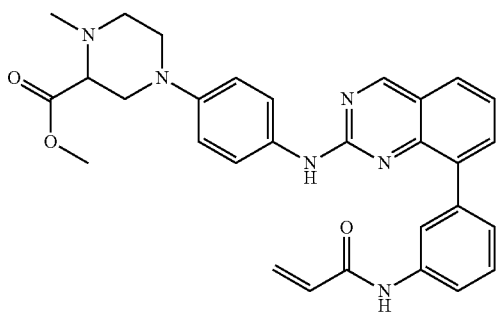

methyl 4-(4-((8-(3-acrylamidophenyl)quinazolin-2-yl)amino)phenyl)-1-methylpiperazine-2-carboxylate Methyl 4-(4-((8-(3-acrylamidophenyl)quinazolin-2-yl)amino)phenyl)-1-methylpiperazine-2-carboxylate (34.0 mg) was prepared as described for (S)—N-(3-(2-((4-((1-acetylpyrrolidin-3-yl)oxy)phenyl)amino)quinazolin-8-yl)phenyl)acrylamide. LRMS (M+H+) m/z calculated 523.2, found 523.2. $^1$H NMR (CD$_3$OD, 400 MHz) δ 9.16 (s, 1H), 8.05 (s, 1H), 7.92 (d, 1H), 7.84 (d, 2H), 7.75 (d, 2H), 7.40-7.53 (m, 3H), 6.79 (d, 2H), 6.38-6.51 (m, 2H), 5.79 (dd, 1H), 3.82 (s, 3H), 3.47 (d, 1H), 3.31 (d, 1H), 3.18 (dd, 1H), 3.03-3.07 (m, 1H), 2.87-2.97 (m, 2H), 2.45-2.51 (m, 1H), 2.40 (s, 1H).

Example 81: Preparation of N-(3-(7-fluoro-2-((4-(4-(2-fluoroethyl)piperazin-1-yl)phenyl)amino)quinazolin-8-yl)phenyl)acrylamide

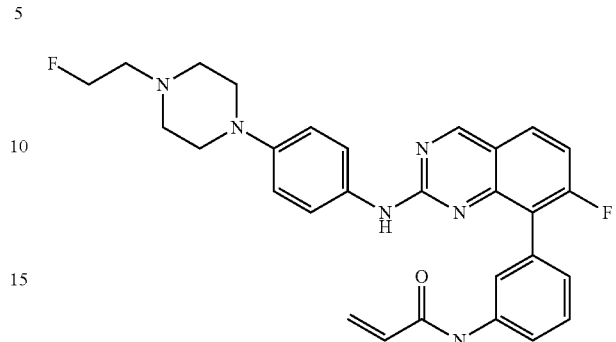

N-(3-(7-fluoro-2-((4-(4-(2-fluoroethyl)piperazin-1-yl)phenyl)amino)quinazolin-8-yl)phenyl)acrylamide N-(3-(7-fluoro-2-((4-(4-(2-fluoroethyl)piperazin-1-yl)phenyl)amino)quinazolin-8-yl)phenyl)acrylamide (34.0 mg) was prepared as described for (S)—N-(3-(2-((4-((1-acetylpyrrolidin-3-yl)oxy)phenyl)amino)quinazolin-8-yl)phenyl)acrylamide. LRMS (M+H+) m/z calculated 515.2, found 515.2. $^1$H NMR (CD$_3$OD, 400 MHz) δ 9.11 (s, 1H), 8.01 (d, 1H), 7.88 (dd, 1H), 7.82 (s, 1H), 7.64 (d, 2H), 7.52 (t, 1H), 7.21-7.30 (m, 2H), 6.77 (d, 2H), 6.39-6.61 (m, 2H), 5.79 (dd, 1H), 4.72 (t, 1H), 4.60 (t, 1H), 3.12 (t, 4H), 2.86 (t, 1H), 2.75-2.80 (m, 5H).

Example 82: Preparation of N-(3-(2-((4-(2-oxoxazolidin-3-yl)phenyl)amino)quinazolin-8-yl)phenyl)acrylamide

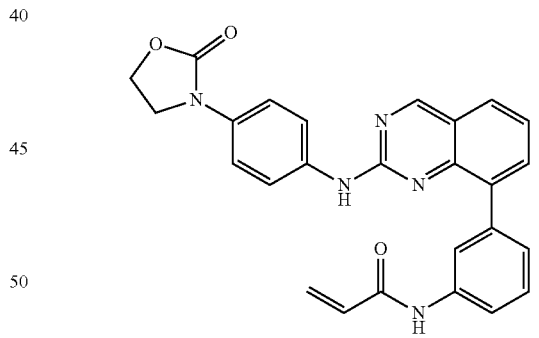

N-(3-(2-((4-(2-oxooxazolidin-3-yl)phenyl)amino)quinazolin-8-yl)phenyl)acrylamide N-(3-(2-((4-(2-oxooxazolidin-3-yl)phenyl)amino)quinazolin-8-yl)phenyl)acrylamide (71.0 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 452.2, found 452.1. $^1$H NMR (DMSO-d6, 400 MHz) δ10.30 (s, 1H), 9.95 (s, 1H), 9.36 (s, 1H), 8.06 (s, 1H), 7.81-7.96 (m, 5H), 7.48 (q, 2H), 7.41 (d, 1H), 7.29 (d, 2H), 6.43-6.47 (m, 1H), 6.26 (d, 1H), 5.75 (d, 1H), 4.42 (t, 2H), 3.97 (t, 2H).

Example 83: Preparation of 4-(4-((8-(3-acrylamidophenyl)quinazolin-2-yl)amino)phenyl)-1-methylpiperazine-2-carboxylic acid

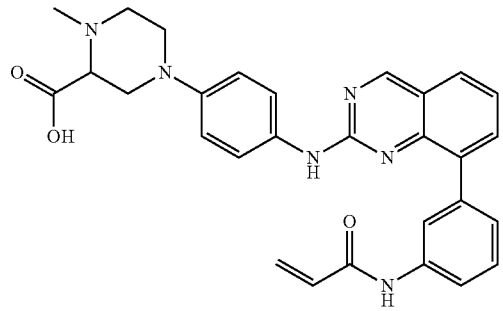

4-(4-((8-(3-acrylamidophenyl)quinazolin-2-yl)amino)phenyl)-1-methylpiperazine-2-carboxylic acid 4-(4-((8-(3-Acrylamidophenyl)quinazolin-2-yl)amino)phenyl)-1-methylpiperazine-2-carboxylic acid (32.3 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 509.2, found 509.2. $^1$H NMR (CD$_3$OD, 400 MHz) δ 9.06 (s, 1H), 8.12 (s, 1H), 7.68-7.77 (m, 5H), 7.32-7.47 (m, 3H), 6.77 (d, 2H), 6.36-6.53 (m, 2H), 5.80 (d, 1H), 3.78 (d, 1H), 3.45 (d, 1H), 3.23-3.34 (m, 2H), 2.82-2.91 (m, 3H), 2.70 (s, 3H).

Example 84: Preparation of N-(3-(2-((4-(1H-imidazol-1-yl)phenyl)amino)quinazolin-8-yl)phenyl)acrylamide

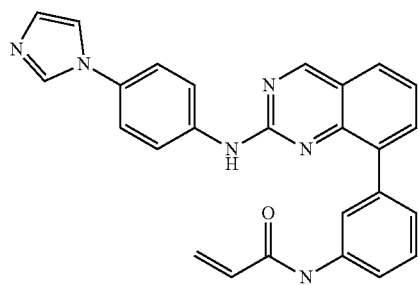

N-(3-(2-((4-(1H-imidazol-1-yl)phenyl)amino)quinazolin-8-yl)phenyl)acrylamide

N-(3-(2-((4-(1H-imidazol-1-yl)phenyl)amino)quinazolin-8-yl)phenyl)acrylamide (41.2 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 433.2, found 433.1. $^1$H NMR (CD$_3$OD, 400 MHz) δ 9.13 (s, 1H), 7.89-7.98 (m, 4H), 7.74-7.79 (m, 3H), 7.31-7.44 (m, 4H), 7.17 (d, 2H), 7.07 (s, 1H), 6.17-6.31 (m, 2H), 5.58 (dd, 1H).

Example 85: Preparation of 4-(4-((8-(3-acrylamidophenyl)quinazolin-2-yl)amino)phenyl)-1-methylpiperazine-2-carboxamide

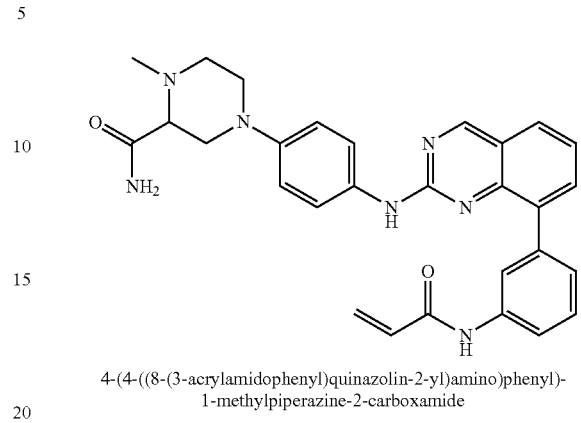

4-(4-((8-(3-acrylamidophenyl)quinazolin-2-yl)amino)phenyl)-1-methylpiperazine-2-carboxamide 4-(4-((8-(3-Acrylamidophenyl)quinazolin-2-yl)amino)phenyl)-1-methylpiperazine-2-carboxamide (74.0 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 508.2, found 508.2. $^1$H NMR (DMSO-d6, 400 MHz) δ10.32 (s, 1H), 9.72 (s, 1H), 9.30 (s, 1H), 8.06 (s, 1H), 7.73-8.06 (m, 5H), 7.17-7.50 (m, 5H), 6.71 (d, 2H), 6.43-651 (m, 1H), 6.30 (d, 1H), 5.75 (dd, 1H), 3.34-3.42 (m, 2H), 2.87 (t, 1H), 2.60-2.71 (m, 3H), 2.18-2.21 (m, 4H).

Example 86: Preparation of N-(3-(2-((4-(4-(methylsulfonyl)piperazin-1-yl)phenyl)amino)quinazolin-8-yl)phenyl)acrylamide

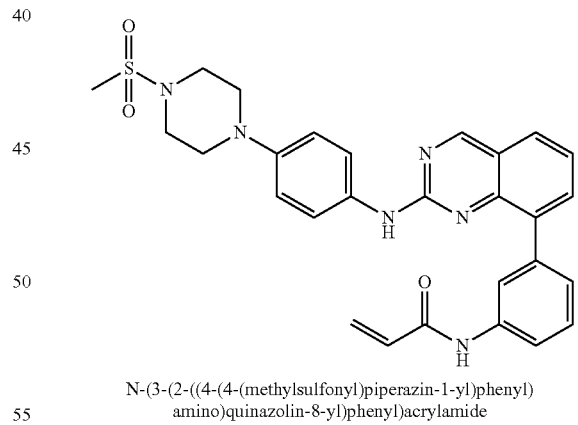

N-(3-(2-((4-(4-(methylsulfonyl)piperazin-1-yl)phenyl)amino)quinazolin-8-yl)phenyl)acrylamide N-(3-(2-((4-(4-(methylsulfonyl)piperazin-1-yl)phenyl)amino)quinazolin-8-yl)phenyl)acrylamide (24.0 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 529.2, found 529.1. $^1$H NMR (DMSO-d6, 400 MHz) δ10.33 (s, 1H), 9.74 (s, 1H), 9.31 (s, 1H), 8.02 (s, 1H), 7.76-7.93 (m, 5H), 7.41-7.50 (m, 2H), 7.34 (d, 1H), 7.75 (d, 2H), 6.42-6.50 (m, 1H), 6.28 (d, 1H), 5.77 (d, 1H), 3.22 (brs, 4H), 3.08 (brs, 4H), 2.93 (s, 3H).

Example 87: Preparation of N-(3-(2-((4-(3-oxomorpholino)phenyl)amino)quinazolin-8-yl)phenyl)acrylamide

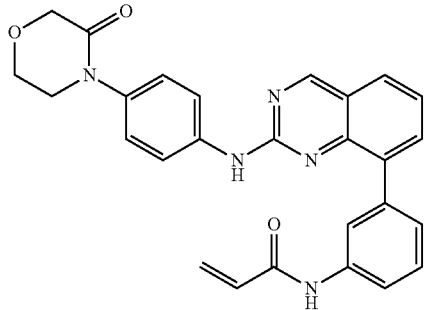

N-(3-(2-((4-(3-oxomorpholino)phenyl)amino)quinazolin-8-yl)phenyl)acrylamide

N-(3-(2-((4-(3-oxomorpholino)phenyl)amino)quinazolin-8-yl)phenyl)acrylamide (98.0 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 466.2, found 466.2. $^1$H NMR (DMSO-d6, 400 MHz) δ10.28 (s, 1H), 10.01 (s, 1H), 9.38 (s, 1H), 8.02 (s, 1H), 7.91-7.97 (m, 3H), 7.83-7.86 (m, 2H), 7.49 (t, 2H), 7.40 (d, 2H), 6.42-6.49 (m, 1H), 6.25 (dd, 1H), 5.75 (d, 1H), 4.17 (s, 2H), 3.95 (t, 2H), 3.62 (t, 2H).

Example 88: Preparation of N-(3-(2-((4-(2-oxopyrrolidin-1-yl)phenyl)amino)quinazolin-8-yl)phenyl)acrylamide

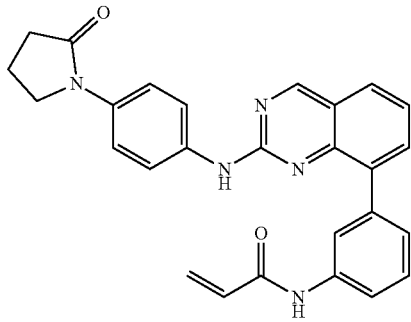

N-(3-(2-((4-(2-oxopyrrolidin-1-yl)phenyl)amino)quinazolin-8-yl)phenyl)acrylamide N-(3-(2-((4-(2-oxopyrrolidin-1-yl)phenyl)amino)quinazolin-8-yl)phenyl)acrylamide (67.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 450.2, found 450.2. $^1$H NMR (DMSO-d6, 400 MHz) δ10.29 (s, 1H), 9.92 (s, 1H), 9.35 (s, 1H), 8.04 (s, 1H), 7.93 (dd, 1H), 7.83-7.88 (m, 4H), 7.45-7.50 (m, 2H), 7.35-7.40 (m, 3H), 6.40-6.47 (m, 1H), 6.25 (dd, 1H), 5.75 (d, 1H), 3.73 (t, 2H), 2.45 (t, 2H), 2.02-2.06 (m, 2H).

Example 89: Preparation of N-(3-(2-((4-(2-oxoimidazolidin-1-yl)phenyl)amino)quinazolin-8-yl)phenyl)acrylamide

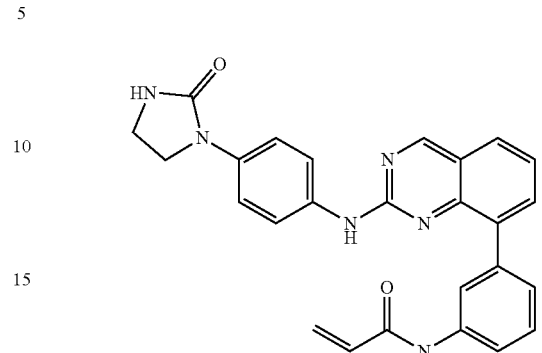

N-(3-(2-((4-(2-oxoimidazolidin-1-yl)phenyl)amino)quinazolin-8-yl)phenyl)acrylamide N-(3-(2-((4-(2-oxoimidazolidin-1-yl)phenyl)amino)quinazolin-8-yl)phenyl)acrylamide (12.0 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 451.2, found 451.1. $^1$H NMR (DMSO-d6, 400 MHz) δ 10.43 (s, 1H), 9.82 (s, 1H), 9.34 (s, 1H), 8.08 (s, 1H), 7.94 (d, 1H), 7.82-7.88 (m, 4H), 7.40-7.50 (m, 3H), 7.30 (d, 2H), 6.82 (s, 1H), 6.50-6.54 (m, 1H), 6.25-6.29 (m, 1H), 5.75-5.78 (m, 1H), 3.74-3.78 (m, 2H), 3.35-3.39 (m, 2H).

Example 90: Preparation of N-(3-(2-((4-((1-(2-hydroxyethyl)azetidin-3-yl)amino)phenyl)amino)quinazolin-8-yl)phenyl)acrylamide

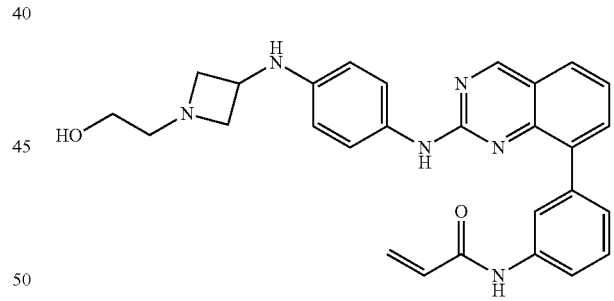

N-(3-(2-((4-((1-(2-hydroxyethyl)azetidin-3-yl)amino)phenyl)amino)quinazolin-8-yl)phenyl)acrylamide N-(3-(2-((4-((1-(2-hydroxyethyl)azetidin-3-yl)amino)phenyl)amino)quinazolin-8-yl)phenyl)acrylamide (52.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 481.2, found 481.2. $^1$H NMR (DMSO-d6, 400 MHz) δ10.27 (s, 1H), 9.49 (s, 1H), 9.24 (s, 1H), 8.00 (s, 1H), 7.84-7.87 (m, 2H), 7.77 (d, 1H), 7.58 (d, 2H), 7.43-7.46 (m, 1H), 7.36-7.40 (m, 2H), 6.45-6.51 (m, 1H), 6.26-6.31 (m, 3H), 5.75-5.78 (m, 1H), 5.62 (d, 1H), 4.38-4.41 (m, 1H), 4.08-4.12 (m, 1H), 3.80-3.85 (m, 2H), 3.33-3.38 (m, 2H), 2.73-2.77 (m, 2H), 2.46-2.50 (m, 2H).

Example 91: Preparation of N-(3-(2-((4-(3-hydroxypyrrolidin-1-yl)phenyl)amino)quinazolin-8-yl)phenyl)acrylamide

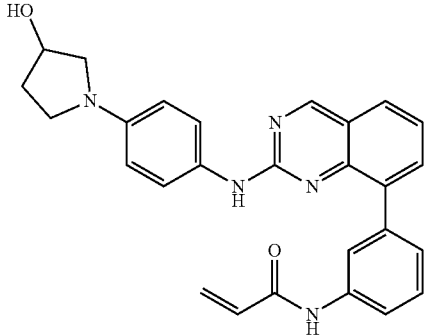

N-(3-(2-((4-(3-hydroxypyrrolidin-1-yl)phenyl)amino)quinazolin-8-yl)phenyl)acrylamide N-(3-(2-((4-(3-hydroxypyrrolidin-1-yl)phenyl)amino)quinazolin-8-yl)phenyl)acrylamide (30.8 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 452.2, found 452.2. $^1$H NMR (DMSO-d6, 400 MHz) δ10.29 (s, 1H), 9.52 (s, 1H), 9.24 (s, 1H), 8.04 (s, 1H), 7.85-7.87 (m, 2H), 7.77 (d, 1H), 7.66 (d, 2H), 7.43-7.47 (m, 1H), 7.36-7.40 (m, 1H), 7.32-7.33 (m, 1H), 6.45-6.51 (m, 1H), 6.24-6.31 (m, 3H), 5.74-5.77 (m, 1H), 4.90 (s, 1H), 4.36 (s, 1H), 3.30-3.37 (m, 1H), 3.21-3.23 (m, 1H), 3.13-3.15 (m, 1H), 2.95-2.98 (m, 1H), 1.94-2.06 (m, 1H), 1.76-1.88 (m, 1H).

Example 92: Preparation of N-(4-cyano-3-(2-((4-(4-methylpiperazin-1-yl)phenyl)amino)quinazolin-8-yl)phenyl)acrylamide

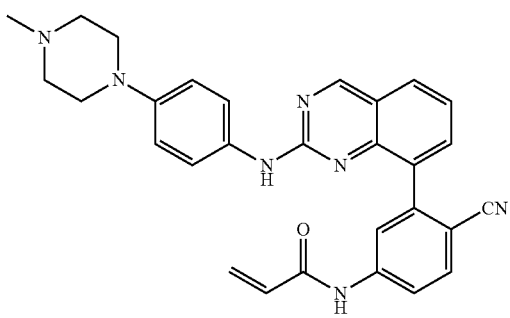

N-(4-cyano-3-(2-((4-(4-methylpiperazin-1-yl)phenyl)amino)quinazolin-8-yl)phenyl)acrylamide N-(4-cyano-3-(2-((4-(4-methylpiperazin-1-yl)phenyl)amino)quinazolin-8-yl)phenyl)acrylamide (41.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 490.2, found 490.2. $^1$H NMR (DMSO-d6, 400 MHz) δ10.70 (s, 1H), 9.77 (s, 1H), 9.33 (s, 1H), 7.87-8.07 (m, 5H), 7.57 (d, 2H), 7.45-7.48 (m, 1H), 6.65 (d, 2H), 6.42-6.47 (m, 1H), 6.28-6.33 (m, 1H), 5.82-5.85 (m, 1H), 2.95-2.31 (m, 4H), 2.42-2.46 (m, 4H), 2.23 (s, 3H).

Example 93: Preparation of methyl 2-acrylamido-6-(2-((4-(4-methylpiperazin-1-yl)phenyl)amino)quinazolin-8-yl)benzoate

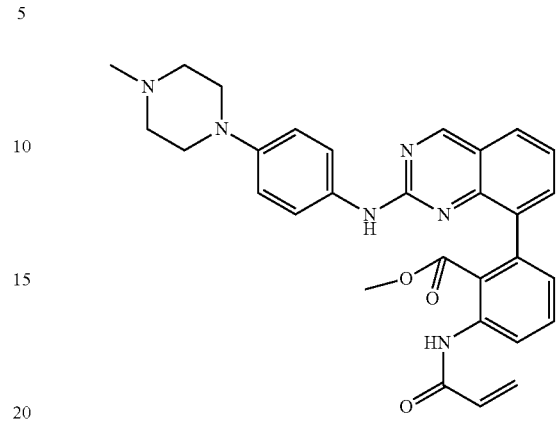

methyl 2-acrylamido-6-(2-((4-(4-methylpiperazin-1-yl)phenyl)amino)quinazolin-8-yl)benzoate Methyl 2-acrylamido-6-(2-((4-(4-methylpiperazin-1-yl)phenyl)amino)quinazolin-8-yl)benzoate (21.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 523.2, found 523.2. $^1$H NMR (CD$_3$OD, 400 MHz) δ 9.13 (s, 1H), 8.34 (d, 1H), 7.65-7.83 (m, 3H), 7.54-7.57 (m, 2H), 7.41-7.44 (m, 1H), 7.28 (d, 1H), 6.77 (d, 2H), 6.39-6.42 (m, 2H), 5.83-5.87 (m, 1H), 3.13-3.18 (m, 7H), 2.90-2.94 (m, 4H), 2.60 (s, 3H).

Example 94: Preparation of methyl 2-((8-(3-acrylamidophenyl)quinazolin-2-yl)amino)-5-(4-methylpiperazin-1-yl)benzoate

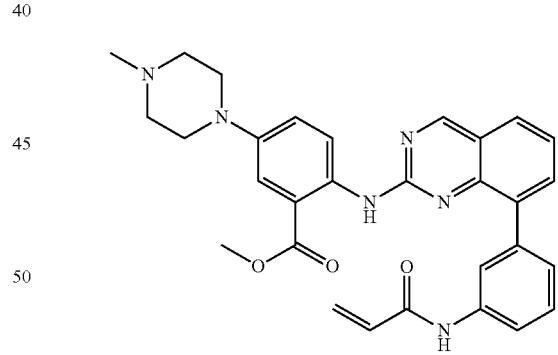

methyl 2-((8-(3-acrylamidophenyl)quinazolin-2-yl)amino)-5-(4-methylpiperazin-1-yl)benzoate Methyl 2-((8-(3-acrylamidophenyl)quinazolin-2-yl)amino)-5-(4-methylpiperazin-1-yl)benzoate (10.9 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 523.2, found 523.2. $^1$H NMR (CD$_3$OD, 400 MHz) δ7.69 (s, 1H), 7.44 (d, 1H), 7.40-7.43 (m, 2H), 7.25-7.28 (m, 3H), 7.09-7.13 (m, 2H), 6.98-7.03 (m, 2H), 6.24-6.28 (m, 2H), 5.64-5.68 (m, 1H), 3.19-3.24 (m, 3H), 3.08-3.17 (m, 4H), 2.67-2.69 (m, 4H), 2.37 (s, 3H).

Example 95: Preparation of N-(3-(2-((4-(1,4-oxazepan-4-yl)phenyl)amino)quinazolin-8-yl)phenyl)acrylamide

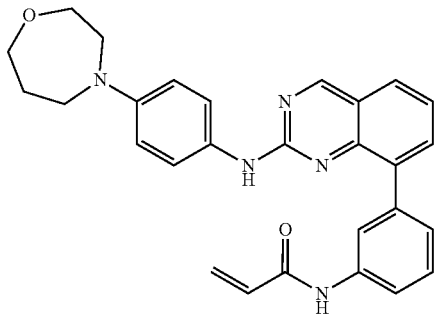

N-(3-(2-((4-(1,4-oxazepan-4-yl)phenyl)amino)quinazolin-8-yl)phenyl)acrylamide

N-(3-(2-((4-(1,4-oxazepan-4-yl)phenyl)amino)quinazolin-8-yl)phenyl)acrylamide (38.0 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 466.2, found 466.2. ¹H NMR (DMSO-d6, 400 MHz) δ 10.30 (s, 1H), 9.54 (s, 1H), 9.25 (s, 1H), 8.02 (s, 1H), 7.87 (d, 2H), 7.78 (d, 1H), 7.65 (d, 2H), 7.39-7.47 (m, 2H), 7.30 (d, 1H), 6.44-6.51 (m, 3H), 6.24-6.29 (m, 1H), 5.75-5.78 (m, 1H), 3.63-3.67 (m, 2H), 3.46-3.52 (m, 6H), 1.83-1.86 (m, 2H).

Example 96: Preparation of N-(3-(2-((4-(4-methyl-2-oxopiperazin-1-yl)phenyl)amino)quinazolin-8-yl)phenyl)acrylamide

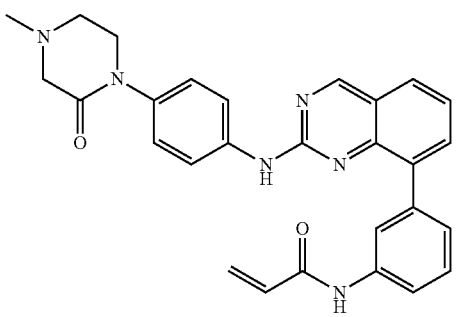

N-(3-(2-((4-(4-methyl-2-oxopiperazin-1-yl)phenyl)amino)quinazolin-8-yl)phenyl)acrylamide N-(3-(2-((4-(4-methyl-2-oxopiperazin-1-yl)phenyl)amino)quinazolin-8-yl)phenyl)acrylamide (32.1 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 479.2, found 479.2. ¹H NMR (DMSO-d6, 400 MHz) δ10.28 (s, 1H), 9.99 (s, 1H), 9.37 (s, 1H), 8.03 (s, 1H), 7.81-7.97 (m, 5H), 7.47-7.50 (m, 2H), 7.36-7.39 (m, 1H), 7.02 (d, 2H), 6.42-6.54 (m, 1H), 6.22-6.27 (m, 1H), 5.73-5.75 (m, 1H), 3.49-3.56 (m, 2H), 3.06 (s, 2H), 2.64-2.71 (m, 2H), 2.32 (s, 3H).

Example 97: Preparation of N-(3-(2-((4-(2-methoxyethoxy)phenyl)amino)quinazolin-8-yl)phenyl)acrylamide

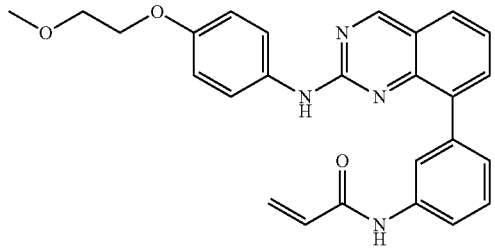

N-(3-(2-((4-(2-methoxyethoxy)phenyl)amino)quinazolin-8-yl)phenyl)acrylamide

N-(3-(2-((4-(2-methoxyethoxy)phenyl)amino)quinazolin-8-yl)phenyl)acrylamide (85.0 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 441.2, found 441.2. ¹H NMR (CD₃OD, 400 MHz) δ 9.01 (s, 1H), 7.89 (s, 1H), 7.59-7.76 (m, 5H), 7.25-7.38 (m, 3H), 6.60-6.63 (m, 3H), 6.24-6.34 (m, 2H), 5.64-5.67 (m, 1H), 3.89-3.91 (m, 2H), 3.58-3.60 (m, 2H), 3.31 (s, 3H).

Example 98: Preparation of N-(3-(2-((4-(2-hydroxyethoxy)phenyl)amino)quinazolin-8-yl)phenyl)acrylamide

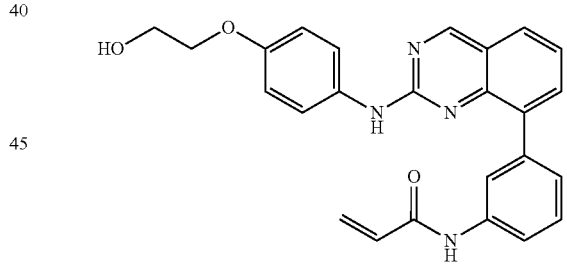

N-(3-(2-((4-(2-hydroxyethoxy)phenyl)amino)quinazolin-8-yl)phenyl)acrylamide

N-(3-(2-((4-(2-hydroxyethoxy)phenyl)amino)quinazolin-8-yl)phenyl)acrylamide (37.1 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 427.2, found 427.1. ¹H NMR (DMSO-d6, 400 MHz) δ 10.33 (s, 1H), 9.75 (s, 1H), 9.31 (s, 1H), 8.05 (s, 1H), 7.91 (d, 1H), 7.76-7.82 (m, 4H), 7.41-7.50 (m, 2H), 7.36 (d, 1H), 6.69 (d, 2H), 6.45-6.49 (m, 1H), 6.24-6.28 (m, 1H), 5.74-5.77 (m, 1H), 4.81 (s, 1H), 3.85-3.88 (m, 2H), 3.66-3.69 (m, 2H).

Example 99: Preparation of N-(3-(2-((4-(2-(dimethylamino)ethoxy)phenyl)amino)quinazolin-8-yl)phenyl)acrylamide

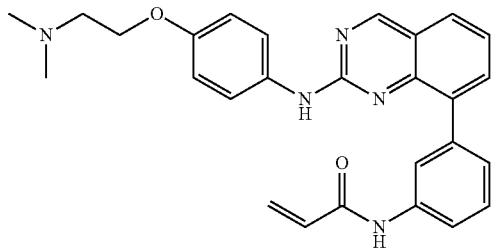

N-(3-(2-((4-(2-(dimethylamino)ethoxy)phenyl)amino)quinazolin-8-yl)phenyl)acrylamide N-(3-(2-((4-(2-(dimethylamino)ethoxy)phenyl)amino)quinazolin-8-yl)phenyl)acrylamide (98.5 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 454.2, found 454.2. ¹H NMR (DMSO-d6, 400 MHz) δ10.32 (s, 1H), 9.77 (s, 1H), 9.32 (s, 1H), 8.01 (s, 1H), 7.79-7.93 (m, 5H), 7.36-7.50 (m, 3H), 6.69 (d, 2H), 6.67-6.73 (m, 1H), 6.24-6.28 (m, 1H), 5.74-5.77 (m, 1H), 4.01-4.04 (m, 2H), 2.90 (s, 2H), 2.44 (s, 6H).

Example 100: Preparation of N-(3-(2-((4-(2-(azetidin-1-yl)ethoxy)phenyl)amino)quinazolin-8-yl)phenyl)acrylamide

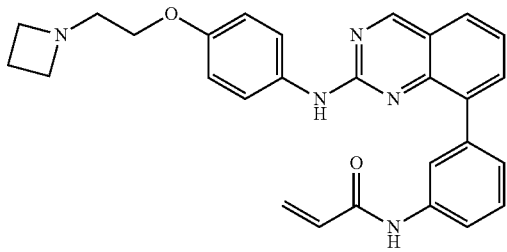

N-(3-(2-((4-(2-(azetidin-1-yl)ethoxy)phenyl)amino)quinazolin-8-yl)phenyl)acrylamide N-(3-(2-((4-(2-(azetidin-1-yl)ethoxy)phenyl)amino)quinazolin-8-yl)phenyl)acrylamide (41.4 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 466.2, found 466.2. ¹H NMR (CD₃OD, 400 MHz) δ 9.04 (s, 1H), 7.79-7.83 (m, 2H), 7.64-7.72 (m, 4H), 7.28-7.37 (m, 3H), 6.63-6.70 (m, 3H), 6.28-6.37 (m, 2H), 5.68 (d, 1H), 4.08-4.12 (m, 4H), 3.99-4.01 (m, 2H), 3.20-3.24 (m, 2H), 2.39-2.43 (m, 2H).

Example 101: Preparation of (S)—N-(3-(2-((4-((tetrahydrofuran-3-yl)amino)phenyl)amino)quinazolin-8-yl)phenyl)acrylamide

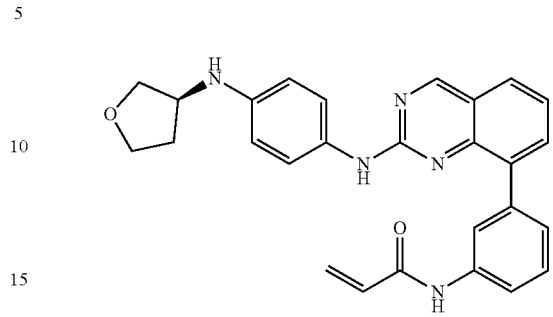

(S)-N-(3-(2-((4-((tetrahydrofuran-3-yl)amino)phenyl)amino)quinazolin-8-yl)phenyl)acrylamide (S)—N-(3-(2-((4-((tetrahydrofuran-3-yl)amino)phenyl)amino)quinazolin-8-yl)phenyl)acrylamide (55.9 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 452.2, found 452.2. ¹H NMR (DMSO-d6, 400 MHz) δ10.27 (s, 1H), 9.50 (s, 1H), 9.24 (s, 1H), 7.98 (s, 1H), 7.86-7.88 (m, 2H), 7.76-7.78 (m, 1H), 7.59 (d, 2H), 7.35-7.46 (m, 3H), 6.24-6.51 (m, 4H), 5.74-5.77 (m, 1H), 5.42-5.44 (m, 1H), 3.67-3.86 (m, 4H), 3.42-3.46 (m, 1H), 2.09-2.14 (m, 1H), 1.66-1.72 (m, 1H).

Example 102: Preparation of N-(3-(2-((4-((tetrahydro-2H-pyran-4-yl)oxy)phenyl)amino)quinazolin-8-yl)phenyl)acrylamide

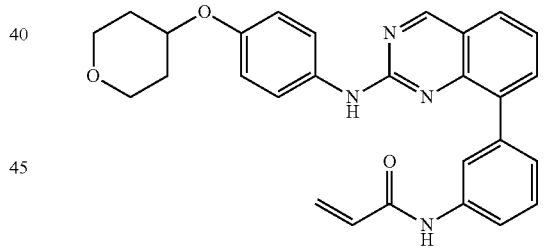

N-(3-(2-((4-((tetrahydro-2H-pyran-4-yl)oxy)phenyl)amino)quinazolin-8-yl)phenyl)acrylamide N-(3-(2-((4-((tetrahydro-2H-pyran-4-yl)oxy)phenyl)amino)quinazolin-8-yl)phenyl)acrylamide (103 mg) was prepared as described for (S)—N-(3-(2-((4-((1-acetylpyrrolidin-3-yl)oxy)phenyl)amino)quinazolin-8-yl)phenyl)acrylamide. LRMS (M+H⁺) m/z calculated 467.2, found 467.2. ¹H NMR (DMSO-d6, 400 MHz) δ10.30 (s, 1H), 9.76 (s, 1H), 9.31 (s, 1H), 8.04 (s, 1H), 7.77-7.92 (m, 5H), 7.32-7.50 (m, 3H), 6.71 (d, 2H), 6.44-6.50 (m, 1H), 6.24-6.29 (m, 1H), 5.75-5.78 (m, 1H), 4.34-4.38 (m, 1H), 3.82-3.86 (m, 2H), 3.42-3.48 (m, 2H), 1.87-1.92 (m, 2H), 1.47-1.56 (m, 2H).

Example 103: Preparation of (S)—N-(3-(2-((4-((tetrahydrofuran-3-yl)oxy)phenyl)amino)quinazolin-8-yl)phenyl)acrylamide

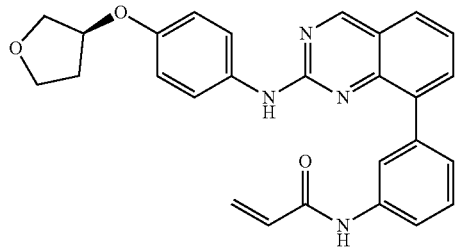

(S)-N-(3-(2-((4-((tetrahydrofuran-3-yl)oxy)phenyl)amino)quinazolin-8-yl)phenyl)acrylamide (S)—N-(3-(2-((4-((tetrahydrofuran-3-yl)oxy)phenyl)amino)quinazolin-8-yl)phenyl)acrylamide (85 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 453.2, found 453.1. $^1$H NMR (DMSO-d6, 300 MHz) δ10.29 (s, 1H), 9.77 (s, 1H), 9.31 (s, 1H), 8.04 (s, 1H), 7.77-7.93 (m, 5H), 7.33-7.51 (m, 3H), 6.65 (d, 2H), 6.43-6.52 (m, 1H), 6.22-6.28 (m, 1H), 5.74-5.78 (m, 1H), 4.84-4.88 (m, 1H), 3.69-3.87 (m, 4H), 2.12-2.19 (m, 1H), 1.85-1.94 (m, 1H).

Example 104: Preparation of N-(3-(2-((4-((tetrahydro-2H-pyran-4-yl)amino)phenyl)amino)quinazolin-8-yl)phenyl)acrylamide

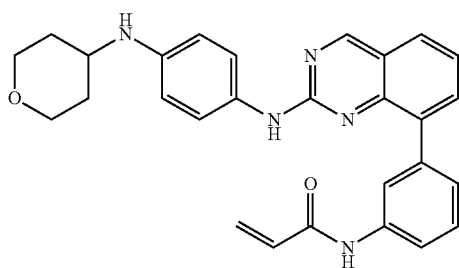

N-(3-(2-((4-((tetrahydro-2H-pyran-4-yl)amino)phenyl)amino)quinazolin-8-yl)phenyl)acrylamide N-(3-(2-((4-((tetrahydro-2H-pyran-4-yl)amino)phenyl)amino)quinazolin-8-yl)phenyl)acrylamide (62.7 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 466.2, found 466.2. $^1$H NMR (DMSO-d6, 300 MHz) δ10.25 (s, 1H), 9.47 (s, 1H), 9.24 (s, 1H), 7.75-7.96 (m, 4H), 7.34-7.59 (m, 5H), 6.30-6.47 (m, 4H), 5.74-5.78 (m, 1H), 5.07-5.10 (m, 1H), 3.84-3.88 (m, 2H), 3.28-3.44 (m, 2H), 1.79-1.83 (m, 2H), 1.29-1.32 (m, 2H).

Example 105: Preparation of (R)—N-(3-(2-((4-((tetrahydrofuran-3-yl)amino)phenyl)amino)quinazolin-8-yl)phenyl)acrylamide

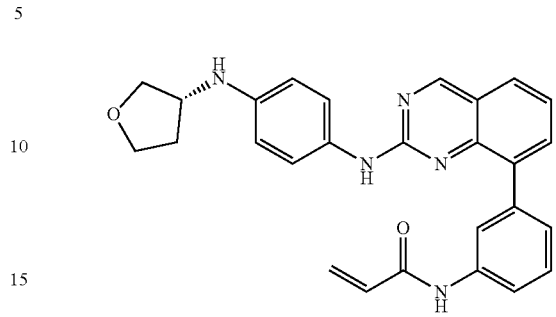

(R)-N-(3-(2-((4-((tetrahydrofuran-3-yl)amino)phenyl)amino)quinazolin-8-yl)phenyl)acrylamide (R)—N-(3-(2-((4-((tetrahydrofuran-3-yl)amino)phenyl)amino)quinazolin-8-yl)phenyl)acrylamide (37.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 452.2, found 452.2. $^1$H NMR (DMSO-d6, 400 MHz) δ10.26 (s, 1H), 9.49 (s, 1H), 9.24 (s, 1H), 7.98 (s, 1H), 7.87 (d, 2H), 7.76 (d, 1H), 7.59 (d, 2H), 7.35-7.46 (m, 3H), 6.44-6.51 (m, 1H), 6.37 (d, 2H), 6.24-6.29 (m, 1H), 5.74-5.77 (m, 1H), 5.41-5.43 (m, 1H), 3.68-3.86 (m, 4H), 3.43-3.46 (m, 1H), 2.09-2.14 (m, 1H), 1.66-1.70 (m, 1H).

Example 106: Preparation of (R)—N-(3-(2-((4-((tetrahydrofuran-3-yl)oxy)phenyl)amino)quinazolin-8-yl)phenyl)acrylamide

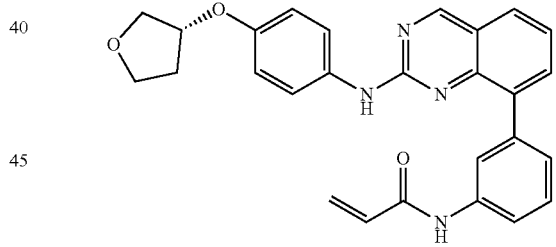

(R)-N-(3-(2-((4-((tetrahydrofuran-3-yl)oxy)phenyl)amino)quinazolin-8-yl)phenyl)acrylamide (R)—N-(3-(2-((4-((tetrahydrofuran-3-yl)oxy)phenyl)amino)quinazolin-8-yl)phenyl)acrylamide (55.0 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 453.2, found 453.1. $^1$H NMR (DMSO-d6, 400 MHz) δ 10.29 (s, 1H), 9.76 (s, 1H), 9.31 (s, 1H), 8.04 (s, 1H), 7.78-7.93 (m, 5H), 7.33-7.50 (m, 3H), 6.66 (d, 2H), 6.44-6.50 (m, 1H), 6.23-6.28 (m, 1H), 5.74-5.77 (m, 1H), 4.85-4.87 (m, 1H), 3.37-3.86 (m, 4H), 2.12-2.17 (m, 1H), 1.89-1.91 (m, 1H).

Example 107: Preparation of (S)—N-(3-(2-((4-((1-methylpyrrolidin-3-yl)oxy)phenyl)amino)quinazolin-8-yl)phenyl)acrylamide

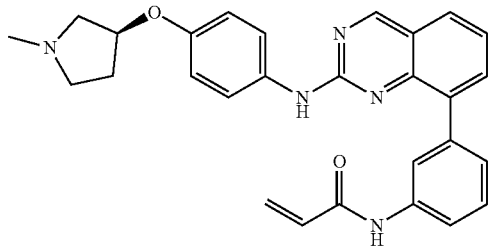

(S)-N-(3-(2-((4-((1-methylpyrrolidin-3-yl)oxy)phenyl)amino)quinazolin-8-yl)phenyl)acrylamide (S)—N-(3-(2-((4-((1-methylpyrrolidin-3-yl)oxy)phenyl)amino)quinazolin-8-yl)phenyl)acrylamide (71.7 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 466.2, found 466.2. $^1$H NMR (DMSO-d6, 400 MHz) δ10.41 (s, 1H), 9.81 (s, 1H), 9.33 (s, 1H), 8.00 (s, 1H), 7.80-7.94 (m, 5H), 7.43-7.50 (m, 2H), 7.37 (d, 1H), 6.70 (d, 2H), 6.48-6.53 (m, 1H), 6.25-6.29 (m, 1H), 5.75-5.78 (m, 1H), 4.95 (s, 1H), 3.43 (m, 1H), 3.27-3.33 (m, 1H), 3.16-3.17 (m, 1H), 2.77 (s, 3H), 2.31-2.39 (m, 1H), 1.96-2.04 (m, 1H).

Example 108: Preparation of N-(3-(2-((4-((1-acetylpiperidin-4-yl)amino)phenyl)amino)quinazolin-8-yl)phenyl)acrylamide

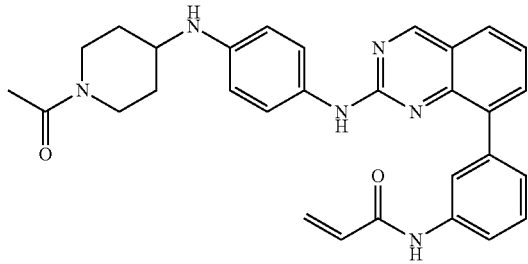

N-(3-(2-((4-((1-acetylpiperidin-4-yl)amino)phenyl)amino)quinazolin-8-yl)phenyl)acrylamide N-(3-(2-((4-((1-acetylpiperidin-4-yl)amino)phenyl)amino)quinazolin-8-yl)phenyl)acrylamide (39.6 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 507.2, found 507.2. $^1$H NMR (DMSO-d6, 300 MHz) δ 10.28 (s, 1H), 9.48 (s, 1H), 9.24 (s, 1H), 7.75-7.96 (m, 4H), 7.76 (d, 2H), 7.35-7.44 (m, 3H), 6.30-6.44 (m, 4H), 5.79 (d, 1H), 5.10 (d, 1H), 4.17-4.21 (m, 1H), 3.73-3.78 (m, 1H), 3.34 (s, 1H), 3.11-3.18 (m, 1H), 2.74-2.81 (m, 1H), 2.01 (s, 3H), 1.83-1.87 (m, 2H), 1.14-1.24 (m, 2H).

Example 109: Preparation of N-(3-(2-((4-(4-methyl-3-oxopiperazin-1-yl)phenyl)amino)quinazolin-8-yl)phenyl)acrylamide

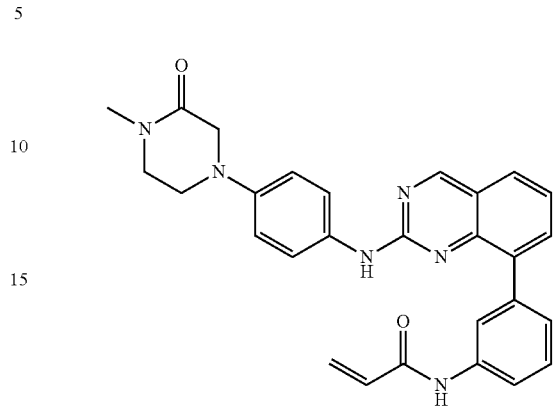

N-(3-(2-((4-(4-methyl-3-oxopiperazin-1-yl)phenyl)amino)quinazolin-8-yl)phenyl)acrylamide N-(3-(2-((4-(4-methyl-3-oxopiperazin-1-yl)phenyl)amino)quinazolin-8-yl)phenyl)acrylamide (72.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 479.2, found 479.2. $^1$H NMR (DMSO-d6, 400 MHz) δ10.30 (s, 1H), 9.71 (s, 1H), 9.30 (s, 1H), 8.05 (s, 1H), 7.75-7.91 (m, 5H), 7.34-7.51 (m, 3H), 6.72 (d, 2H), 6.44-6.51 (m, 1H), 6.25-6.30 (m, 1H), 5.75 (dd, 1H), 3.60 (s, 2H), 3.38-3.40 (m, 2H), 3.31-3.32 (m, 2H), 2.89 (s, 3H).

Example 110: Preparation of (R)—N-(3-(2-((4-((1-methylpyrrolidin-3-yl)oxy)phenyl)amino)quinazolin-8-yl)phenyl)acrylamide

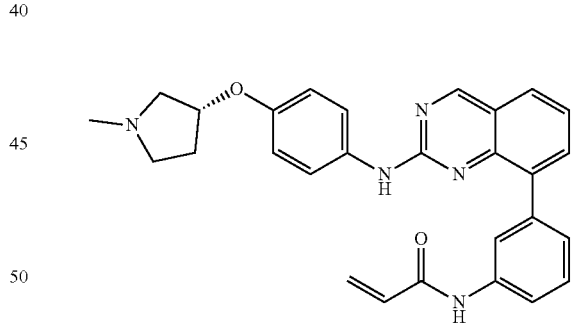

(R)-N-(3-(2-((4-((1-methylpyrrolidin-3-yl)oxy)phenyl)amino)quinazolin-8-yl)phenyl)acrylamide (R)—N-(3-(2-((4-((1-methylpyrrolidin-3-yl)oxy)phenyl)amino)quinazolin-8-yl)phenyl)acrylamide (131.7 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 466.2, found 466.2. $^1$H NMR (DMSO-d6, 400 MHz) δ10.30 (s, 1H), 9.74 (s, 1H), 9.31 (s, 1H), 8.05 (s, 1H), 7.76-7.92 (m, 5H), 7.32-7.50 (m, 3H), 6.61 (d, 2H), 6.44-6.51 (m, 1H), 6.24-6.28 (m, 1H), 5.76 (dd, 1H), 4.68-4.71 (m, 1H), 2.59-2.74 (m, 2H), 2.50-2.52 (m, 1H), 2.18-2.37 (m, 5H), 1.68-1.73 (m, 1H).

Example 111: Preparation of N-(3-(2-((4-((1-acetylazetidin-3-yl)amino)phenyl)amino)quinazolin-8-yl)phenyl)acrylamide

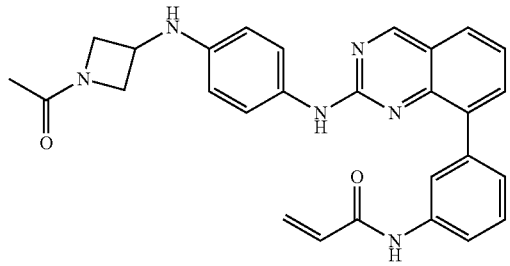

N-(3-(2-((4-((1-acetylazetidin-3-yl)amino)phenyl)amino)quinazolin-8-yl)phenyl)acrylamide N-(3-(2-((4-((1-acetylazetidin-3-yl)amino)phenyl)amino)quinazolin-8-yl)phenyl)acrylamide (105.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 479.2, found 479.2. $^1$H NMR (DMSO-d6, 400 MHz) δ 10.27 (s, 1H), 9.54 (s, 1H), 9.26 (s, 1H), 7.98 (s, 1H), 7.87 (d, 2H), 7.78 (d, 1H), 7.63 (d, 2H), 7.36-7.47 (m, 3H), 6.46-6.52 (m, 1H), 6.26-6.31 (m, 3H), 5.92 (d, 1H), 5.77 (dd, 1H), 4.37-4.41 (m, 1H), 4.02-4.15 (m, 2H), 3.75-3.78 (m, 1H), 3.55-3.58 (m, 1H), 1.77 (s, 3H).

Example 112: Preparation of N-(3-(2-((4-((1-acetylazetidin-3-yl)oxy)phenyl)amino)quinazolin-8-yl)phenyl)acrylamide

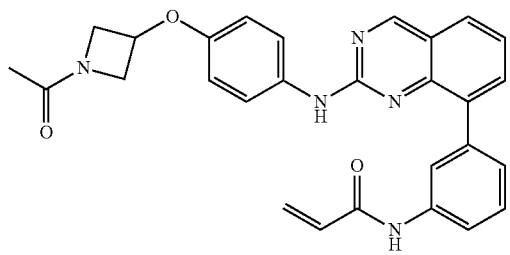

N-(3-(2-((4-((1-acetylazetidin-3-yl)oxy)phenyl)amino)quinazolin-8-yl)phenyl)acrylamide N-(3-(2-((4-((1-acetylazetidin-3-yl)oxy)phenyl)amino)quinazolin-8-yl)phenyl)acrylamide (66.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 480.2, found 480.2. $^1$H NMR (DMSO-d6, 400 MHz) δ 10.30 (s, 1H), 9.80 (s, 1H), 9.32 (s, 1H), 8.04 (s, 1H), 7.92 (d, 1H), 7.79-7.83 (m, 4H), 7.34-7.51 (m, 3H), 6.59 (d, 2H), 6.45-6.52 (m, 1H), 6.25-6.29 (m, 1H), 5.75-5.78 (m, 1H), 4.86-4.89 (m, 1H), 4.47-4.51 (m, 1H), 4.21-4.26 (m, 1H), 4.00-4.03 (m, 1H), 3.69-3.72 (m, 1H), 1.79 (s, 3H).

Example 113: Preparation of N-(3-(2-((4-(3-oxopiperazin-1-yl)phenyl)amino)quinazolin-8-yl)phenyl)acrylamide

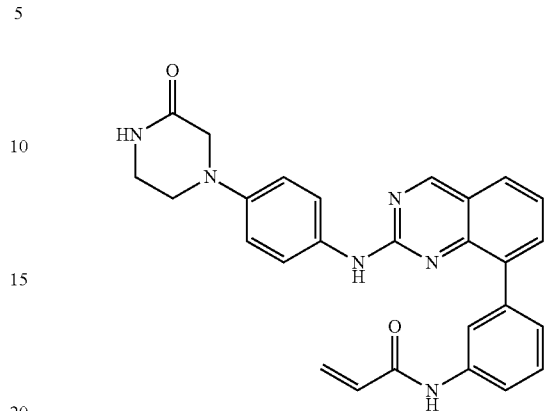

N-(3-(2-((4-(3-oxopiperazin-1-yl)phenyl)amino)quinazolin-8-yl)phenyl)acrylamide

N-(3-(2-((4-(3-oxopiperazin-1-yl)phenyl)amino)quinazolin-8-yl)phenyl)acrylamide (8.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 465.2, found 465.2. $^1$H NMR (DMSO-d6, 400 MHz) δ 10.31 (s, 1H), 9.71 (s, 1H), 9.30 (s, 1H), 8.05 (d, 2H), 7.89 (d, 1H), 7.75-7.84 (m, 4H), 7.33-7.50 (m, 3H), 6.72 (dd, 2H), 6.44-6.50 (m, 1H), 6.25-6.29 (m, 1H), 5.74-5.77 (m, 1H), 3.56 (s, 2H), 3.23-3.27 (m, 4H).

Example 114: Preparation of (S)—N-(3-(2-((4-((1-methylpyrrolidin-3-yl)amino)phenyl)amino)quinazolin-8-yl)phenyl)acrylamide

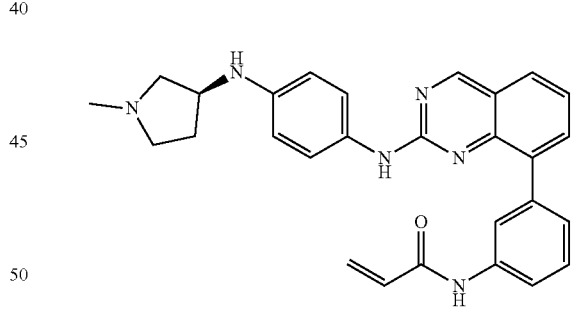

(S)-N-(3-(2-((4-((1-methylpyrrolidin-3-yl)amino)phenyl)amino)quinazolin-8-yl)phenyl)acrylamide (S)—N-(3-(2-((4-((1-methylpyrrolidin-3-yl)amino)phenyl)amino)quinazolin-8-yl)phenyl)acrylamide (14 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 465.2, found 465.2. $^1$H NMR (DMSO-d6, 400 MHz) δ 10.26 (s, 1H), 9.47 (s, 1H), 9.24 (s, 1H), 7.98 (s, 1H), 7.87 (d, 2H), 7.76 (d, 1H), 7.56 (d, 2H), 7.36-7.47 (m, 3H), 6.46-6.51 (m, 1H), 6.24-6.36 (m, 3H), 5.75 (dd, 1H), 5.27 (d, 1H), 3.75-3.76 (m, 1H), 2.67-2.70 (m, 1H), 2.04-2.70 (m, 7H), 1.49-1.51 (m, 1H).

Example 115: Preparation of (R)—N-(3-(2-((4-((1-acetylpyrrolidin-3-yl)amino)phenyl)amino)quinazolin-8-yl)phenyl)acrylamide

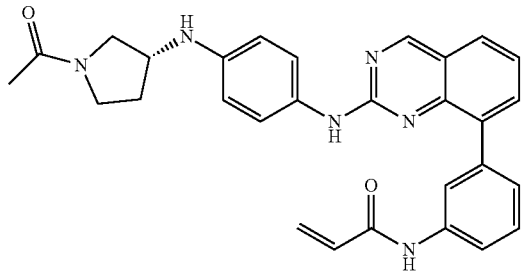

(R)-N-(3-(2-((4-((1-acetylpyrrolidin-3-yl)amino)phenyl)amino)-quinazolin-8-yl)phenyl)acrylamide (R)—N-(3-(2-((4-((1-acetylpyrrolidin-3-yl)amino)phenyl)amino)quinazolin-8-yl)phenyl)acrylamide (36.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 493.2, found 493.2. $^1$H NMR (DMSO-d6, 400 MHz) δ 10.28 (t, 1H), 9.52 (d, 1H), 9.25 (s, 1H), 7.96 (s, 1H), 7.86 (d, 2H), 7.76 (d, 1H), 7.61 (d, 2H), 7.35-7.49 (m, 3H), 6.38-6.53 (m, 3H), 6.27 (d, 1H), 5.76 (d, 1H), 5.48 (dd, 1H), 3.48-3.54 (m, 2H), 3.31-3.40 (m, 2H), 3.14-3.19 (m, 1H), 2.47-2.50 (m, 1H), 1.94 (d, 3H), 1.80-1.92 (m, 1H).

Example 116: Preparation of (R)—N-(3-(2-((4-((1-methylpyrrolidin-3-yl)amino)phenyl)amino)quinazolin-8-yl)phenyl)acrylamide

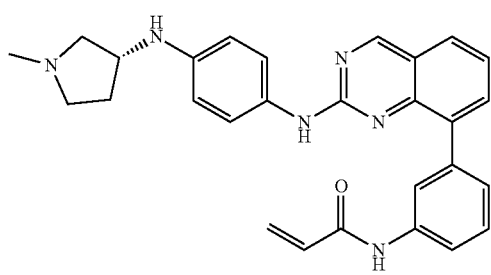

(R)-N-(3-(2-((4-((1-methylpyrrolidin-3-yl)amino)phenyl)amino)-quinazolin-8-yl)phenyl)acrylamide (R)—N-(3-(2-((4-((1-methylpyrrolidin-3-yl)amino)phenyl)amino)quinazolin-8-yl)phenyl)acrylamide (54.8 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 465.2, found 465.2. $^1$H NMR (CD$_3$OD, 400 MHz) δ 9.11 (s, 1H), 7.99 (d, 1H), 7.78-7.82 (m, 3H), 7.63 (d, 2H), 7.35-7.49 (m, 3H), 6.36-6.50 (m, 4H), 6.29 (dd, 1H), 5.79 (dd, 1H), 4.14-4.17 (m, 1H), 3.54-3.61 (m, 2H), 3.31-3.38 (m, 2H), 2.96 (s, 3H), 2.85-2.88 (m, 1H), 2.02-2.05 (m, 1H).

Example 117: Preparation of (S)—N-(3-(2-((4-((1-acetylpyrrolidin-3-yl)amino)phenyl)amino)quinazolin-8-yl)phenyl)acrylamide

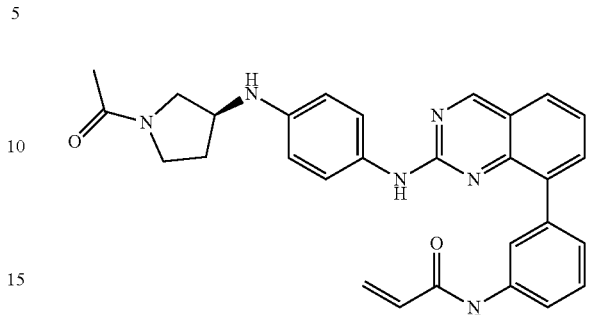

(S)-N-(3-(2-((4-((1-acetylpyrrolidin-3-yl)amino)phenyl)amino)-quinazolin-8-yl)phenyl)acrylamide (S)—N-(3-(2-((4-((1-acetylpyrrolidin-3-yl)amino)phenyl)amino)quinazolin-8-yl)phenyl)acrylamide (57.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 493.2, found 493.2. $^1$H NMR (DMSO-d6, 400 MHz) δ 10.27 (d, 1H), 9.51 (s, 1H), 9.25 (s, 1H), 7.97 (s, 1H), 7.66-7.88 (m, 3H), 7.61 (d, 2H), 7.37-7.47 (m, 3H), 6.39-6.52 (m, 3H), 6.26 (d, 1H), 5.76 (d, 1H), 5.47 (dd, 1H), 3.49-3.91 (m, 4H), 3.15-3.18 (m, 1H), 2.05-2.14 (m, 1H), 1.94 (d, 3H), 1.73-1.85 (m, 1H).

Example 118: Preparation of N-(3-(2-((4-(4-methylpiperazin-1-yl)phenyl)amino)quinazolin-8-yl)-1H-pyrazol-5-yl)acrylamide

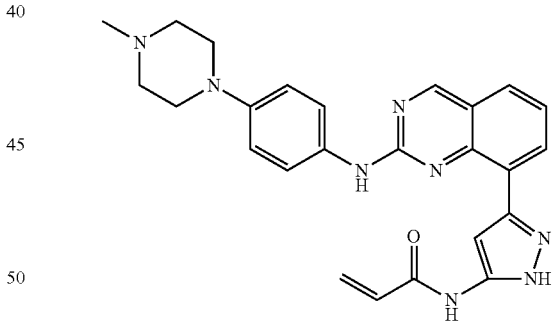

N-(3-(2-((4-(4-methylpiperazin-1-yl)phenyl)amino)quinazolin-8-yl)-1H-pyrazol-5-yl)acrylamide N-(3-(2-((4-(4-methylpiperazin-1-yl)phenyl)amino)quinazolin-8-yl)-1H-pyrazol-5-yl)acrylamide (6.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 455.2, found 455.2. $^1$H NMR (DMSO-d6, 400 MHz) δ 13.02 (s, 1H), 10.73 (s, 1H), 9.91 (t, 1H), 9.33 (s, 1H), 8.15 (d, 1H), 7.88 (d, 1H), 7.62 (d, 2H), 7.37-7.41 (m, 1H), 7.30 (s, 1H), 6.96 (d, 2H), 6.52-6.59 (m, 1H), 6.29 (d, 1H), 5.76 (d, 1H), 3.08 (t, 4H), 2.46 (t, 4H), 2.34 (s, 3H).

Example 119: Preparation of N-(2-methoxy-3-(2-((4-(4-methylpiperazin-1-yl)phenyl)amino)quinazolin-8-yl)phenyl)acrylamide

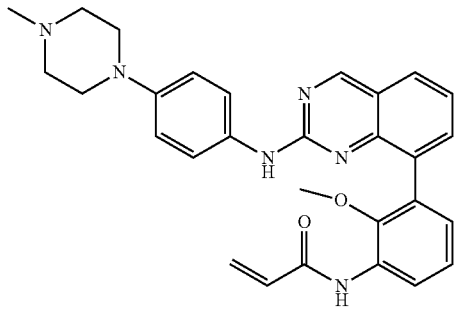

N-(2-methoxy-3-(2-((4-(4-methylpiperazin-1-yl)phenyl)-amino)quinazolin-8-yl)phenyl)acrylamide N-(2-methoxy-3-(2-((4-(4-methylpiperazin-1-yl)phenyl)amino)quinazolin-8-yl)phenyl)acrylamide (30.1 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 495.2, found 426.2. $^1$H NMR (DMSO-d6, 400 MHz) δ 9.60 (d, 1H), 9.27 (s, 1H), 9.37 (s, 1H), 8.37 (d, 1H), 7.92 (d, 1H), 7.80 (d, 1H), 7.56 (d, 2H), 7.42 (t, 1H), 7.21 (t, 1H), 7.04 (d, 1H), 6.81-6.88 (m, 1H), 6.62 (d, 2H), 6.30 (d, 1H), 5.75 (d, 1H), 3.34 (s, 3H), 3.25 (t, 4H), 2.42 (t, 4H), 1.99 (s, 3H).

Example 120: Preparation of N-(3-(2-((4-((2-fluoroethyl)(methyl)amino)phenyl)amino)quinazolin-8-yl)phenyl)acrylamide

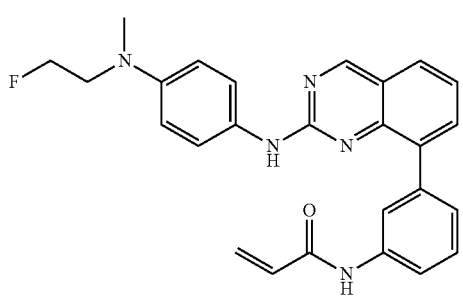

N-(3-(2-((4-((2-fluoroethyl)(methyl)amino)phenyl)-amino)quinazolin-8-yl)phenyl)acrylamide N-(3-(2-((4-((2-fluoroethyl)(methyl)amino)phenyl)amino)quinazolin-8-yl)phenyl)acrylamide (30.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 442.2, found 442.2. $^1$H NMR (CDCl$_3$, 400 MHz) δ 9.05 (s, 1H), 8.01 (s, 1H), 7.85 (s, 1H), 7.81 (d, 1H), 7.69 (d, 1H), 7.59 (d, 2H), 7.48 (d, 2H), 7.33-7.36 (m, 1H), 7.26-7.28 (m, 1H), 7.14 (d, 1H), 6.61 (d, 2H), 6.41-6.45 (m, 1H), 6.21-6.24 (m, 1H), 5.74-5.77 (m, 1H), 4.63 (t, 1H), 4.52 (t, 1H), 3.54-3.61 (m, 2H), 2.95 (s, 3H).

Example 121: Preparation of N-(2-fluoro-3-(2-((4-((2-fluoroethyl)(methyl)amino)phenyl)amino)quinazolin-8-yl)phenyl)acrylamide

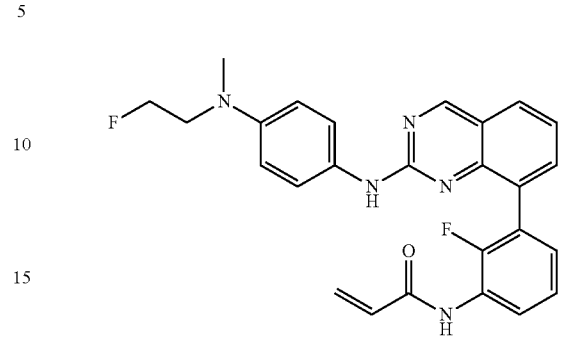

N-(2-fluoro-3-(2-((4-((2-fluoroethyl)(methyl)amino)phenyl)-amino)quinazolin-8-yl)phenyl)acrylamide N-(2-fluoro-3-(2-((4-((2-fluoroethyl)(methyl)amino)phenyl)amino)quinazolin-8-yl)phenyl)acrylamide (32.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 460.2, found 460.2. $^1$H NMR (CDCl$_3$, 400 MHz) δ 9.06 (s, 1H), 8.58 (m, 1H), 7.76 (d, 2H), 7.57-7.58 (m, 1H), 7.46 (d, 2H), 7.37 (t, 1H), 7.30 (t, 1H), 7.20-7.23 (m, 1H), 7.14 (d, 1H), 6.53 (d, 2H), 6.44-6.49 (m, 1H), 6.24-6.31 (m, 1H), 5.79-5.82 (m, 1H), 4.62 (t, 1H), 4.50 (t, 1H), 3.51-3.60 (m, 2H), 2.93 (s, 3H).

Example 122: Preparation of N-(3-(2-((4-((2-hydroxyethyl)amino)phenyl)amino)quinazolin-8-yl)phenyl)acrylamide

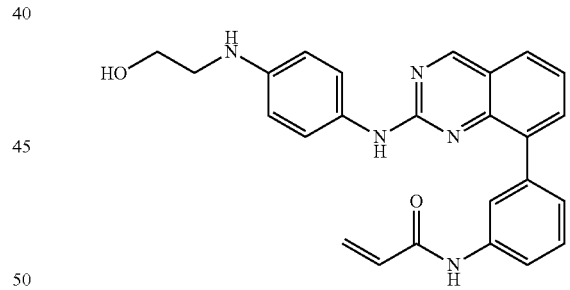

N-(3-(2-((4-((2-hydroxyethyl)amino)phenyl)amino)quinazolin-8-yl)phenyl)acrylamide N-(3-(2-((4-((2-hydroxyethyl)amino)phenyl)amino)quinazolin-8-yl)phenyl)acrylamide (34.4 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 426.2, found 426.2. $^1$H NMR (DMSO-d6, 400 MHz) δ 10.30 (s, 1H), 10.00 (s, 1H), 9.37 (s, 1H), 7.83-7.97 (m, 6H), 7.42-7.51 (m, 3H), 6.96-6.99 (m, 2H), 6.44-6.51 (m, 1H), 6.24-6.29 (m, 1H), 5.75-5.78 (m, 1H), 3.58 (t, 2H), 3.21 (t, 2H).

Example 123: Preparation of N-(4-fluoro-3-(2-((4-(4-methylpiperazin-1-yl)phenyl)amino)quinazolin-8-yl)phenyl)acrylamide

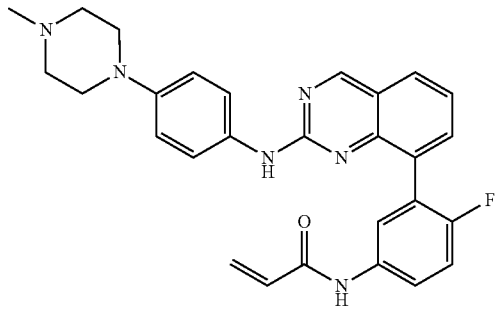

N-(4-fluoro-3-(2-((4-(4-methylpiperazin-1-yl)phenyl)amino)-quinazolin-8-yl)phenyl)acrylamide N-(4-fluoro-3-(2-((4-(4-methylpiperazin-1-yl)phenyl)amino)quinazolin-8-yl)phenyl)acrylamide (38.7 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 483.2, found 483.2. $^1$H NMR (CD$_3$OD, 400 MHz) δ 9.14 (s, 1H), 7.80-7.96 (m, 4H), 7.64 (d, 1H), 7.39 (t, 1H), 7.27 (t, 1H), 6.76 (d, 2H), 6.62 (d, 2H), 6.36-6.45 (m, 2H), 5.78 (dd, 1H), 3.11 (t, 4H), 2.67 (t, 4H), 2.40 (s, 3H).

Example 124: Preparation of 1-(4-(2-((4-(4-methylpiperazin-1-yl)phenyl)amino)quinazolin-8-yl)piperazin-1-yl)prop-2-en-1-one

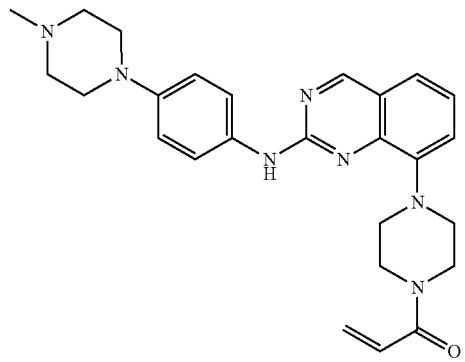

1-(4-(2-((4-(4-methylpiperazin-1-yl)phenyl)amino)quinazolin-8-yl)piperazin-1-yl)prop-2-en-1-one 1-(4-(2-((4-(4-Methylpiperazin-1-yl)phenyl)amino)quinazolin-8-yl)piperazin-1-yl)prop-2-en-1-one (10.5 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 458.2, found 458.2. $^1$H NMR (CDCl$_3$, 400 MHz) δ 9.06 (s, 1H), 7.72 (d, 2H), 7.39-7.43 (m, 2H), 7.18-7.30 (m, 2H), 7.00 (d, 2H), 6.65-6.72 (m, 1H), 6.40 (d, 1H), 5.79 (d, 1H), 4.06 (s, 2H), 3.89 (s, 2H), 3.41 (t, 4H), 3.24 (t, 4H), 2.66 (t, 4H), 2.41 (s, 3H).

Example 125: Preparation of (R)—N-(3-(2-((4-((1-acetylpyrrolidin-3-yl)oxy)phenyl)amino)quinazolin-8-yl)phenyl)acrylamide

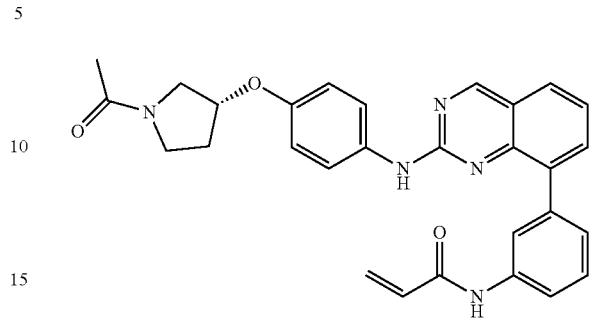

(R)-N-(3-(2-((4-((1-acetylpyrrolidin-3-yl)oxy)phenyl)amino)-quinazolin-8-yl)phenyl)acrylamide (R)—N-(3-(2-((4-((1-acetylpyrrolidin-3-yl)oxy)phenyl)amino)quinazolin-8-yl)phenyl)acrylamide (89.3 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 494.2, found 494.2. $^1$H NMR (DMSO-d6, 400 MHz) δ 10.31 (s, 1H), 9.79 (s, 1H), 9.32 (s, 1H), 8.04 (s, 1H), 7.93 (d, 1H), 7.79-7.91 (m, 4H), 7.42-7.51 (m, 2H), 7.36 (d, 1H), 6.71 (t, 2H), 6.45-6.51 (m, 1H), 6.26 (d, 1H), 5.74-5.77 (m, 1H), 4.90 (dd, 1H), 3.48-3.76 (m, 4H), 3.28-3.33 (m, 1H), 1.96-2.16 (m, 5H).

Example 126: Preparation of N-(3-(2-((4-((2-fluoroethyl)amino)phenyl)amino)quinazolin-8-yl)phenyl)acrylamide

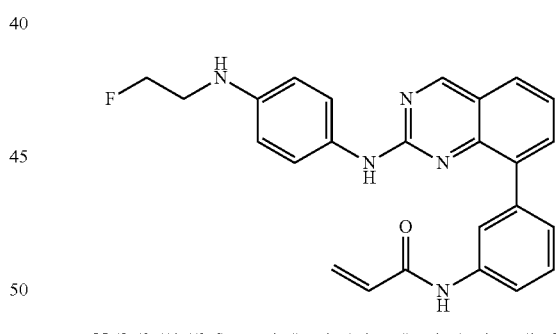

N-(3-(2-((4-((2-fluoroethyl)amino)phenyl)amino)quinazolin-8-yl)phenyl)acrylamide N-(3-(2-((4-((2-fluoroethyl)amino)phenyl)amino)quinazolin-8-yl)phenyl)acrylamide (25.7 mg) was prepared as described for (S)—N-(3-(2-((4-((1-acetylpyrrolidin-3-yl)oxy)phenyl)amino)quinazolin-8-yl)phenyl)acrylamide. LRMS (M+H+) m/z calculated 428.2, found 428.2. $^1$H NMR (DMSO-d6, 300 MHz) δ 10.26 (s, 1H), 9.50 (s, 1H), 9.25 (s, 1H), 7.97 (d, 1H), 7.76-7.88 (m, 3H), 7.59-7.63 (m, 2H), 7.36-7.48 (d, 2H), 6.24-6.49 (m, 4H), 5.74-5.78 (m, 1H), 5.40-5.43 (m, 1H), 4.59 (t, 1H), 4.43 (t, 1H), 3.36-3.31 (m, 2H).

Example 127: Preparation of N-(3-(2-((4-((2,2-difluoroethyl)amino)phenyl)amino)quinazolin-8-yl)phenyl)acrylamide

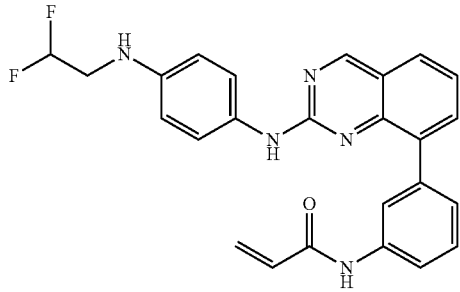

N-(3-(2-((4-((2,2-difluoroethyl)amino)phenyl)amino)quinazolin-8-yl)phenyl)acrylamide N-(3-(2-((4-((2,2-difluoroethyl)amino)phenyl)amino)quinazolin-8-yl)phenyl)acrylamide (29.6 mg) was prepared as described for (S)—N-(3-(2-((4-((1-acetylpyrrolidin-3-yl)oxy)phenyl)amino)quinazolin-8-yl)phenyl)acrylamide. LRMS (M+H+) m/z calculated 446.2, found 446.2. $^1$H NMR (CD$_3$OD, 400 MHz) δ 9.01 (s, 1H), 7.86 (s, 1H), 7.56-7.78 (m, 1H), 7.68-7.70 (m, 2H), 7.49 (d, 2H), 7.25-7.39 (m, 3H), 6.26-6.45 (m, 4H), 5.66-5.80 (m, 2H), 3.28-3.36 (m, 2H).

Example 128: Preparation of N-(3-(2-((4-(4-(2-amino-2-oxoethyl)piperazin-1-yl)phenyl)amino)quinazolin-8-yl)phenyl)acrylamide

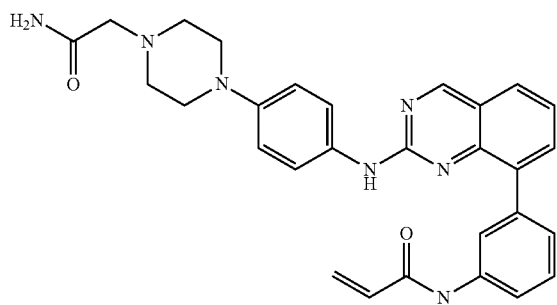

N-(3-(2-((4-(4-(2-amino-2-oxoethyl)piperazin-1-yl)phenyl)amino)-quinazolin-8-yl)phenyl)acrylamide N-(3-(2-((4-(4-(2-amino-2-oxoethyl)piperazin-1-yl)phenyl)amino)quinazolin-8-yl)phenyl)acrylamide (79.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 508.2, found 508.2. $^1$H NMR (DMSO-d6, 400 MHz) δ 10.29 (s, 1H), 9.66 (s, 1H), 9.29 (s, 1H), 8.02 (s, 1H), 7.73-7.91 (m, 5H), 7.14-7.49 (m, 5H), 6.70 (d, 2H), 6.45-6.47 (m, 1H), 6.28-6.29 (m, 1H), 5.75-5.78 (m, 1H), 3.01-3.03 (m, 4H), 2.92 (s, 2H), 2.55-2.57 (m, 4H).

Example 129: Preparation of N-(3-(2-((4-(4-(2-methoxyethyl)piperazin-1-yl)phenyl)amino)quinazolin-8-yl)phenyl)acrylamide

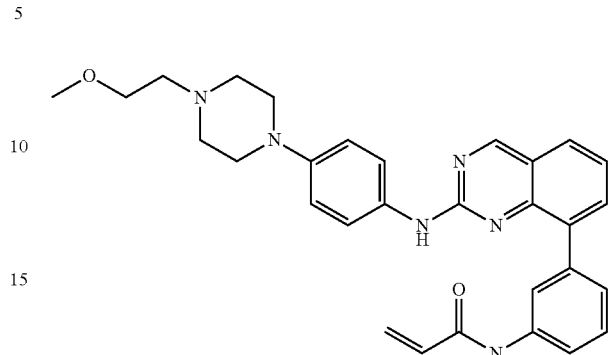

N-(3-(2-((4-(4-(2-methoxyethyl)piperazin-1-yl)phenyl)amino)uinazolin-8-yl)phenyl)acrylamide N-(3-(2-((4-(4-(2-methoxyethyl)piperazin-1-yl)phenyl)amino)quinazolin-8-yl)phenyl)acrylamide (58.2 mg) was prepared as described for (S)—N-(3-(2-((4-((1-acetylpyrrolidin-3-yl)oxy)phenyl)amino)quinazolin-8-yl)phenyl)acrylamide. LRMS (M+H$^+$) m/z calculated 509.3, found 509.2. $^1$H NMR (DMSO-d6, 400 MHz) δ 10.30 (s, 1H), 9.66 (s, 1H), 9.29 (s, 1H), 7.73-8.03 (m, 6H), 7.32-7.50 (m, 3H), 6.70 (d, 2H), 6.45-6.50 (m, 1H), 6.26-6.30 (m, 1H), 5.76 (d, 1H), 3.46-3.48 (m, 2H), 3.26 (s, 3H), 2.97 (m, 4H), 2.50-2.53 (m, 6H).

Example 130: Preparation of N-(3-(2-((4-((3-fluoro-1-methylpiperidin-4-yl)oxy)phenyl)amino)quinazolin-8-yl)phenyl)acrylamide

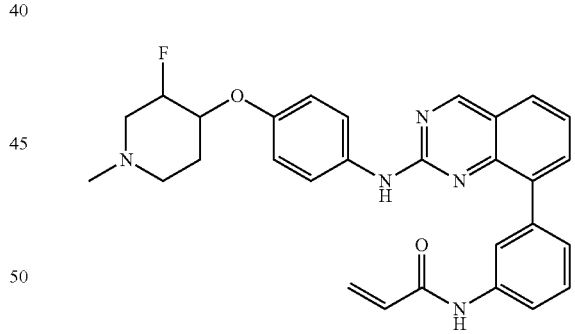

N-(3-(2-((4-((3-fluoro-1-methylpiperidin-4-yl)oxy)phenyl)amino)quinazolin-3-yl)phenyl)acrylamide

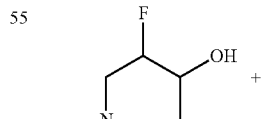

+

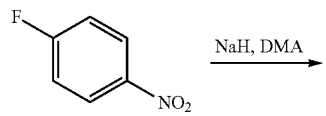

NaH, DMA →

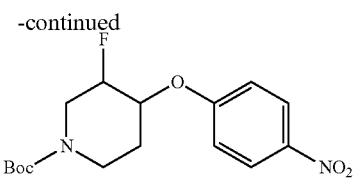

To a solution of tert-butyl 3-fluoro-4-hydroxypiperidine-1-carboxylate (10.07 g, 46 mmol, 1 eq.) in DMA (200 mL) cooled at 0° C. was added NaH (3.7 g, 92 mmol, 2 eq.) in small portions and the resulting mixture was stirred at 0° C. for 30 min. Then 1-fluoro-4-nitrobenzene (4.9 mL, 46 mmol, 1 eq.) was added slowly and the mixture was stirred at r.t. overnight. The mixture was poured into ice-water (1000 mL), extracted with EA (3×200 mL) and the organic layers were combined, washed with brine (600 mL), dried over anhydrous Na$_2$SO$_4$, concentrated and purified via column chromatography (PE/EA=2/1) to afford tert-butyl 3-fluoro-4-(4-nitrophenoxy)piperidine-1-carboxylate (8.7 g, 55.6%) as a yellow solid.

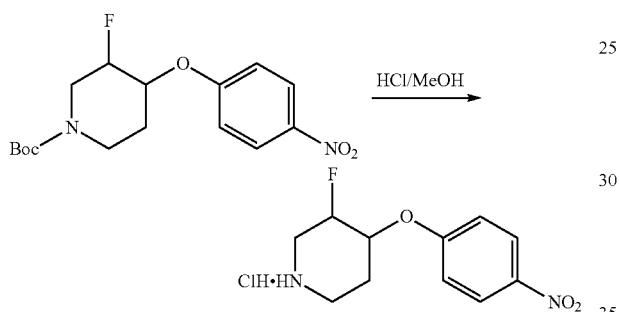

To a solution of HCl in MeOH (20 mL) was added tert-butyl 3-fluoro-4-(4-nitrophenoxy)piperidine-1 1-carboxylate (1.7 g, 5 mmol) and the resulting mixture was stirred at r.t. for 1 h. Then the solution was concentrated to afford 3-fluoro-4-(4-nitrophenoxy)piperidine hydrochloride (1.38 g, 100%) as yellow solid.

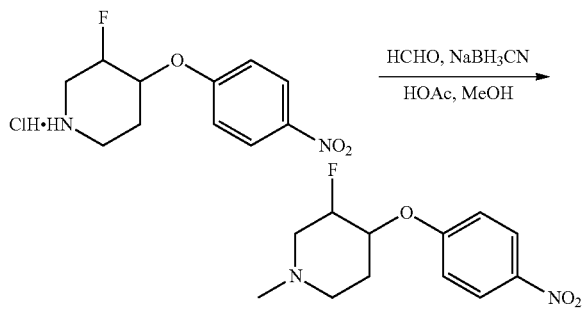

To a solution of 3-fluoro-4-(4-nitrophenoxy)piperidine hydrochloride (1.38 g, 5 mmol, 1 eq.) in MeOH (20 mL) was added HOAc (2 mL) and HCHO (0.77 mL, 10 mmol, 2 eq.) followed by NaBH$_3$CN (630 mg, 10 mmol, 2 eq.) and the resulting mixture was stirred at r.t. for 30 min. Then sat. Na$_2$CO$_3$ (50 mL) was added, extracted with EA (3×50 mL) and the organic layers were combined, washed with brine (200 mL), dried over anhydrous Na$_2$SO$_4$ and concentrated to afford 3-fluoro-1-methyl-4-(4-nitrophenoxy)piperidine (1.26 g, 100%) as yellow oil.

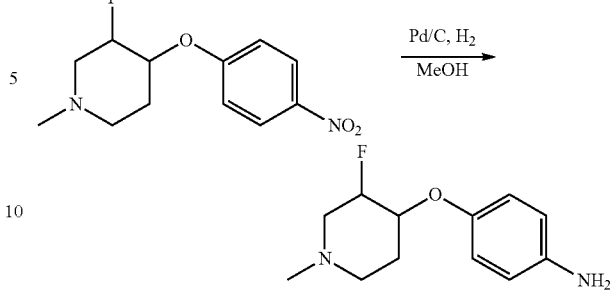

To a solution of 3-fluoro-1-methyl-4-(4-nitrophenoxy) piperidine (1.26 g, 5 mmol) in MeOH (20 mL) was added Pd/C (250 mg) and the resulting mixture was stirred at r.t. overnight. The Pd/C was removed by filtration and the filtrate was concentrated to afford 4-((3-fluoro-1-methylpiperidin-4-yl)oxy)aniline (1.04 g, 93%).

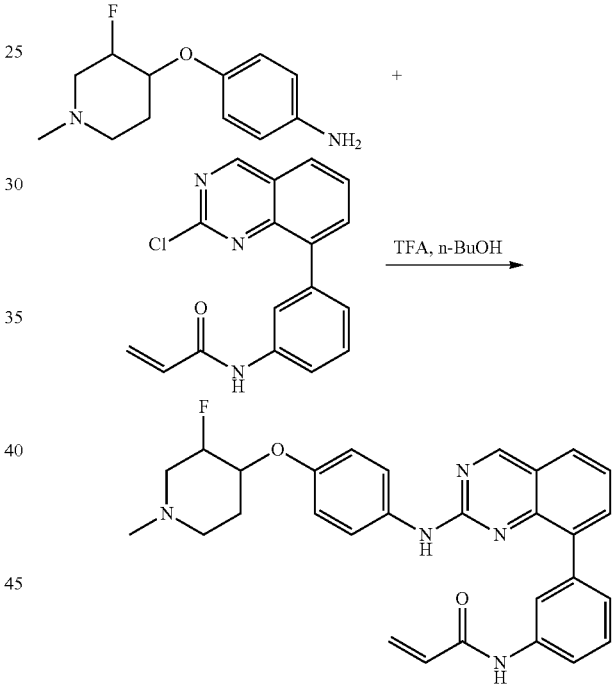

To a suspension of 4-((3-fluoro-1-methylpiperidin-4-yl) oxy)aniline (1.04 g, 4.6 mmol, 1.2 eq.) and N-(3-(2-chloroquinazolin-8-yl)phenyl)acrylamide (1.17 g, 3.8 mmol, 1 eq.) in n-BuOH (20 mL) was added TFA (2.6 g, 23 mmol, 5 eq.) and the resulting mixture was stirred at 90° C. overnight. The mixture was concentrated, diluted with DCM (50 mL), washed with sat. Na$_2$CO$_3$ (50 mL), dried over anhydrous Na$_2$SO$_4$, concentrated and purified via column chromatography (DCM/MeOH=20/1) to afford N-(3-(2-((4-((3-fluoro-1-methylpiperidin-4-yl)oxy)phenyl)amino)quinazolin-8-yl) phenyl)acrylamide (1.1 g, 58.2%) as yellow solid. LRMS (M+H$^+$) m/z calculated 498.2, found 498.2. $^1$H NMR (CDCl$_3$, 400 MHz) δ 9.07 (s, 1H), 7.88-7.91 (m, 2H), 7.82 (d, 1H), 7.71 (d, 1H), 7.66 (d, 2H), 7.36-7.51 (m, 5H), 6.82 (d, 2H), 6.44 (d, 1H), 6.21-6.28 (m, 1H), 5.78 (d, 1H), 4.77-4.91 (m, 1H), 4.33-4.35 (m, 1H), 3.61-4.22 (m, 1H), 3.01-3.03 (m, 1H), 2.74-2.75 (m, 2H), 2.35-2.44 (m, 4H), 2.10-2.17 (m, 1H), 1.86-1.91 (m, 1H).

Example 131: Preparation of N-(2-fluoro-3-(2-((4-((3-fluoro-1-methylpiperidin-4-yl)oxy)phenyl)amino)quinazolin-8-yl)phenyl)acrylamide

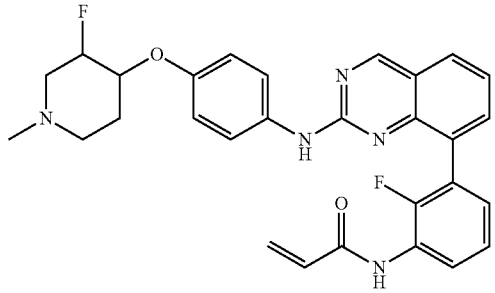

N-(2-fluoro-3-(2-((4-((3-fluoro-1-methylpiperidin-4-yl)oxy)phenyl)amino)quinazolin-8-yl)phenyl)acrylamide N-(2-fluoro-3-(2-((4-((3-fluoro-1-methylpiperidin-4-yl)oxy)phenyl)amino)quinazolin-8-yl)phenyl)acrylamide (31.4 mg) was prepared as described for N-(3-(2-((4-((3-fluoro-1-methylpiperidin-4-yl)oxy)phenyl)amino)quinazolin-8-yl)phenyl)acrylamide. LRMS (M+H) m/z calculated 516.2, found 516.2. $^1$H NMR (CDCl$_3$, 400 MHz) δ 8.82 (s, 1H), 8.56-8.60 (m, 1H), 7.79 (d, 2H), 7.50-7.62 (m, 3H), 7.40-7.44 (m, 1H), 7.26-7.33 (m, 1H), 7.22-7.24 (m, 1H), 6.76-6.88 (m, 2H), 6.48 (d, 1H), 6.25-6.32 (m, 1H), 5.82 (d, 1H), 4.73-4.88 (m, 1H), 4.28-4.32 (m, 1H), 2.98-3.02 (m, 1H), 2.69-2.74 (m, 1H), 2.32-2.38 (m, 5H), 2.03-2.17 (m, 2H), 1.83-1.87 (m, 1H).

Example 132: Preparation of N-(3-(2-((4-((1-(2-fluoroethyl)azetidin-3-yl)oxy)phenyl)amino)quinazolin-8-yl)phenyl)acrylamide

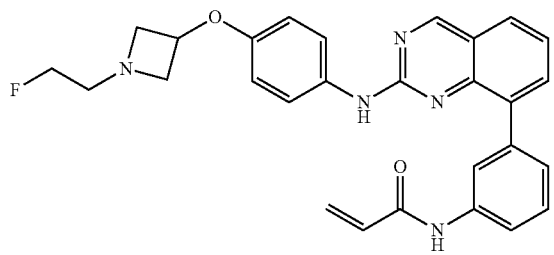

N-(3-(2-((4-((1-(2-fluoroethyl)azetidin-3-yl)oxy)phenyl)amino)quinazolin-8-yl)phenyl)acrylamide N-(3-(2-((4-((1-(2-fluoroethyl)azetidin-3-yl)oxy)phenyl)amino)quinazolin-8-yl)phenyl)acrylamide (87.7 mg) was prepared as described for N-(3-(2-((4-((3-fluoro-1-methylpiperidin-4-yl)oxy)phenyl)amino)quinazolin-8-yl)phenyl)acrylamide. LRMS (M+H$^+$) m/z calculated 484.2, found 484.2. $^1$H NMR (CDCl$_3$, 400 MHz) δ 9.06 (s, 1H), 8.09 (s, 1H), 7.91 (s, 1H), 7.81 (d, 1H), 7.70 (d, 2H), 7.62 (d, 2H), 7.45 (d, 2H), 7.35-7.38 (m, 2H), 6.62 (d, 2H), 6.41-6.45 (m, 1H), 6.30-6.32 (m, 1H), 5.74 (d, 1H), 4.81-4.84 (m, 1H), 4.60 (t, 1H), 4.47 (t, 1H), 4.01 (t, 2H), 3.27 (t, 2H), 2.86-2.96 (m, 2H).

Example 133: Preparation of N-(3-(2-((4-((1-acetylpiperidin-4-yl)oxy)phenyl)amino)quinazolin-8-yl)phenyl)acrylamide

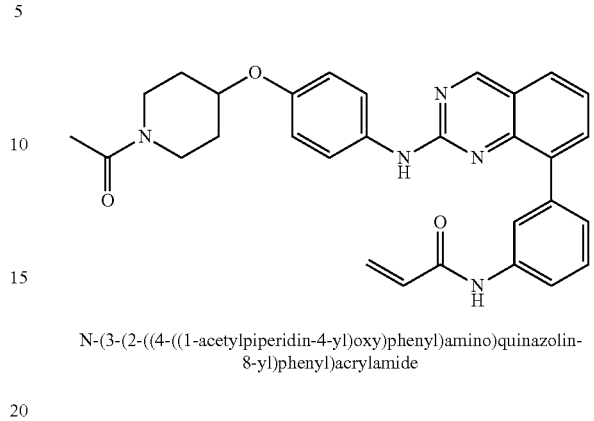

N-(3-(2-((4-((1-acetylpiperidin-4-yl)oxy)phenyl)amino)quinazolin-8-yl)phenyl)acrylamide N-(3-(2-((4-((1-acetylpiperidin-4-yl)oxy)phenyl)amino)quinazolin-8-yl)phenyl)acrylamide (101.7 mg) was prepared as described for N-(3-(2-((4-((3-fluoro-1-methylpiperidin-4-yl)oxy)phenyl)amino)quinazolin-8-yl)phenyl)acrylamide. LRMS (M+H$^+$) m/z calculated 508.2, found 508.2. $^1$H NMR (DMSO-d6, 400 MHz) δ10.29 (s, 1H), 9.76 (s, 1H), 9.31 (s, 1H), 8.03 (d, 1H), 7.77-7.92 (m, 5H), 7.33-7.50 (m, 3H), 6.73 (d, 2H), 6.44-6.50 (m, 1H), 6.24-6.28 (m, 1H), 5.74-5.77 (m, 1H), 4.40-4.42 (m, 1H), 3.76-3.78 (m, 1H), 3.62-3.63 (m, 1H), 3.16-3.33 (m, 2H), 2.02 (s, 3H), 1.79-1.90 (m, 2H), 1.44-1.56 (m, 2H).

Example 134: Preparation of N-(3-(2-((4-((1-methylpiperidin-4-yl)oxy)phenyl)amino)quinazolin-8-yl)phenyl)acrylamide

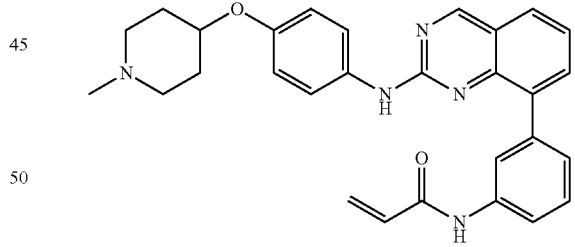

N-(3-(2-((4-((1-methylpiperidin-4-yl)oxy)phenyl)amino)quinazolin-8-yl)phenyl)acrylamide N-(3-(2-((4-((1-methylpiperidin-4-yl)oxy)phenyl)amino)quinazolin-8-yl)phenyl)acrylamide (94.3 mg) was prepared as described for N-(3-(2-((4-((3-fluoro-1-methylpiperidin-4-yl)oxy)phenyl)amino)quinazolin-8-yl)phenyl)acrylamide. LRMS (M+H$^+$) m/z calculated 480.2, found 480.2. $^1$H NMR (DMSO-d6, 400 MHz) δ10.29 (s, 1H), 9.74 (s, 1H), 9.31 (s, 1H), 8.04 (s, 1H), 7.76-7.92 (m, 4H), 7.41-7.49 (m, 2H), 6.33 (d, 1H), 6.68 (d, 2H), 6.44-6.50 (m, 1H), 6.25-6.29 (m, 1H), 5.76 (d, 1H), 4.14-4.16 (m, 1H), 2.57-2.58 (m, 2H), 2.11-2.17 (m, 5H), 1.81-1.83 (m, 2H), 1.55-1.59 (m, 2H).

Example 135: Preparation of N-(3-(2-((4-((1-(2-fluoroethyl)piperidin-4-yl)oxy)phenyl)amino)quinazolin-8-yl)phenyl)acrylamide

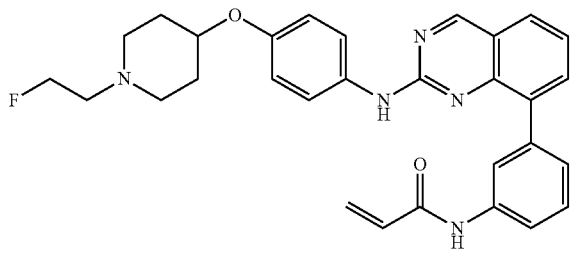

N-(3-(2-((4-((1-(2-fluoroethyl)piperidin-4-yl)oxy)phenyl)amino)quinazolin-8-yl)phenyl)acrylamide N-(3-(2-((4-((1-(2-fluoroethyl)piperidin-4-yl)oxy)phenyl)amino)quinazolin-8-yl)phenyl)acrylamide (62.1 mg) was prepared as described for N-(3-(2-((4-((3-fluoro-1-methylpiperidin-4-yl)oxy)phenyl)amino)quinazolin-8-yl)phenyl)acrylamide. LRMS (M+H$^+$) m/z calculated 512.2, found 512.2. $^1$H NMR (DMSO-d6, 400 MHz) δ 10.29 (s, 1H), 9.75 (s, 1H), 9.31 (s, 1H), 8.04 (s, 1H), 7.91 (d, 1H), 7.76-7.87 (m, 4H), 7.42-7.50 (m, 2H), 7.33 (d, 1H), 6.69 (d, 2H), 6.44-6.51 (m, 1H), 6.27 (dd, 1H), 5.76 (dd, 1H), 4.60 (t, 1H), 4.48 (t, 1H), 4.17-4.19 (m, 1H), 2.59-2.74 (m, 4H), 2.26-2.32 (m, 2H), 1.85-1.89 (m, 2H), 1.54-1.57 (m, 2H).

Example 136: Preparation of N-(3-(2-((4-((1-(2-hydroxyethyl)piperidin-4-yl)oxy)phenyl)amino)quinazolin-8-yl)phenyl)acrylamide

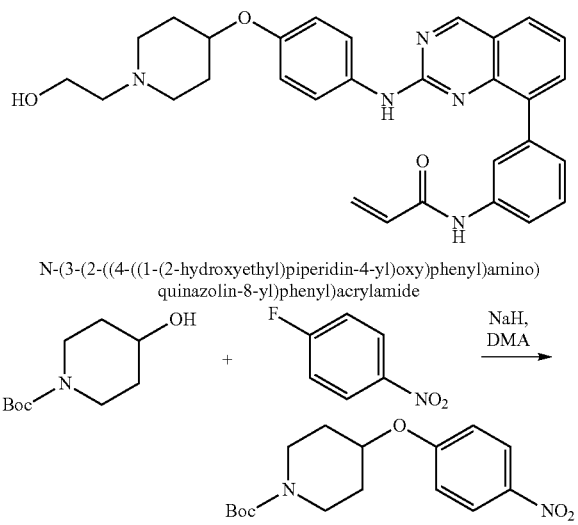

N-(3-(2-((4-((1-(2-hydroxyethyl)piperidin-4-yl)oxy)phenyl)amino)quinazolin-8-yl)phenyl)acrylamide To a solution of tert-butyl 4-hydroxypiperidine-1-carboxylate (603 mg, 3 mmol, 1 eq.) in DMA (10 mL) cooled at 0° C. was added NaH (180 mg, 4.5 mmol, 1.5 eq.) in small portions and the resulting mixture was stirred at 0° C. for 30 min. Then 1-fluoro-4-nitrobenzene (423 mg, 3 mmol, 1 eq.) was added slowly. The mixture was stirred at r.t. overnight. The mixture was poured into ice-water (100 mL), extracted with EA (3×20 mL) and the organic layers were combined, washed with brine (60 mL), dried over Na$_2$SO$_4$, concentrated and purified via column chromatography (PE/EA=2/1) to afford tert-butyl 4-(4-nitrophenoxy)piperidine-1-carboxylate (818 mg, 85%) as a yellow solid.

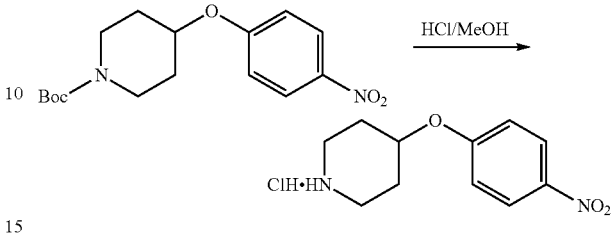

To a solution of HCl in MeOH (20 mL) was added tert-butyl 4-(4-nitrophenoxy)piperidine-1-carboxylate (818 mg, 2.5 mmol). The resulting mixture was stirred at r.t. for 1 h. The mixture was concentrated to afford 4-(4-nitrophenoxy)piperidine hydrochloride (760 mg, 100%) as a yellow solid.

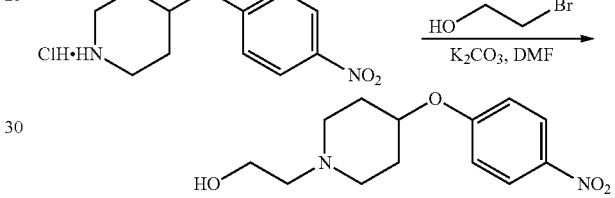

To a solution of 4-(4-nitrophenoxy)piperidine hydrochloride (516 mg, 2 mmol, 1 eq.) in DMF (10 mL) was added K$_2$CO$_3$ (828 mg, 6 mmol, 3 eq.) followed by 2-bromoethanol (273 mg, 2.2 mmo, 1.1 eq.) and the resulting mixture was stirred at 90° C. for 12 h. The mixture was purified via column chromatography (DCM/MeOH=10/1) to afford 2-(4-(4-nitrophenoxy)piperidin-1-yl)ethanol (240 mg, 45%) as a white solid.

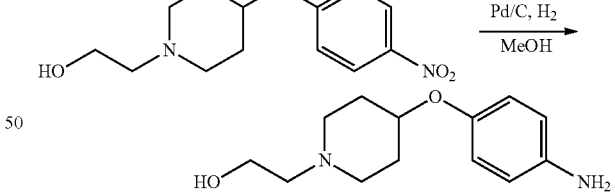

To a solution of 2-(4-(4-nitrophenoxy)piperidin-1-yl)ethanol (240 mg, 0.9 mmol) in MeOH (10 mL) was added Pd/C (50 mg) and the resulting mixture was stirred at r.t. overnight. The Pd/C was removed by filtration and the filtrate was concentrated to afford 2-(4-(4-aminophenoxy)piperidin-1-yl)ethanol (200 mg, 94%) as colorless oil.

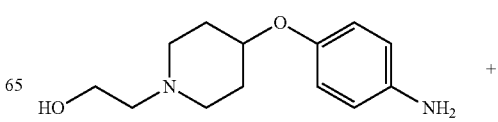

-continued

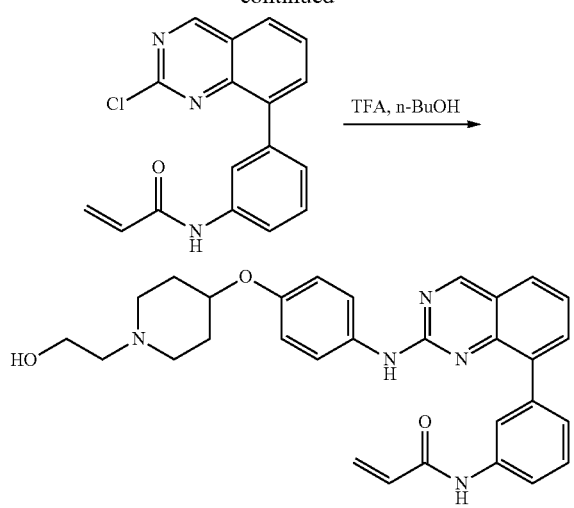

To a suspension of 2-(4-(4-aminophenoxy)piperidin-1-yl)ethanol (83 mg, 0.35 mmol, 1.1 eq.) and N-(3-(2-chloroquinazolin-8-yl)phenyl)acrylamide (100 mg, 0.32 mmol, 1 eq.) in n-BuOH (10 mL) was added TFA (180 mg, 1.6 mmol, 5 eq.) and the resulting mixture was stirred at 90° C. overnight. The mixture was concentrated, diluted with DCM (20 mL), washed with Na₂CO₃ solution (20 mL), dried over Na₂SO₄, concentrated and purified via column chromatography (DCM/MeOH=20/1) to afford N-(3-(2-((4-((1-(2-hydroxyethyl)piperidin-4-yl)oxy)phenyl)amino)quinazolin-8-yl)phenyl)acrylamide (65.8 mg, 40%) as yellow solid. LRMS (M+H⁺) m/z calculated 510.2, found 510.2. ¹H NMR (DMSO-d6, 400 MHz) δ 10.45 (s, 1H), 9.78 (s, 1H), 9.32 (s, 1H), 8.05 (s, 1H), 7.78-7.94 (m, 5H), 7.37-7.48 (m, 3H), 6.74 (d, 2H), 6.44-6.76 (m, 1H), 6.27 (d, 1H), 5.76 (d, 1H), 5.07 (s, 1H), 3.70-4.45 (m, 4H), 2.94-3.27 (m, 4H), 1.80-2.06 (m, 4H).

Example 137: Preparation of N-(3-(2-((4-((3-fluoro-1-methylpiperidin-4-yl)amino)phenyl)amino)quinazolin-8-yl)phenyl)acrylamide

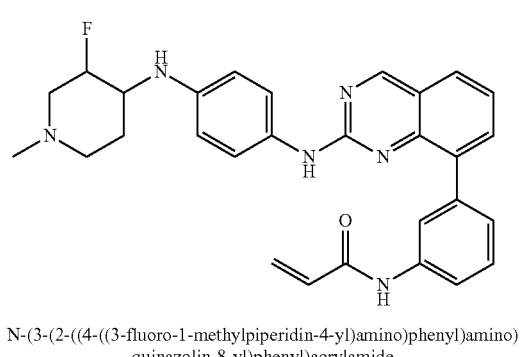

N-(3-(2-((4-((3-fluoro-1-methylpiperidin-4-yl)amino)phenyl)amino)quinazolin-8-yl)phenyl)acrylamide

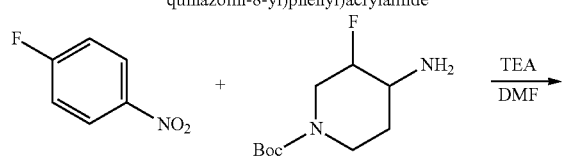

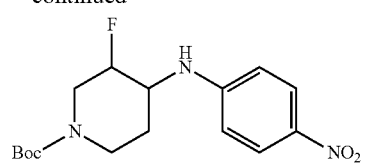

To a solution of tert-butyl 4-amino-3-fluoropiperidine-1-carboxylate (1.1 g, 4 mmol, 1.2 eq.) in DMSO (4 mL) was added TEA (1.2 mL 8 mmol, 2 eq.) followed by 1-fluoro-4-nitrobenzene (465 mg, 3.3 mmol, 1 eq.) and the mixture was stirred at 90° C. overnight. The mixture was poured into ice-water (40 mL), and the precipitate was collected by filtration, dried in vacuum to afford tert-butyl 3-fluoro-4-((4-nitrophenyl)amino)piperidine-1-carboxylate (1.1 g, 100%) as yellow solid.

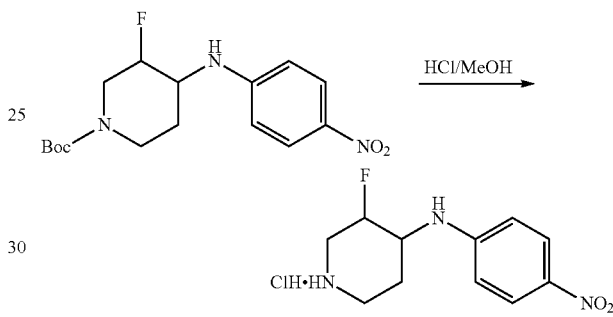

To a solution of HCl in MeOH (10 mL) was added tert-butyl 3-fluoro-4-((4-nitrophenyl)amino)piperidine-1-carboxylate (678 mg, 2 mmol) and the resulting mixture was stirred at r.t. for 1 h. Then the solution was concentrated to afford 3-fluoro-N-(4-nitrophenyl)piperidin-4-amine hydrochloride (624 mg, 100%) as yellow solid.

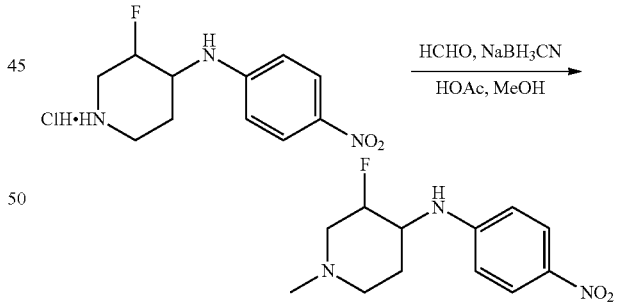

To a solution of 3-fluoro-N-(4-nitrophenyl)piperidin-4-amine hydrochloride (624 mg, 2 mmol, 1 eq.) in MeOH (5 mL) was added HOAc (1 mL) and HCHO (0.3 mL, 4 mmol, 2 eq.) followed by NaBH₃CN (252 mg, 4 mmol, 2 eq.) and the resulting mixture was stirred at r.t. for 30 min. Then to the mixture was added Na₂CO₃ solution (10 mL). The mixture was extracted with EA (3×10 mL) and the organic layers were combined, washed with brine (40 mL), dried over, concentrated and purified via column chromatography (DCM/MeOH=30/1) to afford 3-fluoro-1-methyl-N-(4-nitrophenyl)piperidin-4-amine (310 mg, 61%).

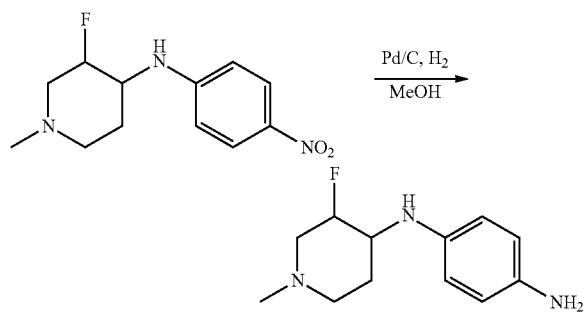

To a solution of 3-fluoro-1-methyl-N-(4-nitrophenyl)piperidin-4-amine (253 mg, 1 mmol) in MeOH (5 mL) was added Pd/C (50 mg) and the resulting mixture was stirred at r.t. overnight. The Pd/C was removed by filtration and the filtrate was concentrated to afford N1-(3-fluoro-1-methylpiperidin-4-yl)benzene-1,4-diamine (210 mg, 96%) as dark oil.

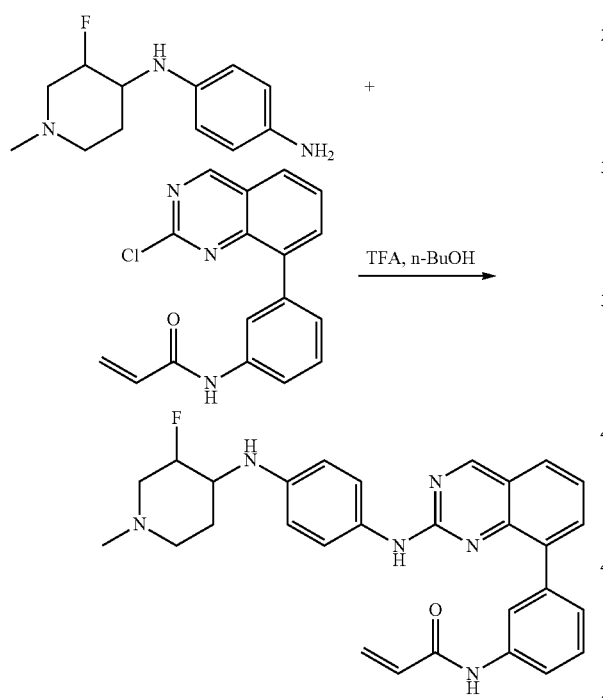

To a suspension of N1-(3-fluoro-1-methylpiperidin-4-yl)benzene-1,4-diamine (210 mg, 0.95 mmol, 1 eq.) and N-(3-(2-chloroquinazolin-8-yl)phenyl)acrylamide (290 mg, 0.95 mmol, 1 eq.) in n-BuOH (10 mL) was added TFA (520 mg, 4.8 mmol, 5 eq.) and the resulting mixture was stirred at 90° C. overnight. The mixture was concentrated, diluted with DCM (20 mL), washed with Na$_2$CO$_3$ solution (20 mL), dried over Na$_2$SO$_4$, concentrated and purified via column chromatography (DCM/MeOH=10/1) to afford N-(3-(2-((4-((3-fluoro-1-methylpiperidin-4-yl)amino)phenyl)amino)quinazolin-8-yl)phenyl)acrylamide (44.4 mg, 9.4%) as yellow solid. LRMS (M+H$^+$) m/z calculated 497.2, found 497.2. $^1$H NMR (DMSO-d6, 400 MHz) δ 10.26 (s, 1H), 9.49 (s, 1H), 9.24 (s, 1H), 7.76-7.96 (m, 4H), 7.56-7.60 (m, 2H), 7.35-7.47 (m, 3H), 6.43-6.51 (m, 3H), 6.25-6.30 (m, 1H), 5.77 (d, 1H), 5.03 (d, 1H), 4-73 (d, 1H), 2.99-3.04 (m, 1H), 2.75-2.78 (m, 1H), 2.44-2.59 (m, 1H), 2.15-2.27 (m, 5H), 1.66-1.67 (m, 2H).

Example 138: Preparation of N-(3-(2-((4-((1-methylpiperidin-4-yl)amino)phenyl)amino)quinazolin-8-yl)phenyl)acrylamide

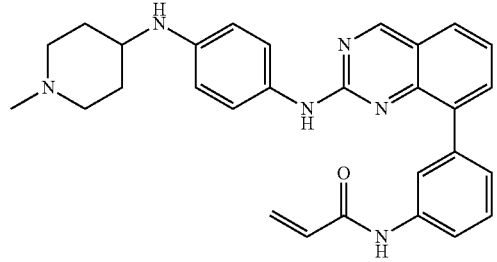

N-(3-(2-((4-((1-methylpiperidin-4-yl)amino)phenyl)amino)quinazolin-8-yl)phenyl)acrylamide

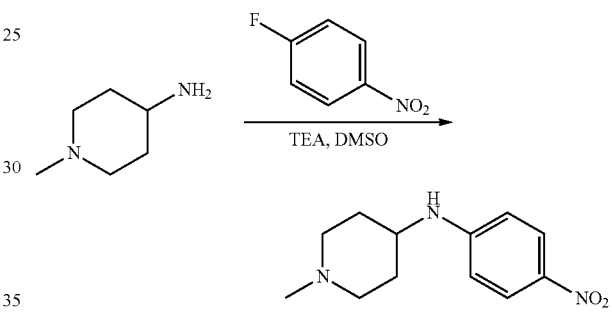

To a solution of 1-methylpiperidin-4-amine (1.25 g, 11 mmol, 1.1 eq.) in DMSO (20 mL) was added TEA (4.2 mL 30 mmol, 3 eq.) followed by 1-fluoro-4-nitrobenzene (1.41 g, 10 mmol, 1 eq.) and the mixture was stirred at 90° C. overnight. The mixture was poured into ice-water (40 mL), and the precipitate was collected by filtration, dried in vacuum to afford 1-methyl-N-(4-nitrophenyl)piperidin-4-amine (2 g, 85%) as a white solid.

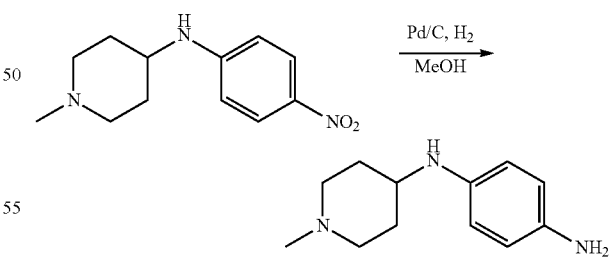

To a solution of 1-methyl-N-(4-nitrophenyl)piperidin-4-amine (2 g, 8.5 mmol) in MeOH (20 mL) was added Pd/C (200 mg) and the resulting mixture was stirred at r.t. overnight. The Pc/C was removed by filtration and the filtrate was concentrated to afford N1-(1-methylpiperidin-4-yl)benzene-1,4-diamine (1.7 g, 99%) as a yellow solid.

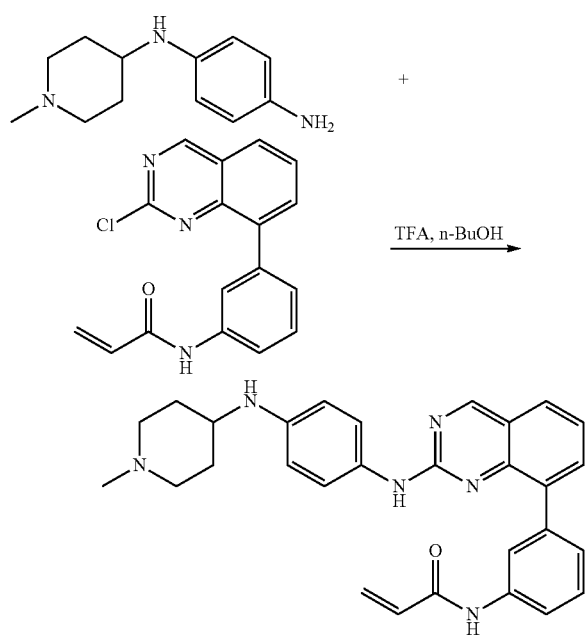

To a suspension of N1-(1-methylpiperidin-4-yl)benzene-1,4-diamine (103 mg, 0.5 mmol, 1 eq.) and N-(3-(2-chloroquinazolin-8-yl)phenyl)acrylamide (155 mg, 0.5 mmol, 1 eq.) in n-BuOH (10 mL) was added TFA (290 mg, 2.5 mmol, 5 eq.) and the resulting mixture was stirred at 90° C. overnight. The mixture was concentrated, diluted with DCM (20 mL), washed with Na$_2$CO$_3$ solution (20 mL), dried over Na$_2$SO$_4$, concentrated and purified via column chromatography (DCM/MeOH=10/1) to afford N-(3-(2-((4-((1-methylpiperidin-4-yl)amino)phenyl)amino)quinazolin-8-yl)phenyl)acrylamide (13.9 mg, 31%) as yellow solid. LRMS (M+H$^+$) m/z calculated 479.2, found 479.2. $^1$H NMR (DMSO-d6, 400 MHz) δ 10.24 (s, 1H), 9.45 (s, 1H), 9.23 (s, 1H), 7.97 (s, 1H), 7.85-7.89 (m, 2H), 7.76 (m, 1H), 7.56 (d, 2H), 7.35-7.43 (m, 3H), 6.30-6.37 (m, 4H), 5.77 (d, 1H), 4.99 (d, 1H), 2.69-2.72 (m, 2H), 2.17 (s, 3H), 1.99 (t, 2H), 1.79-1.82 (m, 2H), 1.29-1.32 (m, 2H).

Example 139: Preparation of N-(3-(2-((4-((1-(2-fluoroethyl)piperidin-4-yl)amino)phenyl)amino)quinazolin-8-yl)phenyl)acrylamide

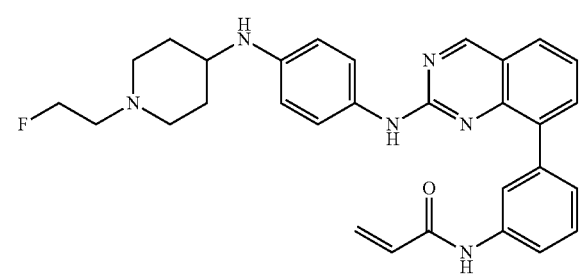

N-(3-(2-((4-((1-(2-fluoroethyl)piperidin-4-yl)amino)phenyl)amino)quinazolin-8-yl)phenyl)acrylamide

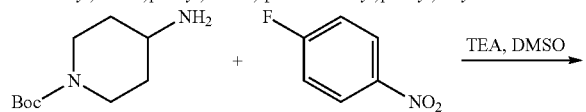

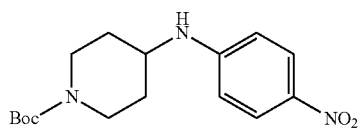

To a solution of tert-butyl 4-aminopiperidine-1-carboxylate (5 g, 25 mmol, 1.1 eq.) in DMSO (50 mL) was added TEA (7.5 mL 54 mmol, 2.2 eq.) followed by 1-fluoro-4-nitrobenzene (5.4 g, 36 mmol, 1.4 eq.) and the mixture was stirred at 90° C. overnight. The mixture was poured into ice-water (500 mL), and the precipitate was collected by filtration, dried in vacuum to afford tert-butyl 4-((4-nitrophenyl)amino)piperidine-1-carboxylate (6.7 g, 84%) as a white solid.

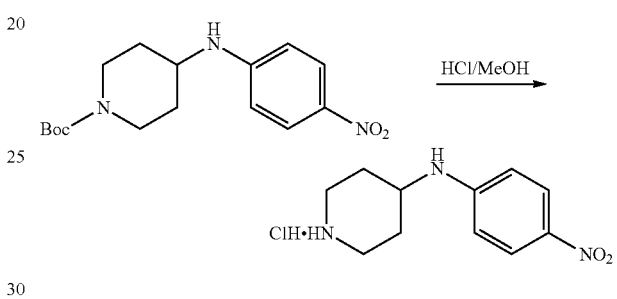

To a solution of HCl in MeOH (40 mL) was added tert-butyl 4-((4-nitrophenyl)amino)piperidine-1-carboxylate (3.7 g, 11.5 mmol). The resulting mixture was stirred at r.t. for 1 h. The Pd/C was removed by filtration and the filtrate was concentrated to to afford N-(4-nitrophenyl)piperidin-4-amine hydrochloride (2.96 g, 100%) as a yellow solid.

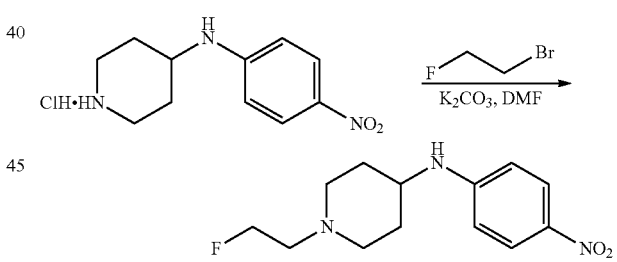

To a solution of N-(4-nitrophenyl)piperidin-4-amine hydrochloride (1.48 g, 5.8 mmol, 1 eq.) in DMF (15 mL) was added K$_2$CO$_3$ (2.38 g, 17.3 mmol, 3 eq.) followed by 1-bromo-2-fluoroethane (1.08 g, 8.6 mmol, 1.5 eq.) and the resulting mixture was stirred at 120° C. for 2 h in microwave reactor. The mixture was purified via column chromatography (DCM/MeOH=30/1) to afford 1-(2-fluoroethyl)-N-(4-nitrophenyl)piperidin-4-amine (700 mg, 45%) as a brown oil.

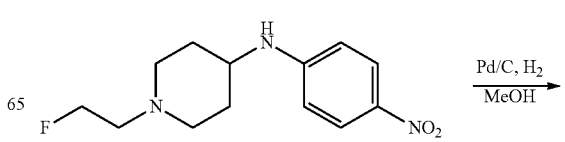

-continued

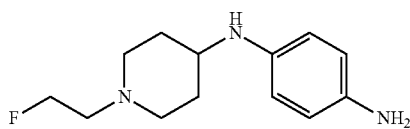

To a solution of 1-(2-fluoroethyl)-N-(4-nitrophenyl)piperidin-4-amine (150 mg, 0.56 mmol) in MeOH (20 mL) was added Pd/C (20 mg) and the resulting mixture was stirred at r.t. overnight. The Pd/C was removed by filtration and the filtrate was concentrated to afford N1-(1-(2-fluoroethyl)piperidin-4-yl)benzene-1,4-diamine (133 mg, 100%) as a brown oil.

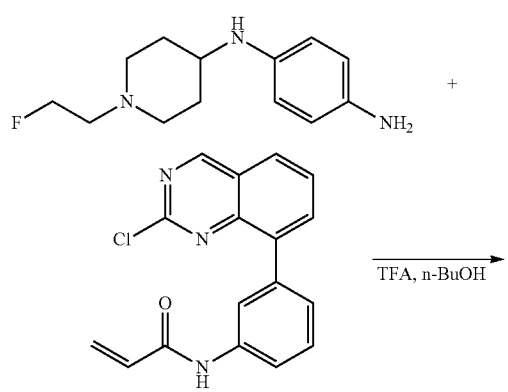

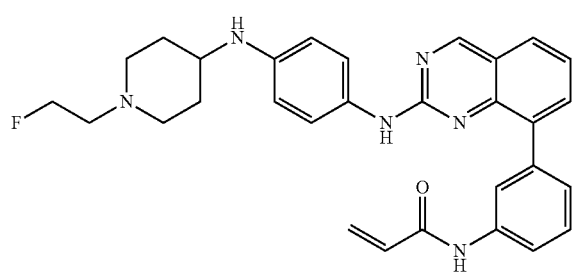

To a suspension of N1-(1-(2-fluoroethyl)piperidin-4-yl)benzene-1,4-diamine (133 mg, 0.56 mmol, 1.7 eq.) and N-(3-(2-chloroquinazolin-8-yl)phenyl)acrylamide (100 mg, 0.32 mmol, 1 eq.) in n-BuOH (15 mL) was added TFA (290 mg, 2.5 mmol, 5 eq.) and the resulting mixture was stirred at 90° C. overnight. The mixture was concentrated, diluted with DCM (20 mL), washed with Na₂CO₃ solution (20 mL), dried over Na₂SO₄, concentrated and purified via column chromatography (DCM/MeOH=20/1) to afford N-(3-(2-((4-((1-(2-fluoroethyl)piperidin-4-yl)amino)phenyl)amino)quinazolin-8-yl)phenyl)acrylamide (27 mg, 16.3%) as yellow solid. LRMS (M+H⁺) m/z calculated 511.3, found 511.2. ¹H NMR (DMSO-d6, 300 MHz) δ 10.25 (s, 1H), 9.46 (s, 1H), 9.24 (s, 1H), 7.97 (s, 1H), 7.85-7.97 (m, 3H), 7.76 (dd, 1H), 7.57 (d, 2H), 7.35-7.45 (m, 3H), 6.25-6.53 (m, 4H), 5.76 (dd, 1H), 5.00 (d, 1H), 4.61 (t, 1H), 4.45 (t, 1H), 3.05-3.06 (m, 1H), 2.82-2.86 (m, 2H), 2.56-2.69 (m, 2H), 2.10-2.18 (m, 2H), 1.80-1.85 (m, 2H), 1.29-1.33 (m, 2H).

Example 140: Preparation of N-(3-(2-((4-((1-(2-hydroxyethyl)piperidin-4-yl)amino)phenyl)amino)quinazolin-8-yl)phenyl)acrylamide

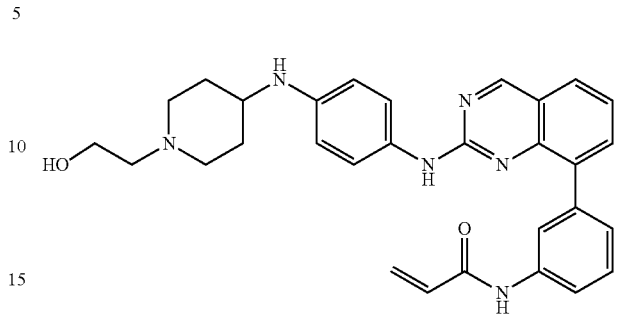

N-(3-(2-((4-((1-(2-hydroxyethyl)piperidin-4-yl)amino)phenyl)amino)quinazolin-8-yl)phenyl)acrylamide

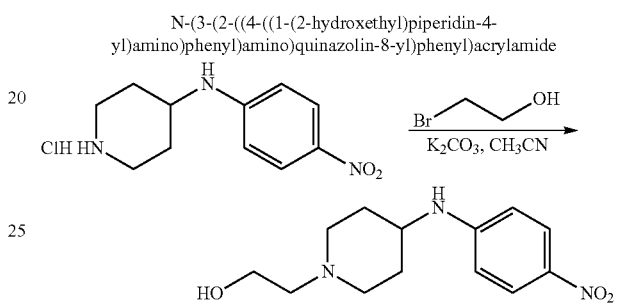

To a solution of N-(4-nitrophenyl)piperidin-4-amine hydrochloride (1.48 g, 5.8 mmol, 1 eq.) in DMF (15 mL) was added K₂CO₃ (2.38 g, 17.3 mmol, 3 eq.) followed by 1-bromo-2-fluoroethane (0.86 g, 6.9 mmol, 1.2 eq.) and the resulting mixture was stirred at 90° C. overnight. The mixture was poured into ice-water (100 mL), extracted by EA (3×40 mL), and the organic layers were combined, washed with brine (150 mL), concentrated and purified via column chromatography (DCM/MeOH=30/1) to afford 2-(4-((4-nitrophenyl)amino)piperidin-1-yl)ethanol (700 mg, 45%) as a brown oil.

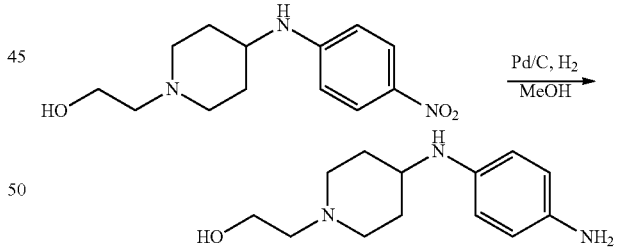

To a solution of 2-(4-((4-nitrophenyl)amino)piperidin-1-yl)ethanol (150 mg, 0.56 mmol) in MeOH (15 mL) was added Pd/C (15 mg) and the resulting mixture was stirred at r.t. overnight. The Pd/C was removed by filtration and the filtrate was concentrated to afford 2-(4-((4-aminophenyl)amino)piperidin-1-yl)ethanol (133 mg, 100%) as brown oil.

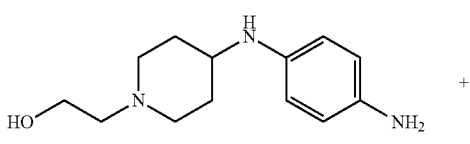

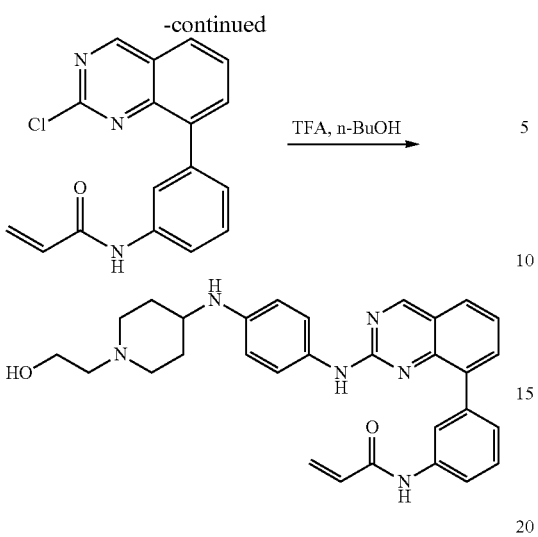

To a suspension of 2-(4-((4-aminophenyl)amino)piperidin-1-yl)ethanol (153 mg, 0.56 mmol, 1.75 eq.) and N-(3-(2-chloroquinazolin-8-yl)phenyl)acrylamide (100 mg, 0.32 mmol, 1 eq.) in n-BuOH (10 mL) was added TFA (0.3 mL, 2.5 mmol, 5 eq.) and the resulting mixture was stirred at 90° C. overnight. The mixture was concentrated, diluted with DCM (20 mL), washed with Na₂CO₃ solution (20 mL), dried over Na₂SO₄, concentrated and purified via column chromatography (DCM/MeOH=10/1) to afford N-(3-(2-((4-((1-(2-hydroxyethyl)piperidin-4-yl)amino)phenyl)amino)quinazolin-8-yl)phenyl)acrylamide (51 mg, 31%) as yellow solid. LRMS (M+H⁺) m/z calculated 509.3, found 509.2. ¹H NMR (DMSO-d6, 400 MHz) δ 10.25 (s, 1H), 9.46 (s, 1H), 9.24 (s, 1H), 7.97 (s, 1H), 7.85-7.90 (m, 2H), 7.76 (dd, 1H), 7.57 (d, 2H), 7.35-7.46 (m, 3H), 6.44-6.51 (m, 1H), 6.26-6.34 (m, 3H), 5.76 (dd, 1H), 4.99 (d, 1H), 4.37-4.38 (m, 1H), 3.47-3.52 (m, 2H), 3.03-3.06 (m, 1H), 2.80-2.83 (m, 2H), 2.40 (t, 2H), 2.05-2.11 (m, 2H), 1.78-1.83 (m, 2H), 1.29-1.34 (m, 2H).

Example 141: Preparation of N-(3-(2-((4-((1-(2-fluoroethyl)azetidin-3-yl)amino)phenyl)amino)quinazolin-8-yl)phenyl)acrylamide

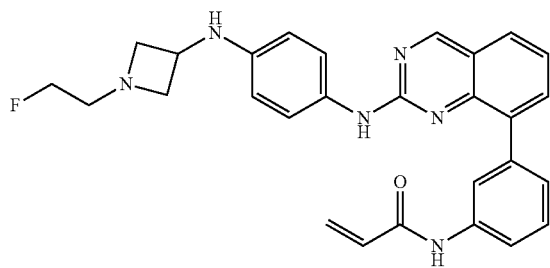

N-(3-(2-((4-((1-(2-fluoroethyl)azetidin-3-yl)amino)phenyl)amino)quinazolin-8-yl)phenyl)acrylamide N-(3-(2-((4-((1-(2-fluoroethyl)azetidin-3-yl)amino)phenyl)amino)quinazolin-8-yl)phenyl)acrylamide (117 mg) was prepared as described for N-(3-(2-((4-((3-fluoro-1-methylpiperidin-4-yl)amino)phenyl)amino)quinazolin-8-yl)phenyl)acrylamide. LRMS (M+H⁺) m/z calculated 483.2, found 483.2. ¹H NMR (DMSO-d6, 400 MHz) δ 10.27 (s, 1H), 9.50 (s, 1H), 9.24 (s, 1H), 8.00 (s, 1H), 7.84-7.87 (m, 2H), 7.76 (d, 1H), 7.59 (d, 2H), 7.35-7.47 (m, 3H), 6.45-6.52 (m, 1H), 6.26-6.31 (m, 3H), 5.75-5.78 (m, 1H), 5.64 (d, 1H), 4.33-4.48 (m, 2H), 3.83-3.87 (m, 1H), 3.64-3.68 (m, 2H), 2.79-2.83 (m, 2H), 2.71-2.74 (m, 1H), 2.64-2.66 (m, 1H).

Example 142: Preparation of N-(3-(2-((2-fluoro-4-((1-methylpiperidin-4-yl)amino)phenyl)amino)quinazolin-8-yl)phenyl)acrylamide

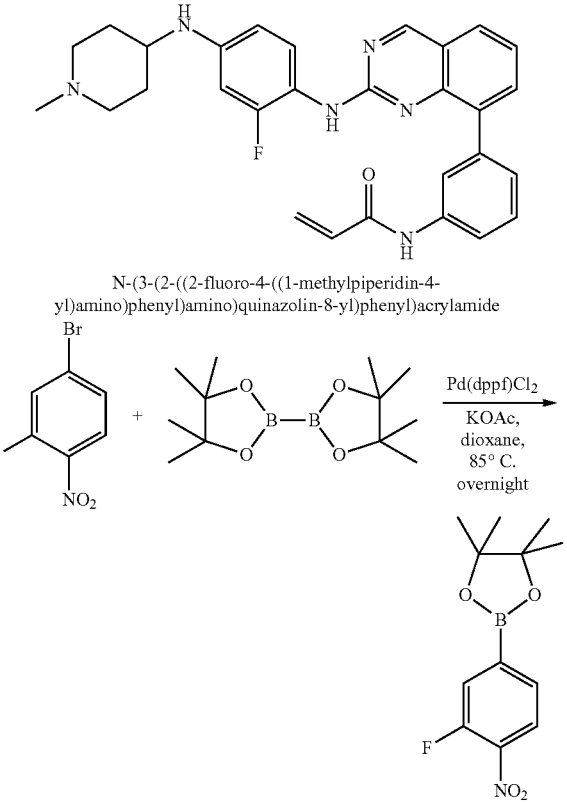

N-(3-(2-((2-fluoro-4-((1-methylpiperidin-4-yl)amino)phenyl)amino)quinazolin-8-yl)phenyl)acrylamide To a solution of 4-bromo-2-fluoro-1-nitrobenzene (2.2 g, 10 mmol, 1 eq.) and 3-(4,4,5,5-tetramethyl-1,3,2-dioxaborolan-2-yl)aniline (3.81 g, 15 mmol, 1.5 eq.) in dioxane (80 mL) was added KOAc (1.96 g, 20 mmol, 2 eq.), followed by Pd(dppf)Cl₂ (408 mg, 0.5 mmol, 0.05 eq.) under N₂ protection. The mixture was stirred at 90° C. for 12 h, then cooled to r.t. and concentrated. The resulting residue was purified via column chromatography (PE/EA=20/1-5/1, v/v) to afford 2-(3-fluoro-4-nitrophenyl)-4,4,5,5-tetramethyl-1,3,2-dioxaborolane as a white solid (2.1 g, 78.6% yield).

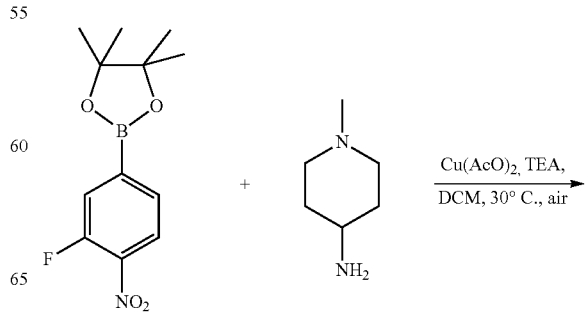

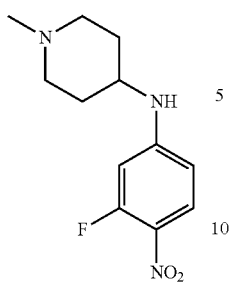

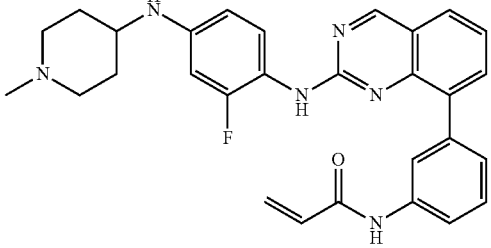

To a solution of 1-methylpiperidin-4-amine (674 mg, 5.9 mmol, 1 eq.) and TEA (323 mg, 18.9 mmol, 3.2 eq.) in DCM (80 mL) was added a pre-mixed slurry of Cu(AcO)$_2$ and 2-(3-fluoro-4-nitrophenyl)-4,4,5,5-tetramethyl-1,3,2-dioxaborolane (1.58 g, 5.9 mmol, 1 eq.). The blue mixture was then warmed to 30° C. and stirred for 24 hs open to the air with a condenser. The resulting residue was purified via column chromatography (DCM/MeOH=20/1, v/v) to afford N-(3-fluoro-4-nitrophenyl)-1-methylpiperidin-4-amine as a yellow oil (224 g, 14.9% yield).

To a solution of 3-fluoro-N1-(1-methylpiperidin-4-yl)benzene-1,4-diamine (127 mg, 0.57 mmol, 1.2 eq.) and N-(3-(2-chloroquinazolin-8-yl)phenyl)acrylamide (100 mg, 0.47 mmol, 1 eq.) in n-BuOH (10 mL) was added TFA (0.14 mL, 1.8 mmol, 1.2 eq.). The mixture was stirred at 90° C. for 12 h. The solution was then cooled to r.t. and concentrated. The resulting residue was dissolved in DCM (20 mL), washed with aqueous Na$_2$CO$_3$ solution, dried over anhydrous Na$_2$SO$_4$ and concentrated. The resulting residue was purified via column chromatography (DCM/MeOH=10:1, v/v) to afford N-(3-(2-((2-fluoro-4-((1-methylpiperidin-4-yl)amino)phenyl)amino)quinazolin-8-yl)phenyl)acrylamide (23.0 mg, 10% yield). LRMS (M+H$^+$) m/z calculated 497.2, found 497.2. $^1$H NMR (DMSO-d6, 300 MHz) δ 10.18 (s, 1H), 9.26 (s, 1H), 8.81 (s, 1H), 7.86-7.90 (m, 2H), 7.75-7.78 (m, 1H), 7.34-7.41 (m, 3H), 6.30-6.47 (m, 5H), 5.77 (d, 1H), 5.51 (d, 1H), 3.02-3.07 (m, 1H), 2.62-2.76 (m, 2H), 2.29 (s, 1H), 1.84-2.19 (m, 2H), 1.29-1.33 (m, 2H).

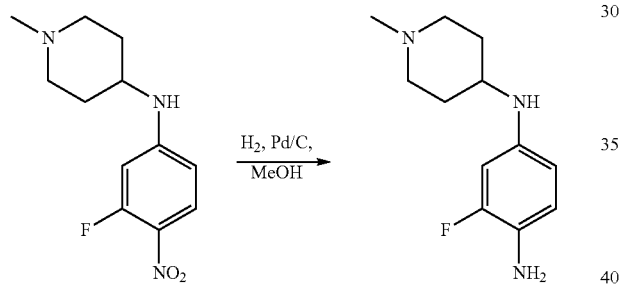

Example 143: Preparation of N-(3-(2-((4-(1H-pyrazol-1-yl)phenyl)amino)quinazolin-8-yl)phenyl)acrylamide

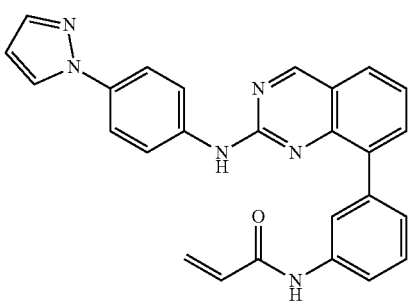

N-(3-(2-((4-(1H-pyrazol-1-yl)phenyl)amino)quinazolin-8-yl)phenyl)acrylamide

To a solution of N-(3-fluoro-4-nitrophenyl)-1-methylpiperidin-4-amine (224 mg, 0.88 mmol, 1 eq.) in MeOH (15 mL) was added Pd/C (50 mg, w/w>50%). under H$_2$ atmosphere (1 atm) and stirred overnight, then filtered and concentrated to afford 3-fluoro-N1-(1-methylpiperidin-4-yl)benzene-1,4-diamine (127 mg, 64.5% yield).

N-(3-(2-((4-(1H-pyrazol-1-yl)phenyl)amino)quinazolin-8-yl)phenyl)acrylamide (78.6 mg) was prepared as described for N-(3-(2-((2-fluoro-4-((1-methylpiperidin-4-yl)amino)phenyl)amino)quinazolin-8-yl)phenyl)acrylamide. LRMS (M+H$^+$) m/z calculated 433.2, found 433.2. $^1$H NMR (DMSO-d6, 400 MHz) δ 10.30 (s, 1H), 10.07 (s, 1H), 9.39 (s, 1H), 8.28 (d, 1H), 7.41-8.07 (m, 12H), 6.20-6.51 (m, 3H), 5.70 (dd, 1H).

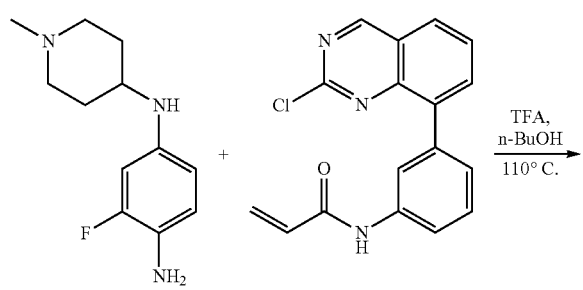

Example 144: Preparation of N-(3-(2-((4-(1H-pyrazol-4-yl)phenyl)amino)quinazolin-8-yl)phenyl)acrylamide

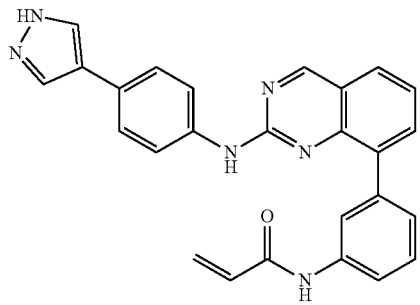

N-(3-(2-((4-(1H-pyrazol-4-yl)phenyl)amino)quinazolin-8-yl)phenyl)acrylamide

N-(3-(2-((4-(1H-pyrazol-4-yl)phenyl)amino)quinazolin-8-yl)phenyl)acrylamide (28.9 mg) was prepared as described for N-(3-(2-((2-fluoro-4-((1-methylpiperidin-4-yl)amino)phenyl)amino)quinazolin-8-yl)phenyl)acrylamide. LRMS (M+H$^+$) m/z calculated 433.2, found 433.2. $^1$H NMR (DMSO-d6, 300 MHz) δ 10.31 (s, 1H), 9.88 (s, 1H), 9.35 (s, 1H), 7.31-8.06 (m, 14H), 6.28-6.51 (m, 2H).

Example 145: Preparation of N-(3-(2-((2-fluoro-4-((1-methylpiperidin-4-yl)oxy)phenyl)amino)quinazolin-8-yl)phenyl)acrylamide

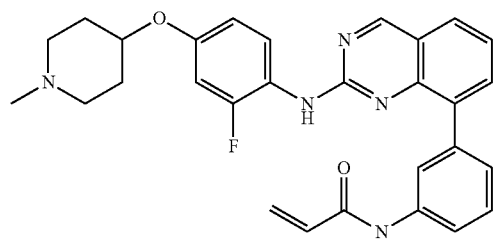

N-(3-(2-((2-fluoro-4-((1-methylpiperidin-4-yl)oxy)phenyl)amino)quinazolin-8-yl)phenyl)acrylamide

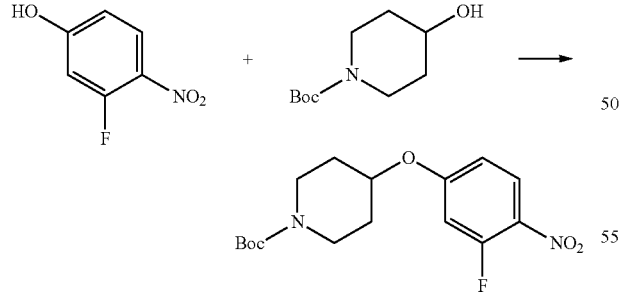

To a suspension of 3-fluoro-4-nitrophenol (1.57 g, 10 mmol, 1 eq.), tert-butyl 4-hydroxypiperidine-1-carboxylate (2.01 g, 10 mmol, 1 eq.) and PPh3 (3.9 g, 15 mmol, 1.5 eq.) in THF (100 mL) was added DIAD (3.0 g, 15 mmol, 1.5 eq.) dropwise at 0° C. and the resulting mixture was stirred at r.t. overnight. The mixture was concentrated and purified via column chromatography (PE/EA=10/1) to afford tert-butyl 4-(3-fluoro-4-nitrophenoxy)piperidine-1-carboxylate (2.5 g, 67%) as colorless oil.

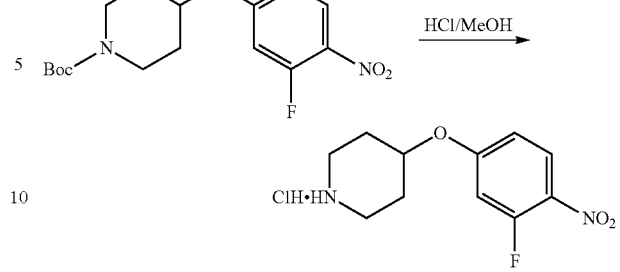

To a solution of HCl in MeOH (20 mL) was added tert-butyl 4-(3-fluoro-4-nitrophenoxy)piperidine-1-carboxylate (2.5 g, 7.3 mmol) and the resulting mixture was stirred at r.t. for 1 h. Then the solution was concentrated to afford 4-(3-fluoro-4-nitrophenoxy)piperidine hydrochloride (1.83 g, 91%) as white solid.

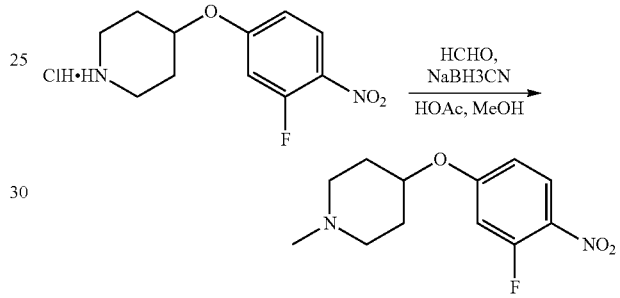

To a solution of 4-(3-fluoro-4-nitrophenoxy)piperidine hydrochloride (500 mg, 1.8 mmol, 1 eq.) in MeOH (10 mL) was added HOAc (0.2 mL) and HCHO (0.2 mL, 3.6 mmol, 2 eq.) followed by NaBH3CN (342 mg, 5.4 mmol, 3 eq.) and the resulting mixture was stirred at r.t. for 30 min. Then sat. Na2CO$_3$ (20 mL) was added, extracted with EA (3×20 mL) and the organic layers were combined, washed with brine (50 mL), dried over anhydrous Na$_2$SO$_4$, concentrated to afford 4-(3-fluoro-4-nitrophenoxy)-1-methylpiperidine (450 mg, 98%) as red oil.

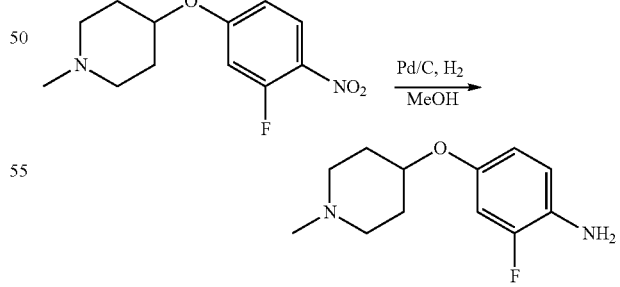

To a solution of 4-(3-fluoro-4-nitrophenoxy)-1-methylpiperidine (450 mg, 1.8 mmol) in MeOH (10 mL) was added Pd/C (25 mg) and the resulting mixture was stirred at r.t. overnight. The Pd/C was removed by filtration and the filtrate was concentrated to afford 2-fluoro-4-((1-methylpiperidin-4-yl)oxy)aniline (401 mg, 98%) as yellow oil.

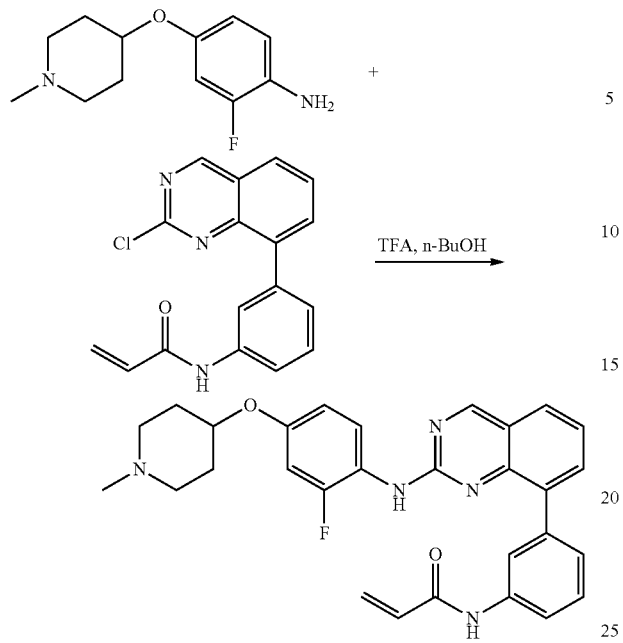

To a suspension of 2-fluoro-4-((1-methylpiperidin-4-yl)oxy)aniline (87 mg, 0.39 mmol, 1.2 eq) and N-(3-(2-chloroquinazolin-8-yl)phenyl)acrylamide (100 mg, 0.32 mmol) in n-BuOH (5 mL) was added TFA (0.4 mL, 1.6 mmol, 5 eq.) and the resulting mixture was stirred at 90° C. overnight. The mixture was concentrated, diluted with DCM (20 mL), washed with sat. Na$_2$CO$_3$ (20 mL), dried over anhydrous Na$_2$SO$_4$, concentrated and purified via column chromatography (DCM/MeOH=10/1) to afford N-(3-(2-((2-fluoro-4-((1-methylpiperidin-4-yl)oxy)phenyl)amino)quinazolin-8-yl)phenyl)acrylamide (35.5 mg, 18%) as yellow solid. LRMS (M+H$^+$) m/z calculated 498.2, found 498.2. $^1$H NMR (CD$_3$OD, 300 MHz) δ 9.23 (s, 1H), 8.32 (t, 1H), 7.86-7.94 (m, 4H), 7.42-7.50 (m, 3H), 6.77-6.81 (m, 1H), 6.38-6.55 (m, 3H), 5.80-5.83 (m, 1H), 4.41 (m, 1H), 2.89-2.92 (m, 2H), 2.65-2.66 (m, 2H), 2.51 (s, 3H), 2.01-2.07 (m, 2H), 2.02-2.07 (m, 2H).

Example 146: Preparation of N-(3-(2-((3-fluoro-4-(4-(2-hydroxyethyl)piperazin-1-yl)phenyl)amino)quinazolin-8-yl)phenyl)acrylamide

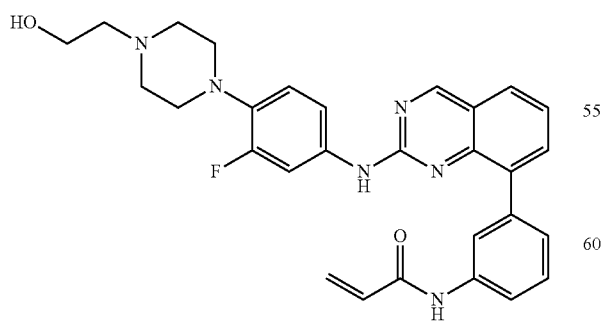

N-(3-(2-((3-fluoro-4-(4-(2-hydroxyethyl)piperazin-1-yl)phenyl)amino)quinazolin-8-yl)phenyl)acrylamide N-(3-(2-((3-fluoro-4-(4-(2-hydroxyethyl)piperazin-1-yl)phenyl)amino)quinazolin-8-yl)phenyl)acrylamide (88 mg) was prepared as described for N-(3-(2-((2-fluoro-4-((1-methylpiperidin-4-yl)oxy)phenyl)amino)quinazolin-8-yl)phenyl)acrylamide. LRMS (M+H$^+$) m/z calculated 513.2, found 513.2. $^1$H NMR (DMSO-d6, 400 MHz) δ 10.26 (s, 1H), 9.92 (s, 1H), 9.35 (s, 1H), 8.04 (s, 1H), 7.77-7.95 (m, 4H), 7.36-7.57 (m, 4H), 6.79 (m, 1H), 6.43-6.50 (m, 1H), 6.22-6.27 (m, 1H), 4.33 (m, 1H), 5.73 (d, 1H), 4.43-4.44 (m, 1H), 3.53-3.56 (m, 2H), 3.17-3.18 (m, 2H), 2.89 (m, 4H), 2.46-2.56 (m, 4H).

Example 147: Preparation of N-(3-(2-((3-fluoro-4-(4-(2-hydroxy-2-methylpropyl)piperazin-1-yl)phenyl)amino)quinazolin-8-yl)phenyl)acrylamide

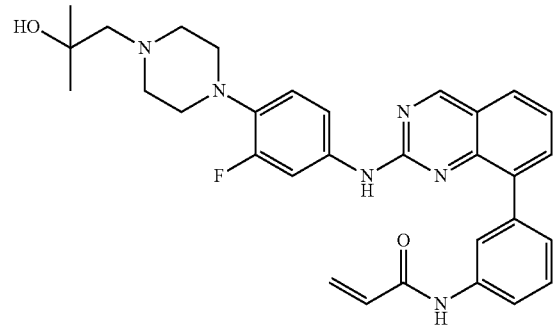

N-(3-(2-((3-fluoro-4-(4-(2-hydroxy-2-methylpropyl)piperazin-1-yl)phenyl)amino)quinazolin-8-yl)phenyl)acrylamide N-(3-(2-((3-fluoro-4-(4-(2-hydroxy-2-methylpropyl)piperazin-1-yl)phenyl)amino)quinazolin-8-yl)phenyl)acrylamide (46.2 mg) was prepared as described for N-(3-(2-((2-fluoro-4-((1-methylpiperidin-4-yl)oxy)phenyl)amino)quinazolin-8-yl)phenyl)acrylamide. LRMS (M+H$^+$) m/z calculated 541.3, found 541.2. $^1$H NMR (DMSO-d6, 400 MHz) δ 10.24 (s, 1H), 9.90 (s, 1H), 9.34 (s, 1H), 8.03 (s, 1H), 7.72-7.95 (m, 4H), 7.35-7.61 (m, 4H), 6.78 (t, 1H), 6.42-6.49 (m, 1H), 5.71-5.75 (m, 1H), 4.09 (s, 1H), 2.87 (m, 4H), 2.64 (m, 4H), 2.25 (s, 2H), 1.23 (s, 6H).

Example 148: Preparation of N-(3-(2-((4-(4-(2-hydroxy-2-methylpropyl)piperazin-1-yl)phenyl)amino)quinazolin-8-yl)phenyl)acrylamide

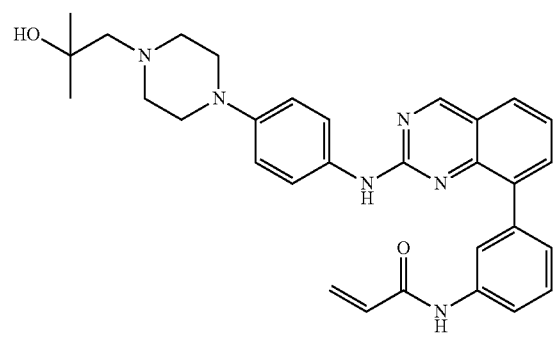

N-(3-(2-((4-(4-(2-hydroxy-2-methylpropyl)piperazin-1-yl)phenyl)amino)quinazolin-8-yl)phenyl)acrylamide N-(3-(2-((4-(4-(2-hydroxy-2-methylpropyl)piperazin-1-yl)phenyl)amino)quinazolin-8-yl)phenyl)acrylamide (64.6 mg) was prepared as described for N-(3-(2-((2-fluoro-4-((1-methylpiperidin-4-yl)oxy)phenyl)amino)quinazolin-8-yl)phenyl)acrylamide. LRMS (M+H) m/z calculated 523.3, found 523.2. ¹H NMR (DMSO-d6, 300 MHz) δ 10.30 (s, 1H), 9.68 (s, 1H), 9.28 (s, 1H), 8.03 (s, 1H), 7.72-7.92 (m, 5H), 7.30-7.50 (m, 3H), 6.67 (d, 2H), 6.23-6.52 (m, 2H), 5.74 (dd, 1H), 4.13 (s, 1H), 2.96 (m, 4H), 2.64 (m, 4H), 2.24 (s, 2H), 1.11 (s, 6H).

Example 149: Preparation of N-(3-(2-((3,5-difluoro-4-(4-methylpiperazin-1-yl)phenyl)amino)quinazolin-8-yl)phenyl)acrylamide

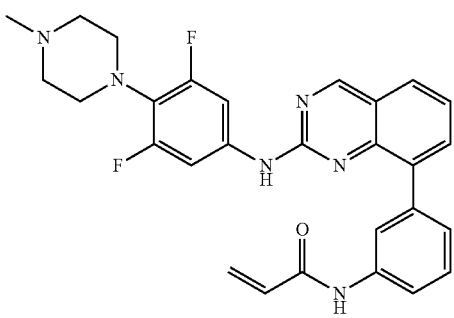

N-(3-(2-((3,5-difluoro-4-(4-methylpiperazin-1-yl)phenyl)amino)quinazolin-8-yl)phenyl)acrylamide N-(3-(2-((3,5-difluoro-4-(4-methylpiperazin-1-yl)phenyl)amino)quinazolin-8-yl)phenyl)acrylamide (27.2 mg) was prepared as described for N-(3-(2-((2-fluoro-4-((1-methylpiperidin-4-yl)oxy)phenyl)amino)quinazolin-8-yl)phenyl)acrylamide. LRMS (M+H) m/z calculated 501.2, found 501.2. ¹H NMR (DMSO-d6, 400 MHz) δ 10.20 (s, 1H), 10.13 (s, 1H), 9.39 (s, 1H), 7.82-8.05 (m, 4H), 7.37-7.60 (m, 5H), 6.41-6.44 (m, 1H), 6.23-6.24 (m, 1H), 5.71 (d, 1H), 2.97 (m, 4H), 2.38 (m, 4H), 2.21 (s, 3H).

Example 150: Preparation of N-(3-(2-((2-fluoro-4-(4-(2-hydroxyethyl)piperazin-1-yl)phenyl)amino)quinazolin-8-yl)phenyl)acrylamide

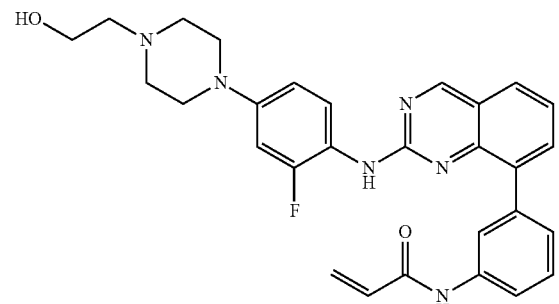

N-(3-(2-((2-fluoro-4-(4-(2-hydroxyethyl)piperazin-1-yl)phenyl)amino)quinazolin-8-yl)phenyl)acrylamide

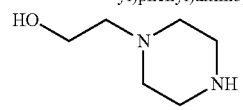

+

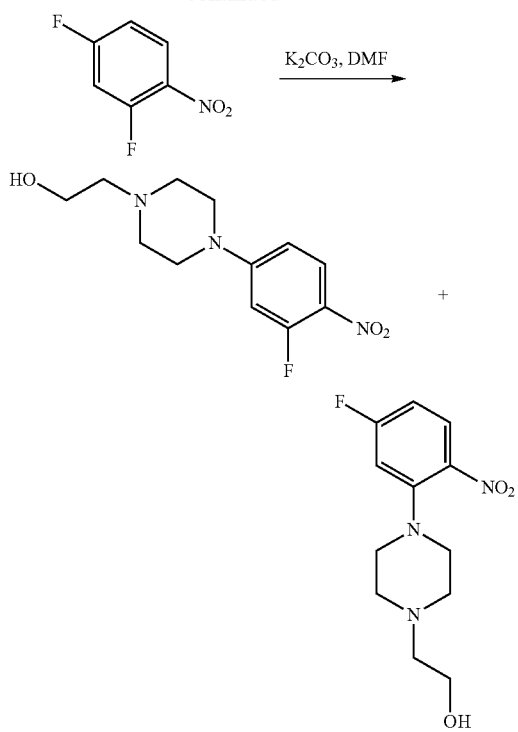

To a solution of 2-(piperazin-1-yl)ethanol (1.56 g, 12 mmol, 1.2 eq.) in DMF (20 mL) was added K₂CO₃ (2.76 g, 20 mmol, 2 eq.) followed by 2,4-difluoro-1-nitrobenzene (1.59 g, 10 mmol, 1 eq.) and the mixture was stirred at 90° C. overnight. The mixture was poured into ice-water (200 mL), extracted by EA (3×40 mL), and the organic layers were combined, washed with brine (150 mL), concentrated to afford the mixture of 2-(4-(3-fluoro-4-nitrophenyl)piperazin-1-yl)ethanol and 2-(4-(5-fluoro-2-nitrophenyl)piperazin-1-yl)ethanol (2 g) which was used without further purification.

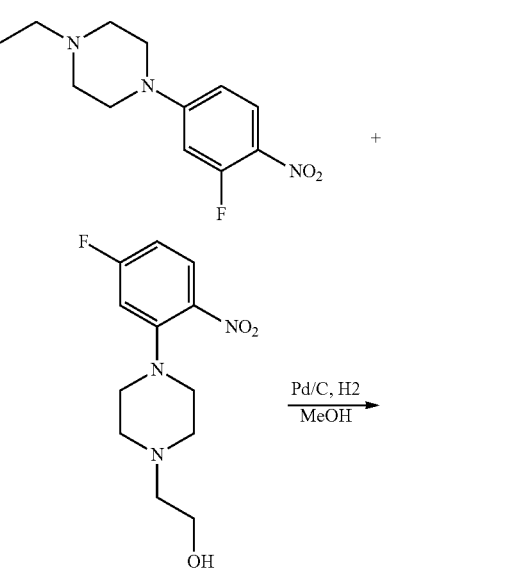

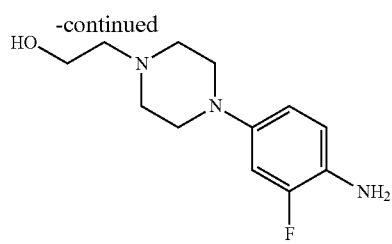

To a solution of the mixture of 2-(4-(3-fluoro-4-nitrophenyl)piperazin-1-yl)ethanol and 2-(4-(5-fluoro-2-nitrophenyl)piperazin-1-yl)ethanol (2 g in MeOH (50 mL) was added Pd/C (200 mg) and the resulting mixture was stirred at r.t. overnight. Pd/C was removed by filtration and the filtrate was concentrated and purified via column chromatography (10-95% CH3CN—H2O) to afford 2-(4-(4-amino-3-fluorophenyl)piperazin-1-yl)ethanol (500 mg, 25% for two steps) as a brown solid.

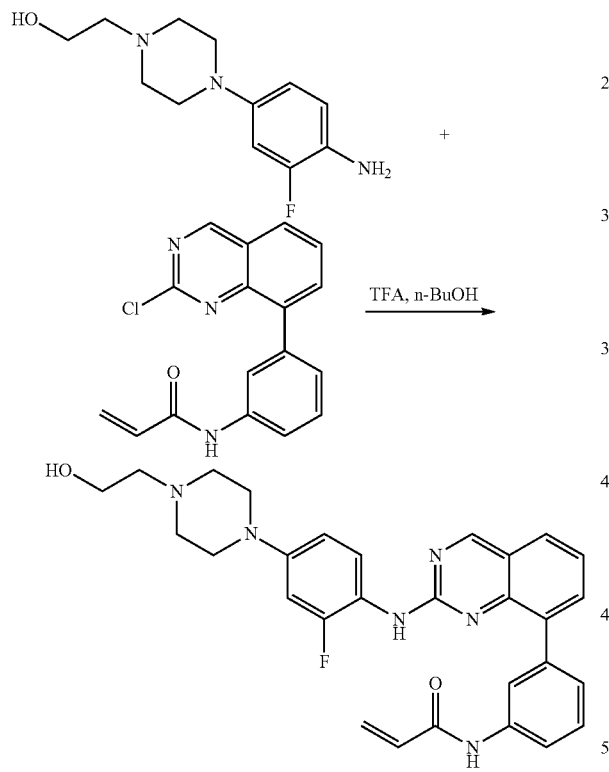

To a suspension of 2-(4-(4-amino-3-fluorophenyl)piperazin-1-yl)ethanol (76 mg, 0.32 mmol, 1 eq.) and N-(3-(2-chloroquinazolin-8-yl)phenyl)acrylamide (100 mg, 0.32 mmol, 1 eq.) in n-BuOH (10 mL) was added TFA (0.2 mL, 1.6 mmol, 5 eq.) and the resulting mixture was stirred at 90° C. overnight. The mixture was concentrated, diluted with DCM (20 mL), washed with Na₂CO₃ solution (20 mL), dried over anhydrous Na₂SO₄, concentrated and purified via column chromatography (DCM/MeOH=10/1) to afford N-(3-(2-((2-fluoro-4-(4-(2-hydroxyethyl)piperazin-1-yl)phenyl)amino)quinazolin-8-yl)phenyl)acrylamide (54 mg, 33%) as yellow solid. LRMS (M+H⁺) m/z calculated 513.2, found 513.2. ¹H NMR (DMSO-d6, 400 MHz) δ 10.22 (s, 1H), 9.30 (s, 1H), 8.97 (s, 1H), 7.76-7.93 (m, 5H), 7.36-7.45 (m, 3H), 6.78 (d, 1H), 6.46-6.52 (m, 2H), 6.26-6.30 (m, 1H), 5.77 (d, 1H), 4.44 (t, 1H), 3.53-3.57 (m, 2H), 3.06 (m, 4H), 2.51-2.54 (m, 4H), 2.44 (t, 2H).

Example 151: Preparation of N-(3-(2-((2,6-difluoro-4-(4-methylpiperazin-1-yl)phenyl)amino)quinazolin-8-yl)phenyl)acrylamide

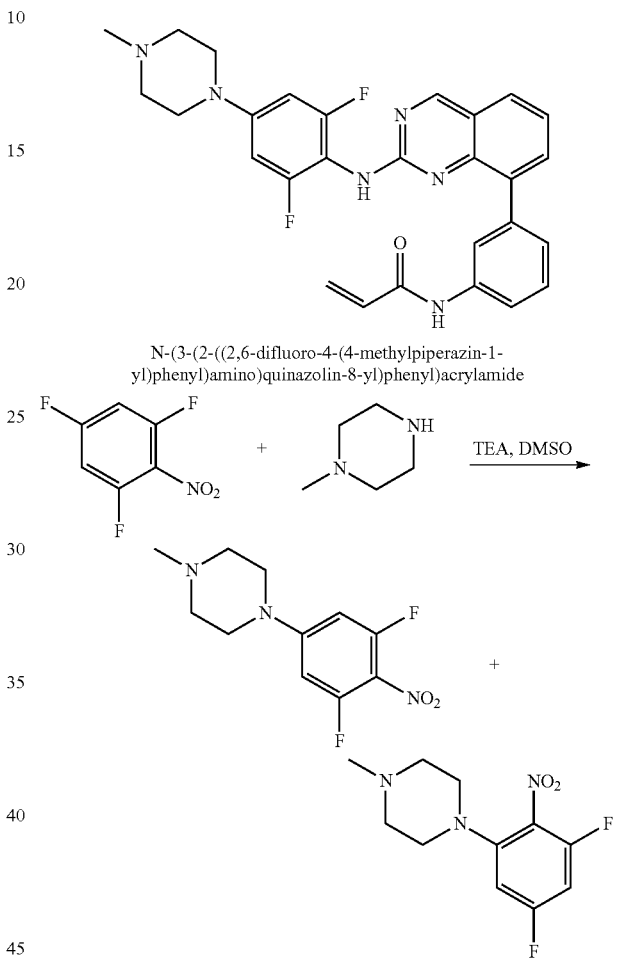

N-(3-(2-((2,6-difluoro-4-(4-methylpiperazin-1-yl)phenyl)amino)quinazolin-8-yl)phenyl)acrylamide To a solution of 1,3,5-trifluoro-2-nitrobenzene (500 mg, 5 mmol, 1.1 eq.) in DMSO (20 mL) was added TEA (1.4 mL 10 mmol, 2 eq.) followed by 1-methylpiperazine (885 mg, 5 mmol, 1 eq.) and the mixture was stirred at 90° C. overnight. The mixture was poured into ice-water (200 mL), extracted with EA (3×50 mL), and the organic phase were combined, washed with brine (150 mL), dried over Na₂SO₄ and concentrated to afford a mixture of two isomers (2 g, 90%) as brown solid.

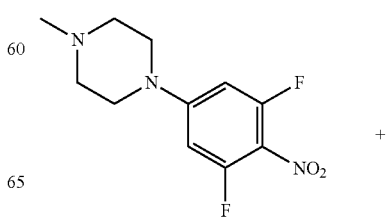

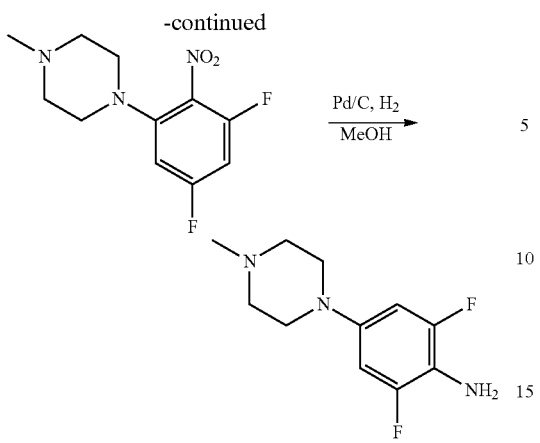

To a solution of a mixture of two isomers (200 mg, 0.8 mmol) in MeOH (20 mL) was added Pd/C (20 mg) and the resulting mixture was stirred at r.t. overnight. The Pd/C was removed by filtration and the filtrate was concentrated and purified via column chromatography (10-95% $CH_3CN$—$H_2O$) to afford 2,6-difluoro-4-(4-methylpiperazin-1-yl)aniline (160 mg, 94%) as brown oil.

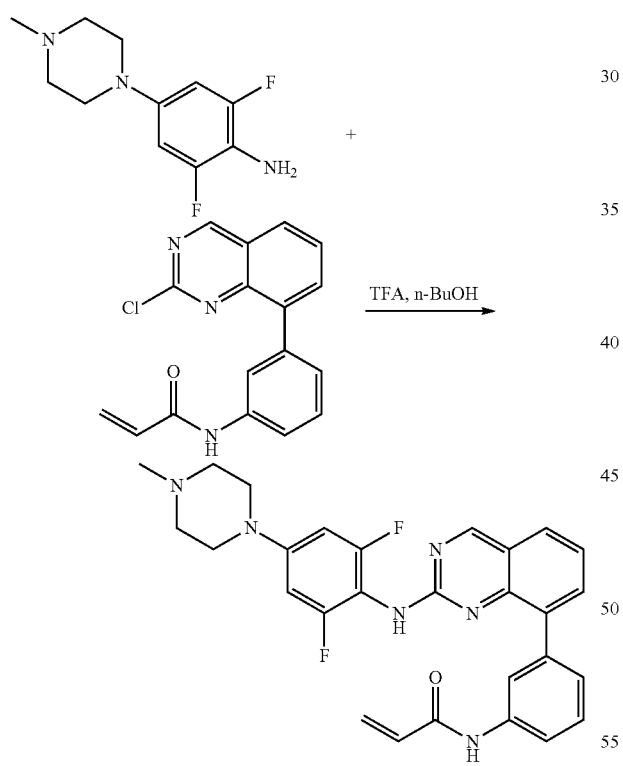

To a suspension of 2,6-difluoro-4-(4-methylpiperazin-1-yl)aniline (73 mg, 0.32 mmol, 1 eq.) and N-(3-(2-chloroquinazolin-8-yl)phenyl)acrylamide (100 mg, 0.32 mmol, 1 eq.) in n-BuOH (10 mL) was added TFA (180 mg, 1.6 mmol, 5 eq.) and the resulting mixture was stirred at 90° C. overnight. The mixture was concentrated, diluted with DCM (20 mL), washed with $Na_2CO_3$ solution (20 mL), dried over anhydrous $Na_2SO_4$, concentrated and purified via column chromatography afford N-(3-(2-((2,6-difluoro-4-(4-methylpiperazin-1-yl)phenyl)amino)quinazolin-8-yl)phenyl)acrylamide (4.7 mg, 2%) as yellow solid. LRMS (M+H⁺) m/z calculated 501.2, found 501.2. ¹H NMR (CD3Cl, 400 MHz) δ 9.11 (s, 1H), 7.71-7.83 (m, 4H), 7.30-7.46 (m, 4H), 6.30-6.52 (m, 5H), 5.78 (d, 1H), 3.16-3.18 (m, 4H), 2.53-2.56 (m, 4H), 2.35 (s, 3H).

Example 152: Preparation of N-(3-(2-((2-fluoro-4-(4-(2-hydroxy-2-methylpropyl)piperazin-1-yl)phenyl)amino)quinazolin-8-yl)phenyl)acrylamide

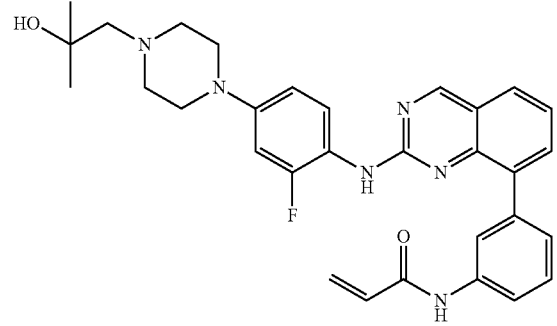

N-(3-(2-((2-fluoro-4-(4-(2-hydroxy-2-methylpropyl)piperazin-1-yl)phenyl)amino)quinazolin-8-yl)phenyl)acrylamide N-(3-(2-((2-fluoro-4-(4-(2-hydroxy-2-methylpropyl)piperazin-1-yl)phenyl)amino)quinazolin-8-yl)phenyl)acrylamide (16.4 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 541.3, found 541.2. ¹H NMR (DMSO-d6, 400 MHz) δ 10.29 (s, 1H), 9.30 (s, 1H), 8.90 (s, 1H), 7.78-7.92 (m, 5H), 7.38-7.45 (m, 3H), 6.75 (dd, 1H), 6.48-6.52 (m, 2H), 6.30-6.38 (m, 1H), 5.75 (d, 1H), 4.12 (s, 1H), 3.03-3.05 (m, 4H), 2.63-2.65 (m, 4H), 2.25 (s, 2H).

Example 153: Preparation of N-(3-(2-((2,3-difluoro-4-(4-(2-hydroxyethyl)piperazin-1-yl)phenyl)amino)quinazolin-8-yl)phenyl)acrylamide

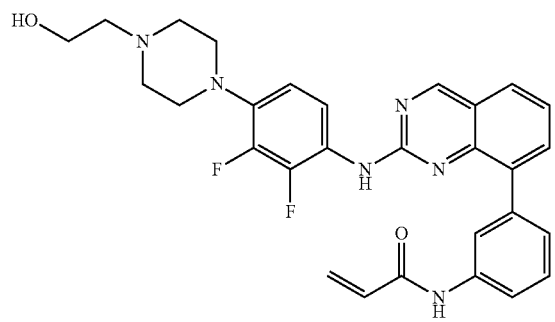

N-(3-(2-((2,3difluoro-4-(4-(2-hydroxyethyl)piperazin-1-yl)phenyl)amino)quinazolin-8-yl)phenyl)acrylamide

243

-continued

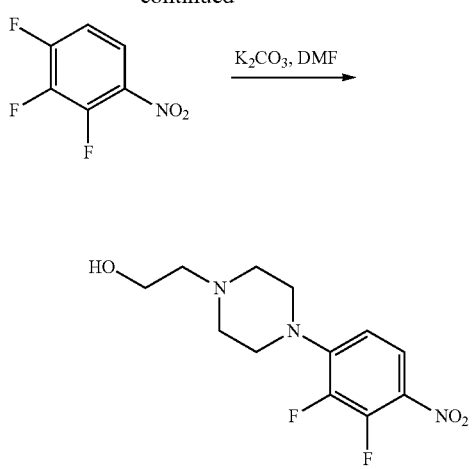

To a solution of 1,2,3-trifluoro-4-nitrobenzene (2.5 g, 14 mmol, 1.0 eq.) in DMF (20 mL) was added K₂CO₃ (3.8 g, 28 mmol, 2.0 eq.) followed by 2-(piperazin-1-yl)ethanol (1.8 g, 14 mmol, 1.0 eq.) at 0° C. and the mixture was stirred at r.t. overnight. The mixture was poured into ice-water (200 mL), filtered and dried in vacuo to afford 2-(4-(2,3-difluoro-4-nitrophenyl)piperazin-1-yl)ethanol (2.7 g, 67.5%).

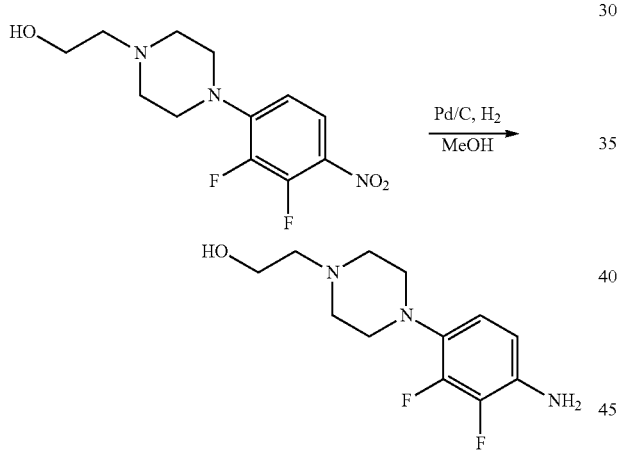

To a solution of 2-(4-(2,3-difluoro-4-nitrophenyl)piperazin-1-yl)ethanol (2.7 g, 9.0 mmol) in MeOH (30 mL) was added Pd/C (270 mg) and the resulting mixture was stirred at r.t. overnight. The Pd/C was removed by filtration and the filtrate was concentrated to afford 2-(4-(4-amino-2,3-difluorophenyl)piperazin-1-yl)ethanol (2.39 g, 99% yield) as off-white solid.

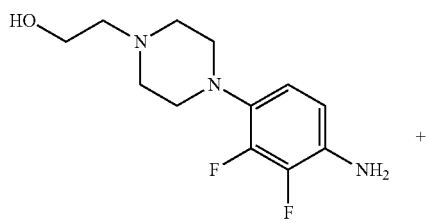

+

244

-continued

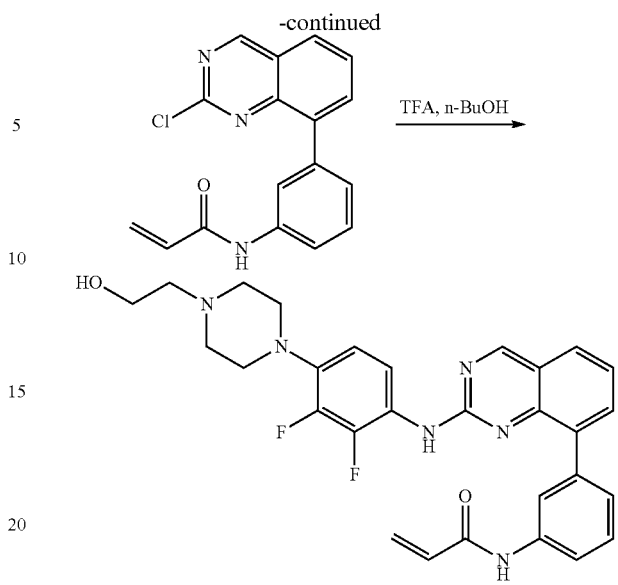

To a suspension of 2-(4-(4-amino-2,3-difluorophenyl)piperazin-1-yl)ethanol (83 mg, 0.32 mmol, 1 eq.) and N-(3-(2-chloroquinazolin-8-yl)phenyl)acrylamide (100 mg, 0.32 mmol, 1 eq.) in n-BuOH (5 mL) was added TFA (68 mg, 0.64 mmol, 2 eq.) and the resulting mixture was stirred at 90° C. overnight. The mixture was concentrated, diluted with DCM (20 mL), washed with Na₂CO₃ solution (20 mL), dried over anhydrous Na₂SO₄, concentrated and the residue was purified via column chromatography (MeOH/DCM=1/30, v:v) to afford N-(3-(2-((2,3-difluoro-4-(4-(2-hydroxyethyl)piperazin-1-yl)phenyl)amino)quinazolin-8-yl)phenyl)acrylamide as a yellow solid (16.3 mg, 9.5% yield). LRMS (M+H⁺) m/z calculated 531.2, found 531.2. ¹H NMR (CD₃OD, 400 MHz) δ 9.21 (s, 1H), 7.19-8.01 (m, 10H), 8.90 (s, 1H), 6.41-6.49 (m, 3H), 5.86 (m, 1H), 3.98-4.01 (m, 3H), 3.70-3.76 (m, 3H), 3.40-3.49 (m, 2H), 3.37-3.39 (m, 4H), 3.18 (m, 2H).

Example 154: Preparation of N-(3-(2-((4-(4-(2-amino-2-oxoethyl)piperazin-1-yl)-2-fluorophenyl)amino)quinazolin-8-yl)phenyl)acrylamide

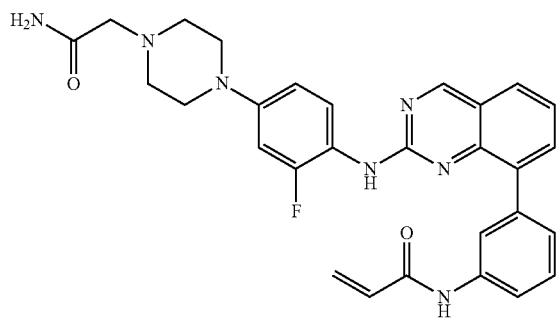

N-(3-(2-((4-(4-(2-amino-2-oxoethyl)piperazin-1-yl)-2-fluorophenyl)amino)quinazolin-8-yl)phenyl)acrylamide N-(3-(2-((4-(4-(2-amino-2-oxoethyl)piperazin-1-yl)-2-fluorophenyl)amino)quinazolin-8-yl)phenyl)acrylamide (152.7 mg) was prepared as described for N-(3-(2-((2-fluoro-4-(4-(2-hydroxyethyl)piperazin-1-yl)phenyl)amino)

quinazolin-8-yl)phenyl)acrylamide. LRMS (M+H⁺) m/z calculated 526.2, found 526.2. ¹H NMR (DMSO-d6, 400 MHz) δ 10.23 (s, 1H), 9.31 (s, 1H), 8.99 (s, 1H), 7.77-7.93 (m, 5H), 7.15-7.45 (m, 5H), 6.79 (dd, 1H), 6.46-6.52 (m, 2H), 6.25-6.30 (m, 1H), 5.78 (d, 1H), 3.09-3.12 (m, 4H), 2.93 (s, 2H), 2.54-2.57 (m, 4H).

Example 155: Preparation of N-(3-(2-((4-(4-(2-amino-2-oxoethyl)piperazin-1-yl)-3-fluorophenyl)amino)quinazolin-8-yl)phenyl)acrylamide

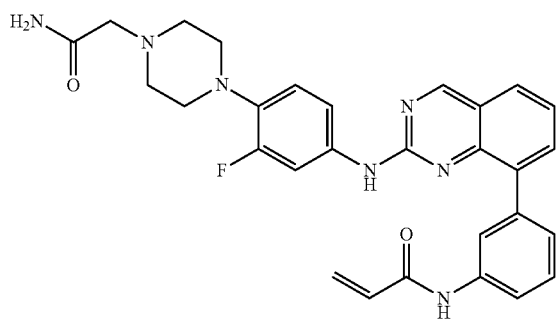

N-(3-(2-((4-(4-(2-amino-2-oxoethyl)piperazin-1-yl)-3-fluorophenyl)amino)quinazolin-8-yl)phenyl)acrylamide N-(3-(2-((4-(4-(2-amino-2-oxoethyl)piperazin-1-yl)-3-fluorophenyl)amino)quinazolin-8-yl)phenyl)acrylamide (30.8 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 526.2, found 526.2. ¹H NMR (CD3Cl, 400 MHz) δ 9.00 (s, 1H), 7.72-7.83 (m, 5H), 7.66 (s, 1H), 7.42-7.45 (m, 3H), 7.34 (t, 1H), 7.16 (d, 1H), 6.98 (m, 1H), 6.72 (t, 1H), 6.16-6.37 (m, 2H), 5.61-5.67 (m, 2H), 3.00 (s, 2H), 2.93-2.96 (m, 4H), 2.62-2.64 (m, 4H).

Example 156: Preparation of N-(3-(2-((2-fluoro-4-(4-(2-methoxyethyl)piperazin-1-yl)phenyl)amino)quinazolin-8-yl)phenyl)acrylamide

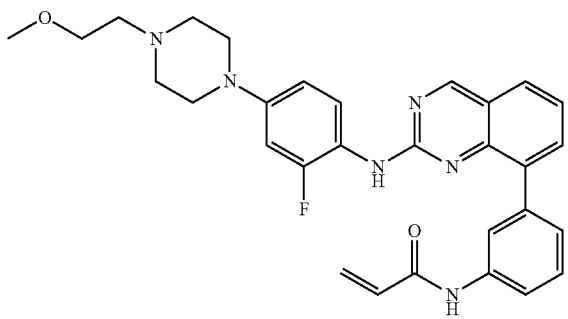

N-(3-(2-((2-fluoro-4-(4-(2-methoxyethyl)piperazin-1-yl)phenyl)amino)quinazolin-8-yl)phenyl)acrylamide N-(3-(2-((2-fluoro-4-(4-(2-methoxyethyl)piperazin-1-yl)phenyl)amino)quinazolin-8-yl)phenyl)acrylamide (60.1 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 528.2, found 528.2. ¹H NMR (DMSO-d6, 400 MHz) δ 10.22 (s, 1H), 9.30 (s, 1H), 8.97 (s, 1H), 7.75-7.93 (m, 5H), 7.36-7.45 (m, 3H), 6.78 (dd, 1H), 6.44-6.52 (m, 2H), 6.25-6.30 (m, 1H), 5.78 (d, 1H), 3.48 (t, 2H), 3.26 (s, 3H), 3.04-3.06 (m, 4H), 2.50-2.53 (m, 6H).

Example 157: Preparation of N-(3-(2-((3-fluoro-4-(4-(2-methoxyethyl)piperazin-1-yl)phenyl)amino)quinazolin-8-yl)phenyl)acrylamide

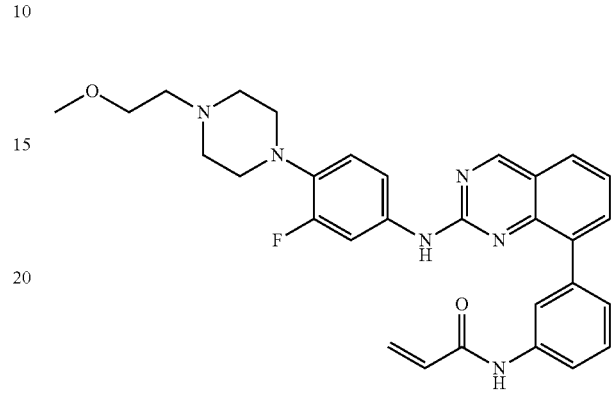

N-(3-(2-((3-fluoro-4-(4-(2-methoxyethyl)piperazin-1-yl)phenyl)amino)quinazolin-8-yl)phenyl)acrylamide N-(3-(2-((3-fluoro-4-(4-(2-methoxyethyl)piperazin-1-yl)phenyl)amino)quinazolin-8-yl)phenyl)acrylamide (92.8 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 527.2, found 527.2. ¹H NMR (DMSO-d6, 300 MHz) δ 10.24 (s, 1H), 9.91 (s, 1H), 9.34 (s, 1H), 7.81-8.04 (m, 4H), 7.38-7.54 (m, 3H), 6.78 (t, 1H), 6.26-6.50 (m, 2H), 5.74 (d, 1H), 4.08 (q, 1H), 3.46 (t, 2H), 3.26 (d, 2H), 2.87 (m, 3H), 2.50-2.53 (m, 8H).

Example 158: Preparation of N-(3-(2-((2,3-difluoro-4-(4-methylpiperazin-1-yl)phenyl)amino)quinazolin-8-yl)phenyl)acrylamide

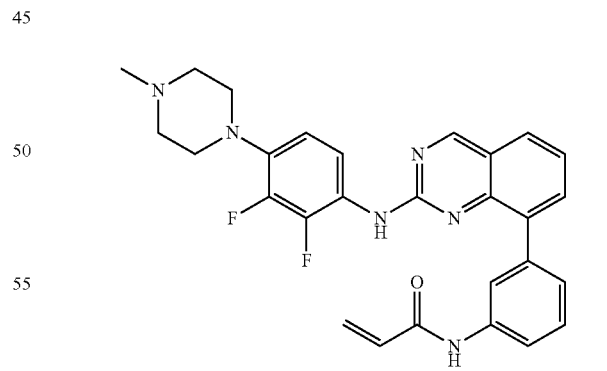

N-(3-(2-((2,3-difluoro-4-(4-methylpiperazin-1-yl)phenyl)amino)quinazolin-8-yl)phenyl)acrylamide

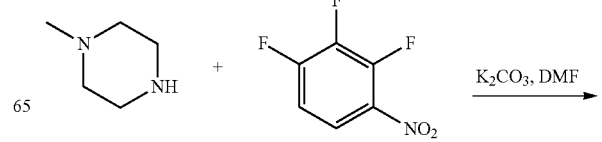

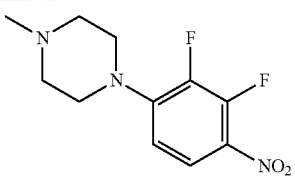

To a solution of 1-methylpiperazine (0.57 g, 5.7 mmol, 1 eq.) in DMF (10 mL) was added K2CO3 (1.56 g, 11.3 mmol, 2 eq.) followed by 1,2,3-trifluoro-4-nitrobenzene (1 g, 5.7 mmol, 1 eq.) and the mixture was stirred at 0° C. for 1 h. The mixture was poured into ice-water (100 mL), extracted by EA (3×40 mL), and the organic layers were combined, washed with brine (150 mL), concentrated and purified via column chromatography (10-95% CH3CN—H2O) to afford (1.3 g, 86%) as a yellow solid.

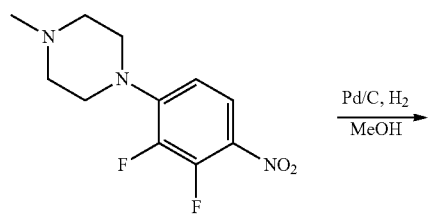

To a solution of 1-(2,3-difluoro-4-nitrophenyl)-4-methylpiperazine (1.3 g, 5.4 mmol) in MeOH (50 mL) was added Pd/C (200 mg) and the resulting mixture was stirred at r.t. overnight. The catalyst was removed by filtration and the filtrate was concentrated to afford 2,3-difluoro-4-(4-methylpiperazin-1-yl)aniline (1.3 g, 100%) as a yellow solid.

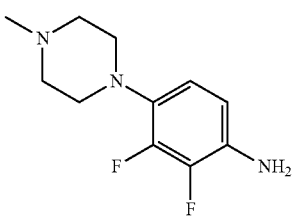

To a suspension of 2,3-difluoro-4-(4-methylpiperazin-1-yl)aniline (154 mg, 0.5 mmol, 1 eq.) and N-(3-(2-chloroquinazolin-8-yl)phenyl)acrylamide (114 mg, 0.5 mmol, 1 eq.) in n-BuOH (10 mL) was added TFA (0.3 mL, 2.5 mmol, 5 eq.) and the resulting mixture was stirred at 90° C. overnight. The mixture was concentrated, diluted with DCM (20 mL), washed with Na2CO3 solution (20 mL), dried, concentrated and purified via silica gel column (DCM/MeOH=10/1) to afford N-(3-(2-((2,3-difluoro-4-(4-methylpiperazin-1-yl)phenyl)amino)quinazolin-8-yl)phenyl)acrylamide (37 mg, 14%) as a yellow solid.

LRMS (M+H$^+$) m/z calculated 501.2, found 501.2. $^1$H NMR (DMSO-d6, 400 MHz) δ 10.24 (s, 1H), 9.35-9.36 (m, 2H), 7.32-7.96 (m, 8H), 6.24-6.57 (m, 3H), 5.78 (d, 1H), 2.94-2.96 (m, 4H), 2.46-2.47 (m, 4H), 2.24 (s, 3H).

Example 159: Preparation of N-(3-(2-((2,5-difluoro-4-(4-methylpiperazin-1-yl)phenyl)amino)quinazolin-8-yl)phenyl)acrylamide

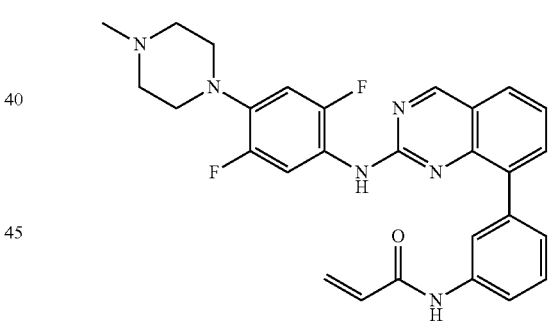

N-(3-(2-((2,5-difluoro-4-(4-methylpiperazin-1-yl)phenyl)amino)quinazolin-8-yl)phenyl)acrylamide

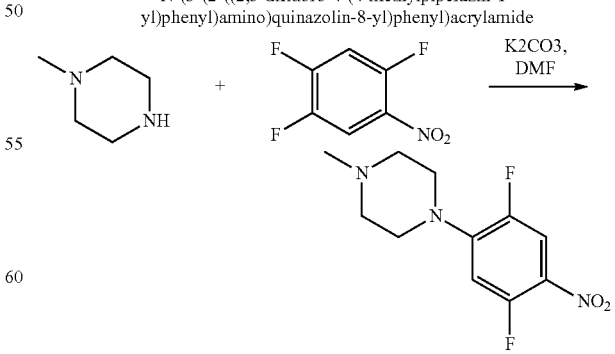

To a solution of 1-methylpiperazine (0.57 g, 5.7 mmol, 1 eq.) in DMF (10 mL) was added K2CO3 (1.56 g, 11.3 mmol, 2 eq.) followed by 1,2,4-trifluoro-5-nitrobenzene (1 g, 5.7 mmol, 1 eq.) and the mixture was stirred at 0° C. for 1 hour. The mixture was poured into ice-water (100 mL), extracted by EA (3×40 mL), and the organic layers were combined, washed with brine (150 mL), concentrated and purified via column chromatography (10-95% CH₃CN—H₂O) to afford 1-(2,5-difluoro-4-nitrophenyl)-4-methylpiperazine (1.4 g, 93%) as yellow solid.

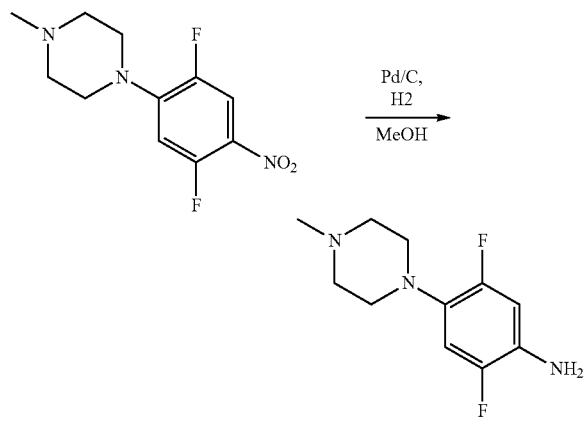

To a solution of 1-(2,5-difluoro-4-nitrophenyl)-4-methylpiperazine (1.4 g, 5.5 mmol) in MeOH (50 mL) was added Pd/C (200 mg) and the resulting mixture was stirred at r.t. overnight. The catalyst was removed by filtration and the filtrate was concentrated to afford 2,5-difluoro-4-(4-methylpiperazin-1-yl)aniline (1.4 g, 100%).

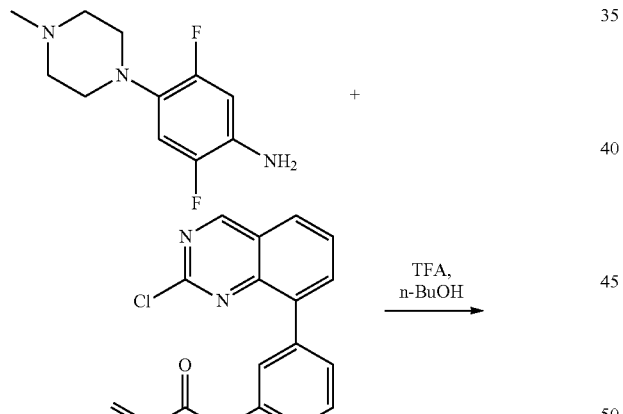

To a suspension of 2,5-difluoro-4-(4-methylpiperazin-1-yl)aniline (154 mg, 0.5 mmol, 1 eq.) and N-(3-(2-chloroquinazolin-8-yl)phenyl)acrylamide (114 mg, 0.5 mmol, 1 eq.) in n-BuOH (10 mL) was added TFA (0.3 mL, 2.5 mmol, 5 eq.) and the resulting mixture was stirred at 90° C. overnight. The mixture was concentrated, diluted with DCM (20 mL), washed with Na₂CO₃ solution (20 mL), dried, concentrated and purified via column chromatography (DCM/MeOH=10/1) to afford N-(3-(2-((2,5-difluoro-4-(4-methylpiperazin-1-yl)phenyl)amino)quinazolin-8-yl)phenyl)acrylamide (42 mg, 16%) as a yellow solid.

LRMS (M+H⁺) m/z calculated 501.2, found 501.2. ¹H NMR (DMSO-d6, 300 MHz) δ 10.17 (s, 1H), 9.37 (s, 1H), 9.17 (s, 1H), 7.75-7.97 (m, 5H), 7.39-7.51 (m, 3H), 6.84-6.89 (m, 1H), 6.19-6.49 (m, 2H), 5.74 (dd, 1H), 2.91-2.94 (m, 4H), 2.45-2.49 (m, 4H), 2.23 (s, 3H).

Example 160: Preparation of N-(3-(2-((2,5-difluoro-4-(4-(2-methoxyethyl)piperazin-1-yl)phenyl)amino)quinazolin-8-yl)phenyl)acrylamide

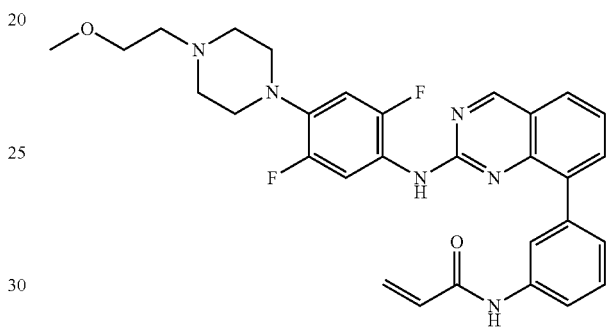

N-(3-(2-((2,5-difluoro-4-(4-(2-methoxyethyl)piperazin-1-yl)phenyl)amino)quinazolin-8-yl)phenyl)acrylamide N-(3-(2-((2,5-difluoro-4-(4-(2-methoxyethyl)piperazin-1-yl)phenyl)amino)quinazolin-8-yl)phenyl)acrylamide (55 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 545.2, found 545.2. ¹H NMR (CD₃OD, 400 MHz) δ 9.13 (s, 1H), 8.31-8.36 (m, 1H), 7.74-7.82 (m, 4H), 7.30-7.40 (m, 3H), 6.77-6.82 (m, 3H), 6.21-6.38 (m, 2H), 5.64-5.66 (m, 1H), 3.65-3.68 (m, 2H), 3.54-3.56 (m, 2H), 3.32-3.37 (m, 3H), 3.17 (m, 6H), 2.99-3.01 (m, 2H).

Example 161: Preparation of N-(3-(2-((2,5-difluoro-4-(4-(2-hydroxyethyl)piperazin-1-yl)phenyl)amino)quinazolin-8-yl)phenyl)acrylamide

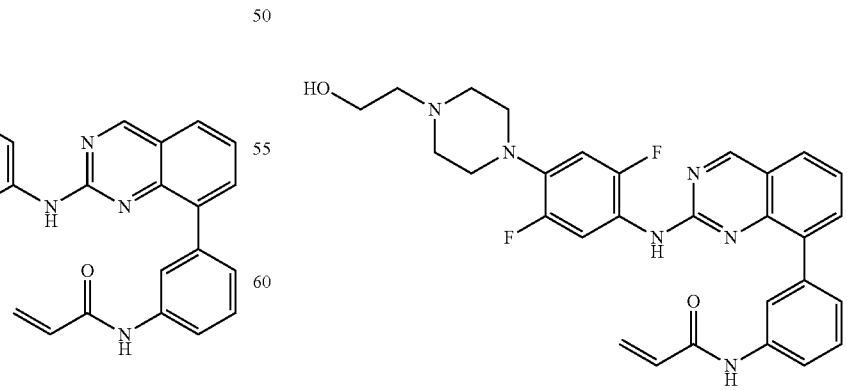

N-(3-(2-((2,5-difluoro-4-(4-(2-hydroxyethyl)piperazin-1-yl)phenyl)amino)quinazolin-8-yl)phenyl)acrylamide

251

-continued

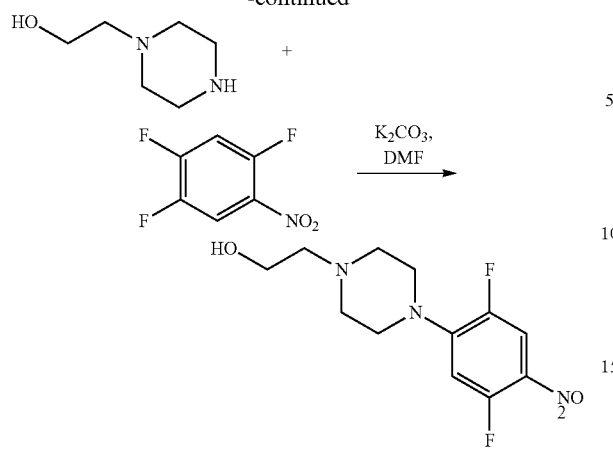

To a solution of 2-(piperazin-1-yl)ethanol (0.73 g, 5.6 mmol, 1 eq.) in DMF (10 mL) was added K$_2$CO$_3$ (1.56 g, 11.3 mmol, 2 eq.) followed by 1,2,4-trifluoro-5-nitrobenzene (1 g, 5.6 mmol, 1 eq.) and the mixture was stirred at 0° C. for 1 hour. The mixture was poured into ice-water (100 mL), extracted by EA (3×40 mL), and the organic layers were combined, washed with brine (150 mL), concentrated and purified via column chromatography (10-95% CH$_3$CN—H$_2$O) to afford 2-(4-(2,5-difluoro-4-nitrophenyl)piperazin-1-yl)ethanol (0.65 g, 41%) as a yellow solid.

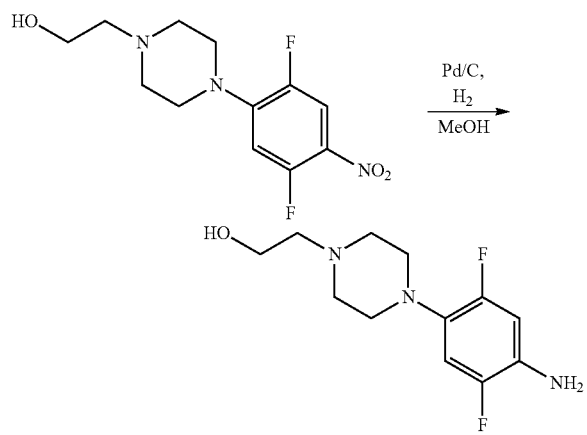

To a solution of 2-(4-(2,5-difluoro-4-nitrophenyl)piperazin-1-yl)ethanol (0.65 g, 2.3 mmol) in MeOH (50 mL) was added Pd/C (100 mg) and the resulting mixture was stirred at r.t. overnight. The Pd/C was removed by filtration and the filtrate was concentrated to afford 2-(4-(4-amino-2,5-difluorophenyl)piperazin-1-yl)ethanol (0.58 g, 99%).

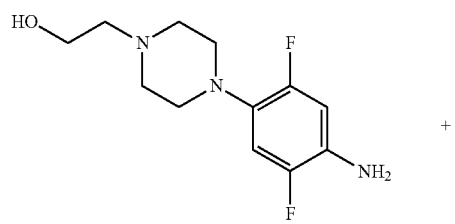

252

-continued

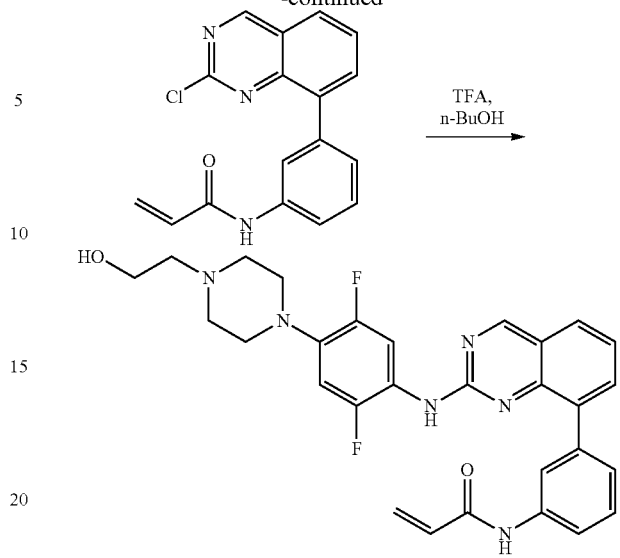

To a suspension of 2-(4-(4-amino-2,5-difluorophenyl)piperazin-1-yl)ethanol (270 mg, 0.88 mmol, 1 eq.) and N-(3-(2-chloroquinazolin-8-yl)phenyl)acrylamide (225 mg, 0.88 mmol, 1 eq.) in n-BuOH (10 mL) was added TFA (0.5 mL, 4.4 mmol, 5 eq.) and the resulting mixture was stirred at 90° C. overnight. The mixture was concentrated, diluted with DCM (20 mL), washed with Na$_2$CO$_3$ solution (20 mL), dried, concentrated and purified via column chromatography (DCM/MeOH=10/1) to afford N-(3-(2-((2,5-difluoro-4-(4-(2-hydroxyethyl)piperazin-1-yl)phenyl)amino)quinazolin-8-yl)phenyl)acrylamide (120 mg, 26%) as yellow solid. LRMS (M+H$^+$) m/z calculated 531.2, found 531.2. 1H NMR (DMSO-d6, 400 MHz) δ 10.18 (s, 1H), 9.37 (s, 1H), 9.17 (s, 1H), 7.97-7.94 (m, 3H), 7.83-7.74 (m, 2H), 7.50-7.39 (m, 3H), 6.90-6.85 (m, 1H), 6.48-6.41 (m, 1H), 6.23 (dd, 1H), 5.73 (dd, 1H), 4.42 (t, 1H), 3.55-3.50 (m, 2H), 2.94-2.91 (m, 4H), 2.55-2.54 (m, 4H), 2.44 (t, 2H).

Example 162: Preparation of N-(3-(2-((2,5-difluoro-4-(4-(2-hydroxy-2-methylpropyl)piperazin-1-yl)phenyl)amino)quinazolin-8-yl)phenyl)acrylamide

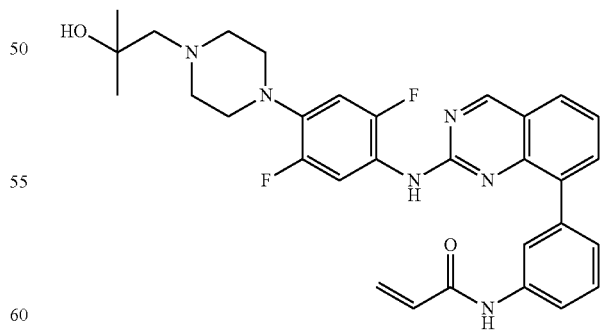

N-(3-(2-((2,5-difluoro-4-(4-(2-hydroxy-2-methylpropyl)piperazin-1-yl)phenyl)amino)quinazolin-8-yl)phenyl)acrylamide N-(3-(2-((2,5-difluoro-4-(4-(2-hydroxy-2-methylpropyl)piperazin-1-yl)phenyl)amino)quinazolin-8-yl)phenyl)acrylamide (42 mg) was prepared as described for N-(3-(2-((2- fluoro-4-(4-(2-hydroxyethyl)piperazin-1-yl)phenyl)amino)quinazolin-8-yl)phenyl)acrylamide. LRMS (M+H⁺) m/z calculated 559.2, found 559.2. ¹H NMR (DMSO-d6, 400 MHz) δ 10.18 (s, 1H), 9.37 (s, 1H), 9.18 (s, 1H), 8.00-7.94 (m, 3H), 7.83-7.74 (m, 2H), 7.50-7.39 (m, 3H), 6.90-6.85 (m, 1H), 6.47-6.41 (m, 1H), 6.22 (dd, 1H), 5.75-5.71 (m, 1H), 4.12 (s, 1H), 2.92-2.91 (m, 4H), 2.65-2.64 (m, 4H), 2.24 (s, 2H), 1.11 (s, 6H).

Example 163: Preparation of N-(3-(2-((2,3-difluoro-4-(4-(2-methoxyethyl)piperazin-1-yl)phenyl)amino)quinazolin-8-yl)phenyl)acrylamide

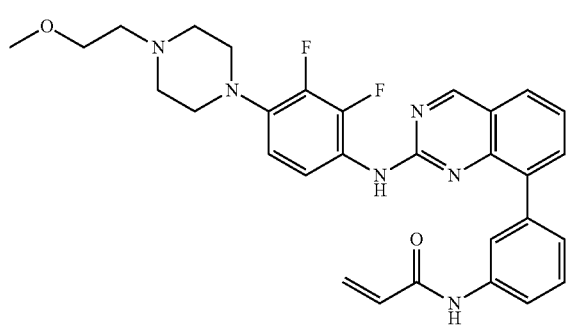

N-(3-(2-((2,3-difluoro-4-(4-(2-methoxyethyl)piperazin-1-yl)phenyl)amino)quinazolin-8-yl)phenyl)acrylamide N-(3-(2-((2,3-difluoro-4-(4-(2-methoxyethyl)piperazin-1-yl)phenyl)amino)quinazolin-8-yl)phenyl)acrylamide (55 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 545.2, found 545.2. ¹H NMR (CD₃OD, 400 MHz) δ 9.13 (s, 1H), 8.09-8.04 (m, 1H), 7.86-7.68 (m, 4H), 7.40-7.27 (m, 3H), 6.48-6.25 (m, 3H), 5.69 (dd, 1H), 3.67 (t, 2H), 3.58-3.55 (m, 2H), 3.36-3.33 (m, 3H), 3.25-3.20 (m, 7H), 3.04-3.01 (m, 2H).

Example 164: Preparation of N-(3-(2-((2,3-difluoro-4-(4-(2-hydroxy-2-methylpropyl)piperazin-1-yl)phenyl)amino)quinazolin-8-yl)phenyl)acrylamide

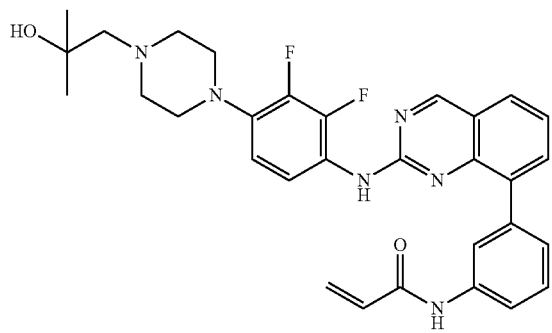

N-(3-(2-((2,3-difluoro-4-(4-(2-hydroxy-2-methylpropyl)piperazin-1-yl)phenyl)amino)quinazolin-8-yl)phenyl)acrylamide N-(3-(2-((2,3-difluoro-4-(4-(2-hydroxy-2-methylpropyl)piperazin-1-yl)phenyl)amino)quinazolin-8-yl)phenyl)acrylamide (33 mg) was prepared as described for N-(3-(2-((2-fluoro-4-(4-(2-hydroxyethyl)piperazin-1-yl)phenyl)amino)quinazolin-8-yl)phenyl)acrylamide. LRMS (M+H⁺) m/z calculated 559.2, found 559.2. ¹H NMR (DMSO-d6, 400 MHz) δ 10.22 (s, 1H), 9.36 (s, 1H), 9.32 (s, 1H), 7.96-7.77 (m, 5H), 7.49-7.34 (m, 3H), 6.46-6.42 (m, 2H), 6.29-6.28 (m, 1H), 5.76 (dd, 1H), 4.11 (s, 1H), 2.95-2.93 (m, 4H), 2.67-2.66 (m, 4H), 2.25 (s, 2H), 1.12 (s, 6H).

Example 165: Preparation of N-(3-(2-((2-fluoro-4-((1-(2-fluoroethyl)piperidin-4-yl)oxy)phenyl)amino)quinazolin-8-yl)phenyl)acrylamide

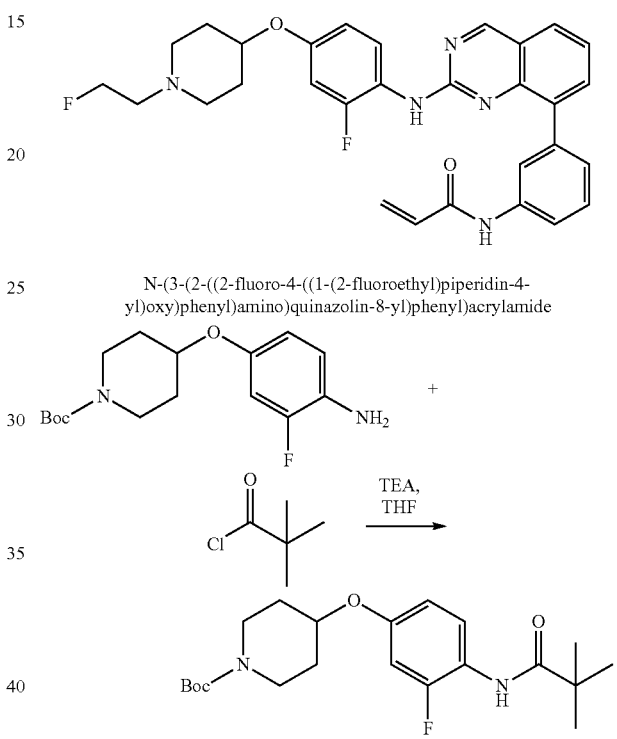

N-(3-(2-((2-fluoro-4-((1-(2-fluoroethyl)piperidin-4-yl)oxy)phenyl)amino)quinazolin-8-yl)phenyl)acrylamide

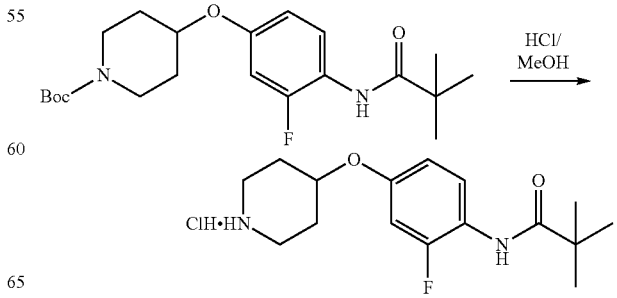

To a solution of tert-butyl 4-(4-amino-3-fluorophenoxy)piperidine-1-carboxylate (1.1 g, 3.6 mmol, 1 eq.) in THF (20 mL) cooled at 0° C. was added TEA (1.1 g, 10.8 mmol, 3 eq.) followed by pivaloyl chloride (0.6 mL, 4.3 mmol, 1.2 eq.) and the resulting mixture was stirred at r.t. for 10 min. The mixture was diluted with EA (20 mL), washed with brine (40 mL) and concentrated to afford tert-butyl 4-(3-fluoro-4-pivalamidophenoxy)piperidine-1-carboxylate (1.4 g, 100%).

To a solution of HCl in MeOH (15 mL) was added tert-butyl 4-(3-fluoro-4-pivalamidophenoxy)piperidine-1-carboxylate (1.4 g, 3.6 mmol) and the resulting mixture was stirred at r.t. for 1 h. Then the solution was concentrated to afford N-(2-fluoro-4-(piperidin-4-yloxy)phenyl)pivalamide hydrochloride (1.2 g, 100%).

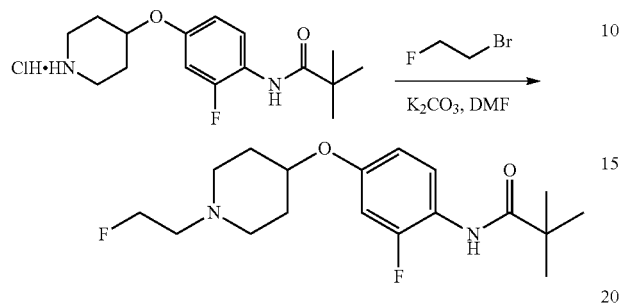

To a solution of N-(2-fluoro-4-(piperidin-4-yloxy)phenyl)pivalamide hydrochloride (1.2 g, 3.6 mmol, 1 eq.) in DMF (10 mL) was added K₂CO₃ (994 mg, 7.2 mmol, 2 eq.) followed by 1-bromo-2-fluoroethane (680 mg, 5.4 mmo, 1.5 eq.) and the resulting mixture was stirred at 120° C. for 2 h in microwave reactor. The mixture was purified via Prep-HPLC to afford N-(2-fluoro-4-((1-(2-fluoroethyl)piperidin-4-yl)oxy)phenyl)pivalamide (430 mg, 35%).

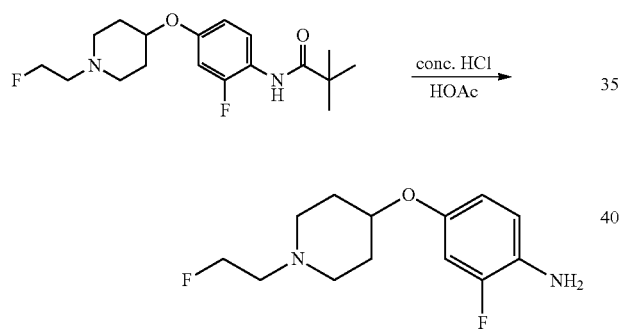

To a solution of N-(2-fluoro-4-((1-(2-fluoroethyl)piperidin-4-yl)oxy)phenyl)pivalamide (430 mg, 1.3 mmol) in HOAc (8 mL) was added conc. HCl (4 mL) and the resulting mixture was stirred at 110° C. for 12 h. The mixture was cooled and poured into ice-water (100 mL), basified with Na₂CO₃ solution to PH=10, extracted with EA and the organic phase was dried, concentrated and purified via column chromatography (DCM/MeOH=10/1) to afford 2-fluoro-4-((1-(2-fluoroethyl)piperidin-4-yl)oxy)aniline (180 mg, 56%).

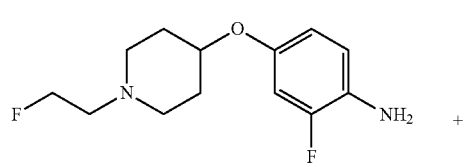

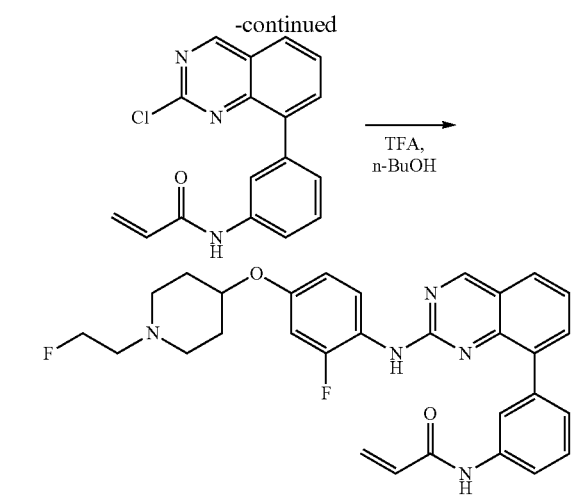

To a suspension of 2-fluoro-4-((1-(2-fluoroethyl)piperidin-4-yl)oxy)aniline (150 mg, 0.6 mmol, 1.2 eq) and N-(3-(2-chloroquinazolin-8-yl)phenyl)acrylamide (154 mg, 0.5 mmol, 1 eq.) in n-BuOH (10 mL) was added TFA (285 mg, 2.5 mmol, 5 eq.) and the resulting mixture was stirred at 90° C. overnight. The mixture was concentrated, diluted with DCM (20 mL), washed with Na₂CO₃ solution (20 mL), dried over Na₂SO₄, concentrated and purified via column chromatography (DCM/MeOH=10/1) and Prep-HPLC to afford N-(3-(2-((2-fluoro-4-((1-(2-fluoroethyl)piperidin-4-yl)oxy)phenyl)amino)quinazolin-8-yl)phenyl)acrylamide (45.8 mg, 17.3%). LRMS (M+H⁺) m/z calculated 530.2, found 530.2. ¹H NMR (DMSO-d6, 400 MHz) δ 10.24 (s, 1H), 9.37 (s, 1H), 8.41-8.45 (m, 1H), 7.76-8.09 (m, 5H), 7.37-7.52 (m, 3H), 7.04 (dd, 1H), 6.23-6.50 (m, 3H), 5.77 (dd, 1H), 4.44-4.58 (m, 3H), 2.52-2.66 (m, 5H), 2.39 (m, 2H), 1.90-1.95 (m, 2H), 1.71-1.76 (m, 2H).

Example 166: Preparation of N-(3-(2-((2-fluoro-4-((1-(2-hydroxyethyl)piperidin-4-yl)oxy)phenyl)amino)quinazolin-8-yl)phenyl)acrylamide

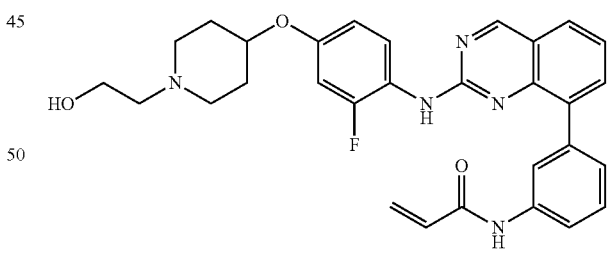

N-(3-(2-((2-fluoro-4-((1-(2-hydroxyethyl)piperidin-4-yl)oxy)phenyl)amino)quinazolin-8-yl)phenyl)acrylamide N-(3-(2-((2-fluoro-4-((1-(2-hydroxyethyl)piperidin-4-yl)oxy)phenyl)amino)quinazolin-8-yl)phenyl)acrylamide (32.3 mg) was prepared as described for N-(3-(2-((2-fluoro-4-((1-(2-fluoroethyl)piperidin-4-yl)oxy)phenyl)amino)quinazolin-8-yl)phenyl)acrylamide. LRMS (M+H⁺) m/z calculated 528.2, found 528.2. ¹H NMR (DMSO-d6, 400 MHz) δ 10.22 (s, 1H), 9.32 (s, 1H), 9.08 (s, 1H), 7.73-7.93 (m, 5H), 7.36-7.45 (m, 3H), 6.87 (d, 1H), 6.44-6.56 (m, 2H), 6.24-6.29 (m, 1H), 5.76 (d, 1H), 4.33 (m, 1H), 3.52-3.56 (m, 2H), 2.75-2.81 (m, 2H), 1.91-1.97 (m, 2H), 1.65-1.71 (m, 2H).

Example 167: Preparation of N-(3-(2-((2-fluoro-4-(4-(2-hydroxyethyl)piperazin-1-yl)phenyl)amino)quinazolin-8-yl)phenyl)acrylamide maleate

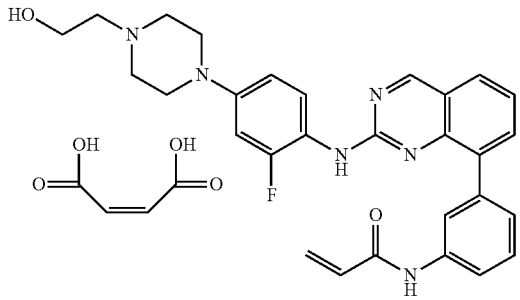

N-(3-(2-((2-fluoro-4-(4-(2-hydroxyethyl)piperazin-1-yl)phenyl)amino)quinazolin-8-yl)phenyl)acrylamide maleate

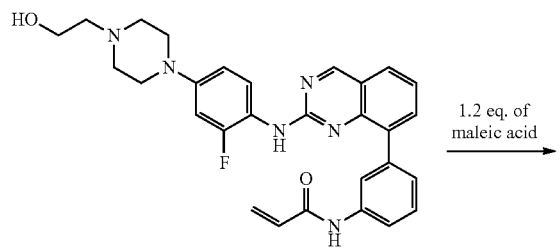

1.2 eq. of maleic acid

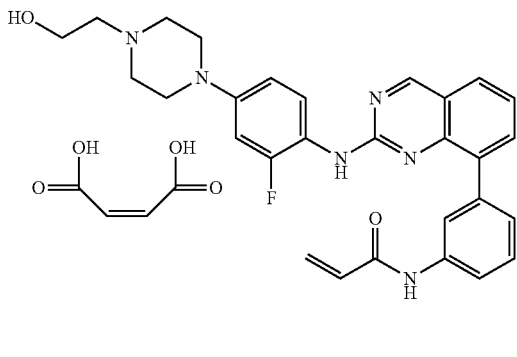

3.8 mL of refluxing EtOH/H2O (20/1) was slowly added to 100 mg of N-(3-(2-((2-fluoro-4-(4-(2-hydroxyethyl)piperazin-1-yl)phenyl)amino)quinazolin-8-yl)phenyl)acrylamide and 1.2 eq of maleic acid till all solid was dissolved, the mixture was slowly cooled down and stood overnight, the precipitate was collected by filtration to give N-(3-(2-((2-fluoro-4-(4-(2-hydroxyethyl)piperazin-1-yl)phenyl)amino)quinazolin-8-yl)phenyl)acrylamide maleate (86.7 mg).

LRMS (M+H$^+$) m/z calculated 513.2, found 513.2. $^1$H NMR (DMSO-d6, 400 MHz) δ 10.23 (s, 1H), 9.31 (s, 1H), 9.07 (s, 1H), 7.93-7.79 (m, 5H), 7.46-7.38 (m, 3H), 6.92-6.87 (m, 1H), 6.58-6.47 (m, 2H), 6.34 (dd, 1H), 6.03 (s, 2H), 5.77 (dd, 1H), 5.33 (s, 1H), 4.34 (s, 1H), 3.76-3.44 (m, 2H), 3.46-3.11 (m, 12H), 1.05 (t, 3H).

Example 168: Preparation of N-(3-(2-((4-(4-methylpiperazin-1-yl)phenyl)amino)quinazolin-8-yl)phenyl)acrylamide maleate

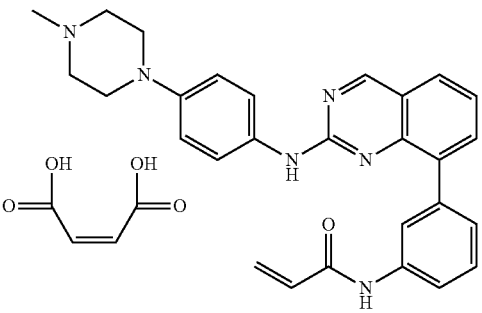

N-(3-(2-((4-(4-methylpiperazin-1-yl)phenyl)amino)quinazolin-8-yl)phenyl)acrylamide maleate N-(3-(2-((4-(4-methylpiperazin-1-yl)phenyl)amino)quinazolin-8-yl)phenyl)acrylamide maleate was prepared as described for N-(3-(2-((2-fluoro-4-(4-(2-hydroxyethyl)piperazin-1-yl)phenyl)amino)quinazolin-8-yl)phenyl)acrylamide maleate. LRMS (M+H$^+$) m/z calculated 465.2, found 465.2. $^1$H NMR (DMSO-d6, 400 MHz) δ 10.27 (s, 1H), 9.72 (s, 1H), 9.31 (s, 1H), 7.92-7.90 (m, 3H), 7.83-7.77 (m, 3H), 7.50-7.36 (m, 3H), 6.76 (d, 2H), 6.51-6.44 (m, 1H), 6.28 (dd, 1H), 6.03 (s, 2H), 5.77 (dd, 1H), 3.31-3.19 (m, 8H), 2.83 (s, 3H).

Example 169: Preparation of N-(3-(2-((4-(4-(2-hydroxyethyl)piperazin-1-yl)phenyl)amino)quinazolin-8-yl)phenyl)acrylamide maleate

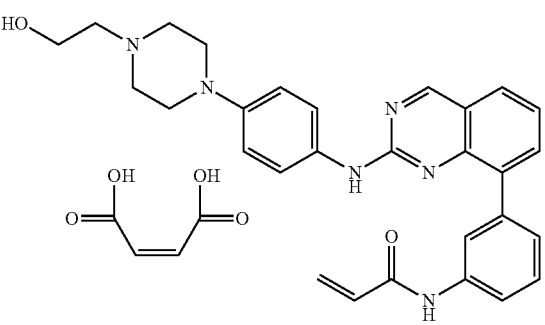

N-(3-(2-((4-(4-(2-hydroxyethyl)piperazin-1-yl)phenyl)amino)quinazolin-8-yl)phenyl)acrylamide maleate N-(3-(2-((4-(4-(2-hydroxyethyl)piperazin-1-yl)phenyl)amino)quinazolin-8-yl)phenyl)acrylamide maleate was prepared as described for N-(3-(2-((2-fluoro-4-(4-(2-hydroxyethyl)piperazin-1-yl)phenyl)amino)quinazolin-8-yl)phenyl)acrylamide maleate. LRMS (M+H$^+$)m/z calculated 495.2, found 495.2. $^1$H NMR (DMSO-d6, 400 MHz) δ 10.31 (s, 1H), 9.64 (s, 1H), 9.28 (s, 1H), 8.02 (s, 1H), 7.91-7.71 (m, 5H), 7.49-7.33 (m, 3H), 6.69 (d, 2H), 6.46-6.43 (m, 1H), 6.29-6.28 (m, 1H), 5.75 (dd, 1H), 4.43 (s, 1H), 3.53 (t, 2H), 3.33 (t, 2H), 2.98-2.95 (m, 4H), 2.53-2.40 (m, 4H).

Example 170: Preparation of N-(3-(2-((2,3-difluoro-4-(4-(2-hydroxyethyl)piperazin-1-yl)phenyl)amino)quinazolin-8-yl)phenyl)acrylamide maleate

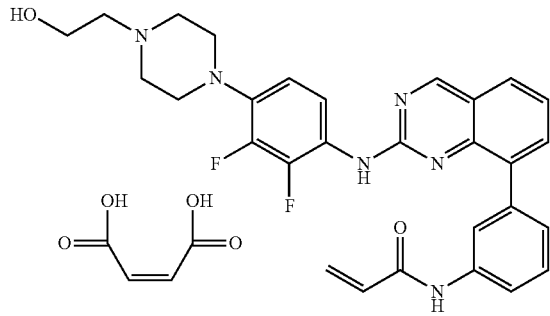

N-(3-(2-((2,3-difluoro-4-(4-(2-hydroxyethyl)piperazin-1-yl)phenyl)amino)quinazolin-8-yl)phenyl)acrylamide maleate N-(3-(2-((2,3-difluoro-4-(4-(2-hydroxyethyl)piperazin-1-yl)phenyl)amino)quinazolin-8-yl)phenyl)acrylamide maleate was prepared as described for N-(3-(2-((2-fluoro-4-(4-(2-hydroxyethyl)piperazin-1-yl)phenyl)amino)quinazolin-8-yl)phenyl)acrylamide maleate. LRMS (M+H+) m/z calculated 531.2, found 531.2. 1H NMR (DMSO-d6, 400 MHz) δ 10.22 (s, 1H), 9.43 (s, 1H), 9.37 (s, 1H), 7.96 (dd, 1H), 7.84-7.81 (m, 3H), 7.69 (t, 1H), 7.48 (t, 1H), 7.41-7.37 (m, 2H), 6.65 (t, 1H), 6.50-6.44 (m, 1H), 6.28 (dd, 1H), 6.02 (d, 2H), 5.77 (dd, 1H), 3.75-3.72 (m, 2H), 3.44-3.06 (m, 12H).

Example 171: Preparation of N-(3-(2-((2,3-difluoro-4-(4-methylpiperazin-1-yl)phenyl)amino)quinazolin-8-yl)phenyl)acrylamide maleate

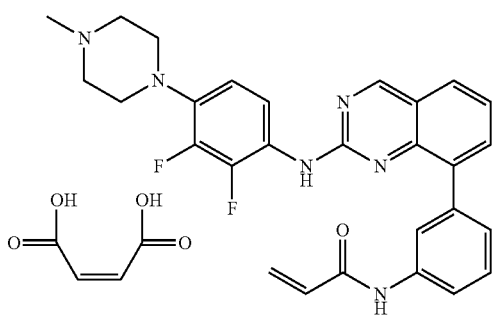

RX-2013-0522-162-03
N-(3-(2-((2,3-difluoro-4-(4-methylpiperazin-1-yl)phenyl)amino)quinazolin-8-yl)phenyl)acrylamide maleate N-(3-(2-((2,3-difluoro-4-(4-methylpiperazin-1-yl)phenyl)amino)quinazolin-8-yl)phenyl)acrylamide maleate was prepared as described for N-(3-(2-((2-fluoro-4-(4-(2-hydroxyethyl)piperazin-1-yl)phenyl)amino)quinazolin-8-yl)phenyl)acrylamide maleate. LRMS (M+H$^+$) m/z calculated 501.2, found 501.2. $^1$H NMR (DMSO-d6, 400 MHz) δ 10.28 (s, 1H), 9.44 (s, 1H), 9.38 (s, 1H), 7.98 (dd, 1H), 7.81-7.95 (m, 3H), 7.71 (t, 1H), 7.48 (t, 1H), 7.41-7.37 (m, 2H), 6.65 (t, 1H), 6.50-6.44 (m, 1H), 6.28 (dd, 1H), 6.02 (s, 1.4H), 5.77 (dd, 1H), 2.86 (s, 3H).

Example 172: Preparation of N-(3-(2-((2-fluoro-4-(4-(2-hydroxyethyl)piperazin-1-yl)phenyl)amino)quinazolin-8-yl)phenyl)acrylamide maleate

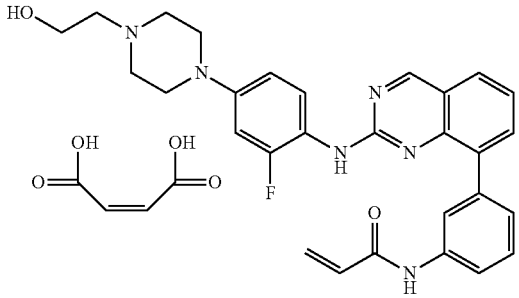

N-(3-(2-((2-fluoro-4-(4-(2-hydroxyethyl)piperazin-1-yl)phenyl)amino)quinazolin-8-yl)phenyl)acrylamide maleate

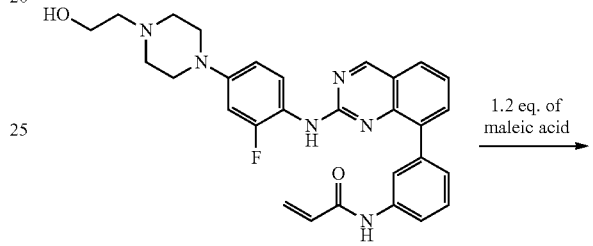

1.2 eq. of maleic acid

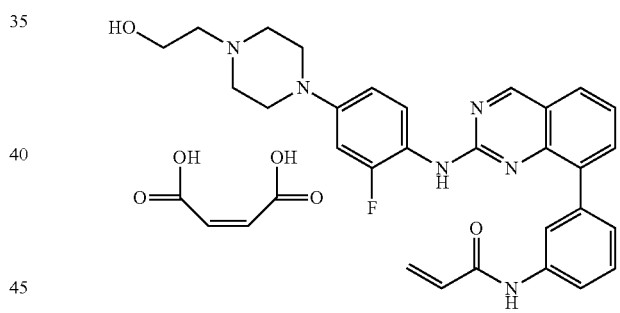

4.6 mL of refluxing iPrOH/H$_2$O (20/1) was slowly added to 100 mg of N-(3-(2-((2-fluoro-4-(4-(2-hydroxyethyl)piperazin-1-yl)phenyl)amino)quinazolin-8-yl)phenyl)acrylamide and 1.2 eq of maleic acid till all solid was dissolved, the mixture was slowly cooled down and stood overnight, the precipitate was collected by filtration to give N-(3-(2-((2-fluoro-4-(4-(2-hydroxyethyl)piperazin-1-yl)phenyl)amino)quinazolin-8-yl)phenyl)acrylamide maleate (72 mg).

LRMS (M+H$^+$) m/z calculated 513.2, found 513.2. $^1$H NMR (DMSO-d6, 400 MHz) δ 10.23 (s, 1H), 9.32 (s, 1H), 9.07 (s, 1H), 7.93-7.79 (m, 5H), 7.46-7.38 (m, 3H), 6.92-6.87 (m, 1H), 6.58-6.47 (m, 2H), 6.27 (dd, 1H), 6.03 (s, 2H), 5.80-5.76 (m, 1H), 5.33 (s, 1H), 3.76-3.75 (m, 2H), 3.42-3.08 (m, 11H).

Example 173: Preparation of N-(3-(2-((2,3-difluoro-4-(4-methylpiperazin-1-yl)phenyl)amino)quinazolin-8-yl)phenyl)acrylamide maleate

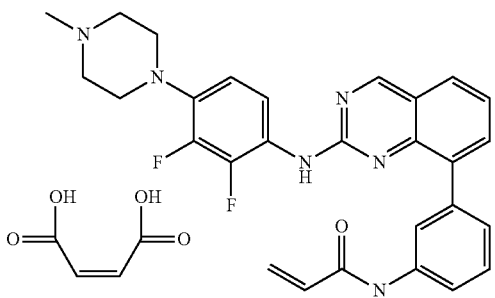

N-(3-(2-((2,3-difluoro-4-(4-methylpiperazin-1-yl)phenyl)amino)quinazolin-8-yl)phenyl)acrylamide maleate N-(3-(2-((2,3-difluoro-4-(4-methylpiperazin-1-yl)phenyl)amino)quinazolin-8-yl)phenyl)acrylamide maleate was prepared as described for N-(3-(2-((2-fluoro-4-(4-(2-hydroxyethyl)piperazin-1-yl)phenyl)amino)quinazolin-8-yl)phenyl)acrylamide maleate. LRMS (M+H$^+$) m/z calculated 501.2, found 501.2. $^1$H NMR (DMSO-d6, 400 MHz) δ 10.28 (s, 1H), 9.44 (s, 1H), 9.38 (s, 1H), 7.98 (dd, 1H), 7.81-7.95 (m, 3H), 7.71 (t, 1H), 7.48 (t, 1H), 7.41-7.37 (m, 2H), 6.65 (t, 1H), 6.50-6.44 (m, 1H), 6.28 (dd, 1H), 6.02 (s, 1.2H), 5.77 (dd, 1H), 2.86 (s, 3H).

Example 174: Preparation of N-(3-(2-((4-(4-methylpiperazin-1-yl)phenyl)amino)quinazolin-8-yl)phenyl)acrylamide hydrochloride

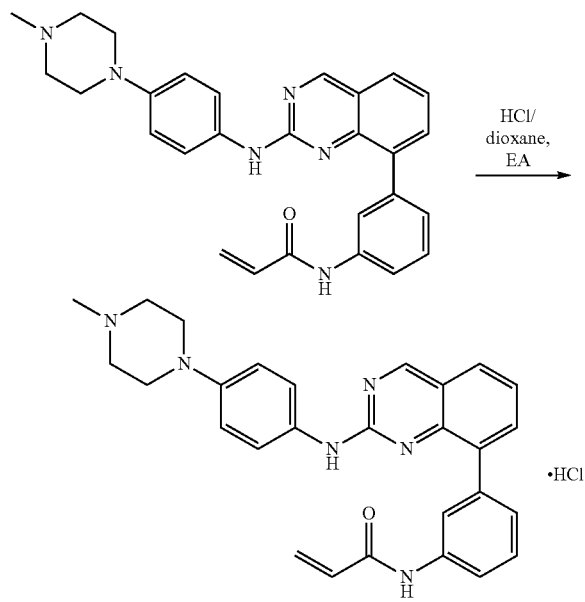

To a suspension of N-(3-(2-((4-(4-methylpiperazin-1-yl)phenyl)amino)quinazolin-8-yl)phenyl)acrylamide (80 mg, 0.17 mol) in EA (10 mL) was added a solution of HCl in dioxane (3M, 1 mL) dropwise at 0° C. which resulted in the formation of precipitate gradually. The precipitate was filtered 30 min later to afford N-(3-(2-((4-(4-methylpiperazin-1-yl)phenyl)amino)quinazolin-8-yl)phenyl)acrylamide hydrochloride as a brown solid (56 mg, 65% yield). LRMS (M+H+) m/z calculated 465.2, found 465.2. $^1$H NMR (DMSO-d6, 300 MHz) 10.8 (br, 1H), 10.5 (s, 1H), 9.77 (s, 1H), 9.31 (s, 1H), 8.02 (s, 1H), 7.77-7.93 (m, 5H), 7.42-7.51 (m, 2H), 7.35 (d, 1H), 6.77 (d, 2H), 6.50-6.55 (m, 1H), 6.23-6.30 (m, 1H), 5.76-5.79 (m, 1H), 3.60-3.64 (m, 2H), 3.45-3.50 (m, 2H), 2.98-3.15 (m, 4H), 2.81 (d, 3H).

Example 175: Inhibitory Activity Against EGFR, EGFR Mutants and Several Other Kinases Inhibitory activities of compounds against BTK, EGFR and EGFR mutants (EGFR L858R, EGFR T790M, EGFR L858R/T790M), FGFR1, FGFR2, JAK2, JAK3 and KDR were measured by Invitrogen using Z'-LYTE® Method as briefly described in the following.

Test Compounds are screened in 1% DMSO (final) in the well. For 10 point titrations, 3-fold serial dilutions are conducted from the starting concentration. All ATP Solutions are diluted to a 4× working concentration in Kinase Buffer (50 mM HEPES pH 7.5, 0.01% BRIJ-35, 10 mM MgCl$_2$, 1 mM EGTA). Peptide/Kinase Mixtures are diluted to a 2× working concentration in the appropriate Kinase Buffers as described below.

(i) Peptide/Kinase Mixtures for measurement of EGFR (ErbB1):

The 2×EGFR (ErbB1)/Tyr 04 mixture is prepared in 50 mM HEPES pH 7.5, 0.01% BRIJ-35, 10 mM MgCl$_2$, 4 mM MnCl$_2$, 1 mM EGTA, 2 mM DTT. The final 10 μL Kinase Reaction consists of 1.1-5.25 ng EGFR (ErbB1) and 2 μM Tyr 04 in 50 mM HEPES pH 7.5, 0.01% BRIJ-35, 10 mM MgCl$_2$, 2 mM MnCl$_2$, 1 mM EGTA, 1 mM DTT. After the 1 hour Kinase Reaction incubation, 5 μL of a 1:64 dilution of Development Reagent B is added.

(ii) Peptide/Kinase Mixtures for measurement of EGFR (ErbB1) L858R:

The 2×EGFR (ErbB1) L858R/Tyr 04 mixture is prepared in 50 mM HEPES pH 7.5, 0.01% BRIJ-35, 10 mM MgCl$_2$, 4 mM MnCl$_2$, 1 mM EGTA, 2 mM DTT. The final 10 μL Kinase Reaction consists of 0.2-1.68 ng EGFR (ErbB1) L858R and 2 μM Tyr 04 in 50 mM HEPES pH 7.5, 0.01% BRIJ-35, 10 mM MgCl$_2$, 2 mM MnCl$_2$, 1 mM EGTA, 1 mM DTT. After the 1 hour Kinase Reaction incubation, 5 μL of a 1:64 dilution of Development Reagent B is added.

(iii) Peptide/Kinase Mixtures for measurement of EGFR (ErbB1) T790M:

The 2×EGFR (ErbB1) T790M/Tyr 04 mixture is prepared in 50 mM HEPES pH 6.5, 0.01% BRIJ-35, 10 mM MgCl$_2$, 1 mM EGTA, 0.02% NaN$_3$. The final 10 μL Kinase Reaction consists of 3.9-30.2 ng EGFR (ErbB1) T790M and 2 μM Tyr 04 in 50 mM HEPES pH 7.0, 0.01% BRIJ-35, 10 mM MgCl$_2$, 1 mM EGTA, 0.01% NaN3. After the 1 hour Kinase Reaction incubation, 5 μL of a 1:64 dilution of Development Reagent B is added.

(iv) Peptide/Kinase Mixtures for measurement of EGFR (ErbB1) T790M L858R:

The 2×EGFR (ErbB1) T790M L858R/Tyr 04 mixture is prepared in 50 mM HEPES pH 6.5, 0.01% BRIJ-35, 10 mM MgCl$_2$, 1 mM EGTA, 0.02% NaN$_3$. The final 10 μL Kinase Reaction consists of 0.38-4.22 ng EGFR (ErbB1) T790M L858R and 2 μM Tyr 04 in 50 mM HEPES pH 7.0, 0.01% BRIJ-35, 10 mM MgCl$_2$, 1 mM EGTA, 0.01% NaN$_3$. After the 1 hour Kinase Reaction incubation, 5 μL of a 1:64 dilution of Development Reagent B is added.

(v) Peptide/Kinase Mixtures for measurement of BTK:

The 2×BTK/Tyr 01 mixture is prepared in 50 mM HEPES pH 7.5, 0.01% BRIJ-35, 10 mM MgCl2, 1 mM EGTA. The final 10 µL Kinase Reaction consists of 1.04-10.4 ng BTK and 2 µM Tyr 01 in 50 mM HEPES pH 7.5, 0.01% BRIJ-35, 10 mM MgCl2, 1 mM EGTA. After the 1 hour Kinase Reaction incubation, 5 µL of a 1:256 dilution of Development Reagent B is added.

(v) Peptide/Kinase Mixtures for measurement of FGFR1:

The 2×FGFR1/Tyr 04 mixture is prepared in 50 mM HEPES pH 7.5, 0.01% BRIJ-35, 10 mM MgCl2, 4 mM MnCl2, 1 mM EGTA, 2 mM DTT. The final 10 µL Kinase Reaction consists of 0.41-3.5 ng FGFR1 and 2 µM Tyr 04 in 50 mM HEPES pH 7.5, 0.01% BRIJ-35, 10 mM MgCl2, 2 mM MnCl2, 1 mM EGTA, 1 mM DTT. After the 1 hour Kinase Reaction incubation, 5 µL of a 1:64 dilution of Development Reagent B is added.

(v) Peptide/Kinase Mixtures for measurement of FGFR2:

The 2×FGFR2/Tyr 04 mixture is prepared in 50 mM HEPES pH 7.5, 0.01% BRIJ-35, 10 mM MgCl2, 4 mM MnCl2, 1 mM EGTA, 2 mM DTT. The final 10 µL Kinase Reaction consists of 0.19-2.36 ng FGFR2 and 2 µM Tyr 04 in 50 mM HEPES pH 7.5, 0.01% BRIJ-35, 10 mM MgCl2, 2 mM MnCl2, 1 mM EGTA, 1 mM DTT. After the 1 hour Kinase Reaction incubation, 5 µL of a 1:64 dilution of Development Reagent B is added.

(v) Peptide/Kinase Mixtures for measurement of JAK2:

The 2×JAK2/Tyr 06 mixture is prepared in 50 mM HEPES pH 7.5, 0.01% BRIJ-35, 10 mM MgCl2, 1 mM EGTA. The final 10 µL Kinase Reaction consists of 0.06-0.81 ng JAK2 and 2 µM Tyr 06 in 50 mM HEPES pH 7.5, 0.01% BRIJ-35, 10 mM MgCl2, 1 mM EGTA. After the 1 hour Kinase Reaction incubation, 5 µL of a 1:64 dilution of Development Reagent A is added.

(v) Peptide/Kinase Mixtures for measurement of JAK3:

The 2×JAK3/Tyr 06 mixture is prepared in 50 mM HEPES pH 7.5, 0.01% BRIJ-35, 10 mM MgCl2, 1 mM EGTA. The final 10 µL Kinase Reaction consists of 0.29-1.34 ng JAK3 and 2 µM Tyr 06 in 50 mM HEPES pH 7.5, 0.01% BRIJ-35, 10 mM MgCl2, 1 mM EGTA. After the 1 hour Kinase Reaction incubation, 5 µL of a 1:64 dilution of Development Reagent A is added.

(v) Peptide/Kinase Mixtures for measurement of KDR (VEGFR2):

The 2×KDR (VEGFR2)/Tyr 01 mixture is prepared in 50 mM HEPES pH 7.5, 0.01% BRIJ-35, 10 mM MgCl2, 1 mM EGTA. The final 10 µL Kinase Reaction consists of 0.5-11.7 ng KDR (VEGFR2) and 2 µM Tyr01 in 50 mM HEPES pH 7.5, 0.01% BRIJ-35, 10 mM MgCl2, 1 mM EGTA. After the 1 hour Kinase Reaction incubation, 5 µL of a 1:256 dilution of Development Reagent B is added.

Reaction starts by 30-second shaking of mixture consisting of 2.5 µL 4× test compound, 5 µL 2× kinase reaction mixture and 2.5 µL 4×ATP Solution on Bar-coded Corning, low volume NBS, black 384-well plate (Corning Cat. #3676). Then the mixture is incubated for 60-minute at room temperature for the kinase reaction, followed by addition of 5 µL of a 1:1024 dilution of development reagent A and 30-second plate shake. The mixture is then incubated for another 60-minute at room temperature for development reaction. Finally fluorescence is read by plate reader.

Table 2 shows % inhibition against EGFR, EGFR L858R, EGFR T790M and EGFR L858R/T790M at 0.0137, 0.041 or 1 µM of several compounds of the invention using Z'-LYTE® method. The scale utilized in Table 2 is as follows: ++ more than 50% inhibition and + less than 50% inhibition.

TABLE 2

Biological activity of illustrative compounds against BTK, EGFR and EGFR L5858R/T790M

| | EGFR (Compound at 0.041 µM) | EGFR (Compound at 1 µM) | EGFR L858R (Compound at 1 µM) | EGFR T790M (Compound at 1 µM) | EGFR L858R/T790M (Compound at 0.0137 µM) | EGFR L858R/T790M (Compound at 1 µM) |
|---|---|---|---|---|---|---|
| C001 | | ++ | ++ | ++ | + | ++ |
| C002 | | + | + | ++ | | ++ |
| C003 | | ++ | ++ | ++ | ++ | ++ |
| C004 | | + | + | + | | ++ |
| C005 | | ++ | ++ | + | | + |
| C007 | | + | + | + | | + |
| C008 | | + | + | + | | + |
| C009 | | + | + | + | | + |
| C010 | | + | + | + | | + |
| C011 | | + | + | + | | + |
| C012 | | + | + | ++ | | ++ |
| C020 | | | | | | ++ |
| C021 | ++ | | | | ++ | |
| C022 | | | | | | ++ |
| C023 | | + | | | | + |
| C024 | | | | | | ++ |
| C025 | | | | | | ++ |
| C026 | | | | | | ++ |
| C027 | | | | | | ++ |
| C028 | | | | | | ++ |
| C029 | | ++ | | | | ++ |
| C030 | | ++ | | | | ++ |
| C031 | | ++ | | | | ++ |
| C032 | | ++ | | | + | ++ |
| C033 | | ++ | | | | ++ |
| C034 | ++ | ++ | | | | ++ |
| C037 | ++ | | | | | |
| C040 | ++ | | | | | ++ |

TABLE 2-continued

Biological activity of illustrative compounds against BTK, EGFR and EGFR L5858R/T790M

| | EGFR (Compound at 0.041 μM) | EGFR (Compound at 1 μM) | EGFR L858R (Compound at 1 μM) | EGFR T790M (Compound at 1 μM) | EGFR L858R/ T790M (Compound at 0.0137 μM) | EGFR L858R/ T790M (Compound at 1 μM) |
|---|---|---|---|---|---|---|
| C041 | ++ | | | | ++ | |
| C042 | ++ | | | | + | |
| C043 | ++ | | | | ++ | |
| C044 | ++ | | | | ++ | |
| C045 | ++ | | | | ++ | |
| C046 | ++ | | | | ++ | |
| C047 | ++ | | | | ++ | |
| C048 | ++ | | | | ++ | |
| C049 | ++ | | | | ++ | |
| C050 | + | | | | ++ | |
| C051 | + | | | | ++ | |
| C052 | + | | | | ++ | |
| C053 | + | ++ | | | ++ | ++ |
| C054 | ++ | | | | ++ | |
| C055 | + | | | | ++ | |
| C056 | + | | | | + | |
| C057 | ++ | | | | ++ | |
| C058 | + | | | | ++ | |
| C059 | ++ | | | | ++ | |
| C060 | + | | | | ++ | |
| C061 | + | | | | ++ | |
| C062 | ++ | | | | ++ | |
| C063 | ++ | | | | ++ | |
| C064 | + | | | | + | |
| C065 | + | | | | + | |
| C066 | + | | | | + | |
| C067 | ++ | | | | ++ | |
| C068 | ++ | | | | ++ | |
| C069 | ++ | | | | ++ | |
| C070 | + | | | | + | |
| C071 | + | | | | + | |
| C072 | + | | | | ++ | |
| C073 | + | | | | ++ | |
| C074 | + | | | | ++ | |
| C075 | ++ | | | | ++ | |
| C076 | + | | | | + | |
| C077 | + | | | | ++ | |
| C078 | ++ | | | | ++ | |
| C079 | + | | | | ++ | |
| C080 | ++ | | | | ++ | |
| C081 | + | | | | ++ | |
| C082 | + | | | | ++ | |
| C083 | + | | | | ++ | |
| C084 | + | | | | ++ | |
| C085 | + | | | | ++ | |
| C086 | + | | | | ++ | |
| C087 | ++ | | | | ++ | |
| C088 | ++ | | | | ++ | |
| C089 | + | | | | + | |
| C090 | + | | | | ++ | |
| C091 | + | | | | + | |
| C092 | + | | | | + | |
| C093 | + | | | | ++ | |
| C094 | + | | | | + | |
| C095 | + | | | | + | |
| C096 | + | | | | + | |
| C097 | + | | | | + | |
| C098 | + | | | | + | |
| C099 | ++ | | | | ++ | |
| C100 | + | | | | + | |
| C101 | + | | | | ++ | |
| C102 | + | | | | + | |
| C103 | + | | | | ++ | |
| C104 | + | | | | + | |
| C105 | + | | | | ++ | |
| C109 | + | | | | ++ | |
| C110 | + | | | | ++ | |
| C111 | + | | | | + | |
| C112 | + | | | | + | |
| C113 | + | | | | + | |
| C114 | + | | | | + | |

TABLE 2-continued

Biological activity of illustrative compounds against BTK, EGFR and EGFR L5858R/T790M

| | EGFR (Compound at 0.041 μM) | EGFR (Compound at 1 μM) | EGFR L858R (Compound at 1 μM) | EGFR T790M (Compound at 1 μM) | EGFR L858R/ T790M (Compound at 0.0137 μM) | EGFR L858R/ T790M (Compound at 1 μM) |
|---|---|---|---|---|---|---|
| C115 | + | | | | + | |
| C116 | + | | | | + | |
| C117 | + | | | | + | |
| C118 | ++ | | | | ++ | |
| C119 | + | | | | + | |
| C120 | + | | | | + | |
| C121 | + | | | | ++ | |
| C122 | + | | | | + | |
| C123 | ++ | | | | ++ | |
| C124 | + | | | | + | |
| C125 | + | | | | + | |
| C126 | ++ | | | | ++ | |
| C127 | ++ | | | | ++ | |
| C128 | + | | | | + | |
| C129 | ++ | | | | ++ | |
| C130 | + | | | | + | |
| C131 | + | | | | + | |
| C132 | + | | | | + | |
| C133 | + | | | | + | |
| C134 | + | | | | + | |
| C135 | + | | | | + | |
| C136 | + | | | | ++ | |
| C137 | ++ | | | | ++ | |
| C138 | ++ | | | | ++ | |
| C139 | ++ | | | | ++ | |
| C140 | ++ | | | | ++ | |
| C141 | ++ | | | | ++ | |
| C142 | | | | | | |
| C143 | + | | | | ++ | |
| C144 | ++ | | | | ++ | |
| C145 | + | | | | ++ | |
| C146 | + | | | | ++ | |
| C147 | + | | | | ++ | |
| C148 | + | | | | + | |
| C149 | + | | | | + | |
| C150 | + | | | | + | |
| C151 | + | | | | ++ | |
| C152 | + | | | | ++ | |
| C153 | + | | | | + | |
| C154 | + | | | | + | |
| C155 | + | | | | ++ | |
| C157 | | | | | + | |
| C158 | | | | | + | |
| C159 | | | | | + | |
| C160 | | | | | + | |
| C161 | | | | | + | |
| C164 | + | | | | + | |

Table 3 shows 00 inhibition against BTK, JAK2 and FGFR1 at 0.041 μM of several compounds of the invention using Z'-LYTE® method. The scale utilized in Table 3 is as follows: ++ more than 500% inhibition and + less than 50% inhibition.

TABLE 3

Biological activity of illustrative compounds against BTK, JAK2 and FGFR1

| Compound No. | BTK | JAK2 | FGFR1 |
|---|---|---|---|
| C001 | ++ | ++ | ++ |
| C004 | + | ++ | |
| C005 | ++ | + | |
| C008 | + | ++ | + |
| C009 | + | ++ | |
| C012 | ++ | + | |

TABLE 3-continued

Biological activity of illustrative compounds against BTK, JAK2 and FGFR1

| Compound No. | BTK | JAK2 | FGFR1 |
|---|---|---|---|
| C020 | | | ++ |
| C021 | ++ | ++ | ++ |
| C022 | ++ | ++ | ++ |
| C023 | + | + | + |
| C025 | | | ++ |
| C026 | + | ++ | ++ |
| C027 | | | ++ |
| C032 | | | ++ |
| C032 | ++ | ++ | |
| C033 | ++ | + | |
| C036 | | | + |
| C040 | ++ | + | |
| C044 | | | + |

TABLE 3-continued

Biological activity of illustrative compounds against BTK, JAK2 and FGFR1

| Compound No. | BTK | JAK2 | FGFR1 |
|---|---|---|---|
| C051 |  |  | + |
| C053 | ++ | ++ | ++ |
| C054 | ++ | ++ |  |
| C055 | + | + |  |
| C059 |  |  | ++ |
| C075 |  |  | ++ |
| C109 | ++ |  |  |
| C110 | ++ |  |  |
| C111 | ++ |  |  |
| C112 | ++ |  |  |
| C113 | ++ |  |  |
| C114 | ++ |  |  |
| C115 | ++ |  |  |
| C116 | ++ |  |  |
| C117 | ++ |  |  |
| C118 | ++ |  |  |
| C119 | ++ |  |  |
| C120 | ++ |  |  |
| C121 | ++ |  |  |
| C122 | ++ |  |  |
| C123 | ++ |  |  |
| C124 | ++ |  |  |
| C125 | ++ |  |  |
| C126 | ++ |  |  |

To determine $IC_{50}$ of a compound against EGFR, EGFR mutant and other kinases, a series of concentrations of the compound were tested for the inhibition. $IC_{50}$ was calculated by plotting the concentration of compound vs the percentage of inhibition in treated wells using GraphPad Prism 5. Table 4 shows $IC_{50}$ values of several compounds of the invention against EGFR, EGFR L858R/T790M and several other kinases. The scale utilized in Table 4 is as follows: +++ less than 100 nM, ++ 100-500 nM and + greater than 500 nM.

TABLE 4

$IC_{50}$ of several illustrative compounds against EGFR, EGFR L858R/T790M, BTK, FGFR1, FGFR2, KDR and JAK3

| Compound No. | EGFR | EGFR L858R/T790M | BTK | FGFR1 | FGFR2 | KDR | JAK3 |
|---|---|---|---|---|---|---|---|
| C001 |  | +++ |  |  |  |  |  |
| C003 |  | +++ |  |  |  |  |  |
| C021 | +++ | +++ | +++ | +++ | +++ | +++ | +++ |
| C032 | ++ | +++ |  |  |  |  |  |
| C034 | +++ | +++ |  |  |  |  |  |
| C040 | +++ | +++ |  |  |  |  |  |
| C041 | +++ | +++ |  | +++ | +++ | +++ | +++ |
| C044 | +++ | +++ | +++ | ++ |  | ++ | +++ |
| C045 |  | +++ |  |  |  |  |  |
| C048 | +++ | +++ |  |  |  |  |  |
| C049 |  | +++ |  |  |  |  |  |
| C054 |  | +++ |  |  |  |  |  |
| C057 |  | +++ |  |  |  |  |  |
| C059 | +++ | +++ | +++ | +++ | ++ | +++ | +++ |
| C061 |  | +++ |  |  |  |  |  |
| C063 |  | +++ |  |  |  |  |  |
| C067 |  | +++ |  |  |  |  |  |
| C068 |  | +++ |  |  |  |  |  |
| C072 |  | +++ |  |  |  |  |  |
| C074 |  | +++ |  |  |  |  |  |
| C075 |  | +++ |  |  |  |  |  |
| C077 |  | +++ |  |  |  |  |  |
| C078 |  | +++ |  |  |  |  |  |
| C079 | ++ | +++ | +++ |  |  |  |  |
| C080 |  | +++ |  |  |  |  |  |
| C081 |  | +++ |  |  |  |  |  |
| C085 | ++ | +++ | +++ |  |  |  |  |
| C087 |  | +++ |  |  |  |  |  |

TABLE 4-continued $IC_{50}$ of several illustrative compounds against EGFR, EGFR L858R/T790M, BTK, FGFR1, FGFR2, KDR and JAK3

| Compound No. | EGFR | EGFR L858R/T790M | BTK | FGFR1 | FGFR2 | KDR | JAK3 |
|---|---|---|---|---|---|---|---|
| C088 |  | +++ |  |  |  |  |  |
| C099 | +++ | +++ | +++ |  |  |  |  |
| C103 |  | +++ |  |  |  |  |  |
| C105 | +++ | +++ | +++ |  |  |  |  |
| C106 | + | +++ | +++ |  |  |  |  |
| C107 | + | +++ | +++ |  |  |  |  |
| C108 | ++ | +++ | +++ |  |  |  |  |
| C109 |  | +++ |  |  |  |  |  |
| C110 |  | +++ |  |  |  |  |  |
| C118 |  | +++ |  |  |  |  |  |
| C121 |  | +++ |  |  |  |  |  |
| C123 |  | +++ |  |  |  |  |  |
| C126 |  | +++ |  |  |  |  |  |
| C127 |  | +++ |  |  |  |  |  |
| C129 |  | +++ |  |  |  |  |  |
| C137 |  | +++ |  |  |  |  |  |
| C138 |  | +++ |  |  |  |  |  |
| C139 |  | +++ |  |  |  |  |  |
| C140 |  | +++ |  |  |  |  |  |
| C141 |  | +++ |  |  |  |  |  |
| C145 |  | +++ |  |  |  |  |  |
| C147 | +++ | +++ | +++ | ++ | ++ | ++ |  |
| C151 | +++ | +++ | +++ | ++ | ++ | ++ |  |
| C156 | +++ | +++ |  |  |  |  |  |

Example 176: Inhibition of Cancer Cell Growth by Compounds Using MTT Assay

Inhibition of cell growth by compounds was measured using MTT assay (Mosmann, T., *Journal of Immunological Methods*, 1983, 65, 55-63). Tumor cell lines were purchased from ATCC (American Type Culture Collection, Manassas, Va.). All cell lines were maintained in RPMI 1640 (Hyclone) supplemented with 10% fetal bovine serum (FBS, Hyclone), glutamine (2 mM, Hyclone), and antibiotics (penicillin 100 U/mL and streptomycin 50 μg/mL) at 37° C. in a humidified atmosphere of 5% $CO_2$ in air. Taxol (as a positive control, Sigma) and compounds were dissolved in DMSO (Sigma), and the final concentration of DMSO in the medium was 1%. Tumor cells were plated in 96-well plates at densities of about 4000 cells/well of a 96-well plate and allowed to adhere/grow for 24 h. They were then treated with various concentrations of drug for 72 h. 3-(4,5-Dimethylthiazol-2-yl)-2,5-diphenyltetrazolium bromide (MTT, Sigma) was used to determine the number of viable cells at the time of compound addition and the number of cells remaining after 72 h compound exposure. The number of cells remaining after 72 h was compared to the number of viable cells at the time of compound addition by measuring the absorbance at 570 nm, allowing for the calculation of growth inhibition.

All concentrations of compounds were tested in triplicate and controls were averaged over 4 wells. $IC_{50}$ was calculated by plotting the concentration of compound vs the percentage of inhibition in treated wells using GraphPad Prism 5. Data for representative compounds are shown below.

Tables 5 show $IC_{50}$ values of several compounds of the invention in A431, HCT827, H3255, H1299 and H1975 cells. H1299 cells have a mutation on NRAS, HCC827 cells have an exon 19 deletion (del E746-A750), H3255 cells have L858R mutation, and H1975 cells have double EGFR mutations (L858R/T790M). The scale utilized in Tables 5 is as follows: +++ less than 100 nM; ++ between 100 nM and 500 nM; and + greater than 500 nM.

TABLE 5

IC$_{50}$ of several illustrative compounds in A549, A431, H1299, HCC827, H3255 and H1975 cells

| Compound No | A431 | HCC827 | H3255 | H1299 | H1975 |
|---|---|---|---|---|---|
| C001 | + | +++ | + | + | ++ |
| C002 | + | ++ | + | | |
| C003 | + | +++ | + | + | ++ |
| C004 | | + | | | + |
| C005 | | ++ | | + | |
| C007 | | + | | | + |
| C008 | | + | | | + |
| C009 | | + | | | + |
| C010 | | + | | | + |
| C011 | + | + | | | + |
| C012 | + | +++ | | | ++ |
| C020 | | + | | | + |
| C021 | ++ | +++ | ++ | ++ | +++ |
| C022 | | +++ | | | + |
| C023 | | + | | | + |
| C024 | | + | | | + |
| C025 | | + | | | + |
| C026 | | + | | | + |
| C027 | | ++ | | | + |
| C028 | | + | | | + |
| C029 | ++ | +++ | + | | ++ |
| C030 | | ++ | | | ++ |
| C031 | | + | | | + |
| C032 | ++ | +++ | | + | ++ |
| C033 | | +++ | | + | ++ |
| C034 | + | +++ | | + | +++ |
| C035 | + | +++ | | + | +++ |
| C036 | | +++ | | + | + |
| C037 | +++ | +++ | | | +++ |
| C038 | | +++ | | | +++ |
| C039 | | +++ | | + | ++ |
| C040 | ++ | +++ | | ++ | +++ |
| C041 | + | +++ | + | + | ++ |
| C042 | | | | | + |
| C043 | + | | | | ++ |
| C044 | + | | + | + | +++ |
| C045 | ++ | | | | +++ |
| C046 | + | | | + | +++ |
| C047 | + | | | | ++ |
| C048 | + | | | | +++ |
| C049 | + | | | | ++ |
| C050 | | | | | + |
| C051 | + | | | | ++ |
| C052 | | | | | ++ |
| C053 | ++ | | | | +++ |
| C054 | + | | | | ++ |
| C055 | ++ | | | | ++ |
| C056 | + | | | | ++ |
| C057 | ++ | | | | ++ |
| C058 | + | | | | +++ |
| C059 | ++ | +++ | ++ | + | +++ |
| C060 | + | | | | ++ |
| C061 | + | | | | +++ |
| C062 | | | | | ++ |
| C063 | + | | | | +++ |
| C064 | | | | | + |
| C065 | | | | | ++ |
| C066 | | | | | + |
| C067 | | | | | +++ |
| C068 | + | | | | ++ |
| C069 | +++ | | | | +++ |
| C070 | | | | | + |
| C071 | | | | | + |
| C072 | ++ | | | | ++ |
| C073 | | | | | ++ |
| C074 | ++ | | | | ++ |
| C075 | ++ | | | | +++ |
| C076 | | | | | + |
| C077 | | | | | +++ |
| C078 | + | | | | +++ |
| C079 | ++ | | ++ | | +++ |
| C080 | ++ | | | | +++ |
| C081 | | | | | ++ |
| C082 | | | | | ++ |
| C083 | | | | | ++ |
| C084 | | | | | ++ |
| C085 | ++ | | + | + | +++ |
| C086 | | | | | ++ |
| C087 | ++ | | | | ++ |
| C088 | + | | + | + | +++ |
| C089 | | | | | ++ |
| C090 | | | | | ++ |
| C091 | + | | | | ++ |
| C092 | | | | | ++ |
| C093 | | | | | ++ |
| C094 | | | | | ++ |
| C095 | | | | | ++ |
| C096 | | | | | +++ |
| C097 | | | | | ++ |
| C098 | | | | | +++ |
| C099 | ++ | | + | + | +++ |
| C100 | | | | | + |
| C101 | | | | | +++ |
| C102 | | | | | +++ |
| C103 | +++ | | ++ | | +++ |
| C104 | | | | | + |
| C105 | ++ | +++ | +++ | | +++ |
| C106 | +++ | | ++ | | +++ |
| C107 | +++ | | ++ | | +++ |
| C108 | + | | | | +++ |
| C109 | ++ | | | | +++ |
| C110 | +++ | | | | +++ |
| C111 | | | | | +++ |
| C112 | | | | | +++ |
| C113 | | | | | +++ |
| C114 | | | | | +++ |
| C115 | | | | | ++ |
| C116 | | | | | ++ |
| C117 | | | | | ++ |
| C118 | +++ | | ++ | | +++ |
| C119 | | | | | +++ |
| C120 | | | | | +++ |
| C121 | ++ | | | | +++ |
| C122 | | | | | +++ |
| C123 | +++ | | | | +++ |
| C124 | | | | | +++ |
| C125 | | | | | +++ |
| C126 | +++ | | | | +++ |
| C127 | +++ | | ++ | | +++ |
| C128 | | | | | +++ |
| C129 | +++ | | | | +++ |
| C130 | | | | | +++ |
| C131 | | | | | +++ |
| C132 | | | | | ++ |
| C133 | | | | | ++ |
| C134 | | | | | +++ |
| C135 | | | | | +++ |
| C136 | +++ | | | | +++ |
| C137 | ++ | | + | | +++ |
| C138 | ++ | | | | +++ |
| C139 | +++ | | ++ | | +++ |
| C140 | + | | + | | +++ |
| C141 | ++ | +++ | ++ | | +++ |
| C142 | | | | | +++ |
| C143 | | | | | +++ |
| C144 | | | | | +++ |
| C145 | ++ | +++ | + | | +++ |
| C146 | | | | | +++ |
| C147 | ++ | +++ | + | | +++ |
| C148 | | | | | +++ |
| C149 | | | | | +++ |
| C150 | | | | | +++ |
| C151 | ++ | +++ | + | | +++ |
| C152 | ++ | | ++ | | +++ |
| C153 | | | | | +++ |
| C154 | | | | | ++ |
| C155 | | | | | +++ |
| C156 | ++ | +++ | + | | +++ |
| C157 | | | | | + |
| C158 | | | | | ++ |

TABLE 5-continued

IC$_{50}$ of several illustrative compounds in A549,
A431, H1299, HCC827, H3255 and H1975 cells

| Compound No | A431 | HCC827 | H3255 | H1299 | H1975 |
|---|---|---|---|---|---|
| C159 |  |  |  |  | + |
| C160 |  |  |  |  | ++ |
| C161 |  |  | + |  | ++ |
| C162 |  |  | + |  | ++ |
| C163 |  |  |  |  | ++ |
| C164 |  |  |  |  | ++ |

Example 177: Inhibition of Tumor Growth in Xenograft Model

H1975 cells were implanted in BALB/c female nude mice and grown as tumor xenografts. When tumors achieved 120-200 mm$^3$, mice were assigned into treatment and control groups using randomized block design based upon their tumor volumes. Each group contained 6 tumor-bearing mice. Tumors were measured twice weekly in two dimensions using a caliper, and the tumor volume was calculated from two-dimensional measurements using the equation $V=0.5 \times a \times b^2$ where a and b are the long and short diameters of the tumor, respectively. Relative tumor volume (RTV) was defined as $TV_t/TV_i$, the ratio of the volume on a given day ($TV_t$) and the volume at the start of treatment ($TV_i$). Relative tumor growth rate (T/C) was defined as $RTV_T/RTV_C$, the ratio of relative tumor volume of treatment group ($RTV_T$) and relative tumor volume of control group ($RTV_C$) on a given day. Inhibition of tumor growth in a H1975 tumor xenograft model by some compounds is shown below in Table 6 and Table 7.

TABLE 6

In vivo activity of illustrative compounds in H1975 tumor model

| Compound No. | Dose (mg/kg) | Route | Schedule | Tumor Volume Pre-treatment (mm$^3$) | Tumor Volume Post-treatment (mm$^3$) | T/C (%) |
|---|---|---|---|---|---|---|
| Vehicle | — | Oral | QD x 14 | 152.8 | 2110.2 | — |
| C021 | 60 | Oral | QD x 14 | 152.5 | 633.5 | 30.5 |
| C041 | 30 | Intra-peritoneal injection | QD x 14 | 151.7 | 1021.2 | 48.7 |
| C059 | 60 | Oral | QD x 14 | 151.6 | 746.4 | 35.3 |
| C103 | 30 | Intra-peritoneal injection | QD x 14 | 150.9 | 748.7 | 35.8 |
| C107 | 30 | Intra-peritoneal injection | QD x 14 | 150.6 | 1341.7 | 63.6 |

TABLE 7

In vivo activity of more illustrative compounds in H1975 tumor model

| Compound No. | Dose (mg/kg) | Route | Schedule | Tumor Volume Pre-treatment (mm3) | Tumor Volume Post-treatment (mm3) | T/C (%) |
|---|---|---|---|---|---|---|
| Vehicle | — | Oral | QD x 14 | 227 | 1613 | — |
| C147 | 60 | Oral | QD x 14 | 240 | 898 | 55.7 |
| C151 | 60 | Oral | QD x 14 | 229 | 462 | 28.6 |
| C156 | 60 | Oral | QD x 14 | 232 | 594 | 36.8 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A method of treating cancer in a patient, wherein said patient has one or more mutations in the EGFR gene, comprising administering to said patient a therapeutically effective amount of a substituted quinazoline compound comprising an electrophilic group capable of forming a covalent bond with a nucleophile, or a pharmaceutically acceptable salt thereof; wherein the cancer is skin cancer or lung cancer.

2. The method of claim 1, wherein the cancer is skin cancer.

3. The method of claim 1, wherein the cancer is lung cancer.

4. The method of claim 3, wherein the lung cancer is lung carcinoma or small cell lung carcinoma.

5. The method of claim 3, wherein the lung cancer is non-small cell lung cancer (NSCLC).

6. The method of claim 1, wherein the mutation is selected from the group consisting of EGFR del E746-A750, EGFR del E747-E749/A750P, EGFR del E747-S752/P753S, EGFR del E747-T751/Sins/A750P, EGFR del S752-1759, EGFR G719S, EGFR G719C, EGFR L861Q, EGFR L858R, EGFR T790M, and EGFR L858R/T790M.

7. The method of claim 1, wherein the patient has an exon 19 deletion mutation.

8. The method of claim 1, wherein the patient has L858R substitution mutation in exon 21.

9. The method of claim 1, wherein the patient has T790M point mutation.

10. The method of claim 1, wherein the patient has both the L858R and T790M mutations.

11. The method of claim 1, wherein the substituted quinazoline compound is administered in a unit dose ranging from about 1 mg to about 1000 mg.

12. The method of claim 1, wherein the substituted quinazoline compound is administered in a unit dose ranging from about 1 mg to 300 mg.

13. The method of claim 1, wherein the substituted quinazoline compound is administered in a unit dose ranging from 10 mg to 200 mg.

14. The method of claim 1, wherein the substituted quinazoline compound is administered in a dosage form comprising one or more unit doses.

15. The method of claim 1, wherein the substituted quinazoline compound is administered in a dosage range of about 0.01 mg/kg of body weight to about 100 mg/kg of body weight per day.

16. The method of claim 1, wherein the substituted quinazoline is substituted at the 8 position with a substituted phenyl group and at the 2 position with a —NHR group, wherein R is an aryl or a heteroaryl substituted with an optionally substituted heterocycloalkyl.

17. The method of claim 16, wherein the substituted phenyl group is substituted with the electrophilic group.

18. The method of claim 1, wherein the electrophilic group is selected from the group consisting of:

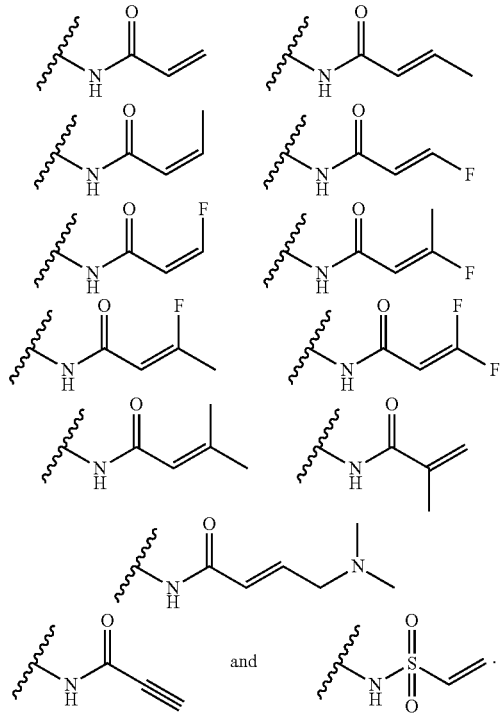

19. The method of claim 18, wherein the electrophilic group is

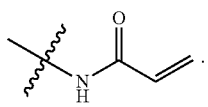 [SMILES: *NC(=O)C=C]

20. The method of claim 18, wherein the electrophilic group is

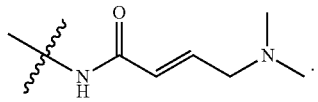 [SMILES: *NC(=O)/C=C/CN(C)C]

21. The method of claim 1, wherein the substituted quinazoline compound is a compound of Formula Ib':

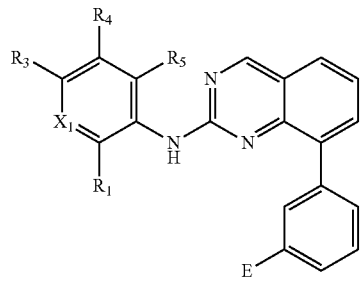

wherein:
X1 is N or C—R2;
each R1, R2, R4, and R5 is independently H or halo;
R3 is optionally substituted heterocycloalkyl; and
E is an electrophilic group capable of forming a covalent bond with a nucleophile.

22. The method of claim 1, wherein the substituted quinazoline compound is selected from the group consisting of N-(3-(2-((4-(4-(2-hydroxyethyl)piperazin-1-yl)phenyl)amino)quinazolin-8-yl)phenyl)acrylamide, N-(3-(2-((2,3-difluoro-4-(4-(2-hydroxyethyl)piperazin-1-yl)phenyl)amino)quinazolin-8-yl)phenyl)acrylamide, N-(3-(2-((2,3-difluoro-4-(4-methylpiperazin-1-yl)phenyl)amino)quinazolin-8-yl)phenyl)acrylamide, N-(3-(2-((2,3-difluoro-4-(4-(2-hydroxy-2-methylpropyl)piperazin-1-yl)phenyl)amino)quinazolin-8-yl)phenyl)acrylamide, N-(3-(2-((2,3-difluoro-4-(4-(2-methoxyethyl)piperazin-1-yl)phenyl)amino)quinazolin-8-yl)phenyl)acrylamide, N-(3-(2-((4-(4-(2-methoxyethyl)piperazin-1-yl)phenyl)amino)quinazolin-8-yl)phenyl)acrylamide, N-(3-(2-((3-fluoro-4-(4-(2-methoxyethyl)piperazin-1-yl)phenyl)amino)quinazolin-8-yl)phenyl)acrylamide, N-(3-(2-((2-fluoro-4-(4-(2-hydroxyethyl)piperazin-1-yl)phenyl)amino)quinazolin-8-yl)phenyl)acryl amide, N-(3-(2-((6-(4-methylpiperazin-1-yl)pyridin-3-yl)amino)quinazolin-8-yl)phenyl)acrylamide, N-(3-(2-((4-(4-methylpiperazin-1-yl)phenyl)amino)quinazolin-8-yl)phenyl)acrylamide, and pharmaceutically acceptable salts thereof.

* * * * *